(12) United States Patent
Pitts et al.

(10) Patent No.: US 7,737,279 B2
(45) Date of Patent: Jun. 15, 2010

(54) 1,6-DIHYDRO-1,3,5,6-TETRAAZA-AS-INDACENE BASED TRICYCLIC COMPOUNDS AND PHARMACEUTICAL COMPOSITIONS COMPRISING SAME

(75) Inventors: William J. Pitts, Newtown, PA (US); James Kempson, Princeton, NJ (US); Junqing Guo, Princeton, NJ (US); Jagabandhu Das, Mercerville, NJ (US); Charles M. Langevine, Brooklyn, NY (US); Steven H. Spergel, Warrington, PA (US); Scott Hunter Watterson, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1007 days.

(21) Appl. No.: 11/430,215

(22) Filed: May 8, 2006

(65) Prior Publication Data

US 2006/0270654 A1    Nov. 30, 2006

Related U.S. Application Data

(60) Provisional application No. 60/679,692, filed on May 10, 2005.

(51) Int. Cl.
C07D 471/14 (2006.01)
A61K 31/437 (2006.01)
A61K 31/4375 (2006.01)

(52) U.S. Cl. .................................. 546/82; 514/290
(58) Field of Classification Search .................. 546/82; 514/279, 290
See application file for complete search history.

(56) References Cited

U.S. PATENT DOCUMENTS

| 6,933,294 | B2 | 8/2005 | Belema et al. |
| 7,071,333 | B2 | 7/2006 | Combs et al. |
| 2004/0204432 | A1 | 10/2004 | Qiu et al. |
| 2005/0101626 | A1 | 5/2005 | Pitts et al. |
| 2006/0106051 | A1 | 5/2006 | Dyckman et al. |
| 2006/0128741 | A1 | 6/2006 | Das et al. |

FOREIGN PATENT DOCUMENTS

| WO | WO 91/10671 | 7/1991 |
| WO | WO 99/43680 | 9/1999 |
| WO | WO 02/12442 | 2/2002 |
| WO | WO 2004/106293 | 12/2004 |
| WO | WO 2005/082367 | 9/2005 |
| WO | WO 2005/105788 | 11/2005 |

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Dorwald F. A. Side Reactions in Organic Synthesis, 2005, Wiley: VCH, Weinheim.*
C. Papamicael et al., Heterocycles, vol. 47, No. 2, 1998, pp. 991-1004.
S. Achab et al., Tetrahedron Letters, "A short route to functionalized imidazo[4,5-c]carbazoles. Synthesis of the first example of the imidazo[4,5-c]β-carboline ring system", vol. 42, 2001, pp. 8825-8828.
Registry File Record for CAS RN 552317-79-0, Jul. 2003.
K. Rupert et al., "Imidazopyrimidines, potent inhibitors of p38 MAP kinase", Bioorganic & Medicinal Chemistry Letters, vol. 13, No. 3, 2003, pp. 37-350.

* cited by examiner

*Primary Examiner*—Rita J Desai
(74) *Attorney, Agent, or Firm*—Mary K. VanAtten

(57) ABSTRACT

The present invention provides for tricyclic compounds having the formula (I),

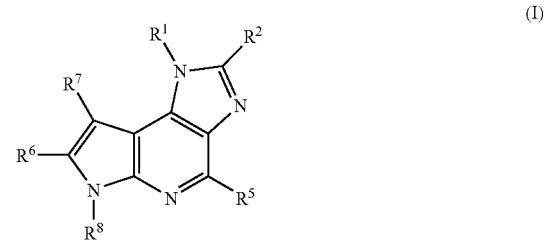

wherein $R^1$, $R^2$, $R^5$, $R^6$, $R^7$, and $R^8$ are as described herein. The present invention further provides pharmaceutical compositions comprising such compounds, as well as the use of such compounds for treating inflammatory and immune diseases.

8 Claims, 1 Drawing Sheet

US 7,737,279 B2

1,6-DIHYDRO-1,3,5,6-TETRAAZA-*AS*-INDACENE BASED TRICYCLIC COMPOUNDS AND PHARMACEUTICAL COMPOSITIONS COMPRISING SAME

CROSS-REFERENCE TO RELATED APPLICATION

This application claims the benefit of U.S. Provisional Application No. 60/679,692, filed May 10, 2005, incorporated herein by reference in its entirety.

FIELD OF THE INVENTION

Disclosed herein are 1,6-dihydro-1,3,5,6-tetraaza-as-indacene based tricyclic compounds, to methods of using the compounds in treating inflammatory and immune diseases, and cancer and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. Additionally, certain neurodegenerative diseases such as Alzheimer's disease, Parkinson's disease, and Creutzfeldt-Jacob disease also are reportedly associated with enhanced TNF-α levels. See, e.g., Arvin et al., "*The Role of Inflammation and Cytokines in Brain Injury*," Neuroscience and Biobehavioral Reviews, Vol. 20, No. 3 (1996), at pp. 445-452. More recently agents which inhibit the action of TNF-α have demonstrated clinical utility in a variety of diseases such as rheumatoid arthritis, psoriasis, and inflammatory bowel disease. See, e.g. Keating, et al. "*Infliximab: An Updated Review of its use in Crohn's Disease and Rheumatoid Arthritis*" BioDrugs Vol 16, (2002) pp. 111-148, and Hanns-Martin, et al. "*Perspectives for TNF-alpha-targeting Therapies.*" Arthritis Res. Vol 4. Supp 3 (2002) pp. S 17-24.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs or P-38 inhibitors). These drugs are useful in treating a variety of diseases. See Dinarello, "*Role of Pro- and Anti-Inflammatory Cytokines During Inflammation: Experimental and Clinical Findings, Review*, Vol. 0393-974X (1997), at pp. 91-103.

Recently, attention has focussed on the role of Nuclear factor κB (NF-κB) in the activation pathway that leads to production of TNF-α and other inflammatory cytokines and gene products. Besides TNF-α, NF-κB is involved in the regulation of a variety of genes involved in immune function and inflammation. These include the cytokines IL-1, IL-2, IL-6, IL-2Rα, and GM-GSF, the chemokines IL-8, MCP-1 (CCR2), and RANTES, the adhesion molecules, intercellular adhesion molecule-1 (ICAM-1), vascular cellular adhesion molecule-1 (VCAM-1) and E-selectin, the proteases matrix metalloproteinase-1 (MMP-1), MMP-9 and MMP-13, and the pro-inflammatory enzymes cyclooxygenase-2 (COX-2), iNOS, and cPLA$_2$. Thus, inhibition of NF-κB and/or its activation pathway provides a means for treating various diseases including autoimmune diseases, inflammatory diseases, Alzheimer's disease, atherosclerosis, oncogenesis, and so forth by a variety of modes of action (i.e. cytokine reduction, chemokine reduction, reduction of adhesion molecule expression, decreased expression of certain proteases implicated in inflammatory and immune disease processes, and decreased production of enzymes which produce pro-inflammatory mediators) which have been implicated in a variety of disease progression. See, e.g., Baldwin, "*The NF-κB and IκB Proteins: New Discoveries and Insights,*" Annual Rev. Immunol., Vol. 14 (1996), at pp. 649-81; see also Christman et al., "*Impact of Basic Research on Tomorrow's Medicine, The Role of Nuclear Factor-κB in Pulmonary Diseases,*" Chest, Vol. 117 (2000), at pp. 1482-87, and Roshak, et al., "*Small-molecule Inhibitors of NF-κB for the Treatment of Inflammatory Joint Disease.*" Current Opinion in Pharmacol. Vol. 2 (2002) pp. 316-321.

Additionally attention has focussed on inhibition of NF-κB and/or its activation pathway to provide a means for treating cancer. Genes which mediate either tumorigenesis or tumor metastasis are regulated by NF-κB. In addition NF-κB is know to be activated by carcinogens and tumor promotors. See e.g., Karin et al.; "*NF-κB in Cancer: From Innocent Bystander to Major Culprit,*" Nature Rev. Cancer., Vol. 2 (2002) at pp. 301-310; see also Bharti et al.; "*Nuclear factor-kappa B and cancer: its role in prevention and therapy*" in Biochem. Pharmocol. at pp. 883-888.

IκB is a cytoplasmic protein that controls NF-κB activity by retaining NF-κB in the cytoplasm. IκB is phosphorylated by the IκB kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Thus inhibitors of IKK-1 and/or IKK-2 would prevent translocation of NF-κB to the nucleus and prevent transcription of the pro-inflammatory gene products described above. For example see Burke, et al. "*BMS-345541 is a Highly Selective Inhibitor of IkB Kinase that Binds at an Allosteric Site of the Enzyme and Blocks NF-kB dependent Transcription in Mice.*" J. Biol. Chem. Vol. 278, (2003) pp. 1450-1456.

The therapeutic effects of glucocorticoids are mediated in part by their ability to inhibit NF-κB activity by two mechanisms, i.e., up-regulating IκB protein levels and inhibiting NF-κB subunits. The deleterious side effects of glucocorticoids (such as osteoporosis, hyperglycemia, fat redistribution, etc.) have been postulated to result from the interaction of glucocorticoids with the glucocorticoid receptor (GR) or the glucocorticoid response element (GRE). For example see Schacke, et al. "*Mechanisms Involved in the Side Effects of Glucocorticoids*" Pharmacol. and Therapeutics Vol 96 (2002) pp. 23-43. Thus inhibitors of IKK-1 and/or IKK-2 inhibitors should provide much of the therapeutic benefit of glucocorticoids with a greatly improved side effect profile.

As may be appreciated, those in the field of pharmaceutical research continue to seek to develop new compounds and compositions having increased effectiveness, bioavailability, and solubility, having fewer side effects, and/or providing the physician and patient with a choice of treatment options. Particularly in the area of immune response, individuals respond differently depending upon the type of treatment and chemical agent used. Mechanisms of action continue to be studied to aid in understanding the immune response and in developing compounds effective for treating inflammatory and immune-related disorders.

SUMMARY OF THE INVENTION

Accordingly, presented herein are novel inhibitors of IKK enzyme activity, or pharmaceutically acceptable salts or prodrugs thereof.

Disclosed herein are pharmaceutical compositions comprising a pharmaceutically acceptable carrier and a therapeutically effective amount of at least one of the compounds of the present invention or a pharmaceutically acceptable salt or prodrug form thereof.

Additionally, disclosed herein is a novel process and intermediates for the preparation of the heterocyclic systems described within this document.

Disclosed herein is a method for treating disorders selected from rheumatoid arthritis, asthma, inflammaotry bowel disease, chronic obstructive pulmonary disease, psoriasis, and cancer, comprising administering to a host in need of such treatment a therapeutically effective amount of at least one of the compounds of the present invention or a pharmaceutically acceptable salt or prodrug form thereof.

Disclosed herein is a method for treating inflammatory diseases, comprising administering to a host in need of such treatment a therapeutically effective amount of at least one of the compounds of the present invention or a pharmaceutically acceptable salt or prodrug form thereof.

Disclosed herein is a method for treating immunological diseases, comprising administering to a host in need of such treatment a therapeutically effective amount of at least one of the compounds of the present invention or a pharmaceutically acceptable salt or prodrug form thereof.

Additionally are disclosed novel compounds for use in therapy.

Additionally, disclosed herein is the use of novel compounds for the manufacture of a medicament for the treatment of inflammatory diseases and cancer.

These and other features, which will become apparent during the following detailed description, have been achieved by the inventors' discovery that compounds of formula (I):

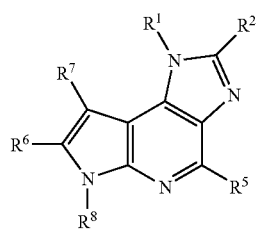

or stereoisomers or pharmaceutically acceptable salts thereof, wherein $R^1$, $R^2$, $R^5$, $R^6$, and $R^8$ are defined below, are effective inhibitors of IKK activity.

DETAILED DESCRIPTION OF EMBODIMENTS

Figure 1:
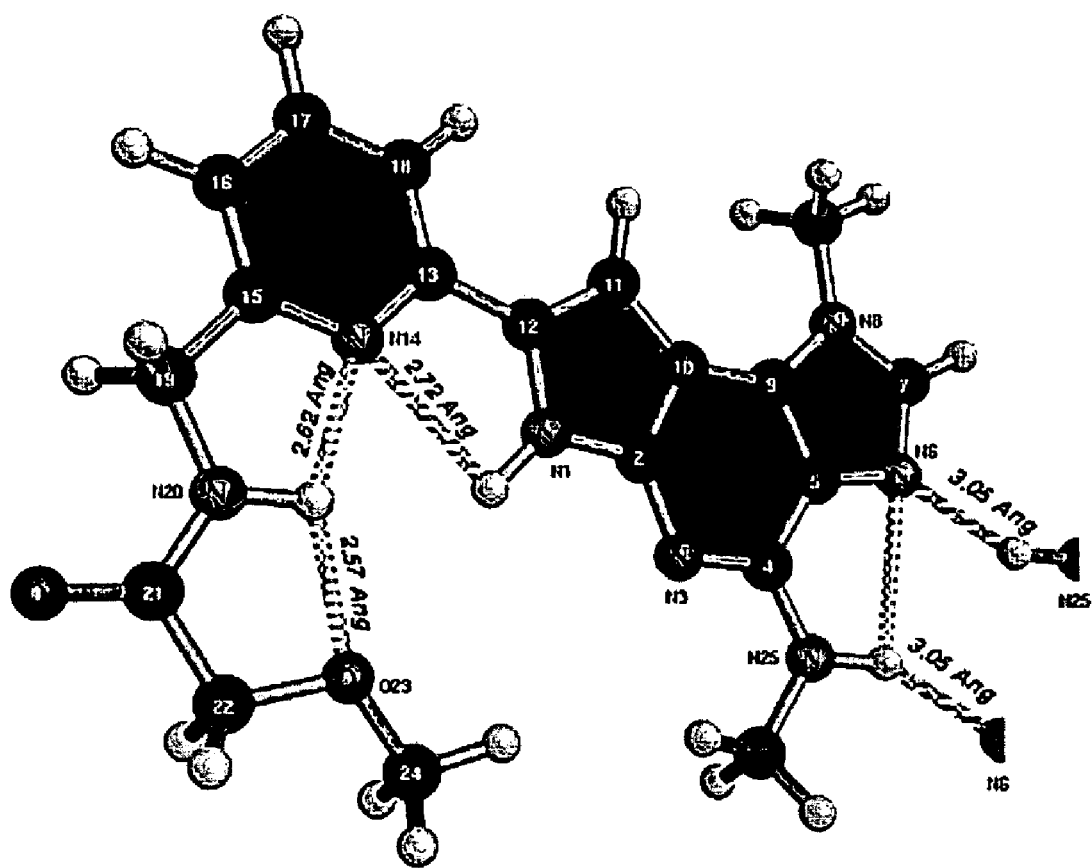
FIG. 1 shows the crystal structure for Example No. A228.

Disclosed herein are compounds of formula (I), useful in treating inflammatory or immune conditions or cancer:

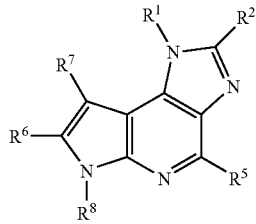

or salts thereof wherein $R^1$ is selected from hydrogen, $C_{1-3}$ alkyl, $C_{2-3}$ alkenyl, and $C_{2-3}$ alkynyl;

$R^2$ is selected from hydrogen, halo, alkyl, alkenyl, alkynyl, and perfluoroalkyl;

$R^5$ is selected from
  (a) hydrogen and halo,
  (b) alkyl, alkenyl, alkynyl, and haloalkyl, any of which may be optionally independently substituted as valence allows with one or more $Z^{1b}$, $Z^{2b}$ and $Z^{3b}$;
  (c) —$OR^{11}$, —$SR^{11}$ and —$NR^3R^4$;

$R^3$ and $R^4$ are independently selected from
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
  (c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12a}R^{13}$, —$N(R^{12})SO_2NR^{12a}R^{13}$, —$C(O)NR^{12}R^{13}$, —$SO_2R^{14}$, or —$SO_2NR^{12}R^{13}$;
  (d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$R^6$ is
  (a) alkyl, alkenyl, alkynyl, any of which is substituted with one or more as valence allows $Z^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
  (b) —$SR^{7a}$, —$SO_2R^{10}$, —$SO_2NR^{8a}R^{9b}$, $C(O)R^{7a}$, —$C(O)OR^{7a}$, or —$C(O)NR^{8a}R^{9a}$;

$R^7$ is
  (a) hydrogen, halo, or cyano,
  (b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1c}$, $Z^{2c}$ and $Z^{3c}$; or $R^{7a}$ is independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^8$ is
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$; or
  - (c) —$SO_2R^{10}$, —$SO_2NR^{8^b}R^{9^b}$, —$C(O)OR^{7^a}$, or —$C(O)NR^{8^a}R^{9^a}$;

$R^{8^a}$, $R^{8^b}$, $R^{9^a}$ and $R^{9^b}$ are independently
  - (a) hydrogen,
  - (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$;
  - (c) $R^{8^a}$ and $R^{9^a}$ together with the nitrogen atom to which they are attached combine to form a 3 to 8 membered heterocyclic ring optionally independently substituted as valence allows with one or more $Z^{1^b}$, $Z^{2^b}$ and $z^{3^b}$; or
  - (d) $R^{8^b}$ and $R^{9^b}$ together with the nitrogen atom to which they are attached combine to form a 3 to 8 membered heterocyclic ring optionally independently substituted as valence allows with one or more $Z^{1^b}$, $Z^{2^b}$ and $Z^{3^b}$;

$R^{10}$, at each occurance, is independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$;

$R^{11}$, $R^{12}$, $R^{12^a}$ and $R^{13}$ are independently
  - (a) hydrogen, or
  - (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;

$Z^{1^a-1^e}$, $Z^{2^a-2^e}$, and $Z^{3^a-3^e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
  - (1) a bond
  - (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more $V^{1-5}$; or where $V^{1-5}$ are independently
  - (1) H
  - (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more of groups (3)-(28) of $V^{1-5}$;
  - (3) —$U^1$—O—$Y^5$,
  - (4) —$U^1$—S—$Y^5$,
  - (5) —$U^1$—$C(O)_t$—H, —$U^1$—$C(O)_t$—$Y^5$ where t is 1 or 2,
  - (6) —$U^1$—$SO_3$—H, or —$U^1$—$S(O)_tY^5$,
  - (7) —$U^1$-halo,
  - (8) —$U^1$-cyano,
  - (9) —$U^1$-nitro,
  - (10) —$U^1$—$NY^2Y^3$,
  - (11) —$U^1$—$N(Y^4)$—$C(O)$—$Y^1$,
  - (12) —$U^1$—$N(Y^4)$—$C(S)$—$Y^1$,
  - (13) —$U^1$—$N(Y^4)$—$C(O)$—$NY^2Y^3$,
  - (14) —$U^1$—$N(Y^4)$—$C(O)$—$C(O)$—$NY^2Y^3$,
  - (15) —$U^1$—$N(Y^4)$—$C(O)$—$C(O)$—$OY^5$,
  - (16) —$U^1$—$N(Y^4)$—$C(S)$—$NY^2Y^3$,
  - (17) —$U^1$—$N(Y^4)$—$C(O)O$—$Y^5$,
  - (18) —$U^1$—$N(Y^4)$—$S(O)_2$—$Y^1$,
  - (19) —$U^1$—$N(Y^4)$—$S(O)_2$—$NY^2Y^3$,
  - (20) —$U^1$—$C(O)$—$NY^2Y^3$,
  - (21) —$U^1$—$OC(O)$—$NY^2Y^3$,
  - (22) —$U^1$—$OC(O)$—$OY^5$,
  - (23) —$U^1$—$S(O)_2$—$N(Y^4)$—$Y^1$,
  - (24) —$U^1$—$N(Y^4)$—$C(=NV^{1^a})$—$NY^2Y^3$,
  - (25) —$U^1$—$N(Y^4)$—$C(=NV^{1^a})$—$Y^1$,
  - (26) —$U^1$—$C(=NV^{1^a})$—$NY^2Y^3$,
  - (27) oxo;
  - (28) —$U^1$—$Y^5$;

$Z^{1^f}$, at each occurrence, is independently selected from
  - (1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with one or more of groups (2) to (25) of $Z^{1^f}$;
  - (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  - (3) —$U^1$—O—$Y^5$,
  - (4) —$U^1$—S—$Y^5$,
  - (5) —$U^1$—$C(O)_t$—H, —$U^1$—$C(O)_t$—$Y^5$ where t is 1 or 2,
  - (6) —$U^1$—$SO_3$—H, or —$U^1$—$S(O)_tY^5$,
  - (7) —$U^1$-halo,
  - (8) —$U^1$-cyano,
  - (9) —$U^1$-nitro,
  - (10) —$U^1$—$NY^2Y^3$,
  - (11) —$U^1$—$N(Y^4)$—$C(O)$—$Y^1$,
  - (12) —$U^1$—$N(Y^4)$—$C(S)$—$Y^1$,
  - (13) —$U^1$—$N(Y^4)$—$C(O)$—$NY^2Y^3$,
  - (14) —$U^1$—$N(Y^4)$—$C(S)$—$NY^2Y^3$,
  - (15) —$U^1$—$N(Y^4)$—$C(O)O$—$Y^5$,
  - (16) —$U^1$—$N(Y^4)$—$S(O)_2$—$Y^1$,
  - (17) —$U^1$—$N(Y^4)$—$S(O)_2$—$NY^2Y^3$,
  - (18) —$U^1$—$C(O)$—$NY^2Y^3$,
  - (19) —$U^1$—$OC(O)$—$NY^2Y^3$
  - (20) —$U^1$—$S(O)_2$—$N(Y^4)$—$Y^1$,
  - (21) —$U^1$—$N(Y^4)$—$C(=NV^{1^a})$—$NY^2Y^3$,
  - (22) —$U^1$—$N(Y^4)$—$C(=NV^{1^a})$—$Y^1$,
  - (23) —$U^1$—$C(=NV^{1^a})$—$NY^2Y^3$,
  - (24) oxo;
  - (25) —$U^1$—$Y^5$;

$V^{1^a}$ is independently hydrogen, alkyl, —CN, —$C(O)Y^1$, —$S(O)_tY^5$, —$C(O)NY^2Y^3$, $S(O)_2NY^2Y^3$;

$Y^1$, $Y^2$, $Y^3$, $Y^4$ and $Y^5$
  - (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $z^6$; or
  - (2) $Y^2$ and $Y^3$ together with the nitrogen atom to which they are attached combine to form a 3 to 8 membered heterocyclic ring optionally independently substituted as valence allows with one or more $Z^4$, $Z^5$ and $Z^6$, or
  - (4) $Y^2$ and $Y^3$ together with the nitrogen atom to which they are attached may combine to form a group —N=$CY^6Y^7$ where $Y^6$ and $Y^7$ are each independently H or alkyl; and $Z^4$, $Z^5$, and $Z^6$ are optional substituents at each occurrence independently selected from
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^{5a}$,
(4) —$U^1$—S—$Y^{5a}$,
(5) —$U^1$—C(O)$_t$—H, —$U^1$—C(O)$_t$—$Y^{5a}$ where t is 1 or 2,
(6) —$U^1$—SO$_3$—H, or —$U^1$—S(O)$_t Y^{5a}$,
(7) —$U^1$-halo,
(8) —$U^1$-cyano,
(9) —$U^1$-nitro,
(10) —$U^1$—N$Y^{2a}Y^{3a}$,
(11) —$U^1$—N($Y^{4a}$)—C(O)—$Y^{1a}$,
(12) —$U^1$—N($Y^{4a}$)—C(S)—$Y^{1a}$,
(13) —$U^1$—N($Y^{4a}$)—C(O)—N$Y^{2a}Y^{3a}$,
(14) —$U^1$—N($Y^{4a}$)—C(S)—N$Y^{2a}Y^{3a}$,
(15) —$U^1$—N($Y^{4a}$)—C(O)O—$Y^{5a}$,
(16) —$U^1$—N($Y^{4a}$)—S(O)$_2$—$Y^{1a}$,
(17) —$U^1$—N($Y^{4a}$)—S(O)$_2$—N$Y^{2a}Y^{3a}$,
(18) —$U^1$—C(O)—N$Y^{2a}Y^{3a}$,
(19) —$U^1$—OC(O)—N$Y^{2a}Y^{3a}$,
(20) —$U^1$—S(O)$_2$—N($Y^{4a}$)—$Y^{1a}$,
(21) —$U^1$—N($Y^{4a}$)—C(=N$V^{1b}$)—N$Y^{2a}Y^{3a}$,
(22) —$U^1$—N($Y^{4a}$)—C(=N$V^{1b}$)—$Y^{1a}$,
(23) —$U^1$—C(=N$V^{1b}$)—N$Y^{2a}Y^{3a}$,
(24) oxo;
(25) —$U^1$—$Y^{5a}$;
$V^{1b}$ is independently hydrogen, alkyl, —CN, —C(O)$Y^{1a}$, —S(O)$_2 Y^{5a}$, S(O)$_2$N$Y^{2a}Y^{3a}$;
$Y^{1a}, Y^{2a}, Y^{3a}, Y^{4a}$ and $Y^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
$U^1$ is independently
(1) a single bond,
(2) alkylene,
(3) alkenylene, or
(4) alkynylene.

Disclosed herein are compounds of formula (I), useful in treating inflammatory or immune conditions or cancer:

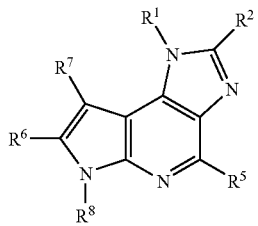

(I)

enantiomers, diastereomers, salts, and solvates thereof wherein
$R^1$ is selected from hydrogen, $C_{1-3}$ alkyl, $C_{2-3}$ alkenyl, and $C_{2-3}$ alkynyl;
$R^2$ is selected from hydrogen, alkyl, alkenyl, alkynyl, and haloalkyl;

$R^5$ is selected from
a) hydrogen and halo,
(b) alkyl, alkenyl, alkynyl, and haloalkyl, any of which may be optionally independently substituted as valence allows with one or more $Z^{1b}, Z^{2b}$ and $Z^{3b}$;
(c) —$R^{11}$, —$SR^{11}$ and —$NR^3R^4$;
$R^3$ and $R^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}, Z^{2b}$ and $Z^{3b}$;
(c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12a}R^{13}$, or —$N(R^{12})SO_2NR^{12a}R^{13}$ or —$C(O)OR^{14}$, —$C(O)R^{11}$, —$C(O)NR^{12}R^{13}$, —$SO_2R^{14}$, —$SO_2NR^{12}R^{13}$;
(d) $R^3$ and $R^4$ together with the nitrogen atom to which they are attached combine to form a 3 to 8 membered heterocyclic ring optionally independently substituted as valence allows with one or more $Z^{1b}, Z^{2b}$ and $Z^{3b}$;
$R^6$ is
(a) alkyl, alkenyl, alkynyl, any of which is substituted with one or more as valence allows $Z^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}, Z^{2d}$ and $Z^{3d}$; or
(b) —$SR^{7a}$, —$SO_2R^{10}$, —$SO_2NR^{8b}R^{9b}$, C(O)$R^{7a}$, —C(O)OR$^{7a}$, or —$C(O)NR^{8a}R^{9a}$;
$R^7$ is
(a) hydrogen, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1c}, Z^{2c}$ and $Z^{3c}$; or
(c) —$SO_2R^{10}$, —$SO_2NR^{8b}R^{9b}$, —$C(O)R^{7a}$, —$C(O)OR^{7a}$, or —$C(O)NR^{8a}R^{9a}$;
$R^{7a}$ and $R^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}, Z^{2e}$ and $Z^{3e}$;
$R^8$ is
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}, Z^{2a}$ and $Z^{3a}$; or
(c) —$SO_2R^{10}$, $SO_2NR^{8b}R^{9b}$, —$C(O)R^{7a}$, —$C(O)OR^{7a}$, or —$C(O)NR^{8a}R^{9a}$;
$R^{8a}, R^{8b}, R^{9a}$ and $R^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}, Z^{2b}$ and $Z^{3b}$;
(c) $R^{8a}$ and $R^{9a}$ together with the nitrogen atom to which they are attached combine to form a 3 to 8 membered heterocyclic ring optionally independently substituted as valence allows with one or more $Z^{1b}, Z^{2b}$ and $Z^{3b}$; or (d) $R^{8b}$ and $R^{9b}$ together with the nitrogen atom to which they are attached combine to form a 3 to 8 membered heterocyclic ring optionally independently substituted as valence allows with one or more $Z^{1b}$, $Z^{2b}$ and $Z^{3}$; $R^{10}$, at each occurance, is independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently (a) hydrogen, or (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently (1) a bond (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more $V^{1-5}$; or where $V^{1-5}$ are independently (1) H (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more of groups (3)-(25) of $V^{1-5}$;

(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—SO$_3$—H, or —$U^1$—S(O)$_t$$Y^5$,
(7) —$U^1$-halo,
(8) —$U^1$-cyano,
(9) —$U^1$-nitro,
(10) —$U^1$—N$Y^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—N$Y^2Y^3$,
(14) —$U^1$—N($Y^4$)—C(S)—N$Y^2Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—N$Y^2Y^3$,
(18) —$U^1$—C(O)—N$Y^2Y^3$,
(19) —$U^1$—OC(O)—N$Y^2Y^3$
(20) —$U^1$—S(O)$_2$—N($Y^4$)—$Y^1$,
(21) —$U^1$—N($Y^4$)—C(=N$V^{1a}$)—N$Y^2Y^3$,
(22) —$U^1$—N($Y^4$)—C(=N$V^{1a}$)—$Y^1$,
(23) —$U^1$—C(=N$V^{1a}$)—N$Y^2Y^3$,
(24) oxo;
(25) —$U^1$—$Y^5$;

$Z^{1f}$, at each occurrence, is independently selected from (1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with one or more of groups (2) to (25) of $Z^{1f}$;

(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—SO$_3$—H, or —$U^1$—S(O)$_t$$Y^5$,
(7) —$U^1$-halo,
(8) —$U^1$-cyano,
(9) —$U^1$-nitro,
(10) —$U^1$—N$Y^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—N$Y^2Y^3$,
(14) —$U^1$—N($Y^4$)—C(S)—N$Y^2Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—N$Y^2Y^3$,
(18) —$U^1$—C(O)—N$Y^2Y^3$,
(19) —$U^1$—OC(O)—N$Y^2Y^3$
(20) —$U^1$—S(O)$_2$—N($Y^4$)—$Y^1$,
(21) —$U^1$—N($Y^4$)—C(=N$V^{1a}$)—N$Y^2Y^3$,
(22) —$U^1$—N($Y^4$)—C(=N$V^{1a}$)—$Y^1$,
(23) —$U^1$—C(=N$V^{1a}$)—N$Y^2Y^3$,
(24) oxo;
(25) —$U^1$—$Y^5$;

$V^{1a}$ is independently hydrogen, alkyl, —CN, —C(O)$Y^1$, —S(O)$_2Y^5$, S(O)$_2$N$Y^2Y^3$;

$Y^1$, $Y^2$, $Y^3$, $Y^4$ and $Y^5$ (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or (2) $Y^2$ and $Y^3$ may together be alkylene or alkenylene, completing a 3- to 8-membered saturated or unsaturated ring together with the atoms to which they are attached, or (4) $Y^2$ and $Y^3$ together with the nitrogen atom to which they are attached may combine to form a group —N=C$Y^6Y^7$ where $Y^6$ and $Y^7$ are each independently H or alkyl; and $Z^4$, $Z^5$, and $Z^6$ are optional substituents at each occurrence independently selected from (1) H (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

(3) —$U^1$—O—$Y^{5a}$,
(4) —$U^1$—S—$Y^{5a}$,
(5) —$U^1$—C(O)$_t$—H, —$U^1$—C(O)$_t$—$Y^{5a}$ where t is 1 or 2,
(6) —$U^1$—SO$_3$—H, or —$U^1$—S(O)$_t$$Y^{5a}$,
(7) —$U^1$-halo,
(8) —$U^1$-cyano,
(9) —$U^1$-nitro,
(10) —$U^1$—N$Y^{2a}Y^{3a}$,
(11) —$U^1$—N($Y^{4a}$)—C(O)—$Y^{1a}$,
(12) —$U^1$—N($Y^{4a}$)—C(S)—$Y^{1a}$,
(13) —$U^1$—N($Y^{4a}$)—C(O)—N$Y^{2a}Y^{3a}$,

(14) —U$^1$—N(Y$^{4a}$)—C(S)—NY$^{2a}$Y$^{3a}$,
(15) —U$^1$—N(Y$^{4a}$)—C(O)O—Y$^{5a}$,
(16) —U$^1$—N(Y$^{4a}$)—S(O)$_2$—Y$^{1a}$,
(17) —U$^1$—N(Y$^{4a}$)—S(O)$_2$—NY$^{2a}$Y$^{3a}$,
(18) —U$^1$—C(O)—NY$^{2a}$Y$^{3a}$,
(19) —U$^1$—OC(O)—NY$^{2a}$Y$^{3a}$
(20) —U$^1$—S(O)$_2$—N(Y$^{4a}$)—Y$^{1a}$,
(21) —U$^1$—N(Y$^{4a}$)—C(=NV$^{1b}$)—NY$^{2a}$Y$^{3a}$,
(22) —U$^1$—N(Y$^{4a}$)—C(=NV$^{1b}$)—Y$^{1a}$,
(23) —U$^1$—C(=NV$^{1b}$)—NY$^{2a}$Y$^{3a}$,
(24) oxo;
(25) —U$^1$—Y$^{5a}$;

V$^{1b}$ is independently hydrogen, alkyl, —CN, —C(O)Y$^{1a}$, —S(O)$_2$Y$^{5a}$, S(O)$_2$NY$^{2a}$Y$^{3a}$;

Y$^{1a}$, Y$^{2a}$, Y$^{3a}$, Y$^{4a}$ and Y$^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

U$^1$ is independently
(1) a single bond,
(2) alkylene,
(3) alkenylene, or
(4) alkynylene.

In another embodiment are compounds of formula (I), wherein

R$^3$ and R$^4$ are independently
(a) hydrogen,
(b) alkyl, haloalkyl, (hydroxy)alkyl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1b}$, Z$^{2b}$ and Z$^{3b}$;
(c) —NR$^{12}$R$^{13}$, C(O)OR$^{14}$, or —C(O)R$^{11}$; or
(d) R$^3$ and R$^4$ together with the nitrogen atom to which they are attached combine to form a 3 to 8 membered heterocyclic ring optionally independently substituted as valence allows with one or more Z$^{1b}$, Z$^{2b}$ and Z$^{3b}$.

In another embodiment are compounds of formula (I), wherein

R$^3$ and R$^4$ are independently
(a) hydrogen,
(b) alkyl, haloalkyl, (hydroxy)alkyl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1b}$, Z$^{2b}$ and Z$^{3b}$;
(c) —NR$^{12}$R$^{13}$; or
(d) R$^3$ and R$^4$ together with the nitrogen atom to which they are attached combine to form a 3 to 8 membered heterocyclic ring optionally independently substituted as valence allows with one or more Z$^{1b}$, Z$^{2b}$ and Z$^{3b}$.

In another embodiment are compounds of formula (I), wherein

R$^6$ is
(a) alkyl, alkenyl, alkynyl, any of which is substituted with one or more as valence allows Z$^{1f}$; aryl, heteroaryl, cycloalkyl, (cycloalkyl)alkyl, heterocyclo, (heterocyclo)alkyl, aryl, (aryl)alkyl, or (heteroaryl)alkyl any of which may be optionally independently substituted as valence allows with one or more Z$^{1d}$, Z$^{2d}$ and Z$^{3d}$; or
(b) —C(O)R$^{7a}$, —C(O)OR$^{7a}$, or —C(O)NR$^{8a}$R$^{9a}$.

In another embodiment are compounds of formula (I), wherein

R$^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$ and Z$^{3c}$.

In another embodiment are compounds of formula (I), wherein

R$^3$ and R$^4$ are independently hydrogen, alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$; —NR$^{12}$R$^{13}$; —C(O)OR$^4$, or —C(O)R$^{11}$; or alternatively, R$^3$ and R$^4$ are independently hydrogen, alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$; —NR$^{12}$R$^{13}$; or alternatively, R$^3$ and R$^4$ together with the nitrogen atom to which they are attached combine to form a 3 to 6 membered heterocyclic ring selected from piperidinyl, morpholinyl, pyrrolidinyl, piperazinyl, and azetidinyl; optionally independently substituted as valence allows with one or more Z$^{1b}$, Z$^{2b}$ and Z$^{3b}$;

R$^6$ is
(a) alkyl, which is substituted with one or more as valence allows Z$^{1f}$; aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1d}$, Z$^{2d}$ and Z$^{3d}$; or
(b) —C(O)R$^{7a}$, or —C(O)NR$^{8a}$R$^{9a}$; or alternatively, (b) —C(O)R$^{7a}$, —C(O)OR$^{7a}$, or —C(O)NR$^{8a}$R$^{9a}$.

In another embodiment are compounds of formula (I), wherein

R$^1$ is hydrogen, methyl, ethyl, propyl, i-propyl, prop-2-enyl, prop-1-enyl; and R$^2$ is hydrogen, methyl, trifluoromethyl, and phenyl.

Compounds of formula (I), useful in treating inflammatory or immune conditions or cancer:

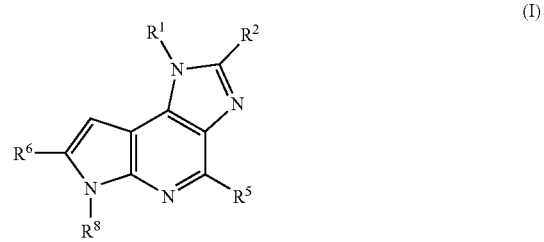

(I)

enantiomers, diastereomers, salts, and solvates thereof wherein

R$^1$ is selected from hydrogen and C$_{1-3}$ alkyl;

R$^6$ is
(a) alkyl, alkenyl, alkynyl, any of which is substituted with one or more as valence allows Z$^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or (b) —C(O)$R^{7a}$, —C(O)O$R^{7a}$, or —C(O)N$R^{8a}R^{9a}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl any of which may be optionally independently substituted as valence allows with one or more of groups (3)-(25) of $V^{1-5}$;
  (3) —$U^1$—O—$Y^5$,
  (4) —$U^1$—S—$Y^5$,
  (5) —$U^1$—C(O)$_t$—H, —$U^1$—C(O)$_t$—$Y^5$ where t is 1 or 2,
  (6) —$U^1$—SO$_3$—H, or —$U^1$—S(O)$_t Y^5$,
  (7) —$U^1$-halo,
  (8) —$U^1$-cyano,
  (9) —$U^1$-nitro,
  (10) —$U^1$—N$Y^2 Y^3$,
  (11) —$U^1$—N($Y^4$)—C(O)—$Y^1$,
  (12) —$U^1$—N($Y^4$)—C(S)—$Y^1$,
  (13) —$U^1$—N($Y^4$)—C(O)—N$Y^2 Y^3$,
  (14) —$U^1$—N($Y^4$)—C(S)—N$Y^2 Y^3$,
  (15) —$U^1$—N($Y^4$)—C(O)O—$Y^5$,
  (16) —$U^1$—N($Y^4$)—S(O)$_2$—$Y^1$,
  (17) —$U^1$—N($Y^4$)—S(O)$_2$—N$Y^2 Y^3$,
  (18) —$U^1$—C(O)—N$Y^2 Y^3$,
  (19) —$U^1$—OC(O)—N$Y^2 Y^3$
  (20) —$U^1$—S(O)$_2$—N($Y^4$)—$Y^1$,
  (21) —$U^1$—N($Y^4$)—C(=N$V^{1a}$)—N$Y^2 Y^3$,
  (22) —$U^1$—N($Y^4$)—C(=N$V^{1a}$)—$Y^1$,
  (23) —$U^1$—C(=N$V^{1a}$)—N$Y^2 Y^3$,
  (24) oxo;
  (25) —$U^1$—$Y^5$;

$Z^{1'}$, at each occurrence, is independently selected from
  (1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with groups (2) to (25);
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^5$,
  (4) —$U^1$—S—$Y^5$,
  (5) —$U^1$—C(O)$_t$—H, —$U^1$—C(O)$_t$—$Y^5$ where t is 1 or 2,
  (6) —$U^1$—SO$_3$—H, or —$U^1$—S(O)$_t Y^5$,
  (7) —$U^1$-halo,
  (8) —$U^1$-cyano,
  (9) —$U^1$-nitro,
  (10) —$U^1$—N$Y^2 Y^3$,
  (11) —$U^1$—N($Y^4$)—C(O)—$Y^1$,
  (12) —$U^1$—N($Y^4$)—C(S)—$Y^1$,
  (13) —$U^1$—N($Y^4$)—C(O)—N$Y^2 Y^3$,
  (14) —$U^1$—N($Y^4$)—C(S)—N$Y^2 Y^3$,
  (15) —$U^1$—N($Y^4$)—C(O)O—$Y^5$,
  (16) —$U^1$—N($Y^4$)—S(O)$_2$—$Y^1$,
  (17) —$U^1$—N($Y^4$)—S(O)$_2$—N$Y^2 Y^3$,
  (18) —$U^1$—C(O)—N$Y^2 Y^3$,
  (19) —$U^1$—OC(O)—N$Y^2 Y^3$
  (20) —$U^1$—S(O)$_2$—N($Y^4$)—$Y^1$,
  (21) —$U^1$—N($Y^4$)—C(=N$V^{1a}$)—N$Y^2 Y^3$,
  (22) —$U^1$—N($Y^4$)—C(=N$V^{1a}$)—$Y^1$,
  (23) —$U^1$—C(=N$V^{1a}$)—N$Y^2 Y^3$,
  (24) oxo;
  (25) —$U^1$—$Y^5$;

$V^{1a}$ is independently hydrogen, alkyl, —CN, —C(O)$Y^1$, —S(O)$_2 Y^5$, S(O)$_2$N$Y^2 Y^3$;

$Y^1$, $Y^2$, $Y^3$, $Y^4$ and $Y^5$
  (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or
  (2) $Y^2$ and $Y^3$ may together be alkylene or alkenylene, completing a 3- to 8-membered saturated or unsaturated ring together with the atoms to which they are attached, or
  (4) $Y^2$ and $Y^3$ together with the nitrogen atom to which they are attached may combine to form a group —N=C$Y^6 Y^7$ where $Y^6$ and $Y^7$ are each independently H or alkyl.

In another embodiment are compounds of formula (I) wherein $R^1$ is selected from hydrogen and $C_{1-3}$ alkyl;

$R^6$ is
  (a) alkyl, alkenyl, alkynyl, any of which is substituted with one or more as valence allows $Z^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
  (b) —C(O)$R^{7a}$, —C(O)O$R^{7a}$, or —C(O)N$R^{8a}R^{9a}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl any of which may be optionally independently substituted as valence allows with one or more of groups (3)-(28) of $V^{1-5}$;
  (3) —$U^1$—O—$Y^5$,
  (4) —$U^1$—S—$Y^5$,
  (5) —$U^1$—C(O)$_t$—H, —$U^1$—C(O)$_t$—$Y^5$ where t is 1 or 2,
  (6) —$U^1$—SO$_3$—H, or —$U^1$—S(O)$_t Y^5$,
  (7) —$U^1$-halo,
  (8) —$U^1$-cyano,
  (9) —$U^1$-nitro,
  (10) —$U^1$—N$Y^2 Y^3$,
  (11) —$U^1$—N($Y^4$)—C(O)—$Y^1$,
  (12) —$U^1$—N($Y^4$)—C(S)—$Y^1$,
  (13) —$U^1$—N($Y^4$)—C(O)—N$Y^2 Y^3$,
  (14) —$U^1$—N($Y^4$)—C(O)—C(O)—N$Y^2 Y^3$,
  (15) —$U^1$—N($Y^4$)—C(O)—C(O)—O$Y^5$,

(16) —U$^1$—N(Y$^4$)—C(S)—NY$^2$Y$^3$,
(17) —U$^1$—N(Y$^4$)—C(O)O—Y$^5$,
(18) —U$^1$—N(Y$^4$)—S(O)$_2$—Y$^1$,
(19) —U$^1$—N(Y$^4$)—S(O)$_2$—NY$^2$Y$^3$,
(20) —U$^1$—C(O)—NY$^2$Y$^3$,
(21) —U$^1$—OC(O)—NY$^2$Y$^3$,
(22) —U$^1$—OC(O)—OY$^5$,
(23) —U$^1$—S(O)$_2$—N(Y$^4$)—Y$^1$,
(24) —U$^1$—N(Y$^4$)—C(=NV$^{1a}$)—NY$^2$Y$^3$,
(25) —U$^1$—N(Y$^4$)—C(=NV$^{1a}$)—Y$^1$,
(26) —U$^1$—C(=NV$^{1a}$)—NY$^2$Y$^3$,
(27) oxo;
(2528) —U$^1$—Y$^5$;

Z$^{1f}$, at each occurrence, is independently selected from
(1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with groups (2) to (25);
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —U$^1$—O—Y$^5$,
(4) —U$^1$—S—Y$^5$,
(5) —U$^1$—C(O)$_t$—H, —U$^1$—C(O)$_t$—Y$^5$ where t is 1 or 2,
(6) —U$^1$—SO$_3$—H, or —U$^1$—S(O)$_t$Y$^5$,
(7) —U$^1$-halo,
(8) —U$^1$-cyano,
(9) —U$^1$-nitro,
(10) —U$^1$—NY$^2$Y$^3$,
(11) —U$^1$—N(Y$^4$)—C(O)—Y$^1$,
(12) —U$^1$—N(Y$^4$)—C(S)—Y$^1$,
(13) —U$^1$—N(Y$^4$)—C(O)—NY$^2$Y$^3$,
(14) —U$^1$—N(Y$^4$)—C(S)—NY$^2$Y$^3$,
(15) —U$^1$—N(Y$^4$)—C(O)O—Y$^5$,
(16) —U$^1$—N(Y$^4$)—S(O)$_2$—Y$^1$,
(17) —U$^1$—N(Y$^4$)—S(O)$_2$—NY$^2$Y$^3$,
(18) —U$^1$—C(O)—NY$^2$Y$^3$,
(19) —U$^1$—OC(O)—NY$^2$Y$^3$
(20) —U$^1$—S(O)$_2$—N(Y$^4$)—Y$^1$,
(21) —U$^1$—N(Y$^4$)—C(=NV$^{1a}$)—NY$^2$Y$^3$,
(22) —U$^1$—N(Y$^4$)—C(=NV$^{1a}$)—Y$^1$,
(23) —U$^1$—C(=NV$^{1a}$)—NY$^2$Y$^3$,
(24) oxo;
(25) —U$^1$—Y$^5$;

V$^{1a}$ is independently hydrogen, alkyl, —CN, —C(O)Y$^1$, —C(O)NY$^2$Y$^3$, —S(O)$_2$Y$^5$, S(O)$_2$NY$^2$Y$^3$;

Y$^1$, Y$^2$, Y$^3$, Y$^4$ and Y$^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more Z$^4$, Z$^5$ and Z$^6$; or
(2) Y$^2$ and Y$^3$ together with the nitrogen atom to which they are attached combine to form a 3 to 8 membered heterocyclic ring optionally independently substituted as valence allows with one or more Z$^4$, Z$^5$ and Z$^6$, or
(4) Y$^2$ and Y$^3$ together with the nitrogen atom to which they are attached may combine to form a group —N=CY$^6$Y$^7$ where Y$^6$ and Y$^7$ are each independently H or alkyl.

In another embodiment are compounds of formula (I) wherein
R$^3$ and R$^4$ are independently
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more Z$^{1b}$, Z$^{2b}$ and Z$^{3b}$;
(c) —NR$^{12}$R$^{13}$; or
(d) R$^3$ and R$^4$ together with the nitrogen atom to which they are attached combine to form a 3 to 8 membered heterocyclic ring optionally independently substituted as valence allows with one or more Z$^{1b}$, Z$^{2b}$ and Z$^{3b}$.

In another embodiment are compounds of formula (I) wherein
R$^6$ is
(a) alkyl, alkenyl, alkynyl any of which is substituted with one or more as valence allows Z$^{1f}$; aryl, heteroaryl, (cycloalkyl)alkyl, (heterocyclo)alkyl, (aryl)alkyl, or (heteroaryl)alkyl any of which may be optionally independently substituted as valence allows with one or more Z$^{1d}$, Z$^{2d}$ and Z$^{3d}$; or
(b) —C(O)R$^{7a}$, —C(O)OR$^{7a}$, or —C(O)NR$^{8a}$R$^{9a}$.

In another embodiment are compounds of formula (I) wherein
R$^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$ and Z$^{3c}$.

In another embodiment are compounds of formula (I) wherein
Z$^{1b}$, Z$^{2b}$ and Z$^{3b}$ are optional substituents independently selected from alkyl, heteroaryl, —OH, —O—Y$^5$, —U$^1$—NY$^2$Y$^3$, —C(O)$_t$H, —C(O)$_t$Y$^5$;
Z$^{1c}$ is
(a) —OH, —OY$^5$ or
(b) aryl optionally substituted with —OH or —OY$^5$;
Z$^{1d}$, Z$^{2d}$ and Z$^{3d}$ are optional substituents independently selected from
(a) cyano, halo, —OH, —OY$^5$, —U$^1$—NY$^2$Y$^3$, —C(O)$_t$H, —C(O)$_t$Y, —S(O)$_t$Y$^5$;
(b) alkyl or alkoxy optionally substituted with one or more cyano, halo, —OH, —OY, —U$^1$—NY$^2$Y$^3$, —C(O)$_t$H, —C(O)$_t$Y, —U$^1$—N(Y$^4$)—C(O)—Y$^1$, —U$^1$—N(Y$^4$)—C(O)—NY$^2$Y$^3$, —U$^1$—N(Y$^4$)—C(O)O—Y$^5$, —U$^1$—N(Y$^4$)—C(=NV$^{1a}$)—NY$^2$Y$^3$, —U$^1$—N(Y$^4$)—C(=NV$^{1a}$)—Y$^1$, —S(O)$_t$Y, —U$^1$-heteroaryl.

In another embodiment are compounds of formula (I) wherein
Z$^{1b}$, Z$^{2b}$ and Z$^{3b}$ are optional substituents independently selected from alkyl, heteroaryl, —OH, —O—Y$^5$, —U$^1$—NY$^2$Y$^3$, —C(O)$_t$H, —C(O)$_t$Y$^5$;
Z$^{1c}$ is
(a) —OH, —OY$^5$ or
(b) aryl optionally substituted with —OH or —OY$^5$;
Z$^{1d}$, Z$^{2d}$ and Z$^{3d}$ are optional substituents independently selected from
(a) cyano, halo, —OH, —OY$^5$, —U$^1$—NY$^2$Y$^3$, —C(O)$_t$H, —C(O)$_t$Y$^1$, —U$^1$—C(O)—NY$^2$Y$^3$, —S(O)$_t$Y$^5$;
(b) alkyl or alkoxy optionally substituted with one or more cyano, halo, —OH, —OY$^5$, —U$^1$—NY$^2$Y$^3$, —C(O)$_t$H, —C(O)$_t$Y$^1$, —U$^1$—C(O)—NY$^2$Y$^3$, —OC(O)—NY$^2$Y$^3$, OC(O)—OY$^5$, —U$^1$—N(Y$^4$)—C(O)—Y$^1$, —U$^1$—N(Y$^4$)—C(O)—NY$^2$Y$^3$, —U$^1$—N(Y$^4$)—C(O)O—Y$^5$, —N(Y$^4$)—S(O)$_2$—Y$^1$, —N(Y$^4$)—C(O)—C(O)—NY$^2$Y$^3$, —N(Y$^4$)—C(O)—C(O)—OY$^5$, —U$^1$—N(Y$^4$)—C(=NV$^{1a}$)—NY$^2$Y$^3$, —U$^1$—N(Y$^4$)—C(=NV$^{1a}$)—Y$^1$, —S(O)$_t$Y, —U$^1$-heteroaryl, or U1-heterocyclo, wherein heteroaryl and heterocyclo are substituted as valence allows with one or more of groups (3)-(28) of V$^{1-5}$.

In another embodiment are compounds of formula (I) wherein
R$^3$ is hydrogen;
R$^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$;
alternatively, R$^3$ and R$^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more Z$^{1b}$, Z$^{2b}$ and Z$^{3b}$;
R$^6$ is
(a) alkynyl optionally substituted with Z$^{1d}$ where Z$^{1d}$ is aryl which may be further optionally independently substituted with one or more cyano, halo, —OH, —OY, —U$^1$—NY$^2$Y$^3$, —C(O)$_t$H, —C(O)$_t$Y, or, —S(O)$_t$Y; or
(b) aryl optionally independently substituted as valence allows with one or more Z$^{1d}$, Z$^{2d}$ and Z$^{3d}$;
(c) heteroaryl optionally independently substituted as valence allows with one or more Z$^{1d}$, Z$^{2d}$ and Z$^{3d}$; or
(d) —C(O)OR$^{7a}$, or —C(O)NR$^{8a}$R$^{9a}$;
where U$^1$ is a bond or alkylene.

In another embodiment are compounds of formula (I) wherein
R$^3$ is hydrogen;
R$^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$;
alternatively, R$^3$ and R$^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more Z$^{1b}$, Z$^{2b}$ and Z$^{3b}$;
R$^6$ is
(a) alkynyl optionally substituted with Z$^{1d}$ where Z$^{1d}$ is aryl which may be further optionally independently substituted with one or more cyano, halo, —OH, —OY, —U$^1$—NY$^2$—Y$^3$, —C(O)$_t$H, —C(O)$_t$Y, or, —S(O)$_t$Y; or
(b) aryl optionally independently substituted as valence allows with one or more Z$^{1d}$, Z$^{2d}$ and Z$^{3d}$;
where U$^1$ is a bond or alkylene;
Z$^{1c}$ is
(a) —OY where Y is aryl, or
(b) aryl optionally substituted with —OH or —OY where Y is alkyl;
Z$^{1d}$, Z$^{2d}$ and Z$^{3d}$ are optional substituents independently selected from
(a) cyano, halo, —OH, —OY, —C(O)$_t$H, —C(O)$_t$Y, —S(O)$_t$Y, or
(b) alkyl or alkoxy optionally substituted with one or more cyano, halo, —OH, —OY, —U$^1$—NY$^2$Y$^3$, —C(O)$_t$H, —C(O)$_t$Y, —U$^1$—N(Y$^4$)—C(O)—Y$^1$, —U$^1$—N(Y$^4$)—C(O)—NY$^2$Y$^3$, —U$^1$—N(Y$^4$)—C(O)O—Y$^5$, —U$^1$—N(Y$^4$)—C(=NV$^{1a}$)—NY$^2$Y$^3$, —U$^1$—N(Y$^4$)—C(=NV$^{1a}$)—Y$^1$, —S(O)$_t$Y, —U$^1$-heteroaryl;
where
U$^1$ is a bond or alkylene.

In another embodiment are compounds of formula (I) wherein
R$^1$ is alkyl; and
R$^2$ is hydrogen.

In another embodiment are compounds of formula (I) wherein
R$^5$ is selected from
(a) hydrogen, or
(b) alkyl, alkenyl, alkynyl, and haloalkyl, any of which may be optionally independently substituted as valence allows with one or more Z$^{1b}$, Z$^{2b}$ and Z$^{3b}$;
R$^6$ is which may be further substituted with with one or more Z$^{1d}$, Z$^{2d}$ and Z$^{3d}$.

In another embodiment are compounds of formula (I) wherein (I)

enantiomers, diastereomers, salts, and solvates thereof wherein
R$^1$ is selected from hydrogen, C$_{1-3}$ alkyl, C$_{2-3}$ alkenyl, and C$_{2-3}$ alkynyl;
R$^2$ is hydrogen, alkyl, alkenyl, alkynyl, haloalkyl,
R$^5$ is selected from
(a) hydrogen and halo,
(b) alkyl, alkenyl, alkynyl, and haloalkyl, any of which may be optionally independently substituted as valence allows with one or more Z$^{1b}$, Z$^{2b}$ and Z$^{3b}$;
(c) —OR$^{11}$, —SR$^{11}$ and —NR$^3$R$^4$;
R$^3$ and R$^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1b}$, Z$^{2b}$ and Z$^{3b}$;
(c) —OR$^{11}$, —NR$^{12}$R$^{13}$, —N(R$^{12}$)C(O)R$^{14}$, —N(R$^{12}$)C(O)OR$^{14}$, —N(R$^{12}$)SO$_2$R$^{14}$, —N(R$^{12}$)C(O)NR$^{12a}$R$^{13}$, or —N(R$^{12}$)SO$_2$NR$^{12a}$R$^{13}$ or —C(O)OR$^{14}$, —C(O)R$^{11}$, —C(O)NR$^{12}$R$^{13}$, —SO$_2$R$^{14}$, —SO$_2$NR$^{12}$R$^{13}$;
(d) R$^3$ and R$^4$ together with the nitrogen atom to which they are attached combine to form a 3 to 8 membered heterocyclic ring optionally independently substituted as valence allows with one or more Z$^{1b}$, Z$^{2b}$ and Z$^{3b}$;

$R^6$ is
- (a) alkyl, alkenyl, alkynyl, any of which is substituted with one or more as valence allows $Z^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
- (b) —$SR^{7a}$, —$SO_2R^{10}$, —$SO_2NR^{8b}R^{9b}$, $C(O)R^{7a}$, —$C(O)OR^{7a}$, or —$C(O)NR^{8a}R^{9a}$;

$R^7$ is
- (a) hydrogen, hydroxy, halo, or cyano,
- (b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1c}$, $Z^{2c}$ and $Z^{3c}$; or
- (c) —$SR^{7a}$, —$SO_2R^{10}$, —$SO_2NR^{8b}R^{9b}$, —$C(O)R^{7a}$, —$C(O)OR^{7a}$, or —$C(O)NR^{8a}R^{9a}$;

$R^{7a}$ and $R^{7b}$ are independently
- (a) hydrogen, or
- (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{8a}$, $R^{8b}$, $R^{9a}$ and $R^{9b}$ are independently
- (a) hydrogen,
- (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;
- (c) $R^{8a}$ and $R^{9a}$ together with the nitrogen atom to which they are attached combine to form a 3 to 8 membered heterocyclic ring optionally independently substituted as valence allows with one or more $Z^{1b}$, $Z^{2b}$ and $Z^{3b}$; or
- (d) $R^{8b}$ and $R^{9b}$ together with the nitrogen atom to which they are attached combine to form a 3 to 8 membered heterocyclic ring optionally independently substituted as valence allows with one or more $Z^{1b}$, $Z^{2b}$ and $Z^3$;

$R^{10}$, at each occurance, is independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
- (a) hydrogen, or
- (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1a\text{-}1e}$, $Z^{2a\text{-}2e}$, and $Z^{3a\text{-}3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1\text{-}5}$ are independently
- (1) a bond
- (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more $V^{1\text{-}5}$; or where $V^{1\text{-}5}$ are independently
- (1) H;
- (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more of groups (3)-(25) of $V^{1\text{-}5}$;
- (3) —$U^1$—O—$Y^5$,
- (4) —$U^1$—S—$Y^5$,
- (5) —$U^1$—$C(O)_t$—H, —$U^1$—$C(O)_t$—$Y^5$ where t is 1 or 2,
- (6) —$U^1$—$SO_3$—H, or —$U^1$—$S(O)_tY^5$,
- (7) —$U^1$-halo,
- (8) —$U^1$-cyano,
- (9) —$U^1$-nitro,
- (10) —$U^1$—$NY^2Y^3$,
- (11) —$U^1$—$N(Y^4)$—$C(O)$—$Y^1$,
- (12) —$U^1$—$N(Y^4)$—$C(S)$—$Y^1$,
- (13) —$U^1$—$N(Y^4)$—$C(O)$—$NY^2Y^3$,
- (14) —$U^1$—$N(Y^4)$—$C(S)$—$NY^2Y^3$,
- (15) —$U^1$—$N(Y^4)$—$C(O)O$—$Y^5$,
- (16) —$U^1$—$N(Y^4)$—$S(O)_2$—$Y^1$,
- (17) —$U^1$—$N(Y^4)$—$S(O)_2$—$NY^2Y^3$,
- (18) —$U^1$—$C(O)$—$NY^2Y^3$,
- (19) —$U^1$—$OC(O)$—$NY^2Y^3$
- (20) —$U^1$—$S(O)_2$—$N(Y^4)$—$Y^1$,
- (21) —$U^1$—$N(Y^4)$—$C(=NV^{1a})$—$NY^2Y^3$,
- (22) —$U^1$—$N(Y^4)$—$C(=NV^{1a})$—$Y^1$,
- (23) —$U^1$—$C(=NV^{1a})$—$NY^2Y^3$,
- (24) oxo;
- (25) —$U^1$—$Y^5$;

$Z^{1f}$, at each occurrence, is independently selected from
- (1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with one or more of groups (2) to (25) of $Z^{1f}$;
- (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
- (3) —$U^1$—O—$Y^5$,
- (4) —$U^1$—S—$Y^5$,
- (5) —$U^1$—$C(O)_t$—H, —$U^1$—$C(O)_t$—$Y^5$ where t is 1 or 2,
- (6) —$U^1$—$SO_3$—H, or —$U^1$—$S(O)_tY^5$,
- (7) —$U^1$-halo,
- (8) —$U^1$-cyano,
- (9) —$U^1$-nitro,
- (10) —$U^1$—$NY^2Y^3$,
- (11) —$U^1$—$N(Y^4)$—$C(O)$—$Y^1$,
- (12) —$U^1$—$N(Y^4)$—$C(S)$—$Y^1$,
- (13) —$U^1$—$N(Y^4)$—$C(O)$—$NY^2Y^3$,
- (14) —$U^1$—$N(Y^4)$—$C(S)$—$NY^2Y^3$,
- (15) —$U^1$—$N(Y^4)$—$C(O)O$—$Y^5$,
- (16) —$U^1$—$N(Y^4)$—$S(O)_2$—$Y^1$,
- (17) —$U^1$—$N(Y^4)$—$S(O)_2$—$NY^2Y^3$,
- (18) —$U^1$—$C(O)$—$NY^2Y^3$,
- (19) —$U^1$—$OC(O)$—$NY^2Y^3$
- (20) —$U^1$—$S(O)_2$—$N(Y^4)$—$Y^1$,
- (21) —$U^1$—$N(Y^4)$—$C(=NV^{1a})$—$NY^2Y^3$,
- (22) —$U^1$—$N(Y^4)$—$C(=NV^{1a})$—$Y^1$,
- (23) —$U^1$—$C(=NV^{1a})$—$NY^2Y^3$,
- (24) oxo;
- (25) —$U^1$—$Y^5$;

$V^{1a}$ is independently hydrogen, alkyl, —CN, —C(O)Y$^1$, —S(O)$_2$Y$^5$, S(O)$_2$NY$^2$Y$^3$;

$Y^1, Y^2, Y^3, Y^4$ and $Y^5$
- (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4, Z^5$ and $Z^6$; or
- (2) $Y^2$ and $Y^3$ may together be alkylene or alkenylene, completing a 3- to 8-membered saturated or unsaturated ring together with the atoms to which they are attached, or
- (4) $Y^2$ and $Y^3$ together with the nitrogen atom to which they are attached may combine to form a group —N=CY$^6$Y$^7$ where $Y^6$ and $Y^7$ are each independently H or alkyl; and $Z^4, Z^5$, and $Z^6$ are optional substituents at each occurrence independently selected from
- (1) H
- (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
- (3) —U$^1$—O—Y$^{5a}$,
- (4) —U$^1$—S—Y$^{5a}$,
- (5) —U$^1$—C(O)$_t$—H, —U$^1$—C(O)$_t$—Y$^{5a}$ where t is 1 or 2,
- (6) —U$^1$—SO$_3$—H, or —U$^1$—S(O)$_t$Y$^{5a}$,
- (7) —U$^1$-halo,
- (8) —U$^1$-cyano,
- (9) —U$^1$-nitro,
- (10) —U$^1$—NY$^{2a}$Y$^{3a}$,
- (11) —U$^1$—N(Y$^{4a}$)—C(O)—Y$^{1a}$,
- (12) —U$^1$—N(Y$^{4a}$)—C(S)—Y$^{1a}$,
- (13) —U$^1$—N(Y$^{4a}$)—C(O)—NY$^{2a}$Y$^{3a}$,
- (14) —U$^1$—N(Y$^{4a}$)—C(S)—NY$^{2a}$Y$^{3a}$,
- (15) —U$^1$—N(Y$^{4a}$)—C(O)O—Y$^{5a}$,
- (16) —U$^1$—N(Y$^{4a}$)—S(O)$_2$—Y$^{1a}$,
- (17) —U$^1$—N(Y$^{4a}$)—S(O)$_2$—NY$^{2a}$Y$^{3a}$,
- (18) —U$^1$—C(O)—NY$^{2a}$Y$^{3a}$,
- (19) —U$^1$—OC(O)—NY$^{2a}$Y$^{3a}$,
- (20) —U$^1$—S(O)$_2$—N(Y$^{4a}$)—Y$^{1a}$,
- (21) —U$^1$—N(Y$^{4a}$)—C(=NV$^{1b}$)—NY$^{2a}$Y$^{3a}$,
- (22) —U$^1$—N(Y$^{4a}$)—C(=NV$^{1b}$)—Y$^{1a}$,
- (23) —U$^1$—C(=NV$^{1b}$)—NY$^{2a}$Y$^{3a}$,
- (24) oxo;
- (25) —U$^1$—Y$^{5a}$;

$V^{1b}$ is independently hydrogen, alkyl, —CN, —C(O)Y$^{1a}$, —S(O)$_2$Y$^{5a}$, S(O)$_2$NY$^{2a}$Y$^{3a}$;

$Y^{1a}, Y^{2a}, Y^{3a}, Y^{4a}$ and $Y^{5a}$
- (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

$U^1$ is independently
- (1) a single bond,
- (2) alkylene,
- (3) alkenylene, or
- (4) alkynylene.

In another embodiment are compounds of formula (I) wherein the compounds are selected from the compounds of the Examples.

Another embodiment is directed to pharmaceutical compositions containing at least one compound of formula (I) and a pharmaceutically-acceptable carrier or diluent, for use in treating inflammatory and immune diseases or cancer. Also included within the invention are methods of treating such diseases comprising administering to a mammal in need of such treatment an effective amount of at least one compound of formula (I).

In another embodiment, $R^6$ is phenyl substituted with 0-3 $Z^{1d}, Z^{2d}$ and $Z^{3d}$.

In another embodiment, $R^6$ is SR$^{7a}$, —SO$_2$R$^{10}$, —SO$_2$NR$^{8b}$R$^{9b}$, C(O)R$^{7a}$, —C(O)OR$^{7a}$, or —C(O)NR$^{8a}$R$^{9a}$.

In another embodiment, $R^1$ is hydrogen, methyl, or ethyl.

In another embodiment, $R^2$ is hydrogen.

In another embodiment, $R^1$ is selected from hydrogen, $C_{1-3}$ alkyl, and $C_{2-3}$ alkenyl; and $R^2$ is hydrogen, alkyl, haloalkyl, or aryl.

In another embodiment, $R^3$ and $R^4$ are independently selected from
- (a) hydrogen,
- (b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1b}, Z^{2b}$ and $Z^{3b}$;
- (c) —NR$^{12}$R$^{13}$; or
- (d) $R^3$ and $R^4$ together with the nitrogen atom to which they are attached combine to form a 3 to 8 membered heterocyclic ring optionally independently substituted as valence allows with one or more $Z^{1b}, Z^{2b}$ and $Z^{3b}$.

In another embodiment, $R^3$ and $R^4$ are independently selected from
- (a) alkyl which may be optionally independently substituted as valence allows with one or more $Z^{1b}, Z^{2b}$ and $Z^{3b}$; or
- (b) —C(O)OR$^{14}$, —C(O)R$^{11}$, —C(O)NR$^{12}$R$^{13}$, —SO$_2$R$^{14}$, —SO$_2$NR$^{12}$R$^{13}$.

In another embodiment, $R^3$ and $R^4$ are independently selected from
- (a) alkyl which may be optionally independently substituted as valence allows with one or more $Z^{1b}, Z^{2b}$ and $Z^{3b}$; or
  wherein $Z^{1b}, Z^{2b}$ and $Z^{3b}$ is H, heterocyclo, heteroaryl, any of which may be optionally independently substituted as valence allows with one or more $Z^4, Z^5$ and $Z^6$; or —U$^1$—NY$^2$Y$^3$,
- (b) —C(O)OR$^{14}$, —C(O)R$^{11}$, —C(O)NR$^{12}$R$^3$, —SO$_2$R$^4$, —SO$_2$NR$^{12}$R$^{13}$.

In another embodiment, $R^3$ and $R^4$ are independently selected from hydrogen, alkyl, (hydroxy)alkyl, or (heteroaryl)alkyl any of which may be optionally independently substituted as valence allows with 1-2 $Z^{1b}, Z^{2b}$ and $Z^{3b}$; —NR$^{12}$R$^{13}$; or $R^3$ and $R^4$ together with the nitrogen atom to which they are attached combine to form a 3 to 8 membered heterocyclic ring optionally independently substituted as valence allows with one or more $Z^{1b}, Z^{2b}$ and $Z^{3b}$;

$Z^{1b}, Z^{2b}$ and $Z^{3b}$ are selected from hydrogen, alkyl, —U$^1$—O—Y$^5$, —U$^1$, —NY$^2$Y$^3$, and $U^1$ is a single bond or alkylene, In another embodiment, $R^3$ and $R^4$ are independently selected from hydrogen, alkyl, substituted as valence allows with 0-2 $Z^{1b}, Z^{2b}$ and $Z^{3b}$.

In another embodiment $R^5$ is selected from —NR$^3$R$^4$.

In another embodiment $R^5$ is hydrogen.

In another embodiment, $R^6$ is selected from
(a) hydrogen, or
(b) alkyl, alkenyl, alkynyl, and haloalkyl, any of which may be optionally independently substituted as valence allows with one or more as valence allows $Z^{1,f}$;
(c) aryl, heteroaryl, which may be further substituted with with one or more $Z^{1^d}$, $Z^{2^d}$ and $Z^{3^d}$; or
(d) —C(O)OR$^{7^a}$, or —C(O)NR$^{8^a}$R$^{9^a}$.

In another embodiment,
$R^6$ is selected from
(a) hydrogen, or
(c) aryl, heteroaryl, which may be further substituted with with one or more $Z^{1^d}$, $Z^{2^d}$ and $Z^{3^d}$; or
(d) —C(O)OR$^{7^a}$, or —C(O)NR$^{8^a}$R$^{9^a}$.

In another embodiment,
$R^6$ is selected from
(a) hydrogen, or
(c) phenyl, or pyridyl, which may be further substituted with with one or more $Z^{1^d}$, $Z^{2^d}$ and $Z^{3^d}$; or
(d) —C(O)OR$^{7^a}$, or —C(O)NR$^{8^a}$R$^{9^a}$.

In another embodiment,
$R^6$ is selected from
(a) hydrogen, or
(b) alkyl, alkenyl, alkynyl, and haloalkyl, any of which may be optionally independently substituted as valence allows with one or more $Z^{1^b}$, $Z^{2^b}$ and $Z^{3^b}$;
$R^6$ is

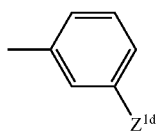

which may be further substituted with with one or more $Z^{1^d}$, $Z^{2^d}$ and $Z^{3^d}$.

In another embodiment, $R^6$ is

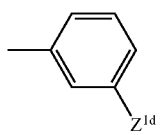

which may be further substituted with with one or more $Z^{1^d}$, $Z^{2^d}$ and $Z^{3^d}$,
and $Z^{1d}$ is selected from
(a) cyano, halo, —OH, —OY$^5$, —U$^1$—NY$^2$Y$^3$, —C(O)$_t$H, —C(O)$_t$Y, —S(O)$_t$Y$^5$;
(b) alkyl or alkoxy optionally substituted with one or more cyano, halo, —OH, —OY, —U$^1$—NY$^2$Y$^3$, —C(O)$_t$H, —C(O)$_t$Y, —U$^1$—N(Y$^4$)—C(O)—Y$^1$, —U$^1$—N(Y$^4$)—C(O)—NY$^2$Y$^3$, —U$^1$—N(Y$^4$)—C(O)O—Y$^5$, —U$^1$—N(Y$^4$)—C(=NV$^{1^a}$)—NY$^2$Y$^3$, —U$^1$—N(Y$^4$)—C(=NV$^{1^a}$)—Y$^1$, —S(O)$_t$Y, —U$^1$-heteroaryl.

In another embodiemtn, $Z^{1d}$, $Z^{2d}$ and $Z^{3d}$ are optional substituents independently selected from
(a) cyano, halo, —OH, —OY$^5$, —U$^1$—NY$^2$Y$^3$, —C(O)$_t$H, —C(O)$_t$Y$^1$, —U$^1$—C(O)—NY$^2$Y$^3$, —S(O)$_t$Y$^5$;
(b) alkyl or alkoxy optionally substituted with one or more cyano, halo, —OH, —OY$^5$, —U$^1$—NY$^2$Y$^3$, —C(O)$_t$H, —C(O)$_t$Y$^1$, —U$^1$—C(O)—NY$^2$Y$^3$, —OC(O)—NY$^2$Y$^3$, OC(O)—OY$^5$, —U$^1$—N(Y$^4$)—C(O)—Y$^1$, —U$^1$—N(Y$^4$)—C(O)—NY$^2$Y$^3$, —U$^1$—N(Y$^4$)—C(O)O—Y$^5$, —N(Y$^4$)—S(O)$_2$—Y$^1$, —N(Y$^4$)—C(O)—C(O)—NY$^2$Y$^3$, —N(Y$^4$)—C(O)—C(O)—OY$^5$, —U$^1$—N(Y$^4$)—C(=NV$^{1^a}$)—NY$^2$Y$^3$, —U$^1$—N(Y$^4$)—C(=NV$^{1^a}$)—Y$^1$, —S(O)$_t$Y, —U$^1$-heteroaryl, or U1-heterocyclo, wherein heteroaryl and heterocyclo are substituted as valence allows with one or more of groups (3)-(28) of V$^{1-5}$.

In another embodiment, Y$^5$ is H or alkyl, wherein the alkyl is selected from methyl, ethyl, propyl, i-propyl, butyl, i-butyl, t-butyl, pentyl, and hexyl;
Y$^2$ and Y$^3$ are independently selected from alkyl wherein the alkyl is selected from methyl, ethyl, propyl, i-propyl, butyl, i-butyl, t-butyl, pentyl, and hexyl.

In another embodiment, $R^3$ and $R^4$ are independently selected from hydrogen, alkyl, wherein the alkyl is selected from methyl, ethyl, propyl, i-propyl, butyl, i-butyl, t-butyl, pentyl, and hexyl; (hydroxy)alkyl, or (heteroaryl)alkyl, wherein (heteroaryl)alkyl is (tetrazolyl)methyl; any of which may be optionally independently substituted with 1 $Z^{1^b}$; —NR$^{12}$R$^{13}$; or R$^3$ and R$^4$ together with the nitrogen atom to which they are attached combine to form a 3 to 8 membered heterocyclic ring, wherein the ring is selected from piperidinyl, and morpholinyl, optionally independently substituted with 1 $Z^{1^b}$.

In another embodiment, $R^3$ is hydrogen;
$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$;
alternatively, R$^3$ and R$^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1^b}$, $Z^{2^b}$ and $Z^{3^b}$.

In another embodiment, $R^6$ is
(a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or
(b) —SR$^{7a}$, —SO$_2$R$^{10}$, —SO$_2$NR$^{8^b}$R$^{9^b}$, C(O)R$^{7^a}$, —C(O)OR$^{7^a}$, or —C(O)NR$^{8^a}$R$^{9^a}$.

In another embodiment, $R^6$ is
(a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or
(b) —SR$^{7a}$, —SO$_2$R$^{10}$, —SO$_2$NR$^{8^b}$R$^{9^b}$, C(O)R$^{7^a}$, —C(O)OR$^{7^a}$, or —C(O)NR$^{8^a}$R$^{9^a}$;
wherein $Z^{1^d}$, $Z^{2^d}$ and $Z^{3^d}$ is —W$^4$—V$^4$; where W$^4$ is independently
(1) a bond
(2) alkyl, (hydroxy)alkyl, alkenyl, haloalkyl, heteroaryl, or (heteroaryl)alkyl; and
where V$^4$ is independently
(1) H
(2) aryl, (aryl)alkyl, heterocyclo, (heterocyclo)alkyl, heteroaryl, or (heteroaryl)alkyl any of which may be optionally independently substituted as valence allows with one or more of groups (3)-(15) of V$^{1-5}$;
(3) —U$^1$—O—Y$^5$,
(4) —U$^1$—C(O)$_t$—H, —U$^1$—C(O)$_t$—Y$^5$ where t is 1 or 2,
(5) —U$^1$—SO$_3$—H, or —U$^1$—S(O)$_t$Y$^5$,
(6) —U$^1$-halo,
(7) —U$^1$—NY$^2$Y$^3$, (8) —U$^1$—N(Y$^4$)—C(O)—Y$^1$,
(8) —U$^1$—N(Y$^4$)—C(O)—NY$^2$Y$^3$,
(10) —U$^1$—N(Y$^4$)—C(O)O—Y$^5$,
(11) —U$^1$—N(Y$^4$)—S(O)$_2$—Y$^1$,
(12) —U$^1$—N(Y$^4$)—S(O)$_2$—NY$^2$Y$^3$,
(13) —U$^1$—C(O)—NY$^2$Y$^3$,
(14) —U$^1$—OC(O)—NY$^2$Y$^3$
(15) —U$^1$—S(O)$_2$—N(Y$^4$)—Y$^1$; and
U$^1$ is a bond.

In another embodiment, compounds of formula (I) wherein R$^6$ is

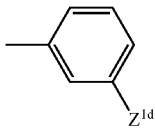

which may be further substituted with with one or more Z$^{1^d}$, Z$^{2^d}$ and Z$^{3^d}$.

In another embodiment, R$^6$ is
(a) alkynyl optionally substituted with Z$^{1^d}$ where Z$^{1^d}$ is aryl which may be further optionally independently substituted with one or more cyano, halo, —OH, —OY, —U$^1$—NY$^2$Y$^3$, —C(O)$_r$H, —C(O)$_t$Y, or, —S(O)$_t$Y;
(b) aryl optionally independently substituted as valence allows with one or more Z$^{1^d}$, Z$^{2^d}$ and Z$^{3^d}$; or
(c) —SR$^{7a}$, —SO$_2$R$^{10}$, or —SO$_2$NR$^{8^b}$R$^{9^b}$;
Z$^{1^b}$, Z$^{2^b}$ and Z$^{3^b}$ are optional substituents independently selected from —OH, —OY, —U$^1$—NY$^2$Y$^3$, —C(O)$_r$H, —C(O)$_t$Y, —U$^1$—N(Y$^4$)—C(O)—Y$^1$, or —U$^1$—N(Y$^4$)—C(O)O—Y$^5$.

In another embodiment R$^6$ is
(a) alkynyl optionally substituted with Z$^{1^d}$ where Z$^{1^d}$ is aryl which may be further optionally independently substituted with one or more cyano, halo, —OH, —OY, —U$^1$—NY$^2$Y$^3$, —C(O)$_r$H, —C(O)$_t$Y, or, —S(O)$_t$Y;
(b) aryl optionally independently substituted as valence allows with one or more Z$^{1^d}$, Z$^{2^d}$ and Z$^{3^d}$; or
(c) —SR$^{7a}$, —SO$_2$R$^{10}$, or —SO$_2$NR$^{8^b}$R$^{9^b}$;
Z$^{1^b}$, Z$^{2^b}$ and Z$^{3^b}$ are optional substituents independently selected from —OH, —OY, —U$^1$—NY$^2$Y$^3$, —C(O)$_r$H, —C(O)$_t$Y, —U$^1$—N(Y$^4$)—C(O)—Y$^1$, or —U$^1$—N(Y$^4$)—C(O)O—Y$^5$,
where
U$^1$ is a bond or alkylene;
Z$^{1^c}$ is
(a) —OY where Y is aryl, or
(b) aryl optionally substituted with —OH or —OY where Y is alkyl;
Z$^{1^d}$, Z$^{2^d}$ and Z$^{3^d}$ are optional substituents independently selected from
(a) cyano, halo, —OH, —OY, —C(O)$_r$H, —C(O)$_t$Y, —S(O)$_t$Y, or
(b) alkyl or alkoxy optionally substituted with one or more cyano, halo, —OH, —OY, —U$^1$—NY$^2$Y$^3$, —C(O)$_r$H, —C(O)$_t$Y, —S(O)$_t$Y, —U$^1$—N(Y$^4$)—C(O)—Y$^1$, —U$^1$—N(Y$^4$)—C(O)—NY$^2$Y$^3$, —U$^1$—N(Y$^4$)—C(O)O—Y$^5$, —U$^1$—N(Y$^4$)—C(=NV$^{1^a}$)—NY$^2$Y$^3$, —U$^1$—N(Y$^4$)—C(=NV$^{1^a}$)—Y$^1$, —U$^1$—N(Y$^4$)—C(O)—Y$^1$, or —U$^1$—N(Y$^4$)—S(O)$_2$—Y$^1$,
where
U$^1$ is a bond or alkylene.

In another embodiment
R$^6$ is
(a) alkynyl optionally substituted with Z$^{1^d}$ where Z$^{1^d}$ is phenyl which may be further optionally independently substituted with 0-1 cyano, halo, —OH, —OY, —U$^1$—NY$^2$Y$^3$, —C(O)$_r$H, —C(O)$_t$Y, or, —S(O)$_t$Y;
(b) phenyl optionally independently substituted as valence allows with one or more Z$^{1^d}$, Z$^{2^d}$ and Z$^{3^d}$; or
(c) —SR$^{7a}$;
Z$^{1^b}$, Z$^{2^b}$ and Z$^{3^b}$ are optional substituents independently selected from —OH, —OY, —U$^1$—NY$^2$Y$^3$, —C(O)$_r$H, —C(O)$_t$Y, —U$^1$—N(Y$^4$)—C(O)—Y$^1$, or —U$^1$—N(Y$^4$)—C(O)O—Y$^5$,
where
U$^1$ is a bond or alkylene, wherein alkylene is selected from methylene, ethylene, propylene, and butylene;
Z$^{1^c}$ is
(a) —OY where Y is phenyl, or
(b) phenyl optionally substituted with 0-1 —OH or —OY where Y is alkyl selected from methyl, ethyl, propyl, i-propyl, butyl, i-butyl, t-butyl, pentyl, hexyl;
Z$^{1^d}$, Z$^{2^d}$ and Z$^{3^d}$ are optional substituents independently selected from
(a) cyano, halo, —OH, —OY, —C(O)$_r$H, —C(O)$_t$Y, —S(O)$_t$Y, or
(b) alkyl or alkoxy optionally substituted with one or more cyano, halo, —OH, —OY, —U$^1$—NY$^2$Y$^3$, —C(O)$_r$H, —C(O)$_t$Y, —S(O)$_t$Y, —U$^1$—N(Y$^4$)—C(O)—NY$^2$Y$^3$, —U$^1$—N(Y$^4$)—C(O)O—Y$^5$, —U$^1$—N(Y$^4$)—C(=NV$^{1^a}$)—NY$^2$Y$^3$, —U$^1$—N(Y$^4$)—C(=NV$^{1^a}$)—Y$^1$, —U$^1$—N(Y$^4$)—C(O)—Y$^1$, —U$^1$—N(Y$^4$)—C(O)—Y$^1$, or —U$^1$—N(Y$^4$)—S(O)$_2$—Y$^1$,
where
U$^1$ is a bond or alkylene, wherein alkylene is selected from methylene, ethylene, propylene, and butylene.

In another embodiment, R$^6$ is
(a) alkynyl optionally substituted with Z$^{1d}$ where Z$^{1d}$ is aryl which may be further optionally independently substituted with one or more cyano, halo, —OH, —OY, —U$^1$—NY$^2$Y$^3$, —C(O)$_r$H, —C(O)$_t$Y, or, —S(O)$_t$Y; or
(b) aryl optionally independently substituted as valence allows with one or more Z$^{1d}$, Z$^{2d}$ and Z$^{3d}$;
(c) heteroaryl optionally independently substituted as valence allows with one or more Z$^{1d}$, Z$^{2d}$ and Z$^{3d}$; or
(d) —C(O)OR$^{7a}$, or —C(O)NR$^{8^a}$R$^{9^a}$.

In another embodiment, R$^7$ is hydrogen, alkyl, alkenyl, alkynyl, or haloalkyl.

In another embodiment, R$^7$ is hydrogen.

In another embodiment, Y$^1$, Y$^2$, Y$^3$, and Y$^4$ are independently selected from hydrogen, alkyl, wherein alkyl is selected from alkyl is selected from methyl, ethyl, propyl, i-propyl, butyl, i-butyl, t-butyl, pentyl, and hexyl; aryl wherein aryl is phenyl, (aryl)alkyl.

Another embodiment is directed to a compound of Formula (I), wherein the compound is selected from the compounds of the Examples or of Tables.

Another embodiment is directed to a pharmaceutical composition, comprising a pharmaceutically acceptable carrier and a therapeutically effective amount of a compound of Formula (I).

Another embodiment is directed to a method of treating an inflammatory or immune disease or disorder comprising administering to a mammal in need thereof a therapuetically-effective amount of at least one compound of formula (I).

Another embodiment is directed to a method of treating cancer comprising administering to a mammal in need thereof a therapuetically-effective amount of at least one compound of formula (I)

Another embodiment is directed to a method of treating an inflammatory or immune disease or disorder selected from, rheumatoid arthritis, asthma, inflammatory bowel disease, chronic obstructive pulmonary disease, and psoriasis.

Another embodiment is directed to the use of a compound of Formula (I) in the preparation of a medicament for the treatment of an inflammatory or immune disease.

Another embodiment is directed to the use of a compound of Formula (I) in the preparation of a medicament for the treatment of cancer.

Another embodiment is directed to the use of a compound of Formula (I) in the preparation of a medicament for the treatment of an inflammatory or immune disease.

Another embodiment is directed to the use of a compound of Formula (I) in the preparation of a medicament for the treatment of cancer.

Another embodiment is directed to the use of a compound of Formula (I) in the preparation of a medicament for the treatment of an inflammatory or immune disease, wherein the disease is selected from, rheumatoid arthritis, asthma, inflammatory bowel disease, chronic obstructive pulmonary disease, and psoriasis.

Another embodiment is directed to the use of a compound of Formula (I) for use in therapy.

The invention may be embodied in other specific forms without departing from the spirit or essential attributes thereof. This invention also encompasses all combinations of alternative aspects and embodiments of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The following are definitions of terms used in this specification. The initial definition provided for a group or term herein applies to that group or term throughout the present specification, individually or as part of another group, unless otherwise indicated.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced. The term "optionally independently substituted as valence allows", as used herein, means that the any one or more hydrogens on the designated variable is independently replaced with a selection from the indicated group, provided that the designated variable's normal valency is not exceeded, and that the substitution results in a stable compound.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

It will be appreciated that the compounds of the present invention may contain one or more asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated. All tautomers of shown or described compounds are also intended.

The term "alkyl" as used herein by itself or as part of another group refers to straight and branched chain hydrocarbons, containing 1 to 20 carbons, alternatively, 1 to 10 carbons, or 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are an alternative embodiment.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The term "alkenyl" as used herein by itself or as part of another group refers to straight or branched chain radicals of 2 to 20 carbons, alternatively, 2 to 12 carbons, or 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, alternatively, 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

When the term "alkyl" is used together with another group, such as in "(aryl)alkyl", this conjunction is meant to refer to a substituted alkyl group wherein at least one of the substituents is the specifically named group in the conjunction. For example, "(aryl)alkyl" refers to a substituted alkyl group as defined above wherein at least one of the substituents is an aryl, such as benzyl.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

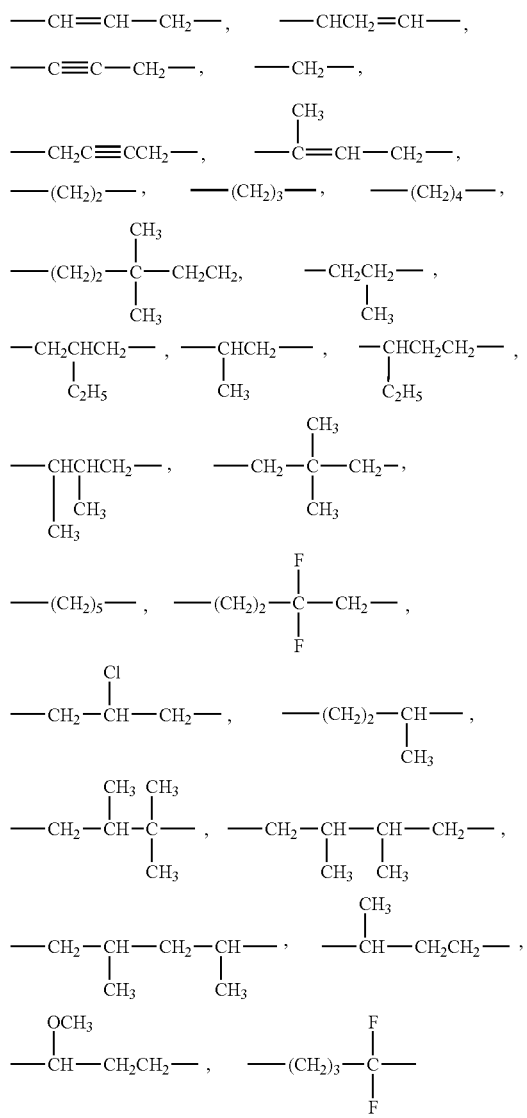

and the like. Alkylene groups may be optionally independently substituted as valence allows with one or more groups provided in the definition of $Z^1$.

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, alternatively, 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

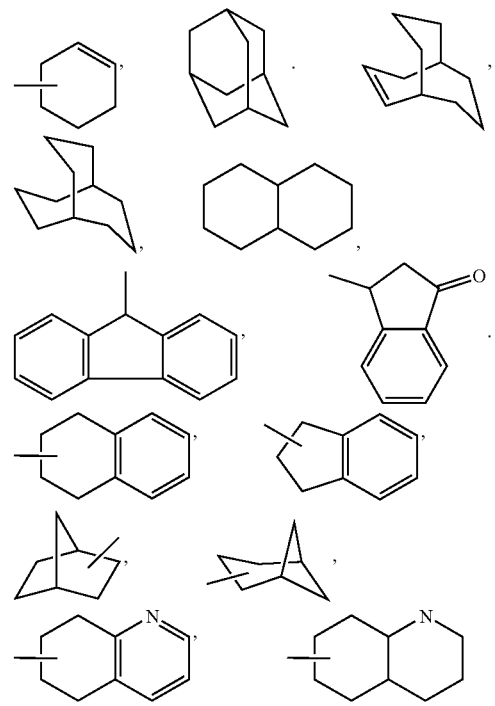

and the like.

The term "cycloalkylene" as employed herein refers to a "cycloalkyl" group which includes free bonds and thus is a linking group such as

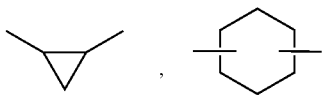

and the like.

One skilled in the field will understand that, when the designation "$CO_2$" is used herein, this is intended to refer to the group

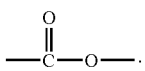

The term "alkoxy" refers to an alkyl or substituted alkyl group as defined above bonded through an oxygen atom (—O—), i.e., the groups —$OR_d$, wherein $R_d$ is alkyl or substituted alkyl.

The term "alkylthio" refers to an alkyl or substituted alkyl group as defined above bonded through a sulfur atom (—S—), i.e., the groups —$SR_d$, wherein $R_d$ is alkyl or substituted alkyl.

The term "acyl" refers to a carbonyl group linked to an organic radical, more particularly, the group $C(=O)R_g$, wherein $R_g$ can be selected from alkyl, alkenyl, substituted alkyl, or substituted alkenyl, as defined herein.

The term "alkoxycarbonyl" refers to a carboxy group

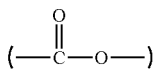

linked to an organic radical ($CO_2R_g$), wherein $R_g$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

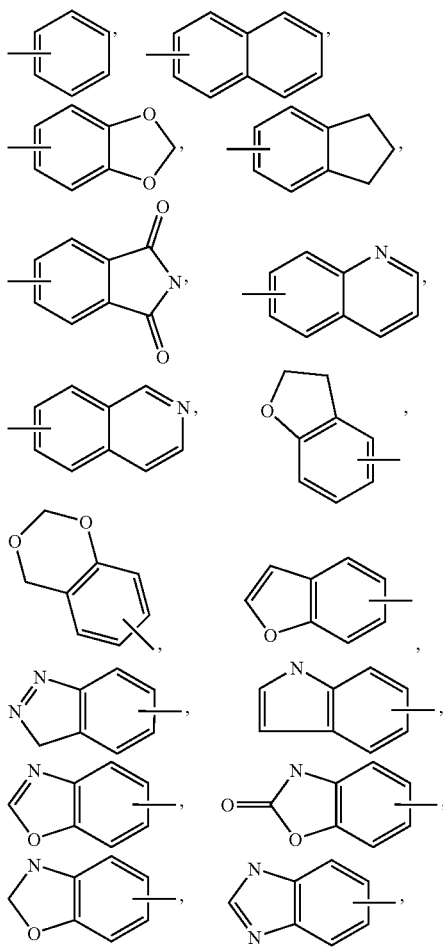

-continued

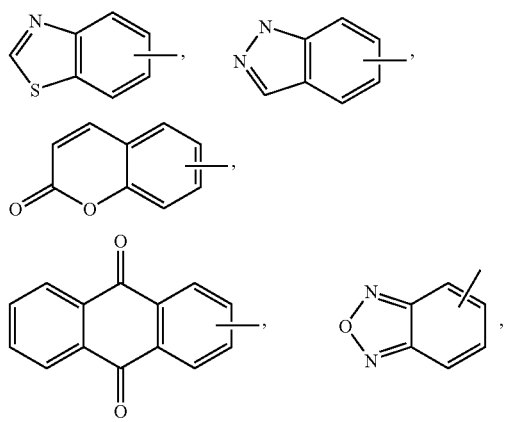

and the like.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

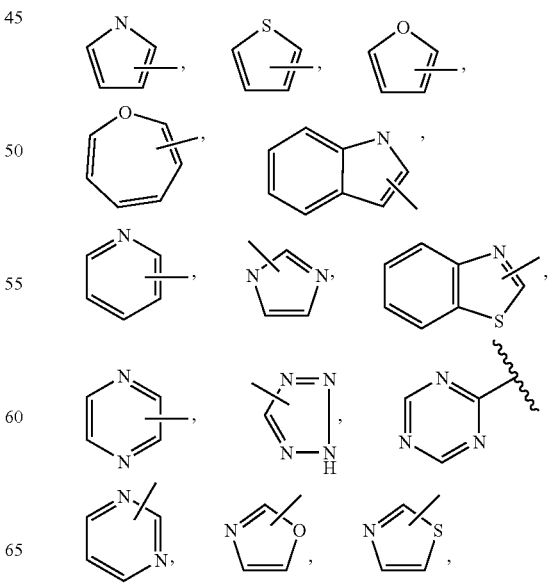

-continued

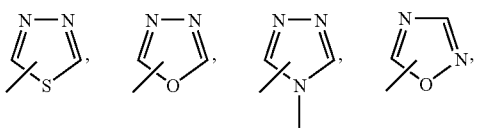

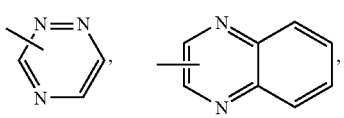

and the like.

In compounds of formula (I), heteroaryl groups include

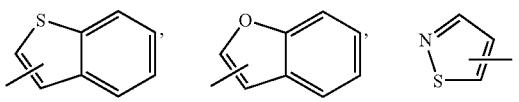

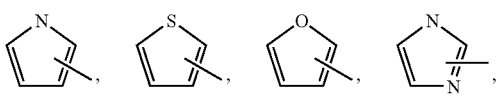

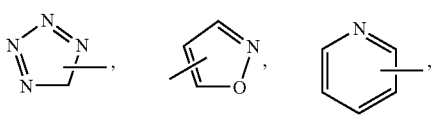

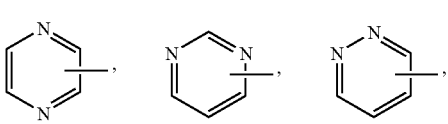

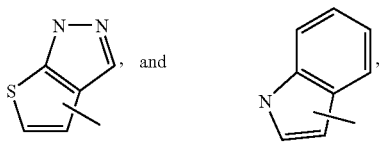, and and the like, which optionally may be substituted at any available carbon or nitrogen atom.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, alternatively, containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

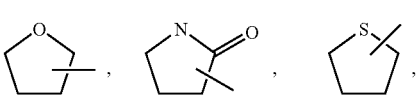

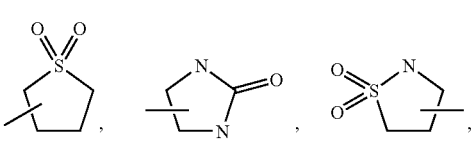

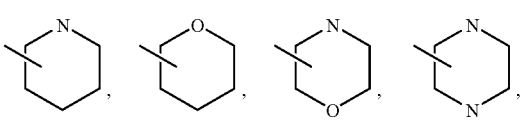

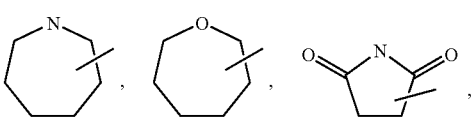

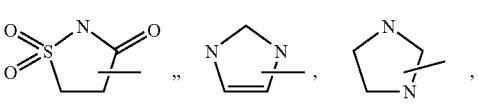

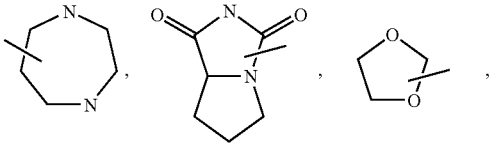

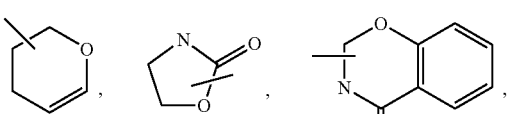

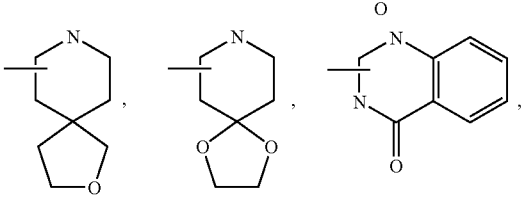

-continued

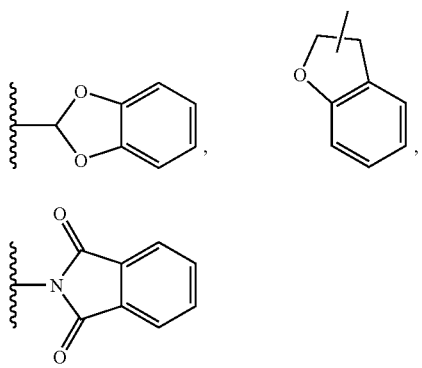

and the like.

Heterocyclo groups in compounds of formula (I) include

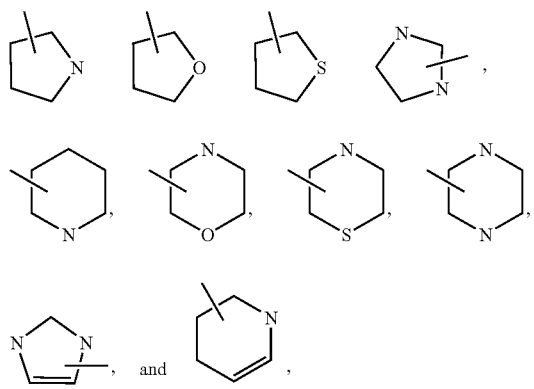

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl).

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, alternativley, 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);
b) *A Textbook of Drug Design and Development*, edited by Krosgaard-Larsen and H. Bundgaard, Chapter 5, "Design and Application of Prodrugs," by H. Bundgaard, at pp. 113-191 (1991);
c) H. Bundgaard, *Advanced Drug Delivery Reviews*, Vol. 8, p. 1-38 (1992);
d) H. Bundgaard, et al., *Journal of Pharmaceutical Sciences*, Vol. 77, p. 285 (1988); and
e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

It should further be understood that solvates (e.g., hydrates) of the compounds of formula I are also contemplated to be within the scope of the present invention.

"Therapeutically effective amount" is intended to include an amount of a compound of the present invention alone or an amount of the combination of compounds claimed or an amount of a compound of the present invention in combination with other active ingredients effective to inhibit IKK or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Methods of Preparation

Compounds of Formula I may be prepared by reference to the methods illustrated in the following Schemes I-V. As shown therein the end product is a compound having the same structural formula as Formula I. It will be understood that any compound of Formula I may be produced by Scheme I-V by the suitable selection of reagents with appropriate substitution. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

The sequence described in Scheme I will produce compounds of Formula I. Nitration of 4-hydroxy pyridine, I-1 to provide the known compound I-2. followed by conversion to the corresponding known chloro-pyridine I-3. Subsequent addition of an amine such as methylamine provides the previously un-described compound I-4. Reduction of both nitro groups and simultaneous chlorination of the intermediate triaminopyridine occurs on treatment of I-4 with tin(II) chloride to produce I-5. This important intermediate can be reacted with triethyl orthoformate to provide fused imidazole I-6. Diazotization of the amine under reductive conditions provides imidazopyridine I-7 which reacts with amines such as methyl amine, ethyl amine, para-methoxybenzyl amine etc. in high regioselectivity which after protection with Boc anhydride or similar reagent provides amino compound I-8. Substitution of the chloro group with an amine can be readily accomplished by what is commonly referred to as a Buchwald amination (for examples see Yin, J., Buchwald, S. L., J. Am. Chem. Soc. 2002, 124(21) 6043-6048). Thus I-8 is reacted with benzophenoneimine or lithium bistrimethylsilylamide (to directly produce I-10) in the presence of a palladium catalyst, preferably with the use of Xantphos® as a ligand to provide I-9 which is readily hydrolyzed to produce amine I-10. Reaction of the aminopyridine I-10 with N-iodosuccinimide or other electrophillic iodine species such as $I_2$ with silver triflate, will provide iodopyridine I-11. A Sonogashira reaction with intermediate I-11 and an acetylene provides intermediate I-12, which can readily undergo 5 endo-dig cyclization in the presence of a base or palladium catalyst to provide I-13. Removal of the Boc protecting group with trifluoroacetic acid with or without the presence of a scavenger such as anisole, or thioanisole provides I-14 which is a compound of Formula I.

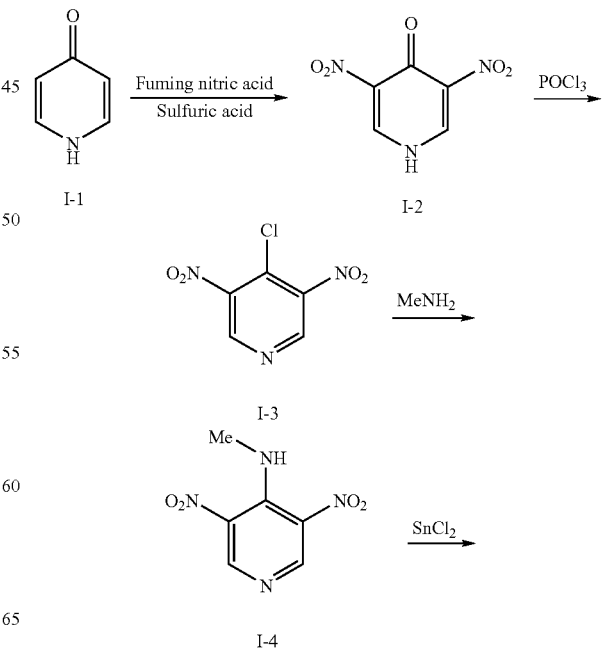

Scheme I

-continued

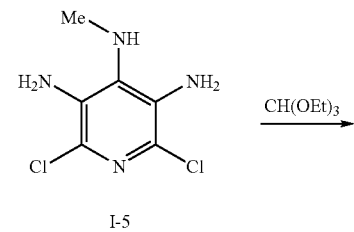
I-5

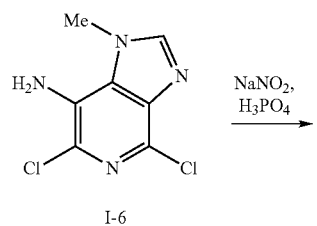
I-6

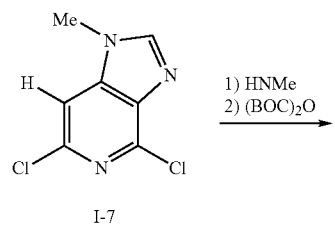
I-7

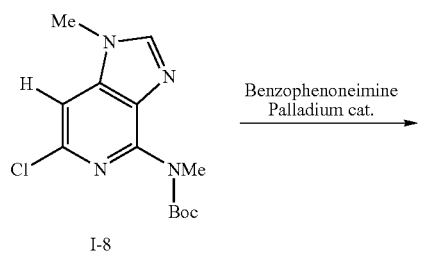
I-8

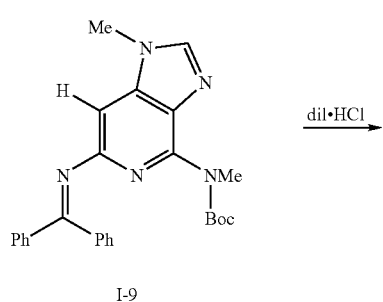
I-9

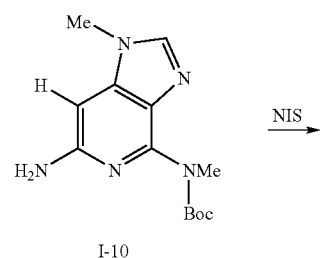
I-10

-continued

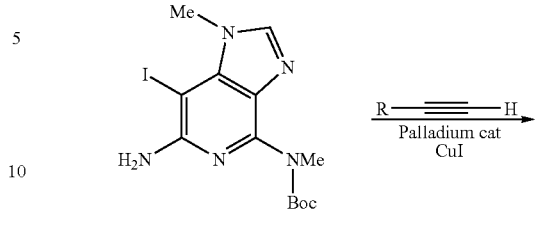
I-11

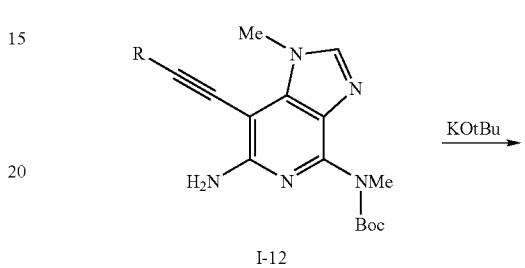
I-12

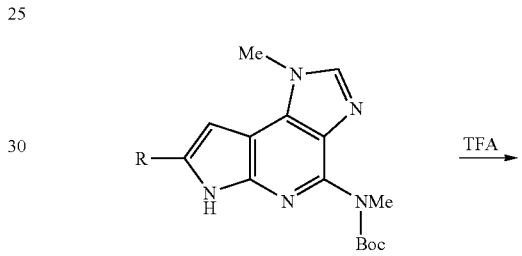
I-13

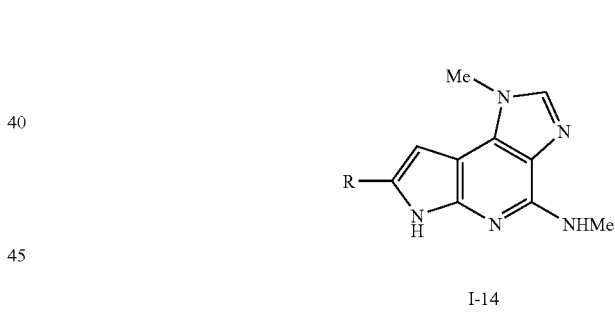
I-14

Entry into compounds substituted at the 8-position of this system can be envisioned to arise by electrophillic aromatic substitution reactions such as halogenation followed by subsequent transformations as depicted in Scheme II. Thus I-14 can readily undergo halogenation with N-chlorosuccinimide, N-bromosuccinimide, N-iodosuccinimide to produce intermediate II-1 (bromo depicted). This versatile intermediate can undergo several transformations. Of particular interest to this application is reaction with zinc cyanide in the presence of palladium, or copper cyanide to produce II-2 which is a compound of Formula I. Also of interest is carbonylation of II-1 to produce II-4, which is also a compound of Formula I. Alternatively II-4 can arise from the carbonylative cyclization of I-12 in the presence of carbon monoxide gas, and a palladium catalyst in the presence of a suitable alcohol to produce II-3 which is readily deprotected with trifluoroacetic acid with or without the presence of anisole, or thioanisole to provide II-4.

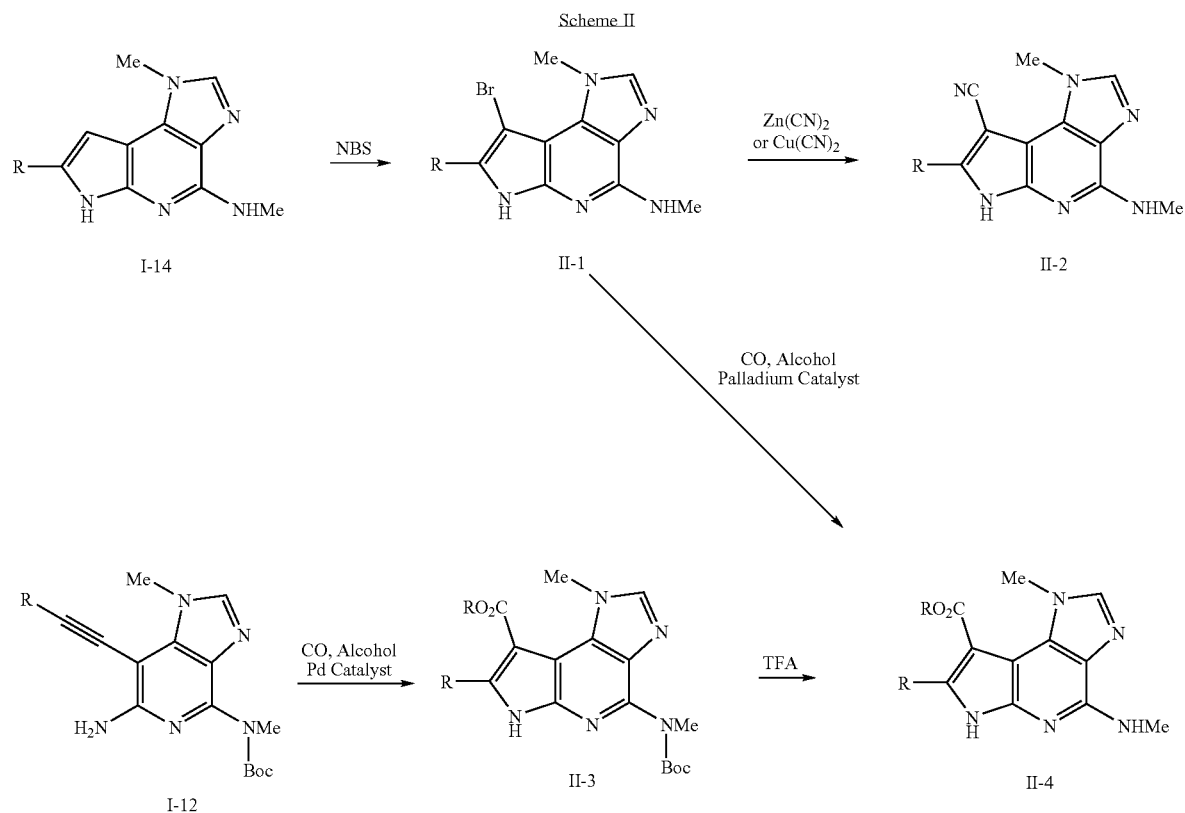

Alternatively a potentially more versatile route to compounds of Formula I is described in Scheme III. III-1 can be prepared as described in Scheme I using trimethylsilylacetylene as the reacting partner with I-11 and proceeding through the cyclization step. Protection of the indole nitrogen can be accomplished with a suitable base such as sodium hydride followed by addition of ditertbutyldicarbonate ((Boc)$_2$O) to provide III-2. Selective deprotonation with n-butyl lithium, or with the milder base lithium diisopropylamide (see Vasquez, E. et. al. J. Org. Chem. 2002, 67 7551-7552.) followed by reaction with a boronating reagent such as triisopropylborate which after hydrolysis provides the versatile intermediate III-3. Intermediate III-3 is able to react with a wide variety of substrated in what is commonly referred to as a Suzuki coupling to produce III-4 which are compounds of Formula I.

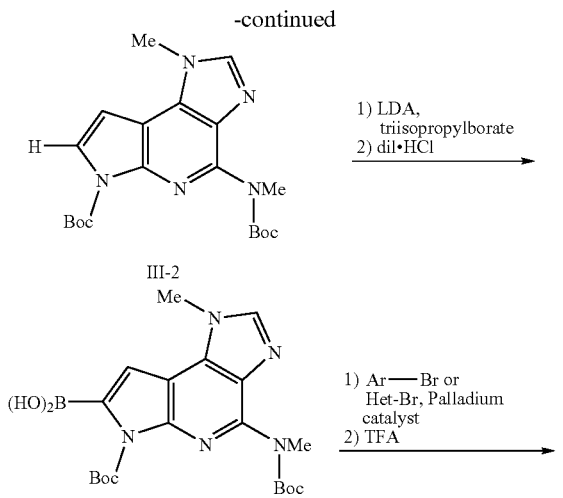

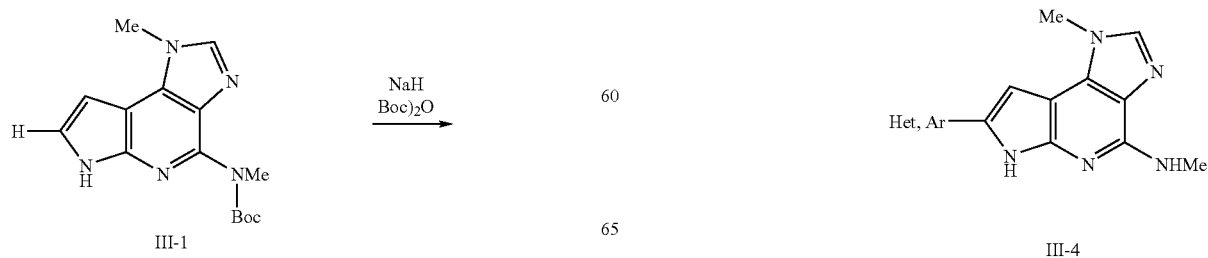

Substitution on the pyrrole nitrogen can be accomplished in general either by direct synthesis using the Buchwald synthesis with the desired amine as described in Scheme I using intermediate I-8. In some case it may be more convenient to perform the desired substitution as described in Scheme IV. Thus deprotonation with a suitable base such as sodium hydride, sodium bis(trimethylsilyl)amide, potassium butoxide, cesium carbonate and the like.

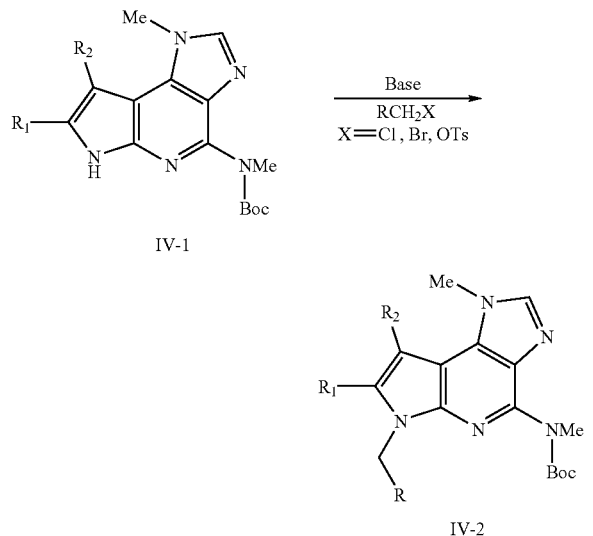

In general substitution at the 4-position of the heterocycle can be envisioned to arise from the active chlorine substituent in intermediate I-7. In some instances it is more convenient to modify the route to the heterocycle. One such instance is described in Scheme V.

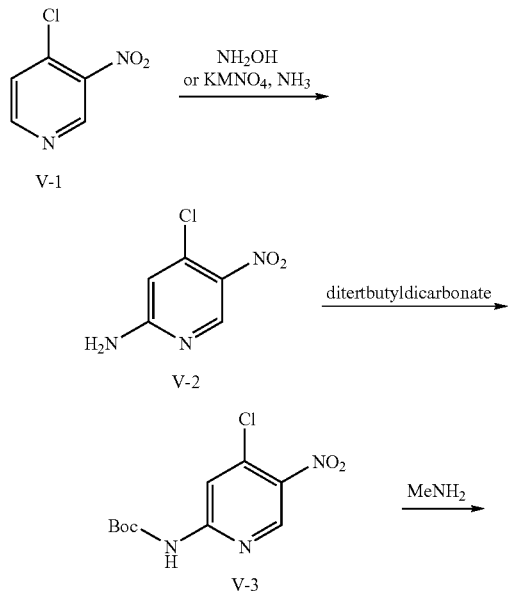

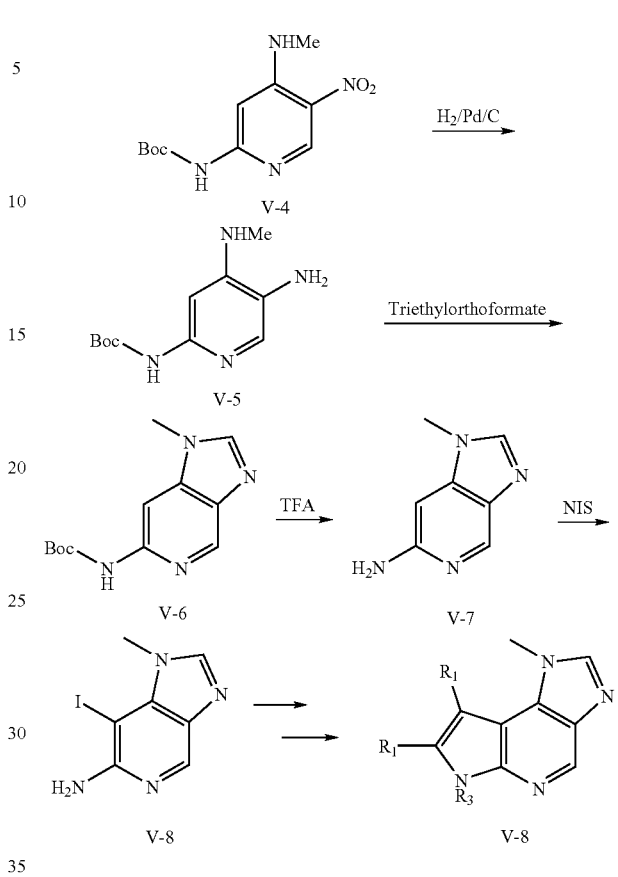

Thus commercially available 4-chloro-3-nitropyridine can undergo what is commonly referred to as a vicarious nucleophillic substitution with either hydroxylamine or ammonia in the presence of potassium permanganate to provide V-2. Protection of the amine as the Boc derivative can be assisted by the use of DMAP as the base to provide V-4. Reduction of the nitro group can be accomplished by a variety of methods generally known such as metal reductions such as zinc, iron, and the like, or alternatively using hydrogen gas at a pressure of atmospheric to 40 psi in the presence of a catalyst such as Palladium on charcoal, platinum oxide, and the like to produce intermediate V-5. Reaction of the diamine V-5 with triethylorthoformate will provide V-6, which after removal of the protecting group using trifluoroacetic acid produces amine V-7. Iodination of V-7 with N-iodosuccinimide or iodine in the presence of a catalyst such as silver triflate will produce V-8. Reaction of the iodoamine species in a manner similar to that described in Schemes 1-4 will provide V-9.

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

Abbreviations
Ac Acetyl
AcOH Acetic acid
aq. Aqueous
CDI Carbonyldiimidazole
Bn Benzyl
Bu Butyl
Boc tert-butoxycarbonyl
DIEA Diisopropylethylamine
DMAP Dimethylaminopyridine
DMA N,N-Dimethylacetamide
DMF dimethylformamide
DMSO Dimethylsulfoxide
EDC 1-(3-Dimethylaminopropyl)-3-ethylcarbodiimide hydrochloride
EtOAc Ethyl acetate
Et Ethyl
EtOH Ethanol
H Hydrogen
h Hours
i iso
HPLC High pressure liquid chromatography
HOAc Acetic acid
HOBT 1-Hydroxybenzotriazole
Lawesson's Reagent [2,4-bis(4-methoxyphenyl)-1,3-dithia-2,4-diphosphetane-2-4-disufide
LC liquid chromatography
Me Methyl
MeOH Methanol
min. Minutes
$M^+$ $(M+H)^+$
$M^{+1}$ $(M+H)^+$
MP Melting point
MS Mass spectrometry
n normal
PhCONCS Benzyolyisothiocyanate
Pd/C Palladium on carbon
Ph Phenyl
Pr Propyl
PSI Pounds per square inch
Ret Time Retention time
rt or RT Room temperature
sat. Saturated
S-Tol-BINAP (S)-(−)-2,2'-Bis(di-p-tolylphosphino)-1,1'-binapthyl
t tert
TFA Trifluoroacetic acid
THF Tetrahydrofuran
Phenominex Phenominex, Macclesfield, Cheshire, UK
Xantphos® (9,9-Dimethyl-9H-xanthene-4,5-diyl)bis[diphenylphosphine]
YMC YMC, Inc, Wilmington, N.C. 20403
HPLC conditions used to determine retention times;
LCMS conditions=A:
2 min gradient 0-100% B in A (A; 0.1% TFA in 90/10 water/methanol; B; 0.1% TFA in 10/90 water/methanol) using a Phenominex 4.6×30 mm S-5 ODS column
LCMS conditions=B:
4 min gradient 0-100% B in A (A; 0.1% TFA in 90/10 water/methanol; B; 0.1% TFA in 10/90 water/methanol) using a Waters Sunfire C18 (4.6×50 mm)
Condition C:
HPLC: Column: YMC S5 ODS 4.6×50 mm; Gradient time: 4 min; Flow rate=4 ml/min; Solvent A=10% MeOH—90% Water—0.2% H3PO4; Solvent B=90% MeOH—10% water—0.2% H3PO4; Start % B=0; Final % B=100.

Condition D:
Chiral HPLC: Column AD 4.6×250 mm; Hexanes/MeOH/Isopropanol (84/8/8) (Isocratic).

Condition E:
Chiral HPLC: Column Chiralpak AD 10 um 4.6×250 mm; Percent B=60% Isocratic; Flow rate=1 ml/min; Solvent A=Heptane; Solvent B=50% MeOH—50% EtOH Condition F:
Chiral HPLC: Column ChiralCEL OJ 10 um 4.6×250 mm; Percent B=20% Isocratic; Flow rate=2 ml/min; Solvent A=$CO_2$; Solvent B MeOH—0.5% DEA.

Condition G:
HPLC: Column: YMC 20×100 mm S-5; Gradient time: 10 min; Flow rate=20 ml/min; Solvent A=10% MeOH—90% Water—0.1% TFA; Solvent B=90% MeOH—10% water—0.1% TFA; Start % B=20; Final % B=100.

Condition H:
Chiral HPLC: Column ChiralCEL OD 10 um 4.6×250 mm; Percent B=35% Isocratic; Flow rate=2 ml/min; Solvent A=$CO_2$; Solvent B MeOH—0.1% DEA.

All systems utilized a detection wavelength of 254 nanometers or 220 nanometers.

In general reactions were conducted under a nitrogen atmosphere unless otherwise noted.

Those experiments which specify they were performed in a microwave were conducted either in a SmithSynthesizer™ manufactured by Personal Chemistry or a Discover™ microwave manufactured by CEM microwave. This microwave oven generates a temperature which can be selected between 60-250° C. The microwave automatically monitors the pressure which is between 0-290 PSI. Reaction times and temperatures are reported.

Example A1

1,6-dihydro-N,1-dimethyl-7-phenyl imidazo[4,5-d]pyrrolo[2,3-b]pyridin-4-amine

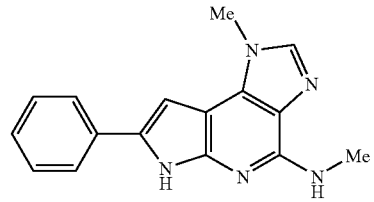

A1

A1.1: 3,5-Dinitro-1H-pyridin-4-one

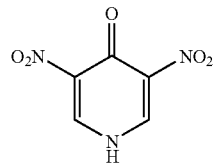

A1.1

4-Hydroxypyridine (40.0 g, 0.42 mol) was added portionwise to fuming nitric acid (140 ml) and sulfuric acid (500 ml). The resulting mixture was heated to 140° C. for 12 hours. The reaction mixture was cooled in an ice-bath and cautiously poured onto ice (500 ml). The yellow solid which precipitated was collected by filtration and dried under vacuum to yield A1.1 (70.0 g, 90%). $^1$H-NMR (DMSO-$d_6$) δ: 4.06 (2H, s). HPLC (B): 98.9%, ret. time=0.173 min., LC/MS $(M-H)^+$=184.

A1.2: (3,5-Dinitro-pyridin-4-yl)methylamine

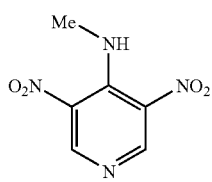

A1.1 (10.0 g, 0.051 mol) was added portionwise to a mixture of phosphorus oxychloride (25 ml) and $PCl_5$ (17.0 g, 0.082 mol). The reaction mixture was heated to reflux under a nitrogen atmosphere for 12 hours. The reaction mixture was allowed to cool to room temperature and the phosphorus oxychloride removed in vacuo. The residue was suspended in dry THF (50 ml) and cooled to 0° C. Methylamine (32 ml, 2.0M in THF, 0.064 mol) was added drop wise over 20 minutes under a nitrogen atmosphere and the resulting solution was allowed to warm to room temperature over 1 hour. The reaction mixture was evaporated in vacuo and the residue suspended in ethyl acetate (200 ml) which was then filtered and the filtrate evaporated in vacuo to leave the crude product. The crude product was recrystallized from methanol (100 ml) to give A1.2 as a tan solid (7.2 g, 71% for two steps). HPLC (B): 98%, ret. time 1.58 min., LC/MS $(M+H)^+$=199.

A1.3: 2,6-Dichloro-N'-methyl-pyridine-3,4,5-triamine

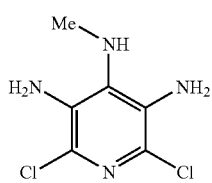

A solution of A1.2 (60.0 g, 0.30 mol) in concentrated hydrochloric acid (300 ml) was heated to 90° C. Tin (II) chloride (85.0 g, 0.45 mol) was added portionwise over 1 hour with vigorous effervescence noted for the first equivalent of tin chloride added. The reaction mixture was heated for a further hour before the addition of more tin chloride (28.0 g, 0.15 mol) and continued heating for 2 more hours. The reaction mixture was cooled to 0° C. and cautiously basified with concentrated ammonium hydroxide (200 ml). The precipitated solid was filtered off and the filtrate extracted with ethyl acetate (5×200 ml). The combined organics were dried (MgSO4) and evaporated in vacuo to leave A1.3 as a brown solid (28.0 g, 46%). HPLC (B): 98%, ret. time=1.58 min., LC/MS $(M+H)^+$=208.

A1.4: 7-Amino-4,6-dichloro-1-methyl-1H-imidazo[4,5-c]pyridine

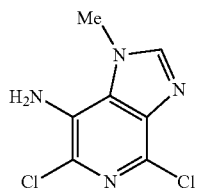

Triethylorthoformate (25.0 ml, 0.15 mol) was added in one portion to a suspension of A1.3 (28 g, 0.14 mol) in dry acetonitrile (400 ml). The reaction mixture was heated to reflux for 4 hours and then cooled to room temperature. The reaction mixture was evaporated in vacuo to leave A1.4 as a brown powder. $^1$H-NMR (DMSO-$d_6$) δ: 8.20 (1H, s), 5.49 (2H, br. s), 4.07 (3H, s). HPLC (A): 98%, ret. time=0.78 min., LC/MS $(M+H)^+$=218.

A1.5: 4,6-Dichloro-1-methyl-1H-imidazo[4,5-c]pyridine

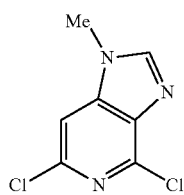

A solution of sodium nitrite (5.28 g; 76.5 mmol) in water (17 ml) was added drop wise over 5 minutes to a stirred solution of A1.4 (11.3 g; 52 mmol) in hypophosphorous acid (50 wt. % solution in water, 150 mL) at 0° C. to 5° C. The reaction mixture was allowed to warm to room temperature and stirred for an additional 40 minutes. The mixture was cooled in an ice bath (0° C. to 5° C.) and the pH was adjusted to >10 by the addition of aqueous sodium hydroxide (55 g in 100 mL of water). The resulting suspension was filtered. The filter cake was rinsed with water and suction dried to afford 9.9 g (97%) of A1.5 as a HPLC: 99%, ret. time=0.92 min., LC/MS $(M+H)^+$=202.06 (204.04, 206.02).

Alternative Route to A1.5

A1.6: 2,6-Dichloro-4-methylamino-pyridine

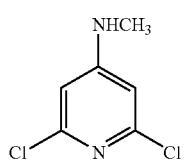

Methylamine (8M solution in ethanol, 5 ml; 40 mmol) was added drop wise to a stirred solution of commercially available 2,4,6-trichloropyridine (5 g; 27.4 mmol) in absolute ethanol (50 ml). After heating to 55-60° C. for 24 hr, the mixture was cooled to rt and concentrated. After adding water (50 ml) to the residue, the resulting suspension was filtered and the white filter cake was washed with water (3×10 ml). After air drying, the solid was suspended in dichloromethane (25 ml) and stirred for 10 minutes. Filtration, rinsing with dichloromethane and drying afforded 2.45 g (51%) of A1.6 as a white solid. HPLC (A): 95%, ret. time=1.16 min., LC/MS (M+H)$^+$=177.00 (178.99).

Alternate Preparation:

2,4,6-Trichloropyridine (1800 g, 9.89 mol) was dissolved in ethanol (1800 mL). Methylamine 40% solution in ethanol (6.3 L) was added over 1 h and 40 min maintaining the reaction temperature between 20-25° C. The reaction was stirred for 14 hours at room temperature and concentrated. The product was filtered, washed with methyl t-butyl ether (1,500 ml) and dried to yield A1.6 (1200 g, 68%)

A1.7: 2,6-Dichloro-4-methylamino-3-nitro-pyridine

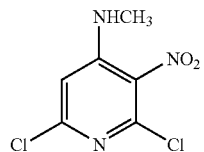

A1.7

Solid A1.6 (3.5 g, 19 mmol) was added portionwise to stirred concentrated sulfuric acid at 0° C. Effervescence was observed. 90% Fuming nitric acid (3.5 ml) was added drop wise at a rate that maintained the internal temperature below 6° C. After the addition was complete (45 minutes), the solution was stirred 10 minutes. The reaction mixture was poured onto ~100 g of ice and the resulting aqueous mixture was extracted with dichloromethane (3×100 ml). The combined organics were washed with water (200 ml), dried (MgSO$_4$/Na$_2$SO$_4$) and concentrated. The residue was dissolved in concentrated sulfuric acid (25 ml) and stirred 30 minutes at rt. Pouring the reaction mixture into ice gave a yellow suspension that was filter and dried to afford 2.45 g (49%) of A1.7 as a yellow solid. HPLC (A): 95%, ret. time=1.16 min., LC/MS (M+H)$^+$=177.00 (178.99).

Alternate Preparation:

Sulfuric acid (1.4 L) was cooled to 0° C. and A1.6 (700 g, 3.95 mol) was added portionwise over a period of 1.5 h while maintaining the temperature between −5° C. and 0° C. Fuming nitric acid (700 mL) was added over 1 h while maintaining the reaction at 0° C. and the reaction was stirred at 0° C. for one hour and poured onto ice. The reaction mixture was extracted with dichloromethane (3×3 L) and the solvent removed under reduced pressure to produce N-(2,6-dichloropyridin-4-yl)-N-methylnitramide (535 g 61%)

Caution—while N-(2,6-dichloropyridin-4-yl)-N-methylnitramide has been prepared without incident such intermediates should be treated with caution (such as avoid mechanical shock and heat and work behind a shield)

Sulfuric acid (1.1 L) was cooled to 0° C. The intermediate nitramide (535 g, 2.4 mol) was added portionwise to the sulfuric acid while maintaining the reaction temperature at 0° C. (~1 h). The reaction mixture was stirred for 1 h. Analysis of an aliquot showed disappearance of the nitramide. The reaction mixture was poured onto ice and after 1.5 h the product was extracted into dichloromethane (3×2 L) and the solvent removed under reduced pressure (temp=35° C.). The residue was crystallized by the addition of n-hexane and the solid collected to yield A1.7 (500 g, 81%)

A1.5: 4,6-Dichloro-1-methyl-1H-imidazo[4,5-c]pyridine

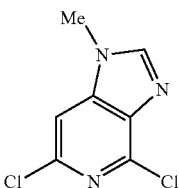

A1.5

A mixture of A1.7 (2.4 g; 10.8 mmol), SnCl$_2$.2H$_2$O (9.7 g; 43 mmol) and concentrated HCl (20 ml) in methanol (80 ml) was refluxed 1 hr. After removing the volatiles in vacuo, the intermediate (3,4-diamino-2,6-dichloro-N$^4$-methylpyridine) was dissolved in methanol (80 ml) and trimethylorthoformate (10 ml) was added. After refluxing 30 minutes, additional trimethylorthoformate (10 ml) was added and heating was continued for 30 minutes. After removing the volatiles in vacuo, the residue was partitioned between ethyl acetate (200 ml) and 2N NaOH (150 ml). The organic layer was washed with 2N NaOH (150 ml) and brine (100 ml). Drying (MgSO$_4$) and concentration afforded 2.12 g (97%) of A1.5 as a tan solid. HPLC (A): 98%, ret. time=0.94 min., LC/MS (M+H)$^+$=202.05 (204.04, 206.02).

Alternate Preparation:

Ammonium chloride (787 g) was added to water (5 L) at room temperature. Iron (1.0 kg, 18 mol) was added and the reaction mixture heated to 90° C. A1.5 (500 g, 2.25 mmol) was added portionwise over ~1 h (frothing observed). The reaction mixture was maintained at 90° C. for 1 hour after which time TLC analysis of the reaction mixture showed no starting material remaining. The reaction mixture was allowed to cool to 30° C. and ethyl acetate (5 L) was added to the reaction and the mixture was filtered to remove the iron. The layers were separated and the water layer washed with additional ethyl acetate. The organic layer was combined and the solvent removed under reduced pressure to provide the intermediate (3,4-diamino-2,6-dichloro-N$^4$-methylpyridine, 360 g, 83%), which was dissolved in ethanol (1,058 mL). Triethylorthoformate (1058 mL, 6.37 mol) was added at room temperature and the reaction mixture slowly heated to 80° C. The reaction mixture was maintained at 80° C. for ~15 h and cooled to 50° C. and the solvent removed by distillation under reduced pressure. n-Hexane was added and the product crystallized and was collected by filtration and dried to yield A1.7 (336 g, 74%, based on A1.5).

A1.8: 4-Methylamino-6-chloro-1-methyl-1H-imidazo[4,5-c]pyridine

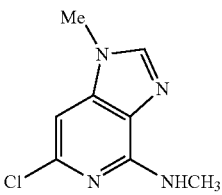

A1.8

A mixture of A1.5 (9.9 g; 49 mmol) and methylamine (8M solution in ethanol, 80 mmol, 100 ml) was heated to 82° C. for 24 hr. After removing the volatiles in vacuo, the residue was triturated with water (30 mL), filtered and dried to afford 8.89 g (93%) of A1.8 as a tan solid. HPLC (A): 99%, ret. time=0.98 min., LC/MS (M+H)$^+$=197.16 (199.06).

Alternate Preparation:

A1.7 (260 g, 1.3 mol) and methylamine 40% in ethanol (3.0 L) were placed in an autoclave and heated between 110-120° C. for 3 h. The reaction mixture was allowed to cool to room temperature and the solvent was removed by distillation under reduced pressure. The residue was triturated with water (15 L) and then washed with hexane (5 L) and dried to yield A1.8 (228 g, 90%).

A1.9: 4-[N-(Methyl)-N-(tertbutyloxycarbonyl)amino]-6-chloro-1-methyl-1H-imidazo[4,5-c]pyridine

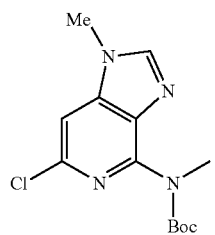

A1.9

A mixture of A1.8 (8.89 g, 45.3 mmol) was dissolved in anhydrous THF (50 mL) and cooled in a bath maintained at −78° C. Sodium bis(trimethylsilyl)amide (1M solution in THF, 56 mL, 56 mmol) was added over 10 min and the reaction mixture stirred at −78° C. for an additional 25 minutes. Di-tert-butyl dicarbonate (10.4 g, 47.6 mmol) was added portionwise and the low temperature bath removed. The reaction mixture was stirred at room temperature for 16 h and the solvent removed under reduced pressure. The crude product was dissolved in 250 mL of ethyl acetate and washed with water (2×100 mL) followed by brine (100 mL). The organic layer was dried over magnesium sulfate, filtered and the solvent removed under reduced pressure. The product was purified by silica gel chromatography (100% ethyl acetate) to provide 9.07 g (68%) of A1.9 LCMS Ret time 2.51 min, M+H+=297.15.

Alternate Preparation:

A1.8 (50 g, 0.26 mol) was dissolved in THF (2.5 L) and maintained between −25° C. and −20° C. Sodium bis(trimethylsilyl)amide 1M solution in THF (400 mL, 0.40 mol) was added over a period of 30 minutes. The reaction mixture was maintained between −25° C. and −20° C. for 30 min and ditertbutyldicarbonate (140 g, 0.64 mol) was added over 30 minutes (a slight exotherm was observed). The reaction mixture was stirred at −20° C. for ~3 h and the solvent removed under reduced pressure. The residue was partitioned between water (2 L) and ethyl acetate (3 L). The layers were separated and the aqueous layer was extracted with additional ethyl acetate (1 L). The combined organic layers were washed with brine. The organic layer was separated, dried and the solvent removed under reduced pressure to produce a crude solid which was stirred for 1 h with n-hexane, filtered, washed with additional hexane and dried to yield A1.9 (62 g, 82%).

A1.10: tert-Butyl 6-(diphenylmethyleneamino)-1-methyl-1H-imidazo[4,5-c]pyridine-4-yl(methyl)carbamate

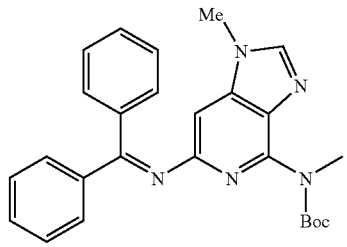

A1.10

A1.9 (9.00 g, 30.64 mmol) was dissolved in dimethylacetamide (100 mL) and benzophenone imine (8.69 g, 46 mmol), tris(dibenzylidineacetone)dipalladium (0) (1.69 g, 1.84 mmol), Xantphos® (1.60 g, 2.76 mmol) and cesium carbonate (16 g, 49 mmol) were added. The reaction mixture was heated to 115° C. for 5 h and allowed to cool to room temperature. The reaction mixture was filtered and concentrated under reduced pressure. The residue was diluted with water (100 mL) and stirred for 10 min. The solid was collected by filtration. Additional product was obtained from evaporation of the solution and purification by silica gel chromatography. The product was combined to yield 13.85 g (~100%) of A1.10, M+H$^+$ 442.24.

Alternate Preparation:

A stream of argon was passed through N,N-Dimethylacetamide (480 mL) for 30 min. A1.9 (40 g, 0.14 mol), benzophenone imine (33.5 mL, 0.20 mol), Xantphos® (1.60 g, 2.76 mmol), tris(dibenzylidineacetone)dipalladium (0) (9.5 g, 0.01 mol), and cesium carbonate (16 g, 49 mmol) were added. Argon was passed through the reaction mixture for and additional 20 min. The reaction mixture was then heated under an argon atmosphere at 110° C. for 8 h. The reaction mixture was cooled to room temperature, filtered and the solvent evaporated under reduced pressure. The residue was triturated with methyl tert-butyl ether and dried to yield A1.10 (44 g, 74%).

A1.11: tert-Butyl 6-amino-1-methyl-1H-imidazo[4,5-c]pyridin-4-yl(methyl)carbamate

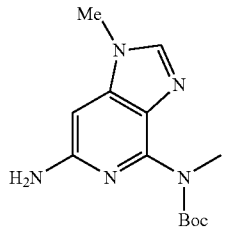

A1.11

A1.10 (13.85 g, 30.6 mmol) was dissolved in THF (100 mL) and cooled in an ice bath. 1N HCl (64 mL) was added dropwise and stirred for an additional 20 min. The organic layer was separated and set aside. The aqueous layer was neutralized by the addition of sodium hydroxide and saturated with sodium chloride and extracted with ethyl acetate (3×100 mL). All organic layers were combined and concentrated. The residue was triturated with anhydrous ether (100 mL) and filtered to provide 8.31 g (98%) of A1.11 M+H⁺=278.29.

Alternate Preparation:

A1.10 (42 g, 0.095 mol) was suspended in THF (310 mL) and cooled in an ice-salt bath. HCl (0.5 N, 392 mL) was added dropwise while maintaining the reaction temperature between 0° C. to 5° C. (~30 minutes). The reaction mixture was washed with ethyl acetate (3×300 mL) and the layers separated. The organic layer was basified with aqeous NaOH (18% solution) until pH 12 and extracted and evaporated to yield A1.11 (21 g, 80%).

A1.12: tert-Butyl 6-amino-7-iodo-1-methyl-1H-imidazo[4,5-c]pyridin-4-yl(methyl)carbamate

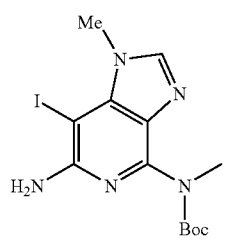

A1.12

A1.11 (8.0 g, 28.9 mmol) was dissolved in acetonitrile (260 mL) and cooled in an ice bath. N-iodosuccinimide (6.87 g, 29 mmol) was added portion wise with stirring. The reaction mixture was stirred for an additional 30 min, then the solvent removed under reduced pressure. The residue was purified on silica gel column (ethyl acetate) to yield 8.73 g (75%) of A1.12. M+H⁺=404.02.

Alternate Preparation:

A1.11 (25.0 g, 90.2 mmol) was suspended in acetonitrile (700 mL) and cooled in an ice-ethanol bath. N-iodosuccinimide (NIS) (19.5 g, 84.7 mmol) dissolved in acetonitrile (200 mL) was then added dropwise over 1 hr to the suspension of A1.11 while maintaining the internal reaction temperature to below 0° C. After 70 mL of NIS addition, the reaction mixture became homogeneous. After complete NIS addition, the reaction mixture was stirred at 0° C. for an additional 15 min before quenching with sodium hydrogen sulfite solution (2M, 500 mL added dropwise over 1 hr at 0° C.). The organic layer was separated and evaporated in vacuo. The remaining aqueous layer was extracted with dichloromethane (3×300 mL) and the combined organics were added to the original evaporated residue and once again evaporated in vacuo. This residue was taken up in dichloromethane (500 mL) and washed with water (500 mL). The organic layer was dried (Na₂SO₄) and stirred with decolorizing charcoal (5 g), before filtering and pre-absorbing on celite. Purification by column chromatography (dichloromethane→ethyl acetate gradient) gave a yellow solid (31.3 g) which was slurried in anhydrous methanol (40 mL), then filtered to give pure A1.12 (26.6 g). The filtrate was evaporated in vacuo and the slurry/filter process repeated (2×) to give a total of 29.4 g (81%) of A1.12. M⁺−100 (100%)=304.19, M⁺+H⁺=404.17, M⁺+Na=426.14. ¹H NMR (400 MHz, DMSO) δ: 7.97 (s, 1H), 5.78 (s, 2H), 3.97 (s, 3H), 3.17 (s, 3H), 1.31 (s, 9H).

A1.13: tert-Butyl 6-amino-1-methyl-7-(2-phenyl-ethynyl)-1H-imidazo[4,5-c]pyridin-4-yl(methyl) carbamate

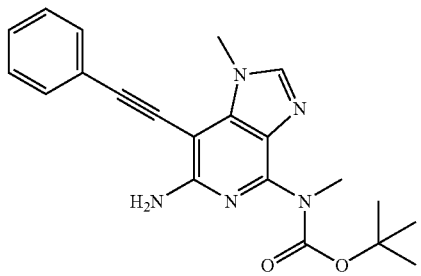

A1.13

Copper iodide (5.0 mg, 0.025 mmol) and dichlorobis (triphenylphosphine) palladium (4.0 mg, 0.050 mmol) were each added in one portion to a mixture of A1.12 (100 mg, 0.25 mmol), phenylacetylene (28 mg, 0.28 mmol) and triethylamine (0.11 ml, 0.75 mmol) in dichloromethane (0.5 ml) at room temperature under a nitrogen atmosphere. The resulting mixture was heated to 40° C. for 24 hrs before cooling to room temperature and evaporating in vacuo. The residue was purified by column chromatography using ethyl acetate as eluent to give 62 mg of A1.13. LC/MS Phenomenex S5 4.6×30 mm (2 min gradient) Found: M+H=378.27 at 1.51 min Alternate Preparation:

A suspension of A1.12 (1.0 g, 248 mmol) in DMF (6.80 mL) was degassed by bubbling argon through the solvent. Phenylacetylene was added (0.68 mL, 6.2 mmol), followed by dichlorobis(triphenyl-phosphine)palladium II (0.10 g, 0.149 mmol), copper (I) iodide (28.4 mg, 0.06 mmol), and degasssed diisopropylamine (9.2 mL). The pressure tube was sealed and immediately immersed in a 60° C. oil bath, and stirred for 30 min. The reaction mixture was evaporated to dryness under vacuum. The crude product was partitioned between EtOAc (45 mL) and water. After separation, the EtOAc layer was washed with water, brine, dried (Na₂SO₄), and concentrated under reduced pressure to yield over 1.0 g of a brown taffy. Flash chromatography on silica gel, eluting with a hexane: EtOAc gradient yielded 0.94 g, (98%) of A1.13 as a pale yellow powder. HPLC (condition C): 92.9%, ret. Time 2.91 min., LC/MS (M+H)⁺=378.4.

A1.14 (Alternate Preparation): tert-butyl methyl(1-methyl-7-phenyl-1,6-dihydroimidazo[4,5-d]pyrrolo[2,3-b]pyridin-4-yl)carbamate

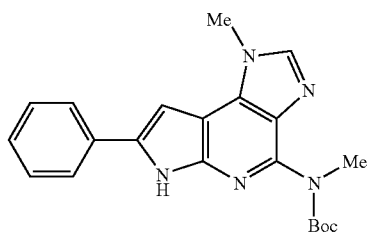

A1.14

Potassium tert-butoxide (2.91 mL of a 1.0M solution in THF, 2.91 mmol) was added to a solution of A1.13 (0.88 g, 2.33 mmol) in DMA (14.7 mL). The reaction solution was stirred at 80° C. for 35 min. Additional potassium tert-butoxide solution was added (0.35 mL, 0.35 mmol), and stirring at 80° C. was continued for 2 h. DMA was removed under vacuum. Water was added (20.0 mL), and after cooling to 0° C., the precipitate was collected by filtration, rinsed with ice-water and dried under vacuum to yield 0.70 g (79.5%) of A1.14 as a pale tan solid HPLC (C): 92.4%, ret. Time 2.76 min., LC/MS (M+H)$^+$=378.27

A1: 1,6-dihydro-N,1-dimethyl-7-phenyl imidazo[4,5-d]pyrrolo[2,3-b]pyridin-4-amine Potssium tert-butoxide (1M in THF, 0.04 ml, 0.04 mmol) was added dropwise to a solution of A1.13 (9.3 mg, 0.025 mmol) in NMP (0.4 ml) under a nitrogen atmosphere. The resulting mixture was heated to 80° C. for 2 hrs before cooling to room temperature, quenching with water (0.5 ml) and extracting with ethyl acetate (3×2 ml). The combined organics were dried (MgSO$_4$) and evaporated in vacuo. The residue (A1.14) was immediately dissolved in TFA and allowed to stir at room temperature for 2 hrs before evaporating in vacuo and purifying by preparative HPLC to provide A1 (3.2 mg) as an off-white solid. LC/MS Phenomenex S5 4.6×30 mm (2 min gradient) Found: M+H$^+$=278.22 at 1.310 min. $^1$H-NMR (MeOD) 8.05 (s, 1H), 7.71-7.66 (m, 2H), 7.40-7.30 (m, 2H), 7.25-7.18 (m, 1H), 7.04 (s, 1H), 4.04 (s, 3H) and 3.22 (s, 3H).

Example A2

3-[1,5-dihydro-1-methyl-4-(methylamino)imidazo[4,5-d]pyrrolo[2,3-b]pyridin-7-yl]benzonitrile

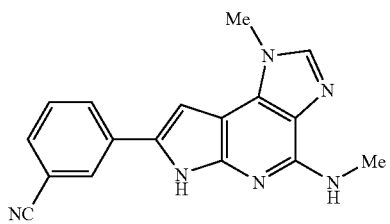

A2

A2.1: 3-(2-(trimethylsilyl)ethynyl)benzonitrile

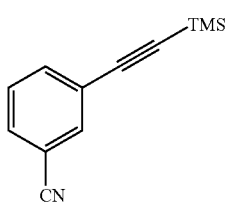

A2.1

To a solution of commercially available 3-iodobenzonitrile (25 g, 0.109 mol), copper (I) iodide (2.08 g, 0.0109 mol), PdCl$_2$(PPh$_3$)$_2$ (3.82 g, 0.0054 mol) and triethylamine (45.7 ml, 0.327 mol) in 250 of dry dichloromethane was added 12.8 g (0.131 mol) of trimethylsilylacetylene drop wise at 0° C. over a period of 10 min. The reaction mixture was stirred at RT over night. The reaction mixture was diluted with additional dichloromethane, filtered over Celite and the filtrate was concentrated. The crude material was purified by silica gel (60-120) column chromatography using 95:5 petrolium ether/ethyl acetate as eluent. A2.1 (20 g, 92%) was obtained as a brown solid $^1$H NMR, 400 MHz, CDCl$_3$: 7.79 (s, 1H), 7.67 (d, 1H), 7.59 (d, 1H), 7.43 (t, 1H), 0.26 (s, 9H).

A2.2: 3-Ethynylbenzonitrile

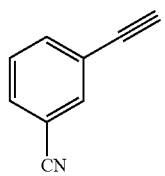

A2.2

To a solution of 20 g (0.01 mol) of A2.1 in 400 ml of methanol was added a solution of 0.28 g (0.005 mol) of potassium hydroxide in 3 ml of water. The reaction mixture was stirred at RT for 1 hr. The reaction mixture was diluted with 600 ml water and extracted with ethyl acetate. The extract was washed with brine and concentrated. The crude product was purified by 60-120 silica gel coloum using 5% of ethyl acetate in petrolium ether to provide A2.2 (10.7 g, 84%) as an off white solid $^1$H NMR, 400 MHz, CDCl$_3$: 7.78 (s, 1H), 7.72 (d, 1H), 7.65 (d, 1H), 7.43 (t, 1H), 3.21 (s, 1H).

A2.3: tert-Butyl 6-amino-7-(2-(3-cyanophenyl)ethynyl)-1-methyl-1H-imidazo[4,5-c]pyridin-4-yl(methyl)carbamate

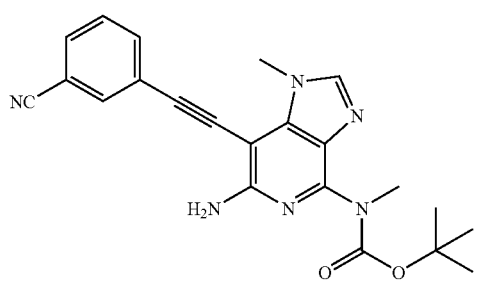

A2.3

A1.12 (1.48 g, 3.66 mmol), dichlorobis(triphenylphosphine)palladium (155 mg, 0.22 mmol), 3-ethynylbenzonitrile (A2.2) (930 mg, 7.32 mmol) and triethylamine (12 mL) were added to N,N-dimethylformamide (8 mL). The reaction mixture was heated at 90° C. for 50 min, cooled and the solvent removed under reduced pressure. The residue was purified by silica gel column chromatography using ethyl acetate as the eluent to provide 960 mg (65%) of A2.3. M+H⁺=403.21.

Alternate Preparation:

A1.12 (8.0 g, 19.85 mmol), dichlorobis(triphenylphosphine)palladium (840 mg, 1.2 mmol), 3-ethynylbenzonitrile (A2.2) (3.2 g, 25.0 mmol) and triethylamine (60 mL) were each added to N,N-dimethylformamide (40 mL), and nitrogen was bubbled through the resulting mixture for 5 min. The reaction mixture was heated at 90° C. for 20 min under a nitrogen atmosphere before cooling to room temperature and evaporating the solvent in vacuo. The residue was purified by silica gel column chromatography using ethyl acetate as eluent to provide 6.5 g (81%) of A2.3 HPLC YMC S-5 4.6×33 mm (2 min grad): retention time 2.80 min, M+H⁺=403.21

A2.4: 3-[1,6-dihydro-1-methyl-4-(N-tert-butyloxycarbonyl-N-methylamino)imidazo[4,5-d]pyrrolo[2,3-b]pyridin-7-yl]benzonitrile

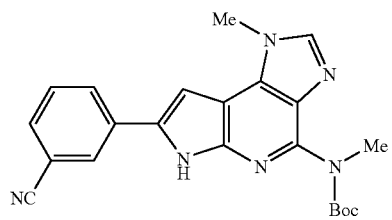

A2.4

A2.3 (960 mg, 2.38 mmol) was dissolved in dimethylacetamide (12 mL). Potassium t-butoxide, 1M in THF (2.6 ml, 2.6 mmol) was added and the reaction was heated in an oil bath maintained at 80° C. for 20 min. The reaction was allowed to cool to room temperature and the solvent was removed under reduced pressure. The residue was purified by Silica gel column chromatography using ethyl acetate as the eluent to yield 517 mg (54%) of A2.4. M+H⁺=403.34.

Alternate Preparation:

A2.3 (6.8 g, 16.84 mmol) was dissolved in dimethylacetamide (85 mL). Potassium t-butoxide, (1M in THF, 16.94 ml, 16.94 mmol) was added and the reaction heated in an oil bath maintained at 80° C. for 20 min. The reaction was allowed to cool to room temperature and the solvent was removed under reduced pressure. The residue was purified by Silica gel column chromatography using ethyl acetate as the eluent to yield 4.33 g (64%) of A2.4. HPLC YMC S-5 4.6×33 mm (2 min grad): retention time 2.80 min, M+H⁺=403.34.

A2.5: 3-[1,6-dihydro-1-methyl-4-(methylamino)imidazo[4,5-d]pyrrolo[2,3-b]pyridin-7-yl]benzonitrile A2.4 (12 mg, 30 mmol) was dissolved in a 1:1 mixture of TFA and methylene chloride, and stirred for 1 h. The volatiles were removed under reduced pressure and the residue purified by reverse phase column chromatography to provide 6.8 mg (75%) of A2. LC/MS Phenomenex S5 4.6×30 mm (2 min gradient) Found: M+H⁺=203.23 at 1.23 min. ¹H-NMR (d₆-DMSO): 12.2 (br s, 1H), 8.32 (br s, 2H) 8.17-8.15 (m, 1H), 7.64-7.59 (m, 3H), 7.45 (s, 1H), 4.09 (s, 3H), 3.04 (s, 3H).

Example A3

7-[3-(Aminomethyl)phenyl]-1,6-dihydro-N,1-dimethyl-imidazo[4,5-d]pyrrolo[2,3-b]pyridin-4-amine trifluoacetate salt

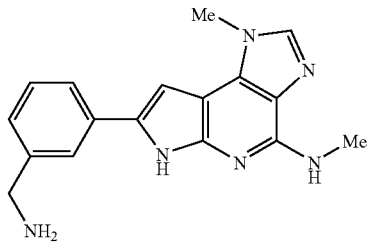

A3

TFA

A3.1 7-[3-(Aminomethyl)phenyl]-1,6-dihydro-N,1-dimethyl-imidazo[4,5-d]pyrrolo[2,3-b]pyridin-4-(t-butyloxycarbonylamine)

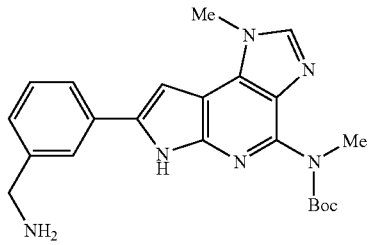

A3.1

A2.4 (1.2 g, 2.9 mmol) was dissolved in ethanol (100 mL, 100% ethanol). The solution was saturated with ammonia gas. Raney nickel (one spatula full ~1 g) was washed with water followed by ethanol and then added to the reaction mixture. A balloon of hydrogen gas was affixed to the reaction mixture and stirred at room temperature for 24 h. The product was filtered and the solvent removed under reduced pressure to yield A3.1 (1.14 g, 94%) M+H⁺=407.28.

Alternate Preparation:

A2.4 (5.6 g, 13.9 mmol) was dissolved in ethanol (300 mL, 100% ethanol) pre-saturated with ammonia gas. Raney nickel (one spatula full ~1 g) was washed with water followed by ethanol and then added to the reaction mixture. A balloon of hydrogen gas was affixed to the reaction mixture and stirred at room temperature for 18 h. The reaction mixture was filtered through celite and the solvent removed under reduced pressure to yield A3.1 (5.7 g, 98%). HPLC YMC S-5 4.6×33 mm (2 min grad): retention time 1.28 min, M+H⁺=407.28.

A3.2 7-[3-(Aminomethyl)phenyl]-1,6-dihydro-N,1-dimethyl-imidazo[4,5-d]pyrrolo[2,3-b]pyridin-4-amine trifluoacetate salt A3.1 (1.14 g, 2.8 mmol) was dissolved in dichloromethane (3 mL) and cooled in an ice bath. Trifluoroacetic acid (3 mL) was added and the reaction mixture was allowed to warm to room temperature and stirred for 30 min. The solvent was removed under reduced pressure to provide A3 (1.32 g, 88%) M+H⁺=307.24. ¹H NMR (MeOD): δ 8.20 (br s 1H), 7.72-7.68 (m, 3H), 7.46 (t, J=7 hz, 1H), 7.28 (d, J=7 hz, 1H), 7.18 (s, 1H). 4.17 (s, 3H), 2.05 (s, 3H).

Example A4

N-[[3-[1,6-dihydro-1-methyl-4-(methylamino)imidazo[4,5-d]pyrrolo[2,3-b]pyridin-7-yl]phenyl]methyl]acetamide, hydrochloride salt

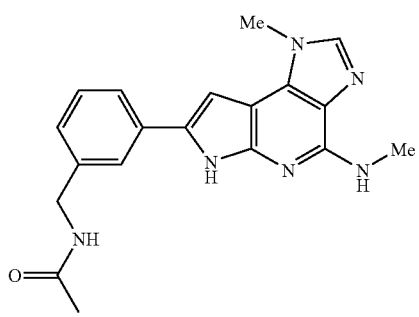

A4

A4.1: N-[3-[1,6-dihydro-1-methyl-4-(methyl-t-butyloxycarbonylamino)imidazo[4,5-d]pyrrolo[2,3-b]pyridin-7-yl]phenyl]methyl]acetamide

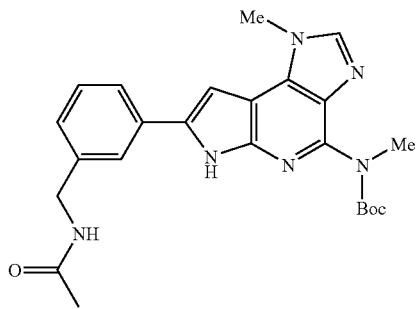

A4.1

A3.1 (30 mg, 0.074 mmol) was dissolved in methylene chloride (0.5 mL) triethyl amine (8.6 mg, 0.085 mmol) was added and the mixture cooled in an ice bath. Acetyl chloride (6.1 mg, 0.078 mmol) was added drop wise and the reaction mixture was stirred for 10 min. Saturated sodium bicarbonate (0.5 mL) was added and the mixture was stirred for an additional 5 minutes, and the product was collected by filtration.

An additional lot was prepared at the same time using the same procedure detailed above using A3.1 (420 mg, 1.03 mmol), triethyl amine (15 mg, 1.55 mmol), acetyl chloride (10.3 mg, 1.34 mmol) and methylene chloride (7 mL). The product of the two lots were combined to yield 437 mg (88%) of A4.1. M+H$^+$=449.18.

A4.2: N-[[3-[1,6-dihydro-1-methyl-4-(methylamino)imidazo[4,5-d]pyrrolo[2,3-b]pyridin-7-yl]phenyl]methyl]acetamide A4.1 (437 mg, 0.98 mmol) was dissolved in methanol (15 mL). 4N HCl in dioxane (5.4 mL) was added and the reaction mixture was heated in an oil bath for 4 hours. The solvent was removed under reduced pressure. The product was triturated with anhydrous ether, filtered and dried under vacuum to provide 350 mg (94%) of A4 as a white solid. M+H$^+$=349.33 $^1$H NMR δ 8.25, (s, 1H), 7.75-7.65 (m, 2H), 7.45 (t, J=7 hz, 1H), 7.28 (d, J=7 hz, 1H), 7.21 (s, 1H), 4.19 (s, 3H), 2.05 (s, 3H).

Examples A5-A52

Examples A5-A52 was prepared by parallel synthesis according to the scheme shown below.

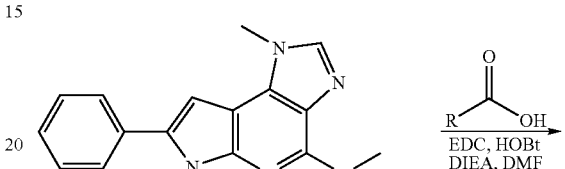

A3

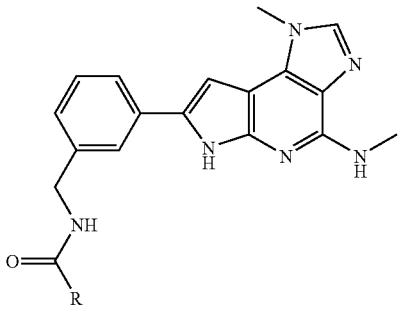

A5-A52

To an individual well in a Bohdan XT® reactor was added 150 uL of a 0.25 M solution of the carboxylic acid in dimethylformamide (DMF) (0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq). The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) to each reactor (that had a BOC group) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS (H$_2$O/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$O/MeOH/0.1% TFA). Examples prepared by this method are described in Table A1.

TABLE A1

| Ex. | R | Name | HPLC Retention (min) | MS Reported |
|---|---|---|---|---|
| A5 | Me, Me (isopropyl) | N-[[3-[1,6-dihydro-1-methyl-4-(methylamino)imidazo[4,5-d]pyrrolo[2,3-b]pyridin-7-yl]phenyl]methyl]-2-methyl-propanamide | 2.39 | 377.19 |
| A6 | t-Bu | N-[[3-[1,6-dihydro-1-methyl-4-(methylamino)imidazo[4,5-d]pyrrolo[2,3-b]pyridin-7-yl]phenyl]methyl]-2,2-dimethyl propanamide | 2.56 | 391.2 |
| A7 | Me-cyclopropyl | N-[[3-[1,6-dihydro-1-methyl-4-(methylamino)imidazo[4,5-d]pyrrolo[2,3-b]pyridin-7-yl]phenyl]methyl]-1-methyl-cyclopropanecarboxamide | 2.49 | 389.16 |
| A8 | HO-cyclopropyl | N-[[3-[1,6-dihydro-1-methyl-4-(methylamino)imidazo[4,5-d]pyrrolo[2,3-b]pyridin-7-yl]phenyl]methyl]-1-hydroxy-cyclopropanecarboxamide | 2.18 | 391.13 |
| A9 | NC-cyclopropyl | 1-cyano-N-[[3-[1,6-dihydro-1-methyl-4-(methylamino)imidazo[4,5-d]pyrrolo[2,3-b]pyridin-7-yl]phenyl]methyl]-cyclopropanecarboxamide | 2.37 | 400.14 |
| A10 | CH$_2$OH | N-[[3-[1,6-dihydro-1-methyl-4-(methylamino)imidazo[4,5-d]pyrrolo[2,3-b]pyridin-7-yl]phenyl]methyl]-2-hydroxy-acetamide | 1.99 | 365.16 |
| A11 | CH$_2$NHC(O)Me | 2-(acetylamino)-N-[[3-[1,6-dihydro-1-methyl-4-(methylamino)imidazo[4,5-d]pyrrolo[2,3-b]pyridin-7-yl]phenyl]methyl]-acetamide | 1.98 | 406.15 |
| A12 | CH$_2$NMe$_2$ | N-[[3-[1,6-dihydro-1-methyl-4-(methylamino)imidazo[4,5-d]pyrrolo[2,3-b]pyridin-7-yl]phenyl]methyl]-2-(dimethylamino)-acetamide | 1.82 | 392.2 |
| A13 | CH$_2$C(O)NH$_2$ | N-[[3-[1,6-dihydro-1-methyl-4-(methylamino)imidazo[4,5-d]pyrrolo[2,3-b]pyridin-7-yl]phenyl]methyl] butanediamide | 1.99 | 406.17 |

TABLE A1-continued

| Ex. | R | Name | HPLC Retention (min) | MS Reported |
|---|---|---|---|---|
| A14 | CH(Me)CH2- (isobutyl, 3-methyl) | N-[[3-[1,6-dihydro-1-methyl-4-(methylamino)imidazo[4,5-d]pyrrolo[2,3-b]pyridin-7-yl]phenyl]methyl]-3-methyl butanamide | 2.6 | 391.2 |
| A15 | C(Me)2CH2- (neopentyl) | N-[[3-[1,6-dihydro-1-methyl-4-(methylamino)imidazo[4,5-d]pyrrolo[2,3-b]pyridin-7-yl]phenyl]methyl]-3,3-dimethyl-butanamide | 2.76 | 405.21 |
| A16 | CH2CH2CH(Me)2 | N-[[3-[1,6-dihydro-1-methyl-4-(methylamino)imidazo[4,5-d]pyrrolo[2,3-b]pyridin-7-yl]phenyl]methyl]-4-methyl-pentanamide | 2.82 | 405.21 |
| A17 | CH2CH2OMe | N-[[3-[1,6-dihydro-1-methyl-4-(methylamino)imidazo[4,5-d]pyrrolo[2,3-b]pyridin-7-yl]phenyl]methyl]-3-methoxy-propanamide | 2.2 | 393.15 |
| A18 | CH2CH2CH2S(O)2Me | 4-(aminosulfonyl)-N-[[3-[1,6-dihydro-1-methyl-4-(methylamino)imidazo[4,5-d]pyrrolo[2,3-b]pyridin-7-yl]phenyl]methyl]-butanamide | 2.03 | 456.12 |
| A19 | 2-chlorophenyl | 2-chloro-N-[[3-[1,6-dihydro-1-methyl-4-(methylamino)imidazo[4,5-d]pyrrolo[2,3-b]pyridin-7-yl]phenyl]methyl]-benzamide | 2.65 | 445.11 |
| A20 | 3-chlorophenyl | 3-chloro-N-[[3-[1,6-dihydro-1-methyl-4-(methylamino)imidazo[4,5-d]pyrrolo[2,3-b]pyridin-7-yl]phenyl]methyl]-benzamide | 2.97 | 445.11 |

TABLE A1-continued

| Ex. | R | Name | HPLC Retention (min) | MS Reported |
|---|---|---|---|---|
| A21 | 4-chlorophenyl | 4-chloro-N-[[3-[1,6-dihydro-1-methyl-4-(methylamino)imidazo[4,5-d]pyrrolo[2,3-b]pyridin-7-yl]phenyl]methyl]-benzamide | 3.01 | 445.12 |
| A22 | benzyl | N-[[3-[1,6-dihydro-1-methyl-4-(methylamino)imidazo[4,5-d]pyrrolo[2,3-b]pyridin-7-yl]phenyl]methyl] benzeneacetamide | 2.64 | 425.19 |
| A23 | phenethyl | N-[[3-[1,6-dihydro-1-methyl-4-(methylamino)imidazo[4,5-d]pyrrolo[2,3-b]pyridin-7-yl]phenyl]methyl] benzenepropanamide | 2.81 | 439.17 |
| A24 | 3-phenylpropyl | N-[[3-[1,6-dihydro-1-methyl-4-(methylamino)imidazo[4,5-d]pyrrolo[2,3-b]pyridin-7-yl]phenyl]methyl]-benzenebutanamide | 2.94 | 453.17 |
| A25 | 3-thienyl | N-[[3-[1,6-dihydro-1-methyl-4-(methylamino)imidazo[4,5-d]pyrrolo[2,3-b]pyridin-7-yl]phenyl]methyl]-3-thiophenecarboxamide | 2.57 | 417.11 |
| A26 | 4-thiazolyl | N-[[3-[1,6-dihydro-1-methyl-4-(methylamino)imidazo[4,5-d]pyrrolo[2,3-b]pyridin-7-yl]phenyl]methyl]-4-thiazolecarboxamide | 2.39 | 418.08 |
| A27 | 4-methyl-1,2,3-thiadiazol-5-yl | N-[[3-[1,6-dihydro-1-methyl-4-(methylamino)imidazo[4,5-d]pyrrolo[2,3-b]pyridin-7-yl]phenyl]methyl]-4-methyl-1,2,3-thiadiazole-5-carboxamide | 2.53 | 433.1 |

TABLE A1-continued

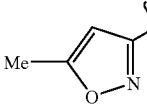

| Ex. | R | Name | HPLC Retention (min) | MS Reported |
|---|---|---|---|---|
| A28 | 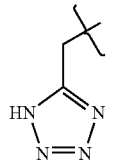 | N-[[3-[1,6-dihydro-1-methyl-4-(methylamino)imidazo[4,5-d]pyrrolo[2,3-b]pyridin-7-yl]phenyl]methyl]-5-methyl-3-isoxazolecarboxamide | 2.5 | 416.14 |
| A29 | 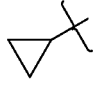 | N-[[3-[1,6-dihydro-1-methyl-4-(methylamino)imidazo[4,5-d]pyrrolo[2,3-b]pyridin-7-yl]phenyl]methyl]-1H-tetrazole-5-acetamide | 2.09 | 417.14 |
| A30 | 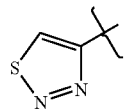 | N-[[3-[1,6-dihydro-1-methyl-4-(methylamino)imidazo[4,5-d]pyrrolo[2,3-b]pyridin-7-yl]phenyl]methyl]-cyclopropanecarboxamide | 2.66 | 375.12 |
| A31 | 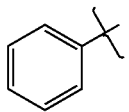 | N-[[3-[1,6-dihydro-1-methyl-4-(methylamino)imidazo[4,5-d]pyrrolo[2,3-b]pyridin-7-yl]phenyl]methyl]-1,2,3-thiadiazole-4-carboxamide | 2.69 | 419.03 |
| A32 | 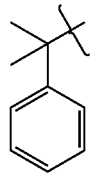 | N-[[3-[1,6-dihydro-1-methyl-4-(methylamino)imidazo[4,5-d]pyrrolo[2,3-b]pyridin-7-yl]phenyl]methyl]-benzamide | 2.96 | 411.10 |
| A33 | 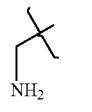 | N-[[3-[1,6-dihydro-1-methyl-4-(methylamino)imidazo[4,5-d]pyrrolo[2,3-b]pyridin-7-yl]phenyl]methyl]-alpha,alpha-dimethylbenzeneacetamide | 3.23 | 453.13 |
| A34 | 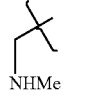 | 2-amino-N-[[3-[1,6-dihydro-1-methyl-4-(methylamino)imidazo[4,5-d]pyrrolo[2,3-b]pyridin-7-yl]phenyl]methyl]-acetamide | 1.74 | 364.42 |
| A35 |  | N-[[3-[1,6-dihydro-1-methyl-4-(methylamino)imidazo[4,5-d]pyrrolo[2,3-b]pyridin-7-yl]phenyl]methyl]-2-(methylamino)-acetamide | 1.74 | 378.36 |

TABLE A1-continued

| Ex. | R | Name | HPLC Retention (min) | MS Reported |
|---|---|---|---|---|
| A36 | (S)-CH(NH₂)CH₃ | 2-amino-N-[[3-[1,6-dihydro-1-methyl-4-(methylamino)imidazo[4,5-d]pyrrolo[2,3-b]pyridin-7-yl]phenyl]methyl]-, (2S)-propanamide | 1.78 | 378.36 |
| A37 | (R)-CH(NH₂)CH₃ | 2-amino-N-[[3-[1,6-dihydro-1-methyl-4-(methylamino)imidazo[4,5-d]pyrrolo[2,3-b]pyridin-7-yl]phenyl]methyl]-, (2R)-propanamide | 1.77 | 378.36 |
| A38 | (S)-CH(NHMe)CH₃ | N-[[3-[1,6-dihydro-1-methyl-4-(methylamino)imidazo[4,5-d]pyrrolo[2,3-b]pyridin-7-yl]phenyl]methyl]-2-(methylamino)-, (2S)-propanamide | 1.81 | 392.39 |
| A39 | CH₂CH₂NH₂ | 3-amino-N-[[3-[1,6-dihydro-1-methyl-4-(methylamino)imidazo[4,5-d]pyrrolo[2,3-b]pyridin-7-yl]phenyl]methyl]-propanamide | 1.76 | 378.36 |
| A40 | 1-aminocyclopropyl | 1-amino-N-[[3-[1,6-dihydro-1-methyl-4-(methylamino)imidazo[4,5-d]pyrrolo[2,3-b]pyridin-7-yl]phenyl]methyl]-cyclopropanecarboxamide | 1.77 | 390.39 |
| A41 | C(CH₃)₂NH₂ | 2-amino-N-[[3-[1,6-dihydro-1-methyl-4-(methylamino)imidazo[4,5-d]pyrrolo[2,3-b]pyridin-7-yl]phenyl]methyl]-2-methyl-propanamide | 1.79 | 329.39 |
| A42 | (S)-CH(NH₂)CH₂CH₃ | 2-amino-N-[[3-[1,6-dihydro-1-methyl-4-(methylamino)imidazo[4,5-d]pyrrolo[2,3-b]pyridin-7-yl]phenyl]methyl]-, (2S)-butanamide | 1.86 | 329.39 |
| A43 | (S)-CH(NH₂)CH(CH₃)₂ | 2-amino-N-[[3-[1,6-dihydro-1-methyl-4-(methylamino)imidazo[4,5-d]pyrrolo[2,3-b]pyridin-7-yl]phenyl]methyl]-3-methyl-, (2S)-butanamide | 1.97 | 406.42 |

TABLE A1-continued

| Ex. | R | Name | HPLC Retention (min) | MS Reported |
|---|---|---|---|---|
| A44 | (isopropyl, NH2) | 2-amino-N-[[3-[1,6-dihydro-1-methyl-4-(methylamino)imidazo[4,5-d]pyrrolo[2,3-b]pyridin-7-yl]phenyl]methyl]-3-methyl-, (2R)-butanamide | 1.97 | 406.42 |
| A45 | (tert-butyl, NH2) | 2-amino-N-[[3-[1,6-dihydro-1-methyl-4-(methylamino)imidazo[4,5-d]pyrrolo[2,3-b]pyridin-7-yl]phenyl]methyl]-3,3-dimethyl-, (2S)-butanamide | 2.09 | 420.36 |
| A46 | (isobutyl, NH2) | 2-amino-N-[[3-[1,6-dihydro-1-methyl-4-(methylamino)imidazo[4,5-d]pyrrolo[2,3-b]pyridin-7-yl]phenyl]methyl]-4-methyl-, (2S)-pentanamide | 2.16 | 420.44 |
| A47 | (phenyl, NH2) | alpha-amino-N-[[3-[1,6-dihydro-1-methyl-4-(methylamino)imidazo[4,5-d]pyrrolo[2,3-b]pyridin-7-yl]phenyl]methyl]-, (alphaS)-benzeneacetamide | 2.05 | 440.32 |
| A48 | (benzyl, NH2) | alpha-amino-N-[[3-[1,6-dihydro-1-methyl-4-(methylamino)imidazo[4,5-d]pyrrolo[2,3-b]pyridin-7-yl]phenyl]methyl]-, (alphaS)-benezenepropanamide | 2.23 | 454.35 |
| A49 | (benzyl, NH2) | alpha-amino-N-[[3-[1,6-dihydro-1-methyl-4-(methylamino)imidazo[4,5-d]pyrrolo[2,3-b]pyridin-7-yl]phenyl]methyl]-, (alphaR)-benezenepropanamide | 2.23 | 454.35 |
| A50 | (pyrrolidinyl) | N-[[3-[1,6-dihydro-1-methyl-4-(methylamino)imidazo[4,5-d]pyrrolo[2,3-b]pyridin-7-yl]phenyl]methyl]-, (2R)-2-pyrrolidinecarboxamide | 1.82 | 404.41 |

TABLE A1-continued

| Ex. | R | Name | HPLC Retention (min) | MS Reported |
|---|---|---|---|---|
| A51 | (H₂N-C(=O)-CH₂-CH(NH₂)-) | N¹-[[3-[1,6-dihydro-1-methyl-4-(methylamino)imidazo[4,5-d]pyrrolo[2,3-b]pyridin-7-yl]phenyl]methyl]-L-aspartamide | 1.67 | 421.39 |
| A52 | (CHPh₂-C(CH₃)-) | N-[[3-[1,6-dihydro-1-methyl-4-(methylamino)imidazo[4,5-d]pyrrolo[2,3-b]pyridin-7-yl]phenyl]methyl]-alpha-phenyl-benzeneacetamide | 3.17 | 501.23 |

Alternate Preparation of Example A6

Example A6

N-[[3-[1,5-dihydro-1-methyl-4-(methylamino)imidazo[4,5-d]pyrrolo[2,3-b]pyridin-7-yl]phenyl]methyl]trimethylacetamide hydrochloride salt

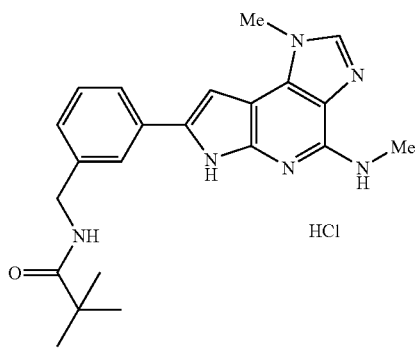

A6

A6.1: N-[[3-[1,5-dihydro-1-methyl-4-(methyl-t-butyloxycarbonylamino)imidazo[4,5-d]pyrrolo[2,3-b]pyridin-7-yl]phenyl]methyl]trimethylacetamide

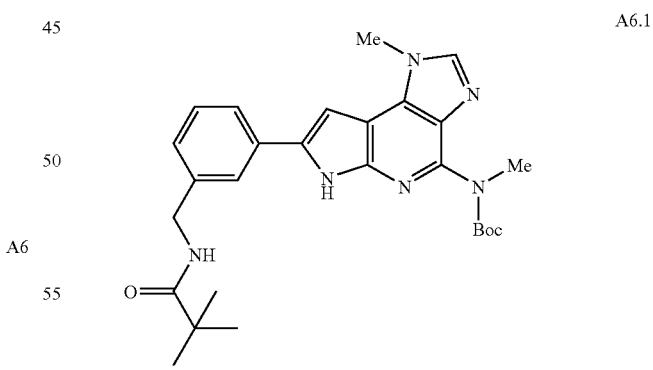

A6.1

A3 (3.0 g, 7.4 mmol) was dissolved in methylene chloride (50 mL). Triethylamine (1.54 mL 11.1 mmol) was added and the mixture cooled in an ice bath. Trimethylacetyl chloride (0.78 mL, 9.24 mmol) was added dropwise and the reaction mixture was stirred for 10 min. Saturated sodium bicarbonate (3.0 mL) was added, the mixture was stirred for an additional 5 minutes, and the product was collected by filtration to yield 3.19 g (88%) of A6.1. HPLC YMC S-5 4.6×33 mm (2 min gradient): retention time 1.75 min, M+H⁺=491.41.

A6.2: N-[[3-[1,5-dihydro-1-methyl-4-(methylamino)imidazo[4,5-d]pyrrolo[2,3-b]pyridin-7-yl]phenyl]methyl]trimethylacetamide hydrochloride salt 4N HCl in dioxane (25.0 mL) was added to A6.1 (3.19 g, 6.51 mmol) and the reaction mixture was stirred at room temperature for 3 hours. The solvent was removed under reduced pressure and the product was triturated with anhydrous ether, filtered and dried under vacuum to provide 2.76 g (94%) of A6 as a yellow powder. HPLC YMC S-5 4.6×33 mm (2 min grad): retention time 1.53 min, M+H$^+$=391.46 $^1$H NMR (500 MHz) δ 8.27, (s, 1H), 7.59-7.56 (m, 2H), 7.37 (t, J=7 hz, 1H), 7.21 (d, J=7 hz, 1H), 7.06 (s, 1H), 4.09 (s, 3H), 3.27 (s, 3H) and 1.21 (s, 9H). $^{13}$C NMR (400 MHz, DMSO) δ 177.8, 144.6, 141.3, 132.8, 131.8, 129.3, 125.6, 123.3, 122.7, 98.0, 95.0, 45.7, 42.5, 38.5, 34.0, 28.0, 27.9, 8.9.

Alternate Preparation of Example A17:

Example A17

N-[[3-[1,5-dihydro-1-methyl-4-(methylamino)imidazo[4,5-d]pyrrolo[2,3-b]pyridin-7-yl]phenyl]methyl]-3-methoxypropanamide hydrochloride salt

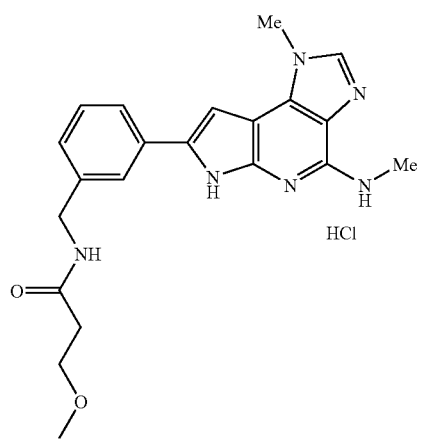

A17

A17.1: N-[[3-[1,5-dihydro-1-methyl-4-(methyl-tert-butyloxycarbonylamino)imidazo[4,5-d]pyrrolo[2,3-b]pyridin-7-yl]phenyl]methyl]-3-methoxypropanamide

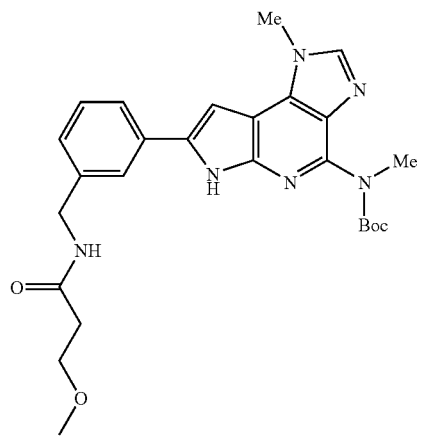

A17.1

EDC (3.21 g, 14.37 mmol) was added in one portion to a mixture of 3-methoxypropionic acid (0.91 g, 9.63 mmol), HOBt (1.72 g, 11.01 mmol) and DIPEA (11 mL) in dry acetonitrile (150 mL). After stirring for 20 min, A3 (2.10 g, 5.17 mmol) was added and the resulting reactiom mixture was allowed to stir at room temperature overnight. The reaction mixture was evaporated in vacuo and the residue was purified by silica gel column chromatography (ethyl acetate) to yield A17.1 (2.1 g, 83%). HPLC YMC S-5 4.6×33 mm (2 min grad): retention time 1.66 min, M+H$^+$=493.48

A17.2: N-[[3-[1,5-dihydro-1-methyl-4-(methylamino)imidazo[4,5-d]pyrrolo[2,3-b]pyridin-7-yl]phenyl]methyl)-3-methoxypropanamide hydrochloride salt 4N HCl in dioxane (25.0 mL) was added to A17.1 (2.0 g, 4.07 mmol) and the reaction mixture was stirred at room temperature for 2 hours. The solvent was removed under reduced pressure and the the product was triturated with anhydrous ether, filtered and dried under vacuum to provide 1.5 g (94%) of A17 as a white powder. HPLC YMC S-5 4.6×33 mm (2 min grad): retention time 1.36 min, M+H$^+$=393.39. $^1$H NMR (500 MHz, DMSO) δ 12.14 (s, 1H), 8.95 (br. s, 1H), 8.44-8.41 (m, 1H), 7.74-7.70 (m, 2H), 7.40 (t, J=7.6 Hz, 1H), 7.26 (d, J=2.0 Hz, 1H), 7.17 (d, J=7.6 Hz, 1H), 4.33 (d, J=5.8 Hz, 2H), 4.17 (s, 3H), 3.59 (t, J=6.4 Hz, 2H), 3.24 (s, 3H), 2.44 (t, J=6.4 Hz, 2H).

Examples A53-A64

Examples A53-A64 was prepared in a manner similar to example A1. Thus intermediate A1.12 was subjected to a what is commonly referred to as a Sonoghasira type coupling (as described in detail for the preparation of A1.13, and conducted in a similar manner) with acetylenes which are either commercially available, or readily prepared (as described for step A2.1 and A2.2 and conducted in a similar manner described below). The acetylene were cyclized to the examples in Table A2 in a manner described in detail in step A1.14. Examples A57 and A58 were resolved by chiral HPLC (Chiralpak AD® 4.6×250 mm, using hexane/methanol/isopropanol 84:8:8 with a flow rate of 1 mL/min) starting from racemic A56.

Acetylene Intermediates

For example A56:

A56.1: 1-(3-bromophenyl)ethanamine

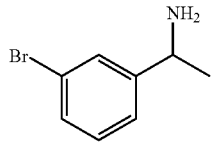

A56.1

A mixture of commercially available 3-bromoacetophenone (30 g, 0.1508 mol), formic acid (47 mL) and formamide (70 mL) was heated to 220° C. for 5 h. The brown liquid obtained was cooled to RT, quenched with water and extracted with ethyl acetate. The organic layer was washed with water, brine and concentrated. The resulting brown liquid was dissolved in ethanol (375 mL) and conc. HCl (75 mL) and the mixture was refluxed over night. Ethanol was removed completely and the aqueous layer was washed with ether and ethyl acetate to remove all non-basic impurities. The aqueous layer was basified with a 10% aqueous sodium hydroxide solution and extracted with ethyl acetate. The ethyl acetate layer was washed with brine, and concentrated to provide 26 g (86.65%) of A56.1. This compound was taken to the next step with out further purification. $^1$H NMR (CDCl$_3$, 300 MHz) δ 1.38 (d, 3H), 4.1 (q, 1H), 7.2 (m, 1H), 7.27 (m, 1H), 7.37 (m, 1H), 7.51 (s, 1H). LS-MS (M–H)$^+$=200.

A56.2: tert-butyl 1-(3-bromophenyl)ethylcarbamate

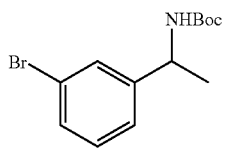

To a solution of A56.1 (15 g, 0.075 mol) in chloroform (150 mL) was added di-tert-butyldicarbonate (18 g, 0.0825 mol) slowly at 0° C. and stirred at RT over night. The solvent was removed under vacuum and the compound was purified by silica gel column chromatography using 5% ethyl acetate in petrolium ether as eluent to obtain 20.6 g (94%) of A56.2 as white solid. $^1$H NMR (CDCl$_3$, 400 MHz) δ 1.4 (m, 12H), 4.8 (bs, 1H), 7.21 (m, 2H), 7.4 (m, 1H), 7.45 (s, 1H). LS-MS (M–H–Boc+CH$_3$CN)$^+$=244.

A56.3: tert-butyl 1-(3-(3-hydroxy-3-methylbut-1-ynyl)phenyl)ethylcarbamate

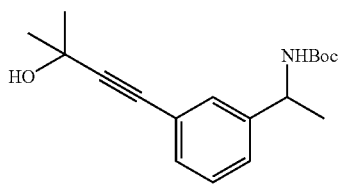

A56.2 (22 g, 0.073 mol) was dissolved in of triethylamine (220 mL) under nitrogen and cuprous iodide (0.695 g, 0.0036 mol) and bis(triphenylphosphine)palladium (II) chloride (1.53 g, 0.0021 mol) were added. To this mixture, 2-methyl-3-butyln-2-ol (9.24 g, 0.109 mol) was added slowly and heated at 80° C. for 12 h. The reaction mixture was concentrated to remove solvents and the residue was dissolved in ethyl acetate, washed with water followed by brine. The organic layer was concentrated under reduced pressure and the residue purified by silica gel column chromatography using 5% of ethyl acetate in petrolium ether to give 20 g (90%) of A56.3. $^1$H NMR (CDCl$_3$, 400 MHz) δ 1.42 (bs, 12H), 1.63 (s, 6H), 4.7 (bs, 1H), 7.29 (m, 3H), 7.36 (s, 1H).

A56.4: tert-butyl 1-(3-ethynylphenyl)ethylcarbamate

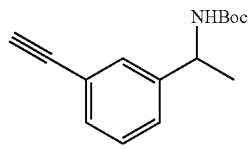

A56.3 (20 g, 0.065 mol) was dissolved in isopropyl alcohol and powdered potassium hydroxide (9.22 g, 0.164 mol) was added. The reaction mixture was heated to 80° C. for 5 h. The reaction mixture was concentrated and the residue was dissolved in ethyl acetate, washed with water, brine and concentrated. The product was purified by column chromatography with petroleum ether/ethyl acetate mixture to give A56.4, 6.5 g (40%). $^1$H NMR (DMSO-d$_6$, 400 MHz) δ 1.22 (d, 3H), 1.36 (s, 9H), 4.17 (s, 1H), 4.59 (t, 1H), 7.32 (m, 3H), 7.40 (s, 1H), 7.45 (s, 1H). LS-MS (M+Na)=268.

For Example A60:

A60.1: (2-(4-chloro-3-methoxyphenyl)ethynyl)trimethylsilane

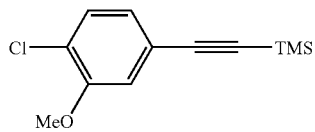

Commercially available 5-bromo-2-chloroanisole (1.0 g, 4.52 mmol), trimethylsilylacetylene (1.07 mL, 7.5 mmol) and triethylamine (15 mL) were added to anhydrous toluene (15 mL) and degassed by purging with nitrogen. Bis(acetato)bis(triphenylphosphine)palladium II (340 mg, 0.45 mmol) was added and the reaction mixture was heated to ~95° C. for 30 min. The reaction mixture was cooled to room temperature, filtered to remove the catalyst, and diluted with ethyl acetate (150 mL). The organic layer was washed with saturated sodium bicarbonate (50 mL) and brine (50 mL) separated, dried over magnesium sulfate, filtered and concentrated. The residue was purified by flash column chromatography over silica gel eluted with hexane/ethyl acetate 20:1 to yield A60.1 (807 mg, 75%). $^1$H NMR (400 MHz): δ 7.40-7.25 (m, 2H), 7.10-7.00 (m, 1H), 3.90, (s, 3H), 0.24 (s, 9H).

A60.2: 1-chloro-4-ethynyl-2-methoxybenzene

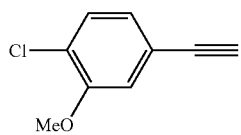

A60.1 (807 mg, 3.38 mmol) was dissolved in anhydrous THF (35 mL) and cooled in an ice bath. Tetra N-butylammonium fluoride 1 M solution in THF (4 mL, 4 mmol) was added and the reaction allowed to warm to room temperature and stirred for an additional 20 min. The reaction mixture was concentrated and diluted in 100 mL of ethyl acetate. The organic layer was washed with water (50 mL) and brine (50 mL), dried over potassium carbonate, filtered and concentrated under reduced pressure to yield A60.2 (686 mg, 82%). $^1$H NMR (400 MHz): δ 7.30-6.90 (complex multiplet, 3H), 3.80 (s, 3H).

TABLE A2

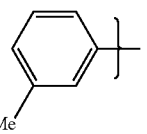

| Ex. | R | Name | HPLC Retention (min) | MS Reported |
|---|---|---|---|---|
| A53 | 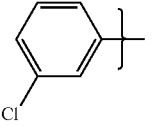 | N,1-dimethyl-7-(3-methylphenyl)-imidazo[4,5-d]pyrrolo[2,3-b]pyridin-4-amine,1,6-dihydro- | 292.21 | 1.542 |
| A54 | 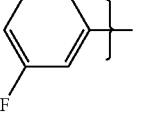 | 7-(3-chlorophenyl)-1,6-dihydro-N,1-dimethyl-imidazo[4,5-d]pyrrolo[2,3-b]pyridin-4-amine | 312.24 | 1.590 |
| A55 | 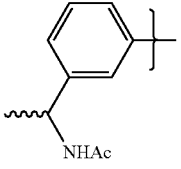 | 7-(3-fluorophenyl)-1,6-dihydro-N,1-dimethyl-imidazo[4,5-d]pyrrolo[2,3-b]pyridin-4-amine | 296.25 | 1.433 |
| A56 | 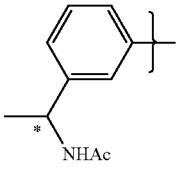 | Racemic N-[1-[3-[1,6-dihydro-1-methyl-4-(methylamino)imidazo[4,5-d]pyrrolo[2,3-b]pyridin-7-yl]phenyl]ethyl]acetamide | 363.34 | 1.333 |
| A57 | 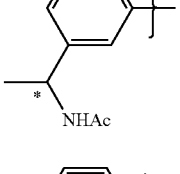 | N-[1-[3-[1,6-dihydro-1-methyl-4-(methylamino)imidazo[4,5-d]pyrrolo[2,3-b]pyridin-7-yl]phenyl]ethyl]acetamide, Faster eluting Enantiomer A | 9.91$^a$ | |
| A58 | 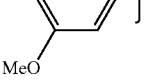 | N-[1-[3-[1,6-dihydro-1-methyl-4-(methylamino)imidazo[4,5-d]pyrrolo[2,3-b]pyridin-7-yl]phenyl]ethyl]acetamide, Slower eluting Enantiomer B | 13.43$^a$ | |
| A59 | | 1,6-dihydro-7-(3-methoxyphenyl)-N,1-dimethyl-imidazo[4,5-d]pyrrolo[2,3-b]pyridin-4-amine | 308.28 | 1.435 |

TABLE A2-continued

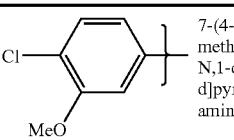

| Ex. | R | Name | HPLC Retention (min) | MS Reported |
|---|---|---|---|---|
| A60 | 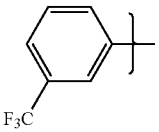 Cl—[ring]—MeO | 7-(4-chloro-3-methoxyphenyl)-1,6-dihydro-N,1-dimethyl-imidazo[4,5-d]pyrrolo[2,3-b]pyridin-4-amine | 342.27 | 1.647 |
| A61 | 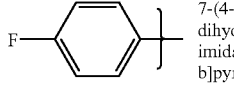 F₃C | 1,6-dihydro-N,1-dimethyl-7-[3-(trifluoromethyl)phenyl]-imidazo[4,5-d]pyrrolo[2,3-b]pyridin-4-amine | 346.28 | 1.682 |
| A62 | F—[ring] | 7-(4-fluorophenyl)-1,6-dihydro-N,1-dimethyl-imidazo[4,5-d]pyrrolo[2,3-b]pyridin-4-amine | 296.25 | 1.415 |
| A63 | MeO—[ring] | 1,6-dihydro-7-(4-methoxyphenyl)-N,1-dimethyl-imidazo[4,5-d]pyrrolo[2,3-b]pyridin-4-amine | 308.28 | 2.380 |
| A64 | Cl—[ring] | 7-(4-fluorophenyl)-1,6-dihydro-N,1-dimethyl-imidazo[4,5-d]pyrrolo[2,3-b]pyridin-4-amine | 312.27 | 1.557 |

[a]Chiralpak AD® 4.6 × 250 mm, using hexane/methanol/isopropanol 84:8:8 with a flow rate of 1 mL/min.

Alternate Preparation of A56 and A57

A56.1a: N-(1-(3-bromophenyl)ethyl)acetamide

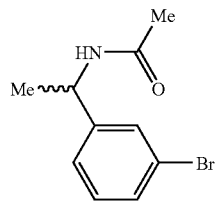

A56.1a

A solution of A56.1 (1.0 g, 5 mmol) and triethylamine (576 mg, 5.63 mmol) in dichloromethane (30 mL) at 0-5° C. was added acetyl chloride (576 mg, 5.7 mmol) and the reaction mixture was stirred at 0-5° C. for 10 minutes, then at room temperature for 10 minutes. The reaction mixture was washed with saturated NaHCO₃ solution (15 ml), water (15 ml), then brine (15 ml) and the organic layer dried over magnesium sulfate. The mixture was filtered and the solution was concentrated under reduced pressure to yield A56.1a (1.125 g, 93%). HPLC: 68%, retention time: 2.448 minute (condition B). LC/MS (M+H)⁺=244.08, ¹H-NMR (60775-143)

A56.1b: N-(1-(3-ethynylphenyl)ethyl)acetamide

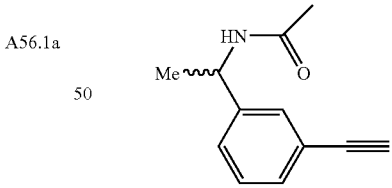

A56.1b

A solution of A56.1a (1.125 g, 4.65 mmol), (trimethylsilyl)acetylene (1.1 ml, 7.7 mmol), Palladium(II)acetate (348 mg, 0.465 mmol) and triethylamine (15 ml) in toluene (15 ml) was degassed by bubbling nitrogen through the solution then stirred at 95° C. for 30 minutes. The solution was filtered and concentrated under reduced pressure. The residue was purified by silica gel column chromatography with ethyl acetate to yield the TMS acetylene intermediate. The product was dissolved in THF (15 ml) at 0-5° C. which was added Bu₄NF (2 ml, 1M in THF) and the reaction mixture was stirred for 10 minutes. The reaction mixture was concentrated and diluted with EtOAc (50 ml). The organic phase was washed with water (20 ml), brine (20 ml) and the organic layer dried over magnesium sulfate. Filtration and concentration under reduced pressure to yield a crude product which was purified by silica gel column chromatography with Hexanes/EtOAc (3/7 to 100% EtOAc) to yield A56.1b (345 mg, 40%). HPLC: 71%, retention time: 2.198 minute (condition B). LC/MS (M+H)+=188.15.

A56.1c: tert-butyl 7-((3-(1-acetamidoethyl)phenyl)ethynyl)-6-amino-1-methyl-1H-imidazo[4,5-c]pyridin-4-yl(methyl)carbamate

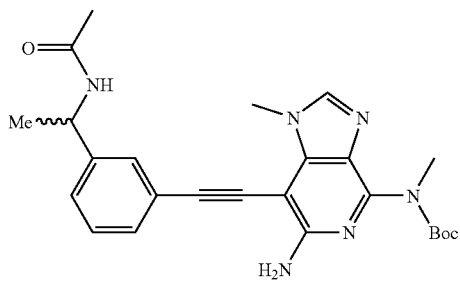

A56.1c

A solution of A1.12 (2.0 g, 4.96 mmol), A56.1b (1.38 g, 7.37 mmol), dichlorobis(triphenylphosphine)palladium(II) (208 mg, 0.296 mmol) and triethylamine (20 ml) in DMF (14 mL) was degassed by bubbling nitrogen through the solvent and was then stirred at 90° C. for 50 minutes. The reaction mixture was concentrated and diluted with CH$_2$Cl$_2$ (200 ml). The organic phase was washed with a saturated NaHCO$_3$ solution (50 ml), the with brine (50 ml) and the separated organic layer was dried over magnesium sulfate. The mixture was filtered and the solvent removed under reduced pressure. The residue was purified on silica gel column with EtOAc/MeOH/NH$_4$OH (200/10/1) to yield A56.1c (844 mg, 37%). HPLC: 96%, retention time: 2.753 minute (condition A). LC/MS (M+H)+=463.2.

A56.1d: N-[1-[3-[1,6-dihydro-1-methyl-4-(N-methyl-tert-butyloxycarbonylamino)imidazo[4,5-d]pyrrolo[2,3-b]pyridin-7-yl]phenyl]ethyl]acetamide

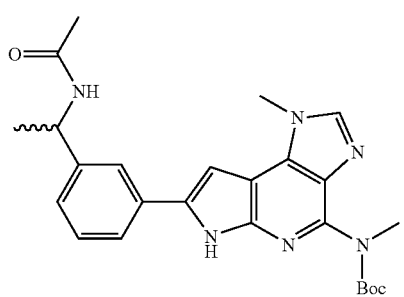

A56.1d

A56.1c (844 mg, 1.83 mmol) was dissolved in dimethylacemide (10 ml). Potassium tert-butoxide (2.6 ml, 1M in THF) was added and the reaction mixture was heated at 80° C. for 50 minutes. The reaction mixture was cooled to room temperature, concentrated and the residue purified on silica gel column with EtOAc/MeOH/NH4OH (200/15/1) to yield A56.1d (648 mg, 77%). HPLC: 96%, retention time: 2.572 minute (condition A). LC/MS (M+H)+=463.3.

A56.1e: Chiral Separation of A56.1d

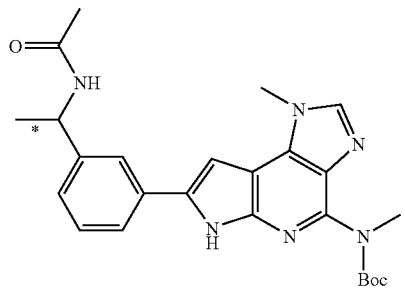

A56.1e

Faster eluting

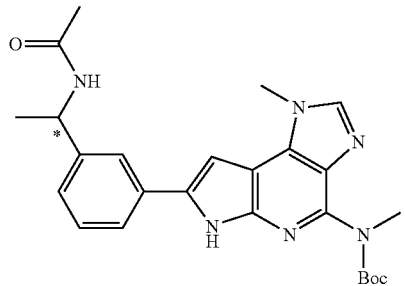

A56.1f

Slower eluting

Compound A56.1d (100 mg, 0.216 mmol) was subjected to chiral separation to yield A56.1e (29.4 mg, 59%). HPLC: >98%, retention time: 2.565 minute (Condition A). Chiral HPLC: 100% ee. retention time: 9.913 minute (condition D). LC/MS (M+H)+=463.3, $^1$H-NMR (400 MHz, CD$_3$OD) δ ppm 8.03 (1 H, s), 7.77 (1 H, s), 7.70 (1 H, d, J=8.14 Hz), 7.37 (1 H, t, J=7.63 Hz), 7.24 (1 H, d, J=7.63 Hz), 7.19 (1 H, s), 5.01 (1 H, q, J=6.95 Hz), 4.13 (3 H, s), 3.32 (3 H, s), 1.93 (3 H, s), 1.45 (3 H, d, J=7.12 Hz), 1.31 (9 H, s), 1.08 (3 H, d, J=6.10 Hz), and A56.1f (30.1 mg, 60%). HPLC: >98%, retention time: 2.577 minute (condition A). Chiral HPLC: 98.4% ee. retention time: 13.427 minute (condition D). LC/MS (M+H)+=463.3, $^1$H-NMR (400 MHz, CD$_3$OD) δ ppm 8.03 (1 H, s), 7.77 (1 H, s), 7.70 (1 H, d, J=8.14 Hz), 7.37 (1 H, t, J=7.88 Hz), 7.24 (1 H, d, J=7.63 Hz), 7.19 (1 H, s), 5.01 (1 H, d, J=7.12 Hz), 4.13 (3 H, s), 3.32 (3 H, s), 1.93 (3 H, s), 1.45 (3 H, d, J=7.12 Hz), 1.31 (9 H, s), 1.08 (3 H, d, J=6.10 Hz).

Example A56

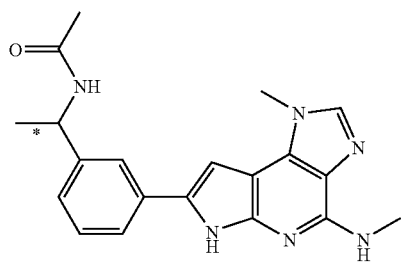

faster eluting enantiomer

A56.1e (29 mg, 0.063 mmol) was dissolved in MeOH (0.5 ml) and 4N HCl in dioxane (1 ml) was added. The reaction mixture was heated at 50° C. for 90 minutes. The mixture was cooled to RT and Et₂O (2 ml) was added and the resulting mixture stirred for 10 minutes. The solid was collected and dried to provide A56 (23.7 mg, 95%). HPLC: >98%, retention time: 1.957 minute (Condition A). Chiral HPLC: >98% ee. retention time: 5.25 minute (condition E). LC/MS (M+H)⁺=363.3, ¹H-NMR (400 MHz, CD₃OD) δ ppm 8.12 (1 H, s), 7.61 (1 H, s), 7.55 (1 H, d, J=7.63 Hz), 7.35 (1 H, t, J=7.88 Hz), 7.23 (1 H, d, J=7.63 Hz), 4.92-5.00 (1 H, m), 4.08 (3 H, s), 3.18 (3 H, s), 1.90 (3 H, s), 1.41 (3 H, d, J=7.12 Hz).

A57

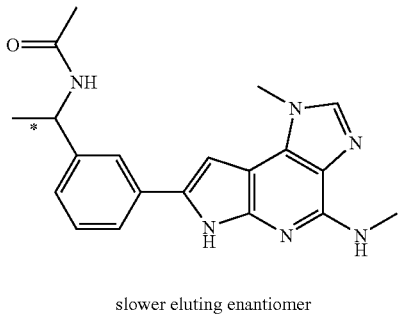

slower eluting enantiomer

A56.1f (30 mg, 0.065 mmol) was dissolved in MeOH (0.5 ml) and 4N HCl in dioxane (1 ml) was added. The reaction mixture was heated at 50° C. for 90 minutes. The reaction mixture was cooled to RT and Et₂O (2 ml) was added. The reaction mixture was stirred for 10 minutes. The solid was collected and dried to provide A57 (23.1 mg, 89%). HPLC: >98%, retention time: 1.975 minute (Condition A). Chiral HPLC: 92% ee. retention time: 7.26 minute (condition E). LC/MS (M+H)⁺=363.3, ¹H-NMR (400 MHz, CD₃OD) δ ppm 7.61 (1 H, s), 7.55 (1 H, d, J=7.63 Hz), 7.35 (1 H, t, J=7.88 Hz), 7.23 (1 H, d, J=7.63 Hz), 7.10 (1 H, s), 6.06 (1 H, s), 4.96 (1 H, d, J=7.12 Hz), 4.08 (3 H, s), 3.18 (3 H, s), 1.90 (3 H, s), 1.41 (3 H, d, J=7.12 Hz).

Example A65

1,6-dihydro-1-methyl-4-(methylamino)-7-phenyl-methyl ester imidazo[4,5-d]pyrrolo[2,3-b]pyridine-8-carboxylic acid

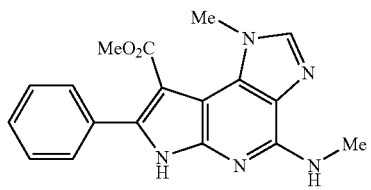

A1.13 (97 mg, 0.26 mmol), sodium acetate (70 mg, 0.51 mmol), potassium carbonate (71 mg, 0.50 mmol) and copper (II) chloride dihydrate (131 mg, 0.77 mmol) were added to anhydrous methanol (6.5 mL) and degassed by purging with nitrogen. Palladium chloride (5.3 mg, 0.03 mmol) was added and the reaction was placed in a stainless steel bomb and pressurized to 20 psi with carbon monoxide. The reaction was heated to 60° C. for 16 h. The reaction was allowed to cool to room temperature, evacuated to remove carbon monoxide and brought to atmospheric pressure by the addition of air. The solvent was removed under reduced pressure. The residue was treated with saturated ammonium chloride solution (5 mL) and concentrated ammonium hydroxide (5 mL), and extracted with chloroform (3×25 mL). The combined organic layers were dried over magnesium sulfate, filtered and concentrated under reduced pressure. The crude product was purified by preparative HPLC to yield 1,6-dihydro-N, 1-dimethyl-N-t-butyloxycarbonyl-7-phenyl imidazo[4,5-d]pyrrolo[2,3-b]pyridin-4-amine. The BOC protected product was dissolved in trifluoroacetic acid (2 mL) stirred for 20 minutes and concentrated under reduced pressure to yield A65 (42 mg, 37%). M+H+=336.26. ¹H NMR (400 MHz) MEOD δ 8.15 (s, 1 H), 7.66 (t, J=2.5 Hz, 2 H), 7.46 (s, 3 H), 4.24 (s, 1.5H), 3.92 (s, 1.5H), 3.29 (s, 3H).

Example A66

N-[[3-[1,6-dihydro-1-methyl-4-(methylamino)imidazo[4,5-d]pyrrolo[2,3-b]pyridin-7-yl]phenyl]methyl]urea

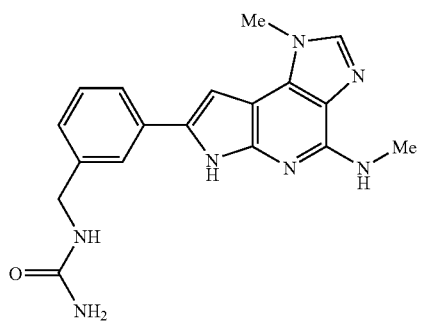

A3.1 (21 mg, 0.05 mmol) was dissolved in dichloromethane (1 mL). Trimethylsilylisocyanate (13.5 μL, 0.1 mmol) was added and the reaction mixture heated to 60° C. for 30 minutes. The reaction mixture was allowed to cool to room temperature then trifluoroacetic acid (0.5 mL) was added and the mixture was stirred for 0.5 h. The solvent was removed under reduced pressure and the product purified by preparatory reverse phase HPLC to yield A66 (7.8 mg, 33%). M+H+=350.35. ¹H NMR (400 MHz) DMSO δ 11.90 (s, 1H), 8.20 (s, 1H). 7.8-7.70 (m, 2H), 7.40-7.30 (t, 1H), 7.18-7.08 (m, 2H), 6.43 (br s, 1H), 4.20 (d, 2H), 4.09 (s, 3H), 3.05 (s, 3H).

Example A67

N-[[3-[1,6-dihydro-1-methyl-4-(methylamino)imidazo[4,5-d]pyrrolo[2,3-b]pyridin-7-yl]phenyl]methyl]guanidine

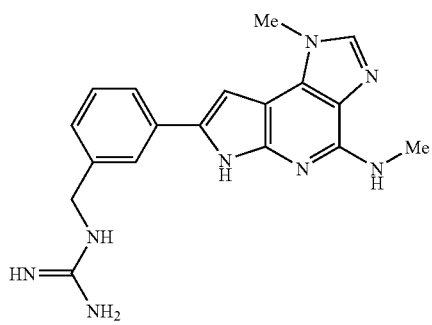

A3.1 (21 mg, 0.05 mmol), and 1,3-bis(t-butoxycarbonyl)-1-methyl-2-thiopseudourea were dissolved in DMF (0.5 mL).

Triethylamine (21 μL, 0.053 mmol) and mercuric chloride (15 mg, 0.055 mmol) were added and the reaction mixture allowed to stir at room temperature for 16 h. The reaction mixture was diluted with 10 mL of ethyl acetate. The solids were removed by filtration and the filtrate evaporated under reduced pressure. The residue was purified on preparatory reverse phase HPLC to yield the boc-protected intermediate N-[[3-[1,6-dihydro-1-methyl-4-(N-tbutyloxycarbonyl-N-methylamino)imidazo[4,5-d]pyrrolo[2,3-b]pyridin-7-yl]phenyl]methyl]guanidine. The solid was dissolved in methylene chloride (0.5 mL). Trifluoroacetic acid (0.5 mL) was added and the reaction mixture stirred for 0.5 h. The solvent was evaporated under reduced pressure to provide A67 (17 mg, 59%). M+H+=349.34. $^1$H NMR (400 MHz) MEOD δ 8.2 (s, 1H), 7.82-7.78 (m, 2H), 7.50 (t, 1H), 7.3 (d, 1H), 7.22 (s, 1H), 4.51 (s, 2H), 4.18 (s, 3H). 3.33 (s, 3H).

Example A68

7-[3-(aminomethyl)phenyl]-1,6-dihydro-1-methyl-imidazo[4,5-d]pyrrolo[2,3-b]pyridin-4-amine

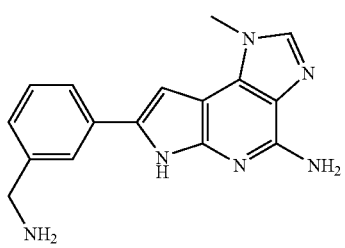

A68

A68.1: N-(4-methoxybenzyl)-6-chloro-1-methyl-1H-imidazo[4,5-c]pyridin-4-amine

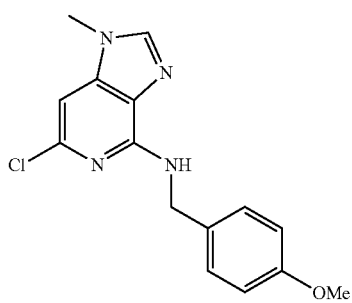

A68.1

A1.5 (17.6 g, 87.6 mmol) and paramethoxybenzyl amine (40 mL) were heated at 110° C. for 4 hours. The reaction mixture was cooled to room temperature and quenched with water. The product precipitated and was collected by filtration and air dried to yield A68.1 (24.6 g, 93%) M+H+=305.25, 305.24.

A68.2: tert-butyl 4-methoxybenzyl(6-chloro-1-methyl-1H-imidazo[4,5-c]pyridin-4-yl)carbamate

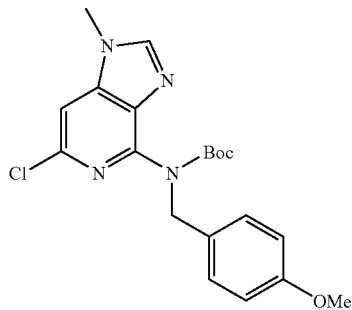

A68.2

A68.1 (5.0 g, 16.6 mmol) was dissolved in THF (300 mL) and cooled to −78° C. Sodium bis(trimethylsilyl)amide 1M in THF (21 mL, 21 mmol) was added over 2 min and allowed to stir at −78° C. for 25 min. Ditertbutyldicarbonate (4.0 g, 18.3 mmol) was added and the reaction mixture was allowed to warm to room temperature and stirred overnight. The solvent was removed under reduced pressure and the residue partitioned between ethyl acetate and water. The organic layer was washed twice with water, separated, dried over magnesium sulfate, filtered and evaporated under reduced pressure. The crude product was purified by flash silica gel column chromatography (ethyl acetate/hexane (1:1) to 100% ethyl acetate) to yield A68.2 (6.4 g, 96%). LCMS: ret time=1.83 min., M+H$^+$=303.23

A68.3: tert-butyl 4-methoxybenzyl(6-(diphenylmethyleneamino)-1-methyl-1H-imidazo[4,5-c]pyridin-4-yl)carbamate

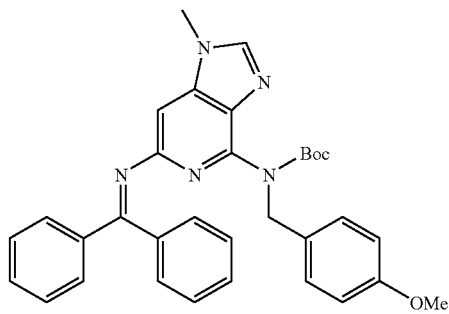

A68.3

A68.2 (6.4 g, 15.9 mmol), benzophenone imine (3.45 g, 19.1 mmol), tris(dibenzylidineacetone)dipalladium (0) (292 mg, 0.32 mmol), Xanthphos® (276 mg 0.48 mmool) and desium carbonate (7.24 g, 22.3 mmol) were added to anhydrous 1,4-dioxane (40 mL). The reaction mixture was heated at 90° C. overnight, allowed to cool to room temperature and the solvent removed under reduced pressure. The residue was partitioned between water and ethyl acetate, and the organic layer was washed twice with water. The organic layer was separated, dried over magnesium sulfate, filtered and the solvent removed under reduced pressure. The residue was purified by flash silica gel column chromatography (ethyl acetate/hexane (1:1) to 100% ethyl acetate) to yield A68.3 (6.78 g, 78%). Electrospray MS: M+H$^+$=548.20.

A68.4: tert-butyl 4-methoxybenzyl(6-amino-1-methyl-1H-imidazo[4,5-c]pyridin-4-yl)carbamate

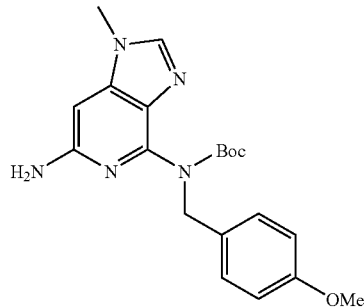

A68.3 (100 mg, 0.18 mmol) was dissolved in anhydrous THF (0.6 mL) and aqueous 1 M HCl (0.4 mL) was added and the reaction mixture was stirred for 2 min. 1 M NaOH (0.8 mL) was added and the reaction mixture was extracted with ethyl acetate. The organic layer was separated, dried over magnesium sulfate, filtered and the solvent removed under reduced pressure. The residue was dried under vacuum for ~1 h and triturated four times with diethyl ether. The residue was dried under vacuum to yield A68.4 (42 mg, 60%). LCMS: ret time=1.48 min., M+H$^+$=384.28, 284.23 (100%, M+H+—Boc). The reaction was repeated on a larger scale using essentially the same procedure. Thus A68.3 (7.18 g, 13.1 mmol) reacted in a similar manner to that described above yielded A68.4 (4.09 g, 81%).

A68.5: tert-butyl 4-methoxybenzyl(6-amino-7-iodo-1-methyl-1H-imidazo[4,5-c]pyridin-4-yl)carbamate

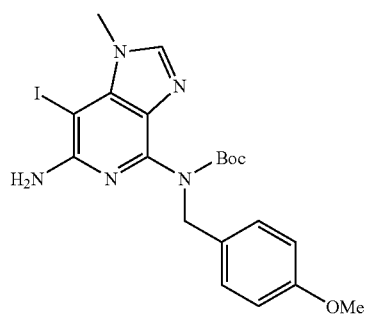

A68.4 (4.07 g, 10.6 mmol) was dissolved in anhydrous acetonitrile (200 mL) and N-iodosuccinimide (2.65 g, 11.3 mmol) was added in one portion. The reaction mixture was stirred for 0.5 h, at which point additional N-iodosuccinimide (200 mg) was added the reaction was stirred for an additional 0.5 h at which point a second addition of N-iodosuccinimide (200 mg) was added and the reaction and stirred for an additional 0.5 h. The solvent was evaporated and the residue was purified by flash silica gel column chromatography, ethyl acetate/hexane 1:1 to ethyl acetate/hexane 2:1, to yield A68.5 (3.72 g, 69%). Electrospray M+H$^+$=510.02.

A68.6: tert-butyl 4-methoxybenzyl(6-amino-7-(2-(3-cyanophenyl)ethynyl)-1-methyl-1H-imidazo[4,5-c]pyridin-4-yl)carbamate

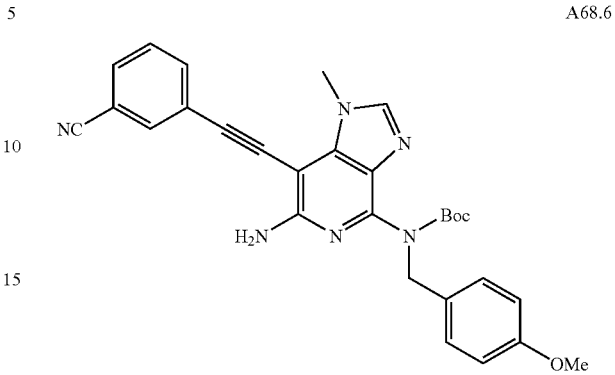

A68.5 (1.0 g, 1.96 mmol), and A2.2 (0.5 g, 3.93 mmol), were added to a mixture of triethylamine (9 mL) and N,N-dimethylformamide (7 mL) and nitrogen bubbled through the mixture. Dichlorobis(triphenylphosphine)palladium (84 mg, 0.12 mmol) was added and the reaction was heated at 90° C. for 4 h. The mixture was allowed to cool to room temperature and the volatiles removed under reduced pressure. The residue was purified by flash silica gel column chromatography eluting with hexane/ethyl acetate 1:1 to yield A68.6 (647 mg, 65%). LCMS: ret time=1.74 min., M+H$^+$=509.31, 409.28 (100%, M+H+—Boc).

A68.7: 3-[1,6-dihydro-1-methyl-4-(N-tert-butyloxycarbonyl-N-(4-methoxyphenylmethyl)amino)imidazo[4,5-d]pyrrolo[2,3-b]pyridin-7-yl]benzonitrile

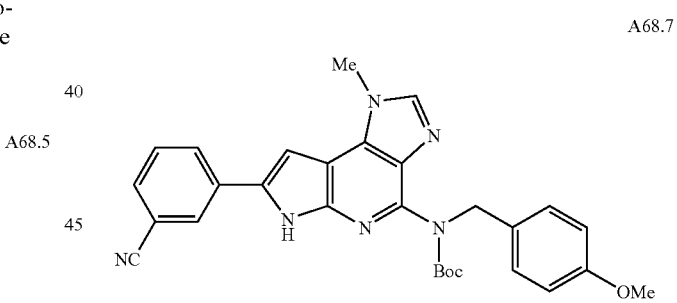

Potassium t-butoxide (172 mg, 1.54 mmol) was dissolved in DMSO (9 mL). A68.6 (623 mg, 1.23 mmol) was dissolved in DMSO (9 ML) and added dropwise to the potassium tert-butoxide solution. After the addition was complete the reaction mixture was heated to 80° C. for 3 h. Additional potassium t-butoxide (100 mg) was added and the reaction heated for an additional 10 min. At which point TLC indicated complete consumption of A68.6. The reaction mixture was allowed to cool to room temperature and diluted with water. The precipitate was filtered under vacuum overnight, during which time the filtrate had evaporated. The filter cake was washed into the filter flask by addition of methanol and the solution collected and evaporated under reduced pressure. The residue was purified by flash silica gel column chromatography eluting with hexane/ethyl acetate 1:1 to yield A68.7 (350 mg, 56%). LCMS: ret time=1.75 min., M+H$^+$=509.31, 409.28 (100%, M+H+—Boc). $^1$H NMR 400 mHz, CDCl$_3$ δ

9.52 (br s, 1H), 7.90, (s, 1H), 7.78-7.72 (m, 1H) 7.66 (s, 1H), 7.60-7.50 (m, 2H), 7.44 (apparent d, 2H), 6.92 (s, 1H), 6.72 (apparent d, 2H).

A68.8: 3-[1,6-dihydro-1-methyl-4-(N-tert-butyloxycarbonyl-N-(4-methoxyphenylmethyl)amino)imidazo[4,5-d]pyrrolo[2,3-b]pyridin-7-yl]benzylamine

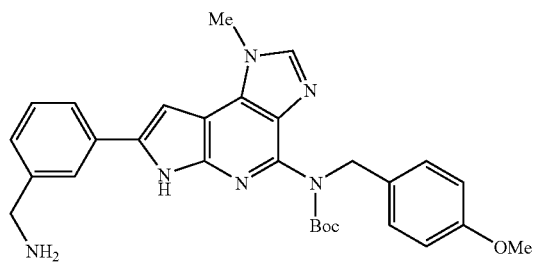

A68.7 (30 mg, 0.06 mmol) was dissolved in 95% ethanol (2 mL). A portion of Raney nickel was washed with ethanol (20 mL). A small spatula full was added and the reaction mixture saturated with ammonia (gas) and a balloon of hydrogen was attached to the reaction vessel. The reaction was complete after 2 h. The mixture was filtered though celite and evaporated under reduced pressure to yield A68.8 (46 mg, 150%). LCMS ret time=1.49 min., M+H$^+$=513.25, 413.26 (100%, M+H+—Boc). The material was used without further purification in the next step.

A68.9: 7-[3-(aminomethyl)phenyl]-1,6-dihydro-1-methyl-imidazo[4,5-d]pyrrolo[2,3-b]pyridin-4-amine A68.8 (46 mg from above) was dissolved in a mixture of trifluoroacetic acid and methylene chloride (1:1, 5 mL) and allowed to stir at room temperature in an open flask overnight. The solvent was evaporated under reduced pressure and dried under vacuum, and the residue was taken up in diethyl ether, which provided a tan solid (40 mg). The solid was taken up in methanol and silica gel was added and the solvent removed under reduced pressure. The silica gel from above was placed on top of additional silica gel and the product eluted with a mixture of methylene chloride/methanol/conc. ammonium hydroxide (100:10:1) to provide 13.3 mg (76% over two steps). LCMS: ret time=0.95 min., M+H$^+$=293.21.

Example A69

N-[[3-(4-Amino-1,6-dihydro-1-methylimidazo[4,5-d]pyrrolo[2,3-b]pyridin-7-yl)phenyl]methyl]acetamide, trifluoroacetate salt

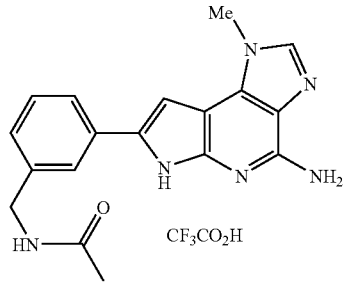

Acetic acid (5 mg, 0.073 mmol), HOBT (15 mg, 0.10 mmol), and diisopropylethylamine (0.1 mL, 0.70 mmol) were added to anhydrous acetonitrile (1 mL). EDC (28 mg, 0.14 mmol) was added and the reaction mixture stirred for 5 minutes. A68.8 (30 mg, 0.058 mmol) was added and the reaction mixture stirred over the weekend. The volatiles were removed under reduced pressure and trifluoroacetic acid (1 mL) was added and the reaction mixture was stirred at room temperature for 4 hours. The solvent was evaporated and the residue purified by preparatory reverse phase column chromatography to yield A69 as the trifluoroacetate salt (16.4 mg, 63%). LCMS: ret time=1.1 min., M+H$^+$=335.29. $^1$H NMR 400 mHz, MeOD δ: 8.15 (s, 1H), 7.76-7.68 (m, 2H), 7.70 (t, J=7.7 Hz, 1H), 7.29 (d, J=7.7 Hz, 1H), 7.20 (s, 1H), 4.49 (s, 22H), 4.16 (s, 3H), 2.04 (s, 3H).

Example A70

7-(3-Fluorophenyl)-1,6-dihydro-1-methylimidazo[4,5-d]pyrrolo[2,3-b]pyridin-4-amine

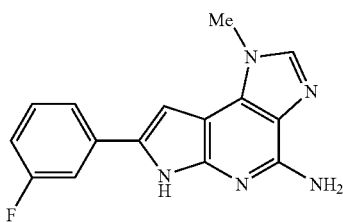

A70.1: tert-Butyl 4-methoxybenzyl(6-amino-7-(2-(3-fluorophenyl)ethynyl)-1-methyl-1H-imidazo[4,5-c]pyridin-4-yl)carbamate

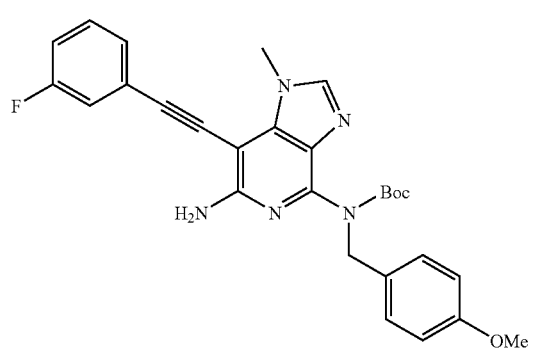

A68.5 (2.0 g, 3.9 mmol) and 3-fluorophenyl acetylene (0.95 g, 7.86 mmol) were dissolved in a mixture of triethylamine (18 mL) and methylene chloride (20 mL) and degassed by passing nitrogen through the solution. Dichlorobis(triphenylphosphine)palladium (200 mg 0.2 mmol) was added and the reaction was heated at 70° C. overnight. The volatiles were removed under reduced pressure and the residue was purified by flash silica gel column chromatography eluting with hexane/ethyl acetate 1:1 to yield A70.1 (1.61 g, 81%). LCMS ret time=1.86 min., M+H$^+$=504.32, 404.32 (100%, M+H+—Boc). $^1$H NMR 400 mHz, CDCl$_3$ δ: 8.30-8.10 (br s, 2H), 7.60 (s, 1H), 7.38-7.26 (m, 4H), 7.26 (d, 1H), 7.08 (t, 1H), 7.66 (d, 2H), 5.04 (s, 2H), 4.04 (s, 3H), 3.74 (s, 3H), 1.40 (s, 9H).

A70.2: 7-(3-Fluorophenyl)-1,6-dihydro-1-methylimi-
dazo[4,5-d]pyrrolo[2,3-b]pyridin-4-(N-(4-methox-
yphenylmethyl)-N-tert-butyloxycarbonylamine A71.1: 7-(3-Fluorophenyl)-1,6-dihydro-1-methyl-8-
chloro-imidazo[4,5-d]pyrrolo[2,3-b]pyridin-4-(N-(4-
methoxyphenylmethyl)-N-tert-butyloxycarbony-
lamine

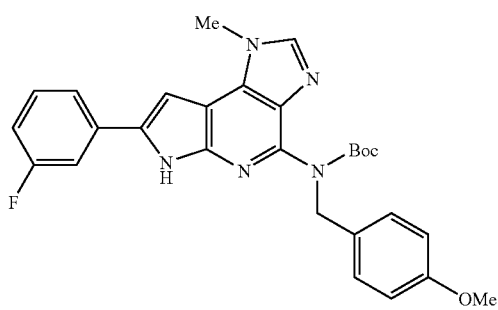

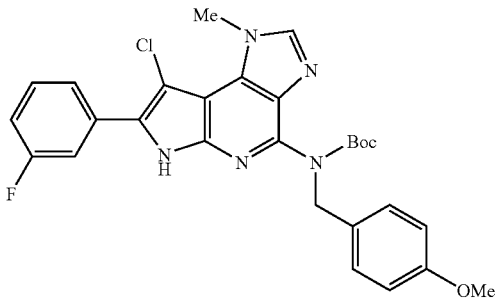

A70.1 (1.61 g, 3.22 mmol) was prepared in a manner similar to that described in step A68.7 to provide A70.2 (0.75 g, 47%). LCMS ret time=1.88 min, M+H$^+$=502.24, 402.24 (100%, M+H+—Boc).

A70.3: 7-(3-Fluorophenyl)-1,6-dihydro-1-methylimi-
dazo[4,5-d]pyrrolo[2,3-b]pyridin-4-amine Trifluoroacetic acid (1.2 mL) was added to a mixture of A70.2 (100 mg, 0.20 mmol) and anisole (0.43 mL). The reaction was stirred overnight at room temperature. The volatiles were removed under reduced pressure and the solid triturated with diethyl ether. The solid was recrystallized from methanol to yield A70 (11 mg, 20%) as the trifluoroacetate salt. LCMS ret time=1.39 min., M+H$^+$=282.23, $^1$H NMR 500 mHz, CD$_3$OD δ: 8.09 (s, 1H), 7.56 (d, 1H), 7.48 (d, 1H), 7.42 (t, 1H), 7.21 (s, 1H), 7.02 (t, 1H), 4.10 (s, 3H).

Example A71

8-chloro-7-(3-fluorophenyl)-1,6-dihydro-1-meth-
ylimidazo[4,5-d]pyrrolo[2,3-b]pyridin-4-amine, trif-
luoroacetate salt A70.2 (100 mg, 0.20 mmol) and N-chlorosuccinimide (27 mg, 0.2 mmol) were dissolved in anhydrous acetonitrile and heated to 100° C. in a sealed vial for 30 min. The reaction mixture was allowed to cool to room temperature during which time the product precipitated. A71.1 (57 mg, 53%) was collected as a white solid. LCMS ret time=1.98 min M+H$^+$=536.27, 436.27 (100%, M+H+—Boc). $^1$H NMR 500 mHz, CD$_3$OD δ: 8.06 (s, 1H). 7.68 (d, J=8 Hz, 1H), 7.65 (d, J=9 Hz, 1H), 7.54-7.46 (m, apparent d of d, 1H), 7.27 (d, J=9 Hz, 2H), 7.18-7.12 (m, apparent t, 1H), 6.72 (d, J=8 Hz, 2H), 5.02 (s, 2H), 4.30 (s, 3H), 3.68 (s, 3H), 1.36 (s, 9H).

A71.2: 8-chloro-7-(3-fluorophenyl)-1,6-dihydro-1-
methylimidazo[4,5-d]pyrrolo[2,3-b]pyridin-4-amine
trifluoroacetate salt Trifluoroacetic acid (1 mL) was added to a mixture of A71.1 (57 mg, 0.11 mmol) and anisole (0.25 mL) and stirred at room temperature overnight. The volatiles were removed under reduced pressure and the solid triturated with diethyl ether and dried to yield A71 (40 mg, 87%). LCMS ret time=1.70 min, M+H+=316.15

Example A72

3-(1-Methyl-4-methylamino-1,6-dihydro-1,3,5,6-
tetraaza-as-indacen-7-yl)-benzoic acid

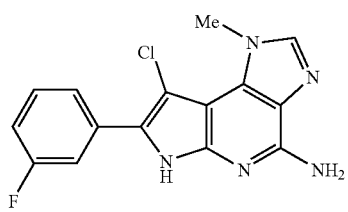

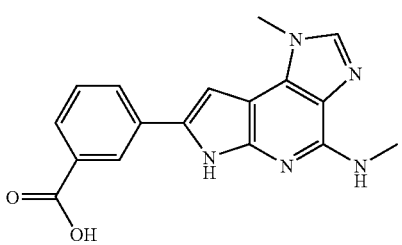

A72.1: 3-[6-Amino-4-(tert-butoxycarbonyl-methyl-amino)-1-methyl-1H-imidazo[4,5-c]pyridin-7-yl-ethynyl]-benzoic acid tert-butyl ester

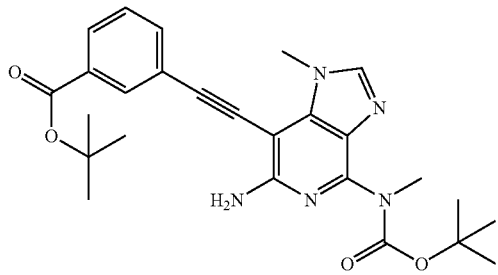

A72.1

Dichlorobis(triphenylphosphine)palladium (104 mg, 0.145 mmol) was added in one portion to a mixture of A1.12 (1.0 g, 2.48 mmol), 3-ethynyl-benzoic acid tert-butyl ester (753 mg, 3.72 mmol) and triethylamine (10 ml) in DMF (7.0 ml) at room temperature under a nitrogen atmosphere. The resulting mixture was heated to 90° C. for 50 min before cooling to room temperature and evaporating in vacuo. The residue was purified by column chromatography using ethyl acetate:hexane as eluent to give 765 mg (65%) of A72.1. Found: M+H=478.21

A72: 3-(1-Methyl-4-methylamino-1,6-dihydro-1,3,5,6-tetraaza-as-indacen-7-yl)-benzoic acid

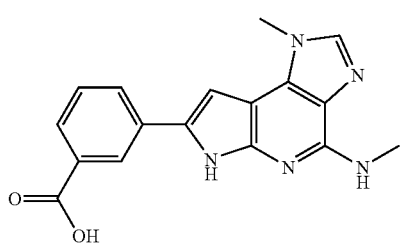

A72

Potssium tert-butoxide (1M in THF, 1.70 ml, 1.70 mmol) was added dropwise to a solution of A72.1 (765.0 mg, 1.60 mmol) in DMA (8.0 ml) under a nitrogen atmosphere. The resulting mixture was heated to 80 C for 20 min before cooling to room temperature, and evaporating in vacuo. The residue was immediately dissolved in TFA and allowed to stir at room temperature for 16 hrs before evaporating in vacuo. MeOH was added to the residue and the mixture stirred at RT for 5 min before collecting the precipitated solid by vacuum filtatrion to provide A72 (210 mg). A portion (15 mg) of this material was further purified by preparative HPLC to provide A72 (3.0 mg) as an off-white solid. LC/MS Phenomenex S5 4.6×30 mm (2 min gradient) Found: M+H$^+$=322.26 at 1.387 min.

Example A73

N-Cyclopropyl-3-(1-methyl-4-methylamino-1,6-dihydro-1,3,5,6-tetraaza-as-indacen-7-yl)-benzamide

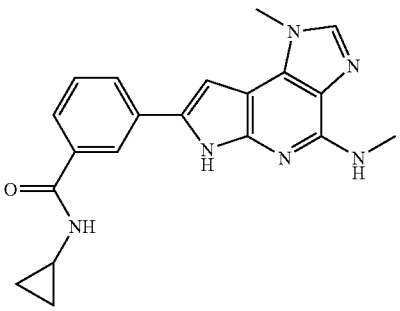

A73

BOP-Cl (85 mg, 0.336 mmol) was added in one portion to a solution of A72 (18.0 mg, 0.056 mmol), cyclopropylamine (7.76 μL, 0.112 mmol) and triethylamine (47 μL, 0.336 mmol) in DMF (0.5 ml) at 0 C under a nitrogen atmosphere. The resulting mixture was warmed to room temperature and stirred for 25 min before evaporating in vacuo and purifying by preparative HPLC to provide A73 (4.0 mg) as an off-white solid. LC/MS Phenomenex S5 4.6×30 mm (2 min gradient) Found: M+H$^+$=361.34 at 1.370 min.

Example A74

[3-(1-Methyl-4-methylamino-1,6-dihydro-1,3,5,6-tetraaza-as-indacen-7-yl)-phenyl]-morpholin-4-yl-methanone

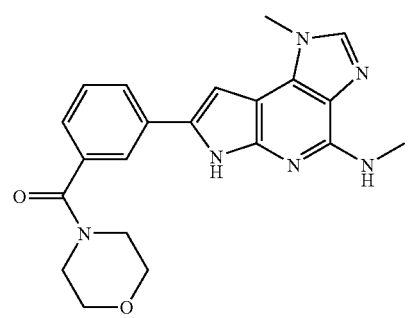

A74

BOP-Cl (85 mg, 0.336 mmol) was added in one portion to a solution of A72 (18.0 mg, 0.056 mmol), morpholine (9.8 μL, 0.112 mmol) and triethylamine (47 μL, 0.336 mmol) in DMF (0.5 ml) at 0 C under a nitrogen atmosphere. The resulting mixture was warmed to room temperature and stirred for 25 min before evaporating in vacuo and purifying by preparative HPLC to provide A74 (10.4.0 mg) as an off-white solid. LC/MS Phenomenex S5 4.6×30 mm (2 min gradient) Found: M+H$^+$=391.25 at 1.295 min.

Example A75

7-(3-bromophenyl)-1,6-dihydro-N,1-dimethyl-imidazo[4,5-d]pyrrolo[2,3-b]pyridin-4-amine

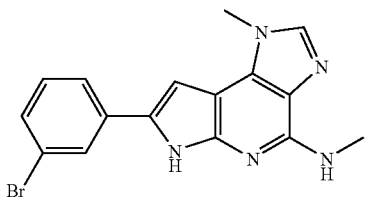

A75.1: tert-Butyl 6-amino-1-methyl-7-(2-(3-bromophenyl)ethynyl)-1H-imidazo[4,5-c]pyridin-4-yl(methyl)carbamate

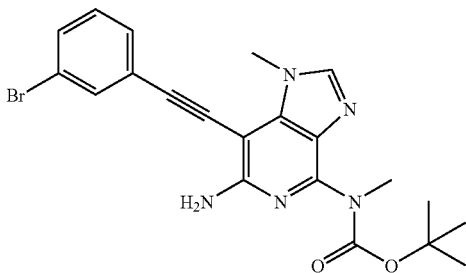

A1.12 (201 mg, 0.5 mmol), bis(triphenylphosphine)palladium dichloride (21 mg, 0.03 mmol), 3-bromophenylacetylene (113 mg, 0.65 mmol) copper iodide (4.3 mg, 0.025 mmol) and diisopropylethylamine (0.2 mL 1.5 mmol) were suspended in DMF (2.5 mL) and degassed by bubbling a stream of nitrogen through the reaction for several minutes. The reaction was then heated to 75° C. for 30 minutes and was concentrated and purified by silica gel chromatography (hexane/ethylacetate gradient) to yield A75.1. (281 mg 123%) LCMS: RT=3.47 min M+H+=458.19. The material was used in the next step without further purification.

A75.2: 7-(3-bromophenyl)-1,6-dihydro-N,1-dimethyl-1-(tertbutyloxycarbonyl)-imidazo[4,5-d]pyrrolo[2,3-b]pyridin-4-amine

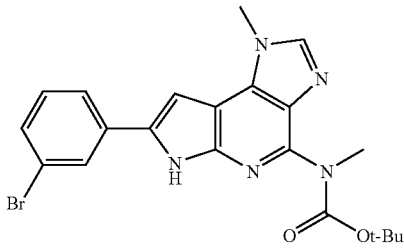

A75.1 (281 mg, 0.61 mmol) and potassium tert-butoxide (1 Molar solution in THF, 900 µL, 0.90 mmol) were dissolved in DMA (2.8 mL) and heated at 70° C. for 10 minutes. The reaction mixture was concentrated and purified by silica gel *ke chromatography (hexane/ethyl acetate gradient) to yield A75.2 (154 mg, 54%). LCMS RT=3.4 min, M+H+=458.19.

A75.3: 7-(3-bromophenyl)-1,6-dihydro-N,1-dimethyl-imidazo[4,5-d]pyrrolo[2,3-b]pyridin-4-amine A75.2 (21 mg, 46 mmol) was dissolved in a mixture of 4N HCl in dioxane (1 mL) and ethanol (1 mL). The reaction mixture was stirred at room temperature for 16 h then at 40° C. for 3 h. The solvent was evaported and the solid collected to yield A75 (6.6 mg, 40%) as the hydrochloride salt. M+H+=356.16. $^1$H NMR (400 MHz, CD$_3$OD) δ ppm 8.13 (1 H, s), 7.87 (1 H, t, J=1.78 Hz), 7.65 (1 H, d, J=8.65 Hz), 7.38 (1 H, d, J=8.65 Hz), 7.28 (1 H, t, J=7.88 Hz), 7.16 (1 H, s), 4.06 (3 H, s), 3.18 (3 H, s)

Example A76

3-[1,6-dihydro-1-methyl-4-(methylamino)imidazo[4,5-d]pyrrolo[2,3-b]pyridin-7-yl]-benzoic acid, ethyl ester

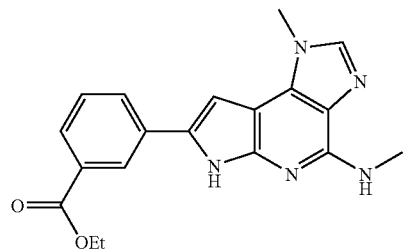

A75.2 (21 mg, 0.046 mmol), palladium acetate (2.25 mg, 0.01 mmol), and 1,3-bis(diphenylphosphino)propane (4.13 mg, 0.01 mmol) were dissolved in ethanol (~1 mL) and potassium carbonate (19 mg, 0.14 mmol) was added. The reaction mixture was placed in a sealed microwave vial and blanked with carbon monoxide. The reaction mixture was heated in a microwave apparatus for 15 minutes at 100° C. The solvent was evaporated and the residue purified on preparatory HPLC to yield the BOC protected product. The BOC protected product was dissolved in a small amount of trifluoroacetic acid and stirred at room temperature for 20 min, and concentrated to yield the crude product which was purified by preparatory thin layer chromatography (methylene chloride methanol, ammonium hydroxide 100:5:1. The appropriate band was collected and washed from the silica gel with additional solvent and evaporated to yield A76 (3.8 mg, 23%). LCMS RT=2.55 min, M+H+=350.29. NMR 400 MHz D$_3$COD: δ 8.3 s, 1H, 8.0-7.7 m, 2H, 7.4-7.2, m, 2H, 7.0 s, 1H, 4.3 q, 2H, 4.0 s, 1H, 3.0, s, 1H, 1.34 t, 3H.

TABLE A2

| Ex. | R | Name | HPLC Retention (min) | MS Reported |
|---|---|---|---|---|
| A77 | (furan-2-ylmethyl)amino | 3-[1,6-dihydro-1-methyl-4-(methylamino)imidazo[4,5-d]pyrrolo[2,3-b]pyridin-7-yl]-N-(2-furanylmethyl)-benzamide | 2.61 | 401.45 |
| A78 | (2S)-2-carbamoylpyrrolidin-1-yl | (2S)-1-[3-[1,6-dihydro-1-methyl-4-(methylamino)imidazo[4,5-d]pyrrolo[2,3-b]pyridin-7-yl]benzoyl]-2-pyrrolidinecarboxamide | 2.11 | 418.44 |
| A79 | 3-hydroxypyrrolidin-1-yl | 1-[3-[1,6-dihydro-1-methyl-4-(methylamino)imidazo[4,5-d]pyrrolo[2,3-b]pyridin-7-yl]benzoyl]-3-pyrrolidinol | 2.04 | 391.46 |
| A80 | (tetrahydrofuran-2-ylmethyl)amino | 3-[1,6-dihydro-1-methyl-4-(methylamino)imidazo[4,5-d]pyrrolo[2,3-b]pyridin-7-yl]-N-[(tetrahydro-2-furanyl)methyl]-benzamide | 2.47 | 405.48 |
| A81 | thiomorpholin-4-yl | 4-[3-[1,6-dihydro-1-methyl-4-(methylamino)imidazo[4,5-d]pyrrolo[2,3-b]pyridin-7-yl]benzoyl]-thiomorpholine | 2.58 | 407.42 |
| A82 | piperidin-1-yl | 1-[3-[1,6-dihydro-1-methyl-4-(methylamino)imidazo[4,5-d]pyrrolo[2,3-b]pyridin-7-yl]benzoyl]-piperidine | 2.72 | 389.48 |
| A83 | 3-carbamoylpiperidin-1-yl | 1-[3-[1,6-dihydro-1-methyl-4-(methylamino)imidazo[4,5-d]pyrrolo[2,3-b]pyridin-7-yl]benzoyl]-3-piperidinecarboxamide | 2.14 | 432.44 |
| A84 | 4-hydroxypiperidin-1-yl | 1-[3-[1,6-dihydro-1-methyl-4-(methylamino)imidazo[4,5-d]pyrrolo[2,3-b]pyridin-7-yl]benzoyl]-4-piperidinol | 2.06 | 405.45 |
| A85 | (pyridin-3-ylmethyl)amino | 3-[1,6-dihydro-1-methyl-4-(methylamino)imidazo[4,5-d]pyrrolo[2,3-b]pyridin-7-yl]-N-(3-pyridinylmethyl)-benzamide | 1.93 | 412.42 |

TABLE A2-continued

| Ex. | R | Name | HPLC Retention (min) | MS Reported |
|---|---|---|---|---|
| A86 | (2-piperidin-1-yl-ethyl)-NH– | 3-[1,6-dihydro-1-methyl-4-(methylamino)imidazo[4,5-d]pyrrolo[2,3-b]pyridin-7-yl]-N-[2-(1-piperidinyl)ethyl]-benzamide | 2.02 | 432.48 |
| A87 | (2-methylpropyl)-NH– | 3-[1,6-dihydro-1-methyl-4-(methylamino)imidazo[4,5-d]pyrrolo[2,3-b]pyridin-7-yl]-N-(2-methylpropyl)-benzamide | 2.8 | 377.48 |
| A88 | Me-CH$_2$-NH– | 3-[1,6-dihydro-1-methyl-4-(methylamino)imidazo[4,5-d]pyrrolo[2,3-b]pyridin-7-yl]-N-ethyl-benzamide | 2.36 | 349.47 |
| A89 | Me-C(O)-NH-CH$_2$CH$_2$-NH– | N-[2-(acetylamino)ethyl]-3-[1,6-dihydro-1-methyl-4-(methylamino)imidazo[4,5-d]pyrrolo[2,3-b]pyridin-7-yl]-benzamide | 2.12 | 406.46 |
| A90 | HO-(CH$_2$)$_4$-NH– | 3-[1,6-dihydro-1-methyl-4-(methylamino)imidazo[4,5-d]pyrrolo[2,3-b]pyridin-7-yl]-N-(4-hydroxybutyl)-benzamide | 2.25 | 393.47 |
| A91 | (Me)$_2$N– (diethyl) | 3-[1,6-dihydro-1-methyl-4-(methylamino)imidazo[4,5-d]pyrrolo[2,3-b]pyridin-7-yl]-N,N-diethyl-benzamide | 2.59 | 377.48 |
| A92 | Me-N(Me)-CH$_2$CH$_2$– | 3-[1,6-dihydro-1-methyl-4-(methylamino)imidazo[4,5-d]pyrrolo[2,3-b]pyridin-7-yl]-N-methyl-N-propyl benzamide | 2.64 | 377.49 |
| A93 | EtO-C(O)-CH$_2$-NH– | N-[3-[1,6-dihydro-1-methyl-4-(methylamino)imidazo[4,5-d]pyrrolo[2,3-b]pyridin-7-yl]benzoyl]-glycine, ethyl ester | 2.45 | 407.43 |
| A94 | EtO-C(O)-CH$_2$CH$_2$-NH– | N-[3-[1,6-dihydro-1-methyl-4-(methylamino)imidazo[4,5-d]pyrrolo[2,3-b]pyridin-7-yl]benzoyl]-beta-alanine, ethyl ester | 2.56 | 421.44 |

TABLE A2-continued

| Ex. | R | Name | HPLC Retention (min) | MS Reported |
|---|---|---|---|---|
| A95 | (EtO-C(=O)-CH2CH2CH2-NH-) | 4-[[3-[1,6-dihydro-1-methyl-4-(methylammo)imidazo[4,5-d]pyrrolo[2,3-b]pyridin-7-yl]benzoyl]amino]-butanoic acid, ethyl ester | 2.69 | 435.44 |
| A96 | (H2N-C(=O)-piperidin-N-) | 1-[3-[1,6-dihydro-1-methyl-4-(methylamino)imidazo[4,5-d]pyrrolo[2,3-b]pyridin-7-yl]benzoyl]-4-piperidinecarboxamide | 1.99 | 432.44 |
| A97 | (Me-C(=O)-N-piperazin-N-) | 1-acetyl-4-[3-[1,6-dihydro-1-methyl-4-(methylamino)imidazo[4,5-d]pyrrolo[2,3-b]pyridin-7-yl]benzoyl]-piperazine | 2.04 | 432.42 |
| A98 | (Me-C(=O)-NH-pyrrolidin-N-) | N-[1-[3-[1,6-dihydro-1-methyl-4-(methylamino)imidazo[4,5-d]pyrrolo[2,3-b]pyridin-7-yl]benzoyl]-3-pyrrolidinyl]-acetamide | 2.06 | 432.43 |
| A99 | (HOCH2-piperidin-N-) | 1-[3-[1,6-dihydro-1-methyl-4-(methylamino)imidazo[4,5-d]pyrrolo[2,3-b]pyridin-7-yl]benzoyl]-4-piperidinemethanol | 2.20 | 419.47 |
| A100 | (2-oxopiperazin-N-) | 4-[3-[1,6-dihydro-1-methyl-4-(methylamino)imidazo[4,5-d]pyrrolo[2,3-b]pyridin-7-yl]benzoyl]-2-piperazinone | 1.85 | 404.42 |

Example A101

3-[1,6-dihydro-1-methyl-4-(methylamino)imidazo[4,5-d]pyrrolo[2,3-b]pyridin-7-yl]-5-fluoro-benzoic acid, methyl ester

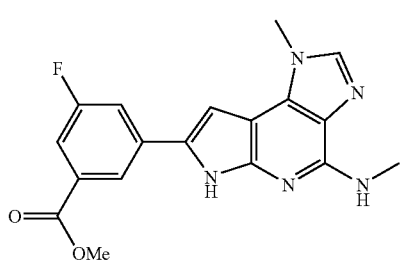

A101

A101.1: 3-Bromo-5-fluorobenzoic acid methyl ester

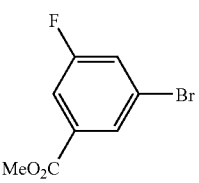

A101.1

Commercially available 3-bromo-5-fluorobenzoic acid (1.0 g, 4.57 mmol) was dissolved in methylene chloride (20 mL) trimethylsilyl diazomethane (2M solution in hexane) (5 mL, 10 mmol) was added and the reaction mixture was stirred for 30 min. at room temperature. The reaction mixture was concentrated and purified by silica gel chromatography (hexane/methylene chloride 2:1) to yield A101.1 (229 mg, 21%).

A101.2: 3-Fluoro-5-(trimethylsilylethynyl)benzoic acid methyl ester

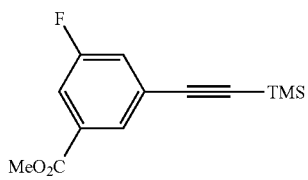

A101.2

A101.1 (229 mg, 0.98 mmol), bis-(triphenylphosphine) palladium diacetate (75 mg, 0.1 mmol), and triethylamine (2.8 mL) were added to toluene (2.8 mL) and degassed by bubbling nitrogen through the solution for a few minutes. Trimethylsilylacetylene (225 µL, 1.6 mmol) was added and the reaction mixture heated to 95° C. for 30 min. The reaction mixture was cooled to room temperature and concentrated under reduced pressure to yield a dark oil which was purified on silica gel chromatography (hexane/methylene chloride 2:1) to yield A101.2 (162 mg, 66%).

A101:3: 3-Ethynyl-5-fluorobenzoic acid methyl ester

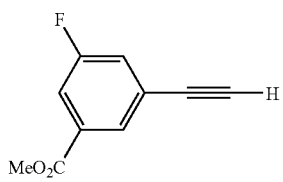

A101.3

A101.2 (162 mg, 0.64 mmol) was added to a solution of aqueous potassium hydroxide (using an aliquot of 5.1 µL of a 200 mg KOH/2 mL water solution) in methanol (1.2 mL) and stirred for 30 min. The mixture was concentrated to yield a dark oil. The product was purified by silica gel chromatography (hexane/dichloromethane 2:1) to yield A101.3 (107 mg, 93%) LCMS: Ret. Time=3.46 min, M+H$^+$=179.16

A101.4: 3-((6-amino-4-(tert-butyloxycarbonyl(methyl)amino)-1-methyl-1H-imidazo[4,5-c]pyridine-7-yl)ethynyl)-5-fluorobenzoic acid, methyl ester

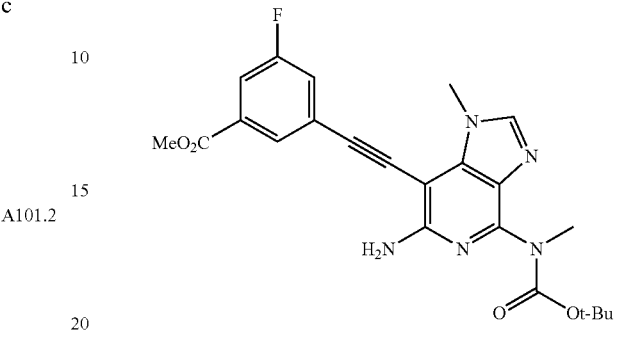

A101.4

A101.3 (107 mg, 0.6 mmol), A1.12 (164 mg, 0.41 mmol) bis(triphenylphophine)palladium dichloride and triethylamine were degassed by bubbling nitrogen through the reaction for several minutes and then heated under a nitrogen atmosphere at 90° C. for 30 minutes. The mixture was concentrated under reduced pressure and the product purified by silica gel chromatography (hexane/ethyl acetate) to yield A101.4 (148 mg, 80%). LCMS: Ret. Time=3.53 min, M+H$^+$=454.39.

A101.5: 3-((4-tert-butyloxycarbonyl(methyl)amino)-1-methyl-6-(2,2,2-trifluoroacetamido)-1H-imidazo[4,5-c]pyridin-7-yl)ethynyl-5-fluorobenzoic acid methyl ester

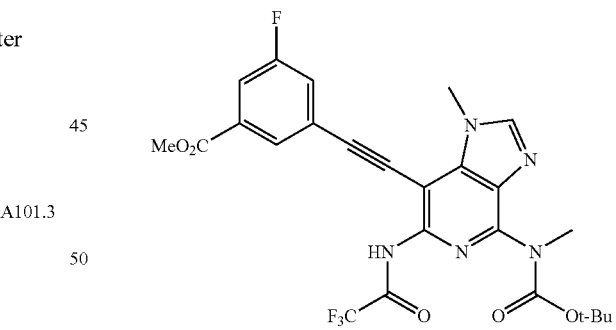

A101.5

A101.4 (148 mg, 0.33 mmol) was dissolved in a mixture of triethylamine (150 µL) in methylene chloride and cooled in a bath maintained between 0° C. and 5° C. Trifluoroacetic anhydride (140 µL, 1.0 mmol) and allowed to warm up to room temperature. The reaction mixture was stirred for an additional 20 minutes and then diluted methylene chloride (10 mL) and washed with saturated sodium bicarbonate (5 mL) followed by brine (5 mL). The organic layer was dried over sodium sulfate, filtered and concentrated under reduced pressure to yield a brown oil. The product was purified by silica gel chromatography (hexane/ethyl acetate 2:3) to yield A101.5 (92.5 mg, 52%). LCMS: ret. Time=3.66 min. M+H$^+$=550.34.

A101.6: 3-[1,6-dihydro-1-methyl-4-((methyl)tertbutoxycarbonylamino)imidazo[4,5-d]pyrrolo[2,3-b]pyridin-7-yl]-5-fluoro-benzoic acid methyl ester

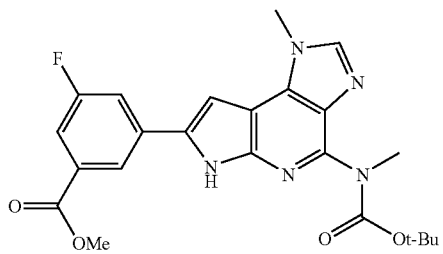

A101.5 (72 mg, 0.036 mmol), potassium carbonate (20 mg) and tetrakis(triphenylphosphine)palladium (0) (9.1 mg) were dissolved in DMA (1.5 mL). The reaction mixture was heated in a microwave apparatus for 45 min at 130° C. The reaction mixture was concentrated under reduced pressure and the residue purified by silica gel chromatography (hexane/ethyl acetate) to yield A101.6 (66 mg, 87%). LCMS: ret time=3.48 min, M+H$^+$=454.25.

A101.7: 3-[1,6-dihydro-1-methyl-4-(methylamino)imidazo[4,5-d]pyrrolo[2,3-b]pyridin-7-yl]-5-fluoro-benzoic acid, methyl ester trifluoacetate salt A101.6 (10 mg) was dissolved in a mixture of trifluoroacetic acid (0.25 mL) and methylene chloride (0.25 mL) and stirred at room temperature for 15 min. The reaction mixture was concentrated under reduced pressure the residue was diluted with methanol (0.25 mL) and stirred for 10 min. The product was filtered and dried to yield A101 (6 mg, 58%) LCMS: ret time=2.67 min, M+H+=354.31

Example A102

3-[1,6-dihydro-1-methyl-4-(methylamino)imidazo[4,5-d]pyrrolo[2,3-b]pyridin-7-yl]-5-fluoro-benzoic acid

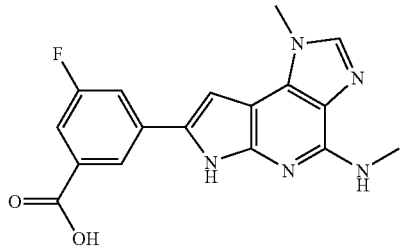

A102.1: 3-[1,6-dihydro-1-methyl-4-((methyl)tert-butyloxycarbonylamino)imidazo[4,5-d]pyrrolo[2,3-b]pyridin-7-yl]-5-fluoro-benzoic acid

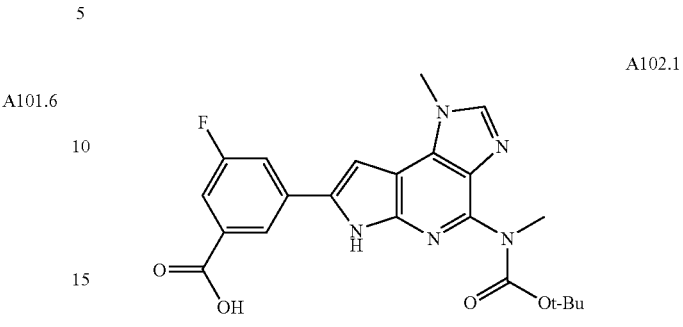

A101.6 (54 mg, 0.12 mmol) was dissolved in a mixture of 1N sodium hydroxide (0.3 mL) and methanol (2.5 mL) and heated in a microwave apparatus at 100° C. for 15 min. The reaction mixture was concentrated under reduced pressure and diluted with water (1 mL). 1N HCl was added until the pH was between 1 and 2 (pH paper). The solid was collected by filtration and dried to yield A102.1 (42 mg, 80%). LCMS: ret time=3.17 min, M+H$^+$=440.32.

A102.2: 3-[1,6-dihydro-1-methyl-4-(methylamino)imidazo[4,5-d]pyrrolo[2,3-b]pyridin-7-yl]-5-fluoro-benzoic acid, trifluoro acetate salt A102.1 (10 mg, 0.022 mmol) was dissolved in a mixture of trifluoroacetic acid (0.25 mL) and methylene chloride (0.25 mL) and stirred at room temperature for 20 min. The reaction mixture was concentrated under reduced pressure. The residue was diluted with methanol (0.5 mL) and stirred for 5 min. The solid was filtered and dried to yield A102 (5 mg, 65%) LCMS: ret time=2.42 min, M+H$^+$=340.33

Example A103

4-[3-[1,6-dihydro-1-methyl-4-(methylamino)imidazo[4,5-d]pyrrolo[2,3-b]pyridin-7-yl]-5-fluorobenzoyl]-morpholine, trifluoacetate salt

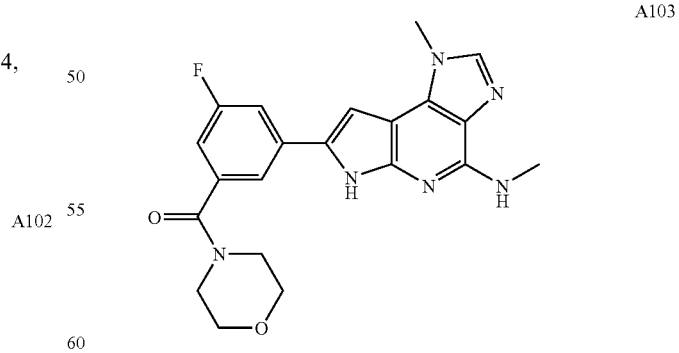

A102.1 (16 mg, 0.036 mmol), morpholine (3.5 µL, 0.04 mmol) and triethylamine (47 µL. 10.3 mmol) were dissolved in DMF in a bath maintained between 0° C. and 5° C. BOP-Cl (85 mg, 0.34 mmol) was added and the reaction allowed to warm to room temperature and stirred for 30 min. The reaction mixture was concentrated under reduced pressure and the residue purified by preparatory reverse phase HPLC to yield the BOC protected derivative (LCMS ret time=2.84 min, M+H⁺=509.32). The intermediate was stirred in a mixture of dichloromethane (0.25 mL) and trifluoroacetic acid (0.25 mL) for 10 minutes and concentrated to yield A103 (9.8 mg, 51%) LCMS: ret time=2.06 min, M+H⁺=409.35.

Example A104

3-[1,6-dihydro-1-methyl-4-(methylamino)imidazo[4,5-d]pyrrolo[2,3-b]pyridin-7-yl]-5-fluoro-N-(2-methoxyethyl)-benzamide, trifluoroacetate salt

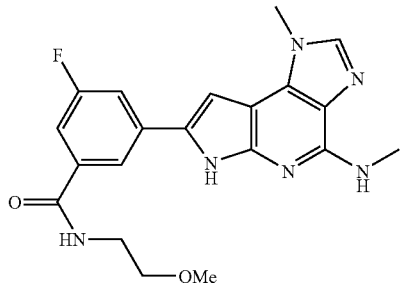

A104

A102.1 (16 mg, 0.036 mmol), HOBT (8.7 mg, 0.64 mmol), and diisoproplyethylamine (76 μL) was dissolved in acetonitrile. EDCI (16.5 mg, 0.086 mmol) was added and the reaction mixture stirred for 5 min. at room temperature. 2-Methoxyethylamine (4 μL, 0.39 mmol) was added and the reaction mixture stirred for 30 minutes at room temperature followed by 30 minutes at 80° C. The reaction mixture was concentrated under reduced pressure and purified by preparatory reverse phase HPLC to yield the BOC protected derivative (M+H⁺=497.28). The intermediate was dissolved in dichloromethane (0.25 mL) and trifluoroacetic acid (0.25 mL), stirred at room temperature for 10 min and concentrated under reduced pressure to yield a clear oil. The residue was washed with diethyl ether and dried under vacuum overnight to yield A104 (14.5 mg 78%). LCMS: ret time=2.26 min, M+H+=397.33

Examples A105-A130

A105a: [7-[4-(aminomethyl)phenyl]-1,6-dihydro-1-methylimidazo[4,5-d]pyrrolo[2,3-b]pyridin-4-yl]methyl-carbamic acid, 1,1-dimethylethyl ester

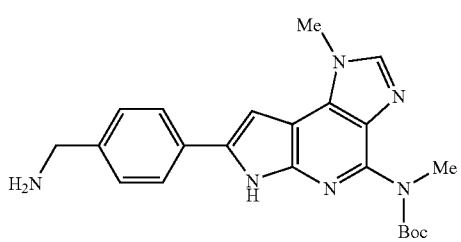

A105a

A105a.1: tert-Butyl 6-amino-7-(2-(4-cyanophenyl)ethynyl)-1-methyl-1H-imidazo[4,5-c]pyridin-4-yl(methyl)carbamate

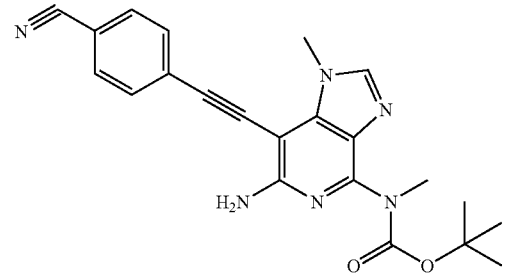

A105a.1

A1.12 (1.0 g, 2.48 mmol), dichlorobis(triphenylphosphine)palladium (24 mg, 0.12 mmol), 4-ethynylbenzonitrile (631 mg, 4.96 mmol) and triethylamine (0.7 mL, 5.0 mmol) were each added to N,N-dimethylformamide (10 mL) and nitrogen bubbled through the resulting mixture for 5 min. The reaction mixture was heated at 90° C. for 20 min under a nitrogen atmosphere before cooling to room temperature and evaporating the solvent in vacuo. The residue was purified by silica gel column chromatography using ethyl acetate as eluent to provide 0.58 g (60%) of A105a.1. HPLC YMC S-5 4.6×33 mm (2 min grad): retention time 1.69 min, M+H⁺=403.35.

A105a.2: 4-[1,5-Dihydro-1-methyl-4-(N-tert-butyloxycarbonyl-N-methylamino)imidazo[4,5-d]pyrrolo[2,3-b]pyridin-7-yl]benzonitrile

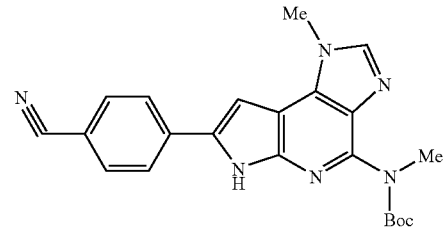

A105a.2

A105a.1 (0.55 g, 1.37 mmol) was dissolved in dimethylacetamide (7 mL). Potassium t-butoxide, 1M in THF (2.10 ml, 2.10 mmol) was added and the reaction heated in an oil bath maintained at 80° C. for 20 min. The reaction was allowed to cool to room temperature and the solvent was removed under reduced pressure. The residue was purified by silica gel column chromatography using ethyl acetate as the eluent to yield 0.73 g (78%) of A105a.2 HPLC YMC S-54.6×33 mm (2 min grad): retention time 1.38 min, M+H⁺=403.31. ¹H NMR (400 MHz, MeOD) δ 8.02 (s, 1H), 7.95 (d, J=8.6 Hz, 2H), 7.70 (d, J=8.6 Hz, 2H), 7.36 (s, 1H), 4.10 (s, 3H), 2.96 (s, 3H), 1.29 (s, 9H).

A105a.3: 7-[4-(Aminomethyl)phenyl]-1,5-dihydro-N,1-dimethyl-imidazo[4,5-d]pyrrolo[2,3-b]pyridin-4-(t-butyloxycarbonylamine)

A105a.2 (0.43 g, 13.9 mmol) was dissolved in ethanol (50 mL, 100% ethanol) pre-saturated with ammonia gas. Raney nickel (~0.5 g) was washed with water followed by ethanol and then added to the reaction mixture. A balloon of hydrogen gas was affixed to the reaction mixture and stirred at room temperature for 18 h. The reaction mixture was filtered through celite and the solvent removed under reduced pressure to yield A105a (0.4 g, 98%) HPLC YMC S-5 4.6×33 mm (2 min grad): retention time 1.24 min, M+H$^+$=407.28.

Examples A105-A130 was prepared by parallel synthesis according to the scheme shown below.

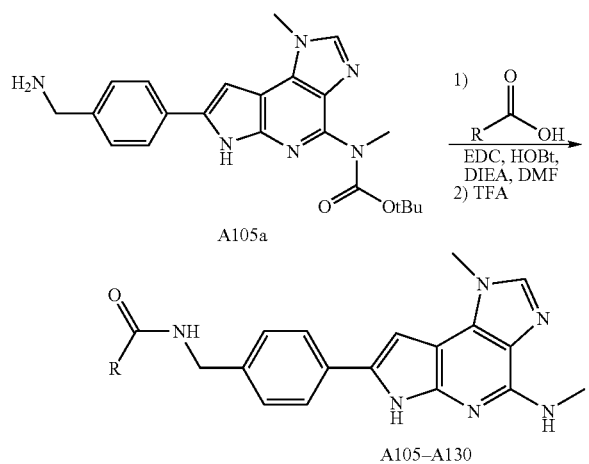

A105a

A105-A130

To an individual well in a Bohdan XT® reactor was added 150 uL of a 0.25 M solution of the carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq). The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS (H$_2$O/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$O/MeOH/0.1% TFA). Examples prepared by this method are described in Table A3.

TABLE A3

| Ex. | R | Name | HPLC Retention (min) | MS Reported |
|---|---|---|---|---|
| A105 | CH$_3$— | N-[[4-[1,6-dihydro-1-methyl-4-(methylamino)imidazo[4,5-d]pyrrolo[2,3-b]pyridin-7-yl]phenyl]methyl]-acetamide | 2.06 | 349.48 |
| A106 | CH$_3$CH$_2$— | N-[[4-[1,6-dihydro-1-methyl-4-(methylamino)imidazo[4,5-d]pyrrolo[2,3-b]pyridin-7-yl]phenyl]methyl]-propanamide | 2.18 | 363.52 |
| A107 | Me-C(Me)- | N-[[4-[1,6-dihydro-1-methyl-4-(methylamino)imidazo[4,5-d]pyrrolo[2,3-b]pyridin-7-yl]phenyl]methyl]-2-methyl propanamide | 2.31 | 377.52 |
| A108 | Me,Me,Me-C- | N-[[4-[1,6-dihydro-1-methyl-4-(methylamino)imidazo[4,5-d]pyrrolo[2,3-b]pyridin-7-yl]phenyl]methyl]-2,2-dimethyl-propanamide | 2.49 | 391.54 |
| A109 | cyclopropyl | N-[[4-[1,6-dihydro-1-methyl-4-(methylamino)imidazo[4,5-d]pyrrolo[2,3-b]pyridin-7-yl]phenyl]methyl]-cyclopropanecarboxamide | 2.27 | 375.48 |

TABLE A3-continued

| Ex. | R | Name | HPLC Retention (min) | MS Reported |
|---|---|---|---|---|
| A110 | Me-cyclopropyl | N-[[4-[1,6-dihydro-1-methyl-4-(methylamino)imidazo[4,5-d]pyrrolo[2,3-b]pyridin-7-yl]phenyl]methyl]-1-methyl-cyclopropanecarboxamide | 2.40 | 389.54 |
| A111 | HO-cyclopropyl | N-[[4-[1,6-dihydro-1-methyl-4-(methylamino)imidazo[4,5-d]pyrrolo[2,3-b]pyridin-7-yl]phenyl]methyl]-1-hydroxy-cyclopropanecarboxamide | 2.12 | 391.48 |
| A112 | NC-cyclopropyl | 1-cyano-N-[[4-[1,6-dihydro-1-methyl-4-(methylamino)imidazo[4,5-d]pyrrolo[2,3-b]pyridin-7-yl]phenyl]methyl]-cyclopropanecarboxamide | 2.32 | 400.48 |
| A113 | HO- | N-[[4-[1,6-dihydro-1-methyl-4-(methylamino)imidazo[4,5-d]pyrrolo[2,3-b]pyridin-7-yl]phenyl]methyl]-2-hydroxy-acetamide | 1.95 | 365.51 |
| A114 | NC- | 2-cyano-N-[[4-[1,6-dihydro-1-methyl-4-(methylamino)imidazo[4,5-d]pyrrolo[2,3-b]pyridin-7-yl]phenyl]methyl]-acetamide | 2.07 | 374.47 |
| A115 | MeO- | N-[[4-[1,6-dihydro-1-methyl-4-(methylamino)imidazo[4,5-d]pyrrolo[2,3-b]pyridin-7-yl]phenyl]methyl]-3-methoxy-propanamide | 2.15 | 393.48 |
| A116 | H$_2$NSO$_2$- | 4-(aminosulfonyl)-N-[[4-[1,6-dihydro-1-methyl-4-(methylamino)imidazo[4,5-d]pyrrolo[2,3-b]pyridin-7-yl]phenyl]methyl]-butanamide | 1.99 | 456.37 |
| A117 | phenyl | N-[[4-[1,6-dihydro-1-methyl-4-(methylamino)imidazo[4,5-d]pyrrolo[2,3-b]pyridin-7-yl]phenyl]methyl]-benzamide | 2.61 | 411.44 |
| A118 | benzyl | N-[[4-[1,6-dihydro-1-methyl-4-(methylamino)imidazo[4,5-d]pyrrolo[2,3-b]pyridin-7-yl]phenyl]methyl]-benzeneacetamide | 2.63 | 425.44 |
| A119 | 3-thienyl | N-[[4-[1,6-dihydro-1-methyl-4-(methylamino)imidazo[4,5-d]pyrrolo[2,3-b]pyridin-7-yl]phenyl]methyl]-3-thiophenecarboxamide | 2.52 | 417.39 |

TABLE A3-continued

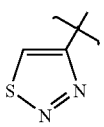

| Ex. | R | Name | HPLC Retention (min) | MS Reported |
|---|---|---|---|---|
| A120 | 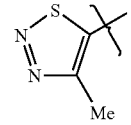 | N-[[4-[1,6-dihydro-1-methyl-4-(methylamino)imidazo[4,5-d]pyrrolo[2,3-b]pyridin-7-yl]phenyl]methyl]-1,2,3-thiadiazole-4-carboxamide | 2.35 | 419.37 |
| A121 | 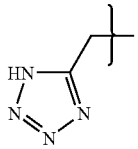 | N-[[4-[1,6-dihydro-1-methyl-4-(methylamino)imidazo[4,5-d]pyrrolo[2,3-b]pyridin-7-yl]phenyl]methyl]-4-methyl-1,2,3-thiadiazole-5-carboxamide | 2.49 | 433.41 |
| A122 | 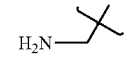 | N-[[4-[1,6-dihydro-1-methyl-4-(methylamino)imidazo[4,5-d]pyrrolo[2,3-b]pyridin-7-yl]phenyl]methyl]-1H-tetrazole-5-acetamide | 2.04 | 417.44 |
| A123 | 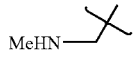 | 2-amino-N-[[4-[1,6-dihydro-1-methyl-4-(methylamino)imidazo[4,5-d]pyrrolo[2,3-b]pyridin-7-yl]phenyl]methyl]-acetamide | 1.77 | 364.49 |
| A124 | 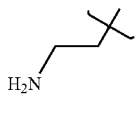 | N-[[4-[1,6-dihydro-1-methyl-4-(methylamino)imidazo[4,5-d]pyrrolo[2,3-b]pyridin-7-yl]phenyl]methyl]-2-(methylamino)-acetamide | 1.78 | 378.48 |
| A125 | 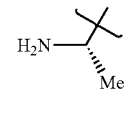 | 3-amino-N-[[4-[1,6-dihydro-1-methyl-4-(methylamino)imidazo[4,5-d]pyrrolo[2,3-b]pyridin-7-yl]phenyl]methyl]-propanamide | 1.81 | 378.48 |
| A126 | 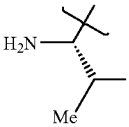 | (2S)-N-[[4-[1,6-dihydro-1-methyl-4-(methylamino)imidazo[4,5-d]pyrrolo[2,3-b]pyridin-7-yl]phenyl]methyl]-2-(methylamino)propanamide | 1.86 | 392.50 |
| A127 |  | (2S)-2-amino-N-[[4-[1,6-dihydro-1-methyl-4-(methylamino)imidazo[4,5-d]pyrrolo[2,3-b]pyridin-7-yl]phenyl]methyl]-4-methylpentanamide | 2.20 | 420.49 |

TABLE A3-continued

| Ex. | R | Name | HPLC Retention (min) | MS Reported |
|---|---|---|---|---|
| A128 | (H₂N, phenyl, dimethyl group) | (alphaS)-alpha-amino-N-[[4-[1,6-dihydro-1-methyl-4-(methylamino)imidazo[4,5-d]pyrrolo[2,3-b]pyridin-7-yl]phenyl]methyl]benzeneacetamide | 2.13 | 440.41 |
| A129 | (pyrrolidine with NH) | (2S)-N-[[4-[1,6-dihydro-1-methyl-4-(methylamino)imidazo[4,5-d]pyrrolo[2,3-b]pyridin-7-yl]phenyl]methyl]-2-pyrrolidinecarboxamide | 1.86 | 404.49 |
| A130 | (4-hydroxy pyrrolidine) | (2S,4R)-N-[[4-[1,6-dihydro-1-methyl-4-(methylamino)imidazo[4,5-d]pyrrolo[2,3-b]pyridin-7-yl]phenyl]methyl]-4-hydroxy-2-pyrrolidinecarboxamide | 1.81 | 420.48 |

Example A131

7-[3-(1-aminoethyl)phenyl]-1,6-dihydro-N,1-dimethyl-imidazo[4,5-d]pyrrolo[2,3-b]pyridin-4-amine

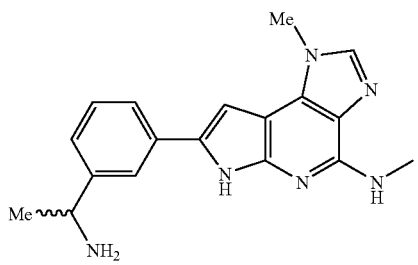

A solution of A56.1d (663 mg, 1.43 mmol) and concentrated HCl solution (4.0 ml) in n-butanol (6.0 ml) was heated to 150° C. for 25 minutes under microwave which was concentrated to yield A131 (525 mg, 93%). HPLC: 91%, retention time: 1.88 minute (condition B). LC/MS (M+H)$^+$=321.3, $^1$H-NMR (400 MHz, CD$_3$OD) δ ppm 8.20 (1 H, s), 7.87 (1 H, s), 7.76 (1 H, d, J=7.63 Hz), 7.50 (1 H, t, J=7.63 Hz), 7.36 (1 H, d, J=7.12 Hz), 7.20 (1 H, s), 4.49 (1 H, d, J=6.61 Hz), 4.08-4.14 (3 H, m), 3.21 (3 H, s), 1.65 (3 H, d, J=7.12 Hz).

Example A132

7-[3-(1-tert-butyloxycarbonylaminoethyl)phenyl]-1,6-dihydro-N,1-dimethyl-imidazo[4,5-d]pyrrolo[2,3-b]pyridin-4-amine

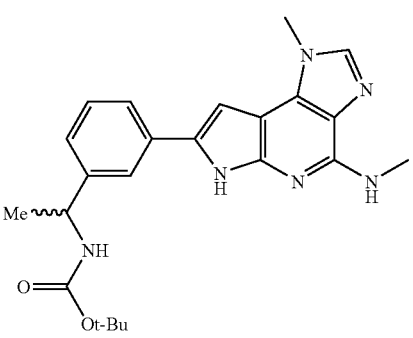

A solution of A131 (515 mg, 1.31 mmol) and Et$_3$N (0.749 ml, 5.18 mmol) in dichloromethane (6.5 ml) and DMF (6.5 ml) at 0-5° C. was added (BOC)$_2$O (300 mg, 1.38 mmol) which was warmed up to RT and stirred for 30 minutes. The reaction mixture was concentrated and diluted with CH$_2$Cl$_2$ (100 ml). The organic phase was washed with saturated NaHCO$_3$ solution (20 ml), water (20 ml), brine (20 ml) and the organic layer was dried over sodium sulfate. Filtration and concentration to yield a crude product which was added Et$_2$O (20 ml) and stirred for 10 minutes. The solid was collected as A132 (432 mg, 79%). HPLC: 97%, retention time: 2.621 minute (condition A). LC/MS (M+H)$^+$=421.4. $^1$H-NMR (400 MHz, CD$_3$OD) δ ppm 7.79 (1 H, s), 7.62 (1 H, s), 7.54 (1 H, d, J=7.63 Hz), 7.27 (1 H, t, J=7.63 Hz), 7.10 (1 H, d, J=8.14 Hz), 6.94 (1 H, s), 4.66 (1 H, s), 4.03 (3 H, s), 3.05 (3 H, s), 1.30-1.44 (12 H, m).

Examples A133 and A134

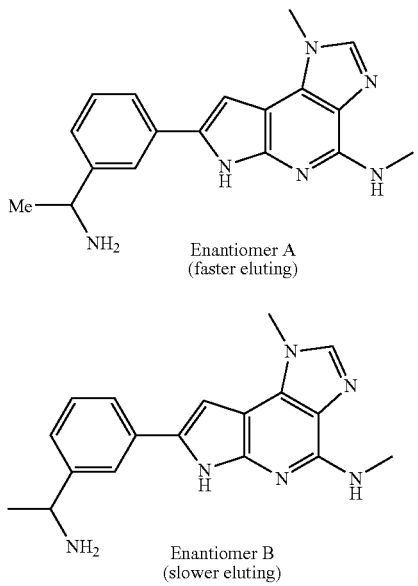

A133.1: 7-[3-(1-tert-butyloxycarbonylaminoethyl) phenyl]-1,6-dihydro-N,1-dimethyl-imidazo[4,5-d] pyrrolo[2,3-b]pyridin-4-tert-butyloxycarbonylamine

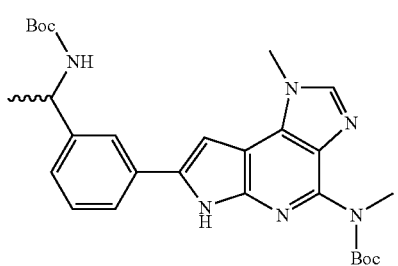

A solution of A131 (721 mg, 1.71 mmol) and DMAP ((21 mg, 0.17 mmol) in CH$_3$CN (13 mL) and DMF (13 mL) at RT was added (BOC)$_2$O (1.30 g, 5.99 mmol) which was heated to 50° C. for 16 hrs. The reaction mixture was concentrated and diluted with CH$_2$Cl$_2$ (100 mL). The organic phase was washed with water (20 ml×2), brine (20 ml) and the organic layer was dried over Sodium sulfate. Filtration and concentration to yield a product A133.1 (965 mg, 100%). HPLC: 84%, retention time: 3.060 minute (condition A). LC/MS (M+H)$^+$=521.3.

A133.2 Chiral Separation of A133.1

Compound A133.1 (965 mg, 1.85 mmol) was subjected to chiral separation to yield A133.2 (312 mg, 65%). HPLC: 97%, retention time: 3.098 minute (LC/MS (M+H)$^+$=521.35. and Compound A133.3 (336 mg, 70%). HPLC: >98%, retention time: 3.113 minute LC/MS (M+H)$^+$=521.34.

Example A133

A solution of A133.2 (336 mg, 0.65 mmol) in CH$_2$Cl$_2$ (2 ml) was added TFA (0.5 ml) dropwise at 0-5° C. which was warmed up to RT and stirred for 1 hr. The reaction mixture was concentrated and added Et$_2$O (20 ml), stirred for 10 minutes. The solid was collected as A133 (335.6 mg, 95%). HPLC: >98%, retention time: 1.860 minute (condition B). Chiral HPLC: 100% ee. retention time: 7.57 minute (condition F). LC/MS (M+H)$^+$=321.3, $^1$H-NMR (400 MHz, CD$_3$OD) δ ppm 8.02 (1 H, s), 7.70-7.82 (1 H, m), 7.45 (1 H, t, J=7.63 Hz), 7.28 (1 H, d, J=7.63 Hz), 7.11 (1 H, s), 4.44 (1 H, d, J=7.12 Hz), 4.05 (3 H, s), 3.15 (3 H, s), 1.61 (3 H, d, J=7.12 Hz).

Example A134

A solution of A133.3 (312 mg, 0.6 mmol) in CH$_2$Cl$_2$ (2 ml) was added TFA (0.5 ml) dropwise at 0-5° C. which was warmed up to RT and stirred for 1 hr. The reaction mixture was concentrated and added Et$_2$O (20 ml), stirred for 10 minutes. The solid was collected as A134 (312.5 mg, 95%). HPLC: >98%, retention time: 1.870 minute (condition B). Chiral HPLC: 100% ee. retention time: 9.47 minute (condition F). LC/MS (M+H)$^+$=321.3, $^1$H-NMR (400 MHz, CD$_3$OD) δ ppm 8.02 (1 H, s), 7.70-7.80 (1 H, m), 7.44 (1 H, t, J=7.63 Hz), 7.29 (1 H, s), 7.10 (1 H, s), 4.44 (1 H, d, J=6.61 Hz), 4.05 (3 H, s), 3.14 (3 H, s), 1.61 (3 H, d, J=6.61 Hz).

Examples A135-A152

Examples A135-A152 was prepared by parallel synthesis according to the scheme shown below.

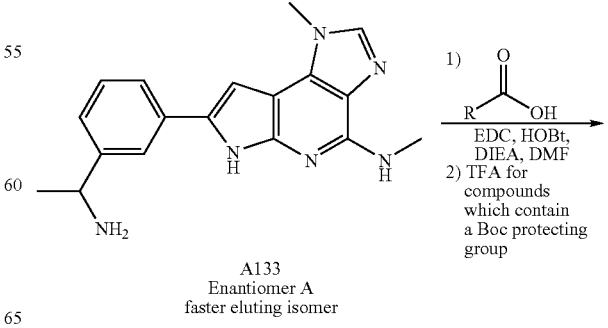

-continued

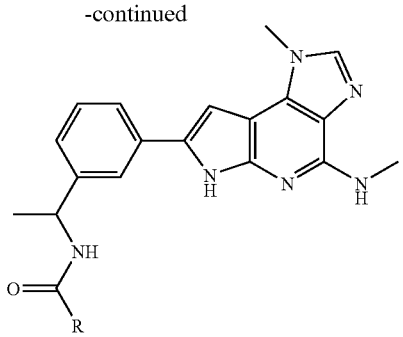

To an individual well in a Bohdan XT® reactor was added 150 uL of a 0.25 M solution of the carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq). The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and for those compounds which contained a BOC group, were removed by adding 600 uL of a 30% by volume solution of trifluoroacetic acid (TFA) in dichloromethane (DCM) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS ($H_2O$/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS ($H_2O$/MeOH/0.1% TFA). Compounds were isolated as trifluoroacetate salts. Examples prepared by this method are described in Table A4.

TABLE A4

Enantiomer A

| Ex. | R | Name | HPLC Retention (min) | MS Reported |
|---|---|---|---|---|
| A135 | $CH_3CH_2$— | N-[1-[3-[1,6-dihydro-1-methyl-4-(methylamino)imidazo[4,5-d]pyrrolo[2,3-b]pyridin-7-yl]phenyl]ethyl]-propanamide | 2.40 | 377.61 |
| A136 | HO— | N-[1-[3-[1,6-dihydro-1-methyl-4-(methylamino)imidazo[4,5-d]pyrrolo[2,3-b]pyridin-7-yl]phenyl]ethyl]-2-hydroxy-acetamide | 2.20 | 379.59 |
| A137 | NC— | 2-cyano-N-[1-[3-[1,6-dihydro-1-methyl-4-(methylamino)imidazo[4,5-d]pyrrolo[2,3-b]pyridin-7-yl]phenyl]ethyl]-acetamide | 2.27 | 388.57 |
| A138 | | N-[1-[3-[1,6-dihydro-1-methyl-4-(methylamino)imidazo[4,5-d]pyrrolo[2,3-b]pyridin-7-yl]phenyl]ethyl]-cyclopropanecarboxamide | 2.47 | 389.60 |

TABLE A4-continued

Enantiomer A

| Ex. | R | Name | HPLC Retention (min) | MS Reported |
|---|---|---|---|---|
| A139 | Me, Me (isopropyl) | N-[1-[3-[1,6-dihydro-1-methyl-4-(methylamino)imidazo[4,5-d]pyrrolo[2,3-b]pyridin-7-yl]phenyl]ethyl]-2-methyl-propanamide | 2.51 | 391.64 |
| A140 | Me-cyclopropyl | N-[1-[3-[1,6-dihydro-1-methyl-4-(methylamino)imidazo[4,5-d]pyrrolo[2,3-b]pyridin-7-yl]phenyl]ethyl]-1-methyl-cyclopropanecarboxamide | 2.63 | 403.60 |
| A141 | HO-cyclopropyl | N-[1-[3-[1,6-dihydro-1-methyl-4-(methylamino)imidazo[4,5-d]pyrrolo[2,3-b]pyridin-7-yl]phenyl]ethyl]-1-hydroxy-cyclopropanecarboxamide | 2.34 | 405.55 |
| A142 | Me, Me (isobutyl) | N-[1-[3-[1,6-dihydro-1-methyl-4-(methylamino)imidazo[4,5-d]pyrrolo[2,3-b]pyridin-7-yl]phenyl]ethyl]-3-methyl-butanamide | 2.72 | 405.61 |
| A143 | Me, Me, Me (tert-butyl) | N-[1-[3-[1,6-dihydro-1-methyl-4-(methylamino)imidazo[4,5-d]pyrrolo[2,3-b]pyridin-7-yl]phenyl]ethyl]-2,2-dimethyl-propanamide | 2.71 | 405.61 |
| A144 | EtO- | N-[1-[3-[1,6-dihydro-1-methyl-4-(methylamino)imidazo[4,5-d]pyrrolo[2,3-b]pyridin-7-yl]phenyl]ethyl]-2-ethoxy-acetamide | 2.55 | 407.61 |
| A145 | MeO- | N-[1-[3-[1,6-dihydro-1-methyl-4-(methylamino)imidazo[4,5-d]pyrrolo[2,3-b]pyridin-7-yl]phenyl]ethyl]-3-methoxy-propanamide | 2.35 | 407.60 |
| A146 | NC-cyclopropyl | 1-cyano-N-[1-[3-[1,6-dihydro-1-methyl-4-(methylamino)imidazo[4,5-d]pyrrolo[2,3-b]pyridin-7-yl]phenyl]ethyl]-cyclopropanecarboxamide | 2.51 | 414.57 |

TABLE A4-continued

Enantiomer A

| Ex. | R | Name | HPLC Retention (min) | MS Reported |
|---|---|---|---|---|
| A147 | Me,Me,Me (tert-butyl-CH2) | N-[1-[3-[1,6-dihydro-1-methyl-4-(methylamino)imidazo[4,5-d]pyrrolo[2,3-b]pyridin-7-yl]phenyl]ethyl]-3,3-dimethyl-butanamide | 2.90 | 419.61 |
| A148 | Me-C(O)-NH-C(Me)2- | 2-(acetylamino)-N-[1-[3-[1,6-dihydro-1-methyl-4-(methylamino)imidazo[4,5-d]pyrrolo[2,3-b]pyridin-7-yl]phenyl]ethyl]-acetamide | 2.18 | 420.58 |
| A149 | Me-C(O)-O-C(Me)2- | 2-(acetyloxy)-N-[1-[3-[1,6-dihydro-1-methyl-4-(methylamino)imidazo[4,5-d]pyrrolo[2,3-b]pyridin-7-yl]phenyl]ethyl]-acetamide | 2.32 | 421.53 |
| A150 | Me,HO,Me | N-[1-[3-[1,6-dihydro-1-methyl-4-(methylamino)imidazo[4,5-d]pyrrolo[2,3-b]pyridin-7-yl]phenyl]ethyl]-3-hydroxy-3-methyl-butanamide | 2.42 | 421.61 |
| A151 | EtO-CH2-C(Me)2- | N-[1-[3-[1,6-dihydro-1-methyl-4-(methylamino)imidazo[4,5-d]pyrrolo[2,3-b]pyridin-7-yl]phenyl]ethyl]-3-ethoxy-propanamide | 2.49 | 421.58 |
| A152 | MeO-C(Me)2- | N-[1-[3-[1,6-dihydro-1-methyl-4-(methylamino)imidazo[4,5-d]pyrrolo[2,3-b]pyridin-7-yl]phenyl]ethyl]-2-methoxy-acetamide | 2.36 | 393.58 |

Examples A153-A167

Examples A153-A167 were prepared by parallel synthesis according to the scheme shown below.

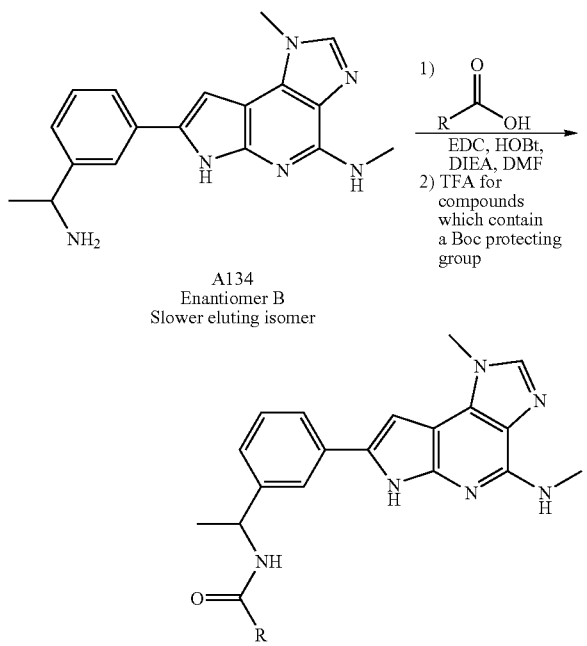

A134
Enantiomer B
Slower eluting isomer

To an individual well in a Bohdan XT® reactor was added 150 uL of a 0.25 M solution of the carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq). The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and for those compounds which contained a BOC group, were removed by adding 600 uL of a 30% by volume solution of trifluoroacetic acid (TFA) in dichloromethane (DCM) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS (H$_2$O/MeOH/0.1% TFA, gradient 35-90% MeOH over 15 min, 20×100 mm 5 µm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$O/MeOH/0.1% TFA). Compounds were isolated as trifluoroacetate salts. Examples prepared by this method are described in Table A5.

TABLE A5

Enantiomer B

| Ex. | R | Name | HPLC Retention (min) | MS Reported |
|---|---|---|---|---|
| A153 | CH$_3$CH$_2$— | N-[1-[3-[1,6-dihydro-1-methyl-4-(methylamino)imidazo[4,5-d]pyrrolo[2,3-b]pyridin-7-yl]phenyl]ethyl]-propanamide | 2.37 | 377.59 |
| A154 | Me, Me (isopropyl) | N-[1-[3-[1,6-dihydro-1-methyl-4-(methylamino)imidazo[4,5-d]pyrrolo[2,3-b]pyridin-7-yl]phenyl]ethyl]-2-methyl-propanamide | 2.51 | 391.61 |
| A155 | Me, Me, Me (tert-butyl) | N-[1-[3-[1,6-dihydro-1-methyl-4-(methylamino)imidazo[4,5-d]pyrrolo[2,3-b]pyridin-7-yl]phenyl]ethyl]-2,2-dimethyl-propanamide | 2.69 | 405.61 |

TABLE A5-continued

Enantiomer B

| Ex. | R | Name | HPLC Retention (min) | MS Reported |
|---|---|---|---|---|
| A156 | cyclopropyl | N-[1-[3-[1,6-dihydro-1-methyl-4-(methylamino)imidazo[4,5-d]pyrrolo[2,3-b]pyridin-7-yl]phenyl]ethyl]-cyclopropanecarboxamide | 2.45 | 389.60 |
| A157 | 1-methylcyclopropyl | N-[1-[3-[1,6-dihydro-1-methyl-4-(methylamino)imidazo[4,5-d]pyrrolo[2,3-b]pyridin-7-yl]phenyl]ethyl]-1-methyl-cyclopropanecarboxamide | 2.61 | 403.59 |
| A158 | 1-hydroxycyclopropyl | N-[1-[3-[1,6-dihydro-1-methyl-4-(methylamino)imidazo[4,5-d]pyrrolo[2,3-b]pyridin-7-yl]phenyl]ethyl]-1-hydroxy-cyclopropanecarboxamide | 2.31 | 404.80 |
| A159 | 1-cyanocyclopropyl | 1-cyano-N-[1-[3-[1,6-dihydro-1-methyl-4-(methylamino)imidazo[4,5-d]pyrrolo[2,3-b]pyridin-7-yl]phenyl]ethyl]-cyclopropanecarboxamide | 2.49 | 414.57 |
| A160 | HOC(CH3)2 | N-[1-[3-[1,6-dihydro-1-methyl-4-(methylamino)imidazo[4,5-d]pyrrolo[2,3-b]pyridin-7-yl]phenyl]ethyl]-2-hydroxy-acetamide | 2.17 | 378.72 |
| A161 | NCC(CH3)2 | 2-cyano-N-[1-[3-[1,6-dihydro-1-methyl-4-(methylamino)imidazo[4,5-d]pyrrolo[2,3-b]pyridin-7-yl]phenyl]ethyl]-acetamide | 2.25 | 388.57 |
| A162 | MeC(O)NHC(CH3)2 | 2-(acetylamino)-N-[1-[3-[1,6-dihydro-1-methyl-4-(methylamino)imidazo[4,5-d]pyrrolo[2,3-b]pyridin-7-yl]phenyl]ethyl]-acetamide | 2.14 | 420.57 |
| A163 | Me2NC(CH3)2 | N-[1-[3-[1,6-dihydro-1-methyl-4-(methylamino)imidazo[4,5-d]pyrrolo[2,3-b]pyridin-7-yl]phenyl]ethyl]-2-(dimethylamino)-acetamide | 2.00 | 406.61 |

TABLE A5-continued

Enantiomer B

[Structure: phenyl-pyrrolopyridine-imidazole core with Me-CH(*)-NH-C(=O)-R substituent]

| Ex. | R | Name | HPLC Retention (min) | MS Reported |
|---|---|---|---|---|
| A164 | Me-CH(Me)-CH2- (isobutyl) | N-[1-[3-[1,6-dihydro-1-methyl-4-(methylamino)imidazo[4,5-d]pyrrolo[2,3-b]pyridin-7-yl]phenyl]ethyl]-3-methyl-butanamide | 2.70 | 405.61 |
| A165 | Me2CH-CH2-CH2- | N-[1-[3-[1,6-dihydro-1-methyl-4-(methylamino)imidazo[4,5-d]pyrrolo[2,3-b]pyridin-7-yl]phenyl]ethyl]-4-methyl-pentanamide | 2.90 | 419.61 |
| A166 | Me3C-CH2- (neopentyl) | N-[1-[3-[1,6-dihydro-1-methyl-4-(methylamino)imidazo[4,5-d]pyrrolo[2,3-b]pyridin-7-yl]phenyl]ethyl]-3,3-dimethyl-butanamide | 2.89 | 419.55 |
| A167 | MeO-CH2-CH2- | N-[1-[3-[1,6-dihydro-1-methyl-4-(methylamino)imidazo[4,5-d]pyrrolo[2,3-b]pyridin-7-yl]phenyl]ethyl]-3-methoxy-propanamide | 2.32 | 407.57 |

Example A168

1,6-dihydro-1-methyl-4-(methylamino)-imidazo[4,5-d]pyrrolo[2,3-b]pyridine-7-carboxylic acid

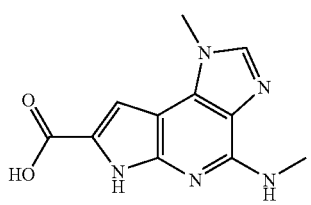

A168

A168.1: 4-[[(1,1-dimethylethoxy)carbonyl]methylamino]-1,6-dihydro-1-methylimidazo[4,5-d]pyrrolo[2,3-b]pyridine-7-carboxylic acid

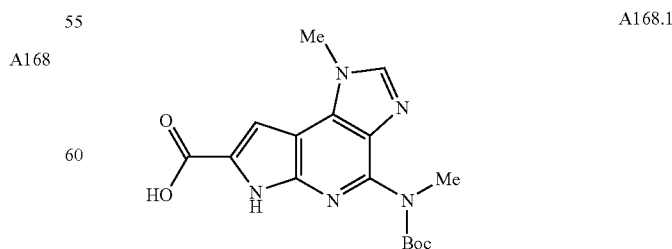

A168.1

A1.12 (0.3 g, 0.74 mmol), pyruvic acid (98 mg, 1.12 mmol), triethylamine and palladium dibenzylidene acetone (68 mg, 0.074 mmol) in dry DMF (3 mL) were heated to 120 C for 15 min in a microwave. The reaction mixture was diluted with water (3 mL) and extracted with ethyl acetate (10 mL). The organic extract was discarded and the aqueous layer acidified to pH 3-4 using 1N HCl. The acidified aqueous layer was then extracted with ethyl acetate (3×20 mL), the combined organics dried (MgSO$_4$) and evaporated in vacuo to give A168.1 (161 mg, 62%). HPLC YMC S-5 4.6×33 mm (2 min grad): retention time 1.32 min, M+H$^+$=346.31, NMR (400 MHz, DMSO) δ 12.49 (s, 1H), 8.16 (s, 1H), 7.47 (s, 1H), 4.04 (s, 3H), 3.29 (s, 3H), 1.30 (s, 9H).

A168.2: 1,6-dihydro-1-methyl-4-(methylamino)-imidazo[4,5-d]pyrrolo[2,3-b]pyridine-7-carboxylic acid A168.1 (20 mg, 0.058 mmol) was dissolved in 4N HCl in dioxane (3 mL) and the resulting suspension stirred at room temperature for 3 hrs. The reaction mixture was evaporated in vacuo, triturated with diethyl ether, then filtered to give A168 (11.2 mg, 88%). HPLC YMC S-5 4.6×33 mm (2 min grad): retention time 0.83 min, M+H$^+$=246.15. NMR (400 MHz, DMSO) δ 8.65 (s, 1H), 7.42 (s, 1H), 4.10 (s, 3H), 3.10 (s, 3H).

Examples A169-A172

Examples A169-A172 were prepared by parallel synthesis according to the scheme shown below.

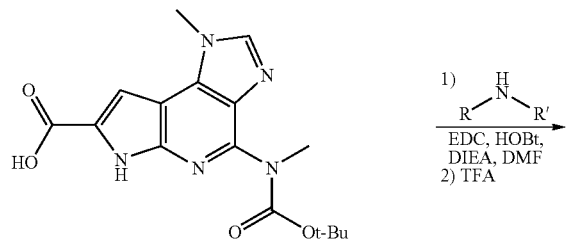

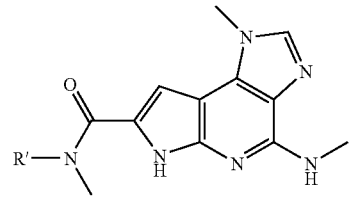

To an individual well in a Bohdan XT® reactor was added 150 uL of a 0.25 M solution of the carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq). The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and the BOC group was removed by adding 600 uL of a 30% by volume solution of trifluoroacetic acid (TFA) in dichloromethane (DCM) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS (H$_2$O/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$O/MeOH/0.1% TFA). Compounds were isolated as trifluoroacetate salts. Examples prepared by this method are described in Table A6.

TABLE A6

| Ex. | R | Name | HPLC Retention (min) | MS Reported |
|---|---|---|---|---|
| A169 | Me, Me (isopropyl) | 1,6-dihydro-1-methyl-4-(methyl amino)-N-(1-methylethyl)-imidazo[4,5-d]pyrrolo[2,3-b]pyridine-7-carboxamide | 1.76 | 287.51 |
| A170 | F$_3$C | 1,6-dihydro-1-methyl-4-(methylamino)-N-(2,2,2-trifluoroethyl)-imidazo[4,5-d]pyrrolo[2,3-b]pyridine-7-carboxamide | 1.81 | 327.52 |

TABLE A6-continued

| Ex. | R | Name | HPLC Retention (min) | MS Reported |
|---|---|---|---|---|
| A171 | Me-CH2-NH- | N-ethyl-1,6-dihydro-1-methyl-4-(methylamino)-imidazo[4,5-d]pyrrolo[2,3-b]pyridine-7-carboxamide | 1.51 | 273.46 |
| A172 | PhCH2-NH- | 1,6-dihydro-1-methyl-4-(phenylmethyl)-imidazo[4,5-d]pyrrolo[2,3-b]pyridine-7-carboxamide | 2.20 | 335.51 |

Examples A173-A213

Examples A173-A213 was prepared by parallel synthesis according to the scheme shown below.

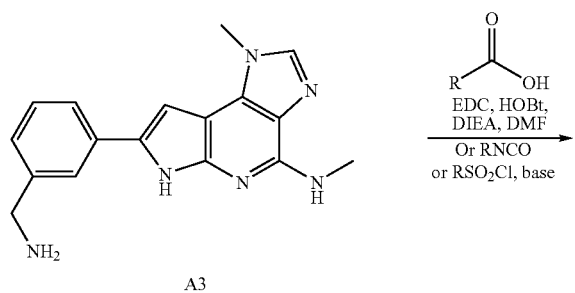

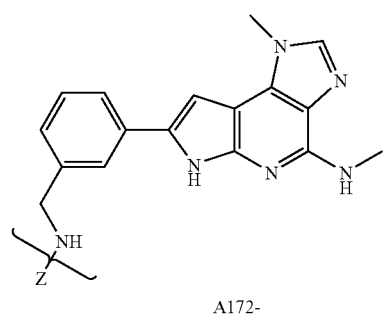

A172-

To an individual well in a Bohdan XT® reactor was added 150 uL of a 0.25 M solution of either a carboxylic acid in dimethylformamide (DMF) (0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq) or an isocyanate or sulfonylchloride reagent with pyridine in similar molar ratio to the carboxylic acid reagent. The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) to each reactor (that had a BOC group) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS ($H_2O$/MeOH/0.1% TFA, gradient 35-90% MeOH over 15 min, 20×100 mm 5 µm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS ($H_2O$/MeOH/0.1% TFA). Compounds were isolated as trifluoroacetate salts. Examples prepared by this method are described in Table A7.

TABLE A7

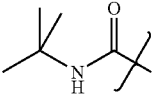

| Ex. | Z | Name | HPLC Retention (min) | MS Reported |
|---|---|---|---|---|
| A173 | 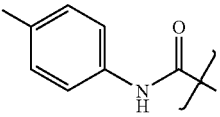 | N-[[3-[1,6-dihydro-1-methyl-4-(methylamino)imidazo[4,5-d]pyrrolo[2,3-b]pyridin-7-yl]phenyl]methyl]-N'-(1,1-dimethylethyl)-urea | 2.68 | 406.62 |
| A174 | 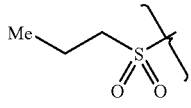 | N-[[3-[1,6-dihydro-1-methyl-4-(methylamino)imidazo[4,5-d]pyrrolo[2,3-b]pyridin-7-yl]phenyl]methyl]-N'-(4-methoxyphenyl)-urea | 2.72 | 456.56 |
| A175 | 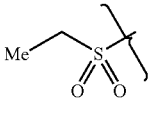 | N-[[3-[1,6-dihydro-1-methyl-4-(methylamino)imidazo[4,5-d]pyrrolo[2,3-b]pyridin-7-yl]phenyl]methyl]-1-propanesulfonamide | 2.54 | 413.55 |
| A176 | 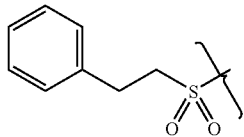 | N-[[3-[1,6-dihydro-1-methyl-4-(methylamino)imidazo[4,5-d]pyrrolo[2,3-b]pyridin-7-yl]phenyl]methyl]-ethanesulfonamide | 2.29 | 399.55 |
| A177 | 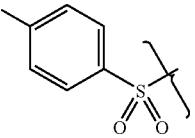 | N-[[3-[1,6-dihydro-1-methyl-4-(methylamino)imidazo[4,5-d]pyrrolo[2,3-b]pyridin-7-yl]phenyl]methyl]-benzeneethanesulfonamide | 2.96 | 475.49 |
| A178 | 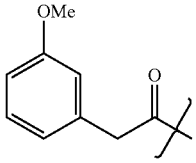 | N-[[3-[1,6-dihydro-1-methyl-4-(methylamino)imidazo[4,5-d]pyrrolo[2,3-b]pyridin-7-yl]phenyl]methyl]-4-methoxy-benzenesulfonamide | 2.79 | 477.48 |
| A179 | 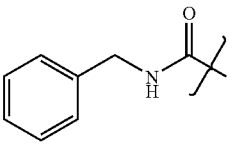 | N-[[3-[1,6-dihydro-1-methyl-4-(methylamino)imidazo[4,5-d]pyrrolo[2,3-b]pyridin-7-yl]phenyl]methyl]-3-methoxy-benzeneacetamide | 2.67 | 455.55 |
| A180 | | N-[[3-[1,6-dihydro-1-methyl-4-(methylamino)imidazo[4,5-d]pyrrolo[2,3-b]pyridin-7-yl]phenyl]methyl]-N'-(phenylmethyl)-urea | 2.69 | 440.57 |

TABLE A7-continued

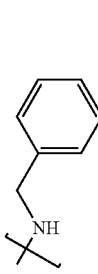

| Ex. | Z | Name | HPLC Retention (min) | MS Reported |
|---|---|---|---|---|
| A181 | 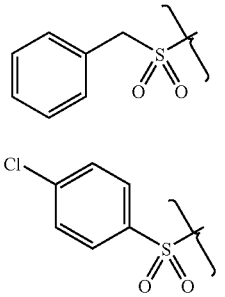 | N-[[3-[1,6-dihydro-1-methyl-4-(methylamino)imidazo[4,5-d]pyrrolo[2,3-b]pyridin-7-yl]phenyl]methyl]-benzenemethanesulfonamide | 2.80 | 461.55 |
| A182 | 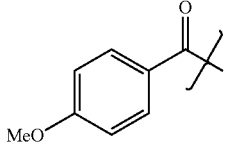 | 4-chloro-N-[[3-[1,6-dihydro-1-methyl-4-(methylamino)imidazo[4,5-d]pyrrolo[2,3-b]pyridin-7-yl]phenyl]methyl]-benzenesulfonamide | 3.00 | 481.46 |
| A183 | 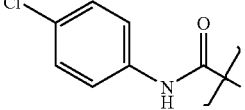 | N-[[3-[1,6-dihydro-1-methyl-4-(methylamino)imidazo[4,5-d]pyrrolo[2,3-b]pyridin-7-yl]phenyl]methyl]-4-methoxy-benzamide | 2.76 | 441.55 |
| A184 | 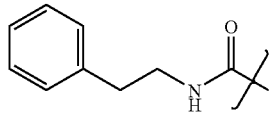 | N-(4-chlorophenyl)-N'-[[3-[1,6-dihydro-1-methyl-4-(methylamino)imidazo[4,5-d]pyrrolo[2,3-b]pyridin-7-yl]phenyl]methyl]-urea | 3.10 | 460.49 |
| A185 | 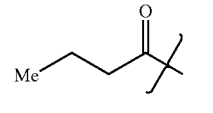 | N-[[3-[1,6-dihydro-1-methyl-4-(methylamino)imidazo[4,5-d]pyrrolo[2,3-b]pyridin-7-yl]phenyl]methyl]-N'-(2-phenylethyl)-urea | 2.87 | 454.61 |
| A186 | 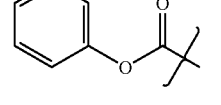 | N-[[3-[1,6-dihydro-1-methyl-4-(methylamino)imidazo[4,5-d]pyrrolo[2,3-b]pyridin-7-yl]phenyl]methyl]-butanamide | 2.47 | 377.64 |
| A187 | 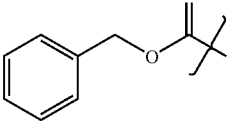 | [[3-[1,6-dihydro-1-methyl-4-(methylamino)imidazo[4,5-yl]phenyl]methyl]-carbamic acid, phenyl ester | 2.83 | 427.55 |
| A188 |  | [[3-[1,6-dihydro-1-methyl-4-(methylamino)imidazo[4,5-d]pyrrolo[2,3-b]pyridin-7-yl]phenyl]methyl]-carbamic acid, phenylmethyl ester | 2.95 | 441.55 |

TABLE A7-continued

| Ex. | Z | Name | HPLC Retention (min) | MS Reported |
|---|---|---|---|---|
| A189 | (ethyl ester group) | [[3-[1,6-dihydro-1-methyl-4-(methylamino)imidazo[4,5-d]pyrrolo[2,3-b]pyridin-7-yl]phenyl]methyl]-carbamic acid, ethyl ester | 2.54 | 379.60 |
| A190 | (2-methylpropyl ester group) | [[3-[1,6-dihydro-1-methyl-4-(methylamino)imidazo[4,5-d]pyrrolo[2,3-b]pyridin-7-yl]phenyl]methyl]-carbamic acid, 2-methylpropyl ester | 2.94 | 407.60 |
| A191 | (4-methoxyphenyl ester group) | [[3-[1,6-dihydro-1-methyl-4-(methylamino)imidazo[4,5-d]pyrrolo[2,3-b]pyridin-7-yl]phenyl]methyl]-carbamic acid, 4-methoxyphenyl ester | 2.95 | 457.55 |
| A192 | (methyl ester group) | [[3-[1,6-dihydro-1-methyl-4-(methylamino)imidazo[4,5-d]pyrrolo[2,3-b]pyridin-7-yl]phenyl]methyl]-carbamic acid, methyl ester | 2.36 | 365.60 |
| A193 | (4-chlorophenyl ester group) | [[3-[1,6-dihydro-1-methyl-4-(methylamino)imidazo[4,5-d]pyrrolo[2,3-b]pyridin-7-yl]phenyl]methyl]-carbamic acid, 4-chlorophenyl ester | 3.12 | 461.49 |
| A194 | (phenyl urea group) | N-[[3-[1,6-dihydro-1-methyl-4-(methylamino)imidazo[4,5-d]pyrrolo[2,3-b]pyridin-7-yl]phenyl]methyl]-N'-phenyl-urea | 2.77 | 426.57 |
| A195 | (benzenesulfonamide group) | N-[[3-[1,6-dihydro-1-methyl-4-(methylamino)imidazo[4,5-d]pyrrolo[2,3-b]pyridin-7-yl]phenyl]methyl]-benzenesulfonamide | 2.75 | 447.53 |
| A196 | (2R-amino hydroxy group) | (2R)-2-amino-N-[[3-[1,6-dihydro-1-methyl-4-(methylamino)imidazo[4,5-d]pyrrolo[2,3-b]pyridin-7-yl]phenyl]methyl]-3-hydroxy-3-methylbutanamide | 1.96 | 422.59 |
| A197 | (2S-amino hydroxy group) | (2S)-2-amino-N-[[3-[1,6-dihydro-1-methyl-4-(methylamino)imidazo[4,5-d]pyrrolo[2,3-b]pyridin-7-yl]phenyl]methyl]-3-hydroxy-3-methylbutanamide | 1.96 | 422.62 |

TABLE A7-continued

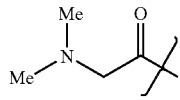

| Ex. | Z | Name | HPLC Retention (min) | MS Reported |
|---|---|---|---|---|
| A198 | 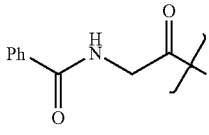 | N-[[3-[1,6-dihydro-1-methyl-4-(methylamino)imidazo[4,5-d]pyrrolo[2,3-b]pyridin-7-yl]phenyl]methyl]-3-(dimethylamino)-propanamide | 1.86 | 406.61 |
| A199 | 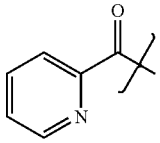 | N-[2-[[[3-[1,6-dihydro-1-methyl-4-(methylamino)imidazo[4,5-d]pyrrolo[2,3-b]pyridin-7-yl]phenyl]methyl]amino]-2-oxoethyl]-benzamide | 2.40 | 468.54 |
| A200 | 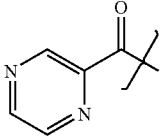 | N-[[3-[1,6-dihydro-1-methyl-4-(methylamino)imidazo[4,5-d]pyrrolo[2,3-b]pyridin-7-yl]phenyl]methyl]-3-pyridinecarboxamide | 2.09 | 412.56 |
| A201 | 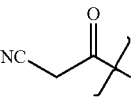 | N-[[3-[1,6-dihydro-1-methyl-4-(methylamino)imidazo[4,5-d]pyrrolo[2,3-b]pyridin-7-yl]phenyl]methyl]-2-pyrazinecarboxamide | 2.37 | 413.55 |
| A202 | 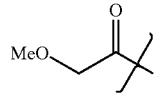 | 2-cyano-N-[[3-[1,6-dihydro-1-methyl-4-(methylamino)imidazo[4,5-d]pyrrolo[2,3-b]pyridin-7-yl]phenyl]methyl]-acetamide | 2.10 | 374.57 |
| A203 | 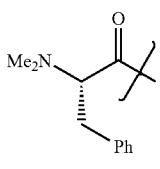 | N-[[3-[1,6-dihydro-1-methyl-4-(methylamino)imidazo[4,5-d]pyrrolo[2,3-b]pyridin-7-yl]phenyl]methyl]-2-methoxy-acetamide | 2.18 | 379.62 |
| A204 | 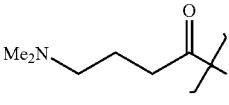 | (alphaS)-N-[[3-[1,6-dihydro-1-methyl-4-(methylamino)imidazo[4,5-d]pyrrolo[2,3-b]pyridin-7-yl]phenyl]methyl]-alpha-(dimethylamino)benzenepropanamide | 2.34 | 482.56 |
| A205 | Me₂N | N-[[3-[1,6-dihydro-1-methyl-4-(methylamino)imidazo[4,5-d]pyrrolo[2,3-b]pyridin-7-yl]phenyl]methyl]-4-(dimethylamino)-butanamide | 1.90 | 420.62 |

TABLE A7-continued

| Ex. | Z | Name | HPLC Retention (min) | MS Reported |
|---|---|---|---|---|
| A206 | | N-[[3-[1,6-dihydro-1-methyl-4-(methylamino)imidazo[4,5-d]pyrrolo[2,3-b]pyridin-7-yl]phenyl]methyl]-1-piperidinepropanamide | 1.98 | 445.84 |
| A207 | | N-[[3-[1,6-dihydro-1-methyl-4-(methylamino)imidazo[4,5-d]pyrrolo[2,3-b]pyridin-7-yl]phenyl]methyl]-cyclohexaneacetamide | 3.00 | 431.61 |
| A208 | | (alphaS)-N-[[3-[1,6-dihydro-1-methyl-4-(methylammo)imidazo[4,5-d]pyrrolo[2,3-b]pyridin-7-yl]phenyl]methyl-alpha-methoxy-alpha-(trifluoromethyl)benzeneacetamide | 3.04 | 523.50 |
| A209 | | (alphaR)-N-[[3-[1,6-dihydro-1-methyl-4-(methylamino)imidazo[4,5-d]pyrrolo[2,3-b]pyridin-7-yl]phenyl]methyl]-alpha-methoxy-alpha-(trifluoromethyl)benzeneacetamide | 3.03 | 523.52 |
| A210 | | N-[[3-[1,6-dihydro-1-methyl-4-(methylamino)imidazo[4,5-d]pyrrolo[2,3-b]pyridin-7-yl]phenyl]methyl]-alpha-hydroxy-alpha-methyl-benzeneacetamide | 2.57 | 455.56 |
| A211 | | N-[[3-[1,6-dihydro-1-methyl-4-(methylamino)imidazo[4,5-d]pyrrolo[2,3-b]pyridin-7-yl]phenyl]methyl]-2,5-dioxo-4-imidazolidineacetamide | 1.96 | 447.54 |
| A212 | | N-[[3-[1,6-dihydro-1-methyl-4-(methylamino)imidazo[4,5-d]pyrrolo[2,3-b]pyridin-7-yl]phenyl]methyl]-3,3,3-trifluoro-2-hydroxy-2-methyl-propanamide | 2.42 | 447.50 |
| A213 | | N-[[3-[1,6-dihydro-1-methyl-4-(methylamino)imidazo[4,5-d]pyrrolo[2,3-b]pyridin-7-yl]phenyl]methyl]-2-hydroxy-2-methyl-propanamide | 2.17 | 393.61 |

Example A214

N-[[6-[1,6-dihydro-1-methyl-4-(methylamino)imidazo[4,5-d]pyrrolo[2,3-b]pyridin-7-yl]-2-pyridinyl]methyl]-acetamide

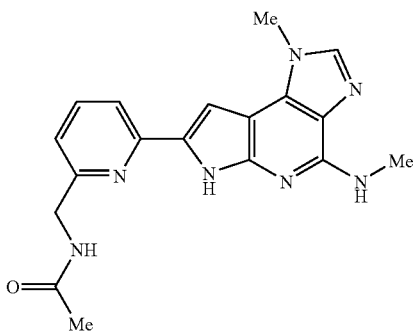

A214

A214.1: 2-((6-Bromopyridin-2-yl)methyl)isoindoline-1,3-dione

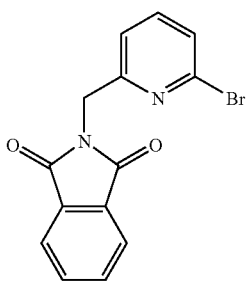

A214.1

A mixture of commercially available (6-bromopyridin-2-yl)methanol (20.0 g, 0.106 mol), phthalimide (20.4 g, 0.138 mol), and triphenylphosphine (36.2 g, 0.138 mol), and 1,1'-(azodicarbonyl)-dipiperidine (34.8 g, 0.138 mol) in anhydrous tetrahydrofuran (1 L) was stirred at room temperature overnight. The precipitate was collected by vacuum filtration and washed with tetrahydrofuran. The filtrate was concentrated under reduced pressure, and the solid residue was triturated with methanol with sonication. A214.1 was collected by vacuum filtration and was dried well to give 24.1 g as a white solid. The filtrate still contained significant product which could be isolated as a second crop with methanol trituration. The compound had an HPLC retention time=2.32 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=317.15 and 319.15.

Alternate Preparation of A214.1

A214.1a: 2-Chloromethyl-6-bromopyridine

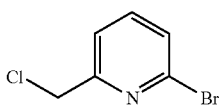

A214.1a

A 1000 mL round bottom flask was flame dried, then cooled under a stream of dry nitrogen. To the flask was added commercially available 6-bromopyridin-2-yl)methanol (25 g, 133 mmol) along with dichloromethane (300 mL). While stirring at room temperature under a nitrogen atmosphere, thionyl chloride (14.5 mL, 199.4 mmol) was added dropwise over 7 to 8 minutes. A white precipitate immediately formed, then redissolved after 10-15 minutes to give a clear, pale yellow solution. After 20-25 minutes post addition, a precipitate re-formed. The reaction was stirred for 3 hours at room temperature then an additional aliquot of thionyl chloride (3.5 mL) was added and the reaction was stirred for 45 minutes. The solution was evaporated to dryness to give the hydrochloride salt of A214.1a as a pale yellow solid (95% purity by HPLC analysis). The material was used for subsequent reactions without further purification. The compound had an HPLC retention time=2.21 min. (Column: Chromolith SpeedROD 4.6×50 mm—4 min.; Solvent A=10% MeOH, 90% $H_2O$, and 0.2% $H_3PO_4$; Solvent B=90% MeOH, 10% $H_2O$, and 0.2% $H_3PO_4$) and a LC/MS $M^{+1}$=208.2 (100% peak).

Alternate Preparation A214.1a 6-bromopyridin-2-yl)methanol (1 kg) was dissolved in dichloromethane (10 L). Thionyl chloride (3 kg) was added dropwise and the reaction mixture stirred at room temperature for 6 h. TLC analysis indicated disappearance of the starting material. The solvent was removed under reduced pressure and diluted with additional dichloromethane (2 L) and the solvent was removed under reduced pressure. The crude product A214.1a (1.25 kg) contained some residual solvent. The material was used in the next step without further purification.

A214.1: 2-((6-Bromopyridin-2-yl)methyl)isoindoline-1,3-dione

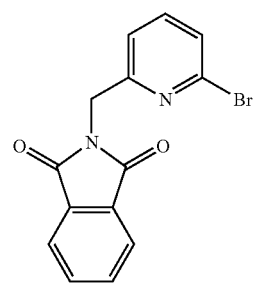

A214.1

Alternate Preparation:

A214.1a (133 mmol) was dissolved in DMF (250 mL) and potassium phthalimide (54.2 g, 293 mmol) was added portionwise to maintain the internal temperature below 30° C. An additional portion of DMF (50 mL) was used to rinse the flask and powder funnel used for the potassium phthalimide addition. The reaction was stirred at room temperature overnight after which the reaction was judged complete by HPLC analysis. Water (600 mL) was added slowly to the reaction and after 30 minutes of stirring the resulting precipitate was collected by filtration, washed with several portions of water (1000 mL total) and allowed to air dry. The resulting solid, which contained the desired product along with excess phthalimide, was resuspended in water (700 mL) and the solution was made basic by addition of 1 N NaOH (3 mL). After slurrying for 20 minutes the solids were collected by filtration, washed with several portions of water and allowed to air dry. The solid still contained some phthalimide so was resuspended in MeOH (50 mL) and water (800 mL) and allowed to stir vigorously for 2 days. The solid was again collected by filtration, then slurried in hot MeOH (200-300 mL), cooled to room temperature and filtered. The solid was air dried to afford the phthalimide adduct, A214.1, along with residual phthalimide as a white solid. This material was used without further purification for the next step.

Alternate Preparation:

Potassium pthalimide (1.23 kg, 6.0 mol), potassium carbonate (2.07 kg, 15 mol) were dissolved in DMF (12.5 L). A214.1a was added slowly and the reaction stirred at room temperature overnight. TLC analysis indicated disappearance of starting material. The product was filtered to yield A214.1 (2.5 kg wet weight—used in next step without further drying).

A214.2: (6-Bromopyridin-2-yl)methanamine

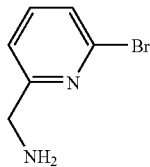

A214.2

A suspension of A214.1 in absolute ethanol (420 mL) was heated at 70° C. for 30 min. To the heterogeneous solution was added hydrazine monohydrate. Within a minute, the reaction mixture became homogeneous. The reaction mixture was heated for 3 hr., during which time the mixture solidified into a white solid. An additional 100 mL of ethanol was added, and the mixture was filtered. The precipitate was washed well with ethanol, and the filtrate was partially concentrated. The solid was collected by vacuum filtration. The filtrated was concentrated to dryness and triturated with methanol. A214.2 was collected by vacuum filtration to give 14.3 g (93%) as a white solid. The compound had an HPLC retention time=0.395 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=187.12 and 189.12.

Alternate Preparation A214.2

A214.1 (1.8 kg, 5.7 mol) was suspended in methanol (18 L) at 65° C. Hydrazine hydrate (1.5 kg, 28 mol) was added over 30 minutes in 500 g batches. After 15 minutes the reaction became homogenious and was heated for 4 hours at 65° C. TLC analysis showed the disappearance of starting material. The reaction mixture was allowed to cool. The product was filtered and washed with additionl methanol, stirred with methyl t-butyl ether, filtered and dried to yield A214.2 (800 g, 75%).

A214.3: N-((6-Bromopyridin-2-yl)methyl)acetamide

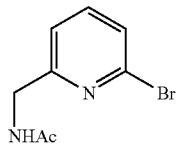

A214.3

To a mixture of A214.2 (14.3 g, 76.5 mmol) and pyridine (14.3 mL) in anhydrous tetrahydrofuran (250 mL) was added acetic anhydride (14.3 mL), and the reaction mixture was stirred for 3 hr at room temperature. The solvent was removed under reduced pressure, and the oily residue was diluted with dichloromethane, washed with water, washed with a saturated aqueous solution of sodium bicarbonate, and dried over anhydrous sodium sulfate. Concentration followed by drying under reduced pressure afforded 16.3 g (93%) of A214.3 as an off-white solid. The compound had an HPLC retention time=0.987 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=229.10 and 231.10.

A214.4: N-((6-((Trimethylsilyl)ethynyl)pyridin-2-yl)methyl)acetamide

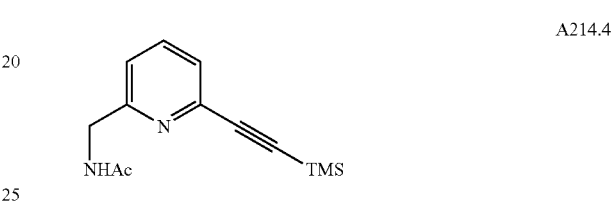

A214.4

To a mixture of A214.3 (8.0 g, 34.9 mmol), dichlorobis(triphenylphosphine)palladium II (1.47 g, 2.09 mmol), and copper iodide (0.332 g, 1.75 mmol) in anhydrous dimethylformamide (90 mL) degassed well with nitrogen was added trimethylsilylacetylene (7.4 mL, 52.4 mmol) followed by triethylamine (24.3 mL, 0.175 mol). The reaction mixture was immersed in an oil bath at 75° C. and stirred for 2 hr. The solvent was removed under reduced pressure, and the residue was purified by flash silica gel chromatography using a mixture of methanol in dichloromethane (2%-5%) to give 7.42 g (86%) of A214.4 as a reddish, viscous oil. The compound had an HPLC retention time=2.42 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=247.20.

A214.5: N-((6-Ethynylpyridin-2-yl)methyl)acetamide

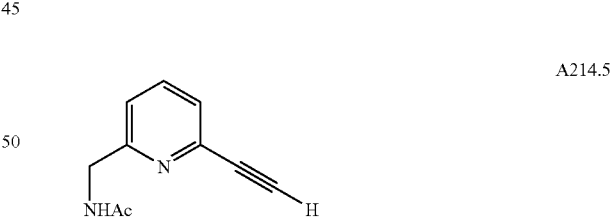

A214.5

A mixture of A214.4 (4.96 g, 20.1 mmol) and catalytic potassium carbonate (0.295 g, 2.13 mmol) in anhydrous methanol (50 mL) was stirred at room temperature for 10 min. The residual potassium carbonate was removed by vacuum filtration, and the filtrate was concentrated under reduced pressure. The residue was purified by flash silica gel chromatography using a mixture of methanol in dichloromethane (2%-5%) to afford 2.64 g (75%) of A214.5 as a tan solid. The compound had an HPLC retention time=0.602 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=175.20.

A214.6 tert-Butyl 7-((6-(acetamidomethyl)pyridin-2-yl)ethynyl)-6-amino-1-methyl-1H-imidazo-[4,5-c]pyridin-4-yl(methyl)carbamate

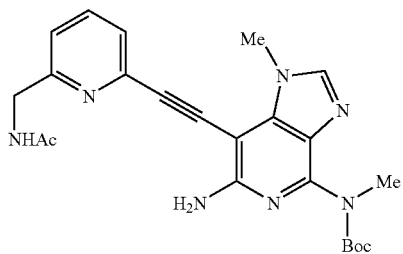

A214.6

To a mixture of A214.5 (1.00 g, 5.74 mmol), tert-Butyl6-amino-7-iodo-1-methyl-1H-imidazo[4,5-c]pyridin-4-yl(methyl)carbamate (1.78 g, 4.42 mmol), dichlorobis(triphenylphosphine)palladium II (0.186 g, 0.265 mmol), and copper iodide (0.042 g, 0.221 mmol) in anhydrous dimethylformamide (12 mL) degassed well with nitrogen was added diisopropylamine (15 mL, 0.111 mol). The reaction mixture was immersed in an oil bath at 75° C. and stirred for 45 min. The solvent was removed under reduced pressure, and the residue was purified by flash silica gel chromatography using a mixture of methanol in dichloromethane (5%-8%) to give 1.88 g (95%) of A214.6 as a tan solid. The compound had an HPLC retention time=2.13 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=450.35.

A214.7: tert-Butyl 7-(6-(acetamidomethyl)pyridin-2-yl)-1-methyl-1,6-dihydroimidazo[4,5-d]pyrrolo[2,3-b]pyridin-4-yl(methyl)carbamate

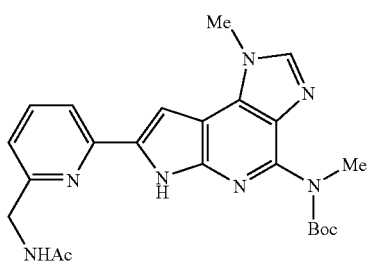

A214.7

To a solution of A214.6 (1.95 g, 4.34 mmol) in 25 mL of anhydrous dimethylacetamide under nitrogen was added a 1.0 M solution of potassium tert-butoxide in tetrahydrofuran (4.8 mL, 4.77 mmol), and the reaction mixture was heated for 10 min. A second 4.8 mL was added, and the reaction was still incomplete after an addition 10 min. A third equivalent was added, and the reaction mixture was stirred for 10 min. by HPLC and TLC, the reaction was complete. The solvent was removed under reduced pressure, and the residue was purified by flash silica gel chromatography using a 5% mixture of methanol in dichloromethane to give 0.780 g of A214.7 as a yellow solid and 0.284 g of 1 as a yellow solid. The combined products represented >55% yield. The compound (1G) had an HPLC retention time=2.20 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=450.37.

A214.8: N-[[6-[1,6-dihydro-1-methyl-4-(methylamino)imidazo[4,5-d]pyrrolo[2,3-b]pyridin-7-yl]-2-pyridinyl]methyl]-acetamide A solution of A214.7 (0.394 g, 0.876 mmol) in trifluoroacetic acid (14 mL) was stirred at room temperature for 10 min. The trifluoroacetic acid was removed under reduced pressure, and the residue was diluted with dichloromethane, washed with a saturated aqueous solution of sodium bicarbonate, and dried over anhydrous sodium sulfate. After filtration, the sodium sulfate remained a bright yellow and was subsequently washed with ethyl acetate followed by a 5% mixture of methanol in dichloromethane, which removed the color. The combined organic layers were concentrated and purified by flash silica gel chromatography using a 5% methanol in dichloromethane to give 275 g (90%) of A214 as a yellow solid. The compound had an HPLC retention time=1.73 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=350.35. $^1$H NMR (400 MHz, DMSO-d6) δ ppm 1.98 (s, 3 H) 2.98 (d, J=4.83 Hz, 3 H) 4.02 (s, 3 H) 4.40 (d, J=5.27 Hz, 2H) 6.69 (d, J=4.83 Hz, 1 H) 7.02 (d, J=7.47 Hz, 1 H) 7.32 (d, J=1.76 Hz, 1 H) 7.67-7.75 (m, 2 H) 7.90 (s, 1 H) 8.56 (t, J=5.27 Hz, 1 H) 11.77 (s, 1 H)

Example A215

7-[6-(aminomethyl)-2-pyridinyl]-1,6-dihydro-N,1-dimethyl-imidazo[4,5-d]pyrrolo[2,3-b]pyridin-4-amine

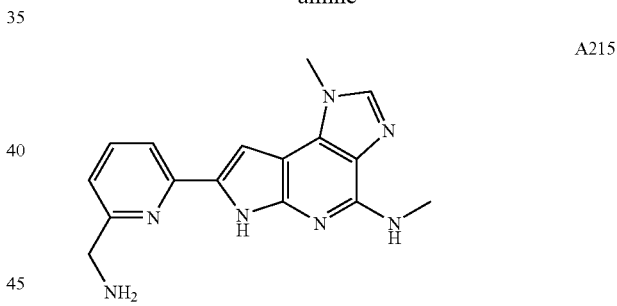

A215

A mixture of A214 (0.168 g, 0.481 mmol), n-butanol (3 mL), and concentrated hydrochloric acid (2 mL) was heated in the microwave at 150° C. for 30 min. The reaction mixture was concentrated to dryness under reduced pressure, and the residue was diluted with dichloromethane, washed with a mixture of saturated aqueous solution of sodium bicarbonate and 1N aqueous sodium hydroxide, and dried over anhydrous sodium sulfate. Concentration under reduced pressure afforded 0.028 g of A215 as a yellow solid. Additional product was still in the aqueous layer. Further extractions with ethyl acetate and dichloromethane afforded an additional 88 mg of A215. The compound had an HPLC retention time=1.66 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS M+$^1$=308.33. $^1$H NMR (400 MHz, CDCl$_3$) δ ppm 1.68 (brs, 2 H) 3.18 (d, J=5.27 Hz, 3 H) 3.94 (d, J=4.39 Hz, 2 H) 3.97-4.02 (m, 1 H) 4.04 (s, 3 H) 5.54 (d, J=5.27 Hz, 1 H) 6.98-7.03 (m, 2 H) 7.49-7.53 (m, 1 H) 7.55-7.63 (m, 2 H) 9.86 (s, 1 H)

A215.1: 7-(6-(Aminomethyl)pyridin-2-yl)-N,1-dimethyl-1,6-dihydroimidazo[4,5-d]pyrrolo[2,3-b]pyridin-4-amine trihydrochloride

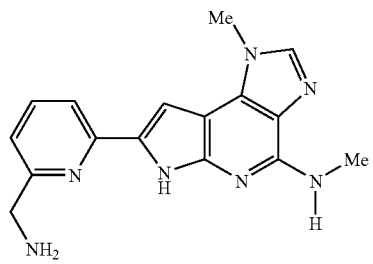

3xHCl
A215.1-trihydrochloride salt

A mixture of A214 (1.60 g, 3.55 mmol), absolute ethanol (30 mL), and concentrated hydrochloric acid (30 mL) was heated at 80° C. for 7 hr. The reaction mixture was concentrated to dryness and dried well under reduced pressure to give 1.48 g (100%) of A215-trihydrochloride salt as a yellow solid. The compound had an HPLC retention time=1.23 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=308.35.

Example A216

N-[[6-[1,6-dihydro-1-methyl-4-(methylamino)imidazo[4,5-d]pyrrolo[2,3-b]pyridin-7-yl]-2-pyridinyl]methyl]-3-methoxy-propanamide

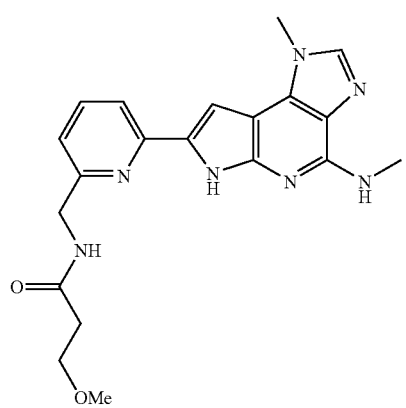

A216

To a mixture of A215 (0.020 g, 0.065 mmol), 1-(3-dimethylaminopropyl)-3-ethylcarbodiimide hydrochloride (0.019 g, 0.098 mmol), 1-hydroxybenzotriazole (0.013 g, 0.098 mmol), and diisopropylethylamine (0.034 mL, 0.195 mmol) in anhydrous dimethylformamide (2 mL) was added 3-methoxypropionic acid (9.20 µL, 0.098 mmol). The reaction mixture was stirred at room temperature overnight (After ~3 hr, the reaction mixture became homogenous). The solvent was removed under reduced pressure, and the residue was diluted with dichloromethane, washed with water, and dried over anhydrous sodium sulfate. Concentration under pressure followed by purification by flash silica gel chromatography using a 5% mixture of methanol in dichloromethane afforded 0.018 g (69%) of A216 as a yellow solid. The compound had an HPLC retention time=1.84 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=394.37. $^1$H NMR (400 MHz, $CDCl_3$) δ ppm 2.62 (t, J=7.15 Hz, 2 H) 3.15 (d, J=6.60 Hz, 3 H) 3.54 (s, 3 H) 3.78 (t, J=7.15 Hz, 2 H) 4.01 (s, 3 H) 4.56 (d, J=6.10 Hz, 2 H) 5.49-5.54 (m, 1 H) 6.96-6.98 (m, 2 H) 7.51-7.58 (m, 3 H) 9.98 (s, 1 H)

Example A217

N-[[6-[1,6-dihydro-1-methyl-4-(methylamino)imidazo[4,5-d]pyrrolo[2,3-b]pyridin-7-yl]-2-pyridinyl]methyl]-2,2-dimethyl-propanamide

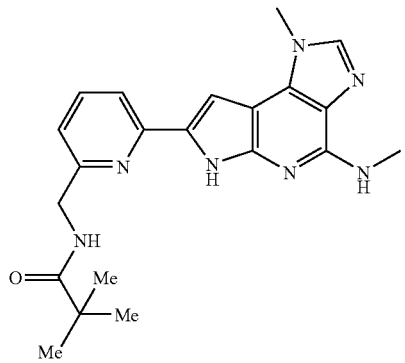

A217

To a mixture of A215 (0.020 g, 0.065 mmol) and triethylamine (0.045 mL, 0.326 mmol) in dichloromethane (2 mL) was added trimethylacetyl chloride (9.00 µL, 0.072 mmol). The reaction mixture was stirred at room temperature for 30 min. The reaction mixture was diluted with dichloromethane, washed with water, and dried over anhydrous sodium sulfate. Concentration under pressure followed afforded 0.020 g (80%) of A217 as a yellow solid. The compound had an HPLC retention time=2.11 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=392.42.

Example A218

N-[[6-[1,6-dihydro-1-methyl-4-(methylamino)imidazo[4,5-d]pyrrolo[2,3-b]pyridin-7-yl]-2-pyridinyl]methyl]-cyclopropanecarboxamide

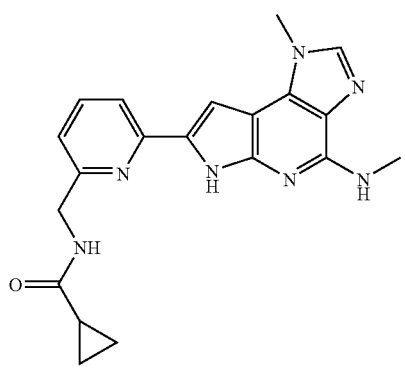

A218

To a mixture of A215 (0.020 g, 0.065 mmol), 1-(3-dimethylaminopropyl)-3-ethylcarbodiimide hydrochloride (0.019 g, 0.098 mmol), 1-hydroxybenzotriazole (0.013 g, 0.098 mmol), and diisopropylethylamine (0.034 mL, 0.195 mmol) in anhydrous dimethylformamide (2 mL) was added cyclopropylcarboxylic acid (8.00 µL, 0.098 mmol). The reaction mixture was stirred at room temperature overnight. Concentration under pressure followed by purification by flash silica gel chromatography using a 5% mixture of methanol in dichloromethane afforded 0.012 g (50%) of A218 as a yellow solid. The compound had an HPLC retention time=1.99 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=376.40.

Examples A219-A245

Examples A219-A245 were prepared by parallel synthesis according to the scheme shown below.

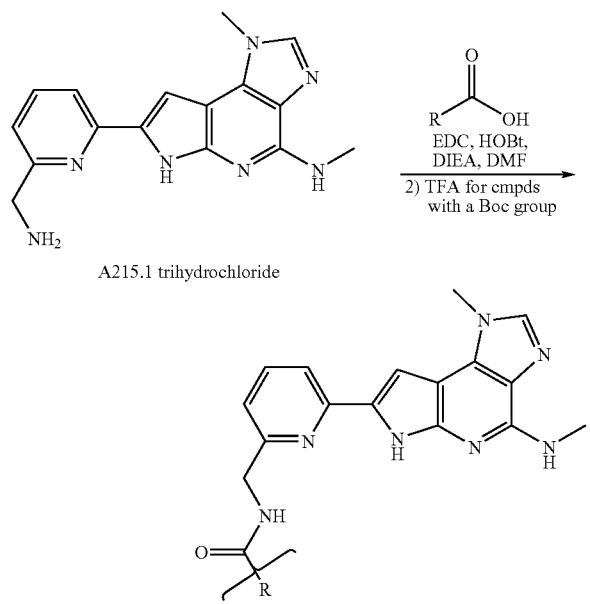

To an individual well in a Bohdan XT® reactor was added 150 uL of a 0.25 M solution of either a carboxylic acid in dimethylformamide (DMF) (0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq) or an isocyanate or sulfonylchloride reagent with pyridine in similar molar ratio to the carboxylic acid reagent. The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) to each reactor (that had a BOC group) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS (H$_2$O/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$O/MeOH/0.1% TFA). Compounds were isolated as trifluoroacetate salts. Examples prepared by this method are described in Table A8.

TABLE A8

| Ex. | R | Name | HPLC Retention (min) | MS Reported |
|---|---|---|---|---|
| A219 | thiadiazolyl | N-[[6-[1,6-dihydro-1-methyl-4-(methylamino)imidazo[4,5-d]pyrrolo[2,3-b]pyridin-7-yl]-2-pyridinyl]methyl]-1,2,3-thiadiazole-4-carboxamide | 2.22 | 420.48 |

TABLE A8-continued

| Ex. | R | Name | HPLC Retention (min) | MS Reported |
|---|---|---|---|---|
| A220 | Me, HO, Me | N-[[6-[1,6-dihydro-1-methyl-4-(methylamino)imidazo[4,5-d]pyrrolo[2,3-b]pyridin-7-yl]-2-pyridinyl]methyl]-3-hydroxy-3-methyl-butanamide | 2.06 | 408.58 |
| A221 | 4-methyl-1,2,3-thiadiazol-5-yl | N-[[6-[1,6-dihydro-1-methyl-4-(methylamino)imidazo[4,5-d]pyrrolo[2,3-b]pyridin-7-yl]-2-pyridinyl]methyl]-4-methyl-1,2,3-thiadiazole-5-carboxamide | 2.37 | 434.53 |
| A222 | Me₂N | N-[[6-[1,6-dihydro-1-methyl-4-(methylamino)imidazo[4,5-d]pyrrolo[2,3-b]pyridin-7-yl]-2-pyridinyl]methyl]-3-(dimethylamino)-propanamide | 1.70 | 407.59 |
| A223 | phenyl | N-[[6-[1,6-dihydro-1-methyl-4-(methylamino)imidazo[4,5-d]pyrrolo[2,3-b]pyridin-7-yl]-2-pyridinyl]methyl]-benzamide | 2.44 | 412.55 |
| A224 | HO | N-[[6-[1,6-dihydro-1-methyl-4-(methylamino)imidazo[4,5-d]pyrrolo[2,3-b]pyridin-7-yl]-2-pyridinyl]methyl]-2-hydroxy-acetamide | 1.71 | 366.56 |
| A225 | Me, Me | N-[[6-[1,6-dihydro-1-methyl-4-(methylamino)imidazo[4,5-d]pyrrolo[2,3-b]pyridin-7-yl]-2-pyridinyl]methyl]-3-methyl-butanamide | 2.43 | 392.61 |
| A226 | Me, HO, Me | N-[[6-[1,6-dihydro-1-methyl-4-(methylamino)imidazo[4,5-d]pyrrolo[2,3-b]pyridin-7-yl]-2-pyridinyl]methyl]-2-hydroxy-2-methyl-propanamide | 1.91 | 394.56 |
| A227 | HO, Me | N-[[6-[1,6-dihydro-1-methyl-4-(methylamino)imidazo[4,5-d]pyrrolo[2,3-b]pyridin-7-yl]-2-pyridinyl]methyl]-3-hydroxy-butanamide | 1.85 | 394.60 |
| A228 | MeO | N-[[6-[1,6-dihydro-1-methyl-4-(methylamino)imidazo[4,5-d]pyrrolo[2,3-b]pyridin-7-yl]-2-pyridinyl]methyl]-2-methoxy-acetamide | 1.95 | 380.60 |

TABLE A8-continued

| Ex. | R | Name | HPLC Retention (min) | MS Reported |
|---|---|---|---|---|
| A229 | Me-cyclopropyl | N-[[6-[1,6-dihydro-1-methyl-4-(methylamino)imidazo[4,5-d]pyrrolo[2,3-b]pyridin-7-yl]-2-pyridinyl]methyl]-1-methyl-cyclopropanecarboxamide | 2.20 | 390.61 |
| A230 | 2-pyridyl | N-[[6-[1,6-dihydro-1-methyl-4-(methylamino)imidazo[4,5-d]pyrrolo[2,3-b]pyridin-7-yl]-2-pyridinyl]methyl]-2-pyridinecarboxamide | 2.35 | 413.55 |
| A231 | pyrazinyl | N-[[6-[1,6-dihydro-1-methyl-4-(methylamino)imidazo[4,5-d]pyrrolo[2,3-b]pyridin-7-yl]-2-pyridinyl]methyl]-2-pyrazinecarboxamide | 2.16 | 414.55 |
| A232 | 3-pyridyl | N-[[6-[1,6-dihydro-1-methyl-4-(methylamino)imidazo[4,5-d]pyrrolo[2,3-b]pyridin-7-yl]-2-pyridinyl]methyl]-3-pyridinecarboxamide | 1.93 | 413.56 |
| A233 | Me, Me (t-Bu type) | N-[[6-[1,6-dihydro-1-methyl-4-(methylamino)imidazo[4,5-d]pyrrolo[2,3-b]pyridin-7-yl]-2-pyridinyl]methyl]-2-methyl-propanamide | 2.10 | 378.29 |
| A234 | H$_2$N, Me | (2S)-2-amino-N-[[6-[1,6-dihydro-1-methyl-4-(methylamino)imidazo[4,5-d]pyrrolo[2,3-b]pyridin-7-yl]-2-pyridinyl]methyl] propanamide | 2.37 | 379.32 |
| A235 | MeHN, Me | (2S)-N-[[6-[1,6-dihydro-1-methyl-4-(methylamino)imidazo[4,5-d]pyrrolo[2,3-b]pyridin-7-yl]-2-pyridinyl]methyl]-2-(methylamino)propanamide | 4.32 | 391.12 |
| A236 | pyrrolidinyl | (2S)-N-[[6-[1,6-dihydro-1-methyl-4-(methylamino)imidazo[4,5-d]pyrrolo[2,3-b]pyridin-7-yl]-2-pyridinyl]methyl]-2-pyrrolidinecarboxamide | 2.49 | 405.40 |
| A237 | MeHN | N-[[6-[1,6-dihydro-1-methyl-4-(methylamino)imidazo[4,5-d]pyrrolo[2,3-b]pyridin-7-yl]-2-pyridinyl]methyl]-2-(methylamino)-acetamide | 1.59 | 378.97 |

TABLE A8-continued

| Ex. | R | Name | HPLC Retention (min) | MS Reported |
|---|---|---|---|---|
| A238 | 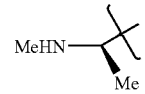 | (2R)-2-amino-N-[[6-[1,6-dihydro-1-methyl-4-(methylamino)imidazo[4,5-d]pyrrolo[2,3-b]pyridin-7-yl]-2-pyridinyl]methyl] propanamide | 2.47 | 379.19 |
| A239 | 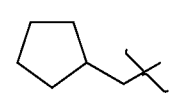 | (2R)-N-[[6-[1,6-dihydro-1-(methylamino)imidazo[4,5-d]pyrrolo[2,3-b]pyridin-7-yl]-2-pyridinyl]methyl]-2-(methylamino)propanamide | 1.60 | 393.26 |
| A240 | 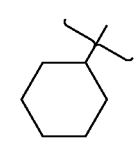 | N-[[6-[1,6-dihydro-1-methyl-4-(methylamino)imidazo[4,5-d]pyrrolo[2,3-b]pyridin-7-yl]-2-pyridinyl]methyl]-cyclopentaneacetamide | 2.74 | 418.36 |
| A241 | 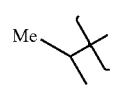 | N-[[6-[1,6-dihydro-1-methyl-4-(methylamino)imidazo[4,5-d]pyrrolo[2,3-b]pyridin-7-yl]-2-pyridinyl]methyl]-cyclohexanecarboxamide | 2.69 | 418.38 |
| A242 | 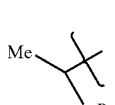 | N-[[6-[1,6-dihydro-1-methyl-4-(methylamino)imidazo[4,5-d]pyrrolo[2,3-b]pyridin-7-yl]-2-pyridinyl]methyl]-2-methyl-butanamide | 2.35 | 392.38 |
| A243 | 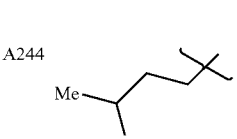 | N-[[6-[1,6-dihydro-1-methyl-4-(methylamino)imidazo[4,5-d]pyrrolo[2,3-b]pyridin-7-yl]-2-pyridinyl]methyl]-2-methyl-pentanamide | 2.59 | 406.35 |
| A244 |  | N-[[6-[1,6-dihydro-1-methyl-4-(methylamino)imidazo[4,5-d]pyrrolo[2,3-b]pyridin-7-yl]-2-pyridinyl]methyl]-4-methyl-pentanamide | 2.70 | 406.38 |
| A245 | | N-[[6-[1,6-dihydro-1-methyl-4-(methylamino)imidazo[4,5-d]pyrrolo[2,3-b]pyridin-7-yl]-2-pyridinyl]methyl]-pentanamide | 2.50 | 392.38 |

Alternate Preparations of Example A228

N-[[6-[1,6-dihydro-1-methyl-4-(methylamino)imidazo[4,5-d]pyrrolo[2,3-b]pyridin-7-yl]-2-pyridinyl]methyl]-2-methoxy-acetamide

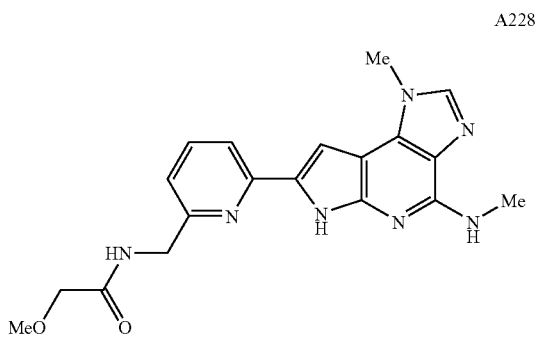

To a mixture of A215.1-trihydrochloride (1.15 g, 2.76 mmol), 1-(3-dimethylaminopropyl)-3-ethylcarbodiimide hydrochloride (0.794 g, 4.14 mmol), 1-hydroxybenzotriazole (0.559 g, 4.14 mmol), and diisopropylethylamine (2.90 mL, 16.6 mmol) in anhydrous dimethylformamide (50 mL) was added methoxyacetic acid (0.320 mL, 4.14 mmol). The reaction mixture was stirred at 80° C. for 20 min. During the first 5 min, the suspension became homogeneous. The solvent was removed under reduced pressure, and the residue was diluted with dichloromethane, washed with a saturated aqueous solution of sodium bicarbonate, and dried over anhydrous sodium sulfate. Concentration under pressure followed by purification by flash silica gel chromatography using a mixture of methanol in dichloromethane (2%-5%) afforded 0.890 g (85%) of A228 as yellowish-brown solid. The solid was triturated with methanol to give 0.660 g of A228 as a yellow solid. The filtrate was re-purified on silica gel to give an additional 0.191 g of A228. The compound had an HPLC retention time=1.81 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=380.33.

Alternate Preparation of Example A228

A228.1: N-((6-Bromopyridin-2-yl)methyl)-2-methoxyacetamide

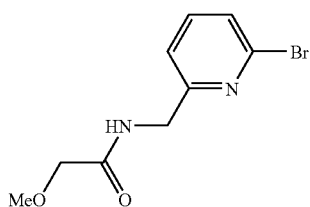

To a mixture of 6-bromo-2-pyridinemethanamine hydrochloride (commercially available or prepared as A214.2) (5.00 g, 222.4 mmol), 1-(3-dimethylaminopropyl)-3-ethylcarbodiimide hydrochloride (6.44 g, 33.6 mmol), 1-hydroxybenzotriazole (4.54 g, 33.6 mmol), and diisopropylethylamine (16.0 mL, 89.6 mmol) in anhydrous dimethylformamide (100 mL) was added methoxyacetic acid (2.60 mL, 33.6 mmol). The reaction mixture was stirred at room temperature for 3 hr and then concentrated under reduced pressure. The residue was diluted with dichloromethane, washed with a saturated aqueous solution of sodium bicarbonate, and dried over anhydrous sodium sulfate. The solvent was removed under reduce pressure, and the residue was dissolved in a minimum amount of ethyl acetate (just enough to fully dissolve), loaded onto a fritted funnel containing a pad of Celite topped with a pad of silica gel, and flushed with ethyl acetate to give 19.0 g (98%) of A228.1 as a white solid. The compound had an HPLC retention time=1.15 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=259.12 and 261.12.

As an alternative method for purification, 4N hydrochloric acid in dioxane (28 mL) was slowly added to a solution of the crude reaction product of A228.1 (~28 g) in ether (400 mL). Filtration and drying under reduced pressure afforded 23.6 g of A228.1 as the hydrochloride salt.

Alternate Preparation of A228.1

A214.2 (800 g, 4.27 mol, processed as 2×400 g batches), 1-(3-dimethylaminopropyl)-3-ethylcarbodiimide hydrochloride (1.22 kg, 6.4 mol), 1-hydroxybenzotriazole (866 g, 6.4 mol), and diisopropylethylamine (830 g, 6.4 mol) in anhydrous dimethylformamide (1.6 L) was added methoxyacetic acid (578 g, 6.4 mol). The reaction mixture was heated at 70° C. for 1 h. TLC analysis of the reaction indicated disappearance of the starting material. The solvent was removed under reduced pressure. The residue was dissolved in dichloromethane, washed with a saturated aqueous solution of sodium bicarbonate, and dried over anhydrous sodium sulfate. The solvent was removed under reduce pressure, and the residue purified by silica gel column chromatography to yield 650 g of A228.1.

A228.2: 2-Methoxy-N-((6-((trimethylsilyl)ethynyl)pyridin-2-yl)methyl)acetamide

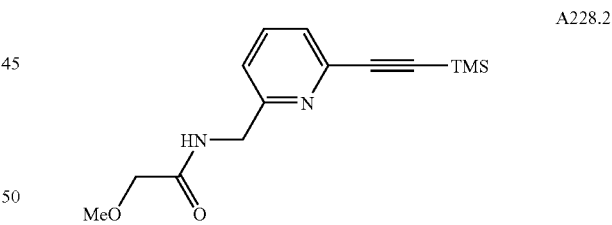

To a mixture of the hydrochloride salt of A228.1 (13.0 g, 44.0 mmol) [The HCl salt is not necessary for the reaction], dichlorobis(triphenylphosphine)palladium II (1.85 g, 2.64 mmol), and copper iodide (0.503 g, 2.64 mmol) in anhydrous dimethylformamide (125 mL) degassed by bubbling nitrogen through the solution and trimethylsilylacetylene (9.30 mL, 66.0 mmol) was added via syringe followed by diisopropylamine (154 mL, 1.10 mol) via cannula. The reaction mixture was immersed in an oil bath at 80° C. and stirred for 30 min. After cooling to room temperature, the salts were removed by vacuum filtration and washed with dimethylformamide. The solvent was removed under reduced pressure, and the residue was dissolved in ether and filtered once again to remove additional salts. The filtrate was concentrated and purified by flash silica gel chromatography using a 50% mixture of ethyl acetate in hexane to give 11.43 g (94%) of the desired product A228.2 as a light tan solid. The compound had an HPLC retention time=2.55 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=277.32.

Alternate Preparation of A228.2

A228.1 (650 g, 2.5 mol) dichlorobis(triphenylphosphine) palladium II (87 g, 0.125 mol), and copper iodide (23.8 g, 0.125 mol) in anhydrous dimethylformamide (7 L) degassed by bubbling nitrogen through the solution for 30 min. Trimethylsilylacetylene (9.30 mL, 66.0 mmol) and diisopropylamine (8.6 L) were added and the reaction mixture immediately placed in a preheated oil bath at 80° C. The reaction mixture was stirred for 1 h at 80° C. TLC analysis indicated the disappearance of starting material. The solvent was removed under reduced pressure and the residue purified by column chromatography to provide A228.2 (280 g, 40%) as a tan solid.

A228.3: N-((6-Ethynylpyridin-2-yl)methyl)-2-methoxyacetamide

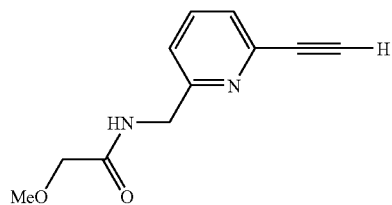

A228.3

A mixture of A228.2 (25.0 g, 90.4 mmol) and a catalytic amount of potassium carbonate (1.38 g, 9.95 mmol) in anhydrous methanol (350 mL) was stirred for 15 min. The reaction mixture was filtered under reduced pressure, and the filtrate was concentrated and further dried on a high-vacuum pump for ~15 min. The residue was dissolved in a small amount of a 2% mixture of methanol in dichloromethane and was loaded on a 2 L coarse fritted funnel containing a pad of Celite topped with a pad of silica gel (~200 g-2 mL/g) and a pad of sand. The product was flushed through with 2% methanol in dichloromethane to give three fractions analyzed by HPLC: A.) 500 mL—no product (clear), B.) 1800 mL—product (yellow), and C.) 1000 mL—no product (pale yellow). Fraction B was concentrated under reduced pressure to give 17.93 g (97%) of A228.3 as a light orange solid, which was ground with a mortal and pestle to give a light tan solid. The compound had an HPLC retention time=0.820 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=205.24. $^1$H NMR (400 MHz, DMSO) δ ppm 3.34 (s, 3 H) 3.88 (s, 2 H) 4.32 (s, 1 H) 4.36 (d, J=6.10 Hz, 2 H) 7.28 (d, J=7.63 Hz, 1 H) 7.43 (d, J=7.63 Hz, 1 H) 7.77 (t, J=7.88 Hz, 1 H) 8.43 (t, J=5.85 Hz, 1 H)

A228.4: tert-Butyl 6-amino-7-((6-((2-methoxyacetamido)methyl)pyridin-2-yl)ethynyl)-1-methyl-1H-imidazo[4,5-c]pyridin-4-yl(methyl)carbamate

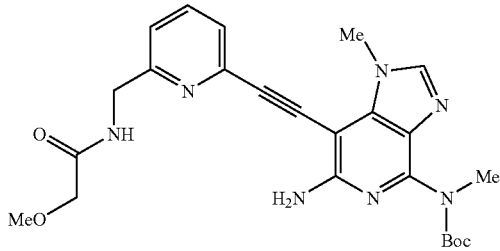

A228.4

To a 1 L three-neck, round bottom flask equipped with a 250 mL addition funnel under nitrogen was added tert-butyl 6-amino-7-iodo-1-methyl-1H-imidazo[4,5-c]pyridin-4-yl (methyl)carbamate (25 g, 62.0 mmol), A228.3 (16.0 g, 78.1 mmol), dichlorobis-(triphenyl-phospine)-palladium (II) (2.61 g, 3.72), and copper iodide (0.590 g, 3.10 mmol). To the mixture was added 170 mL of anhydrous dimethylformamide via syringe. An outlet needle was added, and the mixture was flushed well with a stream of nitrogen for 15 min while stirring rapidly. The nitrogen outlet was removed, and the reaction mixture was maintained under positive pressure with nitrogen. Diisopropylamine (200 mL, 1.43 mol) was added to the addition funnel via cannula over 5 min. The diisopropylamine was then added to the reaction mixture in ~0.5 min. Upon completion, the reaction mixture was quickly immersed in an oil bath at 98° C., the oil bath was allowed to cool to ~85° C., and the reaction mixture was stirred for 45 min at 85° C. After ~1-2 min, the reaction mixture became dark in color. HPLC analysis indicated that there was still approximately 5% of the iodo starting material remaining as well as dimerized acetylene, but no acetylene was observed. The reaction mixture was removed from the bath and allowed to cool to room temperature under nitrogen.

The reaction mixture was concentrated under reduced pressure until only a small amount of dimethylformamide remained (total volume=64 mL). The dark residue was diluted with ~800 mL of ethyl acetate and was poured into a 2 L separatory funnel. The homogeneous solution was washed with ~400 mL of a 10% aqueous solution of lithium chloride. After the washing was complete, the product started crystallizing from the organic layer. The product was allowed to precipitate for 15 min, and the aqueous layer was drained. The organic layer was filtered through a 600 mL fritted funnel (medium porosity), and the precipitate was washed with ~400 mL of ethyl acetate. During this time, a second crop had formed in the aqueous layer. The aqueous mixture was diluted with ethyl acetate and filtered as before to give additional product. By HPLC, both were of equal purity, and both were combined, dried under reduced pressure, and diluted with dichloromethane (~800 mL) (sonication and gentle heating were required). The solution was washed with ~300 mL of a saturated aqueous solution of sodium bicarbonate, and the organic layer was collected. The aqueous layer was extracted with dichloromethane (2×200 mL), and the combined organic layers (~1200 mL) were dried over anhydrous sodium sulfate. Concentration under reduced pressure afforded 21.3 g (72%) of A228.4 as a light-brown solid (HPLC AP=>99%).

The filtrates were washed with a 10% aqueous solution of lithium chloride and dried over anhydrous sodium sulfate. The aqueous layer was extracted with ethyl acetate (3×), and the organic layer was collected and dried over anhydrous sodium sulfate. The fritted funnels from the previous filtrations were rinsed with a 50% mixture of methanol in dichloromethane. All three organic layers were combined and concentrated under reduced pressure to give a brownish-black foamy semi-solid. The mixture was split in two equal portions, and each was purified by flash silica gel chromatography using a mixture of methanol in ethyl acetate (5% to pack, 5% to load, 5% and 10% to run). The combined fractions provided 3.78 g (12.7%) of the product as a dark yellow solid (HPLC AP>99%).

The crude amount of A228.4 was 25.1 g (85%) as a light-brown solid. The compound (21.3 g) was dissolved in isopropyl alcohol (100 mL) and ~4-5 mL of methanol with sonication to give a dark, homogeneous solution. Within a minute of dissolving, the product began to crystallize out of solution. The mixture was stirred at room temperature overnight and filtered through a 600 mL fritted funnel (medium porosity). The columned material (3.78 g) was recrystallized in a similar manner. The resulting solids were washed with isopropyl alcohol and were dried well under reduced pressure to give 19.6 g of A228.4 (pale yellow). The black, homogenous filtrates were combined and concentrated under reduced pressure to give a brown solid (HPCL AP>98%) The compound. had an HPLC retention time=2.21 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS M(-Boc)$^{+1}$=380.26. $^1$H NMR (500 MHz, DMSO-$d_6$) δ ppm 1.31 (s, 9 H) 3.20 (s, 3 H) 3.36 (s, 3 H) 3.90 (s, 2 H) 4.03 (s, 3 H) 4.41 (d, J=6.05 Hz, 2 H) 6.20 (s, 2 H) 7.24 (d, J=7.70 Hz, 1 H) 7.65 (d, J=7.70 Hz, 1 H) 7.80 (t, J=7.84 Hz, 1 H) 7.97 (s, 1 H) 8.42 (t, J=6.05 Hz, 1 H).

A228.5: tert-Butyl 7-(6-((2-methoxyacetamido)methyl)pyridin-2-yl)-1-methyl-1,6-dihydroimidazo[4,5-d]pyrrolo[2,3-b]pyridin-4-yl(methyl)carbamate

A228.5

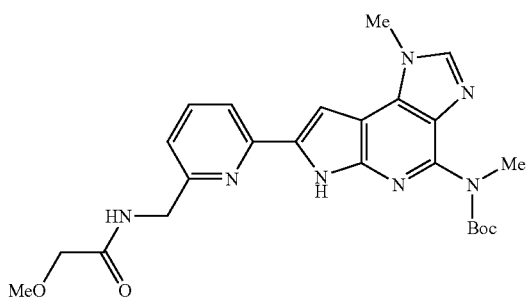

To a 250 mL round bottom flask under nitrogen containing the acetylene intermediate (10.0 g, 20.9 mmol) was added anhydrous dimethylacetamide (100 mL) via cannula without stirring. An outlet needle was added, and the mixture was flushed with a stream of nitrogen for 1 min. The mixture was then sonicated until the solution became homogeneous (~0.5-1 min). An outlet needle was added, and reaction mixture was stirred under a stream of nitrogen for 20 min at room temperature and was then immersed in an oil bath at 85° C. After 5 min, the outlet was removed, and the homogenous mixture was stirred at 85° C., under a positive pressure of nitrogen, for an additional 10 min to allow for complete equilibration. Potassium tert-butoxide (22.9 mL, 22.9 mmol, 1.1 equiv.) was added over 15-30 sec via syringe. After 15 min, a second 1.1 equivalents (22.9 mL, 22.9 mmol) was added, and the reaction mixture was stirred for 15 min, during which time the product precipitated out of solution. The reaction mixture was complete by TLC and was allowed to cool to room temperature. The mixture was cooled with an ice bath and quenched slowly with 20 mL of water to give a homogeneous solution which was transferred to a 1 L separatory funnel with an additional 80 mL of water. The aqueous mixture was extracted with 300 mL of dichloromethane. The aqueous layer was re-extracted with 3×100 mL of dichloromethane, and the organic layers were combined and dried over anhydrous sodium sulfate. Concentration under reduced pressure followed by purification by flash silica gel chromatography using a mixture of methanol in dichloromethane (2%-5%) afforded 8.70 g (87%) of A228.5 as a pale yellow solid $^1$H NMR (500 MHz, DMSO-$d_6$) δ ppm 1.30 (s, 9 H) 3.30 (s, 3 H) 3.38 (s, 3 H) 3.94-3.96 (m, 2 H) 4.10-4.12 (m, 3 H) 4.49 (d, J=5.77 Hz, 2 H) 7.17 (d, J=7.70 Hz, 1 H) 7.53 (d, J=1.92 Hz, 1 H) 7.83 (t, J=7.70 Hz, 1 H) 7.89-7.92 (m, 1 H) 8.14 (s, 1 H) 8.53 (t, J=5.91 Hz, 1 H) 12.38 (d, J=1.92 Hz, 1 H) (The product mixture contained ~8% of A228).

A228.6: N-[[6-[1,6-dihydro-1-methyl-4-(methylamino)imidazo[4,5-d]pyrrolo[2,3-b]pyridin-7-yl]-2-pyridinyl]methyl]-2-methoxy-acetamide A solution of A228.5 (0.781 g, 1.63 mmol) in trifluoroacetic acid (10 mL) was stirred at room temperature for 10 min. The reaction mixture was concentrated under reduced pressure, and the residue was diluted with dichloromethane, washed with a saturated aqueous solution of sodium bicarbonate (2×), and dried over anhydrous sodium sulfate. Concentration under reduced pressure afforded a quantitative yield of the product as a yellow solid. The material was triturated with methanol and filtered under reduced pressure to give 0.532 g (91%) of A228 as a yellow solid MP 263° C. $^1$H NMR (500 MHz, DMSO-$d_6$) δ ppm 2.98 (d, J=4.95 Hz, 3 H) 3.37 (s, 3 H) 3.94 (s, 2 H) 4.02 (s, 3 H) 4.44 (d, J=5.77 Hz, 2 H) 6.67 (q, J=4.58 Hz, 1 H) 7.01 (d, J=7.15 Hz, 1 H) 7.29 (d, J=2.20 Hz, 1 H) 7.68-7.74 (m, 2 H) 7.90 (s, 1 H) 8.53 (t, J=5.77 Hz, 1 H) 11.71 (s, 1 H)

Alternate Preparation of A228

To a 250 mL round bottom flask containing A228.5 (16.0 g, 33.4 mmol) cooled in an ice-water bath was added trifluoroacetic acid (100 mL) slowly. After the addition was complete, the ice bath was removed, and the homogeneous reaction mixture was stirred for 20 min. By HPLC analysis, the reaction was complete. The reaction mixture was concentrated until the total volume was 61 g, a stir bar was added, and the residue was cooled with an ice-water bath. To the stirring mixture was added a 1:1 solution of ammonium hydroxide in water slowly. Once a pH between 9-10 was achieved (~160 mL of the 1:1 ammonium hydroxide/water solution), the product precipitated out of solution. The mixture was stirred at room temperature for 45 min, filtered through a fritted funnel (350 mL, medium porosity) with additional 1:1 ammonium hydroxide/water solution (100 mL), and washed with the 1:1 ammonium hydroxide/water solution (2×100 mL). The resulting off-white cake was air dried overnight. The solid was transferred to a 1 L round bottom flask, diluted with methanol (~500 mL), sonicated for 15 minutes, and concentrated under reduced pressure. During the sonication procedure, the suspension changed from off-white to yellow in color. This sequence was repeated two additional times. The resulting solid was diluted with methanol (~100 mL), filtered under reduced pressure, washed with methanol (~50 mL), and dried well under reduced pressure to give 12.0 g (95%) of A228 as a yellow solid.

Alternate Preparation of A228

To a 2000 mL 3-neck round bottom flask equipped with a mechanic stirrer under nitrogen was charged with A228-methanesulfonic acid salt (67 g) and H$_2$O (670 mL). To this solution at 0° C. was added aqueous NH$_4$OH (7N, 134 mL) drop wise over a period of 30 minutes. During the neutralization, the color was changed from orange to yellow then to colorless. The solution was stirred for addition 90 minutes at 0° C. and the solid was formed. The slurry was filtered and the solid was washed with H$_2$O (2×150 mL), dried in vacuo at 45° C. for 48 hours to A228 as a light yellow solid (33.2 g of product which was 99.7% pure by HPLC).

The structure was confirmed by single crystal x-ray structure described in Table 1 and shown in FIG. 1.

an addition funnel over a period of 20 minutes at this temperature. After the mixture was stirred for additional 45 minutes, MTBE (300 mL) was added and the slurry was cooled to room temperature then to 4° C. and stirred at this temperature for 30 minutes. The slurry was filtered and the solid was collected, washed with 1/1 DCM/MTBE (2×100 mL). The solid was dried in vacuo at 45° C. for 12 hours to give A228 methane sulfonic acid salt as a yellow solid (67.3 g of product which was 99.7% pure by HPLC). $^1$H NMR (500 MHz, DMSO-d$_6$) δ 12.16 (bs, 1 H), 8.53 (t, J=6.05 Hz, 1 H), 8.48 (bs, 1H), 7.89 (m, 2 H), 7.61 (s, 1 H), 7.19 (d, J=7.4 Hz, 1H), 4.51 (d, J=5.75 Hz, 2H), 4.13 (s, 3H), 3.97 (s, 2H), 3.37 (s, 3H), 3.12 (s, 3H), 2.43 (s, 12H), LRMS (M+H)$^+$: 380.33.

TABLE 1

Structure and Properties of Crystal Form

| Form | Solvent Sites for Z' | Solvent %(w/w) | Hot Stage (° C.) | Z' | Vm | sg | dcalc g/cc | T(° C.) | R |
|---|---|---|---|---|---|---|---|---|---|
| N-1 | None | 0.0 | 265-280 (m) | 1 | 460 | P2$_1$/c | 1.370 | 25 | .055 |

A228 Mono-HCl Salt

To a homogenous solution of A228 (2.43 g, 6.40 mmol) in dichloromethane (80 mL) and anhydrous methanol (20 mL) was added a 4M solution of hydrochloric acid in dioxane (1.76 mL, 7.04 mmol) at room temperature. The reaction mixture immediately turned orange and gradually became cloudy. After 15 min, the reaction mixture was concentrated to dryness under reduced pressure, during which time the salt precipitated out of solution as a yellow solid. The residue was diluted with methanol (~75-100 mL), and the suspension was sonicated for 5 min and then gently heated with a heat gun for and additional 5 min. A stir bar was added, and the suspension was stirred overnight. The precipitate was collected by vacuum filtration, washed with methanol, and dried well under reduced pressure to give 2.41 g (90%) of A228 HCl salt as a yellow solid. The compound had an HPLC retention time=1.87 min. (Column: Chromolith SpeedROD 4.6×50 mm—4 min; Solvent A=10% MeOH, 90% H$_2$O, 0.1% TFA; Solvent B=90% MeOH, 10% H$_2$O, 0.1% TFA) and a LC/MS M$^{+1}$=380.25. MP=295° C.

A228—Monohydrate

A228 (200 mg) was suspended in methanol (5 mL) and heated in a bath maintained at 70° C., at which point the solution became homogenious. The reaction mixture was diluted with water (30 mL) and heated at 120° C. for 2.5 h. The mixture was allowed to cool to room temperature and filtered. The product was air dried to yield 150 mg (72%) of A228-monohydrate. MP ~105-140° C. (dhyd) 259-262° C. (dec).

A228—Methanesulfonic Acid Salt

To a 2000 mL 3-neck round bottom flask equipped with a mechanic stirrer under nitrogen containing A228.5 (45.5 g, 0.0938 mol) was added DCM (450 mL). The mixture was heated to 40° C. under nitrogen to obtain a clear solution. Methanesulfonic acid (42 g, 0.437) was added drop wise via Example A246

N-[[6-[1,6-dihydro-1-methyl-4-(methylamino)imidazo[4,5-d]pyrrolo[2,3-b]pyridin-7-yl]-2-pyridinyl]methyl]-N-methyl-acetamide

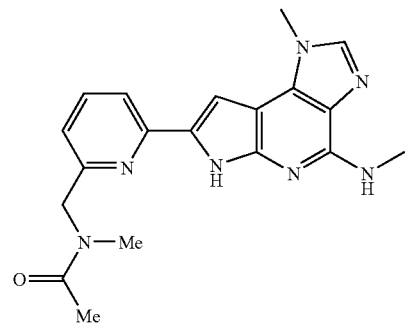

A246

A246.1: tert-Butyl methyl(1-methyl-7-(6-((N-methylacetamido)methyl) pyridin-2-yl)-1,6-dihydro-imidazo[4,5-d]pyrrolo[2,3-b]pyridin-4-yl)carbamate

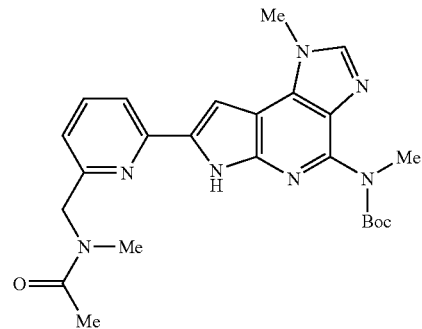

A246.1

To a solution of A214 (0.780 g, 1.74 mmol) in anhydrous tetrahydrofuran (40 mL) at room temperature was added a sodium hydride (0.277 g, 6.94 mmol, 60% in mineral oil). The resulting suspension was stirred for 15 min. Iodomethane (0.12 mL, 1.91 mmol) was added, and the reaction mixture was stirred for 20 min. The reaction was complete by HPLC, quenched with a saturated aqueous solution of ammonium chloride, and the solvent was remove under reduced pressure. The residue was diluted with dichloromethane, washed with a saturated aqueous solution of ammonium chloride, and dried over anhydrous sodium sulfate. Concentration under reduced pressure followed by purification by flash silica gel chromatography using a 5% mixture of methanol in dichloromethane provided 0.685 (85%) of A246.1 as a pale yellow solid. The compound had an HPLC retention time=2.30 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=464.34.

A246.2: N-[[6-[1,6-dihydro-1-methyl-4-(methylamino)imidazo[4,5-d]pyrrolo[2,3-b]pyridin-7-yl]-2-pyridinyl]methyl]-N-methyl-acetamide A solution of A246.1 (0.153 g, 0.330 mmol) in trifluoroacetic acid (5 mL) at room temperature was stirred for 10 min. The trifluoroacetic acid was remove under reduced pressure, and the residue was diluted with dichloromethane, washed with a saturated aqueous solution of sodium bicarbonate, and dried over anhydrous sodium sulfate. Concentration under reduced pressure afforded 0.119 g (99%) of A246 as a yellow solid. The compound had an HPLC retention time=1.93 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=364.38.

Example A247

1,6-dihydro-N,1-dimethyl-7-[6-[(methylamino)methyl]-2-pyridinyl]-imidazo[4,5-d]pyrrolo[2,3-b]pyridin-4-amine

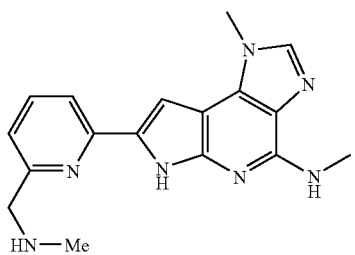

A247

A mixture of A246.1 (0.532 g, 1.15 mmol), absolute ethanol (10 mL), and concentrated hydrochloric acid (10 mL) was stirred at 80° C. overnight. The reaction mixture was concentrated to dryness and dried well under reduced pressure to give a quantitative yield of the tris-hydrochloride salt of A247 as a light brown solid. The salt was diluted with dichloromethane, neutralized with a saturated aqueous solution of sodium bicarbonate, and dried over anhydrous sodium sulfate. Concentration under reduce pressure afforded 0.328 g (89%) of A247 as a light yellow solid. The compound had an HPLC retention time=1.81 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=322.34. $^1$H NMR (500 MHz, $CDCl_3$) δ ppm 2.00 (brs, 1 H) 2.55 (s, 3 H) 3.19 (d, J=4.95 Hz, 3 H) 3.87 (s, 2H) 4.04 (s, 3 H) 5.51 (d, J=4.95 Hz, 1 H) 7.00 (s, 1 H) 7.01 (d, J=7.70 Hz, 1 H) 7.49-7.53 (m, 1 H) 7.55-7.62 (m, 2 H) 9.93 (s, 1 H)

Example A248

N-[[6-[1,6-dihydro-1-methyl-4-(methylamino)imidazo[4,5-d]pyrrolo[2,3-b]pyridin-7-yl]-2-pyridinyl]methyl]-2-methoxy-N-methyl-acetamide

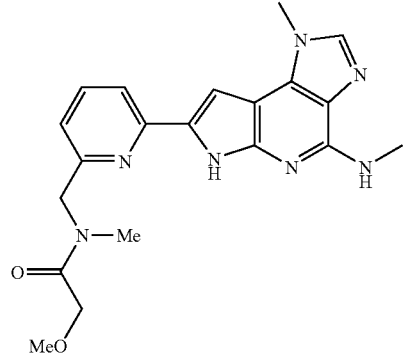

A248

To a mixture of A247 (0.032 g, 99.6 µmol), 1-(3-dimethylaminopropyl)-3-ethylcarbodiimide hydrochloride (0.029 g, 0.149 mmol), 1-hydroxybenzotriazole (0.020 g, 0.149 mmol), and diisopropylethylamine (0.104 mL, 0.598 mmol) in anhydrous dimethylformamide (2 mL) was added methoxyacetic acid (0.012 mL, 0.149 mmol). The homogeneous reaction mixture was heated at 75° C. for 15 min. The solvent was removed under reduced pressure, and the residue was diluted with dichloromethane, washed with a saturated aqueous solution of sodium bicarbonate, and dried over anhydrous sodium sulfate. Concentration under reduced pressure followed by purification by preparative HPLC afforded 0.023 g (59%) of A248 as a light-orange solid. The compound had an HPLC retention time=1.94 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=394.43.

Examples A249-A262

Examples A249-A262 were prepared by parallel synthesis according to the scheme shown below.

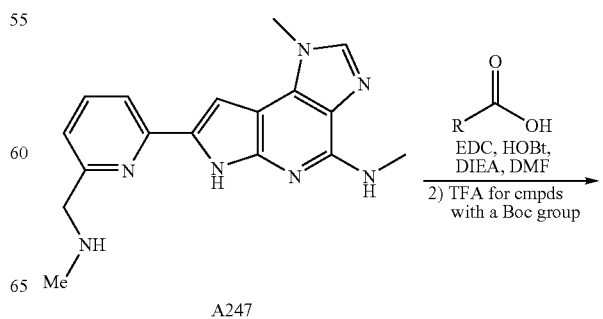

A247

-continued

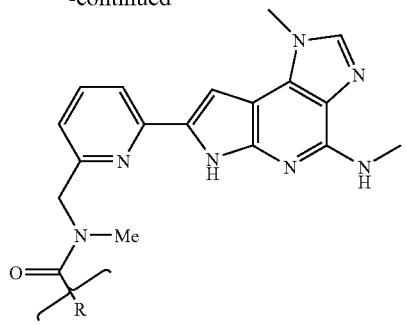

To an individual well in a Bohdan XT® reactor was added 150 uL of a 0.25 M solution of either a carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq) or an isocyanate or sulfonylchloride reagent with pyridine in similar molar ratio to the carboxylic acid reagent. The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) to each reactor (that had a BOC group) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS ($H_2O$/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS ($H_2O$/MeOH/0.1% TFA). Compounds were isolated as trifluoroacetate salts. Examples prepared by this method are described in Table A9.

TABLE A9

| Ex. | R | Name | HPLC Retention (min) | MS Reported |
|---|---|---|---|---|
| A249 | EtO— | N-[[6-[1,6-dihydro-1-methyl-4-(methylamino)imidazo[4,5-d]pyrrolo[2,3-b]pyridin-7-yl]-2-pyridinyl]methyl]-2-ethoxy-N-methyl-acetamide | 2.13 | 409.35 |
| A250 | Ph—C(OMe)— | (alphaS)-N-[[6-[1,6-dihydro-1-methyl-4-(methylamino)imidazo[4,5-d]pyrrolo[2,3-b]pyridin-7-yl]-2-pyridinyl]methyl]-alpha-methoxy-N-methylbenzeneacetamide | 2.48 | 470.32 |
| A251 | Ph—C(OMe)— | (alphaR)-N-[[6-[1,6-dihydro-1-methyl-4-(methylamino)imidazo[4,5-d]pyrrolo[2,3-b]pyridin-7-yl]-2-pyridinyl]methyl]-alpha-methoxy-N-methylbenzeneacetamide | 2.48 | 470.32 |
| A252 | HO-cyclopropyl | N-[[6-[1,6-dihydro-1-methyl-4-(methylamino)imidazo[4,5-d]pyrrolo[2,3-b]pyridin-7-yl]-2-pyridinyl]methyl]-1-hydroxy-N-methyl-cyclopropanecarboxamide | 2.08 | 406.31 |

TABLE A9-continued

| Ex. | R | Name | HPLC Retention (min) | MS Reported |
|---|---|---|---|---|
| A253 | Me, HO, Me (2-hydroxy-2-methylpropyl) | N-[[6-[1,6-dihydro-1-methyl-4-(methylamino)imidazo[4,5-d]pyrrolo[2,3-b]pyridin-7-yl]-2-pyridinyl]methyl]-2-hydroxy-N,2-dimethyl-propanamide | 2.07 | 408.32 |
| A254 | tetrahydrofuran-3-yl | N-[[6-[1,6-dihydro-1-methyl-4-(methylamino)imidazo[4,5-d]pyrrolo[2,3-b]pyridin-7-yl]-2-pyridinyl]methyl]tetrahydro-N-methyl-3-furancarboxamide | 2.04 | 420.31 |
| A255 | (R)-tetrahydrofuran-2-yl | (R)N-[[6-[1,6-dihydro-1-methyl-4-(methylamino)imidazo[4,5-d]pyrrolo[2,3-b]pyridin-7-yl]-2-pyridinyl]methyl]tetrahydro-N-methyl-2-furancarboxamide | 2.15 | 420.31 |
| A256 | tetrahydrofuran-2-yl | N-[[6-[1,6-dihydro-1-methyl-4-(methylamino)imidazo[4,5-d]pyrrolo[2,3-b]pyridin-7-yl]-2-pyridinyl]methyl]tetrahydro-N-methyl-2-furancarboxamide | 2.15 | 420.31 |
| A257 | MeO, Me | (2R)-N-[[6-[1,6-dihydro-1-methyl-4-(methylamino)imidazo[4,5-d]pyrrolo[2,3-b]pyridin-7-yl]-2-pyridinyl]methyl]-2-methoxy-N-methylpropanamide | 2.07 | 408.31 |
| A258 | Me (tert-butyl) | N-[[6-[1,6-dihydro-1-methyl-4-(methylamino)imidazo[4,5-d]pyrrolo[2,3-b]pyridin-7-yl]-2-pyridinyl]methyl]-N-methyl-propanamide | 2.15 | 378.32 |
| A259 | F$_3$C-pyridinyl | N-[[6-[1,6-dihydro-1-methyl-4-(methylamino)imidazo[4,5-d]pyrrolo[2,3-b]pyridin-7-yl]-2-pyridinyl]methyl]-N-methyl-6-(trifluoromethyl)-3-pyridinecarboxamide | 2.59 | 495.21 |
| A260 | MeO | N-[[6-[1,6-dihydro-1-methyl-4-(methylamino)imidazo[4,5-d]pyrrolo[2,3-b]pyridin-7-yl]-2-pyridinyl]methyl]-3-methoxy-N-methyl-propanamide | 2.09 | 408.31 |

TABLE A9-continued

| Ex. | R | Name | HPLC Retention (min) | MS Reported |
|---|---|---|---|---|
| A261 | ![R group with Me and quaternary carbon with two methyls] | N-[[6-[1,6-dihydro-1-methyl-4-(methylamino)imidazo[4,5-d]pyrrolo[2,3-b]pyridin-7-yl]-2-pyridinyl]methyl]-N-methyl-pentanamide | 2.58 | 406.36 |
| A262 | ![R group with Me and quaternary carbon with two methyls] | N-[[6-[1,6-dihydro-1-methyl-4-(methylamino)imidazo[4,5-d]pyrrolo[2,3-b]pyridin-7-yl]-2-pyridinyl]methyl]-N-methyl-butanamide | 2.36 | 392.38 |

Alternate Preparation Example A252

N-[[6-[1,6-dihydro-1-methyl-4-(methylamino)imidazo[4,5-d]pyrrolo[2,3-b]pyridin-7-yl]-2-pyridinyl]methyl]-1-hydroxy-N-methyl-cyclopropanecarboxamide To a mixture of A247 (0.025 g, 76.6 μmol), 1-(3-dimethylaminopropyl)-3-ethylcarbodiimide hydrochloride (0.016 g, 0.115 mmol), 1-hydroxybenzotriazole (0.022 g, 0.115 mmol), and diisopropylethylamine (0.040 mL, 0.230 mmol) in anhydrous dimethylformamide (3 mL) was added 1-hydroxy-1-cyclopropylcarboxylic acid (0.012 mL, 0.115 mmol). The homogeneous reaction mixture was heated at 85° C. for 15 min. The solvent was removed under reduced pressure, and the residue was diluted with dichloromethane, washed with a saturated aqueous solution of sodium bicarbonate, and dried over anhydrous sodium sulfate. Concentration under pressure followed by purification by preparative HPLC afforded 0.016 g (52%) of A252 as a yellow solid. The compound had an HPLC retention time=1.97 min. (Column:

Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=406.38.

Alternate Preparation of A253

N-[[6-[1,6-dihydro-1-methyl-4-(methylamino)imidazo[4,5-d]pyrrolo[2,3-b]pyridin-7-yl]-2-pyridinyl]methyl]-2-hydroxy-N,2-dimethyl-propanamide

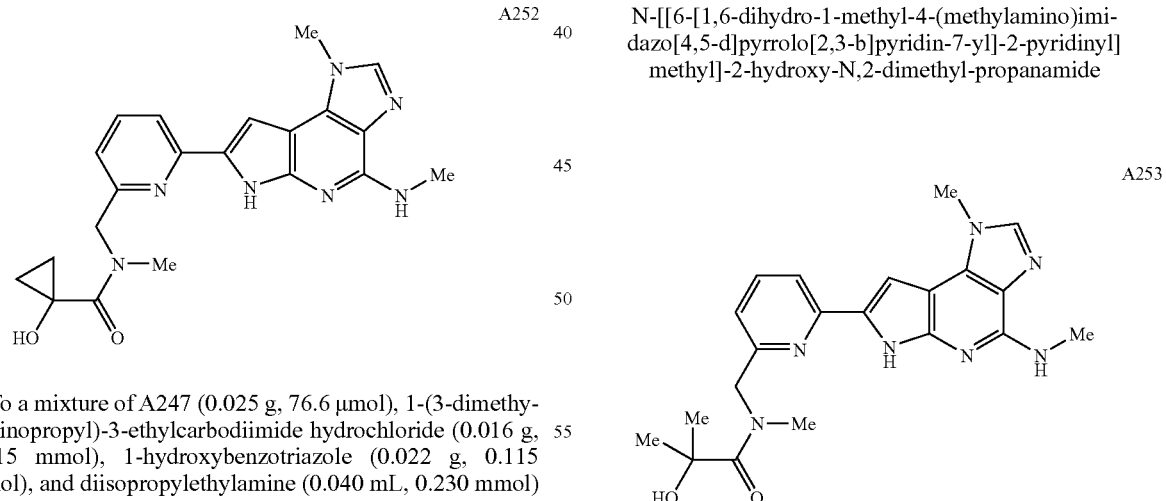

To a mixture of A247 (0.025 g, 76.6 μmol), 1-(3-dimethylaminopropyl)-3-ethylcarbodiimide hydrochloride (0.016 g, 0.115 mmol), 1-hydroxybenzotriazole (0.022 g, 0.115 mmol), and diisopropylethylamine (0.040 mL, 0.230 mmol) in anhydrous dimethylformamide (3 mL) was added 1-hydroxy-1-cyclopropylcarboxylic acid (0.012 mL, 0.115 mmol). The homogeneous reaction mixture was heated at 85° C. for 15 min. The solvent was removed under reduced pressure, and the residue was diluted with dichloromethane, washed with a saturated aqueous solution of sodium bicarbonate, and dried over anhydrous sodium sulfate. Concentration under pressure followed by purification by preparative HPLC afforded 0.013 g (42%) of A253 as a yellow solid. The compound had an HPLC retention time=1.97 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=408.38.

Example A263 and Example A263a

5-[1,6-dihydro-1-methyl-4-(methylamino)imidazo[4,5-d]pyrrolo[2,3-b]pyridin-7-yl]-2-fluoro-benzonitrile and 7-[3-(aminomethyl)-4-fluorophenyl]-1,6-dihydro-N,1-dimethyl-imidazol[4,5-d]pyrrolo[2,3-b]pyridin-4-amine

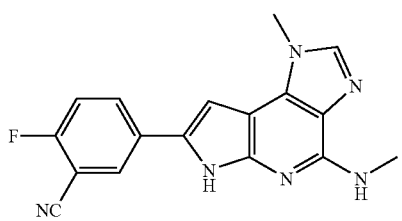

A263

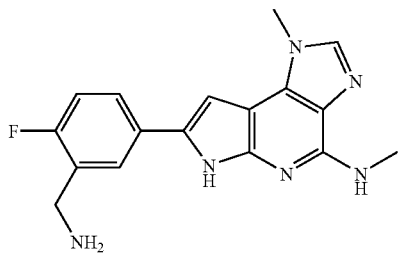

A263a

A263.1: tert-Butyl 6-amino-7-(2-(3-cyano-4-fluorophenyl)ethyl)-1-methyl-1H-imidazo[4,5-c]pyridin-4-yl(methyl)carbamate

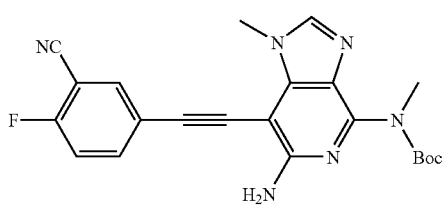

A263.1

A263.1 was prepared in a similar manner as example 2.3 using A1.12 and 3-ethynyl-4-fluorobenzonitrile. HPLC: 82%, retention time: 3.236 minute (condition A). LC/MS (M+H)$^+$=421.4

A263.2: tert-butyl 7-((3-cyano-4-fluorophenyl)ethynyl)-1-methyl-6-(2,2,2-trifluoroacetamido)-1H-imidazo[4,5-c]pyridin-4-yl(methyl)carbamate

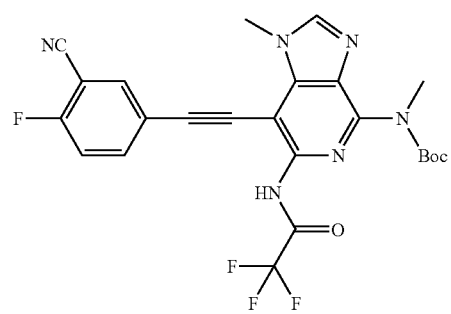

A263.2

To a solution of A263.1 (60 mg, 0.14 mmol) and triethylamine (65 mg, 0.65 mmol) in THF (2 ml) was added trifluoroacetic anhydride (107 mg, 0.51 mmol) dropwise at RT and stirred for 20 minutes. The reaction mixture was concentrated and purified on silica gel column with Hexane/EtOAc (2/3, Isco) to yield A263.2 (51.5 mg, 70%). HPLC: 82%, retention time: 3.506 minute (condition A). LC/MS (M+H)$^+$=517.

A263.3: tert-butyl 7-(3-cyano-4-fluorophenyl)-1-methyl-1,6-dihydroimidazo[4,5-d]pyrrolo[2,3-b]pyridin-4-yl(methyl)carbamate

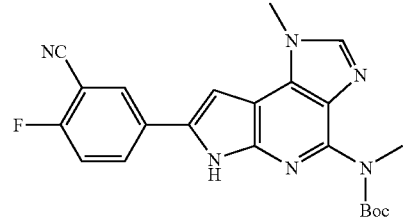

A263.3

A solution of A263.2 (10 mg, 0.019 mmol), K$_2$CO$_3$ (2.68 mg, 0.019 mmol) and tetrakis(triphenylphosphine)Palladium (0) (1.4 mg, 0.0012 mmol) in dimethyl acetamide (0.5 ml) was heated to 90° C. for 16 hrs. The reaction mixture was concentrated and purified on prep. HPLC (condition G) to yield A263.3 (5.7 mg, 70%). HPLC: 99%, retention time: 3.220 minute (condition A). LC/MS (M+H)$^+$=421.4.

A263.4: 5-[1,6-dihydro-1-methyl-4-(methylamino) imidazo[4,5-d]pyrrolo[2,3-b]pyridin-7-yl]-2-fluoro-benzonitrile

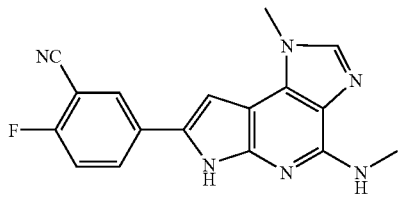

Example A263 was prepared in a similar manner as step A2.4. HPLC: 90%, retention time: 2.407 minute (condition A). LC/MS (M+H)$^+$=321.3, (400 MHz, DMSO-d$_6$) δ ppm 8.34 (1 H, dd, J=5.85, 2.29 Hz), 8.12-8.24 (1 H, m), 7.48-7.66 (2H, m), 7.35 (1 H, s), 4.04 (3 H, s), 2.99 (3 H, s).

A263.5: tert-butyl 7-(3-aminomethyl-4-fluorophenyl)-1-methyl-1,6-dihydroimidazo[4,5-d]pyrrolo[2,3-b]pyridin-4-yl(methyl)carbamate

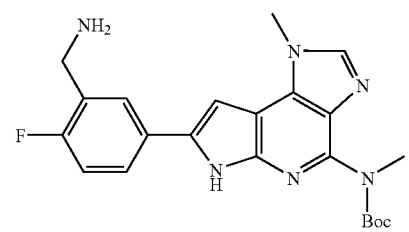

Raney Ni (500 mg) was rinsed with ethanol and A263.3 (890 mg, 2.12 mmol) in ethanol (25 ml) was added. The reaction mixture was saturated with NH$_3$ gas and then it was stirred under hydrogen balloon at RT for 12 hrs. Filtration and concentration to yield a product A263.5 (857 mg, 96%). HPLC: 98%, retention time: 2.108 minute (condition A). LC/MS (M+H)$^+$=425.4.

A263.6: 7-[3-(aminomethyl)-4-fluorophenyl]-1,6-dihydro-N,1-dimethyl-imidazo[4,5-d]pyrrolo[2,3-b]pyridin-4-amine A263a was prepared in a similar manner to Similar method as example A3. HPLC: 93%, retention time: 1.483 minute (condition A). LC/MS (M+H)$^+$=325.3, $^1$H-NMR (400 MHz, CD$_3$OD) δ ppm 7.96 (1 H, s), 7.75-7.82 (1 H, m), 7.41-7.58 (1H, m), 7.21 (1 H, t, J=9.41 Hz), 7.02 (1 H, s), 4.16 (2 H, s), 4.03 (3 H, s), 3.12 (3 H, s).

Examples A264-A292

Examples A264-A292 were prepared by parallel synthesis according to the scheme shown below.

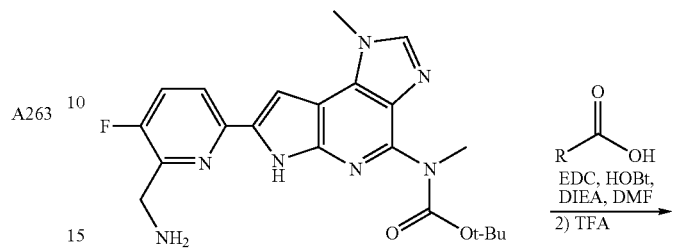

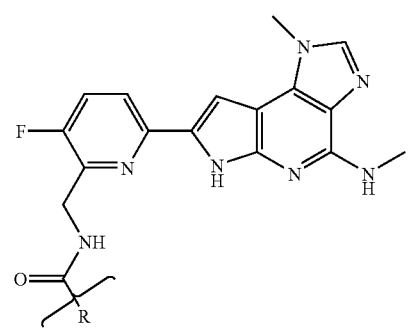

To an individual well in a Bohdan XT® reactor was added 150 uL of a 0.25 M solution of either a carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq) or an isocyanate or sulfonylchloride reagent with pyridine in similar molar ratio to the carboxylic acid reagent. The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) to each reactor (that had a BOC group) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS (H$_2$O/MeOH/0.1% TFA, gradient 35-90% MeOH over 15 min, 20×100 mm 5 μm YMC ODS-A column) utilizing mass-directed fractionation. The purified sample was reconstituted in 1:1N/MeOH:DCE, transferred to a tared 2.5 mL plastic microtube, dried via centrifugal evaporation and weighed. The final product was analyzed by HPLC-MS (H$_2$O/MeOH/0.1% TFA). Compounds were isolated as trifluoroacetate salts. Examples prepared by this method are described in Table A10.

TABLE A10

| Ex. | R | Name | HPLC Retention (min) | MS Reported |
|---|---|---|---|---|
| A264 | HO-C(CH3)2- | N-[[5-[1,6-dihydro-1-methyl-4-(methylamino)imidazo[4,5-d]pyrrolo[2,3-b]pyridin-7-yl]-2-fluorophenyl]methyl]-2-hydroxy-acetamide | 2.14 | 383.31 |
| A265 | (2S)-pyrrolidin-2-yl | (2S)-N-[[5-[1,6-dihydro-1-methyl-4-(methylamino)imidazo[4,5-d]pyrrolo[2,3-b]pyridin-7-yl]-2-fluorophenyl]methyl]-, 2-pyrrolidinecarboxamide | 2.01 | 422.33 |
| A266 | Me-C(OH)(Me)- | N-[[5-[1,6-dihydro-1-methyl-4-(methylamino)imidazo[4,5-d]pyrrolo[2,3-b]pyridin-7-yl]-2-fluorophenyl]methyl]-2-hydroxy-2-methyl-propanamide | 2.33 | 411.31 |
| A267 | HO-CH(Me)- | N-[[5-[1,6-dihydro-1-methyl-4-(methylamino)imidazo[4,5-d]pyrrolo[2,3-b]pyridin-7-yl]-2-fluorophenyl]methyl]-3-hydroxy-butanamide | 2.25 | 411.32 |
| A268 | MeO-C(CH3)2- | N-[[5-[1,6-dihydro-1-methyl-4-(methylamino)imidazo[4,5-d]pyrrolo[2,3-b]pyridin-7-yl]-2-fluorophenyl]methyl]-2-methoxy-acetamide | 2.33 | 397.34 |
| A269 | NC-C(CH3)2- | 2-cyano-N-[[5-[1,6-dihydro-1-methyl-4-(methylamino)imidazo[4,5-d]pyrrolo[2,3-b]pyridin-7-yl]-2-fluorophenyl]methyl]-acetamide | 2.20 | 392.31 |
| A270 | CH3— | N-[[5-[1,6-dihydro-1-methyl-4-(methylamino)imidazo[4,5-d]pyrrolo[2,3-b]pyridin-7-yl]-2-fluorophenyl]methyl]-acetamide | 2.25 | 367.32 |
| A271 | HO-cyclopropyl- | N-[[5-[1,6-dihydro-1-methyl-4-(methylamino)imidazo[4,5-d]pyrrolo[2,3-b]pyridin-7-yl]-2-fluorophenyl]methyl]-1-hydroxy-cyclopropanecarboxamide | 2.29 | 409.31 |
| A272 | NC-cyclopropyl- | 1-cyano-N-[[5-[1,6-dihydro-1-methyl-4-(methylamino)imidazo[4,5-d]pyrrolo[2,3-b]pyridin-7-yl]-2-fluorophenyl]methyl]-cyclopropanecarboxamide | 2.46 | 418.31 |

TABLE A10-continued

| Ex. | R | Name | HPLC Retention (min) | MS Reported |
|---|---|---|---|---|
| A273 | H₂N–C(CH₃)₂–CH₂OH (2S) | (2S)-2-amino-N-[[5-[1,6-dihydro-1-methyl-4-(methylamino)imidazo[4,5-d]pyrrolo[2,3-b]pyridin-7-yl]-2-fluorophenyl]methyl]-3-hydroxypropanamide | 1.91 | 412.31 |
| A274 | MeO-CH₂CH₂-C(CH₃)₂– | N-[[5-[1,6-dihydro-1-methyl-4-(methylamino)imidazo[4,5-d]pyrrolo[2,3-b]pyridin-7-yl]-2-fluorophenyl]methyl]-3-methoxy-propanamide | 2.31 | 411.31 |
| A275 | CH₃CH₂— | N-[[5-[1,6-dihydro-1-methyl-4-(methylamino)imidazo[4,5-d]pyrrolo[2,3-b]pyridin-7-yl]-2-fluorophenyl]methyl]-propanamide | 2.38 | 381.32 |
| A276 | MeO-CH₂CH₂-O-C(CH₃)₂– | N-[[5-[1,6-dihydro-1-methyl-4-(methylamino)imidazo[4,5-d]pyrrolo[2,3-b]pyridin-7-yl]-2-fluorophenyl]methyl]-2-(2-methoxyethoxy)-acetamide | 2.43 | 441.31 |
| A277 | 2-methylpyrrolidin-2-yl (2R) | (2R)-N-[[5-[1,6-dihydro-1-methyl-4-(methylamino)imidazo[4,5-d]pyrrolo[2,3-b]pyridin-7-yl]-2-fluorophenyl]methyl]-2-pyrrolidinecarboxamide | 2.02 | 422.32 |
| A278 | CF₃CH₂— | N-[[5-[1,6-dihydro-1-methyl-4-(methylamino)imidazo[4,5-d]pyrrolo[2,3-b]pyridin-7-yl]-2-fluorophenyl]methyl]-3,3,3-trifluoro-propanamide | 2.53 | 435.26 |
| A279 | (2S,4R)-4-hydroxy-2-methylpyrrolidin-2-yl | (2S,4R)-N-[[5-[1,6-dihydro-1-methyl-4-(methylamino)imidazo[4,5-d]pyrrolo[2,3-b]pyridin-7-yl]-2-fluorophenyl]methyl]-4-hydroxy-2-pyrrolidinecarboxamide | 1.96 | 438.31 |
| A280 | 1-methylcyclopropyl | N-[[5-[1,6-dihydro-1-methyl-4-(methylamino)imidazo[4,5-d]pyrrolo[2,3-b]pyridin-7-yl]-2-fluorophenyl]methyl]-cyclopropanecarboxamide | 2.46 | 393.34 |
| A281 | pyridin-4-yl-C(CH₃)₂– | N-[[5-[1,6-dihydro-1-methyl-4-(methylamino)imidazo[4,5-d]pyrrolo[2,3-b]pyridin-7-yl]-2-fluorophenyl]methyl]-4-pyridinecarboxamide | 2.17 | 430.29 |

TABLE A10-continued

| Ex. | R | Name | HPLC Retention (min) | MS Reported |
|---|---|---|---|---|
| A282 | (2-pyridinyl) | N-[[5-[1,6-dihydro-1-methyl-4-(methylamino)imidazo[4,5-d]pyrrolo[2,3-b]pyridin-7-yl]-2-fluorophenyl]methyl]-2-pyridinecarboxamide | 2.95 | 430.30 |
| A283 | C(Me)(Me)(Me) | N-[[5-[1,6-dihydro-1-methyl-4-(methylamino)imidazo[4,5-d]pyrrolo[2,3-b]pyridin-7-yl]-2-fluorophenyl]methyl]-2,2-dimethyl-propanamide | 2.72 | 409.35 |
| A284 | (3-pyridinyl) | N-[[5-[1,6-dihydro-1-methyl-4-(methylamino)imidazo[4,5-d]pyrrolo[2,3-b]pyridin-7-yl]-2-fluorophenyl]methyl]-3-pyridinecarboxamide | 2.21 | 430.29 |
| A285 | CH(NH$_2$)CH$_2$OCH$_2$Ph | (2S)-2-amino-N-[[5-[1,6-dihydro-1-methyl-4-(methylamino)imidazo[4,5-d]pyrrolo[2,3-b]pyridin-7-yl]-2-fluorophenyl]methyl]-3-(phenylmethoxy)propanamide | 2.45 | 502.33 |
| A286 | 4-(phenylmethoxy)pyrrolidin-2-yl | (2S,4R)-N-[[5-[1,6-dihydro-1-methyl-4-(methylamino)imidazo[4,5-d]pyrrolo[2,3-b]pyridin-7-yl]-2-fluorophenyl]methyl]-4-(phenylmethoxy)2-pyrrolidinecarboxamide | 2.47 | 528.33 |
| A287 | CH(NHMe)CH$_2$OH | (2S)-N-[[5-[1,6-dihydro-1-methyl-4-(methylamino)imidazo[4,5-d]pyrrolo[2,3-b]pyridin-7-yl]-2-fluorophenyl]methyl]-3-hydroxy-2-(methylamino)propanamide | 1.93 | 426.33 |
| A288 | CH$_2$CH(OH)Me | (3S)-N-[[5-[1,6-dihydro-1-methyl-4-(methylamino)imidazo[4,5-d]pyrrolo[2,3-b]pyridin-7-yl]-2-fluorophenyl]methyl]-3-hydroxybutanamide | 2.26 | 411.32 |
| A289 | CH$_2$C(Me)(Me)(OH) | N-[[5-[1,6-dihydro-1-methyl-4-(methylamino)imidazo[4,5-d]pyrrolo[2,3-b]pyridin-7-yl]-2-fluorophenyl]methyl]-3-hydroxy-3-methyl-butanamide | 2.42 | 425.31 |

TABLE A10-continued

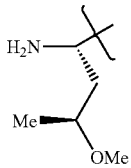

| Ex. | R | Name | HPLC Retention (min) | MS Reported |
|---|---|---|---|---|
| A290 | 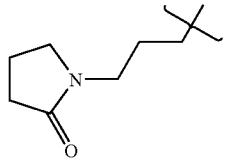 | (2S,3R)-2-amino-N-[[5-[1,6-dihydro-1-methyl-4-(methylamino)imidazo[4,5-d]pyrrolo[2,3-b]pyridin-7-yl]-2-fluorophenyl]methyl]-3-methoxybutanamide | 2.09 | 440.31 |
| A291 | 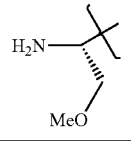 | N-[[5-[1,6-dihydro-1-methyl-4-(methylamino)imidazo[4,5-d]pyrrolo[2,3-b]pyridin-7-yl]-2-fluorophenyl]methyl]-2-oxo-1-pyrrolidinebutanamide | 2.37 | 478.30 |
| A292 | 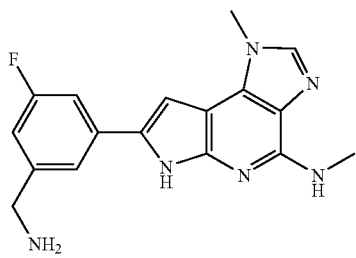 | (2S)-2-amino-N-[[5-[1,6-dihydro-1-methyl-4-(methylamino)imidazo[4,5-d]pyrrolo[2,3-b]pyridin-7-yl]-2-fluorophenyl]methyl]-3-methoxypropanamide | 2.02 | 426.31 |

Example A293

7-[3-(aminomethyl)-5-fluorophenyl]-1,6-dihydro-N,1-dimethyl-imidazo[4,5-d]pyrrolo[2,3-b]pyridin-4-amine

A293

A293.1:
3-fluoro-5-((trimethylsilyl)ethynyl)benzonitrile

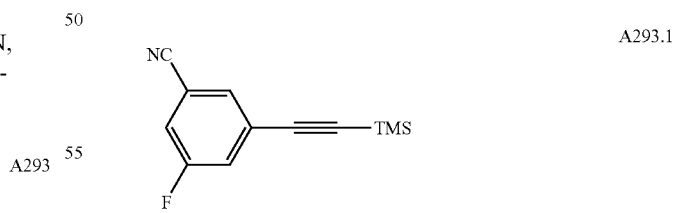

A293.1

A solution of 3-bromo-5-fluorobenzonitrile (2.5 g, 12.5 mmol), (trimethylsilyl)acetylene (2.86 ml, 20 mmol), bis(acetate)bis(triphenylphoshpino) Palladium(II) (936 mg, 1.25 mmol) and triethylamine (35 ml) in toluene (35 ml) was degassed by bubbling nitrogen through the solution and then stirred at 95° C. for 30 minutes. Filtration and concentration to yield a crude product. It was diluted with EtOAc (150 ml). The organic phase was washed with saturated NaHCO₃ solution (50 ml), brine (50 ml) and the organic layer was dried over sodium sulfate. Filtration and concentration to yield a product A293.1 (2.4 g, 88%). HPLC: 95%, retention time: 4.05 minute (condition A). LC/MS (M+H)+=218.2.

A293.2: 3-ethynyl-5-fluorobenzonitrile

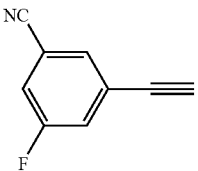

A solution of A293.1 (2.3 g, 10.7 mmol) and KOH (55 mg, 0.98 mmol in 0.55 ml of water) in THF (20 ml) was stirred at RT for 30 minutes. The reaction mixture was concentrated to yield a crude product. It was diluted with EtOAc (100 ml). The organic phase was washed with water (20 ml), brine (20 ml) and the organic layer was dried over sodium sulfate. Filtration and concentration to yield a crude product. It was purified on silica gel column with Hexane/EtOAc (Isco) to yield A293.2 (1.35 g, 87%). HPLC: 72%, retention time: 2.818 minute (condition A). LC/MS (M+H)+=146.1.

A293.3: tert-butyl 6-amino-7-((3-cyano-5-fluorophenyl)ethynyl)-1-methyl-1H-imidazo[4,5-c]pyridin-4-yl(methyl)carbamate

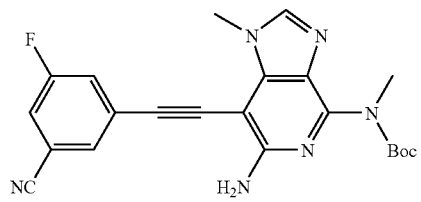

was prepared in a similar manner to example 2.3 using A293.2 as the acetylene.

HPLC: 82%, retention time: 3.281 minute (condition A). LC/MS (M+H)+=421.3.

A293.4: tert-butyl 7-((3-cyano-5-fluorophenyl)ethynyl)-1-methyl-6-(2,2,2-trifluoroacetamido)-1H-imidazo[4,5-c]pyridin-4-yl(methyl)carbamate

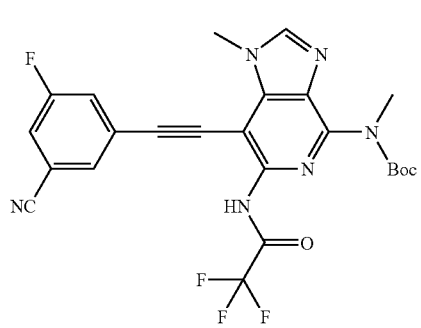

A293.4 was prepared in a similar manner as example A263.2

HPLC: 80%, retention time: 3.486 minute (condition A). LC/MS (M+H)+=517.3.

A293.4: tert-butyl 7-(3-cyano-5-fluorophenyl)-1-methyl-1,6-dihydroimidazo[4,5-d]pyrrolo[2,3-b]pyridin-4-yl(methyl)carbamate

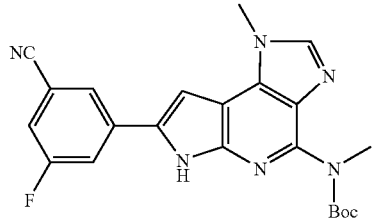

A293.4 was prepared similar to the procedure described for A263.3 HPLC: 99%, retention time: 3.246 minute (condition A). LC/MS (M+H)+=421, ¹H-NMR (400 MHz, DMSO-d₆) δ ppm 8.34 (1 H, s), 8.14-8.21 (2 H, m), 7.70-7.77 (2 H, m), 4.10 (3 H, s), 3.30 (3 H, s), 1.30 (9 H, s).

A293.5: tert-butyl 7-(3-(aminomethyl)-5-fluorophenyl)-1-methyl-1,6-dihydroimidazo[4,5-d]pyrrolo[2,3-b]pyridin-4-yl(methyl)carbamate

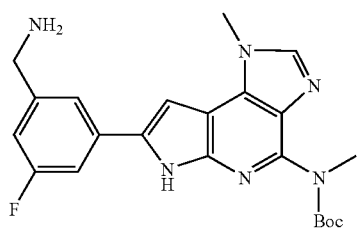

A293 was prepared in a similar manner to A3.1

HPLC: 92%, retention time: 2.098 minute (condition A). LC/MS (M+H)+=425.3, ¹H-NMR (400 MHz, CD₃OD) δ ppm 8.01 (1 H, s), 7.61 (1 H, s), 7.45 (1 H, d, J=9.66 Hz), 7.24 (1 H, s), 7.00 (1 H, d, J=9.66 Hz), 4.09 (3 H, s), 3.82 (2 H, s), 3.29 (3 H, s), 1.28 (9 H, s).

A293.6: 7-[3-(aminomethyl)-5-fluorophenyl]-1,6-dihydro-N, 1-dimethyl-imidazo[4,5-d]pyrrolo[2,3-b]pyridin-4-amine A293a was prepared in a similar manner as step A3.2. HPLC: >98%, retention time: 1.807 minute (condition B). LC/MS (M+H)+=325.3, ¹H-NMR (400 MHz, CD₃OD) δ ppm 8.01 (1 H, s), 7.58 (1 H, s), 7.53 (1 H, d, J=10.17 Hz), 7.16 (1 H, s), 7.03 (1 H, d, J=8.65 Hz), 4.08-4.15 (2 H, m), 4.04 (3 H, s), 3.14 (3 H, s).

Examples A294-A313

Examples A294-A313 were prepared by parallel synthesis according to the scheme shown below.

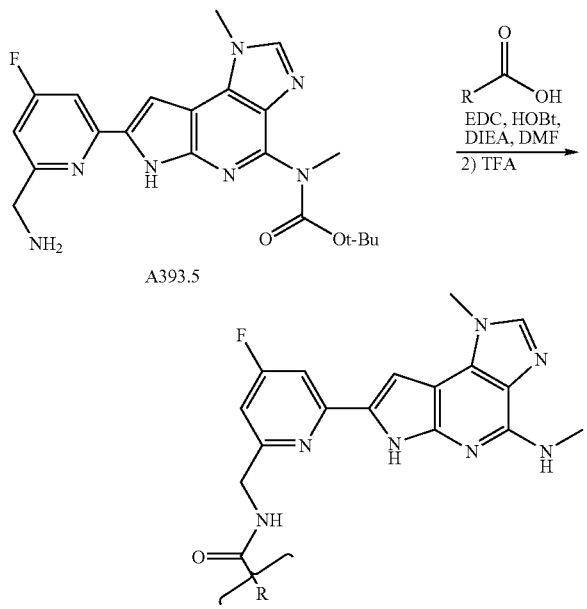

A393.5

To an individual well in a Bohdan XT® reactor was added 150 uL of a 0.25 M solution of either a carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq) or an isocyanate or sulfonylchloride reagent with pyridine in similar molar ratio to the carboxylic acid reagent. The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) to each reactor (that had a BOC group) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS ($H_2O$/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS ($H_2O$/MeOH/0.1% TFA). Compounds were isolated as trifluoroacetate salts. Examples prepared by this method are described in Table A11.

TABLE A11

| Ex. | R | Name | HPLC Retention (min) | MS Reported |
|---|---|---|---|---|
| A294 | cyclopropyl | N-[[3-[1,6-dihydro-1-methyl-4-(methylamino)imidazo[4,5-d]pyrrolo[2,3-b]pyridin-7-yl]-5-fluorophenyl]methyl]-cyclopropanecarboxamide | 2.48 | 393.32 |
| A295 | NC-C(CH3)2- | 2-cyano-N-[[3-[1,6-dihydro-1-methyl-4-(methylamino)imidazo[4,5-d]pyrrolo[2,3-b]pyridin-7-yl]-5-fluorophenyl]methyl]-acetamide | 2.26 | 392.31 |
| A296 | $CH_3CH_2-$ | N-[[3-[1,6-dihydro-1-methyl-4-(methylamino)imidazo[4,5-d]pyrrolo[2,3-b]pyridin-7-yl]-5-fluorophenyl]methyl]-propanamide | 2.40 | 381.31 |
| A297 | (CH3)3C- | N-[[3-[1,6-dihydro-1-methyl-4-(methylamino)imidazo[4,5-d]pyrrolo[2,3-b]pyridin-7-yl]-5-fluorophenyl]methyl]-2,2-dimethyl-propanamide | 2.71 | 409.32 |

TABLE A11-continued

| Ex. | R | Name | HPLC Retention (min) | MS Reported |
|---|---|---|---|---|
| A298 | Me-C(=O)-NH-CH2-C(Me)2- | 2-(acetylamino)-N-[[3-[1,6-dihydro-1-methyl-4-(methylamino)imidazo[4,5-d]pyrrolo[2,3-b]pyridin-7-yl]-5-fluorophenyl]methyl]-acetamide | 2.11 | 424.31 |
| A299 | MeO-CH2-C(Me)2- | N-[[3-[1,6-dihydro-1-methyl-4-(methylamino)imidazo[4,5-d]pyrrolo[2,3-b]pyridin-7-yl]-5-fluorophenyl]methyl]-2-methoxy-acetamide | 2.34 | 397.30 |
| A300 | HOCH$_2$— | N-[[3-[1,6-dihydro-1-methyl-4-(methylamino)imidazo[4,5-d]pyrrolo[2,3-b]pyridin-7-yl]-5-fluorophenyl]methyl]-2-hydroxy-acetamide | 2.15 | 383.30 |
| A301 | Me-C(OH)(Me)- | N-[[3-[1,6-dihydro-1-methyl-4-(methylamino)imidazo[4,5-d]pyrrolo[2,3-b]pyridin-7-yl]-5-fluorophenyl]methyl]-2-hydroxy-2-methyl-propanamide | 2.32 | 411.30 |
| A302 | 1-hydroxy-cyclopropyl | N-[[3-[1,6-dihydro-1-methyl-4-(methylamino)imidazo[4,5-d]pyrrolo[2,3-b]pyridin-7-yl]-5-fluorophenyl]methyl]-1-hydroxy-cyclopropanecarboxamide | 2.30 | 409.30 |
| A303 | (2S)-1-acetyl-pyrrolidin-2-yl | (2S)-1-acetyl-N-[[3-[1,6-dihydro-1-methyl-4-(methylamino)imidazo[4,5-d]pyrrolo[2,3-b]pyridin-7-yl]-5-fluorophenyl]methyl]-2-pyrrolidinecarboxamide | 2.29 | 464.30 |
| A304 | CH$_3$— | N-[[3-[1,6-dihydro-1-methyl-4-(methylamino)imidazo[4,5-d]pyrrolo[2,3-b]pyridin-7-yl]-5-fluorophenyl]methyl]-acetamide | 2.25 | 367.30 |
| A305 | (2S)-pyrrolidin-2-yl | (2S)-N-[[3-[1,6-dihydro-1-methyl-4-(methylamino)imidazo[4,5-d]pyrrolo[2,3-b]pyridin-7-yl]-5-fluorophenyl]methyl]-2-pyrrolidinecarboxamide | 2.03 | 422.31 |

TABLE A11-continued

| Ex. | R | Name | HPLC Retention (min) | MS Reported |
|---|---|---|---|---|
| A306 | (PhCH₂O-pyrrolidine-NH) | (2S,4R)-N-[[3-[1,6-dihydro-1-methyl-4-(methylamino)imidazo[4,5-d]pyrrolo[2,3-b]pyridin-7-yl]-5-fluorophenyl]methyl]-4-(phenylmethoxy)-2-pyrrolidinecarboxamide | 2.50 | 528.27 |
| A307 | MeO-CH₂CH₂-O-C(CH₃)₂- | N-[[3-[1,6-dihydro-1-methyl-4-(methylamino)imidazo[4,5-d]pyrrolo[2,3-b]pyridin-7-yl]-5-fluorophenyl]methyl]-2-(2-methoxyethoxy)-acetamide | 2.43 | 411.31 |
| A308 | (HO-pyrrolidine-NH) | (2S,4R)-N-[[3-[1,6-dihydro-1-methyl-4-(methylamino)imidazo[4,5-d]pyrrolo[2,3-b]pyridin-7-yl]-5-fluorophenyl]methyl]-4-hydroxy-2-pyrrolinecarboxamide | 1.96 | 348.30 |
| A309 | (NAc-pyrrolidine) | (2R)-1-acetyl-N-[[3-[1,6-dihydro-1-methyl-4-(methylamino)imidazo[4,5-d]pyrrolo[2,3-b]pyridin-7-yl]-5-fluorophenyl]methyl]-2-pyrrolidinecarboxamide | 2.27 | 464.31 |
| A310 | CF₃CH₂— | N-[[3-[1,6-dihydro-1-methyl-4-(methylamino)imidazo[4,5-d]pyrrolo[2,3-b]pyridin-7-yl]-5-fluorophenyl]methyl]-3,3,3-trifluoro-propanamide | 2.55 | 435.25 |
| A311 | (4-Me-1,2,3-thiadiazol-5-yl) | N-[[3-[1,6-dihydro-1-methyl-4-(methylamino)imidazo[4,5-d]pyrrolo[2,3-b]pyridin-7-yl]-5-fluorophenyl]methyl]-4-methyl-1,2,3-thiadiazole-5-carboxamide | 2.68 | 451.21 |
| A312 | NC-cyclopropyl- | 1-cyano-N-[[3-[1,6-dihydro-1-methyl-4-(methylamino)imidazo[4,5-d]pyrrolo[2,3-b]pyridin-7-yl]-5-fluorophenyl]methyl]-cyclopropanecarboxamide | 2.51 | 418.24 |
| A313 | (3-morpholinyl) | N-[[3-[1,6-dihydro-1-methyl-4-(methylamino)imidazo[4,5-d]pyrrolo[2,3-b]pyridin-7-yl]-5-fluorophenyl]methyl]-3-morpholinecarboxamide | 1.99 | 438.29 |

Example A314

1,6-dihydro-N,1-dimethyl-7-[3-[(methylamino)methyl]phenyl]-imidazo[4,5-d]pyrrolo[2,3-b]pyridin-4-amine hydrochloride salt

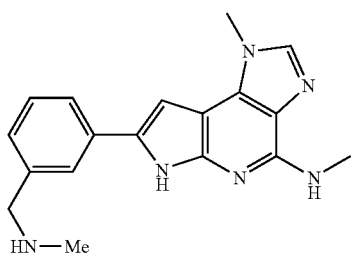

A314

A314.1:
Methyl-(3-trimethylsilanylethynyl-benzyl)-carbamic acid tert-butyl ester

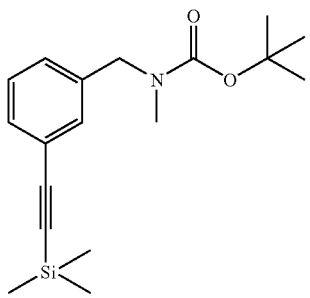

A314.1

TMS-Acetylene (2.2 mL, 15.0 mmol) was added dropwise to commercially available tert-butyl 3-bromobenzyl(methyl)carbamate (3.0 g, 10 mmol), CuI (100 mg, 0.5 mmol) and palladium dichlorobistriphenylphosphine (210 mg, 0.3 mmol) in triethylamine (30 mL) at room temperature under a nitrogen atmosphere. The reaction mixture was heated to 70° C. for 12 hrs before cooling to room temperature and evaporating in vacuo. The residue was triturated with diethyl ether (30 mL), filtered and the filtrate evaporated in vacuo and purified by column chromatography (5% ethyl acetate in hexane) to yield A314.1 (3.2 g, 100%) as a brown oil. HPLC YMC S-5 4.6×33 mm (2 min grad): retention time 2.34 min, $M+Na^+=340.34$

A314.2: (3-Ethynyl-benzyl)-methyl-carbamic acid tert-butyl ester

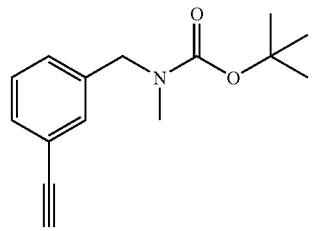

A314.2

Potassium hydroxide solution (1 pellet dissolved in 1 mL of water) was added in one portion to A314.1 (3.2 g) in anhydrous methanol (50 mL). After stirring at room temperature for 2 hrs, the reaction was quenched by the addition of water (25 mL), and the mixture was extracted with hexane (3×100 mL). The combined organics were dried (MgSO4), evaporated in vacuo and purified by column chromatography ((5% ethyl acetate in hexane) to yield A314.2 as an oil (2.54 g, 100%). HPLC YMC S5-4.6×33 mm (2 min gradient): ret. Time=1.41 min, $M+H^+=210.24$

A314.3 (6-Amino-7-{3-[(tert-butoxycarbonyl-methyl-amino)-methyl]-phenylethynyl}-1-methyl-1H-imidazo[4,5-c]pyridin-4-yl)-methyl-carbamic acid tert-butyl ester

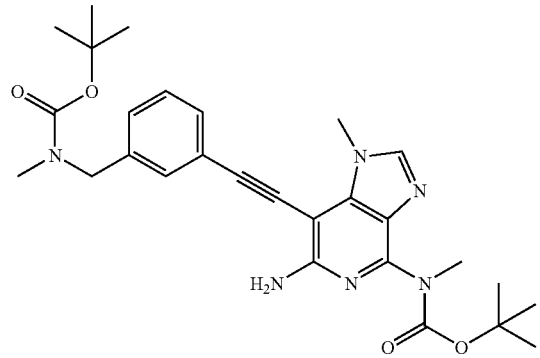

A314.3

A1.12 (1.5 g, 3.72 mmol), dichlorobis(triphenylphosphine)palladium (174 mg, 0.25 mmol), A314.2 (1.14 g, 4.65 mmol) and triethylamine (12 mL) were each added to N,N-dimethylformamide (6 mL) and nitrogen bubbled through the resulting mixture for 5 min. The reaction mixture was heated at 90° C. for 12 hrs under a nitrogen atmosphere before cooling to room temperature and evaporating the solvent in vacuo. The residue was purified by silica gel column chromatography using 1:1 ethyl acetate:hexane as eluent to provide 1.45 g (75%) of A314.3. HPLC YMC S-5 4.6×33 mm (2 min grad): retention time 1.98 min, $M+H^+=521.46$

A314.4: [7-{3-[(tert-Butoxycarbonyl-methyl-amino)-methyl]-phenylethynyl}-1-methyl-6-(2,2,2-trifluoro-acetylamino)-1H-imidazo[4,5-c]pyridin-4-yl]-methyl-carbamic acid tert-butyl ester

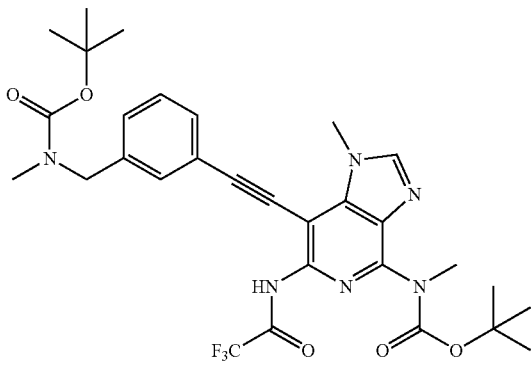

A314.4

Trifluoroacetic anhydride (0.77 mL, 5.54 mmol) was added dropwise over 5 min to a cooled (0 C) solution of A314.3 (1.44 g, 2.77 mmol) and triethylamine (1.16 mL, 8.31 mmol) in THF (40 mL) under a nitrogen atmosphere. The cooling bath was removed after 10 min and the reaction mixture allowed to stir at room temperature for 1 hr before evaporating in vacuo. The residue was taken up in dichloromethane (50 mL) and washed with saturated sodium bicarbonated solution (25 mL). The organic layer was separated and dried (MgSO4), then evaporated in vacuo to yield the crude product A314.4 which was used immediately without further purification (1.76 g). HPLC YMC S-5 4.6×33 mm (2 min grad): retention time 2.08 min, M+H$^+$=617.39.

A314.5: 1,6-dihydro-N, 1-dimethyl-7-[3-[(N-methyl-tert-butyloxycrbonylamino)methyl]phenyl]-imidazo[4,5-d]pyrrolo[2,3-b]pyridin-4-tert-butyloxycarbonylamine

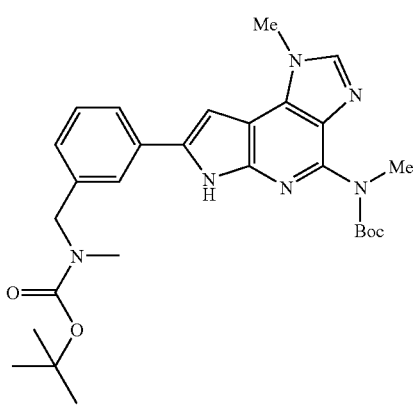

A314.5

Potassium carbonate (400 mg, 2.86 mmol) and dichlorobistriphenylphosphine (210 mg, 0.3 mmol) were each added in one portion to a solution of A314.4 (1.76 g, 2.86 mmol) in dimethylacetamide (30 mL). at room temperature under a nitrogen atmosphere. The reaction was heated to 120 C for 48 hrs before evaporating in vacuo. The residue was partitioned between water (30 mL) and ethyl acetate (50 mL). The separated organic layer was dried (MgSO4), evaporated in vacuo and purified by column chromatography using 2:1 ethyl acetate:hexane to yield A314.5 (1.3 g, 95%). HPLC YMC S-5 4.6×33 mm (2 min grad): retention time 1.99 min, M+H$^+$=521.42

A314.6: 1,6-dihydro-N,1-dimethyl-7-[3-[(methylamino)methyl]phenyl]-imidazo[4,5-d]pyrrolo[2,3-b]pyridin-4-amine A314.5 (1.3 g, 2.5 mmol) was suspended in 4N HCl in dioxane (30 mL) and stirred at room temperature overnight. The reaction mixture was evaporated in vacuo and the residue triturated with diethyl ether to yield A314 (568 mg, 58%). HPLC YMC S-5 4.6×33 mm (2 min grad): retention time 1.10 min, M+H$^+$=321.34. $^1$H NMR (400 MHz, DMSO) δ 12.13 (s, 1H), 9.33 (s, 1H), 8.06 (s, 1H), 7.85 (d, J=8.6 Hz, 1H), 7.50 (t, J=8.6 Hz, 1H), 7.40 (d, J=8.6 Hz, 1H), 7.29 (s, 1H), 4.22 (s, 3H), 2.96 (s, 3H), 2.51 (s, 3H).

Example A315

N-[[3-[1,6-dihydro-1-methyl-4-(methylamino)imidazo[4,5-d]pyrrolo[2,3-b]pyridin-7-yl]phenyl]methyl]-3-methoxy-N-methyl-propanamide

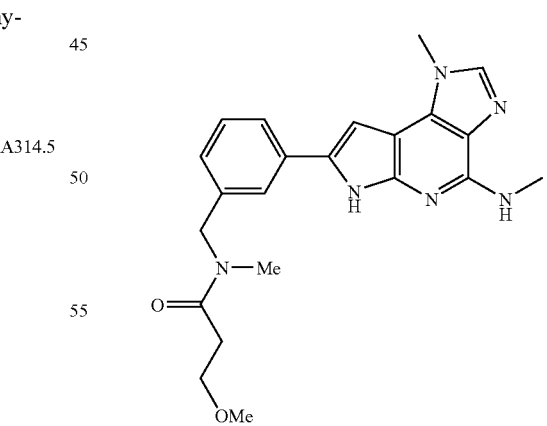

A315

EDC (135 mg, 1.07 mmol) was added in one portion to a mixture of 3-methoxypropionic acid (42 mg, 0.41 mmol), HOBt (73 mg, 0.91 mmol) and DIPEA (0.5 mL) in anhydrous DMF (2 mL) and the resulting mixture was allowed to stir at room temperature for 30 min before addition of the A314 (100 mg, 0.25 mmol). The mixture was heated to 70 C for 48 hrs in a screw-capped vial before cooling to room temperature and evaporating in vacuo. The residue was partitioned between ethyl acetate (5 mL) and water (2 mL). The separated aqueous layer was extracted with ethyl acetate (3×10 mL) and the combined organics dried (MgSO4), evaporated in vacuo and purified by column chromatography (5% MeOH in EtOAc) to yield A315 (62 mg). HPLC YMC S-5 4.6×33 mm (2 min grad): retention time 1.51 min, M+H$^+$=407.41.

Example A316

N-[[3-[1,6-dihydro-1-methyl-4-(methylamino)imidazo[4,5-d]pyrrolo[2,3-b]pyridin-7-yl]phenyl]methyl]-N-methyl-acetamide

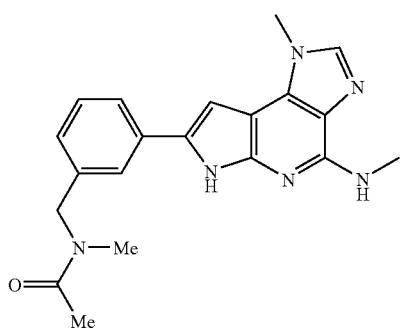

A316

Example A316 was prepared in a similar manner to A315. HPLC YMC S-5 4.6×33 mm (2 min grad): retention time 1.45 min, M+H$^+$=363.42.

Example A317

N-[[3-[1,6-dihydro-1-methyl-4-(methylamino)imidazo[4,5-d]pyrrolo[2,3-b]pyridin-7-yl]phenyl]methyl]-N-methyl-methanesulfonamide

A317

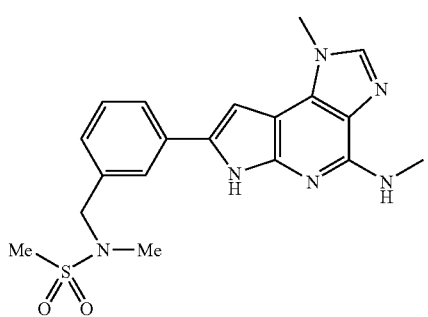

Methansulfonyl chloride (20 mg, 0.26 mmol) was added in one portion to A314 (192 mg, 0.23 mmol) and triethylamine (60 mg, 0.59 mmol) in THF (2 mL). The reaction mixture was stirred at room temperature for 30 minutes. The solvent was evaporated under reduced pressure and the residue purified by preparatory reverse phase chromatography to yield A317. HPLC YMC S-5 4.6×33 mm (2 min grad): retention time 1.50 min, M+H+=399.40.

Examples A318-A331

Examples A318-A331 were prepared by parallel synthesis according to the scheme shown below.

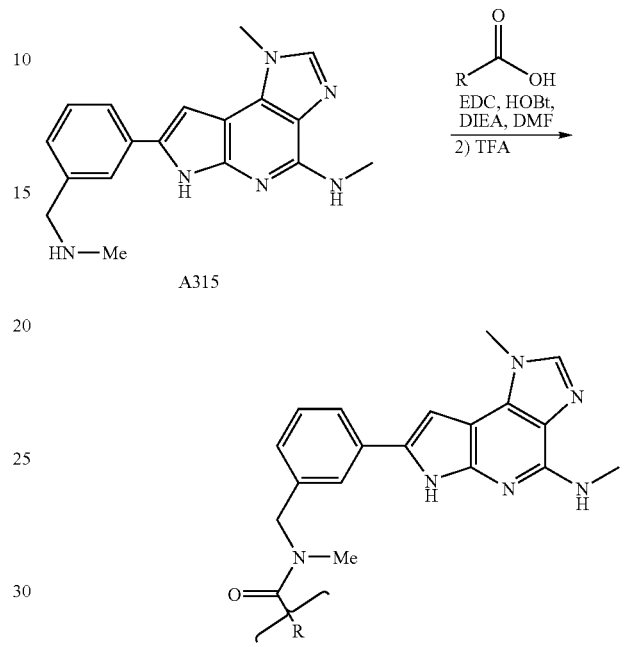

To an individual well in a Bohdan XT® reactor was added 150 uL of a 0.25 M solution of either a carboxylic acid in dimethylformamide (DMF)(0.038 mmol; 1.25 eq), 37.5 uL of a 1 M solution of 1-hydroxybenzotriazol in DMF (0.038 mmol, 1.25 equiv) and 150 uL of a 0.25 M solution of N-(3-dimethylaminopropyl)-N-ethylcarbodiimide hychloride (0.038 mmol; 1.25 eq) or an isocyanate or sulfonylchloride reagent with pyridine in similar molar ratio to the carboxylic acid reagent. The reactor was agitated for 10 minutes via orbital shaker. Then 150 uL of a solution of 0.2 molar amine in DMF (0.03 mmol; 1 eq) and diisopropylethylamine (0.150; 5 eq) was added to each reactor well and the reactor was agitated for 16 hours at 65° C. The library was dried via centrifugal evaporation and BOC groups were removed by adding 600 uL of a 30% by volume solution of trifluoroacetic acid (TFA) in dichloromethane (DCM) to each reactor (that had a BOC group) and the reactor was agitated for 2 hours. The library was dried via centrifugal evaporation and was dissolved in 600 uL of DMF and 600 uL of methanol (MeOH). The entire contents for each reactor were transferred to an STR plate was was purified by standard preparative HPLC-MS (H$_2$O/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$O/MeOH/0.1% TFA). Compounds were isolated as trifluoroacetate salts. Examples prepared by this method are described in Table A12.

TABLE A12

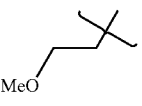

| Ex. | R | Name | HPLC Retention (min) | MS Reported |
|---|---|---|---|---|
| A318 |  | N-[[3-[1,6-dihydro-1-methyl-4-(methylamino)imidazo[4,5-d]pyrrolo[2,3-b]pyridin-7-yl]phenyl]methyl]-2-(2-methoxyethoxy)-N-methyl-acetamide | 2.34 | 437.33 |
| A319 | 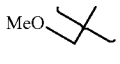 | 1-cyano-N-[[3-[1,6-dihydro-1-methyl-4-(methylamino)imidazo[4,5-d]pyrrolo[2,3-b]pyridin-7-yl]phenyl]methyl]-N-methyl-cyclopropanecarboxamide | 2.49 | 414.34 |
| A320 | 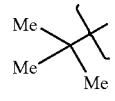 | N-[[3-[1,6-dihydro-1-methyl-4-(methylamino)imidazo[4,5-d]pyrrolo[2,3-b]pyridin-7-yl]phenyl]methyl]-2-methoxy-N-methyl-acetamide | 2.29 | 393.35 |
| A321 |  | N-[[3-[1,6-dihydro-1-methyl-4-(methylamino)imidazo[4,5-d]pyrrolo[2,3-b]pyridin-7-yl]phenyl]methyl]-N,2,2-trimethyl-propanamide | 2.86 | 405.38 |
| A322 | CH$_3$CH$_2$— | N-[[3-[1,6-dihydro-1-methyl-4-(methylamino)imidazo[4,5-d]pyrrolo[2,3-b]pyridin-7-yl]phenyl]methyl]-N-methyl-propanamide | 2.49 | 377.34 |
| A323 |  | N-[[3-[1,6-dihydro-1-methyl-4-(methylamino)imidazo[4,5-d]pyrrolo[2,3-b]pyridin-7-yl]phenyl]methyl]-N-methyl-cyclopropanecarboxamide | 2.55 | 389.38 |
| A324 | 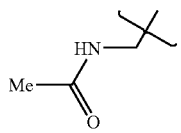 | N-[[3-[1,6-dihydro-1-methyl-4-(methylamino)imidazo[4,5-d]pyrrolo[2,3-b]pyridin-7-yl]phenyl]methyl]-1-hydroxy-N-methyl-cyclopropanecarboxamide | 2.44 | 405.35 |
| A325 | 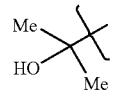 | 2-(acetylamino)-N-[[3-[1,6-dihydro-1-methyl-4-(methylamino)imidazo[4,5-d]pyrrolo[2,3-b]pyridin-7-yl]phenyl]methyl]-N-methyl-acetamide | 2.17 | 420.31 |
| A326 | | N-[[3-[1,6-dihydro-1-methyl-4-(methylamino)imidazo[4,5-d]pyrrolo[2,3-b]pyridin-7-yl]phenyl]methyl]-2-hydroxy-N,2-dimethyl-propanamide | 2.42 | 407.38 |

TABLE A12-continued

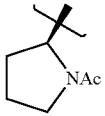

| Ex. | R | Name | HPLC Retention (min) | MS Reported |
|---|---|---|---|---|
| A327 | CF₃CH₂— | N-[[3-[1,6-dihydro-1-methyl-4-(methylamino)imidazo[4,5-d]pyrrolo[2,3-b]pyridin-7-yl]phenyl]methyl]-3,3,3-trifluoro-N-methyl-propanamide | 2.56 | 431.29 |
| A328 | 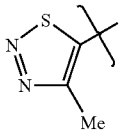 | (2R)-1-acetyl-N-[[3-[1,6-dihydro-1-methyl-4-(methylamino)imidazo[4,5-d]pyrrolo[2,3-b]pyridin-7-yl]phenyl]methyl]-N-methyl-2-pyrrolidinecarboxamide | 2.36 | 460.32 |
| A329 |  | N-[[3-[1,6-dihydro-1-methyl-4-(methylamino)imidazo[4,5-d]pyrrolo[2,3-b]pyridin-7-yl]phenyl]methyl]-N,4-dimethyl-1,2,3-thiadiazole-5-carboxamide | 2.53 | 447.31 |
| A330 | HO⤻ | N-[[3-[1,6-dihydro-1-methyl-4-(methylamino)imidazo[4,5-d]pyrrolo[2,3-b]pyridin-7-yl]phenyl]methyl]-2-hydroxy-N-methyl-acetamide | 2.15 | 379.35 |
| A331 | 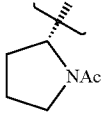 | (2S)-1-acetyl-N-[[3-[1,6-dihydro-1-methyl-4-(methylamino)imidazo[4,5-d]pyrrolo[2,3-b]pyridin-7-yl]phenyl]methyl]-N-methyl-2-pyrrolidinecarboxamide | 2.36 | 460.32 |

Example A332

3-(1-methyl-4-(methylamino)-1,6-dihydroimidazo[4,5-d]pyrrolo[2,3-b]pyridin-7-yl)benzyl 4-isopropylpiperazine-1-carboxylate

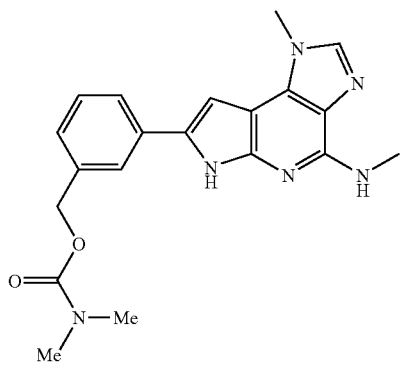

A332

A332.1: 2-(3-Iodo-benzyloxy)-tetrahydro-pyran

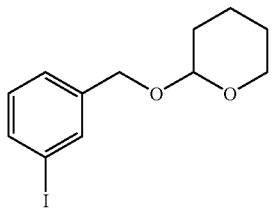

A332.1 para-Toluenesulfonic acid (100 mg, cat.) was added in one portion to a cooled solution (0 C) of 3-iodobenzyl alcohol (4.71 g, 0.02 mol) and dihydropyran (1.86 g, 0.022 mol) in dichloromethane (50 mL) under a nitrogen atmosphere. The cooling bath was removed and the reaction mixture was allowed to warm to room temperature over 1 hr. Diethyl ether (100 mL) was then added followed by saturated sodium hydrogen carbonate solution (100 mL). The organic layer was separated, dried (MgSO$_4$) and evaporated in vacuo to yield the crude product (6.59 g) A332.1, which was used immediately without further purification. HPLC YMC S-5 4.6×33 mm (2 min grad): retention time 2.16 min, no M+H$^+$ observed.

A332.2: Trimethyl-[3-(tetrahydro-pyran-2-yloxymethyl)-phenylethynyl]-silane

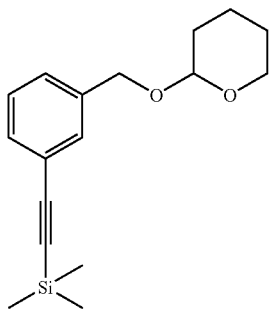

A332.2

TMS-Acetylene (3.2 mL, 22.6 mmol) was added dropwise to A332.1 (6.59 g, 20.6 mmol), CuI (200 mg, 1.0 mol) and palladium dichlorobistriphenylphosphine (1 g, 1.3 mmol) in triethylamine (5.5 mL) and anhydrous DMF (50 mL) at room temperature under a nitrogen atmosphere. The reaction mixture was stirred at room temperature overnight before evaporating in vacuo. Diethyl ether (50 mL) was added to the residue and the slurry filtered. The filtrate was evaporated in vacuo to yield the crude product A332.2 which (8.2 g) which was used immediately without further purification. HPLC YMC S-5 4.6×33 mm (2 min grad): retention time 2.38 min, no M+H$^+$ observed.

A332.3: 2-(3-Ethynyl-benzyloxy)-tetrahydro-pyran

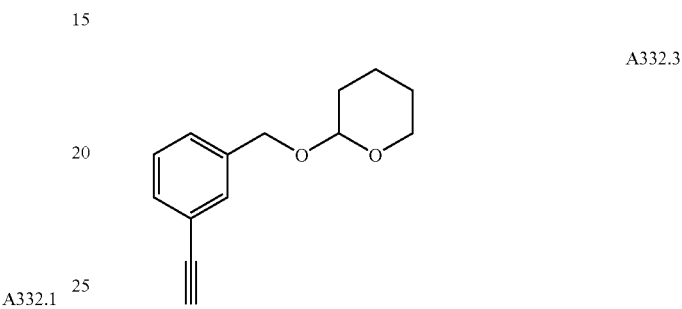

A332.3

Potassium hydroxide solution (1 pellet dissolved in 1 mL of water) was added in one portion to A332.2 (8.2 g) in anhydrous methanol (50 mL). After stirring at room temperature for 2 hrs, the reaction was quenched by the addition of water (25 mL), and the mixture was extracted with hexane (2×250 mL). The combined organics were dried (MgSO4), evaporated in vacuo and purified by column chromatography (10% ethyl acetate in hexane) to yield A332.3 as an oil (2.43 g, 56% over 3 steps). HPLC YMC S-5 4.6×33 mm (2 min grad): retention time 1.93 min, no M+H$^+$ observed.

A332.4: {6-Amino-1-methyl-7-[3-(tetrahydro-pyran-2-yloxymethyl)-phenylethynyl]-1H-imidazo[4,5-c]pyridin-4-yl}-methyl-carbamic acid tert-butyl ester

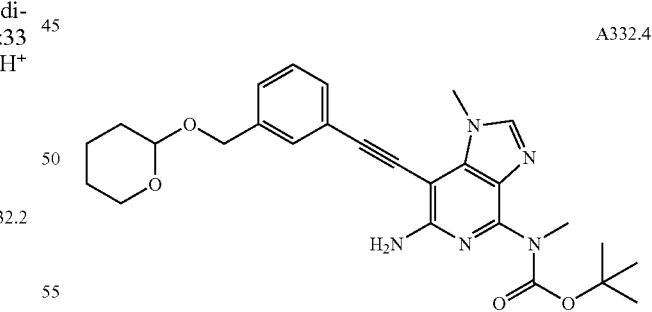

A332.4

A1.12 (1.5 g, 3.72 mmol), dichlorobis(triphenylphosphine)palladium (174 mg, 0.25 mmol), A332.3 (1.0 g, 4.65 mmol) and triethylamine (12 mL) were each added to N,N-dimethylformamide (6 mL) and nitrogen bubbled through the resulting mixture for 5 min. The reaction mixture was heated at 90° C. for 12 hrs under a nitrogen atmosphere before cooling to room temperature and evaporating the solvent in vacuo. Diethyl ether was added to the residue (20 mL) and filtered. The filtrate was evaporated in vacuo purified by silica gel column chromatography using 1:1 ethyl acetate:hexane as eluent to provide 1.62 g (89%) of A332.4. HPLC YMC S-5 4.6×33 mm (2 min grad): retention time 1.92 min, M+H⁺ (−THP)=492.45

A332.5: 3-[1,6-dihydro-1-methyl-4-(N-methyl-tert-buyloxycarbonylamino)imidazo[4,5-d]pyrrolo[2,3-b]pyridin-7-yl]-1-(tetrahydro-pyran-2-yloxymethyl)benzene

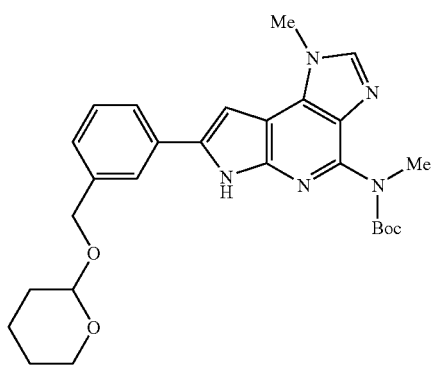

Potassium tert-butoxide (1.0M in THF, 3.3 mL, 3.3 mmol) was added dropwise over 10 min to a solution of the A332.4 (1.62 g, 3.30 mmol) in DMA (15 mL) at room temperature under a nitrogen atmosphere. The reaction was heated to 90° C. for 1 hr before cooling to room temperature and evaporating in vacuo. The residue was purified by column chromatography using ethyl acetate as eluent to yield A332.5 (1.18 g, 73%). HPLC YMC S-5 4.6×33 mm (2 min grad): retention time 1.90 min, M+H⁺ (−THP)=492.45

A332.6: 3-[1,6-dihydro-1-methyl-4-(N-methyl-tert-buyloxycarbonylamino)imidazo[4,5-d]pyrrolo[2,3-b]pyridin-7-yl]-benzenemethanol

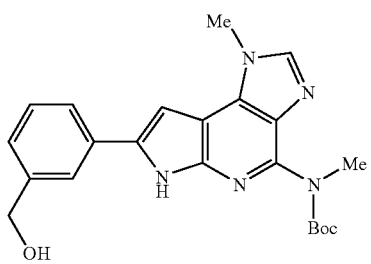

HCl (1.0N aqueous solution, 7.2 mL, 7.2 mmol) was added dropwise over 5 min to a solution of A333.5 (1.18 g, 2.4 mmol) in THF (25 mL) at room temperature. The reaction mixture was stirred at room temperature for 10 hrs before quenching with sodium hydroxide solution (2N, 3.6 mL). The mixture was extracted with ethyl acetate (2×50 mL), the combined organic extracts dried (MgSO4) and evaporated in vacuo to yielded A332.6 (1.04 g) as a yellow solid which was used immediately in the next reaction without further purification. HPLC YMC S-5 4.6×33 mm (2 min grad): retention time 1.74 min, M+H⁺=492.45

A332.7: [7-[3-[[[[(2,5-dioxo-1-pyrrolidinyl)oxy]carbonyl]oxy]methyl]phenyl]-1,6-dihydro-1-methylimidazo[4,5-d]pyrrolo[2,3-b]pyridin-4-yl]methylcarbamic acid, 1,1-dimethylethyl ester

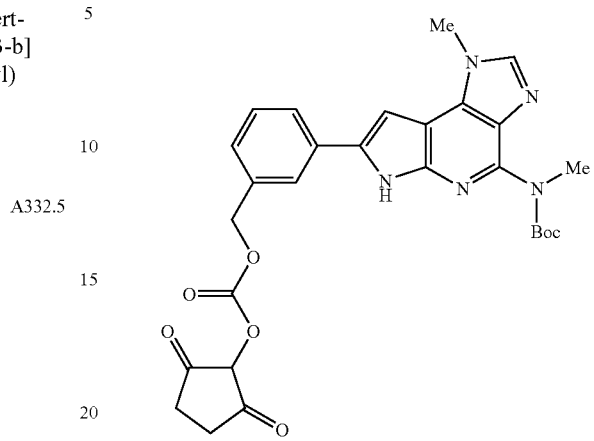

DSC (1 g, 3.85 mmol) was added in one portion to a solution of A332.8 (1.04 g, 2.57 mmol) and triethylamine (1.1 mL, 7.7 mmol) in THF (40 mL) at room temperature under a nitrogen atmosphere. The reaction mixture was heated to 40° C. for 5 hrs before evaporating in vacuo. The residue was dissolved in dichloromethane (50 mL) and washed with 5% aqueous sodium hydrogen carbonate solution (50 mL) then water (50 mL). The organic layer was separated, dried (MgSO₄) and evaporated in vacuo to yield A332.7 (1.2 g) as a yellow solid which was used immediately without further purification. HPLC YMC S-5 4.6×33 mm (2 min grad): retention time 1.56 min, M+H⁺=549.34

A332.8: 3-(1-methyl-4-(methylamino)-1,6-dihydroimidazo[4,5-d∪pyrrolo[2,3-b]pyridin-7-yl)benzyl 4-isopropylpiperazine-1-carboxylate Dimethylamine (2.0M in THF, 1 mL, 2 mmol) was added in one portion to the succinimide carbonate A333.7 (15 mg, 0.027 mmol). The reaction mixture was allowed to stir at room temperature in a screw capped vial for 1 hr before the addition of 4N HCl in dioxane (2 mL) with continued stirring for 2 h. The reaction mixture was evaporated in vacuo and purified by preparative hplc to yield A332 (3.0 mg). HPLC YMC S-5 4.6×33 mm (2 min grad): retention time 1.76 min, M+H⁺=379.37

Example A333

3-[1,6-dihydro-1-methyl-4-(methylamino)imidazo[4,5-d]pyrrolo[2,3-b]pyridin-7-yl]-benzenemethanol

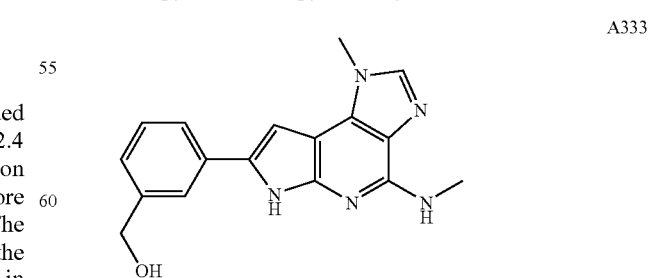

HCl (4.0N in dioxane, 2.0 mL) was added in one portion to A332.6 (20 mg, 0.0049 mol). The reaction mixture was stirred at room temperature for 1 hr before evaporating in vacuo and triturating with diethyl ether (10 mL) to yield A333

(9.12 mg) as a yellow solid. HPLC YMC S-5 4.6×33 mm (2 min grad): retention time 1.22 min, M+H⁺=308.35. ¹H NMR (500 MHz, MeOD) δ 8.19, (s, 1H), 7.73 (s, 1H), 7.64 (d, J=7.7 hz, 1H), 7.41 (t, J=7.7 hz, 1H), 7.30 (d, J=7.7 hz, 1H), 7.15 (s, 1H), 4.66 (s, 2H), 4.13 (s, 3H) and 3.24 (s, 3H).

Examples A334-A390

Examples A334-A390 were prepared by parallel synthesis according to the scheme shown below.

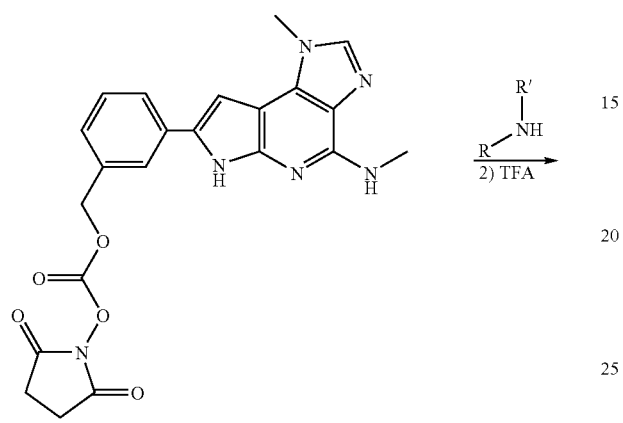

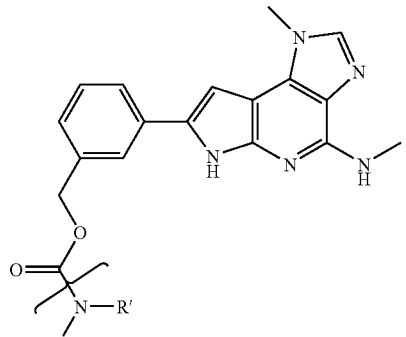

TABLE A13

| Ex. | R | Name | HPLC Retention (min) | MS Reported |
|---|---|---|---|---|
| A334 | MeO-CH₂CH₂-HN— | 3-(1-methyl-4-(methylamino)-1,6-dihydroimidazo[4,5-d]pyrrolo[2,3-b]pyridin-7-yl)benzyl 2-methoxyethylcarbamate | 2.49 | 409.29 |
| A335 | CH₃NH— | 3-(1-methyl-4-(methylamino)-1,6-dihydroimidazo[4,5-d]pyrrolo[2,3-b]pyridin-7-yl)benzyl methyethylcarbamate | 2.45 | 365.25 |
| A336 | cyclopropyl-HN— | 3-(1-methyl-4-(methylamino)-1,6-dihydroimidazo[4,5-d]pyrrolo[2,3-b]pyridin-7-yl)benzyl cyclopropylcarbamate | 2.63 | 391.28 |

TABLE A13-continued

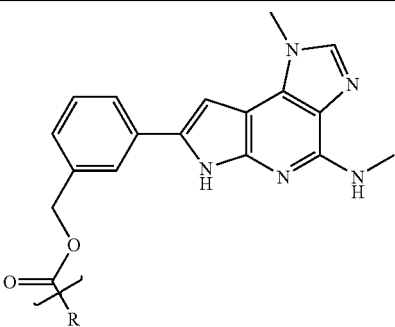

| Ex. | R | Name | HPLC Retention (min) | MS Reported |
|---|---|---|---|---|
| A337 | 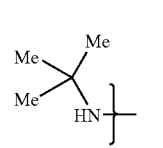 | 3-(1-methyl-4-(methylamino)-1,6-dihydroimidazo[4,5-d]pyrrolo[2,3-b]pyridin-7-yl)benzyl 5-methyl-1,3,4-thiadiazol-2-ylcarbamate | 2.75 | 449.19 |
| A338 | 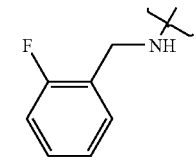 | 3-(1-methyl-4-(methylamino)-1,6-dihydroimidazo[4,5-d]pyrrolo[2,3-b]pyridin-7-yl)benzyl tert-butylcarbamate | 2.94 | 407.29 |
| A339 | 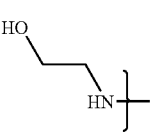 | 3-(1-methyl-4-(methylamino)-1,6-dihydroimidazo[4,5-d]pyrrolo[2,3-b]pyridin-7-yl)benzyl 2-fluorobenzylcarbamate | 3.01 | 459.22 |
| A340 | 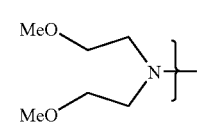 | 3-(1-methyl-4-(methylamino)-1,6-dihydroimidazo[4,5-d]pyrrolo[2,3-b]pyridin-7-yl)benzyl 2-hydroxyethylcarbamate | 2.31 | 395.23 |
| A341 | 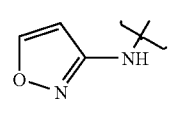 | 3-(1-methyl-4-(methylamino)-1,6-dihydroimidazo[4,5-d]pyrrolo[2,3-b]pyridin-7-yl)benzyl bis(2-methoxyethyl)carbamate | 2.77 | 467.25 |
| A342 | 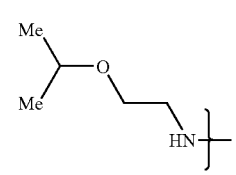 | 3-(1-methyl-4-(methylamino)-1,6-dihydroimidazo[4,5-d]pyrrolo[2,3-b]pyridin-7-yl)benzyl isoxazol-3-ylcarbamate | 2.60 | 418.21 |
| A343 | 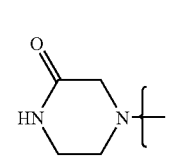 | 3-(1-methyl-4-(methylamino)-1,6-dihydroimidazo[4,5-d]pyrrolo[2,3-b]pyridin-7-yl)benzyl 2-isopropoxyethylcarbamate | 2.82 | 437.28 |
| A344 |  | 3-(1-methyl-4-(methylamino)-1,6-dihydroimidazo[4,5-d]pyrrolo[2,3-b]pyridin-7-yl)benzyl 3-oxopiperazine-1-carboxylate | 2.35 | 434.24 |

TABLE A13-continued

| Ex. | R | Name | HPLC Retention (min) | MS Reported |
|---|---|---|---|---|
| A345 | 4-(hydroxymethyl)piperidin-1-yl | 3-(1-methyl-4-(methylamino)-1,6-dihydroimidazo[4,5-d]pyrrolo[2,3-b]pyridin-7-yl)benzyl 4-(hydroxymethyl)piperidine-1-carboxylate | 2.69 | 449.32 |
| A346 | (R)-3-hydroxypyrrolidin-1-yl | (R)-3-(1-methyl-4-(methylamino)-1,6-dihydroimidazo[4,5-d]pyrrolo[2,3-b]pyridin-7-yl)benzyl 3-hydroxypyrrolidine-1-carboxylate | 2.50 | 421.31 |
| A347 | methyl(1-methylpyrrolidin-3-yl)amino | 3-(1-methyl-4-(methylamino)-1,6-dihydroimidazo[4,5-d]pyrrolo[2,3-b]pyridin-7-yl)benzyl methyl(1-methylpyrrolidin-3-yl)carbamate | 2.20 | 448.33 |
| A348 | 4-acetylpiperazin-1-yl | 3-(1-methyl-4-(methylamino)-1,6-dihydroimidazo[4,5-d]pyrrolo[2,3-b]pyridin-7-yl)benzyl 4-acetylpiperazine-1-carboxylate | 2.51 | 462.31 |
| A349 | (carboxymethyl)amino | 2-((3-(1-methyl-4-(methylamino)-1,6-dihydroimidazo[4,5-d]pyrrolo[2,3-b]pyridin-7-yl)benzyloxy)carbonylamino)acetic acid | 2.23 | 450.35 |
| A350 | 3-(dimethylamino)propyl(methyl)amino | 3-(1-methyl-4-(methylamino)-1,6-dihydroimidazo[4,5-d]pyrrolo[2,3-b]pyridin-7-yl)benzyl 3-(dimethylamino)propyl(methyl)carbamate | 2.23 | 450.35 |
| A351 | 2-(dimethylamino)ethyl(methyl)amino | 3-(1-methyl-4-(methylamino)-1,6-dihydroimidazo[4,5-d]pyrrolo[2,3-b]pyridin-7-yl)benzyl 2-(dimethylamino)ethyl(methyl)carbamate | 2.15 | 436.32 |

TABLE A13-continued

| Ex. | R | Name | HPLC Retention (min) | MS Reported |
|---|---|---|---|---|
| A352 | (S)-MeO-CH2-pyrrolidinyl | (S)-3-(1-methyl-4-(methylamino)-1,6-dihydroimidazo[4,5-d]pyrrolo[2,3-b]pyridin-7-yl)benzyl 3-(methoxymethyl)pyrrolidine-1-carboxylate | 2.93 | 449.32 |
| A353 | Me-CH2-CH2-N(Me)- | 3-(1-methyl-4-(methylamino)-1,6-dihydroimidazo[4,5-d]pyrrolo[2,3-b]pyridin-7-yl)benzyl methyl(propyl)carbamate | 3.04 | 407.33 |
| A354 | (MeCH2)2N- | 3-(1-methyl-4-(methylamino)-1,6-dihydroimidazo[4,5-d]pyrrolo[2,3-b]pyridin-7-yl)benzyl diethylcarbamate | 3.01 | 407.34 |
| A355 | MeCH2-N(Me)- | 3-(1-methyl-4-(methylamino)-1,6-dihydroimidazo[4,5-d]pyrrolo[2,3-b]pyridin-7-yl)benzyl ethyl(methyl)carbamate | 2.85 | 393.33 |
| A356 | PhCH2CH2-N(Me)- | 3-(1-methyl-4-(methylamino)-1,6-dihydroimidazo[4,5-d]pyrrolo[2,3-b]pyridin-7-yl)benzyl methyl(phenethyl)carbamate | 3.29 | 469.32 |
| A357 | PhCH2-N(Me)- | 3-(1-methyl-4-(methylamino)-1,6-dihydroimidazo[4,5-d]pyrrolo[2,3-b]pyridin-7-yl)benzyl benzyl(methyl)carbamate | 3.20 | 455.30 |
| A358 | Me2CH-CH2-CH2-NH- | 3-(1-methyl-4-(methylamino)-1,6-dihydroimidazo[4,5-d]pyrrolo[2,3-b]pyridin-7-yl)benzyl isopentylcarbamate | 3.12 | 421.31 |

TABLE A13-continued

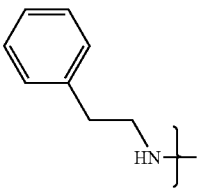

| Ex. | R | Name | HPLC Retention (min) | MS Reported |
|---|---|---|---|---|
| A359 | 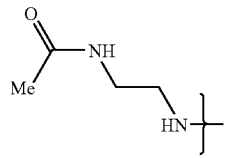 | 3-(1-methyl-4-(methylamino)-1,6-dihydroimidazo[4,5-d]pyrrolo[2,3-b]pyridin-7-yl)benzyl phenethylcarbamate | 3.10 | 455.30 |
| A360 | 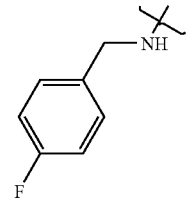 | 3-(1-methyl-4-(methylamino)-1,6-dihydroimidazo[4,5-d]pyrrolo[2,3-b]pyridin-7-yl)benzyl 2-acetamidoethylcarbamate | 2.32 | 436.29 |
| A361 | EtNH— | 3-(1-methyl-4-(methylamino)-1,6-dihydroimidazo[4,5-d]pyrrolo[2,3-b]pyridin-7-yl)benzyl ethylcarbamate | 2.57 | 379.31 |
| A362 | 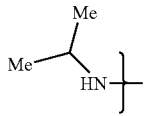 | 3-(1-methyl-4-(methylamino)-1,6-dihydroimidazo[4,5-d]pyrrolo[2,3-b]pyridin-7-yl)benzyl 4-fluorobenzylcarbamate | 3.00 | 459.25 |
| A363 | 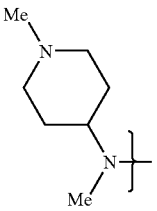 | 3-(1-methyl-4-(methylamino)-1,6-dihydroimidazo[4,5-d]pyrrolo[2,3-b]pyridin-7-yl)benzyl isopropylcarbamate | 2.73 | 393.31 |
| A364 | 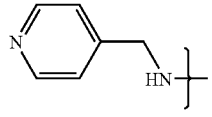 | 3-(1-methyl-4-(methylamino)-1,6-dihydroimidazo[4,5-d]pyrrolo[2,3-b]pyridin-7-yl)benzyl methyl(1-methylpiperidin-4-yl)carbamate | 2.23 | 462.32 |
| A365 |  | 3-(1-methyl-4-(methylamino)-1,6-dihydroimidazo[4,5-d]pyrrolo[2,3-b]pyridin-7-yl)benzyl pyridin-4-ylmethylcarbamate | 2.12 | 442.29 |

TABLE A13-continued

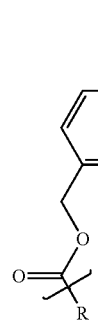

| Ex. | R | Name | HPLC Retention (min) | MS Reported |
|---|---|---|---|---|
| A366 | 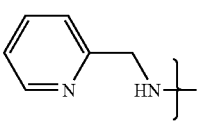 | 3-(1-methyl-4-(methylamino)-1,6-dihydroimidazo[4,5-d]pyrrolo[2,3-b]pyridin-7-yl)benzyl pyridin-3-ylmethylcarbamate | 2.14 | 422.27 |
| A367 | 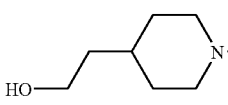 | 3-(1-methyl-4-(methylamino)-1,6-dihydroimidazo[4,5-d]pyrrolo[2,3-b]pyridin-7-yl)benzyl pyridin-2-ylmethylcarbamate | 2.14 | 442.25 |
| A368 | 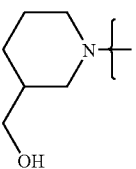 | 3-(1-methyl-4-(methylamino)-1,6-dihydroimidazo[4,5-d]pyrrolo[2,3-b]pyridin-7-yl)benzyl 4-(2-hydroxyethyl)piperidine-1-carboxylate | 2.82 | 463.32 |
| A369 | 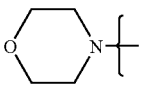 | 3-(1-methyl-4-(methylamino)-1,6-dihydroimidazo[4,5-d]pyrrolo[2,3-b]pyridin-7-yl)benzyl 3-(hydroxymethyl)piperidine-1-carboxylate | 2.74 | 449.32 |
| A370 | 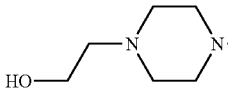 | 3-(1-methyl-4-(methylamino)-1,6-dihydroimidazo[4,5-d]pyrrolo[2,3-b]pyridin-7-yl)benzyl morpholine-4-carboxylate | 2.64 | 421.31 |
| A371 | 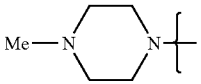 | 3-(1-methyl-4-(methylamino)-1,6-dihydroimidazo[4,5-d]pyrrolo[2,3-b]pyridin-7-yl)benzyl 4-(2-hydroxyethyl)piperazine-1-carboxylate | 2.10 | 464.31 |
| A372 | 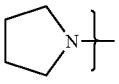 | 3-(1-methyl-4-(methylamino)-1,6-dihydroimidazo[4,5-d]pyrrolo[2,3-b]pyridin-7-yl)benzyl 4-methylpiperazine-1-carboxylate | 2.10 | 434.31 |
| A373 | | 3-(1-methyl-4-(methylamino)-1,6-dihydroimidazo[4,5-d]pyrrolo[2,3-b]pyridin-7-yl)benzyl pyrrolidine-1-carboxylate | 2.91 | 405.32 |

TABLE A13-continued

| Ex. | R | Name | HPLC Retention (min) | MS Reported |
|---|---|---|---|---|
| A374 | Ph-CH2-N(Me)- | 3-(1-methyl-4-(methylamino)-1,6-dihydroimidazo[4,5-d]pyrrolo[2,3-b]pyridin-7-yl)benzyl benzyl(methyl)carbamate | 2.96 | 485.29 |
| A375 | HO-CH2CH2-N(Me)- | 3-(1-methyl-4-(methylamino)-1,6-dihydroimidazo[4,5-d]pyrrolo[2,3-b]pyridin-7-yl)benzyl 2-hydroxyethyl(methyl)carbamate | 2.45 | 409.31 |
| A376 | NC-CH2CH2-N(Me)- | 3-(1-methyl-4-(methylamino)-1,6-dihydroimidazo[4,5-d]pyrrolo[2,3-b]pyridin-7-yl)benzyl 2-cyanoethyl(methyl)carbamate | 2.50 | 418.31 |
| A377 | Ph-N(piperazine)- | 3-(1-methyl-4-(methylamino)-1,6-dihydroimidazo[4,5-d]pyrrolo[2,3-b]pyridin-7-yl)benzyl 4-phenylpiperazine-1-carboxylate | 3.04 | 496.32 |
| A378 | Me-CH(Et)-NH- | 3-(1-methyl-4-(methylamino)-1,6-dihydroimidazo[4,5-d]pyrrolo[2,3-b]pyridin-7-yl)benzyl sec-butylcarbamate | 2.87 | 407.36 |
| A379 | 3-F-C6H4-CH2-NH- | 3-(1-methyl-4-(methylamino)-1,6-dihydroimidazo[4,5-d]pyrrolo[2,3-b]pyridin-7-yl)benzyl 3-fluorobenzylcarbamate | 2.99 | 459.28 |
| A380 | Me2CH-CH2-NH- | 3-(1-methyl-4-(methylamino)-1,6-dihydroimidazo[4,5-d]pyrrolo[2,3-b]pyridin-7-yl)benzyl isobutylcarbamate | 2.92 | 407.36 |
| A381 | 3-hydroxypiperidin-1-yl | 3-(1-methyl-4-(methylamino)-1,6-dihydroimidazo[4,5-d]pyrrolo[2,3-b]pyridin-7-yl)benzyl 3-hydroxypiperidine-1-carboxylate | 2.59 | 435.32 |

TABLE A13-continued

| Ex. | R | Name | HPLC Retention (min) | MS Reported |
|---|---|---|---|---|
| A382 | cyclopropylmethyl-NH- | 3-(1-methyl-4-(methylamino)-1,6-dihydroimidazo[4,5-d]pyrrolo[2,3-b]pyridin-7-yl)benzyl cyclopropylmethylcarbamate | 2.80 | 405.35 |
| A383 | 4-methylhomopiperazin-1-yl | 3-(1-methyl-4-(methylamino)-1,6-dihydroimidazo[4,5-d]pyrrolo[2,3-b]pyridin-7-yl)benzyl 4-methyl-1,4-diazepane-1-carboxylate | 2.08 | 448.34 |
| A384 | (S)-3-acetamidopyrrolidin-1-yl | (S)-3-(1-methyl-4-(methylamino)-1,6-dihydroimidazo[4,5-d]pyrrolo[2,3-b]pyridin-7-yl)benzyl 3-acetamidopyrrolidine-1-carboxylate | 2.48 | 462.32 |
| A385 | 2-methoxyethyl(methyl)amino | 3-(1-methyl-4-(methylamino)-1,6-dihydroimidazo[4,5-d]pyrrolo[2,3-b]pyridin-7-yl)benzyl 2-methoxyethyl(methyl)carbamate | 2.67 | 423.31 |
| A386 | 4-(2-methoxyethyl)piperazin-1-yl | 3-(1-methyl-4-(methylamino)-1,6-dihydroimidazo[4,5-d]pyrrolo[2,3-b]pyridin-7-yl)benzyl 4-(2-methoxyethyl)piperazine-1-carboxylate | 2.09 | 478.32 |
| A387 | (S)-3-hydroxypyrrolidin-1-yl | (S)-3-(1-methyl-4-(methylamino)-1,6-dihydroimidazo[4,5-d]pyrrolo[2,3-b]pyridin-7-yl)benzyl 3-hydroxypyrrolidine-1-carboxylate | 2.45 | 421.31 |
| A388 | (R)-1-carboxyethyl-NH- | (R)-2-((3-(1-methyl-4-(methylamino)-1,6-dihydroimidazo[4,5-d]pyrrolo[2,3-b]pyridin-7-yl)benzyloxy)carbonylamino)propanoic acid | 2.40 | 423.31 |
| A389 | 4-isopropylpiperazin-1-yl | 3-(1-methyl-4-(methylamino)-1,6-dihydroimidazo[4,5-d]pyrrolo[2,3-b]pyridin-7-yl)benzyl 4-isopropylpiperazine-1-carboxylate | 2.08 | 462.36 |

TABLE A13-continued

| Ex. | R | Name | HPLC Retention (min) | MS Reported |
|---|---|---|---|---|
| A390 | 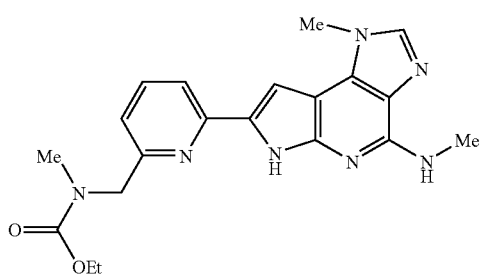 | (S)-3-methyl-2-((3-(1-methyl-4-(methylamino)-1,6-dihydroimidazo[4,5-d]pyrrolo[2,3-b]pyridin-7-yl)benzyloxy)carbonylamino) butanoic acid | 2.71 | 451.32 |

Examples A391

N-[[6-[1,6-dihydro-1-methyl-4-(methylamino)imidazo[4,5-d]pyrrolo[2,3-b]pyridin-7-yl]-2-pyridinyl]methyl]-N,N'-dimethyl-urea

A391

Example A392

Ethyl methyl((6-(1-methyl-4-(methylamino)-1,6-dihydroimidazo[4,5-d]pyrrolo[2,3-b]pyridin-7-yl)pyridin-2-yl)methyl)carbamate

A392

A391.1: N-Methyl-N-((6-(1-methyl-4-(methylamino)-1,6-dihydroimidaza[4,5-d]pyrrolo[2,3-b]pyridine-7-yl)pyridine-2-yl)methyl)-1H-imidazole-1-carboxamide

A391.1

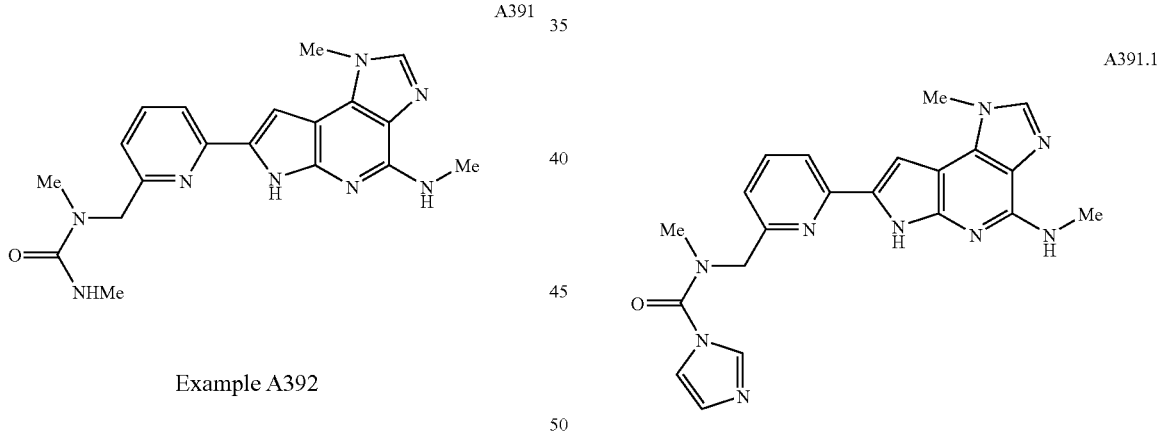

A solution of A247 (10.0 mg, 0.031 mmol), 1,1'-carbonyldiimidazole (40.21 mg, 0.248 mmol), and triethylamine (21.6 µL, 0.16 mmol) in DMF (1.0 mL) was heated at 80° C. for 30 min. After cooling to room temperature, DMF was removed. Water (1.0 mL) and 1:1 THF:EtOAc (2.0 mL) were added, The organic layer was washed with water, brine, dried (Na$_2$SO$_4$), and evaporated under vacuum to yield 9.0 mg M49.1 as a tan solid. HPLC (C): 100.0%, ret. time 1.79 min., MS (D): (M+H)$^+$=416.41; (M–H)=414.41. The acyl imidazole was dissolved in dimethylamine (1.5 mL of a 2.0 M solution in MeOH) and heated at 80° C. for 15 min. The crude product was purified by reverse-phase preparative HPLC to yield A391.1 as an orange solid. HPLC (C): 99.14%, ret. time 2.28 min., LC/MS (M+H)$^+$=380.26.

A391.2: N-[[6-[1,6-dihydro-1-methyl-4-(methylamino)imidazo[4,5-d]pyrrolo[2,3-b]pyridin-7-yl]-2-pyridinyl]methyl]-N,N'-dimethyl-urea and Ethyl methyl((6-(1-methyl-4-(methylamino)-1,6-dihydroimidazo[4,5-d]pyrrolo[2,3-b]pyridin-7-yl)pyridin-2-yl)methyl)carbamate A somewhat cloudy solution of A391.1 (23.5 mg, 0.057 mmol) in methylamine (1.5 mL of a 33% b/w solution in EtOH) was heated at 80° C. for 20 min. After solvent removal, the crude product was combined with crude A392 from a previous reaction and purified by reversed-phase preparative HPLC. Yield: A391 (10.0 mg, yellow solid, 26% assuming 1.0 TFA salt) and A392 (7.5 mg, orange solid, 13% assuming 1.0 TFA salt). HPLC (C): A391, ret. time 1.84 min., LC/MS (M+H)$^+$=379.30. HPLC (C): A392, ret. time 2.48 min., LC/MS (M+H)$^+$=394.23

Examples A393

2-(dimethylamino)ethyl methyl((6-(1-methyl-4-(methylamino)-1,6-dihydroimidazo[4,5-d]pyrrolo[2,3-b]pyridin-7-yl)pyridin-2-yl)methyl)carbamate and isopropyl methyl((6-(1-methyl-4-(methylamino)-1,6-dihydroimidazo[4,5-d]pyrrolo[2,3-b]pyridin-7-yl)pyridin-2-yl)methyl)carbamate

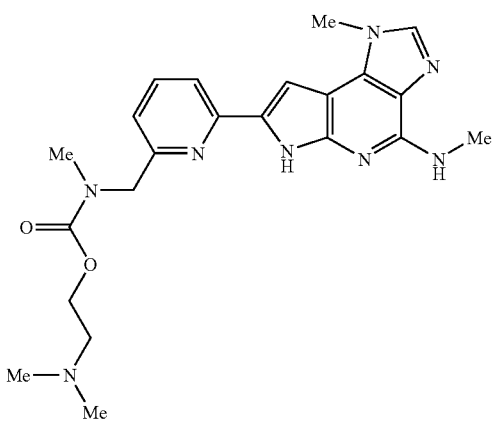

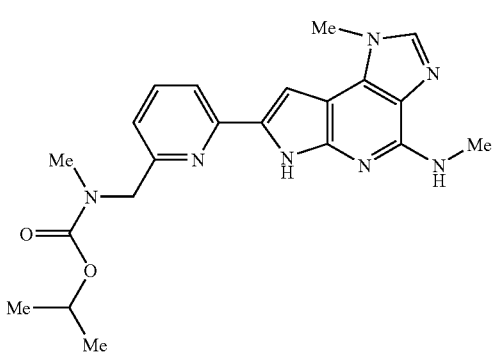

In a procedure similar to A391, A391.1 was reacted with N,N-dimethylethanolamine in isopropanol and purified by reverse phase chromatography. HPLC (C): A393 (tan-orange solid), ret. time 1.84 min., LC/MS (M+H)$^+$=437.33. HPLC (C): A394 (orange solid), ret. time 2.66 min., LC/MS (M+H)$^+$=409.34.

Example A395

N-[[6-[1,6-dihydro-1-methyl-4-(methylamino)imidazo[4,5-d]pyrrolo[2,3-b]pyridin-7-yl]-2-pyridinyl]methyl]-N-methyl-benzenesulfonamide

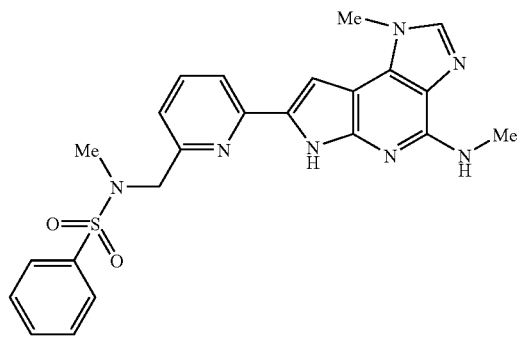

A suspension of A247 (10.0 mg, 0.031 mmol) and benzenesulfonyl chloride (4.77 µL, 0.037 mmol) in pyridine (1.5 mL) was stirred at 80° C. for 2 h. Pyridine was removed under vacuum. MeOH was added (3.0 mL), the precipitate was collected by filtration, rinsed with MeOH, and dried under vacuum to yield A395 (7.0 mg, 49%, white solid). HPLC (C): 100%, ret. time 2.66 min., LC/MS (M+H)$^+$=462.24.

Example A396

N-[[6-[1,6-dihydro-1-methyl-4-(methylamino)imidazo[4,5-d]pyrrolo[2,3-b]pyridin-7-yl]-2-pyridinyl]methyl]-N-methyl-methanesulfonamide

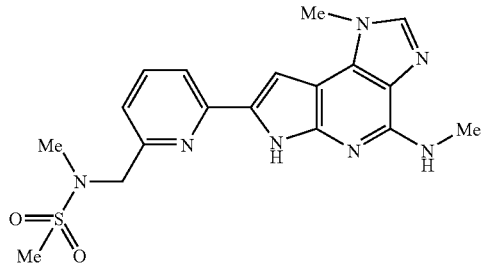

In a manner similar to A394, A247 was reacted with methanesulfonylchloride to yield A396. HPLC (C): 100%, ret. time 2.10 min., LC/MS (M+H)$^+$=400.28.

Example A397

N-[[6-[1,6-dihydro-1-methyl-4-(methylamino)imidazo[4,5-d]pyrrolo[2,3-b]pyridin-7-yl]-2-pyridinyl]methyl]-2-methoxy-N-prop-2-enyl-acetamide

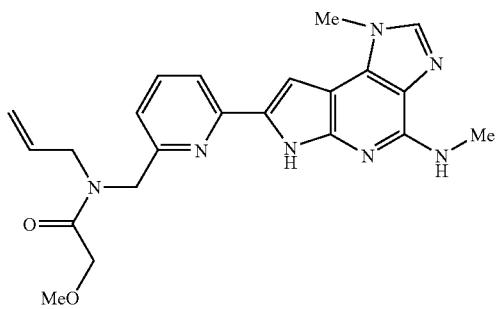

A397

A397.1: N-[[6-[1,6-dihydro-1-methyl-4-(N-methyl-tert-butyloxycarbonylamino)imidazo[4,5-d]pyrrolo[2,3-b]pyridin-7-yl]-2-pyridinyl]methyl]-2-methoxy-N-prop-2-enyl-acetamide

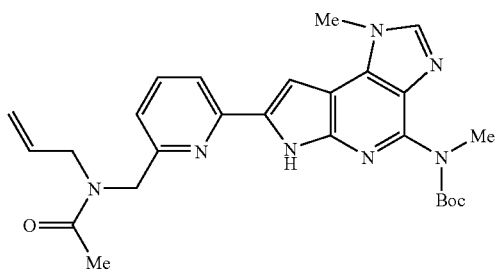

A397.1

NaH (0.10 g of a 60% mineral oil dispersion, 2.54 mmol) was added to a solution of 1G (0.38 g, 0.845 mmol) in DMF (4.0 mL). After 10 min., allyl bromide was added (36.6 µL, 0.42 mmol) and the reaction mixture was stirred for 30 min. More allyl bromide was added (36.6 µL, 0.42 mmol) and stirring was continued for 2 h. After quenching with saturated aq NH₄Cl solution (1.0 mL), DMF was removed under vacuum and the crude product was purified by reverse-phase preparative HPLC to yield A397.1 (0.30 g) as a tan-orange oil (83:17 A397.1: 1G by HPLC analysis). HPLC (C): 92.0%, ret. time 2.72 min., LC/MS (M+H)$^+$=490.31.

A397.2: N-[[6-[1,6-dihydro-1-methyl-4-(methylamino)imidazo[4,5-d]pyrrolo[2,3-b]pyridin-7-yl]-2-pyridinyl]methyl]-N-prop-2-enyl-amine

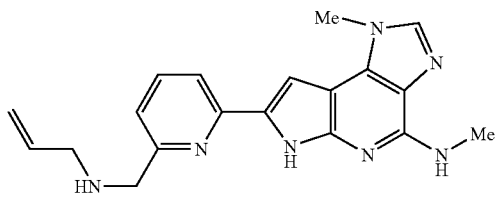

A397.2

In a procedure similar to A247, A397.1 was treated with acid. The crude product was neutralized with saturated aqueous NaHCO₃ solution, and the reaction mixture was evaporated to dryness under vacuum. The free base was then dissolved in MeOH and the inorganic material was removed by filtration. Yield after evaporation of MeOH under vacuum: 0.2525 g of A397.2 as a tan solid (>100%). HPLC (C): 78.5%, ret. time 2.12 min., LC/MS (M+H)$^+$=348.31.

A397.3: N-[[6-[1,6-dihydro-1-methyl-4-(methylamino)imidazo[4,5-d]pyrrolo[2,3-b]pyridin-7-yl]-2-pyridinyl]methyl]-2-methoxy-N-prop-2-enyl-acetamide In a procedure similar to A248, A397.2 was reacted with methoxyacetic acid to yield A397. HPLC (C): 92.0%, ret. time 2.31 min., LC/MS (M+H)$^+$=420.33.

Examples A398-A413

Examples A398-A413 were prepared from A247 in a similar fashion to A248.

For examples A398 and A399, the carboxylate salts A398.1 and A399.1 were prepared as follows:

A398.1:
(R)-(+)-2,2-dimethyl-1,3dioxalan-4-carboxylic acid, potassium salt

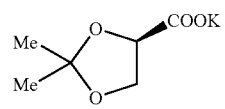

A398.1

A solution of KOH (0.35 g, 6.24 mmol) in MeOH (7.24 mL) was added dropwise to a solution of commercially available (R)-(+)-2,2-dimethyl-1,3 dioxalan-4-carboxylic acid, methyl ester (1.0 g, 6.24 mmol) in MeOH (10.9 mL). The reaction mixture was stirred for 16 h. More KOH was added (0.07 g in 27 µL of MeOH) and after 2 h the reaction mixture was evaporated to dryness. Ether was added (15.0 mL), and after a 30 sec. sonication, the precipitate was collected by filtration, rinsed with ether, and dried under vacuum to yield A398.1 (1.03 g, 90%) as a white solid. HPLC (C): 100%, ret. time 0.645 min., LC/MS (M+H+ Na)$^+$=169.11.

A399.1: (S)-(−)-2,2-dimethyl-1,3 dioxalan-4-carboxylic acid, potassium salt

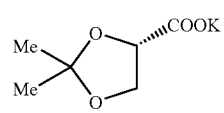

M59.1

A399.1 was prepared in a similar fashion to A398.1. HPLC (C): 100%, ret. time 0.645 min., LC/MS (M+H+ Na)$^+$=169.11.

TABLE A14

| Ex. | R | Name | HPLC Retention (min) | MS Reported |
|---|---|---|---|---|
| A398 | 2,2-dimethyl-1,3-dioxolane (R) | (R)-N,2,2-trimethyl-N-((6-(1-methyl-4-(methylamino)-1,6-dihydroimidazo[4,5-d]pyrrolo[2,3-b]pyridin-7-yl)pyridine-2-yl)methyl)-1,3-dioxolane-4-carboxamide | 2.33 | 450.31 |
| A399 | 2,2-dimethyl-1,3-dioxolane (S) | (S)-N,2,2-trimethyl-N-((6-(1-methyl-4-(methylamino)-1,6-dihydroimidazo[4,5-d]pyrrolo[2,3-b]pyridin-7-yl)pyridine-2-yl)methyl)-1,3-dioxolane-4-carboxamide | 2.34 | 450.31 |
| A400 | (R)-CH(OH)CH2OH | (R)-2,3-dihydroxy-N-methyl-N-((6-(1-methyl-4-(methylamino)-1,6-dihydroimidazo[4,5-d]pyrrolo[2,3-b]pyridin-7-yl)pyridine-2-yl)methyl)propanamide | 1.81 | 410.31 |
| A401 | (S)-CH(OH)CH2OH | (S)-2,3-dihydroxy-N-methyl-N-((6-(1-methyl-4-(methylamino)-1,6-dihydroimidazo[4,5-d]pyrrolo[2,3-b]pyridin-7-yl)pyridine-2-yl)methyl)propanamide | 1.81 | 410.31 |
| A402 | -CH2NHS(O)2Me | N-methyl-N-((6-(1-methyl-4-(methylamino)-1,6-dihydroimidazo[4,5-d]pyrrolo[2,3-b]pyridin-7-yl)pyridin-2-yl)methyl)-2-(methylsulfonamido)acetamide | 1.93 | 457.23 |
| A403 | -CH2CH2N(Me)2 | 3-(dimethylamino)-N-methyl-N-((6-(1-methyl-4-(methylamino)-1,6-dihydroimidazo[4,5-d]pyrrolo[2,3-b]pyridin-7-yl)pyridin-2-yl)methyl)propanamide | 1.75 | 421.36 |
| A404 | 1H-imidazol-5-yl | N-methyl-N-((6-(1-methyl-4-(methylamino)-1,6-dihydroimidazo[4,5-d]pyrrolo[2,3-b]pyridin-7-yl)pyridin-2-yl)methyl)-1H-imidazole-5-carboxamide | 1.71 | 416.29 |
| A405 | -CH2CH2CH2S(O)2NH2 | N-methyl-N-((6-(1-methyl-4-(methylamino)-1,6-dihydroimidazo[4,5-d]pyrrolo[2,3-b]pyridin-7-yl)pyridin-2-yl)methyl)-4-sulfamoylbutanamide | 1.91 | 471.31 |

TABLE A14-continued

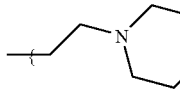

| Ex. | R | Name | HPLC Retention (min) | MS Reported |
|---|---|---|---|---|
| A406 | 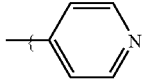 | N-methyl-N-((6-(1-methyl-4-(methylamino)-1,6-dihydroimidazo[4,5-d]pyrrolo[2,3-b]pyridin-7-yl)pyridin-2-yl)methyl)-3-(piperidin-1-yl)propanamide | 1.86 | 461.43 |
| A407 | 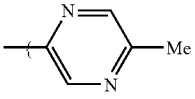 | N-methyl-N-((6-(1-methyl-4-(methylamino)-1,6-dihydroimidazo[4,5-d]pyrrolo[2,3-b]pyridin-7-yl)pyridin-2-yl)methyl)isonicotinamide | 1.84 | 427.38 |
| A408 |  | N,5-dimethyl-N-((6-(1-methyl-4-(methylamino)-1,6-dihydroimidazo[4,5-d]pyrrolo[2,3-b]pyridin-7-yl)pyridin-2-yl)methyl)pyrazine-2-carboxamide | 2.24 | 442.30 |
| A409 | 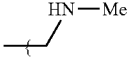 | 2-hydroxy-N-methyl-N-((6-(1-methyl-4-(methylamino)-1,6-dihydroimidazo[4,5-d]pyrrolo[2,3-b]pyridin-7-yl)pyridin-2-yl)methyl)propanamide | 2.01 | 408.38 |
| A410 | HN—Me | N-methyl-N-((6-(1-methyl-4-(methylamino)-1,6-dihydroimidazo[4,5-d]pyrrolo[2,3-b]pyridin-7-yl)pyridin-2-yl)methyl)-2-(methylamino)acetamide | 1.66 | 393.39 |
| A411 | 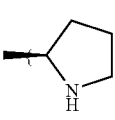 | (R)-N-methyl-N-((6-(1-methyl-4-(methylamino)-1,6-dihydroimidazo[4,5-d]pyrrolo[2,3-b]pyridin-7-yl)pyridin-2-yl)methyl)pyrrolidine-2-carboxamide | 1.74 | 419.32 |
| A412 | 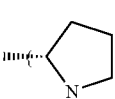 | (S)-N-methyl-N-((6-(1-methyl-4-(methylamino)-1,6-dihydroimidazo[4,5-d]pyrrolo[2,3-b]pyridin-7-yl)pyridin-2-yl)methyl)pyrrolidine-2-carboxamide | 1.74 | 419.31 |
| A413 | 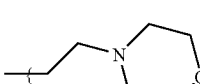 | N-methyl-N-((6-(1-methyl-4-(methylamino)-1,6-dihydroimidazo[4,5-d]pyrrolo[2,3-b]pyridin-7-yl)pyridin-2-yl)methyl)-3-morpholinopropanamide | 1.75 | 463.40 |

Example A414

7-(6-chloropyridin-2-yl)-N,1-dimethyl-1,6-dihydroimidazo[4,5-c]pyrrolo[2,3-b]pyridine-4-amine

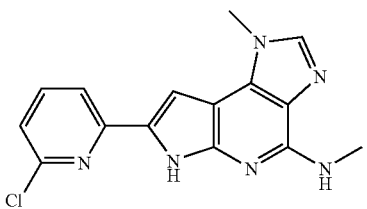

A414

A414.1: Tert-butyl-6-amino-7-(6-chloropyridin-2-yl) ethynyl)-1-methyl-1H-imidazo[4,5-c]pyridine-4-yl (methyl)carbamate

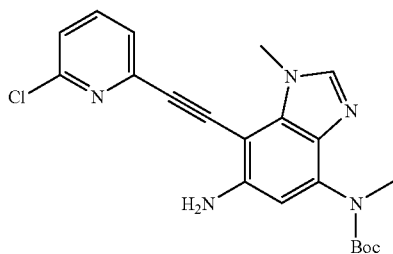

A1.12 (150 mg, 37 mmol), palladiumdichlorobistriphenylphosphine (22 mg, 0.032 mmol), Copper iodide (7 mg, 0.032 mmol) and triethylamine (0.5 ml, 3.7 mmol) in 5 ml DMF was degassed with nitrogen for fifteen minutes. The stirred reaction mixture was heated to 80° C. 2-chloro-6-ethynylpyridine (51 mg, 0.367 mmol) was quickly added and the reaction mixture heated at 80° C. for 1 hour. The reaction mixture was cooled to room temperature concentrated in vacuo. The crude product mixture taken up in dichloromethane and filtered. The filtrate was concentrated in vacuo and the crude product chromatographed on Silica Gel (230-400 Mesh) eluting with 2% MeOH/98% $CH_2Cl_2$ to yield A414.1 (55 mg, 50% yield). M+H+=413.18, 415.18. $^1$H NMR (400 MHz) MeOD δ 7.82 (s, 1H), 7.69 (m, 1H), 7.53 (d, 1H), 7.32 (d, 1H), 4.03 (s, 3H), 3.20 (s, 3H), 1.31 (s, 9H)

Alternate Preparation of A414.1

A solution of A1.12 (1.0 g, 2.48 mmol) and 2-chloro-6-ethynylpyridine (0.68 g, 4.96 mmol) DMF (6.80 mL) was degassed by bubbling nitrogen through the solution. Dichlorobis(triphenylphosphine)Palladium II (0.104 g, 0.148 mmol) and Copper(I) iodide (28.2 mg, 0.148 mmol) were added, and the reaction mixture was heated at 60° C. for 2 h. Additional 2-chloro-6-ethynylpyridine was added (0.17 g, 1.24 mmol) and stirring at 70° C. was continued for 3.0 h. DMF was removed under vacuum. The crude product was partitioned between EtOAc (45.0 mL) and water; after separation, the EtOAc layer was washed with water, brine, dried ($Na_2SO_4$), and concentrated under vacuum. Flash chromatography of the residue on silica gel, eluting with an EtOAc: hexane gradient followed by an EtOAC:MeOH gradient yielded 0.56 g of A414.1 pale tan solid (55%). HPLC (C): 80.5%, ret. Time 2.91 min., LC/MS (M+H)$^+$=413.29.

A414.2: 7-(6-chloropyridin-2-yl)-N,1-dimethyl-1,6-dihydroimidazo[4,5-c]pyrrolo[2,3-b]pyridine-4-amine A414.1 (35 mg, 0.085 mmol), was dissolved in DMA (5 mL) and the solution heated to 70° C. One equivalent of 1.0M potassium t-butoxide in THF (0.1 ml, 0.09 mmol) was quickly added and the reaction heated at 70° C. for thirty minutes. A second equivalent of 1.0M potassium t-butoxide in THF (0.1 ml, 0.09 mmol) was quickly added and the reaction mixture stirred an additional thirty minutes. The reaction mixture was concentrated in vacuo. The crude product residue was chromatographed on Silica Gel (230-400 Mesh) eluting with 2-5% MeOH/$CH_2Cl_2$ to give the Boc-protected intermediate, tert-butyl-7-(6-chloropyridin-2-yl)-1-methyl-1,6-dihydroimidazo[4,5-d]pyrrolo[2,3-b]pyridine-4-yl(methyl)carbamate as an off-white solid. (20 mg, 57% yield). The solid was dissolved in methylene chloride (0.5 mL) and trifluoroacetic acid (0.5 mL) was added and the reaction mixture stirred for 0.25 h. The solvent was evaporated under reduced pressure to provide A414 (12 mg, 57%). M+H+=313.18, 315.18. $^1$H NMR (400 MHz) MEOD δ 8.02 (s, 1H), 7.75 (m, 2H), 7.41 (s, 1H), 7.20 (d, 1H), 4.05 (s, 3 h), 3.15 (s, 3H).

Alternate Preparation of A414

Potassium tert-butoxide (0.94 mL of a 1.0M solution in THF, 0.94 mmol) in DMA (4.5 mL) was added to a solution of A414.1 (0.30 g, 0.73 mmol) in DMA (4.5 mL) under Ar and the reaction mixture was immediately placed in a pre-heated 80° C. oil bath. Stirring was carried out for 17.0 min. The reaction mixture was evaporated to dryness under vacuum. Brine was added (10.0 mL), and after 2.0 min. of sonication, the precipitate was collected by filtration, rinsed with water, and dried under vacuum to yield 0.2775 g of tert-butyl-7-(6-chloropyridin-2-yl)-1-methyl-1,6-dihydroimidazo[4,5-d] pyrrolo[2,3-b]pyridine-4-yl(methyl)carbamate as a light tan powder. Flash chromatography on silica gel, eluting with an EtOAc:MeOH gradient, yielded 0.2315 g of a light tan solid (77.0%). HPLC (C): 91.7%, ret. Time 2.92 min., LC/MS (M+H)$^+$=413.29. The Boc protected intermediate tert-butyl-7-(6-chloropyridin-2-yl)-1-methyl-1,6-dihydroimidazo[4,5-d]pyrrolo[2,3-b]pyridine-4-yl(methyl)carbamate, (940 mg, 22 mmol) was dissolved in 4N HCl in dioxane (10 mL) the resulting suspension was stirred for 15 minutes and the solvent evaporated under reduced pressure. The product was evaporated from methanol and then diethylether, and dried under vacuum to yield A414 as a tan powder (~100%). M+H$^+$=313.26, 315.27.

Example A415

1,6-dihydro-7-[6-[(2-methoxyethyl)amino]-2-pyridinyl]-N,1-dimethyl-imidazo[4,5-d]pyrrolo[2,3-b]pyridin-4-amine

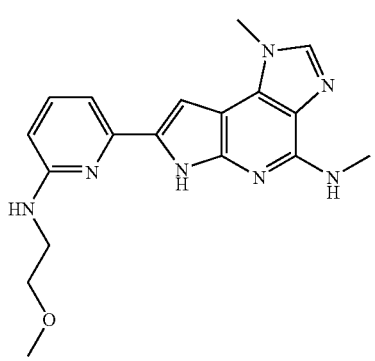

A415

A414 (15 mg, 0.048 mmol), 2-methoxyethylamine (1 ml, 11.5 mmol), 2-tert-butylimino-2-diethylamino-1,3-dimethyl-perhydro-1,3,2-diazaphosphorine on polystyrene [BEMP] (1 g, 2.2 mmol) in NMP was heated at 175° C. for four hours. The reaction mixture was filtered. The filtrate was concentrated in vacuo. The crude product was purified using Reverse Phase-Preparative HPLC/Phenomenex LUNA 5μ, 100×21.2 mm to give the product as an off-white solid. (10 mg, 60% yield). M+H 352.36. $^1$H NMR (400 MHz) MEOD). δ 8.08 (s, 1H), 7.75 (m, 1H), 7.39 (m, 1H), 7.20 (d, 1H), 6.70 (d, 1H). 4.10 (s, 3H), 3.66 (s, 3H), 3.65 (d, 2H), 3.41 (d, 2H), 3.17 (s, 3H).

Example A416

(2S)-3-[[6-[1,6-dihydro-1-methyl-4-(methylamino)imidazo[4,5-d]pyrrolo[2,3-b]pyridin-7-yl]-2-pyridinyl]amino]-1,2-propanediol

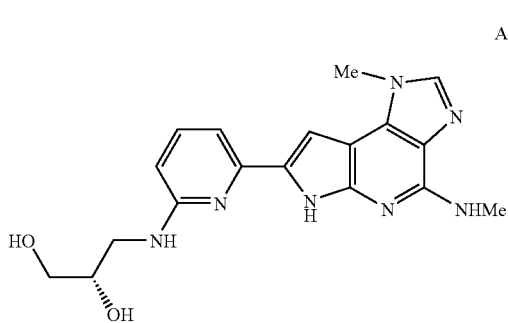

A416

A solution of A414 (15.0 mg, 0.043 mmol) and 1,8-Diazabicyclo[5.4.0]undec-7-ene (96.4 μL, 0.86 mmol) in (S)-(−)-3-Amino-1,2-propanediol (0.60 mL) was heated at 175° C. in a sealed tube for 20.0 hrs. The reaction mixture was concentrated in a 100° C. oil bath with a stream of nitrogen. Reverse-phase preparative HPLC purification yielded 14.7 mg of A416 as a tan solid (71% assuming a 1.0 TFA salt). HPLC (C): 96.5%, ret. Time 1.53 min., LC/MS (M+H)$^+$=368.36.

Examples A417-A435

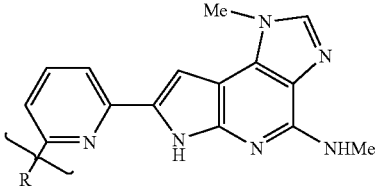

Examples A417-A435 were prepared in a fashion similar to that for A416.

TABLE A15

| Ex. | R | Name | HPLC Retention (min) | MS Reported |
|---|---|---|---|---|
| A417 | —NH—CH₂CH₂—OH | 2-[[6-[1,6-dihydro-1-methyl-4-(methylamino)imidazo[4,5-d]pyrrolo[2,3-b]pyridin-7-yl]-2-pyridinyl]amino]-ethanol | 1.67 | 338.33 |
| A418 | —NH—CH₂CH₂—NH—C(O)Me | N-[2-[[6-[1,6-dihydro-1-methyl-4-(methylamino)imidazo[4,5-d]pyrrolo[2,3-b]pyridin-7-yl]-2-pyridinyl]amino]ethyl]-acetamide | 1.71 | 379.37 |
| A419 | —NH—(CH₂)₃—OMe | 1,6-dihydro-7-[6-[(3-methoxypropyl)amino]-2-pyridinyl]-N,1-dimethyl-imidazo[4,5-d]pyrrolo[2,3-b]pyridin-4-amine | 1.13 | 366.38 |
| A420 | —N(morpholinyl) | 1,6-dihydro-N,1-dimethyl-7-[6-(4-morpholinyl)-2-pyridinyl]-imidazo[4,5-d]pyrrolo[2,3-b]pyridin-4-amine | 2.47 | 364.38 |
| A421 | —N(pyrrolidinyl) | 1,6-dihydro-N,1-dimethyl-7-[6-(1-pyrrolidinyl)-2-pyridinyl]-imidazo[4,5-d]pyrrolo[2,3-b]pyridin-4-amine | 1.91 | 348.35 |

TABLE A15-continued

| Ex. | R | Name | HPLC Retention (min) | MS Reported |
|---|---|---|---|---|
| A422 | 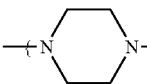 | 4-[6-[1,6-dihydro-1-methyl-4-(methylamino)imidazo[4,5-d]pyrrolo[2,3-b]pyridin-7-yl]-2-pyridinyl]-1-piperazineethanol | 1.87 | 407.41 |
| A423 | 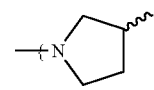 | 1-[6-[1,6-dihydro-1-methyl-4-(methylamino)imidazo[4,5-d]pyrrolo[2,3-b]pyridin-7-yl]-2-pyridinyl]-3-pyrrolidinol | 1.64 | 364.38 |
| A424 | 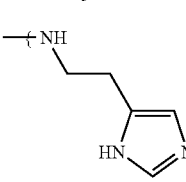 | 1,6-dihydro-7-[6-[[2-(1H-imidazol-4-yl)ethyl]amino]-2-pyridinyl]-N,1-dimethyl-imidazo[4,5-d]pyrrolo[2,3-b]pyridin-4-amine | 1.62 | 388.35 |
| A425 | 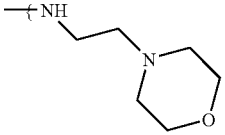 | 1,6-dihydro-N,1-dimethyl-7-[6-[[2-(4-morpholinyl)ethyl]amino]-2-pyridinyl]-imidazo[4,5-d]pyrrolo[2,3-b]pyridin-4-amine | 1.73 | 407.40 |
| A426 | 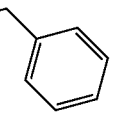 | 1,6-dihydro-N,1-dimethyl-7-[6-[(2-phenylethyl)amino]-2-pyridinyl]-imidazo[4,5-d]pyrrolo[2,3-b]pyridin-4-amine | 1.31 | 398.36 |
| A427 | 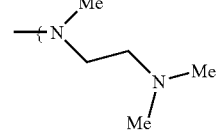 | N-[6-[1,6-dihydro-1-methyl-4-(methylamino)imidazo[4,5-d]pyrrolo[2,3-b]pyridin-7-yl]-2-pyridinyl]-N,N',N'-trimethyl-1,2-ethanediamine | 2.14 | 379.37 |
| A428 | 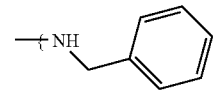 | 1,6-dihydro-N,1-dimethyl-7-[6-[(phenylmethyl)amino]-2-pyridinyl]-imidazo[4,5-d]pyrrolo[2,3-b]pyridin-4-amine | 2.39 | 384.34 |
| A429 | 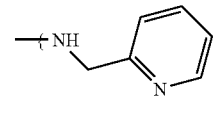 | 1,6-dihydro-N,1-dimethyl-7-[6-[(3-pyridinylmethyl)amino]-2-pyridinyl]-imidazo[4,5-d]pyrrolo[2,3-b]pyridin-4-amine | 1.67 | 385.37 |
| A430 | 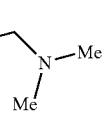 | N'-[6-[1,6-dihydro-1-methyl-4-(methylamino)imidazo[4,5-d]pyrrolo[2,3-b]pyridin-7-yl]-2-pyridinyl]-N,N-dimethyl-1,2-ethanediamine | 1.67 | 365.41 |
| A431 | 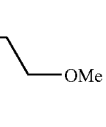 | 7-[6-[(3-ethoxypropyl)amino]-2-pyridinyl]-1,6-dihydro-N,1-dimethyl-imidazo[4,5-d]pyrrolo[2,3-b]pyridin-4-amine | 2.16 | 380.40 |
| A432 | 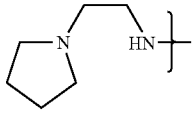 | 1,6-dihydro-N,1-dimethyl-7-[6-[[2-(1-pyrrolidinyl)ethyl]amino]-2-pyridinyl]-imidazo[4,5-d]pyrrolo[2,3-b]pyridin-4-amine | 1.73 | 391.38 |

TABLE A15-continued

| Ex. | R | Name | HPLC Retention (min) | MS Reported |
|---|---|---|---|---|
| A433 | Me—N⟨piperazinyl⟩— | 1,6-dihydro-N,1-dimethyl-7-[6-(4-methyl-1-piperazinyl)-2-pyridinyl]-imidazo[4,5-d]pyrrolo[2,3-b]pyridin-4-amine | 1.87 | 377.34 |
| A434 | EtO-C(O)-CH2-N⟨piperazinyl⟩-N— | 4-[6-[1,6-dihydro-1-methyl-4-(methylamino)imidazo[4,5-d]pyrrolo[2,3-b]pyridin-7-yl]-2-pyridinyl]-1-piperazineacetic acid, ethyl ester | 2.06 | 449.31 |
| A435 | Me-C(O)-N⟨piperazinyl⟩-N— | 1-acetyl-4-[6-[1,6-dihydro-1-methyl-4-(methylamino)imidazo[4,5-d]pyrrolo[2,3-b]pyridin-7-yl]-2-pyridinyl]-piperazine | ND | 405.20 |

Example A436

N-[6-[1,6-dihydro-1-methyl-4-(methylamino)imidazo[4,5-d]pyrrolo[2,3-b]pyridin-7-yl]-2-pyridinyl]-acetamide

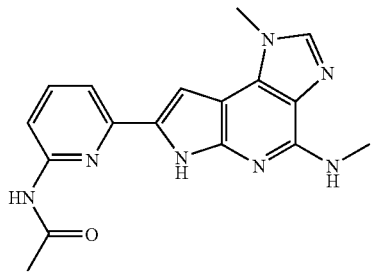

A436

A436.1: N-(6-ethynylpyrdin-2-yl)acetamide

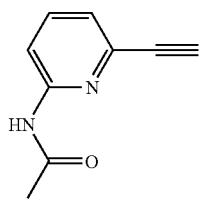

A436.1

Anhydrous potassium carbonate (110 mg, 0.8 mmoles) was added to a solution of N-(6-(((trimethylsilyl)ethynyl)pyridine-2-yl)acetamide (1.86 g, 8 mmol) in 20 ml anhydrous methanol. The reaction mixture was stirred at room temperature for fifteen minutes then filtered. The filtrate was concentrated in vacuo. The crude product mixture was chromatographed on Silica Gel (230-400 Mesh) eluting with 2.5% MeOH/98% $CH_2Cl_2$ to yield A436.1 as an off-white solid.

(770 mg, 60% yield). M+H+=218.20 $^1H$ NMR (400 MHz) MEOD δ 8.13 (m, 1H), 7.75 (m, 1H), 7.27 (m, 1H), 3.65 (s, 1H), 2.18 (s, 3H).

A436.2: tert-Butyl-6-amino-7-(6-acetamidopyridin-2-yl)ethynyl)-1-methyl-1H-imidazo[4,5-c]pyridine-4-yl(methyl)carbamate

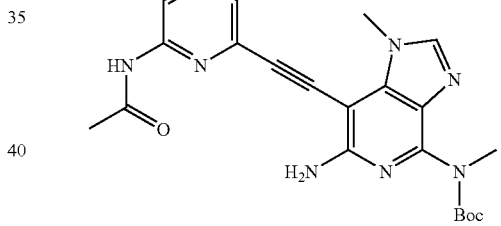

A436.2

A1.12 (200 mg, 0.63 mmol), palladiumdichlorobistriphenylphosphine (44 mg, 0.06 mmol), Copper iodide (12 mg, 0.06 mmol) and dsiisopropylamine (15 ml, 9.45 mmol) in 5 ml DMF was degassed with nitrogen for fifteen minutes. The stirred reaction mixture was heated to 80° C. A436.1 (100 mg, 0.63 mmol) was quickly added and the reaction mixture heated at 80° C. for 1 hour. The reaction mixture was cooled to room temperature and concentrated in vacuo. The crude product mixture taken up in dichloromethane and filtered. The filtrate was concentrated in vacuo and the crude product mixture chromatographed on Silica Gel (230-400 Mesh) eluting with 2.5% MeOH/97.5% $CH_2Cl_2$ to yield A436.2 (135 mg, 50% yield). M+H+=436.31 $^1H$ NMR (400 MHz) MEOD δ 8.02 (s, 1H), 7.50 (s, 1H), 7.35 ((d, 1H), 6.95 (d, 1H), 4.33 (s, 3H), 3.44 (s, 3H), 3.30 ((s, 3H), 1.55 (s, 9H).

A436.3: N-[6-[1,6-dihydro-1-methyl-4-(methylamino)imidazo[4,5-d]pyrrolo[2,3-b]pyridin-7-yl]-2-pyridinyl]-acetamide A436.2 (55 mg, 0.13 mmol), was dissolved in DMA (5 mL) and the solution heated to 70° C. One equivalent of 1.0M potassium t-butoxide in THF (0.14 ml, 0.14 mmol) was quickly added and the reaction heated at 70° C. for thirty minutes. A second equivalent of 1.0M potassium t-butoxide in THF (0.14 ml, 0.14 mmol) was quickly added and the reaction mixture stirred an additional thirty minutes. The reaction mixture was concentrated in vacuo. The crude product residue was chromatographed on Silica Gel (230-400 Mesh) eluting with 2-5% MeOH/CH$_2$Cl$_2$ to give the Boc-protected intermediate, tert-butyl-7-(6-acetamidopyridin-2-yl)-1-methyl-1,6-dihydroimidazo[4,5-d]pyrrolo[2,3-b]pyridine-4-yl(methyl)carbamate as an off-white solid. (26 mg, 60% yield). The solid was dissolved in methylene chloride (0.5 mL) and trifluoroacetic acid (0.5 mL) was added and the reaction mixture stirred for 0.25 h. The solvent was evaporated under reduced pressure to provide A436 (20 mg, 60%). M+H+=336.34 $^1$H NMR (400 MHz) MEOD δ 9.20 (s, 1H), 8.02 (m, 1H), 7.78 (m, 1H), 7.71 (d, 1H), 7.56 (s, 1H), 4.33 (s, 3H), 3.45 (s, 3H), 2.19 (s, 3H).

Example A437

6-[1,6-dihydro-1-methyl-4-(methylamino)imidazo[4,5-d]pyrrolo[2,3-b]pyridin-7-yl]-2-pyridinemethanol

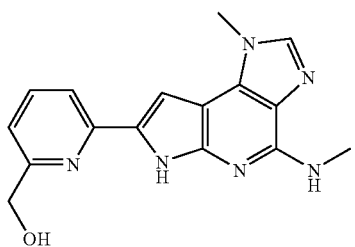

A437

A437.1: 2-((tetrahydro-2H-pyran-2yloxy)methyl)-6-((trimethylsilyl)ethynyl)pyridine

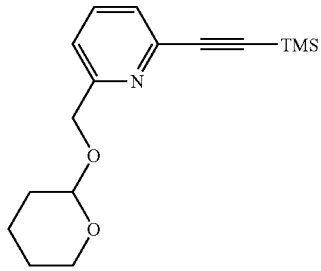

A437.1

2-Bromo-6-(tetrahydro-2H-pyran-2yloxy)methyl)pyridine (952 mg, 3.5 mmol), palladiumdichlorobistriphenylphosphine (120 mg, 0.17 mmol), Copper iodide (33 mg, 0.17 mmol) and diisopropylamine (5 ml, 35 mmol) in 5 ml DMF was degassed with nitrogen for fifteen minutes. The stirred reaction mixture was heated to 80° C. Trimethylsilylacetylene (1.5 ml, 14 mmol) was quickly added and the reaction mixture heated at 80° C. for 1 hour. The reaction mixture was cooled to room temperature concentrated in vacuo. The crude product mixture taken up in dichloromethane and filtered. The filtrate was concentrated in vacuo and the crude product purified by flash Silica Gel (230-400 Mesh) column chromatography eluting with 1% MeOH/98% CH$_2$Cl$_2$ to yield A437.1 (758 mg, 75% yield). M+H+=290.31
$^1$H NMR (400 MHz) MEOD δ 7.51 (m, 1H), 7.33 (m, 1H), 7.19 (m, 1H), 4.68 (m, 3H), 3.66 (m, 1H), 3.25 (m, 1H), 1.48 (m, 6H), 0.08 (s, 9H).

A437.2: 2-ethynyl-6-(tetrahydro-2H-pyran-2yloxy)methyl)pyridine

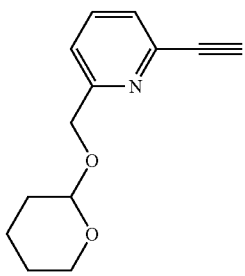

A437.2

Anhydrous potassium carbonate (36 mg, 0.26 mmoles) was added to a solution of A437.1 (752 mg, 2.6 mmol) in 10 ml anhydrous methanol. The reaction mixture was stirred at room temperature for fifteen minutes then filtered. The filtrate was concentrated in vacuo. The crude product mixture was chromatographed on Silica Gel (230-400 Mesh) eluting with 2.5% MeOH/98% CH$_2$Cl$_2$ to yield A437.2 as an off-white solid. (406 mg, 65% yield). M+H+=218.20 $^1$H NMR (400 MHz) MeOD δ 7.87 (m, 1H), 7.58 (m, 1H), 7.50 (m, 1H), 4.61 (d, 1H), 3.92 (m, 3H), 3.58 (m, 2H), 1.93 (m, 6H).

A437.3: Tert-butyl-6-amino-1-methyl-7-(6-((tetrahydro-2H-pyran-2-yloxy)methyl)pyridin-2-yl)ethynyl)-1H-imidazo[4,5-c]pyridine-4-yl(methyl)carbamate

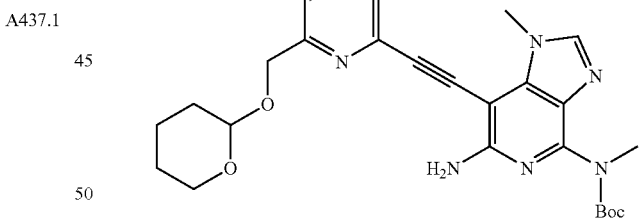

A437.3

A1.12 (2.01 g, 5 mmol), palladiumdichlorobistriphenylphosphine (175 mg, 0.25 mmol), Copper iodide (48 mg, 0.25 mmol) and dsiisopropylamine (21 ml, 150 mmol) in 21 ml DMF was degassed with nitrogen for fifteen minutes. The stirred reaction mixture was heated to 80° C. A437.2 (3.26 g, 15 mmol) was quickly added and the reaction mixture heated at 80° C. for 1 hour. The reaction mixture was cooled to room temperature and concentrated in vacuo. The crude product mixture taken up in dichloromethane and filtered. The filtrate was concentrated in vacuo and the crude product mixture chromatographed on Silica Gel (230-400 Mesh) eluting with 2.5% MeOH/97.5% CH$_2$Cl$_2$. (2.3 g, 88% yield). M+H+=493.21 $^1$H NMR (400 MHz) MeOD δ 7.96 (s, 1H) 7.92 (m, 1H), 7.59 (m, 2H), 4.86 (dd, 2H), 4.18 (s, 3H), 3.93 (t, 1H), 3.52 (m, 2H), 3.50 (s, 3H), 1.64 (m, 6H), 1.43 (s, 9H).

A437.4: 6-[1,6-dihydro-1-methyl-4-(methylamino) imidazo[4,5-d]pyrrolo[2,3-b]pyridin-7-yl]-2-pyridinemethanol A437.3 (2.6 g, 5 mmol), was dissolved in DMA (5 mL) and the solution heated to 70° C. One equivalent of 1.0M potassium t-butoxide in THF (5.5 ml, 5.5 mmol) was quickly added and the reaction heated at 70° C. for thirty minutes. A second equivalent of 1.0M potassium t-butoxide in THF (5.5 ml, 5.5 mmol) was quickly added and the reaction mixture stirred an additional thirty minutes. The reaction mixture was concentrated in vacuo. The crude product residue was chromatographed on Silica Gel (230-400 Mesh) eluting with 2-5% MeOH/CH$_2$Cl$_2$ to give the Boc-protected intermediate, tert-butylmethyl(1-methyl-7-(6-(tetrahydro-2H-pyran-2-yloxy) methyl)pyridine-2-yl)-1,6-dihydroimidazo[4,5-d]pyrrolo[2,3-b]carbamate as an off-white solid. (1.8 g, 88% yield). The solid was dissolved in THF (30 mL) and 6N HCl (30 mL) was added and the reaction mixture heated at 50° C. for one h. The solvent was evaporated under reduced pressure to provide the product as a HCl salt. (1.28 g, 80%). The HCl salt was stirred with 50 ml sat'd Na$_2$CO$_3$ solution and 100 ml dichloromethane. The dichloromethane extract was separated, dried (Na$_2$SO$_4$) and concentrated in vacuo to give the product A437 (0.90 g, 80%). M+H+=309.32 $^1$H NMR (400 MHz) MeOD δ 8.54 (s, 1H), 8.34 (m, 1H), 8.17 (d, 1H), 7.89 (s, 1H), 7.72 (d, 1H), 4.91 (s, 2H), 4.16 (s, 1H), 3.18 (s, 1H).

Example A438

6-[1,6-dihydro-1-methyl-4-(methylamino)imidazo[4,5-d]pyrrolo[2,3-b]pyridin-7-yl]-2-pyridinemethanol, methylcarbamate (ester)

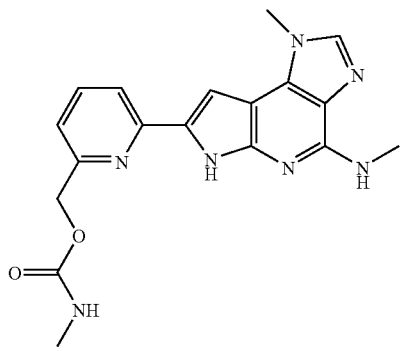

Methylisocyanate (50 mg, 0.88 mmol) was added to a stirred mixture of A437 (50 mg, 0.16 mmol), triethylamine (1 ml) in tetrahydrofuran (5 ml) at room temperature. After complete addition the reaction mixture was stirred at room temperature for sixteen hours. The reaction mixture was concentrated in vacuo. The crude product residue was washed with diethyl ether to give the product as a tan solid. A438 (45 mg, 76% yield). M+H 366.36 $^1$H NMR (400 MHz) MeOD δ 7.95 (s, 1H), 7.68 (m, 2H), 7.30 (s, 1H), 7.10 (d, 1H), 5.06 (s, 2H), 3.99 (s, 3H), 3.18 (s, 3H), 2.61 (s, 3H).

Example A439

(6-(1-methyl-4-(methylamino)-1,6-dihydroimidazo[4,5-d]pyrrolo[2,3-b]pyridin-7-yl)pyridin-2-yl)methyl ethylcarbamate

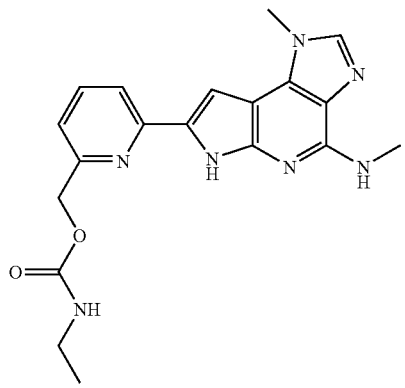

Ethylisocyanate (17 mg, 0.24 mmol) was added to a stirred mixture of A437 (31 mg, 0.10 mmol), triethylamine (1 ml) in tetrahydrofuran (5 ml) at room temperature. After complete addition the reaction mixture was stirred at room temperature for sixteen hours. The reaction mixture was concentrated in vacuo. The crude product residue was chromatographed using Reverse Phase-Preparative HPLC/Phenomenex LUNA 5µ, 100×21.2 mm to give the product as a tan solid. A439 (20 mg, 50% yield). M+H 380.33 $^1$H NMR (400 MHz) MEOD δ 8.11 (s, 1H), 7.85 (m, 2H), 7.47 (s, 1H), 7.32 (d, 1H), 5.24 (s, 2H), 4.20 (s, 3H), 3.33 (s, 3H), 3.14 (m, 2H), 1.35 (t, 3H).

Example A440

(6-(1-methyl-4-(methylamino)-1,6-dihydroimidazo[4,5-d]pyrrolo[2,3-b]pyridin-7-yl)pyridin-2-yl)methyl 1-(2,2,2-trifluoroacetyl)piperidin-4-ylcarbamate

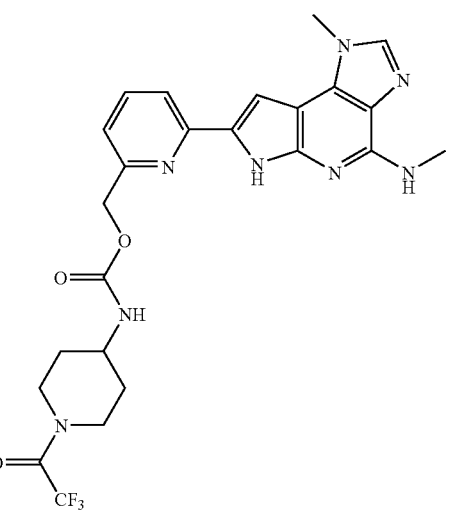

2,2,2-trifluoro-1-(4-isocyanatopiperidin-1-yl)ethanone (40 mg, 0.18 mmol) was added to a stirred mixture of A437 (50 mg, 0.166 mmol), triethylamine (1 ml) in tetrahydrofuran (5 ml) at room temperature. After complete addition the reaction mixture was stirred at room temperature for sixteen hours. The reaction mixture was concentrated in vacuo. The crude product residue was chromatographed using Reverse Phase-Preparative HPLC/Phenomenex LUNA 5µ, 100×21.2 mm to give the product as a tan solid. A440 (23 mg, 27% yield). M+H 531.27.

Example A441

(6-(1-methyl-4-(methylamino)-1,6-dihydroimidazo[4,5-d]pyrrolo[2,3-b]pyridin-7-yl)pyridin-2-yl)methyl 4-(2-methoxyethyl)piperazine-1-carboxylate

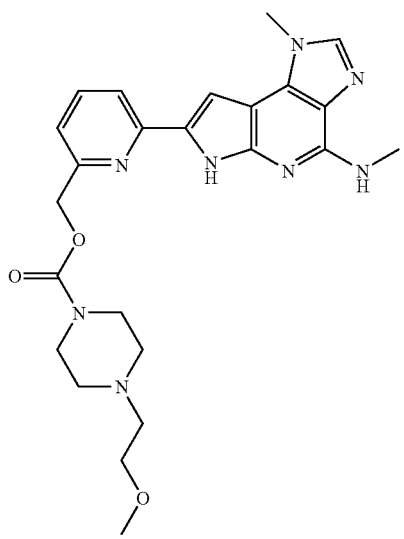

A441

A441.1: (6-(1-methyl-4-(methylamino)-1,6-dihydroimidazo[4,5-d]pyrrolo[2,3-b]pyridin-7-yl)pyridin-2-yl)methyl 1H-imidazole-1-carboxylate

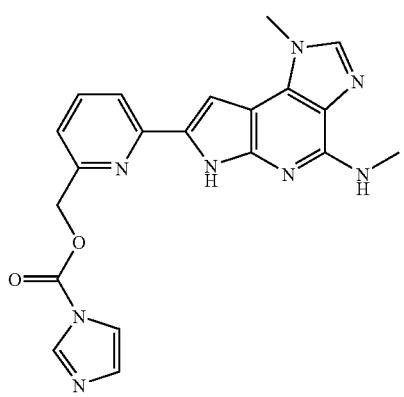

A441.1

1,1-carbonyl diimidazole (81 mg, 0.50 mmol) was added in portions to a stirred mixture of A437 (103 mg, 0.38 mmol) in chloroform (20 ml) heated at 60° C. After complete addition the reaction mixture was heated at 60° C. for one hour. The reaction mixture was cooled to room temperature and washed with 3×25 ml water. The chloroform extract was separated, dried (Na$_2$SO$_4$), and concentrated in vacuo to give the product as an off-white solid. A441.1 (100 mg, 76% yield). M+H 403.23. $^1$H NMR (400 MHz) MEOD δ 8.02 (s, 1H), 7.76 (m, 3H), 7.36 (m, 2H), 7.20 (m, 1H), 5.20 (s, 2H), 4.0 (s, 3H), 3.15 (s, 3H).

A441.2: (6-(1-methyl-4-(methylamino)-1,6-dihydroimidazo[4,5-d]pyrrolo[2,3-b]pyridin-7-yl)pyridin-2-yl)methyl 4-(2-methoxyethyl)piperazine-1-carboxylate A mixture of 1-(2-methoxyethyl)piperazine (29 mg, 0.20 mmol), A441.1 (40 mg, 0.10 mmol), triethylamine (0.5 ml) in chloroform (20 ml) was stirred at room temperature for sixteen hours. The reaction mixture was concentrated in vacuo. The crude product residue was chromatographed using Reverse Phase-Preparative HPLC/Phenomenex LUNA 5µ, 100×21.2 mm to give the product as a tan solid. A441 (25 mg, 52% yield). M+H 479.35. $^1$H NMR (400 MHz) CDCl3, δ 8.73 (d, 1H), 8.03 (s, 1H), 8.01 (d, 1H), 7.60 (s, 1H), 7.34 (d, 1H), 5.46 (s, 2H), 4.13 (s, 3H), 3.57 (d, 2H), 3.37 (m, 13H).

Example A442

(6-(1-methyl-4-(methylamino)-1,6-dihydroimidazo[4,5-d]pyrrolo[2,3-b]pyridin-7-yl)pyridin-2-yl)methyl 2-(dimethylamino)ethyl(methyl)carbamate

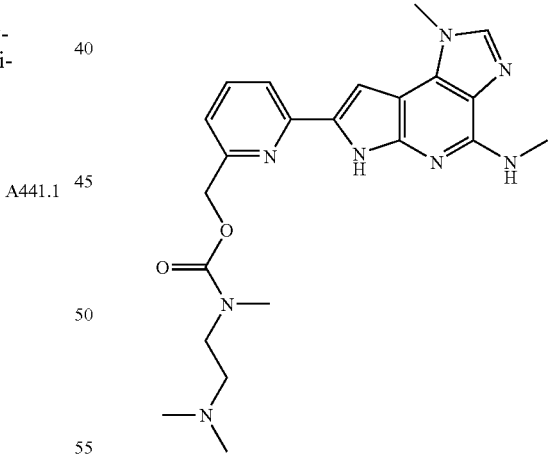

A442

A mixture of N,N,N-trimethylethylenediamine (21 mg, 0.20 mmol), A441.1 (40 mg, 0.10 mmol), triethylamine (0.5 ml) in chloroform (20 ml) was stirred at room temperature for sixteen hours. The reaction mixture was concentrated in vacuo. The crude product residue was purified using Reverse Phase-Preparative HPLC/Phenomenex LUNA 5µ, 100×21.2 mm to give A442 as a tan solid (15 mg, 34% yield). M+H 437.39. $^1$H NMR (400 MHz) MEOD δ 8.13 (s, 1H), 7.87 (m, 2H), 7.44 (s, 1H), 7.30 (m, 1H), 5.32 (s, 2H), 4.15 (s, 3H), 3.80 (m, 4H), 3.40 (m, 3H), 3.32 (s, 3H), 3.00 (s, 3H), 2.88 (s, 3H).

Example A443

(6-(1-methyl-4-(methylamino)-1,6-dihydroimidazo[4,5-d]pyrrolo[2,3-b]pyridin-7-yl)pyridin-2-yl)methyl 4-fluorobenzylcarbamate

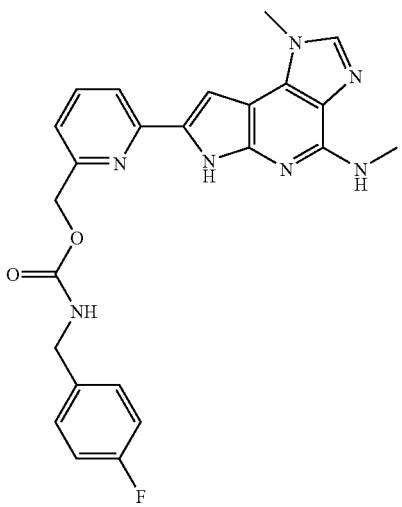

A443

A mixture of 4-fluorobenzylamine (25 mg, 0.20 mmol), A441.1 (40 mg, 0.10 mmol), triethylamine (0.5 ml) in chloroform (20 ml) was stirred at room temperature for sixteen hours. The reaction mixture was concentrated in vacuo. The crude product residue was purified using Reverse Phase-Preparative HPLC/Phenomenex LUNA 5μ, 100×21.2 mm to yield A443 as a tan solid (20 mg, 44% yield). M+H 460.33. $^1$H NMR (400 MHz) MEOD δ 8.129 s, 1H), 7.84 (d, 2H), 7.48 (s, 1H), 7.36 (m, 3H), 7.04 (m, 2H), 5.27 (s, 2H), 4.34 (s, 2H), 4.16 (s, 3H), 3.26 (s, 3H)

Example A444

(6-(1-methyl-4-(methylamino)-1,6-dihydroimidazo[4,5-d]pyrrolo[2,3-b]pyridin-7-yl)pyridin-2-yl)methyl 2-acetamidoethylcarbamate

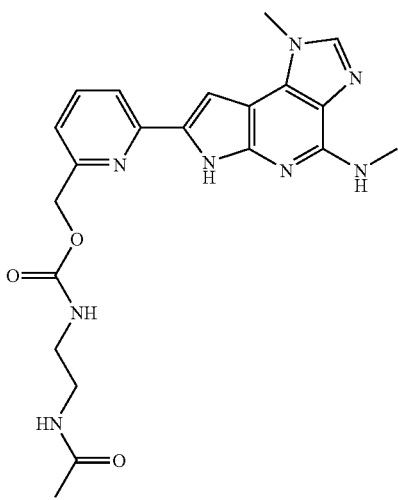

A444

A mixture of N-(aminoethyl)acetamide (21 mg, 0.20 mmol), A441.1 (40 mg, 0.10 mmol), triethylamine (0.5 ml) in chloroform (20 ml) was stirred at room temperature for sixteen hours. The reaction mixture was concentrated in vacuo. The crude product residue was chromatographed using Reverse Phase-Preparative HPLC/Phenomenex LUNA 5μ, 100×21.2 mm to give the product as a tan solid. A444 (12 mg, 27% yield). M+H 437.33. $^1$H NMR (400 MHz) MEOD δ 8.09 (s, 1H), 7.90 (m, 2H), 7.36 (s, 1H), 7.30 (d, 1H), 5.28 (d, 2H), 4.12 (s, 3H), 3.33 (m, 4H), 3.19 (s, 3H), 1.97 (s, 3H).

Example A445

(6-(1-methyl-4-(methylamino)-1,6-dihydroimidazo[4,5-d]pyrrolo[2,3-b]pyridin-7-yl)pyridin-2-yl)methyl 2-(methylamino)ethylcarbamate

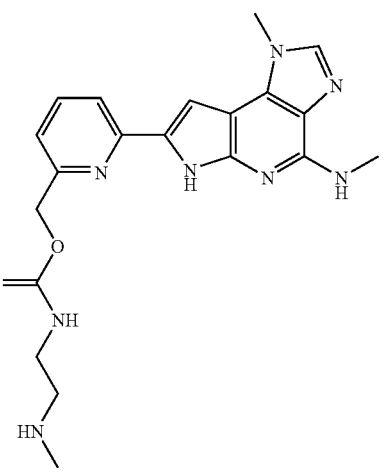

A445

A mixture of N-methylethylenediamine (15 mg, 0.20 mmol), A441.1 (40 mg, 0.10 mmol), triethylamine (0.5 ml) in chloroform (20 ml) was stirred at room temperature for sixteen hours. The reaction mixture was concentrated in vacuo. The crude product residue was purified using Reverse Phase-Preparative HPLC/Phenomenex LUNA 5μ, 100×21.2 mm to yield A445 as a tan solid. (15 mg, 37% yield). M+H 409.35. $^1$H NMR (400 MHz) MEOD δ 8.13 (s, 1H), 7.84 (m, 2H), 7.43 (s, 1H), 7.34 (m, 1H), 5.29 (s, 2H), 4.15 (s, 2H), 3.55 (m, 4H), 3.19 (s, 3H), 2.75 (s, 3H).

Example A446

(6-(1-methyl-4-(methylamino)-1,6-dihydroimidazo[4,5-d]pyrrolo[2,3-b]pyridin-7-yl)pyridin-2-yl)methyl 4-methylpiperazine-1-carboxylate

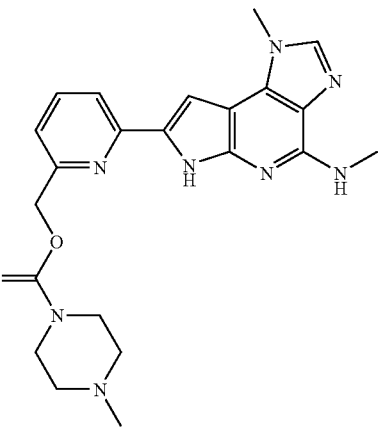

A446

A mixture of 1-methylpiperazine (20 mg, 0.20 mmol), A441.1 (40 mg, 0.10 mmol), triethylamine (0.5 ml) in chloroform (20 ml) was stirred at room temperature for sixteen hours. The reaction mixture was concentrated in vacuo. The crude product residue was chromatographed using Reverse Phase-Preparative HPLC/Phenomenex LUNA 5μ, 100×21.2 mm to give the product as a tan solid. A446 (14 mg, 33% yield). M+H 435.35. $^1$H NMR (400 MHz) MEOD δ 8.16 (s, 1H), 7.89 (m, 2H), 7.51 (s, 1H), 7.35 (m, 1H), 5.33 (s, 2H), 4.18 (s, 3H), 3.32 (m, 11H), 2.96 (s, 3H).

Example A447 ethyl(6-(1-methyl-4-(methylamino)-1,6-dihydroimidazo[4,5-d]pyrrolo[2,3-b]pyridin-7-yl)pyridin-2-yl)methyl carbonate

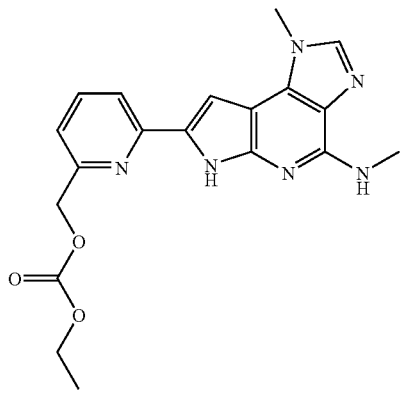

A447

Ethylchloroformate (20 mg, 0.18 mmol) was slowly added to a stirred solution of A437 (50 mg, 0.16 mmol), triethylamine (0.5 ml) in tetrahydrofuran cooled to 0° C. After complete adition the reaction was allowed to warm to room temperature then stirred for four hours. The reaction mixture was quenched with one ml. of 10% HCl(aq) solution and extracted with ethyl acetate (3/20 ml). The ethyl acetate extracts were combined, dried (Na$_2$SO$_4$) and concentrated in vacuo. The crude product residue was chromatographed using Reverse Phase-Preparative HPLC/Phenomenex LUNA 5μ, 100×21.2 mm to give the product as a tan solid. A447 (25 mg, 65% yield). M+H 381.30. $^1$H NMR (400 MHz) MEOD δ 8.04 (s, 1H), 7.78 (m, 2H), 7.36 (s, 1H), 7.25 (m, 1H), 5.23 (s, 2H), 4.23 (m, 2H), 4.08 (s, 3H), 3.19 (s, 3H), 1.30 (m, 3H).

Example A448

6-(1-methyl-4-(methylamino)-1,6-dihydroimidazo[4,5-d]pyrrolo[2,3-b]pyridin-7-yl)pyridin-2-yl)methyl-2-methoxyacetate

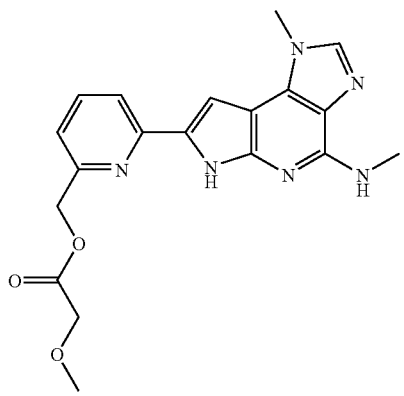

A448

2-methoxyacetylchloride (20 mg, 0.18 mmol) was slowly added to a stirred solution of A437 (50 mg, 0.16 mmol), triethylamine (0.5 ml) in tetrahydrofuran cooled to 0° C. After complete adition the reaction was allowed to warm to room temperature then stirred for four hours. The reaction mixture was quenched with one ml. of 10% HCl(aq) solution and extracted with ethyl acetate (3/20 ml). The ethyl acetate extracts were combined, dried (Na$_2$SO$_4$) and concentrated in vacuo. The crude product residue was purified using Reverse Phase-Preparative HPLC/Phenomenex LUNA 5μ, 100×21.2 mm to give A448 as a tan solid. (25 mg, 65% yield). M+H 381.30. $^1$H NMR (400 MHz) MeOD δ 8.02 (s, 1H), 7.96 (m, 1H), 7.40 (d, 1H), 7.70 (s, 1H), 5.40 (s, 2H), 4.34 (s, 2H), 4.25 (s, 3H), 3.52 (s, 3H), 3.26 (s, 3H).

Example A449

1,6-dihydro-7-[6-[[(3-methoxypropyl)amino]methyl]-2-pyridinyl]-N,1-dimethyl-imidazo[4,5-d]pyrrolo[2,3-b]pyridin-4-amine

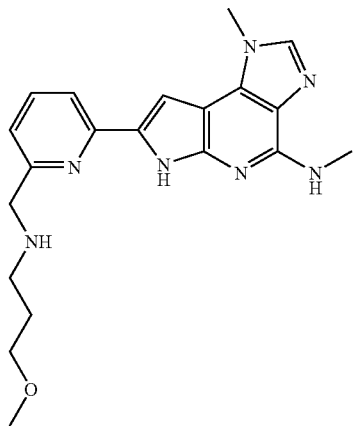

A449

A solution of A216 (62 mg, 16 mmol) in THF was cooled to 0° C. A 1.0M solution of lithium aluminium hydride (0.2 ml, 0.20 mmol) was slowly added to the cooled solution. After complete addition the reaction mixture was stirred at room temperature two hours then heated at reflux for two hours. The reaction mixture was carefully quenched with 0.2 ml H$_2$O, followed by the addition of 0.2 ml 15% NaOH, then followed by the addition of 0.6 ml H$_2$O. The organic layer was separated and concentrated in vacuo. The crude product residue was purified using Reverse Phase-Preparative HPLC/Phenomenex LUNA 5μ, 100×21.2 mm to provide A449 as a tan solid. (20 mg, 30% yield). M+H 381.30. $^1$H NMR (400 MHz) MEOD δ 8.12 (s, 1H), 7.90 (m, 2H), 7.52 (s, 1H), 7.30 (m, 1H), 4.50 (s, 2H), 4.18 (s, 3H), 3.74 (m, 2H), 3.579 m, 2H), 3.33 (s, 3H), 3.36 (s, 3H), 1.89 m, 2H).

Example A450

N-[2-[6-[1,6-dihydro-1-methyl-4-(methylamino)imidazo[4,5-d]pyrrolo[2,3-b]pyridin-7-yl]-2-pyridinyl]ethyl]-acetamide

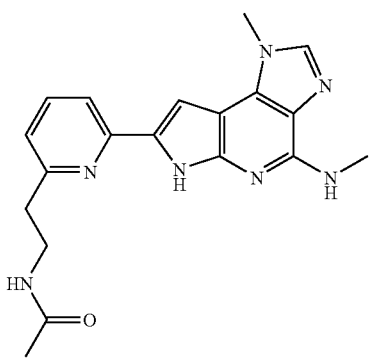

A450

A450.2: N-(2-(6-(trimethylsilyl)ethynyl)pyridine-2-yl)acetamide

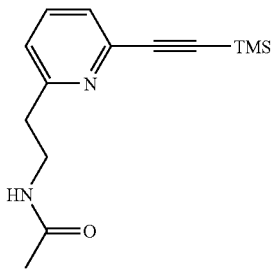

A450.2

A450.1 (840 mg, 3.5 mmol), palladiumdichlorobistriphenylphosphine (120 mg, 0.17 mmol), Copper iodide (33 mg, 0.177 mmol) and diisopropylamine (5 ml, 35 mmol) in 5 ml DMF was degassed with nitrogen for fifteen minutes. The stirred reaction mixture was heated to 80° C. Trimethylsilylacetylene. (1.5 ml, 14 mmol) was quickly added and the reaction mixture heated at 80° C. for 1 hour. The reaction mixture was cooled to room temperature concentrated in vacuo. The crude product mixture taken up in dichloromethane and filtered. The filtrate was concentrated in vacuo and the crude product purified by Silica Gel chromatography (230-400 Mesh) eluting with 1% MeOH/98% CH$_2$Cl$_2$ to yield A450.2 (682 mg, 75% yield) M+H+=261.28 $^1$H NMR (400 MHz) MEOD δ 8.08 (m, 1H), 7.59 (m, 2H), 3.65 (m, 2H), 3.21 (m, 2H), 1.88 (s, 3H), 0.23 (s, 9H).

A450.3: N-(2-(6-ethynylpyridin-2-yl)ethyl)acetamide

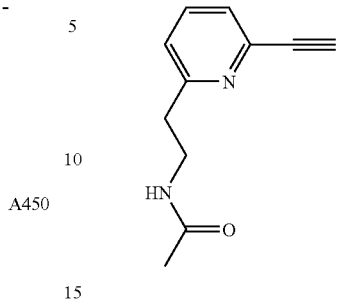

A450.3

Anhydrous potassium carbonate (36 mg, 0.26 mmoles) was added to a solution of A450.2 (682 mg, 2.6 mmol) in 10 ml anhydrous methanol. The reaction mixture was stirred at room temperature for fifteen minutes then filtered. The filtrate was concentrated in vacuo. The crude product mixture was purified by Silica Gel (230-400 Mesh) chromatography eluting with 2.5% MeOH/98% CH$_2$Cl$_2$ to give A450.3 as an off-white solid. (220 mg, 55% yield). M+H+=189.16 $^1$H NMR (400 MHz) MEOD δ 8.15 (m, 1H), 7.58 (m, 2H), 4.57 (s, 1H), 3.66 (m, 2H), 3.22 (m, 2H), 1.90 (s, 3H).

A450.4: tert-butyl 7-((6-(2-acetamidoethyl)pyridin-2-yl)ethynyl)-6-amino-1-methyl-1H-imidazo[4,5-c]pyridin-4-yl(methyl)carbamate

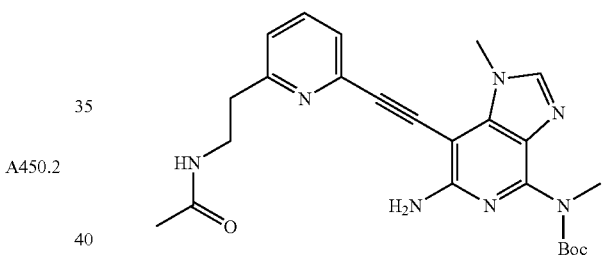

A450.4

A1.12 (604 mg, 1.5 mmol), palladiumdichlorobistriphenylphosphine (72 mg, 0.11 mmol), Copper iodide (21 mg, 0.11 mmol) and diisopropylamine (0.5 ml, 3.7 mmol) in 5 ml DMF was degassed by bubbling nitrogen through the mixture for thirty minutes. The stirred reaction mixture was heated to 80° C. A450.3 (353 mg, 1.88 mmol) was quickly added and the reaction mixture heated at 80° C. for 1 hour. The reaction mixture was cooled to room temperature and concentrated in vacuo. The crude product mixture taken up in dichloromethane and filtered. The filtrate was concentrated in vacuo and the crude product mixture chromatographed on Silica Gel (230-400 Mesh) eluting with 2% MeOH/98% CH$_2$Cl$_2$ to give A450.4 (247 mg, 53% yield). M+H+=464.30.

A450.5: N-[2-[6-[1,6-dihydro-1-methyl-4-(methylamino)imidazo[4,5-d]pyrrolo[2,3-b]pyridin-7-yl]-2-pyridinyl]ethyl]-acetamide A450.4 (147 mg, 0.30 mmol), was dissolved in DMA (5 mL) and the solution heated to 77° C. One equivalent of 1.0M potassium t-butoxide in THF (0.3 ml, 0.30 mmol) was quickly added and the reaction heated at 70° C. for thirty minutes. A second equivalent of 1.0M potassium t-butoxide in THF (0.3 ml, 0.30 mmol) was quickly added and the reaction mixture stirred an additional thirty minutes. The reaction mixture was concentrated in vacuo. The crude product residue was purified by Silica Gel (230-400 Mesh) chromatography eluting with 2-5% MeOH/CH$_2$Cl$_2$ to give the Boc-protected intermediate, tert-butyl-7-(6-(2-acetamidoethyl)pyridin-2-yl)-1-methyl-1,6-dihydroimidazo[4,5-d]pyrrolo[2,3-b]pyridine-4-yl (methyl)carbamate as an off-white solid. (76 mg, 52% yield). The solid was dissolved in methylene chloride (0.5 mL) and trifluoroacetic acid (0.5 mL) was added and the reaction mixture stirred for 0.25 h. The solvent was evaporated under reduced pressure to provide A450 (37 mg, 63%). M+H+=364.26. 1H NMP (400 MHz) MEOD δ 8.14 (s, 1H), 7.84 (m, 2H), 7.52 (s, 1H), 7.30 (m, 1H), 4.18 (s, 3H), 3.77 (m, 2H), 3.29 (s, 3H), 3.11 (m, 2H), 1.94 (s, 3H).

Example A451

7-(6-(2-aminomethyl)pyridine-2-yl)-N-1-dimethyl-1,6-dihydroimidazo[4,5-d]pyrrolo[2,3-b]pyridine-4-amine

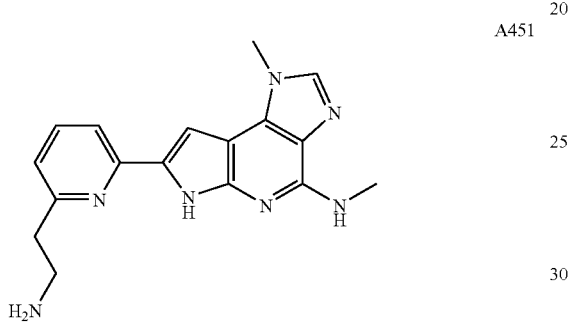

A451

A450 (24 mg, 0.05 mmol), was dissolved in ethanol (5 mL) and 6N HCl (aq) solution and the solution was heated 80° C. for sixteen hours. The reaction mixture was concentrated in vacuo to give the hydrochloride salt as a yellow solid. The solid was stirred in a mixture of sat'd sodium carbonate(aq) solution and dichloromethane for 1 h. The dichloromethane extract was separated, dried (Na2SO4), and concentrated in vacuo to provide A451 as a yellow solid. (16 mg, 96%). M+H+=322.31. $^1$H NMR (400 MHz) MeOD δ 7.45 (s, 1H), 7.20 (m, 2H), 6.90 (s, 1H), 6.55 (m, 1H), 3.33 (s, 3H), 2.75 (m, 4H), 2.49 (s, 3H).

Example A452

[[6-[1,6-dihydro-1-methyl-4-(methylamino)imidazo[4,5-d]pyrrolo[2,3-b]pyridin-7-yl]-2-pyridinyl]methyl]methyl-carbamic acid methyl ester

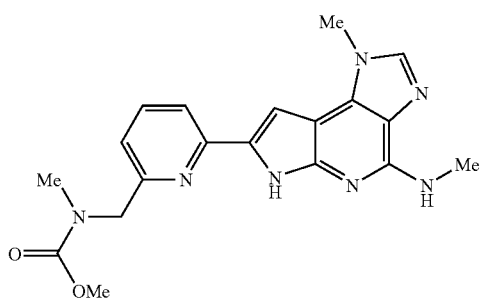

A452

A solution of A247 (10.0 mg, 0.031 mmol), 1,1'-carbonyldiimidazole (40.21 mg, 0.248 mmol), and triethylamine (21.6 μL, 0.16 mmol) in DMF (1.0 mL) was heated at 80° C. for 30 min. After cooling to room temperature, DMF was removed. Water (1.0 mL) and 1:1 THF:EtOAc (2.0 mL) were added, The organic layer was washed with water, brine, dried (Na$_2$SO$_4$), and evaporated under vacuum to yield 9.0 mg M49.1 as a tan solid. HPLC (C): 100.0%, ret. time 1.79 min., MS (D): (M+H)$^+$=416.41; (M−H)=414.41. The acyl imidazole was dissolved in dimethylamine (1.5 mL of a 2.0 M solution in MeOH) and heated at 80° C. for 15 min. The solvent was evaporated under reduced pressure and the crude product was purified by reversed-phase preparative HPLC to yield A452 an orange solid. HPLC (C): 99.14%, ret. time 2.28 min., LC/MS (M+H)$^+$=380.26.

Example A453

N-[[3-[1,6-dihydro-1-methyl-4-(methylamino)imidazo[4,5-d]pyrrolo[2,3-b]pyridin-7-yl]phenyl]methyl]-methanesulfonamide

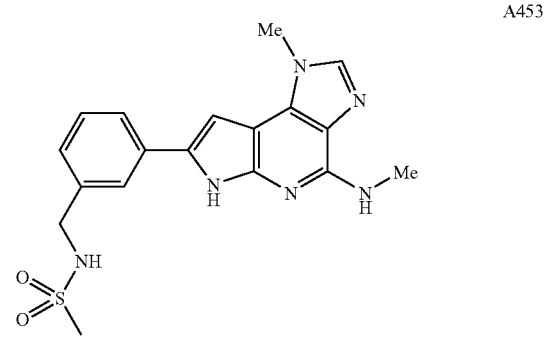

A453

Methanesulfonyl chloride (18.3 mg, 0.16 mmol) was added in one portion to A3 (50 mg, 0.12 mmol) and triethylamine (18.7 mg, 0.19 mmol) in THF (2 mL) at 0 C under a nitrogen atmosphere. The mixture was allowed to warm to room temperature over 3 hrs, before quenching with water (1 mL) and extracting with ethyl acetate (2×10 mL). The combined organics were dried (MgSO$_4$), evaporated in vacuo and the residue treated with 4N HCl in dioxane (2 mL). After stirring at room temperature for 2 hrs, the mixture was evaporated in vacuo. The residue suspended in hot methanol (1 mL) before filtering to yield A453 (10 mg) as a white solid. HPLC YMC S-5 4.6×33 mm (2 min grad): retention time 1.33 min, M+H+=385.38. $^1$H NMR (400 MHz, DMSO) δ 11.93 (s, 1H), 7.70 (br. s, 1H), 7.63 (d, J=7.7 Hz, 1H), 7.47 (t, J=6.2 Hz, 1H), 7.29 (t, J=7.7 Hz, 1H), 7.14-7.12 (m, 2H), 4.09 (d, J=6.1 Hz, 1H), 4.03 (s, 3H), 2.96 (s, 3H), 2.78 (s, 3H).

Example A454

N-[[3-[1,6-dihydro-1-methyl-4-(methylamino)imidazo[4,5-d]pyrrolo[2,3-b]pyridin-7-yl]phenyl]methyl]-N-(2-methoxyethyl)-methanesulfonamide

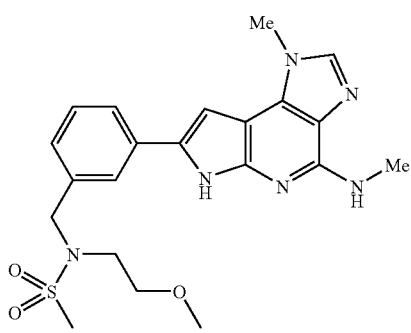

A454

TMAD (9 mg, 0.052 mmol) was added in one portion to A453 (25 mg, 0.052 mmol), 2-methoxyethanol (4 mg, 0.052 mmol) and tributylphosphine (11 mg, 0.052 mmol) in anhydrous DMF (0.2 mL). The reaction mixture was heated to 140° C. for 10 min in the microwave before cooling to room temperature, evaporating in vacuo and purifying by preparative HPLC to yield A454 (1 mg). HPLC YMC S-5 4.6×33 mm (2 min grad): retention time 1.64 min, M+H+=443.34.

Example A455

1,6-dihydro-N-(2-methoxyethyl)-1-methyl-4-(methylamino)-imidazo[4,5-d]pyrrolo[2,3-b]pyridine-7-carboxamide

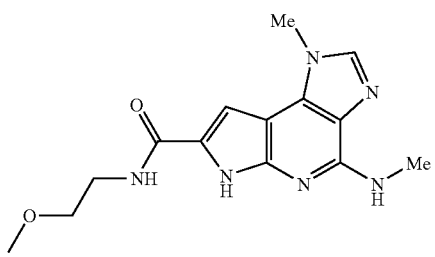

A455

EDC (8.2 mg, 0.065 mmol) was added in one portion to a mixture of the acid A168.1 (10 mg, 0.029 mmol), HOBt (4 mg, 0.05 mmol) and DIPEA (0.06 mL) in anhydrous acetonitrile (0.5 mL) and the resulting mixture was allowed to stir at room temperature for 30 min before addition of 2-methoxyethylamine (4 mg, 0.05 mmol). The mixture was heated overnight to 80° C. in a screw-capped vial before cooling to room temperature, evaporating in vacuo and treating with 4N HCl in dioxane (2 mL). After continued stirring for 2 hr, the mixture was purified by preparative HPLC to yield A455 (5.6 mg, 98%) HPLC YMC S-5 4.6×33 mm (2 min grad): retention time 0.98 min, M+H+=303.30.

Example A456

4-[[6-[1,6-dihydro-1-methyl-4-(methylamino)imidazo[4,5-d]pyrrolo[2,3-b]pyridin-7-yl]-2-pyridinyl]carbonyl]-morpholine

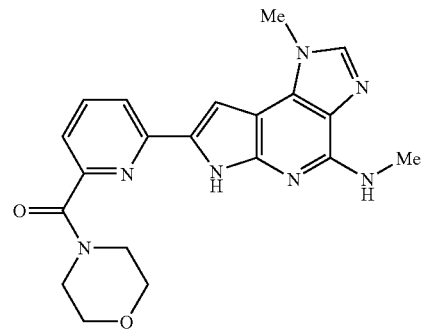

A456

A456.1: 6-Trimethylsilanylethynyl-pyridine-2-carboxylic acid ethyl ester

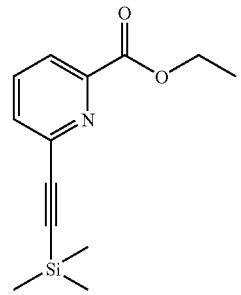

A456.1

TMS-Acetylene (1.36 mL, 9.61 mmol) was added dropwise to the commercially available 2-bromo-5-carboxypyridine ethyl ester (2.0 g, 8.73 mmol), CuI (83 mg, 0.44 mmol) and palladium dichlorobistriphenylphosphine (400 mg, 0.58 mmol) in triethylamine (30 mL) at room temperature under a nitrogen atmosphere. The reaction mixture was stirred at room temperature for 1 hr before evaporating in vacuo. Diethyl ether (50 mL) was added to the residue and the slurry filtered. The filtrate was evaporated in vacuo to yield the crude product A456.1 which (2.68 g) which was used immediately without further purification.

A456.2: 6-Ethynyl-pyridine-2-carboxylic acid methyl ester

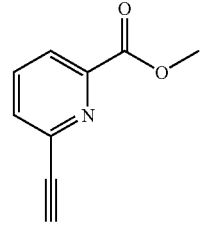

A456.2

Potassium hydroxide solution (1 pellet dissolved in 1 mL of water) was added in one portion to A456.1 (2.68 g) in anhydrous methanol (30 mL). After stirring at room temperature for 1 hr, the reaction was evaporated in vacuo and diethyl ether (50 mL) added to the residue. The slurry was filtered to yield A446.2 (1.38 g) as a brown powder which was used immediately without further purification. HPLC YMC S-5 4.6×33 mm (2 min grad): retention time 0.93 min, M+H$^+$=162.12

A456.3: 6-[6-Amino-4-(tert-butoxycarbonyl-methyl-amino)-1-methyl-1H-imidazo[4,5-c]pyridin-7-yl-ethynyl]-pyridine-2-carboxylic acid methyl ester

A456.3

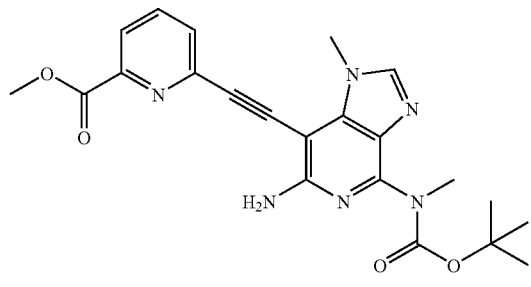

A1.12 (2.0 g, 4.96 mmol), dichlorobis(triphenylphosphine)palladium (232 mg, 0.33 mmol), A456.2 (2.91 g, 19.85 mmol) and triethylamine (18 mL) were each added to N,N-dimethylformamide (20 mL) and nitrogen bubbled through the resulting mixture for 5 min. The reaction mixture was heated at 90° C. for 1 hr under a nitrogen atmosphere before cooling to room temperature and evaporating the solvent in vacuo. Water (50 mL) was added to the residue and the mixture sonicated for 10 min before filtering. The solid (6 g) was purified by column using 10% MeOH in dichloromethane as eluent to provide 2.55 g (100%) of A456.3 as a dark solid. HPLC YMC S-5 4.6×33 mm (2 min grad): retention time 1.53 min, M+H$^+$=437.33

A456.4: 6-[4-(tert-Butoxycarbonyl-methyl-amino)-1-methyl-6-(2,2,2-trifluoro-acetylamino)-1H-imidazo[4,5-c]pyridin-7-ylethynyl]-pyridine-2-carboxylic acid methyl ester

A456.4

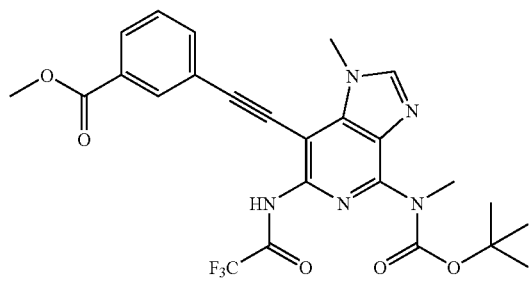

Trifluoroacetic anhydride (1.63 mL, 11.70 mmol) was added dropwise over 5 min to a cooled (0° C.) solution of A456.3 (2.55 g, 5.85 mmol) and triethylamine (2.5 mL, 17.55 mmol) in THF (50 mL) under a nitrogen atmosphere. The cooling bath was removed after 10 min and the reaction mixture allowed to stir at room temperature for 1 hr before evaporating in vacuo. The residue was taken up in dichloromethane (50 mL) and washed with saturated sodium bicarbonate solution (25 mL). The organic layer was separated and dried (MgSO$_4$), then evaporated in vacuo to yield the crude product A456.4 which was used immediately without further purification (2.78 g). HPLC YMC S-5 4.6×33 mm (2 min grad): retention time 1.67 min, M+H$^+$=533.27

A456.5: 6-[1,6-dihydro-1-methyl-4-(N-methyl-tert-butoxycarbonylamino)imidazo[4,5-d]pyrrolo[2,3-b]pyridin-7-yl]-2-pyridinecarboxylic acid

A456.5

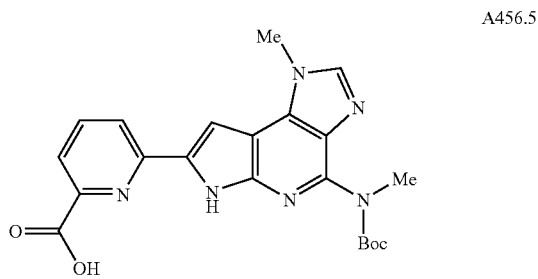

Potassium carbonate (250 mg, 1.79 mmol) and dichlorobistriphenylphosphine (68 mg, 0.097 mmol) were each added in one portion to a solution of A456.4 (0.86 g, 1.62 mmol) in dimethylacetamide (20 mL). at room temperature under a nitrogen atmosphere. The reaction was heated to 130° C. for 1 hr before cooling to room temperature and evaporating in vacuo. The residue was partitioned between water (30 mL) and ethyl acetate (50 mL). The separated organic layer was dried (MgSO4), evaporated in vacuo and purified by column chromatography using 5% MeOH in ethyl acetate to yield azaindole ester (258 mg). The aqueous layer was purified by preparative hplc to yield the desired carboxylic acid A456.5 (220 mg). HPLC YMC S-5 4.6×33 mm (2 min grad): retention time 1.44 min, M+H$^+$=423.31. $^1$H NMR (400 MHz, DMSO) δ 12.88 (s, 1H), 8.51 (s, 1H), 8.37-8.35 (m, 1H), 8.16-8.11 (m, 1H), 8.01-7.98 (m, 1H), 7.82 (s, 1H), 4.19 (s, 3H), 3.36 (s, 3H), 1.34 (s, 9H).

A456.6: 4-[[6-[1,6-dihydro-1-methyl-4-(methylamino)imidazo[4,5-d]pyrrolo[2,3-b]pyridin-7-yl]-2-pyridinyl]carbonyl]-morpholine BOP-Cl (11 mg, 0.44 mmol) was added in one portion to a mixture of A456.5 (20 mg, 0.048 mmol), morpholine (5 mg, 0.0521 mmol) and DIPEA (0.06 mL) in anhydrous DMF (0.5 mL) and the resulting mixture was allowed to stir at room temperature for 30 min in a screw-capped vial before evaporating in vacuo and treating with 4N HCl in dioxane (2 mL). After continued stirring for 2 hr, the mixture was purified by preparative HPLC to yield A456 (10 mg, 98%) HPLC YMC S-5 4.6×33 mm (2 min grad): retention time 1.78 min, M+H$^+$=392.18

Examples A457

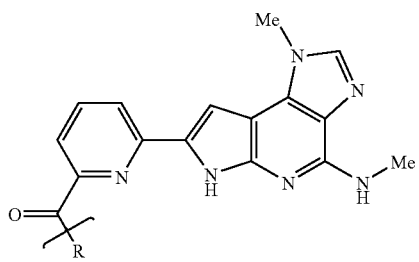

The compounds in Table 16 were prepared in a similar manner to A456 starting with A456.5 and using the appropriate amine.

TABLE A16

| Ex. | R | Name | HPLC Retention (min) | MS Reported |
|---|---|---|---|---|
| A457 | ![piperidinol] | 1-[[6-[1,6-dihydro-1-methyl-4-(methylamino)imidazo[4,5-d]pyrrolo[2,3-b]pyridin-7-yl]-2-pyridinyl]carbonyl]-4-piperidinol | 1.62 | 406.19 |
| A458 | ![methoxymethylpyrrolidine] | (2R)-1-[[6-[1,6-dihydro-1-methyl-4-(methylamino)imidazo[4,5-d]pyrrolo[2,3-b]pyridin-7-yl]-2-pyridinyl]carbonyl]-2-(methoxymethyl)pyrrolidine | 1.53 | 420.40 |
| A459 | ![pyrrolidinol] | (3R)-1-[[6-[1,6-dihydro-1-methyl-4-(methylamino)imidazo[4,5-d]pyrrolo[2,3-b]pyridin-7-yl]-2-pyridinyl]carbonyl]-3-pyrrolidinol | 1.28 | 392.35 |
| A460 | ![cyclopropyl] | N-cyclopropyl-6-[1,6-dihydro-1-methyl-4-(methylamino)imidazo[4,5-d]pyrrolo[2,3-b]pyridin-7-yl]-2-pyridinecarboxamide | 1.82 | 362.34 |

Example A461

N-[1-[6-[1,6-dihydro-1-methyl-4-(methylamino)imidazo[4,5-d]pyrrolo[2,3-b]pyridin-7-yl]-2-pyridinyl]ethyl]-acetamide

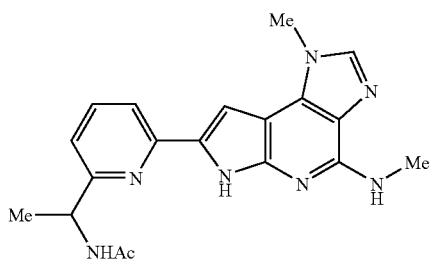

A461.1: (Z)-1-(6-Bromopyridin-2-yl)ethanone oxime

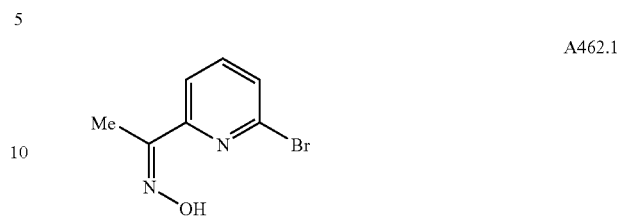

A mixture of 2-acetyl-6-bromopyridine (commercially available) (1.00 g, 5.00 mmol) and hydroxylamine hydrochloride (0.694 g, 10.0 mmol) in pyridine (6 mL) was stirred at room temperature overnight. The solvent was removed under reduced pressure, and the residue was diluted with dichloromethane, washed with water, and dried over anhydrous sodium sulfate. Concentration under reduced pressure afforded a quantitative yield of A461.1 as a white solid. The compound had an HPLC retention time=1.95 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=215 and 217.05.

Alternate Preparation of A461.1

A mixture of 2-acetyl-6-bromopyridine (10.0 g, 0.050 mol) and hydroxylamine hydrochloride (6.90 g, 0.10 mol) in pyridine (50 mL) was stirred at room temperature overnight. The solvent was removed under reduced pressure, and the residue was diluted with ethyl acetate (200 mL), washed with water (100 mL), and dried over anhydrous sodium sulfate.

Concentration under reduced pressure afforded a 10.75 g of A461.1 as an off-white solid.

A461.2: 1-(6-Bromopyridin-2-yl)ethanamine

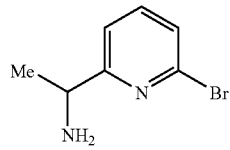

A461.2

To a solution of A461.1 (1.08 g, 5.00 mmol) in trifluoroacetic acid (8 mL) was added zinc dust (1.96 g, 30.0 mmol) slowly in small portions. After the addition was complete, the reaction mixture was stirred for 30 min. The mixture was carefully poured into a solution of 2M aqueous sodium hydroxide (68 mL) and dichloromethane (34 mL) cooled with an ice bath. The resulting mixture was filtered under reduced pressure, and the organic layer was collected, washed with water, and dried over anhydrous sodium sulfate. Concentration under reduced pressure afforded 0.738 g, 74%) of A461.2 as a yellow oil. The compound had an HPLC retention time=0.667 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=201.09 and 203.09.

Alternate Preparation of A461.2

To a stirring suspension of A461.1 (10.75 g, 0.050 mol) in acetic acid (200 mL) and water (100 mL) was slowly added zinc dust (11.0 g, 0.170 mol) in portions over 1 hr. The reaction mixture was filtered through Celite and concentrated under reduced pressure. The residue was neutralized with a 25% aqueous solution of ammonium hydroxide and extracted with dichloromethane (3×100 mL). The organic layers were combined, washed with brine, and dried over anhydrous sodium sulfate. Concentration under reduced pressure afforded 9.90 g (98%) of A461.2 as brownish oil.

A461.3: N-(1-(6-Bromopyridin-2-yl)ethyl)acetamide

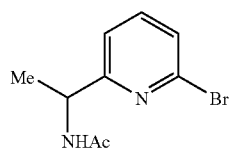

A461.3

A mixture of A461.2 (0.738 g, 3.67 mmol), acetic anhydride (0.74 mL), and pyridine (0.74 mL) was stirred at room temperature for 3 hr. The reaction mixture was concentrated under reduced pressure, and the residue was diluted with dichloromethane, washed with water, wash with a saturated aqueous solution of sodium bicarbonate, and dried over anhydrous sodium sulfate. Concentration under reduced pressure followed by purification by flash silica gel chromatography using mixture of methanol in dichloromethane (1%-2.5%-5%) to give A461.3 (0.474 g, 53%) as a viscous yellow oil. The compound had an HPLC retention time 1.29 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=243 and 245.04.

Alternate Preparation of A461.3

A mixture of A461.2 (9.90 g, 0.050 mol), acetic anhydride (6 mL), and pyridine (10 mL) in anhydrous tetrahydrofuran (50 mL) was stirred at room temperature overnight. The reaction mixture was diluted with ethyl acetate (200 mL), washed with water (100 mL), and dried over anhydrous sodium sulfate. Concentration under reduced pressure afforded A461.3 (12.03 g, 98%) as a viscous yellow oil.

A461.4: N-(1-(6-((Trimethylsilyl)ethynyl)pyridin-2-yl)ethyl)acetamide

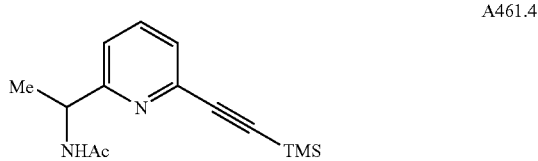

A461.4

A mixture of A461.3 (0.474 g, 1.95 mmol), dichlorobis(triphenylphospine) palladium II (0.082 g, 0.117 mmol), and copper iodide (0.019 g, 0.098 mmol) in anhydrous dimethylformamide (8 mL) was degassed well under nitrogen. To the mixture was added the acetylene (0.413 mL, 2.92 mmol) and triethylamine (1.36 mL, 9.75 mmol), and the reaction mixture was stirred at room temperature for 10 min. and then heated at 75° C. for 3 hr. The reaction mixture was filtered through a pad of Celite topped with a pad of silica gel, and the pad was rinsed with dichloromethane. Concentration under reduced pressure followed by purification by flash silica gel chromatography using a 5% mixture of methanol in dichloromethane afforded 0.365 g (70%) of A461.4 as a light brown viscous oil. The product had an HPLC retention time=2.69 min. (Column: Chromolith SpeedROD 4.6×50 mm—4 min.; Solvent A=10% MeOH, 90% $H_2O$, and 0.1% TFA; Solvent B=90% MeOH, 10% $H_2O$, and 0.1% TFA) and a LC/MS $M^{+1}$=261.28.

Alternate Preparation of A461.4

To a mixture of A461.3 (10.0 g, 0.041 mol), dichlorobis(triphenylphospine) palladium II (1.43 g, 2.00 mmol), copper iodide (0.390 g, 2.00 mmol), and diisopropylamine (57 mL, 0.41 mol) in anhydrous dimethylformamide (57 mL) degassed well under nitrogen at 77° C. was added trimethylacetylene (7.0 mL, 0.062 mol). The reaction mixture was stirred at 77° C. for 1 hr, cooled to room temperature, and filtered. Concentration under reduced pressure followed by purification by flash silica gel chromatography using a mixture of methanol in dichloromethane (0%-1%) provided 6.66 g (96%) of A461.4 as a orange viscous oil.

A461.5 N-(1-(6-Ethynylpyridin-2-yl)ethyl)acetamide

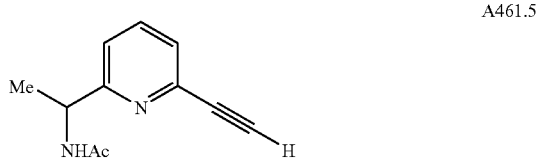

A461.5

A mixture of A461.4 (0.356 g, 1.37 mmol) and potassium carbonate (0.020 g, 0.144 mmol) in methanol (3 mL) was stirred at room temperature for 80 min. The reaction mixture was concentrated under reduced pressure, and the residue was purified by flash silica gel chromatography using a mixture of methanol in dichloromethane (1%-5%) to give 0.167 g (64%) of A461.5 as a yellowish-orange solid. The compound had an HPLC retention time=0.807 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=189.18.

Alternate Preparation of A461.5

A mixture of A461.4 (6.66 g, 0.026 mol) and potassium carbonate (0.350 g, 2.60 mmol) in anhydrous methanol (52 mL) was stirred at room temperature for 15 min. The reaction mixture was filtered and concentrated under reduced pressure, and the residue was purified by flash silica gel chromatography using a mixture of methanol in dichloromethane (0%-2%) to give 3.70 g (70%) of A461.5 as a viscous orange oil.

A461.6: Tert-butyl 7-((6-(1-acetamidoethyl)pyridin-2-yl)ethynyl)-6-amino-1-methyl-1H-imidazo-[4,5-c]pyridin-4-yl(methyl)carbamate

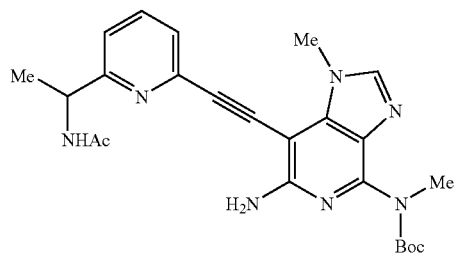

A461.6

A mixture of A461.5 (0.167 g, 0.887 mmol), A1.12 (0.311 g, 0.771 mmol), dichlorobis(triphenyl-phosphine)palladium II (0.032 g, 0.046 mmol), copper (I) iodide (0.007 g, 0.039 mmol), and triethylamine (0.540 mL, 3.86 mmol) in anhydrous dimethylformamide (3 mL) was degassed well with nitrogen. The reaction mixture was immersed in an oil bath at 80° C. and stirred for 45 min. The solvent was removed under reduced pressure, and the residue was purified by flash silica gel chromatography using a mixture of methanol in dichloromethane (1%-10%) to give 0.271 g (76%) of A461.6 as a light orange solid. The compound had an HPLC retention time=2.27 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=464.34.

Alternate Preparation fo A461.6

A mixture of A1.12 (4.03 g, 0.010 mol), dichlorobis(triphenylphosphine) palladium II (0.35 g, 5.00 mmol), copper (I) iodide (0.095 g, 5.00 mmol), and diisopropylamine (21 mL, 0.150 mmol) in anhydrous dimethylformamide (21 mL) was degassed well with nitrogen and heated at 77° C. Acetylene A461.5 (2.82 mL, 0.015 mol) in 5 mL of anhydrous dimethylformamide was added, and the reaction mixture was stirred at 77° C. for 60 min. The solvent was removed under reduced pressure, and the residue was purified by flash silica gel chromatography using a mixture of methanol in dichloromethane (0%-2.5%) to give 5.42 g of crude product as a brown solid. The compound was dissolved in 10 mL of dichloromethane and then pipetted into 100 mL of diethyl ether with stirring. The suspension was filtered and dried well to give 4.50 g (97%) of A461.6 as a tan solid.

A461.7: Tert-butyl 7-(6-(1-acetamidoethyl)pyridin-2-yl)-1-methyl-1,6-dihydroimidazo[4,5-d]pyrrolo-[2,3-b]pyridin-4-yl(methyl)carbamate

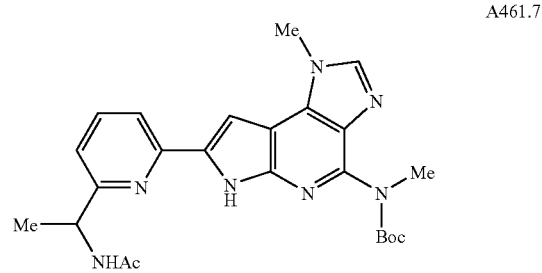

A461.7

To a solution of A461.6 (2.09 g, 0.451 mmol) in anhydrous dimethylacetamide (2.5 mL) under nitrogen was added a 1.0 M solution of potassium tert-butoxide in tetrahydrofuran (0.50 mL, 0.496 mmol), and the reaction mixture was heated for 20 min. A second 0.50 mL was added, and the reaction mixture was stirred for an additional 10 min. The solvent was removed under reduced pressure, and the residue was purified by flash silica gel chromatography using a 5% mixture of methanol in dichloromethane to give 0.125 g (60%) of A461.7 as a yellow solid. The compound had an HPLC retention time=2.41 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=464.34.

Alternate Preparation of A461.7

A solution of A61.6 (4.00 g, 9.00 mmol) in anhydrous dimethylacetamide (20 mL) was stirred under a stream of nitrogen for 20 min. The reaction mixture was immersed into an oil bath at 80° C. and stirred for 5 min. A 1.0 M solution of potassium tert-butoxide in tetrahydrofuran (10.0 mL, 10.0 mmol) was added, and the reaction mixture was heated for 15 min. A second addition of potassium tert-butoxide (1M solution in THF, 10.0 mL) was added, and the reaction mixture was stirred for an additional 15 min, cooled to room temperature, and quenched with a saturated aqueous solution of sodium bicarbonate (50 mL). The aqueous mixture was extracted with dichloromethane (3×100 mL), and the organic layers were combined and concentrated under reduced pressure. Purification by flash silica gel chromatography using a mixture of methanol in dichloromethane (1%-2.5%) provided 3.60 g (85%) of A461.7 as a yellow solid.

A461.8: N-[1-[6-[1,6-dihydro-1-methyl-4-(methylamino)imidazo[4,5-d]pyrrolo[2,3-b]pyridin-7-yl]-2-pyridinyl]ethyl]-acetamide A solution of A461.7 (0.123 g, 0.265 mmol) in trifluoroacetic acid (4.5 mL) was stirred at room temperature for 30 min. The trifluoroacetic acid was removed under reduced pressure, and the residue was diluted with dichloromethane, washed with a saturated aqueous solution of sodium bicarbonate, and dried over anhydrous sodium sulfate. Concentration under reduced pressure provided 0.90 g (94%) of A461 as a yellow solid. The compound had an HPLC retention time=2.01 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=364.31. $^1$H NMR (500 MHz, DMSO-d$_6$) δ ppm 1.36 (d, J=6.60 Hz, 3 H) 1.94 (s, 3 H) 2.99 (d, J=4.40 Hz, 3 H) 4.03 (s, 3 H) 5.01-5.07 (m, 1 H) 6.67 (d, J=4.40 Hz, 1 H) 7.05 (d, J=7.15 Hz, 1 H) 7.33 (d, J=2.20 Hz, 1 H) 7.66-7.72 (m, 2 H) 7.90 (s, 1 H) 8.53 (d, J=8.80 Hz, 1 H) 11.75 (s, 1 H)

Example A462 and Example A463

A461 (50 mg) was separated using a ChiralPAK AD 250× 4.6 mm 10 micron column (CO$_2$/IPA with 0.1% Diethylamine—70/30 at 100 Bar; 35° C.; 2 mL/min.) Enantiomer A (fast eluting) A462 had a chiral HPLC retention time=7.02 min. (99.687% ee). Enantiomer B (slow eluting) A463 chiral HPLC retention time=9.56 min. (99.655% ee)—[Column: ChiralPAK AD 250×4.6 mm 10 micron (CO$_2$/IPA with 0.1% Diethylamine—70/30 at 100 Bar; 35° C.; 2 mL/min.)].

Example A464

7-[6-(1-aminoethyl)-2-pyridinyl]-1,6-dihydro-N,1-dimethyl-imidazo[4,5-d]pyrrolo[2,3-b]pyridin-4-amine

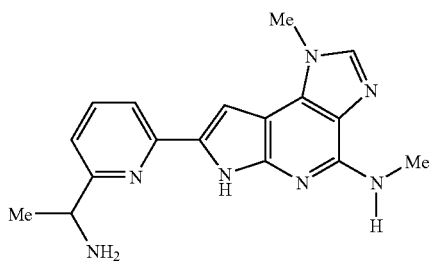

A464

A homogeneous solution of A461 (0.012 g 0.033 mmol) in concentrated hydrochloric acid (1.5 mL) was heated in the microwave at 150° C. for 30 min. The hydrochloric acid was removed under reduced pressure, and the residue was diluted with dichloromethane, neutralized with a saturated aqueous solution of sodium bicarbonate, and dried over anhydrous sodium sulfate. Concentration under reduced pressure followed by purification by silica gel chromatography using a mixture of 10% methanol in dichloromethane (+05% NH$_4$OH) afforded 10.0 mg (91%) of A464 as a yellow solid. The compound had an HPLC retention time=1.95 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=322.30. $^1$ H NMR (500 MHz, CDCl$_3$) δ ppm 1.46 (d, J=6.60 Hz, 3 H) 1.79 (brs, 2 H) 3.19 (d, J=4.95 Hz, 3 H) 4.03 (s, 3 H) 4.10 (d, J=6.60 Hz, 1 H) 5.54 (d, J=4.95 Hz, 1 H) 7.00 (s, 1 H) 7.02 (d, J=7.70 Hz, 1 H) 7.50 (d, J=7.70 Hz, 1 H) 7.56-7.60 (m, 2 H) 9.87 (s, 1 H)

Example A465

N-[1-[6-[1,6-dihydro-1-methyl-4-(methylamino) imidazo[4,5-d]pyrrolo[2,3-b]pyridin-7-yl]-2-pyridinyl]ethyl]-2-methoxy-acetamide chiral, absolute stereochemistry unassigned

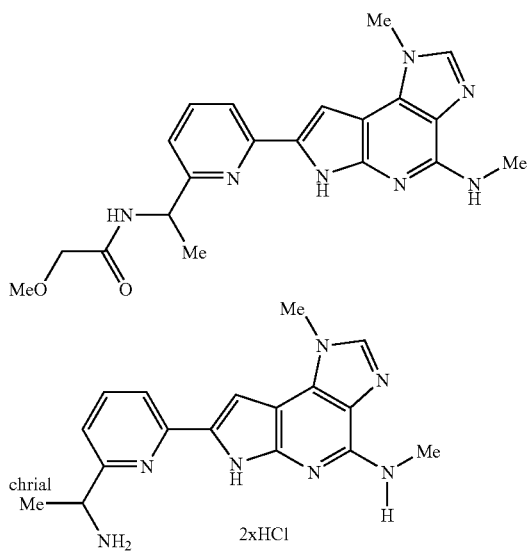

A465

A465.1: 7-[6-(1-aminoethyl)-2-pyridinyl]-1,6-dihydro-N,1-dimethyl-imidazo[4,5-d]pyrrolo[2,3-b]pyridin-4-amine A solution of Enantiomer A463 (0.021 g, 0.058 mmol), absolute ethanol (2.5 mL) and concentrated hydrochloric acid (2.5 mL) was heated at 55° C. overnight. By HPLC and LC/MS, starting material was still present. The residue was concentrated under reduced pressure and re-subjected to the reaction conditions. The reaction mixture was stirred at 55° C. for 2.5 days, at which point, it was complete. Concentration under reduced pressure provided a quantitative yield of the bishydrochloride salt A465.1 as a light orange solid. The compound had an HPLC retention time=1.48 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=322.31.

A465.2: N-[1-[6-[1,6-dihydro-1-methyl-4-(methylamino)imidazo[4,5-d]pyrrolo[2,3-b]pyridin-7-yl]-2-pyridinyl]ethyl]-2-methoxy-acetamide To a mixture of A465.1 (0.023 g, 0.58 mmol), 1-(3-dimethylaminopropyl)-3-ethylcarbodiimide hydrochloride (0.012 g, 0.087 mmol), 1-hydroxybenzotriazole (0.017 g, 0.087 mmol), and diisopropylethylamine (0.060 mL, 0.347 mmol) in anhydrous dimethylformamide (2.5 mL) was added methoxyacetic acid (0.0066 mL, 0.087 mmol). The homogeneous reaction mixture was heated at 75° C. for 1 hr. The solvent was removed under reduced pressure, and the residue was diluted with dichloromethane, washed with a saturated aqueous solution of sodium bicarbonate, and dried over anhydrous sodium sulfate. Concentration under pressure followed by purification by flash silica gel chromatography using a 5% mixture of methanol in dichloromethane afforded 0.019 g (83%) of A465 as a light tan solid. The compound had an HPLC retention time=2.08 min. (Column: Chromolith SpeedROD 4.6×50 mm—4 min.; Solvent A=10% MeOH, 90% H$_2$O, and 0.1% TFA; Solvent B=90% MeOH, 10% H$_2$O, and 0.1% TFA) and a LC/MS M$^{+1}$=394.36, $^1$H NMR (500 MHz, d$^6$-DMSO) δ ppm 1.42 (d, J=6.60 Hz, 3 H) 2.98 (d, J=4.40 Hz, 3 H) 3.34 (s, 3 H) 3.86-3.94 (m, 2 H) 4.02 (s, 3 H) 5.05-5.11 (m, 1 H) 6.69 (d, J=4.40 Hz, 1 H) 7.07 (d, J=7.15 Hz, 1 H) 7.31 (s, 1 H) 7.67-7.74 (m, 2 H) 7.90 (s, 1 H) 8.47 (d, J=8.25 Hz, 1H) 11.79 (s, 1 H)

Example A466

N-[1-[6-[1,6-dihydro-1-methyl-4-(methylamino) imidazo[4,5-d]pyrrolo[2,3-b]pyridin-7-yl]-2-pyridinyl]propyl]-acetamide

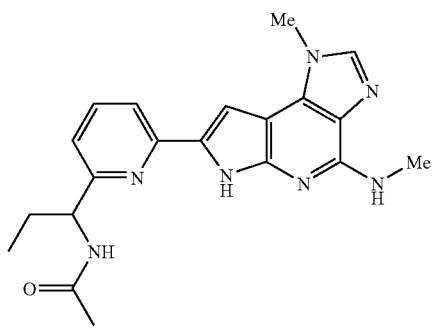

A446.1: 6-Bromo-pyridine-2-carboxylic acid tert-butylamide

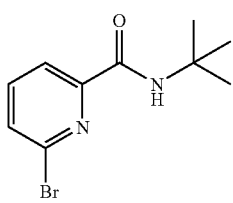

2,6-Dibromopyridine (40 g, 170 mmol) in THF (200 mL) was added dropwise over 1 hr to a cooled (−78 C) solution of n-butyllithium (2.0M in pentane, 85 mL, 170 mmol) in THF (100 mL) under a nitrogen atmosphere. The mixture was allowed to stir for an additional 15 min, then tert-butyl isocyanate was added dropwise over 5 min. The resulting reaction mixture was allowed to warm slowly to room temperature overnight before quenching with saturated ammonium chloride solution (200 mL) and extracting with ethyl acetate (2×100 mL). The combined organics were dried (MgSO$_4$) and evaporated in vacuo to yield the cude product A466.1 (42.4 g) as a dark brown oil which was used immediately without further purification. HPLC YMC S-5 4.6×33 mm (2 min grad): retention time 1.76 min, M+H$^+$=203.08

A466.2: 6-Bromo-pyridine-2-carbonitrile

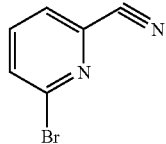

Thionyl chloride (10 mL, 138 mmol) was added in one portion to the amide A466.1 (1.07 g, 4.18 mmol) at room temperature under a nitrogen atmosphere. The resulting mixture was heated to 85° C. for 1 hr before cooling to room temperature and evaporating in vacuo. The residue was basified to pH14 using sodium hydroxide solution (5M, 20 mL). This aqueous phase was then extracted with ethyl acetate (2×25 mL), the combined organics dried (MgSO$_4$), evaporated in vacuo and the residue purified by column chromatography using ethyl acetate as eluent to yield A466.2 (0.5 g) as a beige solid. HPLC YMC S-5 4.6×33 mm (2 min grad): retention time 1.02 min, M+H$^+$=185.06

A466.3: 1-(6-Bromo-pyridin-2-yl)-propylamine

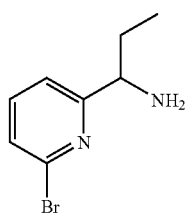

Ethyl magnesium bromide (3.0 mL, 3.0 mmol) was added dropwise over 10 min to a solution of the pyridine nitrile A466.2 (500 mg, 2.75 mmol) in THF (5 mL) at room temperature under a nitrogen atmosphere. After strring for 30 min at room temperature, the reaction mixture was then cooled to 0° C. and anhydrous methanol added (2.75 mL) followed by sodium borohydride (15 mg, 3.0 mmol). The mixture was allowed to warm to room temperature over 1 hr before quenching with saturated ammonium chloride solution (10 mL) and stirring overnight at room temperature. The mixture was diluted with water (20 mL) and extracted with ethyl acetate (3×30 mL). The combined organics were dried (MgSO4), evaporated in vacuo and purified by column chromatography using 10% MeOH in ethyl acetate as eluant to yield A466.3 (237 mg). HPLC YMC S-5 4.6×33 mm (2 min grad): retention time 0.87 min, M+H$^+$=217.15

A466.4:
N-[1-(6-Bromo-pyridin-2-yl)-propyl]-acetamide

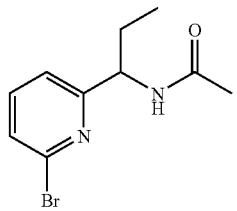

Acetyl chloride (0.087 mL, 1.22 mmol) was added dropwise to a mixture of the amine A466.3 (237 mg, 1.11 mmol) and triethylamine (0.34 mL, 2.44 mmol) in THF (3 mL) at 0 C under a nitrogen atmosphere. The cooling bath was removed and the reaction allowed to warm to room temperature over 1 hr. The reaction mixture was filtered to remove the triethylamine-hydrochloride salt and the filtrate was evaporated in vacuo to yield the crude product A466.4 (299 mg) which was used immediately without further purification. HPLC YMC S-5 4.6×33 mm (2 min grad): retention time 1.31 min, M+H$^+$=259.16

A466.5: N-[1-(6-Trimethylsilanylethynyl-pyridin-2-yl)-propyl]-acetamide

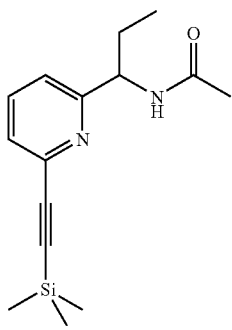

A466.5

TMS-Acetylene (0.21 mL, 1.46 mmol) was added dropwise to the pyridine bromide A466.4 (299 mg, 1.17 mmol), copper (I) iodide (11 mg, 0.06 mmol) and palladium dichlorobistriphenylphosphine (55 mg, 0.078 mmol) in triethylamine (5 mL) and DMF (1 mL) at room temperature under a nitrogen atmosphere. The reaction mixture was heated to 80° C. for 30 min before cooling to room temperature and evaporating in vacuo. Diethyl ether was added (20 mL) and the salt filtered. The filtrate was evaporated in vacuo and purified by column chromatography using 1:1 ethyl acetate:hexane as eluent to yield A466.5 (250 mg). HPLC YMC S-5 4.6×33 mm (2 min grad): retention time 1.84 min, M+H$^+$=275.32

A466.6: N-[1-(6-Ethynyl-pyridin-2-yl)-propyl]-acetamide

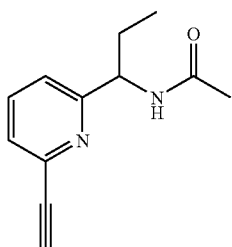

A466.6

Sodium hydroxide (2N, 0.5 mL) was added in one portion to the TMS-acetylene A466.5 (250 mg) in THF (3 mL) at room temperature. After strring for 1 hr, the reaction mixture was diluted with water (5 mL) and extracted with ethyl acetate (2×15 mL). The combined organics were dried (MgSO4) and evaporated in vacuo to yield the crude product A466.6 (141 mg, 77%) which was used immediately without further purification. HPLC YMC S-5 4.6×33 mm (2 min grad): retention time 0.95 min, M+H$^+$=203.26

A466.7: {7-[6-(1-Acetylamino-propyl)-pyridin-2-ylethynyl]-6-amino-1-methyl-1H-imidazo[4,5-c]pyridin-4-yl}-methyl-carbamic acid tert-butyl ester

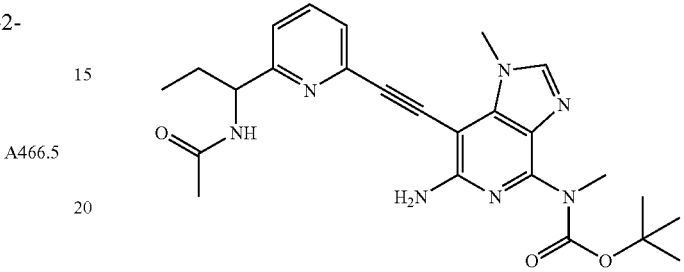

A466.7

A1.12 (225 mg, 0.56 mmol), dichlorobis(triphenylphosphine)palladium (26 mg, 0.037 mmol), A466.6 (141 mg, 0.70 mmol) and triethylamine (2 mL) were each added to N,N-dimethylformamide (2 mL) and nitrogen bubbled through the resulting mixture for 5 min. The reaction mixture was heated at 80° C. for 1 hr under a nitrogen atmosphere before cooling to room temperature and evaporating the solvent in vacuo. Diethyl ether was added to the residue (10 mL) and filtered. The filtrate was evaporated in vacuo purified by silica gel column chromatography using 10% MeOH in ethyl acetate as eluent to provide 172 mg of A466.7. HPLC YMC S-5 4.6×33 mm (2 min grad): retention time 1.47 min, M+H$^+$=478.36.

A466.8: N-[1-[6-[1,6-dihydro-1-methyl-4-(methylamino)imidazo[4,5-d]pyrrolo[2,3-b]pyridin-7-yl]-2-pyridinyl]propyl]-acetamide

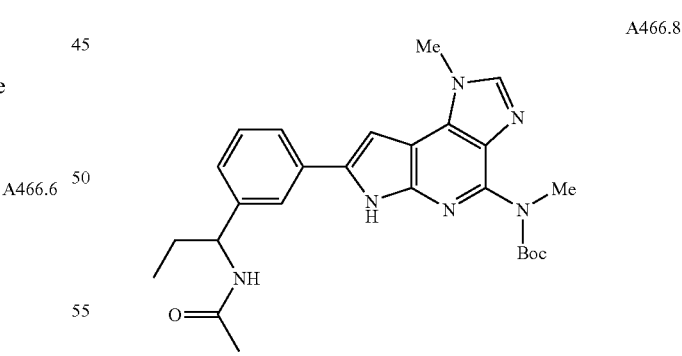

A466.8

Potassium tert-butoxide (1.0M in THF, 0.9 mL, 0.9 mmol) was added dropwise over 2 min to a solution of A466.7 (172 mg, 0.36 mmol) in DMA (4 mL) at room temperature under a nitrogen atmosphere. The reaction was heated to 90° C. for 1 hr before cooling to room temperature and evaporating in vacuo. The residue was purified by column chromatography using 5% MeOH in ethyl acetate as eluent to yield A466.8 (91 mg). HPLC YMC S-5 4.6×33 mm (2 min grad): retention time 1.58 min, M+H$^+$=478.36.

A466.9: N-[1-[6-[1,6-dihydro-1-methyl-4-(methylamino)imidazo[4,5-d]pyrrolo[2,3-b]pyridin-7-yl]-2-pyridinyl]propyl]-acetamide Trifluoroacetic acid in dichloromethane (20% solution, 5 mL) was added in one portion to A466.8 and the resulting reaction mixture was stirred at room temperatuire for 1 hr before evaporating in vacuo. The residue was partitioned between ethyl acetate (5 mL) and saturated sodium hydrogen carbonate solution (5 mL). The aqueous phase was extracted with ethyl acetate (2×10 mL) and the combined organics were dried (MgSO$_4$) and evaporated in vacuo to yield A466 (39 mg) as a tan powder. HPLC YMC S-5 4.6×33 mm (2 min grad): retention time 1.47 min, M+H$^+$=378.38

Examples A467 and A468

Separation of enantiomers was achieved using a chiracel AD column 4.6×250 mm, 10 micron, Hex/MeOH/EtOH/DEA=75:12.5:12.5:0.1 to yield enantiomer one at time t=9.26 min and enantiomer 2 at time t=11.36 min.

Example A469

(gammaS)-gamma-amino-6-[1,6-dihydro-1-methyl-4-(methylamino)imidazol-[4,5-d]pyrrolo[2,3-b]pyridin-7-yl]-2-pyridinepropanol trihydrochloride

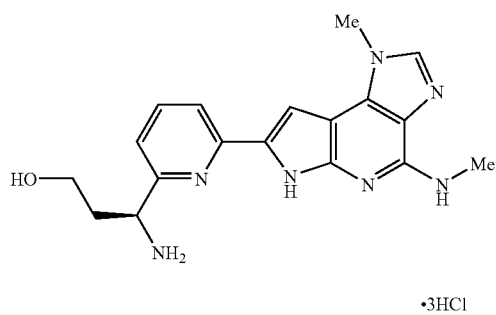

A469

·3HCl

A469.1: (S)-2-{[1-(6-Bromo-pyridin-2-yl)-meth-(E)-ylidene]-amino}-3-methyl-butyric acid methyl ester

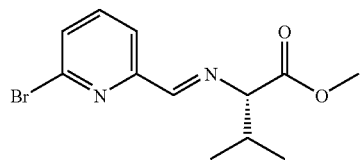

A469.1

Anhydrous magnesium sulfate (5.4 g), 6-bromopyridine-2-carboxaldehyde (5.0 g, 26.9 mmol) and triethylamine (3.75 mL, 26.9 mmol) were each added sequentially in one portion to a cooled (0° C.) solution of (L)-valine methyl ester hydrochloride (4.51 g, 26.9 mmol) and the reaction mixture was allowed to warm slowly to room temperature overnight under a nitrogen atmosphere. The mixture was then filtered and the filter cake washed with diethyl ether (100 mL) before evaporating the filtrate in vacuo. The residue was purified by column chromatography using 5:1 hexane/ethyl acetate as eluent to yield A469.1 (7.1 g, 88%). HPLC YMC S-5 4.6×33 mm (2 min grad): retention time 0.86 min, M+H$^+$=202.08

A469.2: (S)-2-[(S)-1-(6-Bromo-pyridin-2-yl)-allylamino]-3-methyl-butyric acid methyl ester

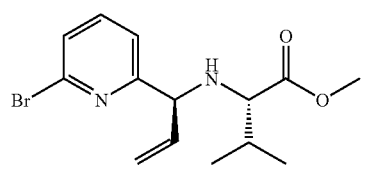

A469.2

Dimethyl zinc (2.0M in toluene, 9.85 mL, 19.7 mmol) was added to anhydrous THF (10 mL) under a nitrogen atmosphere and the solution cooled to −78° C. Vinylmagnesium bromide (1.0M in THF, 19.7 mL, 19.7 mmol) was then added dropwise over 10 min and the solution allowed to stir at −78° C. under a nitrogen atmosphere for 30 min. A solution of the imine A469.1 (5.87 g, 19.7 mmol) in THF (10 mL) was then added dropwise to the zincate solution at −78° C. over 1 hr. The resulting reaction mixture was then allowed to stir for an additional 1 hr at −78° C. before quenching with 10% sodium hydrogen carbonate solution (100 mL) and warming to room temperature. The mixture was diluted with water (50 mL) and extracted with diethyl ether (2×200 mL), the combined organic phases were then dried (MgSO$_4$) and evaporated in vacuo to yield A469.2 (6.35 g, 99%) which was used immediately without further purification. HPLC YMC S-5 4.6×33 mm (2 min grad): retention time 1.21 min, M+H$^+$=329.21

A469.3: (S)-2-[(S)-1-(6-Bromo-pyridin-2-yl)-allylamino]-3-methyl-butan-1-ol

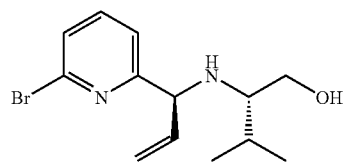

A469.3

Lithium aluminium hydride (2.0M in THF, 6.10 mL, 12.19 mmol) was added dropwise over 30 min to a cooled (−5° C.) solution of the ester A469.2 (3.98 g, 12.19 mmol) in THF (40 mL) under a nitrogen atmosphere. The reaction mixture was allowed to stir for 1 hr before quenching at −5° C. with water (0.46 mL), 15% sodium hydroxide solution (0.46 mL) and water (1.4 mL) each added dropwise. The mixture was then allowed to warm to room temperature before filtering and washing with diethyl ether (30 mL). The filtrate was washed with water (30 mL) and the separated organic layer was dried (MgSO$_4$), evaporated in vacuo and purified by column chromatography using 4:1 hexane:ethyl acetate as eluent to yield A469.3 (2.68 g). HPLC YMC S-5 4.6×33 mm (2 min grad): retention time 1.13 min, M+H+=301.18

A469.4: (S)-1-(6-Bromo-pyridin-2-yl)-allylamine

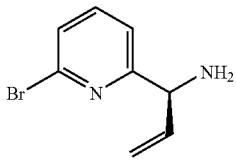

A469.4

40% Aqueous methylamine solution (8.25 mL) followed by periodic acid (5.63 g in 80 mL of water) were each added in one portion to a solution of the alcohol A469.3 (2.04 g, 6.85 mmol) in methanol/THF (9:1 v/v, 80 mL). The reaction mixture was stirred at room temperature for 3 hrs before adding water (90 mL). The methanol was removed in vacuo and the residue extracted with diethyl ether (3×200 mL). The combined organic layers were dried (MgSO$_4$) and evaporated in vacuo to yield A469.4 (1.72 g) which was used immediately without further purification. HPLC YMC S-5 4.6×33 mm (2 min grad): retention time 0.76 min, M+H$^+$=215.10

A469.5: [(S)-1-(6-Bromo-pyridin-2-yl)-allyl]-carbamic acid tert-butyl ester

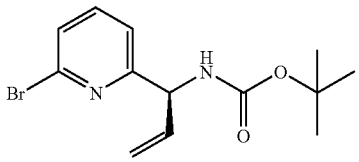

A469.5

Triethylamine (6.1 mL, 43.65 mmol) and BOC-anhydride (2.0 g, 9.17 mmol) were each added in one portion to a cooled (0° C.) solution of the amine A469.4 (1.72 g, 8.73 mmol) in anhydrous dichloromethane (100 mL) under a nitrogen atmosphere. The reaction mixture was allowed to warm slowly to room temperature overnight before quenching with saturated sodium hydrogen carbonate solution (50 mL). The organic layer was dried (MgSO$_4$) and evaporated in vacuo to give a crude residue which was purified by column chromatography using 10:1 hexane:ethyl acetate as eluent to yield A469.5 (2.22 g, 86%). HPLC YMC S-5 4.6×33 mm (2 min grad): retention time 2.01 min, M+H$^+$ (−Boc)=215.10

A469.6: [(S)-1-(6-Bromo-pyridin-2-yl)-3-hydroxy-propyl]-carbamic acid tert-butyl ester

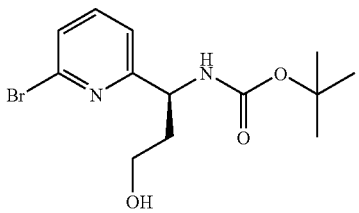

A469.6

9-BBN (0.5M in THF, 6.75 mL) was added dropwise over 2 min to a solution of A469.5 (1.0 g, 3.37 mmol) in THF (20 mL) at room temperature under a nitrogen atmosphere. The reaction mixture was allowed to stir at room temperature for 2 hrs before cooling to 0° C. and adding hydrogen peroxide (30%, 1.69 mL) and sodium hydroxide (3M, 1.69 mL). The mixture was then heated to 50° C. for 1 hr before cooling to room temperature. The aqueous layer was separated and extracted with diethyl ether (2×30 mL), the combined organic layers dried (MgSO$_4$), evaporated in vacuo and purified by column chromatography using 2:1 hexane/ethyl acetate as eluent to give A469.6 (818 mg, 63%). HPLC YMC S-5 4.6× 33 mm (2 min grad): retention time 1.51 min, M+Na$^+$=355.19

A469.7: [(S)-1-(6-Bromo-pyridin-2-yl)-3-(tetrahydro-pyran-2-yloxy)-propyl]-carbamic acid tert-butyl ester

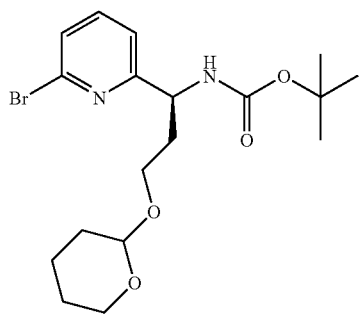

A469.7 para-Toluenesulfonic acid monohydrate (116 mg, 0.61 mmol) was added in one portion to a solution of the alcohol A469.6 (802 mg, 2.43 mmol) and dihydropyran (0.23 mL, 2.55 mmol) in dichloromethane (10 mL) at 0 C under a nitrogen atmosphere. The cooling bath was removed and the reaction mixture allowed to warm to room temperature over 2 h before quenching with saturated sodium hydrogen carbonate solution (10 mL). The organic layer was dried (MgSO$_4$) and evaporated in vacuo to yield A469.7 (1.12 g) which was used immediately without further purification. HPLC YMC S-5 4.6×33 mm (2 min grad): retention time 1.88 min, M+Na$^+$=439.19.

A469.8: [(S)-3-(Tetrahydro-pyran-2-yloxy)-1-(6-trimethylsilanylethynyl-pyridin-2-yl)-propyl]-carbamic acid tert-butyl ester

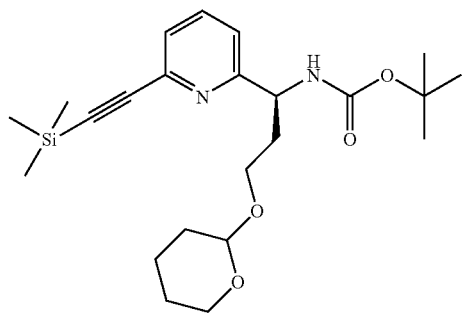

A469.8

TMS-Acetylene (0.98 mL, 6.91 mmol) was added dropwise to the pyridine bromide A469.7 (2.29 g, 5.53 mmol), CuI (53 mg, 0.28 mmol) and palladium dichlorobistriphenylphosphine (260 mg, 0.37 mmol) in triethylamine (30 mL) at room temperature under a nitrogen atmosphere. The reaction mixture was heated to 80 C for 30 min before cooling to room temperature and evaporating in vacuo. Diethyl ether was added (20 mL) and the salt filtered. The filtrate was evaporated in vacuo yield A469.8 (2.50 g) which was used immediately without further purification. HPLC YMC S-5 4.6×33 mm (2 min grad): retention time 2.12 min, M+H$^+$=433.32

A469.9: [(S)-1-(6-Ethynyl-pyridin-2-yl)-3-(tetrahydro-pyran-2-yloxy)-propyl]-carbamic acid tert-butyl ester

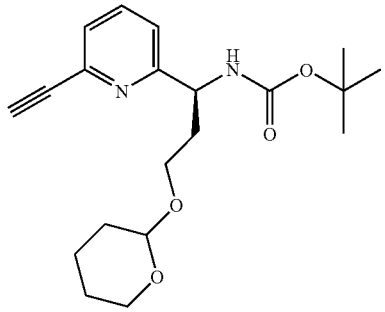

A469.9

Sodium hydroxide (2N, 5.8 mL) was added in one portion to the A469.8 (2.5 g, 5.79 mmol) in THF (50 mL) at room temperature. After stirring for 1 hr, the reaction mixture was diluted with water (20 mL) and extracted with diethyl ether (2×30 mL). The combined organics were dried (MgSO4), evaporated in vacuo and purified by column chromatography using 2:1 hexane/ethyl acetate as eluent to yield A469.9 (1.31 g). HPLC YMC S-5 4.6×33 mm (2 min grad): retention time 1.77 min, M+H$^+$=361.34

A469.10: (6-Amino-7-{6-[(S)-1-tert-butoxycarbonylamino-3-(tetrahydro-pyran-2-yloxy)-propyl]-pyridin-2-ylethynyl}-1-methyl-1H-imidazo[4,5-c]pyridin-4-yl)methyl-carbamic acid tert-butyl ester

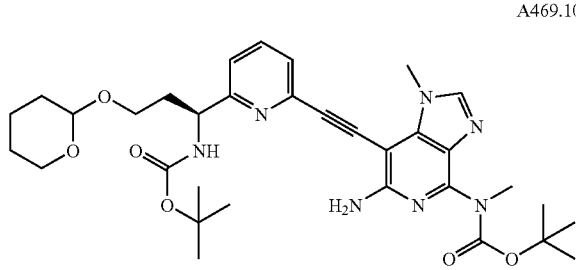

A469.10

A1.12 (484 mg, 1.2 mmol), dichlorobis(triphenylphosphine)palladium (56 mg, 0.08 mmol), A469.9 (540 mg, 1.5 mmol) and triethylamine (4 mL) were each added to N,N-dimethylformamide (2 mL) and nitrogen bubbled through the resulting mixture for 5 min. The reaction mixture was heated at 75° C. for 3 hrs under a nitrogen atmosphere before cooling to room temperature and evaporating the solvent in vacuo. The residue was purified by silica gel column chromatography using 2:1 ethyl acetate/hexane as eluent to provide 449 mg (59%) of A469.10. HPLC YMC S-5 4.6×33 mm (2 min grad): retention time 1.81 min, M+H$^+$=636.40

A469.11: [7-{6-[(S)-1-tert-Butoxycarbonylamino-3-(tetrahydro-pyran-2-yloxy)propyl]-pyridin-2-ylethynyl}-1-methyl-6-(2,2,2-trifluoro-acetylamino)-1H-imidazo[4,5-c]pyridin-4-yl]-methyl-carbamic acid tert-butyl ester

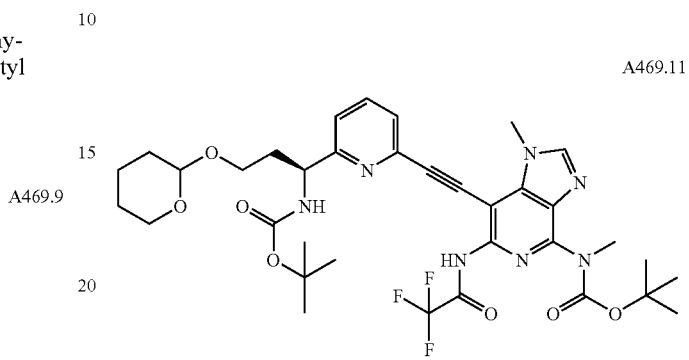

A469.11

Trifluoroacetic anhydride (0.185 mL, 1.33 mmol) was added dropwise over 5 min to a cooled (0 C) solution of A469.10 (423 mg, 0.67 mmol) and triethylamine (0.28 mL, 2.00 mmol) in THF (10 mL) under a nitrogen atmosphere. The cooling bath was removed after 10 min and the reaction mixture allowed to stir at room temperature for 1 hr before evaporating in vacuo. The residue was taken up in dichloromethane (50 mL) and washed with saturated sodium bicarbonate solution (25 mL). The organic layer was separated and dried (MgSO$_4$), then evaporated in vacuo to yield the crude product A469.11 which was used immediately without further purification (513 mg). HPLC YMC S-5 4.6×33 mm (2 min grad): retention time 1.97 min, M+H$^+$=732.34

A469.12: (S)-tert-butyloxycarbonylamino-6-[1,6-dihydro-1-methyl-4-(methylamino)imidazo[4,5-d]pyrrolo[2,3-b]pyridin-7-yl]-2-pyridin-3-(tetrahydro-pyran-2-yl)propanol

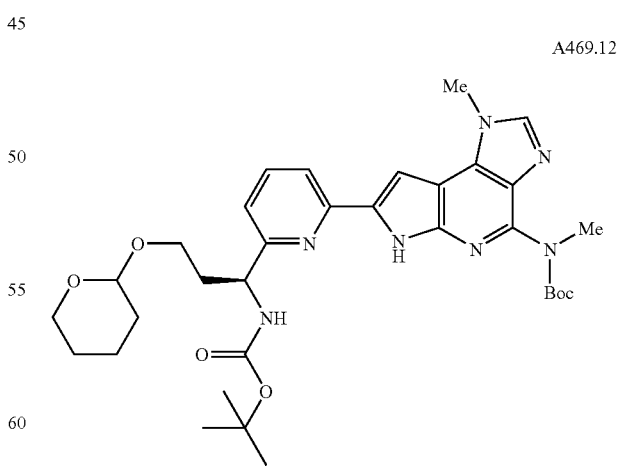

A469.12

Potassium carbonate (107 mg, 0.772 mmol) and dichlorobistriphenylphosphine palladium (II) (30 mg, 0.042 mmol) were each added in one portion to a solution of A469.11 (513 g, 0.7 mmol) in dimethylacetamide (8 mL). at room temperature under a nitrogen atmosphere. The reaction was heated to 120° C. for 2 hrs before evaporating in vacuo and purifying by column chromatography using 2:1 ethyl acetate:hexane to yield A469.12 (305 mg, 72% over two steps). HPLC YMC S-5 4.6×33 mm (2 min grad): retention time 1.87 min, M+H$^+$=636.35

A469.13: (S)-amino-6-[1,6-dihydro-1-methyl-4-(methylamino)imidazo[4,5-d]pyrrolo[2,3-b]pyridin-7-yl]-2-pyridinepropanol Concentrated hydrochloric acid (assuming 10M, 0.44 mL, 4.36 mmol) was added dropwise to a solution of A469.12 (277 mg, 0.436 mmol) in THF (10 mL) and the reaction mixture stirred at room temperature for 3 hrs before evaporating in vacuo. Diethyl ether (20 mL) was added to the residue and the solid filtered to yield A469 (194 mg, 88%). HPLC YMC S-5 4.6×33 mm (2 min grad): retention time 1.06 min, M+H$^+$=352.29.

Column: Chiralpak AD 250×4.6 mm ID; 10 μm
Temperature: 35° C.
Mobil Phase: Hex/EtOH/DEA=20:80:0.1
Flow rate: 1.0 mL/min
Injection volume: 5~15 μl
UV Detection: 368 nm Retention time=12.3 min, 95.6% enantiomeric excess.

Example A470

N-[(1S)-1-[6-[1,6-dihydro-1-methyl-4-(methylamino)imidazo[4,5-d]pyrrolo[2,3-b]pyridin-7-yl]-2-pyridinyl]-3-hydroxypropyl]-2-methoxy-acetamide

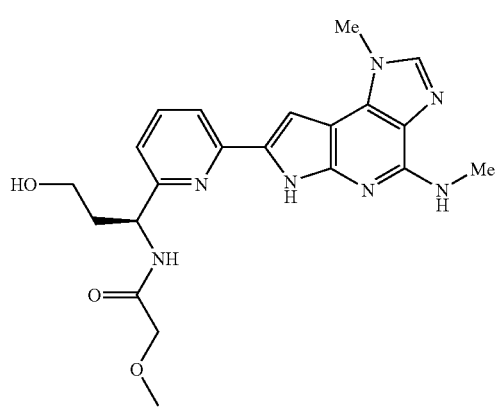

A470

EDC (23 mg, 0.12 mmol) was added in one portion to a mixture of methoxyacetic acid (11 mg, 0.12 mmol), HOBt (16 mg, 0.12 mmol) and DIPEA (0.041 mL) in anhydrous DMF (2 mL) and the resulting mixture was allowed to stir at room temperature for 30 min before addition of A469 (50 mg, 0.109 mmol). The mixture was heated to 70° C. for 2 hrs in a screw-capped vial before cooling to room temperature and evaporating in vacuo. The residue was partitioned between ethyl acetate (5 mL) and water (2 mL). The separated aqueous layer was adjusted to a pH of 7-8 and extracted with ethyl acetate (3×30 mL). The combined organics were dried (MgSO$_4$), evaporated in vacuo and purified by column chromatography (5% MeOH in EtOAc) to yield A470 (29 mg). HPLC YMC S-5 4.6×33 mm (2 min grad): retention time 1.13 min, M+H$^+$=424.28

The compounds in Table A17 were prepared in a similar manner to A470 by reacting A469 and the appropriate carboxylic acid.

TABLE A17

| Ex. | R | Name | HPLC Retention (min) | MS Reported |
|---|---|---|---|---|
| A471 | CH$_3$— | N-[(1S)-1-[6-[1,6-dihydro-1-methyl-4-(methylamino)imidazo[4,5-d]pyrrolo[2,3-b]pyridin-7-yl]-2-pyridinyl]-3-hydroxypropyl]-acetamide | 1.11 | 394.30 |
| A472 | | N-[(1S)-1-[6-[1,6-dihydro-1-methyl-4-(methylamino)imidazo[4,5-d]pyrrolo[2,3-b]pyridin-7-yl]-2-pyridinyl]-3-hydroxypropyl]-3-methoxy-propanamide | 1.14 | 438.29 |

Example A473

(S)-7-(6-(1-amino-3-methoxypropyl)pyridin-2-yl)-N,1-dimethyl-1,6-dihydroimidazo[4,5-d]pyrrolo[2,3-b]pyridin-4-amine

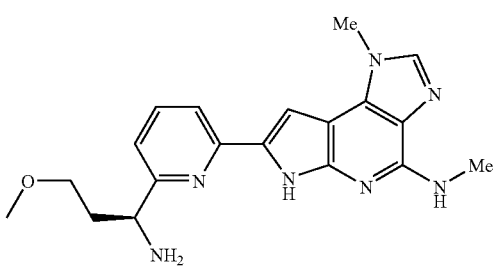

A473

285

A473.1: [(S)-1-(6-Ethynyl-pyridin-2-yl)-3-methoxy-propyl]-carbamic acid tert-butyl ester

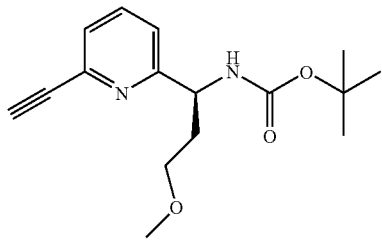

A473.1

Sodium hydride (60% dispersion in oil, 80 mg, 1.99 mmol) was added in one portion to a solution of the alcohol derived from A469.9 by treatment with 1N HCl (440 mg, 1.59 mmol) in anhydrous THF (8 mL) cooled to 0° C. under a nitrogen atmosphere. The reaction mixture was stirred for 10 min before the dropwise addition of methyl iodide (0.10 mL, 1.67 mmol). The reaction mixture was allowed to warm slowly to room temperature overnight before quenching with water (5 mL) and extracting diethyl ether (2×20 mL). The combined organics were dired (MgSO$_4$), evaporated in vacuo and purified by column chromatography using 3:1 hexane:ethyl acetate to yield A473.1 (205 mg). HPLC YMC S-5 4.6×33 mm (2 min grad): retention time 1.60 min, M+H$^+$=291.27

A473.2: {6-Amino-7-[6-((S)-1-tert-butoxycarbonylamino-3-methoxy-propyl)pyridin-2-ylethynyl]-1-methyl-1H-imidazo[4,5-c]pyridin-4-yl}-methyl-carbamic acid tert-butyl ester

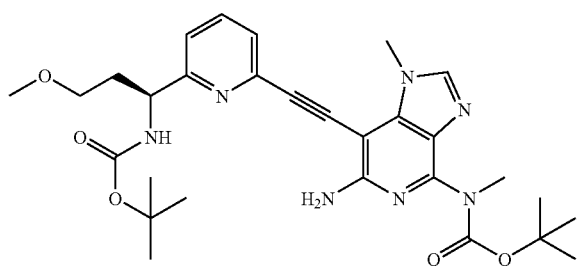

A473.2

A1.12 (239 mg, 0.593 mmol), dichlorobis(triphenylphosphine)palladium II (28 mg, 0.04 mmol), A473.1 (189 mg, 0.652 mmol) and diisopropylamine (2 mL) were each added to N,N-dimethylformamide (1.7 mL) and nitrogen bubbled through the resulting mixture for 5 min. The reaction mixture was heated at 95° C. for 20 min under a nitrogen atmosphere before cooling to room temperature and evaporating the solvent in vacuo. The residue was purified by silica gel column chromatography using ethyl acetate as eluent to provide 334 mg of A473.2. HPLC YMC S-5 4.6×33 mm (2 min grad): retention time 1.72 min, M+H$^+$=566.34.

286

A473.3: [7-[6-((S)-1-tert-Butoxycarbonylamino-3-methoxy-propyl)-pyridin-2-ylethynyl]-1-methyl-6-(2,2,2-trifluoro-acetylamino)-1H-imidazo[4,5-c]pyridin-4-yl]-methyl-carbamic acid tert-butyl ester

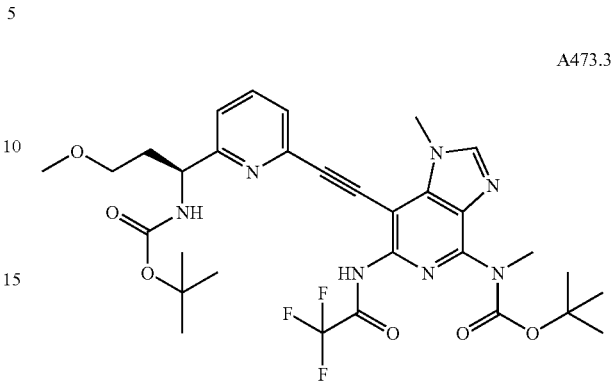

A473.3

Trifluoroacetic anhydride (0.164 mL, 1.18 mmol) was added dropwise over 5 min to a cooled (0° C.) solution of A473.2 (334 mg, 0.592 mmol) and triethylamine (0.25 mL, 1.78 mmol) in THF (10 mL) under a nitrogen atmosphere. The cooling bath was removed after 10 min and the reaction mixture allowed to stir at room temperature for 1 h before evaporating in vacuo. The residue was taken up in dichloromethane (50 mL) and washed with saturated sodium bicarbonate solution (25 mL). The organic layer was separated and dried (MgSO$_4$), then evaporated in vacuo to yield the crude product A473.3 which was used immediately without further purification (369 mg). HPLC YMC S-5 4.6×33 mm (2 min grad): retention time 1.87 min, M+H$^+$=662.32

A473.4 (S)-7-(6-(1-tertbutyloxycarbonylamino-3-methoxypropyl)pyridin-2-yl)-N,1-dimethyl-1,6-dihydroimidazo[4,5-d]pyrrolo[2,3-b]pyridin-4-tert-butyloxycarbonylamine

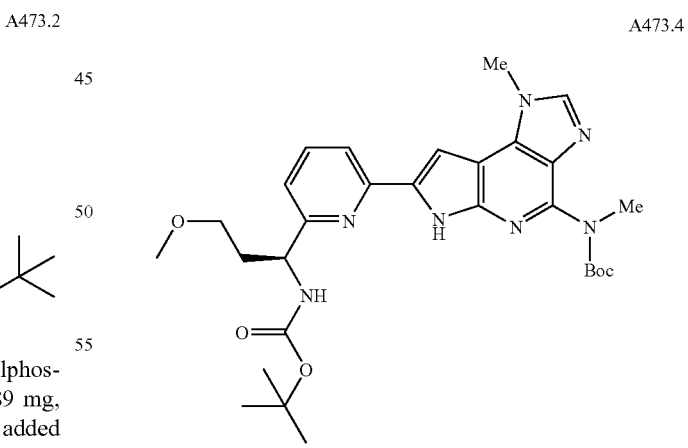

A473.4

Potassium carbonate (85 mg, 0.615 mmol) and dichlorobistriphenylphosphine palladium II (24 mg, 0.034 mmol) were each added in one portion to a solution of the trifluoroacetamide A473.3 (369 mg, 0.56 mmol) in dimethylacetamide (6 mL) at room temperature under a nitrogen atmosphere. The reaction was heated to 120° C. for 3 hrs before evaporating in vacuo and purifying by column chromatography using ethyl acetate to yield A473.4 (283 mg, 90%). HPLC YMC S-5 4.6∴33 mm (2 min grad): retention time 1.73 min, M+H⁺=566.32.

A473.5: (S)-7-(6-(1-amino-3-methoxypropyl)pyridin-2-yl)-N,1-dimethyl-1,6-dihydroimidazo[4,5-d]pyrrolo[2,3-b]pyridin-4-amine Trifluoroacetic acid in dichloromethane (20% solution, 10 mL) was added in one portion to A473.4 (283 mg) and the resulting reaction mixture was stirred at room temperature for 1 hr before evaporating in vacuo. The residue was partitioned between ethyl acetate (5 mL) and saturated aqueous sodium hydrogen carbonate solution (5 mL). The aqueous phase was extracted with ethyl acetate (2×10 mL) and the combined organics were dried (MgSO₄) and evaporated in vacuo to yield A473 (178 mg) as a tan powder. HPLC YMC S-5 4.6×33 mm (2 min grad): retention time 1.33 min, M+H⁺=366.31.

Example A474

(S)-2-methoxy-N-(3-methoxy-1-(6-(1-methyl-4-(methylamino)-1,6-dihydroimidazo[4,5-d]pyrrolo[2,3-b]pyridin-7-yl)pyridin-2-yl)propyl)acetamide

A474

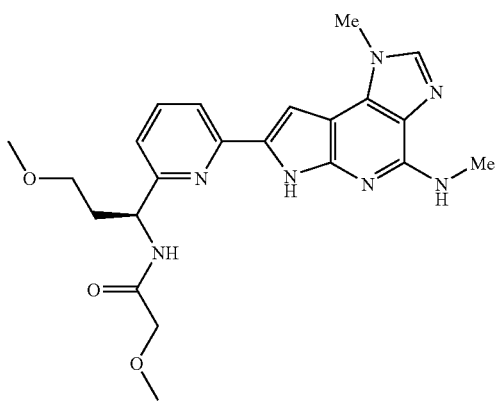

EDC (9 mg, 0.045 mmol) was added in one portion to a mixture of methoxyacetic acid (5 mg, 0.05 mmol), HOBt (7 mg, 0.045 mmol) and DIPEA (0.02 mL) in anhydrous DMF (0.5 mL) and the resulting mixture was allowed to stir at room temperature for 30 min before addition of A473 (15 mg, 0.041 mmol). The mixture was heated to 70° C. for 2 h in a screw-capped vial before cooling to room temperature and evaporating in vacuo. The residue was purified by preparative HPLC to yield amide A474 (8 mg). HPLC YMC S-5 4.6×33 mm (2 min grad): retention time 1.30 min, M+H⁺=438.29

The examples in Table A18 were prepared in a manner similar to that for A474 by the reaction of A473 and the appropriate carboxylic acid.

TABLE A18

| Ex. | R | Name | HPLC Retention (min) | MS Reported |
|---|---|---|---|---|
| A475 | CH₃— | (S)-N-(3-methoxy-1-(6-(1-methyl-4-(methylamino)-1,6-dihydroimidazo[4,5-d]pyrrolo[2,3-b]pyridin-7-yl)pyridin-2-yl)propyl)acetamide | 1.36 | 408.31 |
| A476 | | (S)-3-methoxy-N-(3-methoxy-1-(6-(1-methyl-4-(methylamino)-1,6-dihydroimidazo[4,5-d]pyrrolo[2,3-b]pyridin-7-yl)pyridin-2-yl)propyl)propanamide | 1.31 | 452.32 |
| A477 | | (S)-2-methoxy-N-((S)-3-methoxy-1-(6-(1-methyl-4-(methylamino)-1,6-dihydroimidazo[4,5-d]pyrrolo[2,3-b]pyridin-7-yl)pyridin-2-yl)propyl)propanamide | 1.42 | 452.32 |
| A478 | | (S)-N-(3-methoxy-1-(6-(1-methyl-4-(methylamino)-1,6-dihydroimidazo[4,5-d]pyrrolo[2,3-b]pyridin-7-yl)pyridin-2-yl)propyl)-3-morpholinopropanamide | 1.34 | 507.32 |
| A479 | | (S)-2-(1H-imidazol-4-yl)-N-(3-methoxy-1-(6-(1-methyl-4-(methylamino)-1,6-dihydroimidazo[4,5-d]pyrrolo[2,3-b]pyridin-7-yl)pyridin-2-yl)propyl)acetamide | 1.27 | 488.30 |
| A480 | | (S)-2-cyano-N-(3-methoxy-1-(6-(1-methyl-4-(methylamino)-1,6-dihydroimidazo[4,5-d]pyrrolo[2,3-b]pyridin-7-yl)pyridin-2-yl)propyl)acetamide | 1.36 | 433.29 |

Example A481

(gammaR)-gamma-amino-6-[1,6-dihydro-1-methyl-4-(methylamino)imidazo[4,5-d]pyrrolo[2,3-b]pyridin-7-yl]-2-pyridinepropanol trihydrochloride

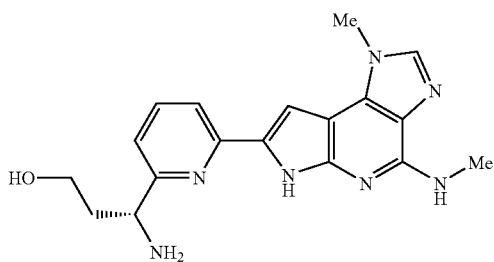

A481

Analogous chemistry utilized to prepare A469 was used to produce A481 with (R)-stereochemistry (starting from D-valine methyl ester hydrochloride):
Column: Chiralpak AD 250×4.6 mm ID; 10 μm
Temperature: 35° C.
Mobil Phase: Hex/EtOH/DEA=20:80:0.1
Flow rate: 1.0 mL/min
Injection volume: 5~15 μl
UV Detection: 368 nm Retention time=6.7 min, 91.4 enantiomeric excess.

Example A482

N-[(1R)-1-[6-[1,6-dihydro-1-methyl-4-(methylamino)imidazo[4,5-d]pyrrolo[2,3-b]pyridin-7-yl]-2-pyridinyl]-3-hydroxypropyl]-2-methoxy-acetamide

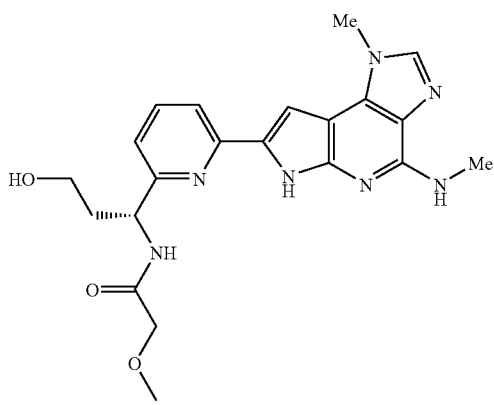

A482

EDC (23 mg, 0.12 mmol) was added in one portion to a mixture of methoxyacetic acid (11 mg, 0.12 mmol), HOBt (16 mg, 0.12 mmol) and DIPEA (0.041 mL) in anhydrous DMF (2 mL) and the resulting mixture was allowed to stir at room temperature for 30 min before addition of A481 (50 mg, 0.109 mmol). The mixture was heated to 70° C. for 2 h in a screw-capped vial before cooling to room temperature and evaporating in vacuo. The residue was partitioned between ethyl acetate (5 mL) and water (2 mL). The separated aqueous layer was adjusted to a pH of 7-8 and extracted with ethyl acetate (3×30 mL). The combined organics were dried (MgSO$_4$), evaporated in vacuo and purified by column chromatography (5% MeOH in EtOAc) to yield amide A482 (29 mg). HPLC YMC S-5 4.6×33 mm (2 min grad): retention time 1.13 min, M+H$^+$424.28

The examples in Table A19 were prepared in a similar manner to Example A482 utilizing A481 and the appropriate carboxylic acid.

TABLE A19

| Ex. | R | Name | HPLC Retention (min) | MS Reported |
|---|---|---|---|---|
| A483 | CH$_3$— | N-[(1R)-1-[6-[1,6-dihydro-1-methyl-4-(methylamino)imidazo[4,5-d]pyrrolo[2,3-b]pyridin-7-yl]-2-pyridinyl]-3-hydroxypropyl]-acetamide | 1.11 | 394.30 |
| A484 | | N-[(1R)-1-[6-[1,6-dihydro-1-methyl-4-(methylamino)imidazo[4,5-d]pyrrolo[2,3-b]pyridin-7-yl]-2-pyridinyl]-3-hydroxypropyl]-3-methoxy-propanamide | 1.14 | 438.29 |

Example A485

(S)-7-(6-(1-amino-4-methoxybutyl)pyridin-2-yl)-N,1-dimethyl-1,6-dihydroimidazo[4,5-d]pyrrolo[2,3-b]pyridin-4-amine

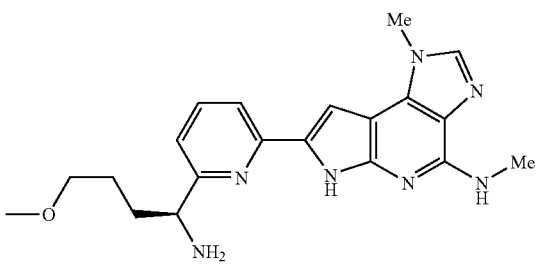

A485

A485.1: (S)-2-[(S)-1-(6-Bromo-pyridin-2-yl)-but-3-enylamino]-3-methyl-butyric acid methyl ester

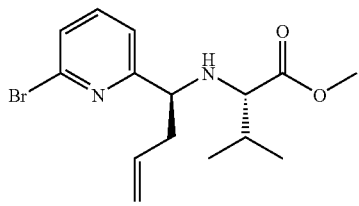

A485.1

Dimethyl zinc (2.0M in toluene, 25.5 mL, 51.0 mmol) was added to anhydrous THF (30 mL) under a nitrogen atmosphere and the solution cooled to −78° C. Allylmagnesium bromide (1.0M in diethyl ether, 51 mL, 51.0 mmol) was then added dropwise over 30 min and the solution allowed to stir at −78 C under a nitrogen atmosphere for 30 min. A solution of the imine [prepared in an analogous manner as example A469.1 substituting D-Valine methyl ester hydrochloride] (15.2 g, 51.0 mmol) in THF (60 mL) was then added dropwise to the zincate solution at −78° C. over 1 hr. The resulting reaction mixture was then allowed to stir for an additional 1 hr at −78° C. before quenching with 10% sodium hydrogen carbonate solution (200 mL) and warming to room temperature. The mixture was diluted with water (50 mL) and extracted with diethyl ether (2×200 mL), the combined organic phases were then dried (MgSO$_4$) and evaporated in vacuo and purified by column chromatography using 9:1 hexane/ethyl acetate to yield A485.1 (11.6 g).

A485.2: (S)-2-[(S)-1-(6-Bromo-pyridin-2-yl)-but-3-enylamino]-3-methyl-butan-1-ol

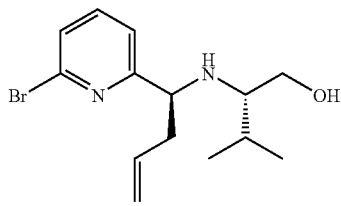

A485.2

Lithium aluminium hydride (2.0M in THF, 17.05 mL, 34.1 mmol) was added dropwise over 30 min to a cooled (−5° C.) solution of the ester A485.1 (11.6 g, 34.1 mmol) in THF (100 mL) under a nitrogen atmosphere. The reaction mixture was allowed to stir for 1 hr before quenching at −5° C. with water (1.3 mL), 15% aqeuous sodium hydroxide solution (1.3 mL) and water (3.9 mL) each added dropwise. The mixture was then allowed to warm to room temperature before filtering and washing with diethyl ether (60 mL). The filtrate was washed with water (30 mL) and the separated organic layer was dried (MgSO$_4$), evaporated in vacuo and purified by column chromatography using 3:1 hexane/ethyl acetate as eluent to yield A485.2 (5.8 g). HPLC YMC S-5 4.6×33 mm (2 min grad): retention time 1.27 min, M+H$^+$=315.16.

A485.3: (S)-1-(6-Bromo-pyridin-2-yl)-but-3-enylamine

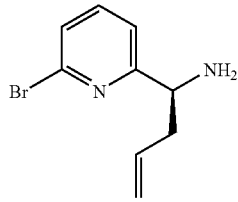

A485.3

40% Aqueous methylamine solution (22 mL) followed by periodic acid (15.26 g in 100 mL of water) were each added in one portion to a solution of the alcohol X (5.8 g, 18.59 mmol) in methanol/THF (9:1 v/v, 200 mL). The reaction mixture was stirred at room temperature for 3 hrs before adding water (90 mL). The methanol was removed in vacuo and the residue extracted with diethyl ether (3×300 mL). The combined organic layers were dried (MgSO$_4$) and evaporated in vacuo to yield A485.3 (3.5 g, 83%) which was used immediately without further purification. HPLC YMC S-5 4.6×33 mm (2 min grad): retention time 0.92 min, M+H$^+$=229.10

A485.4: [(S)-1-(6-Bromo-pyridin-2-yl)-but-3-enyl]-carbamic acid tert-butyl ester

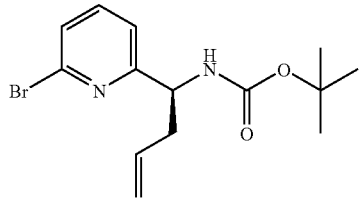

A485.4

Triethylamine (10.8 mL) and BOC-anhydride (3.6 g, 16.5 mmol) were each added in one portion to a cooled (0° C.) solution of the amine A485.3 (3.5 g, 15.5 mmol) in anhydrous dichloromethane (200 mL) under a nitrogen atmosphere. The reaction mixture was allowed to warm slowly to room temperature overnight before quenching with aqueous saturated sodium hydrogen carbonate solution (10 mL). The organic layer was dried (MgSO$_4$) and evaporated in vacuo t give a crude residue which was purified by column chromatography using 9:1 hexane/ethyl acetate as eluent to yield A485.4 (4.0 g, 79%). HPLC YMC S-5 4.6×33 mm (2 min grad): retention time HPLC YMC S-5 4.6×33 mm (2 min grad): retention time 1.95 min, M+H$^+$−Bu$^{tert}$=273.11.

A485.5: [(S)-1-(6-Bromo-pyridin-2-yl)-4-hydroxy-butyl]-carbamic acid tert-butyl ester

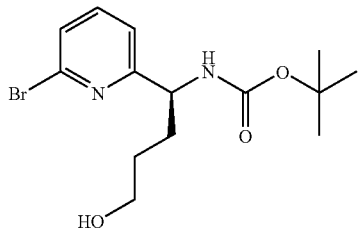

A485.5

9-BBN (0.5M in THF, 12.27 mL, 6.13 mmol) was added dropwise over 10 min to a solution of A485.4 (2.0 g, 6.13 mmol) in THF (40 mL) at room temperature under a nitrogen atmosphere. The reaction mixture was allowed to stir at room temperature for 2 hrs before cooling to 0° C. and adding hydrogen peroxide (30%, 3.1 mL) and sodium hydroxide (3M, 3.1 mL). The mixture was then heated to 50° C. for 1 hr before cooling to room temperature. The aqueous layer was separated and extracted with diethyl ether (2×30 mL), the combined organic layers dried (MgSO$_4$), evaporated in vacuo and purified by column chromatography using 1:1 hexane/ethyl acetate as eluent to give A485.5 (1.52 g). HPLC YMC S-5 4.6×33 mm, 2 min gradient; ret. Time=1.69 min, M+H$^+$–Boc=247.12

A485.6: [(S)-1-(6-Bromo-pyridin-2-yl)-4-methoxy-butyl]-carbamic acid tert-butyl ester

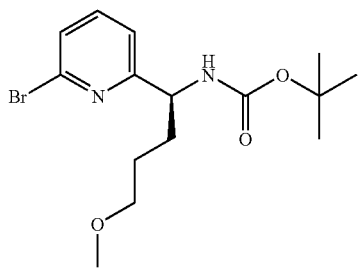

A485.6

Sodium hydride (60% dispersion in oil, 150 mg, 3.63 mmol) was added in one portion to a solution of the alcohol A485.5 (1.0 g, 2.91 mmol) in anhydrous THF (15 mL) cooled to 0° C. under a nitrogen atmosphere. The reaction mixture was stirred for 10 min before the dropwise addition of methyl iodide (0.221 mL, 2.91 mmol). The reaction mixture was allowed to warm slowly to room temperature overnight before quenching with water (5 mL) and extracting diethyl ether (2×20 mL). The combined organics were dired (MgSO$_4$), evaporatred in vacuo and purified by column chromatography using 4:1 hexane/ethyl acetate to yield A485.6 (900 mg). HPLC YMC S-5 4.6×33 mm (2 min grad): retention time 1.95 min, M+Na$^+$=383.18

A485.7: [(S)-4-Methoxy-1-(6-trimethylsilanylethynyl-pyridin-2-yl)-butyl]-carbamic acid tert-butyl ester

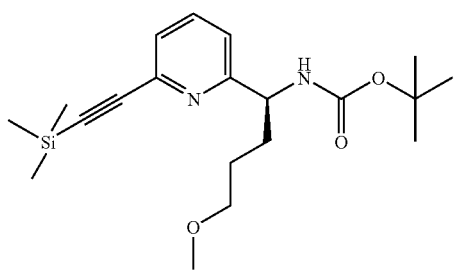

A485.7

TMS-Acetylene (0.39 mL, 2.76 mmol) was added dropwise to A485.6 (0.9 g, 2.51 mmol), CuI (24 mg, 0.13 mmol) and palladium dichlorobistriphenylphosphine palladium II (117 mg, 0.17 mmol) in triethylamine (10 mL) at room temperature under a nitrogen atmosphere. The reaction mixture was stirred at room temperature overnight before evaporating in vacuo. Diethyl ether was added (20 mL) and the salt filtered. The filtrate was evaporated in vacuo and purified by column chromatography using 4:1 hexane:ethyl acetate to yield A485.7 (1.04 g). HPLC YMC S-5 4.6×33 mm (2 min grad): retention time 2.22 min, M+H$^+$=377.36

A485.8: {6-Amino-7-[6-((S)-1-tert-butoxycarbonylamino-4-methoxy-butyl)-pyridin-2-ylethynyl]-1-methyl-1H-imidazo[4,5-c]pyridin-4-yl}-methyl-carbamic acid tert-butyl ester

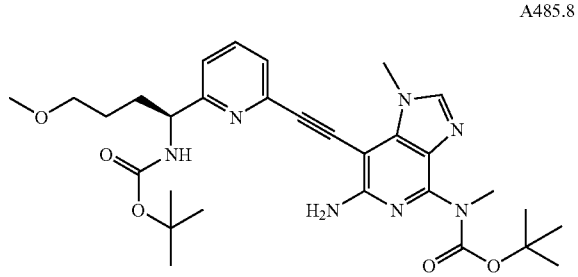

A485.8

Sodium hydroxide (2N, 2.8 mL) was added in one portion to the TMS-acetylene A485.7 (1.04, 2.77 mmol) in THF (20 mL) at room temperature. After stirring for 1 hr, the reaction mixture was diluted with water (20 mL) and extracted with diethyl ether (2×30 mL). The combined organics were dried (MgSO₄), evaporated in vacuo and purified by column chromatography using 4:1 hexane:ethyl acetate as eluent to yield [(S)-1-(6-Ethynyl-pyridin-2-yl)-4-methoxy-butyl]-carbamic acid tert-butyl ester (667 mg, 79%).

A1.12 (804 mg, 1.99 mmol), dichlorobis(triphenylphosphine)palladium (93 mg, 0.14 mmol), [(S)-1-(6-Ethynyl-pyridin-2-yl)-4-methoxy-butyl]-carbamic acid tert-butyl ester (667 mg, 2.19 mmol) and diisopropylamine (7 mL) were each added to N,N-dimethylformamide (5 mL) and nitrogen bubbled through the resulting mixture for 5 min. The reaction mixture was heated at 95° C. for 20 min under a nitrogen atmosphere before cooling to room temperature and evaporating the solvent in vacuo. The residue was purified by silica gel column chromatography using ethyl acetate as eluent to provide 1.09 g of A485.8. HPLC YMC S-5 4.6×33 mm (2 min grad): retention time 3.45 min, M+H⁺=580.25

A485.9: [7-[6-((S)-1-tert-Butoxycarbonylamino-4-methoxy-butyl)-pyridin-2-ylethynyl]-1-methyl-6-(2,2,2-trifluoro-acetylamino)-1H-imidazo[4,5-c]pyridin-4-yl]-methyl-carbamic acid tert-butyl ester

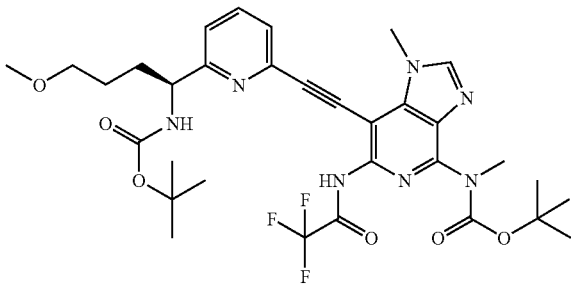

A485.9

Trifluoroacetic anhydride (0.52 mL, 3.77 mmol) was added dropwise over 5 min to a cooled (0 C) solution of aminopyridine A485.8 (1.09 mg, 1.88 mmol) and triethylamine (0.79 mL, 5.64 mmol) in THF (30 mL) under a nitrogen atmosphere. The cooling bath was removed after 10 min and the reaction mixture allowed to stir at room temperature for 1 hr before evaporating in vacuo. The residue was taken up in dichloromethane (50 mL) and washed with saturated sodium bicarbonate solution (25 mL). The organic layer was separated and dried (MgSO₄), then evaporated in vacuo to yield the crude product A485.9 which was used immediately without further purification (1.23 g). HPLC YMC S-5 4.6×33 mm (2 min grad): retention time 3.52 min, M+H⁺=676.30

A485.10: (S)-7-(6-(1-tert-butyloxycarbonylamino-4-methoxybutyl)pyridin-2-yl)-N,1-dimethyl-1,6-dihydroimidazo[4,5-d]pyrrolo[2,3-b]pyridin-4-tert-butyloxycarbonylamine

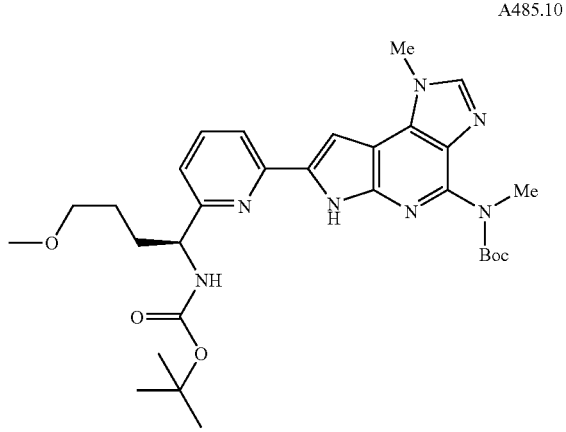

A485.10

Potassium carbonate (280 mg, 2.0 mmol) and dichlorobis-triphenylphosphine palladium II (80 mg, 0.109 mmol) were each added in one portion to a solution of the trifluoroacetamide A485.9 (1.23 g, 1.82 mmol) in dimethylacetamide (20 mL) at room temperature under a nitrogen atmosphere. The reaction was heated to 120° C. for 3 hrs before evaporating in vacuo and purifying by column chromatography using ethyl acetate to yield A485.10 (809 mg). HPLC YMC S-5 4.6×33 mm (2 min grad): retention time 3.45 min, M+H⁺=580.25

A485.11: (S)-7-(6-(1-amino-4-methoxybutyl)pyridin-2-yl)-N,1-dimethyl-1,6-dihydroimidazo[4,5-d]pyrrolo[2,3-b]pyridin-4-amine Trifluoroacetic acid in dichloromethane (20% solution, 10 mL) was added in one portion to A485.10 (809 mg) and the resulting reaction mixture was stirred at room temperatuire for 1 hr before evaporating in vacuo. The residue was partitioned between ethyl acetate (5 mL) and saturated sodium hydrogen carbonate solution (5 mL). The aqueous phase was extracted with ethyl acetate (2×10 mL) and the combined organics were dried (MgSO₄) and evaporated in vacuo to yield A485 (530 mg) as a tan powder. HPLC YMC S-5 4.6×33 mm (2 min grad): retention time 1.073 min, M+H⁺=380.47

Amine A485 was reacted with carboxylic acids in an analogous amide formation procedure to prepare compounds in Table A20.

TABLE A20

| Ex. | R | Name | HPLC Retention (min) | MS Reported |
|---|---|---|---|---|
| A486 | CH₃— | (S)-N-(4-methoxy-1-(6-(1-methyl-4-(methylamino)-1,6-dihydroimidazo[4,5-d]pyrrolo[2,3-b]pyridin-7-yl)pyridin-2-yl)butyl)acetamide | 1.45 | 422.34 |
| A487 | 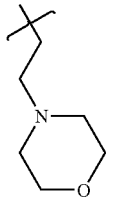 | (S)-2-methoxy-N-(4-methoxy-1-(6-(1-methyl-4-(methylamino)-1,6-dihydroimidazo[4,5-d]pyrrolo[2,3-b]pyridin-7-yl)pyridin-2-yl)butyl)acetamide | 1.46 | 452.32 |
| A488 | 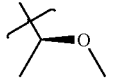 | (S)-N-(4-methoxy-1-(6-(1-methyl-4-(methylamino)-1,6-dihydroimidazo[4,5-d]pyrrolo[2,3-b]pyridin-7-yl)pyridin-2-yl)butyl)-3-morpholinopropanamide | 1.39 | 521.33 |
| A489 |  | (S)-2-methoxy-N-((S)-4-methoxy-1-(6-(1-methyl-4-(methylamino)-1,6-dihydroimidazo[4,5-d]pyrrolo[2,3-b]pyridin-7-yl)pyridin-2-yl)butyl)propanamide | 1.51 | 466.34 |
| A490 | 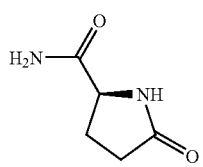 | (S)-2-cyano-N-(4-methoxy-1-(6-(1-methyl-4-(methylamino)-1,6-dihydroimidazo[4,5-d]pyrrolo[2,3-b]pyridin-7-yl)pyridin-2-yl)butyl)acetamide | 1.45 | 447.32 |
| A491 | 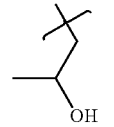 | (S)-N-((S)-4-methoxy-1-(6-(1-methyl-4-(methylamino)-1,6-dihydroimidazo[4,5-d]pyrrolo[2,3-b]pyridin-7-yl)pyridin-2-yl)butyl)-5-oxopyrrolidine-2-carboxamide | 1.39 | 491.28 |
| A492 |  | 3-hydroxy-N-((S)-4-methoxy-1-(6-(1-methyl-4-(methylamino)-1,6-dihydroimidazo[4,5-d]pyrrolo[2,3-b]pyridin-7-yl)pyridin-2-yl)butyl)butanamide | 1.40 | 466.34 |

TABLE A20-continued

| Ex. | R | Name | HPLC Retention (min) | MS Reported |
|---|---|---|---|---|
| A493 | ⋯OH (isobutyl, OH) | (S)-2-hydroxy-N-((S)-4-methoxy-1-(6-(1-methyl-4-(methylamino)-1,6-dihydroimidazo[4,5-d]pyrrolo[2,3-b]pyridin-7-yl)pyridin-2-yl)butyl)-3-methylbutanamide | 1.52 | 480.34 |
| A494 | 2-pyridyl | (S)-N-(4-methoxy-1-(6-(1-methyl-4-(methylamino)-1,6-dihydroimidazo[4,5-d]pyrrolo[2,3-b]pyridin-7-yl)pyridin-2-yl)butyl)picolinamide | 1.55 | 485.27 |
| A495 | NHAc (isobutyl, NHAc) | 2-acetamido-N-((S)-4-methoxy-1-(6-(1-methyl-4-(methylamino)-1,6-dihydroimidazo[4,5-d]pyrrolo[2,3-b]pyridin-7-yl)pyridin-2-yl)butyl)-3-methylbutanamide | 1.47 | 521.34 |
| A496 | 1-acetyl-4-hydroxypyrrolidin-2-yl | 1-acetyl-4-hydroxy-N-((S)-4-methoxy-1-(6-(1-methyl-4-(methylamino)-1,6-dihydroimidazo[4,5-d]pyrrolo[2,3-b]pyridin-7-yl)pyridin-2-yl)butyl)pyrrolidine-2-carboxamide | 1.30 | 535.31 |
| A497 | CH2NMe2 | (S)-2-(dimethylamino)-N-(4-methoxy-1-(6-(1-methyl-4-(methylamino)-1,6-dihydroimidazo[4,5-d]pyrrolo[2,3-b]pyridin-7-yl)pyridin-2-yl)butyl)acetamide | 1.35 | 465.36 |
| A498 | 2-pyrazinyl | (S)-N-(4-methoxy-1-(6-(1-methyl-4-(methylamino)-1,6-dihydroimidazo[4,5-d]pyrrolo[2,3-b]pyridin-7-yl)pyridin-2-yl)butyl)pyrazine-2-carboxamide | 1.47 | 486.28 |
| A499 | CH(OH)CH2CH(CH3)2 | 2-hydroxy-N-((S)-4-methoxy-1-(6-(1-methyl-4-(methylamino)-1,6-dihydroimidazo[4,5-d]pyrrolo[2,3-b]pyridin-7-yl)pyridin-2-yl)butyl)-4-methylpentanamide | 1.49 | 494.32 |

TABLE A20-continued

| Ex. | R | Name | HPLC Retention (min) | MS Reported |
|---|---|---|---|---|
| A500 | (HO, Cl-phenyl) | (S)-3-chloro-2-hydroxy-N-(4-methoxy-1-(6-(1-methyl-4-(methylamino)-1,6-dihydroimidazo[4,5-d]pyrrolo[2,3-b]pyridin-7-yl)pyridin-2-yl)butyl)benzamide | 1.82 | 534.25 |
| A501 | (1-methylimidazol-4-yl)methyl | (S)-N-(4-methoxy-1-(6-(1-methyl-4-(methylamino)-1,6-dihydroimidazo[4,5-d]pyrrolo[2,3-b]pyridin-7-yl)pyridin-2-yl)butyl)-2-(1-methyl-1H-imidazol-4-yl)acetamide | 1.35 | 502.32 |

Examples A502–A511

Examples A502–A511 was prepared in a manner similar to example A1. Thus intermediate A1.12 was subjected to a what is commonly referred to as a Sonoghasira type coupling (as described in detail for the preparation of A1.13, and conducted in a similar manner) with acetylenes which are either commercially available, or readily prepared (as described for step A2.1 and A2.2). The acetylene were cyclized to the examples in Table A2 in a manner described in detail in step A1.14

TABLE A21

| Ex. | R | Name | HPLC Retention (min) | MS Reported |
|---|---|---|---|---|
| A502 | 2-fluorophenyl | 7-(2-fluorophenyl)-1,6-dihydro-N,1-dimethyl-imidazo[4,5-d]pyrrolo[2,3-b]pyridin-4-amine | 2.28 | 296.25 |
| A503 | cyclopropyl | 7-cyclopropyl-1,6-dihydro-N,1-dimethyl-imidazo[4,5-d]pyrrolo[2,3-b]pyridin-4-amine | 1.72 | 242.33 |

TABLE A21-continued

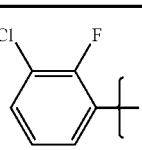

| Ex. | R | Name | HPLC Retention (min) | MS Reported |
|---|---|---|---|---|
| A504 | 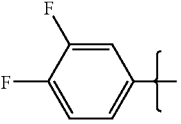 | 7-(3-chloro-2-fluorophenyl)-1,6-dihydro-N,1-dimethyl-imidazo[4,5-d]pyrrolo[2,3-b]pyridin-4-amine | 2.65 | 330.26 |
| A505 | 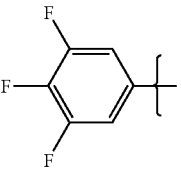 | 7-(3,4-difluorophenyl)-1,6-dihydro-N,1-dimethyl-imidazo[4,5-d]pyrrolo[2,3-b]pyridin-4-amine | 2.59 | 314.29 |
| A506 | 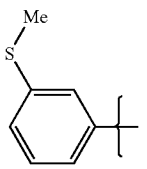 | 1,6-dihydro-N,1-dimethyl-7-(3,4,5-trifluorophenyl)-imidazo[4,5-d]pyrrolo[2,3-b]pyridin-4-amine | 2.82 | 332.32 |
| A507 | 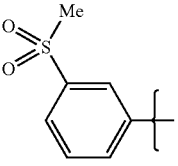 | 1,6-dihydro-N,1-dimethyl-7-[3-(methylthio)phenyl]-imidazo[4,5-d]pyrrolo[2,3-b]pyridin-4-amine | 2.71 | 324.33 |
| A508 | 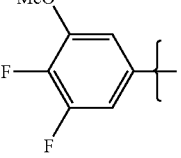 | 1,6-dihydro-N,1-dimethyl-7-[3-(methylsulfonyl)phenyl]-imidazo[4,5-d]pyrrolo[2,3-b]pyridin-4-amine | 2.04 | 356.35 |
| A509 | 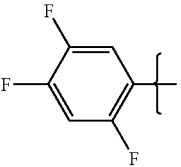 | 7-(3,4-difluoro-5-methoxyphenyl)-1,6-dihydro-N,1-dimethyl-imidazo[4,5-d]pyrrolo[2,3-b]pyridin-4-amine | 2.72 | 344.28 |
| A510 |  | 1,6-dihydro-N,1-dimethyl-7-(2,4,5-trifluorophenyl)-imidazo[4,5-d]pyrrolo[2,3-b]pyridin-4-amine | 2.59 | 332.32 |

TABLE A21-continued

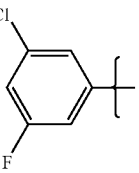

| Ex. | R | Name | HPLC Retention (min) | MS Reported |
|---|---|---|---|---|
| A511 | 3-chloro-5-fluorophenyl | 7-(3-chloro-5-fluorophenyl)-1,6-dihydro-N,1-dimethyl-imidazo[4,5-d]pyrrolo[2,3-b]pyridin-4-amine | 2.99 | 330.25 |

Example A512

1,6-dihydro-N,1-dimethyl-7-[3-(methylsulfinyl)phenyl]-imidazo[4,5-d]pyrrolo[2,3-b]pyridin-4-amine

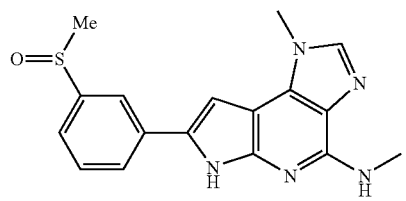
A512

A512.1: trimethyl((3-(methylthio)phenyl)ethynyl)silane

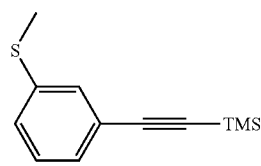
A512.1

Was prepared as described for step A2.1 HPLC: 94%, retention time: 4.303 minute (condition A). LC/MS (M+H)⁺=221.2.

A512.2: (3-ethynylphenyl)(methyl)sulfane

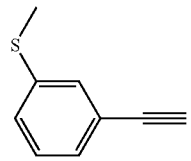

Was prepared as described in step A2.2. HPLC: 90%, retention time: 3.418 minute

A512.3: tert-butyl 6-amino-1-methyl-7-((3-(methylthio)phenyl)ethynyl)-1H-imidazo[4,5-c]pyridin-4-yl(methyl)carbamate

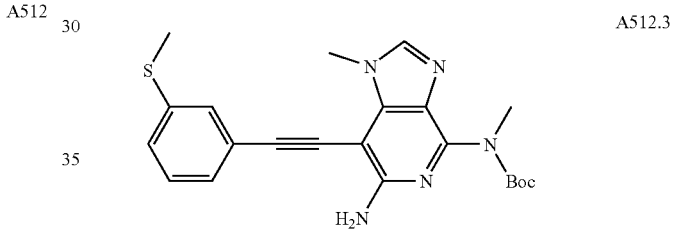
A512.3

Was prepared in a similar manner to A1.13

HPLC: 92%, retention time: 3.555 minute (condition B) LC/MS (M+H)⁺=424.3.

A512.4: tert-butyl methyl(1-methyl-7-(3-(methylthio)phenyl)-1,6-dihydroimidazo[4,5-d]pyrrolo[2,3-b]pyridin-4-yl)carbamate

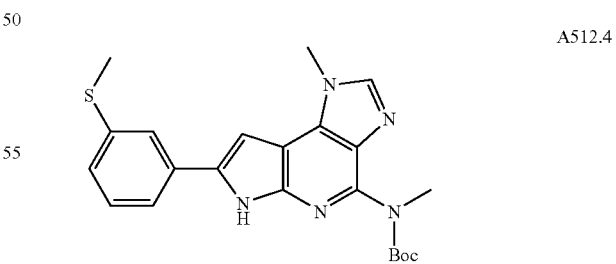
A512.4

Was prepared in a similar manner to A2.4

HPLC: 98%, retention time; (condition B) 3.371 minute LC/MS (M+H)⁺=424.4, ¹H-NMR (400 MHz, CD₃OD) δ ppm 7.90 (1 H, s), 7.57 (1 H, s), 7.43-7.48 (1 H, m), 7.39 (1 H, t, J=7.63 Hz), 7.23 (1 H, s), 7.00 (1 H, d, J=2.54 Hz), 4.15 (3 H, s), 3.52 (3 H, s), 2.56 (3 H, s), 1.46 (9 H, s).

A512.5: 1,6-dihydro-N,1-dimethyl-7-[3-(methylsulfinyl)phenyl]-imidazo[4,5-d]pyrrolo[2,3-b]pyridin-4-amine A solution of A512.4 (46 mg, 0.109 mmol) in acetic acid (0.5 ml) at 0-5° C. was added 30% $H_2O_2$ (41 uL, 0.4 mmol) and warmed up to RT. The reaction mixture was concentrated to yield a crude product which was diluted with dichloromethane (4 ml). The organic phase was washed with saturated aqueous $NaHCO_3$ solution (1 ml), water (1 ml), brine (1 ml) and the organic layer was dried over sodium sulfate. The mixture was filtered and the solvent evaporated under reduced pressure to yield a Boc protected intermediate which was dissolved in $CH_2Cl_2$ (1 ml) was added TFA (0.5 ml) dropwise at 0-5° C. which was warmed up to RT and stirred for 1 hr. The reaction mixture was concentrated and triturated with diethyl ether (~5 ml) for ~10 minutes. The solid was collected as A512. HPLC: >95%, retention time: 1.947 minute LC/MS (M+H)$^+$=340.3, $^1$H-NMR (400 MHz, $CD_3OD$) δ ppm 8.14 (1 H, s), 8.02 (1 H, s), 7.88 (1 H, d, J=7.63 Hz), 7.47-7.63 (2 H, m), 7.24 (1 H, s), 4.09 (3 H, s), 3.19 (3 H, s), 2.80 (3 H, s).

Examples A513 and A514

1,6-dihydro-N,1-dimethyl-7-[3-(methylsulfinyl)phenyl]-imidazo[4,5-d]pyrrolo[2,3-b]pyridin-4-amine

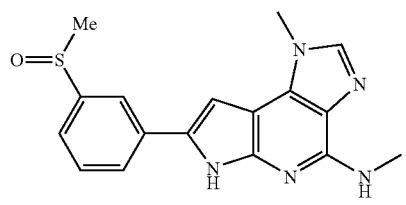

A513 faster eluting enantiomer

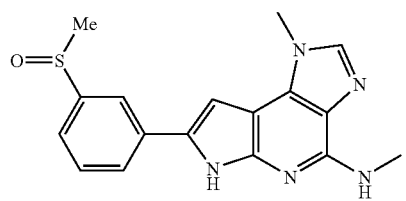

A514

Slower eluting enantiomer

A512 (43 mg, 0.095 mmol) was subjected to chiral separation to yield A513 (9.2 mg, 57%). HPLC: 98%, retention time: 1.845 minute (condition A). Chiral HPLC: 100% ee. retention time: 8.17 minute (condition H). LC/MS (M+H)$^+$=340. $^1$H NMR (400 MHz, DMSO-d6) δ ppm 8.06 (1 H, s), 7.96 (1 H, d, J=7.63 Hz), 7.89 (1 H, s), 7.55 (1 H, t, J=7.88 Hz), 7.44 (1 H, d, J=7.63 Hz), 7.22 (1 H, d, J=2.54 Hz), 6.64 (1H, d, J=5.09 Hz), 4.10 (1 H, q, J=5.26 Hz), 4.02 (3 H, s), 3.15 (1 H, d, J=5.09 Hz), 2.97 (3 H, d, J=4.58 Hz), 2.81 (3 H, s) and A514 (9 mg, 56%). HPLC: 94%, retention time: 1.873 minute (condition A). Chiral HPLC: 100% ee. retention time: 10.53 minute (condition H). LC/MS (M+H)$^+$=340. $^1$H NMR (400 MHz, DMSO-d6) δ ppm 8.06 (1 H, s), 7.96 (1 H, d, J=8.14 Hz), 7.89 (1 H, s), 7.55 (1 H, t, J=7.63 Hz), 7.41-7.47 (1 H, m), 7.22 (1 H, d, J=2.03 Hz), 6.60-6.67 (1 H, m), 4.10 (1 H, q, J=5.26 Hz), 4.02 (3 H, s), 3.15 (1 H, d, J=5.09 Hz), 2.97 (3 H, d, J=4.58 Hz), 2.81 (3 H, s).

Example A515

N-[[3-[1,6-dihydro-1-methyl-4-(methylamino)imidazo[4,5-d]pyrrolo[2,3-b]pyridin-7-yl]-5-fluorophenyl]methyl]-3-methoxy-propanamide

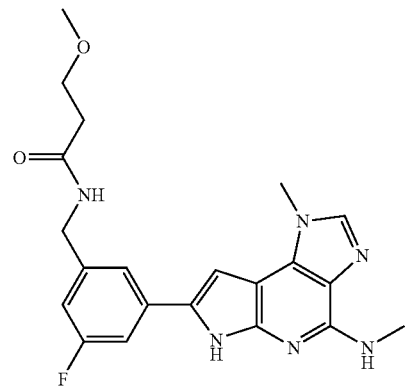

A515

3-methoxypropionic acid (7.34 uL, 0.075 mmol), HOBt (17 mg, 0.125 mmol), and diisopropylethylamine (0.148 ml) was dissolved in $CH_3CN$ (1 ml). EDCI (30 mg, 0.167 mmol) was added and the reaction mixture was stirred at RT for 5 minutes. A293.5 (30 mg, 0.071 mmol) was added and the reaction mixture heated to 80° C. for 30 minutes. The reaction mixture was concentrated and purified on prep. HPLC (condition G) to yield the Boc protected intermediate.

The intermediate was dissolved in $CH_2Cl_2$ (0.25 ml) and added TFA (0.25 ml) dropwise at 0-5° C. which was warmed up to RT and stirred for 30 minutes. The reaction mixture was concentrated to yield A515 (10 mg, 27%). HPLC: 97%, retention time: 2.190 minute (condition B). LC/MS (M+H)$^+$=411.3, $^1$H-NMR (400 MHz, $CD_3OD$) δ ppm 8.48 (1 H, s), 8.11 (1 H, s), 7.42 (1 H, s), 7.27-7.37 (1 H, m), 7.13 (1 H, s), 6.91 (1 H, d, J=7.63 Hz), 4.36 (2 H, s), 4.06 (3 H, s), 3.60 (2 H, t, J=6.10 Hz), 3.25 (3H, s), 3.16 (3 H, s), 2.43 (2 H, t, J=5.85 Hz).

Example A516

N-[[3-[1,6-dihydro-1-methyl-4-(methylamino)imidazo[4,5-d]pyrrolo[2,3-b]pyridin-7-yl]-5-fluorophenyl]methyl]-4-morpholinecarboxamide

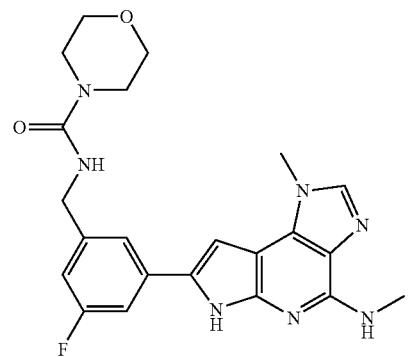

A516

A293.5 (57 mg, 0.134 mmol), 1,1'-carbonyldiimidazole (44 mg, 0.268 mmol), and triethylamine (34 mg, 0.336 mmol) were dissolved in a mixture of dichloroethane (1 ml)/DMF (0.25 ml) and stirred at RT for 30 minutes. Morpholine (0.25 ml, 2.86 mmol) was added and the reaction mixture was heated to 80° C. for 30 minutes. The solvent was concentrated under reduced pressure and the residue purified by prep. HPLC (condition G) to yield the Boc protected intermediate.

The product was dissolved in $CH_2Cl_2$ (0.5 ml) and TFA (0.5 ml) was added dropwise at 0-5° C. which was warmed up to RT and stirred for 30 minutes. The reaction mixture was concentrated under reduced pressure to yield A516 (23.3 mg, 32%). HPLC: 97%, retention time: 2.315 minute (condition B). LC/MS $(M+H)^+$=438.4, $^1$H-NMR (400 MHz, $CD_3OD$) δ ppm 8.11 (1 H, s), 7.41 (1 H, s), 7.30 (1 H, d, J=10.17 Hz), 7.12 (1 H, s), 6.89 (1 H, d, J=8.65 Hz), 4.32 (2 H, s), 4.05 (3 H, s), 3.53-3.62 (4 H, m), 3.28-3.37 (4 H, m), 3.16 (3 H, s).

Examples A517-A525

Examples A517-A525 was prepared in a manner similar to example A516.

TABLE A22

| Ex. | R | Name | HPLC Retention (min) | MS Reported |
|---|---|---|---|---|
| A517 | MeO⌒⌒HN— | N-[[3-[1,6-dihydro-1-methyl-4-(methylamino)imidazo[4,5-d]pyrrolo[2,3-b]pyridin-7-yl]-5-fluorophenyl]methyl]-N'-(2-methoxyethyl)-urea | 2.12 | 426.34 |
| A518 | HO⌒⌒HN— | N-[[3-[1,6-dihydro-1-methyl-4-(methylamino)imidazo[4,5-d]pyrrolo[2,3-b]pyridin-7-yl]-5-fluorophenyl]methyl]-N'-(2-hydroxyethyl)-urea | 2.01 | 412.32 |
| A519 | HN(piperazinyl)N— | N-[[3-[1,6-dihydro-1-methyl-4-(methylamino)imidazo[4,5-d]pyrrolo[2,3-b]pyridin-7-yl]-5-fluorophenyl]methyl]-1-piperazinecarboxamide | 1.98 | 437.39 |
| A520 | $CH_3NH$— | N-[[3-[1,6-dihydro-1-methyl-4-(methylamino)imidazo[4,5-d]pyrrolo[2,3-b]pyridin-7-yl]-5-fluorophenyl]methyl]-N'-methyl-urea | 2.18 | 382.36 |
| A521 | HO-(piperidinyl)N— | N-[[3-[1,6-dihydro-1-methyl-4-(methylamino)imidazo[4,5-d]pyrrolo[2,3-b]pyridin-7-yl]-5-fluorophenyl]methyl]-4-hydroxy-1-piperidinecarboxamide | 2.14 | 452.38 |
| A522 | NC⌒⌒N(Me)— | N-(2-cyanoethyl)-N'-[[3-[1,6-dihydro-1-methyl-4-(methylamino)imidazo[4,5-d]pyrrolo[2,3-b]pyridin-7-yl]-5-fluorophenyl]methyl]-N-methyl-urea | 2.12 | 435.36 |
| A523 | MeO⌒⌒N(Me)— | N'-[[3-[1,6-dihydro-1-methyl-4-(methylamino)imidazo[4,5-d]pyrrolo[2,3-b]pyridin-7-yl]-5-fluorophenyl]methyl]-N-(2-methoxyethyl)-N-methyl-urea | 2.30 | 440.37 |

TABLE A22-continued

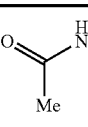

| Ex. | R | Name | HPLC Retention (min) | MS Reported |
|---|---|---|---|---|
| A524 | (acetylamino-pyrrolidine group) | 3-(acetylamino)-N-[[3-[1,6-dihydro-1-methyl-4-(methylamino)imidazo[4,5-d]pyrrolo[2,3-b]pyridin-7-yl]-5-fluorophenyl]methyl]-1-pyrrolidinecarboxamide | 2.09 | 479.33 |
| A525 | (3-hydroxypyrrolidine group) | N-[[3-[1,6-dihydro-1-methyl-4-(methylamino)imidazo[4,5-d]pyrrolo[2,3-b]pyridin-7-yl]-5-fluorophenyl]methyl]-3-hydroxy-1-pyrrolidinecarboxamide | 2.08 | 485.35 |

Examples A526–A528

Examples A526 was prepared in a manner similar to example A515. Examples A527 (retention time: 5.99 minute) and A528 (retention time: 13.5 minute) were separated by chiral chromatography of A526. Chiral HPLC: Column ChiralCEL OD 10 um 4.6×250 mm; Percent B=35% Isocratic; Flow rate=2 ml/min; Solvent A=$CO_2$; Solvent B MeOH—0.1% DEA.

TABLE A23

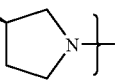

| Ex. | R | Name | HPLC Retention (min) | MS Reported |
|---|---|---|---|---|
| A526 | (racemic morpholine) | Racemic-N-[[3-[1,6-dihydro-1-methyl-4-(methylamino)imidazo[4,5-d]pyrrolo[2,3-b]pyridin-7-yl]-5-fluorophenyl]methyl]-3-morpholinecarboxamide | 1.62 | 438 |

TABLE A23-continued

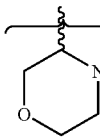

| Ex. | R | Name | HPLC Retention (min) | MS Reported |
|---|---|---|---|---|
| A527 | (morpholine *) | N-[[3-[1,6-dihydro-1-methyl-4-(methylamino)imidazo[4,5-d]pyrrolo[2,3-b]pyridin-7-yl]-5-fluorophenyl]methyl]-3-morpholinecarboxamide-faster eluting enantiomer | 1.67 | 438 |
| A528 | (morpholine *) | N-[[3-[1,6-dihydro-1-methyl-4-(methylamino)imidazo[4,5-d]pyrrolo[2,3-b]pyridin-7-yl]-5-fluorophenyl]methyl]-3-morpholinecarboxamide-slower eluting enantiomer | 1.67 | 438 |

Example A529

N''-cyano-N-[[3-[1,6-dihydro-1-methyl-4-(methylamino)imidazo[4,5-d]pyrrolo[2,3-b]pyridin-7-yl]-5-fluorophenyl]methyl]-N'-methyl-guanidine

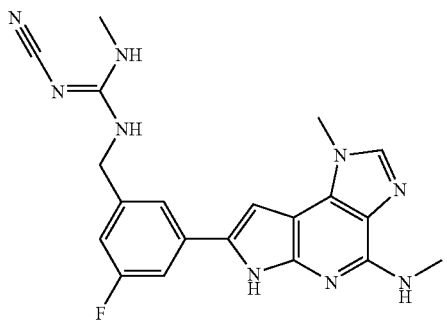

A529

A solution of A293 (32.5 mg, 0.059 mmol), triethylamine (9 uL, 0.065 mmol) and phenyl cyanocarbonimidate (14.3 mg, 0.06 mmol) in ethanol (1 ml) was heated to 100° C. for 10 minutes under microwave. Methylamine (0.185 ml, 0.37 mmol, 2M in THF)) was added and then it was heated to 120° C. for 15 minutes under microwave. The solid was collected as A529 (13.8 mg, 58%), HPLC: 95%, retention time: 2.322 minute (condition B). LC/MS (M+H)$^+$=406, $^1$H-NMR (400 MHz, CD$_3$OD) δ ppm 7.76 (1 H, s), 7.39 (1 H, s), 7.29 (1 H, d, J=10.17 Hz), 6.96 (1 H, s), 6.76 (1 H, d, J=8.14 Hz), 4.36 (2 H, s), 3.98 (3 H, s), 3.01 (3 H, s), 2.74 (3 H, s).

Examples A530-537

Examples A530-A537 was prepared in a manner similar to example A529.

TABLE A24

| Ex. | R | Name | HPLC Retention (min) | MS Reported |
|---|---|---|---|---|
| A530 | morpholinyl-N- | N'-cyano-N-[[3-[1,6-dihydro-1-methyl-4-(methylamino)imidazo[4,5-d]pyrrolo[2,3-b]pyridin-7-yl]-5-fluorophenyl]methyl]-4-morpholinecarboximidamide | 2.44 | 462.34 |
| A531 | MeO-CH$_2$CH$_2$-HN- | N''-cyano-N-[[3-[1,6-dihydro-1-methyl-4-(methylamino)imidazo[4,5-d]pyrrolo[2,3-b]pyridin-7-yl]-5-fluorophenyl]methyl]-N'-(2-methoxyethyl)-guanidine | 2.45 | 450.29 |
| A532 | MeO-CH$_2$CH$_2$-N(Me)- | N''-cyano-N'-[[3-[1,6-dihydro-1-methyl-4-(methylamino)imidazo[4,5-d]pyrrolo[2,3-b]pyridin-7-yl]-5-fluorophenyl]methyl]-N-(2-(methoxyethyl)-N-methyl-guanidine | 2.49 | 464.34 |
| A533 | MeC(O)NH-pyrrolidinyl- | N-[1-[(E)-(cyanoimino)[[[3-[1,6-dihydro-1-methyl-4-(methylamino)imidazo[4,5-d]pyrrolo[2,3-b]pyridin-7-yl]-5-fluorophenyl]methyl]amino]methyl]-3-pyrrolidinyl]-acetamide | 2.34 | 503.34 |

TABLE A24-continued

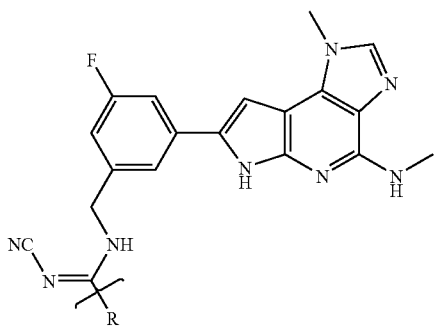

| Ex. | R | Name | HPLC Retention (min) | MS Reported |
|---|---|---|---|---|
| A534 | HO-piperidine-N- | N'-cyano-N-[[3-[1,6-dihydro-1-methyl-4-(methylamino)imidazo[4,5-d]pyrrolo[2,3-b]pyridin-7-yl]-5-fluorophenyl]methyl]-4-hydroxy-1-piperidinecarboximidamide | 2.34 | 476.36 |
| A535 | HO-CH2CH2-HN- | N''-cyano-N-[[3-[1,6-dihydro-1-methyl-4-(methylamino)imidazo[4,5-d]pyrrolo[2,3-b]pyridin-7-yl]-5-fluorophenyl]methyl]-N'-(2-hydroxyethyl)-guanidine | 2.30 | 436.36 |
| A536 | Me-N(piperazine)N- | N'-cyano-N-[[3-[1,6-dihydro-1-methyl-4-(methylamino)imidazo[4,5-d]pyrrolo[2,3-b]pyridin-7-yl]-5-fluorophenyl]methyl]-4-methyl-1-piperazinecarboximidamide | 2.09 | 475.36 |
| A537 | cyclopropyl-HN- | N''-cyano-N-cyclopropyl-N'-[[3-[1,6-dihydro-1-methyl-4-(methylamino)imidazo[4,5-d]pyrrolo[2,3-b]pyridin-7-yl]-5-fluorophenyl]methyl]-guanidine | 2.46 | 432.35 |

Examples A538-540

Examples A538-A540 was prepared in a manner similar to example A529 starting with A215.

TABLE A25

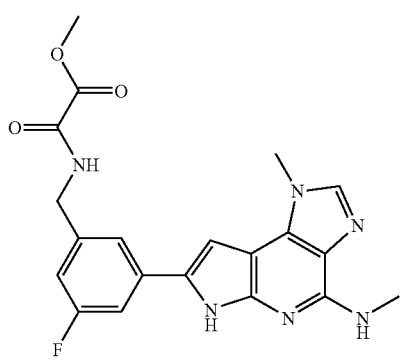

| Ex. | R | Name | HPLC Retention (min) | MS Reported |
|---|---|---|---|---|
| A538 | (morpholine group) | N'-cyano-N-[[6-[1,6-dihydro-1-methyl-4-(methylamino)imidazo[4,5-d]pyrrolo[2,3-b]pyridin-7-yl]-2-pyridinyl]methyl]-4-morpholinecarboximidamide | 1.94 | 445.28 |
| A539 | (cyclopropyl-HN) | N''-cyano-N-cyclopropyl-N'-[[6-[1,6-dihydro-1-methyl-4-(methylamino)imidazo[4,5-d]pyrrolo[2,3-b]pyridin-7-yl]-2-pyridinyl]methyl]-guanidine | 2.00 | 415.29 |
| A540 | HO-CH2CH2-HN | N''-cyano-N-[[6-[1,6-dihydro-1-methyl-4-(methylamino)imidazo[4,5-d]pyrrolo[2,3-b]pyridin-7-yl]-2-pyridinyl]methyl]-N'-(2-hydroxyethyl)-guanidine | 1.90 | 419.30 |

A541

[[[3-[1,6-dihydro-1-methyl-4-(methylamino)imidazo[4,5-d]pyrrolo[2,3-b]pyridin-7-yl]-5-fluorophenyl]methyl]amino]oxo-acetic acid, methyl ester

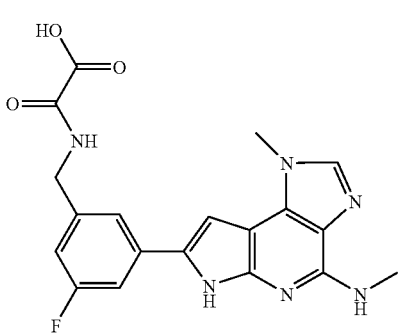

A541.1: Methyl 2-(3-(4-(tert-butoxycarbonyl(methyl)amino)-1-methyl-1,6-dihydroimidazo[4,5-d]pyrrolo[2,3-b]pyridin-7-yl)-5-fluorobenzylamino)-2-oxoacetate

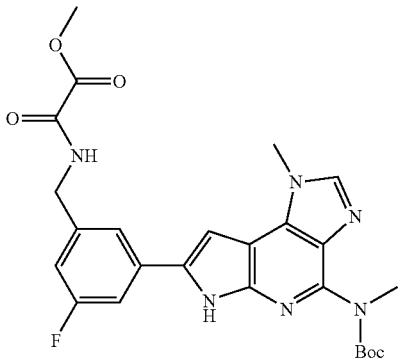

A solution of A293.5 (85 mg, 0.2 mmol) and triethylamine (35 uL, 0.25 mmol) in dichloromethane (2 mL) at 0-5° C. was added methyl chlorooxoacetate (20 uL, 0.22 mmol) and the reaction mixture was warmed up to room temperature and stirred for 30 minutes. The reaction mixture was concentrated and purified on silica gel column with $CH_2Cl_2$/MeOH (20/1) to yield A541.1 (78 mg, 76%). HPLC: 98%, retention time: 2.633 minute (condition B). LC/MS (M+H)$^+$=511, $^1$H-NMR (400 MHz, CDCl$_3$) δ ppm 7.95 (1 H, s), 7.82 (1 H, s), 7.42 (1 H, s), 7.22-7.32 (1 H, m), 6.90-7.06 (1 H, m), 6.90-7.02 (2 H, m), 4.59 (2 H, d, J=6.10 Hz), 4.11 (3 H, s), 3.88-4.00 (3 H, m), 3.52 (3 H, s).

A541.2: [[[3-[1,6-dihydro-1-methyl-4-(methylamino)imidazo[4,5-d]pyrrolo[2,3-b]pyridin-7-yl]-5-fluorophenyl]methyl]amino]oxo-acetic acid, methyl ester A541 was prepared in a similar manner as described for step A2.5. HPLC: 99%, retention time: 2.283 minute (condition B). LC/MS (M+H)$^+$=411, $^1$H-NMR (400 MHz, CD$_3$OD) δ ppm 8.15 (1 H, s), 7.47 (1 H, s), 7.39 (1 H, s), 7.17 (1 H, s), 6.96 (1 H, s), 4.42-4.49 (2 H, m), 4.08 (3 H, s), 3.82 (3 H, s), 3.19 (3 H, s).

Example A542

[[[3-[1,6-dihydro-1-methyl-4-(methylamino)imidazo[4,5-d]pyrrolo[2,3-b]pyridin-7-yl]-5-fluorophenyl]methyl]amino]oxo-acetic acid

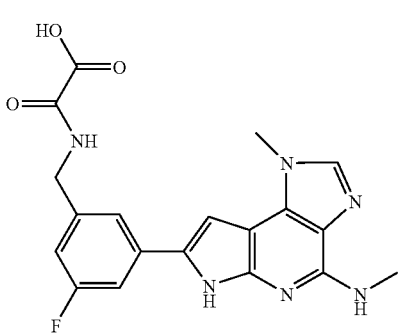

A542.1: 2-(3-(4-(tert-butoxycarbonyl(methyl) amino)-1-methyl-1,6-dihydroimidazo[4,5-d]pyrrolo [2,3-b]pyridin-7-yl)-5-fluorobenzylamino)-2-oxoacetic acid

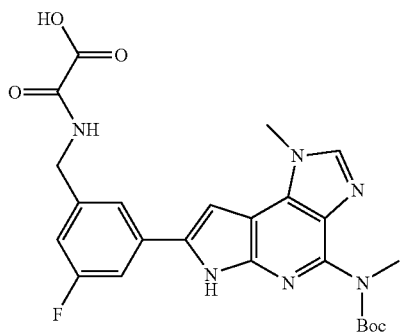

A542.1

A solution of A541.1 (67.2 mg, 0.134 mmol) and 1N NaOH (0.28 ml, 0.28 mmol) in MeOH (2.8 ml) was heated to 100° C. for 15 minutes under micromave and the reaction mixture was concentrated to yield a crude product. It was added water (1 ml) and acidified with 1N HCl solution until PH about 2 at 0-5° C. The solid was collected as A542.1 (60.5 mg, 93%). HPLC: 97%, retention time: 2.558 minute (condition B). LC/MS (M+H)$^+$=497, $^1$H-NMR (400 MHz, CD$_3$OD) δ ppm 8.26 (1H, s), 7.68 (1 H, s), 7.56 (1 H, d, J=10.68 Hz), 7.34 (1 H, s), 7.06 (1 H, s), 4.53 (2 H, s), 4.22 (3 H, s), 3.40 (3 H, s), 1.39 (9 H, s).

A542.2: [[[3-[1,6-dihydro-1-methyl-4-(methylamino)imidazo[4,5-d]pyrrolo[2,3-b]pyridin-7-yl]-5-fluorophenyl]methyl]amino]oxo-acetic acid A solution of A542.1 (10 mg, 0.02 mmol) in CH$_2$Cl$_2$ (0.25 ml) was added TFA (0.25 ml) dropwise at 0-5° C. which was warmed up to RT and stirred for 10 minutes. The reaction mixture was concentrated to yield A542 (9.6 mg, 93%). HPLC: >85%, retention time: 2.025 minute (condition B). LC/MS (M+H)$^+$=397, $^1$H-NMR (400 MHz, DMSO-d6) δ ppm 12.09 (1 H, s), 9.33-9.46 (1 H, m), 8.40 (1 H, s), 7.52-7.69 (3 H, m), 7.28 (1 H, s), 6.85-6.99 (1 H, m), 4.37 (2 H, d, J=6.10 Hz), 4.09 (3 H, s), 3.04 (3 H, s).

Example A543

N-cyclopropyl-N'-[[3-[1,6-dihydro-1-methyl-4-(methylamino)imidazo[4,5-d]pyrrolo[2,3-b]pyridin-7-yl]-5-fluorophenyl]methyl]-ethanediamide

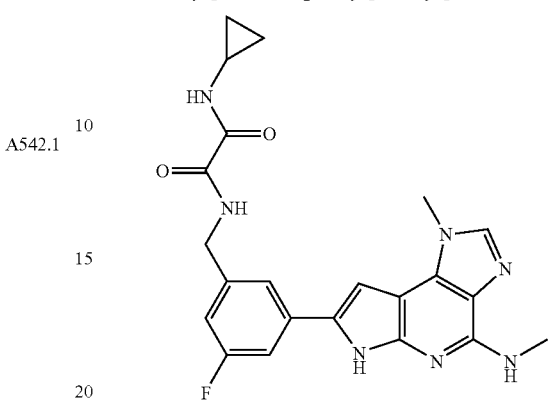

A543

A solution of A542.1 (10 mg, 0.02 mmol), HOBt (4.86 mg, 0.036 mmol), diisopropylethylamine (0.042 ml) in CH$_3$CN (1 ml) was added EDCI (9 mg, 0.047 mmol) and then the reaction mixture was stirred at RT for 5 minutes. It was added cyclopropylamine (1.26 mg, 0.022 mmol) and heated to 80° C. for 30 minutes. The reaction mixture was concentrated and purified on prep. HPLC (condition G) to yield a product.

The product was dissolved in CH$_2$Cl$_2$ (0.25 ml) and added TFA (0.25 ml) dropwise at 0-5° C. which was warmed up to RT and stirred for 30 minutes. The reaction mixture was concentrated to yield A543 (6.6 mg, 60%). HPLC: >98%, retention time: 2.220 minute (condition B). LC/MS (M+H)$^+$=436, $^1$ H-NMR (400 MHz, DMSO-d6) δ ppm 12.04 (1 H, s), 9.25-9.39 (1 H, m), 8.82 (1 H, d, J=5.09 Hz), 8.33 (1 H, s), 7.51-7.69 (2 H, m), 7.25 (1 H, s), 6.89 (1 H, s), 4.35 (2 H, d, J=6.61 Hz), 4.08 (3 H, s), 3.02 (3 H, s), 2.76 (1 H, dd, J=16.79, 5.09 Hz), 0.53-0.72 (4 H, m)

Examples A544-A546

Examples A544-A546 was prepared in a manner similar to example 543 using the appropriate amine.

TABLE A26

| Ex. | R | Name | HPLC Retention (min) | MS Reported |
|---|---|---|---|---|
| A544 | (morpholine) | N-[[3-[1,6-dihydro-1-methyl-4-(methylamino)imidazo[4,5-d]pyrrolo[2,3-b]pyridin-7-yl]-5-fluorophenyl]methyl]-alpha-oxo-4-morpholineacetamide | 2.86 | 466.31 |

TABLE A26-continued

| Ex. | R | Name | HPLC Retention (min) | MS Reported |
|---|---|---|---|---|
| A545 | (piperazinyl) | N-[[3-[1,6-dihydro-1-methyl-4-(methylamino)imidazo[4,5-d]pyrrolo[2,3-b]pyridin-7-yl]-5-fluorophenyl]methyl]-alpha-oxo-1-piperazineacetamide | 1.97 | 465.30 |
| A546 | HO-CH2CH2-NH- | N-[[3-[1,6-dihydro-1-methyl-4-(methylamino)imidazo[4,5-d]pyrrolo[2,3-b]pyridin-7-yl]-5-fluorophenyl]methyl]-N'-(2-hydroxyethyl)-ethanediamide | 1.90 | 419.30 |

Examples A547-A50

Examples A547-A50 was prepared in a manner similar to example A529 starting with A215.

TABLE A27

| Ex. | R | Name | HPLC Retention (min) | MS Reported |
|---|---|---|---|---|
| A547 | CH₃NH— | N''-cyano-N-[[6-[1,6-dihydro-1-methyl-4-(methylamino)imidazo[4,5-d]pyrrolo[2,3-b]pyridin-7-yl]-2-pyridinyl]methyl]-N'-methyl-guanidine | 1.96 | 389.31 |
| A548 | HO-CH(Me)-CH2-HN— | N''-cyano-N-[[6-[1,6-dihydro-1-methyl-4-(methylamino)imidazo[4,5-d]pyrrolo[2,3-b]pyridin-7-yl]-2-pyridinyl]methyl]-N'-(2-hydroxypropyl)-guanidine | 2.06 | 433.32 |
| A549 | MeO-CH2CH2-HN— | N''-cyano-N-[[6-[1,6-dihydro-1-methyl-4-(methylamino)imidazo[4,5-d]pyrrolo[2,3-b]pyridin-7-yl]-2-pyridinyl]methyl]-N'-(2-methoxyethyl)-guanidine | 2.12 | 433.32 |

TABLE A27-continued

| Ex. | R | Name | HPLC Retention (min) | MS Reported |
|---|---|---|---|---|
| A550 | HO-CH2-CH(OH)-CH2-HN- | N''-cyano-N-[[6-[1,6-dihydro-1-methyl-4-(methylamino)imidazo[4,5-d]pyrrolo[2,3-b]pyridin-7-yl]-2-pyridinyl]methyl]-N'-(2,3-dihydroxypropyl)-guanidine | 2.06 | 449.28 |

Example A551

N-[(1E)-[[[3-[1,6-dihydro-1-methyl-4-(methylamino)imidazo[4,5-d]pyrrolo[2,3-b]pyridin-7-yl]-5-fluorophenyl]methyl]amino][(2-methoxyethyl)amino]methylene]-urea

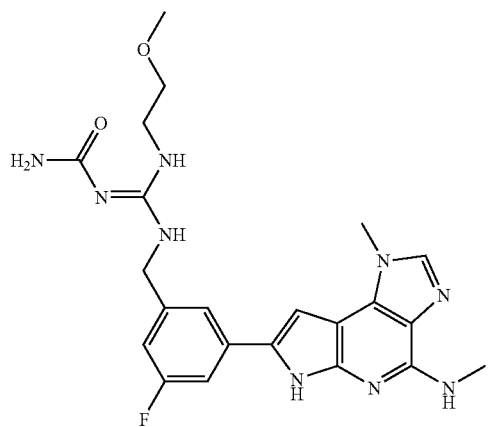

A551

A solution of A293.3 (30 mg, 0.071 mmol) and phenyl cyanocarbonimidate (17.4 mg, 0.071 mmol) in n-butanol (1 ml) was heated to 100° C. for 10 minutes under micromave. A portion of 2-methoxyethylamine (200 uL) was added and then it was heated to 120° C. for 15 minutes under microwave. The reaction mixture was concentrated and puritfied on prep. HPLC (condition G) to yield the Boc protected intermediate which was dissolved in CH$_2$Cl$_2$ (0.25 ml) and added TFA (0.25 ml) dropwise at 0-5° C. which was warmed up to RT and stirred for 30 minutes. The reaction mixture was concentrated to yield A551 (11 mg, 33%). HPLC: >95%, retention time: 1.758 minute (condition A). LC/MS (M+H)$^+$=468, $^1$H-NMR (400 MHz, DMSO-d6) δ ppm 9.58 (1 H, s), 8.14 (1 H, s), 7.47-7.71 (3 H, m), 7.26 (1 H, s), 6.96 (2 H, s), 4.58 (2 H, s), 4.04 (3 H, s), 3.50 (4 H, m), 3.25 (3 H, s), 3.00 (3 H, s).

Example A552

N-[(1Z)-[[[3-[1,6-dihydro-1-methyl-4-(methylamino)imidazo[4,5-d]pyrrolo[2,3-b]pyridin-7-yl]-5-fluorophenyl]methyl]amino](methylamino)methylene]-urea

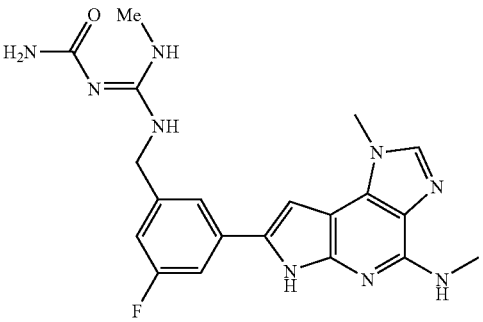

A552

Example A552 was prepared in a similar manner to A551. HPLC: 96%, retention time: 1.918 minute (condition B). LC/MS (M+H)$^+$=424 $^1$H-NMR (400 MHz, CD$_3$OD) δ ppm 8.02 (1 H, s), 7.38-7.53 (2 H, m), 7.14 (1 H, s), 6.92 (1 H, d, J=9.16 Hz), 4.51 (2 H, s), 4.03 (3 H, s), 3.13 (3 H, s), 2.86-2.96 (3 H, s).

Example A553 and A553a

N,1-dimethyl-7-(3-vinylphenyl)-1,6-dihydroimidazo[4,5-d]pyrrolo[2,3-b]pyridin-4-amine and N,1-dimethyl-7-(3'-vinylbiphenyl-3-yl)-1,6-dihydroimidazo[4,5-d]pyrrolo[2,3-b]pyridin-4-amine

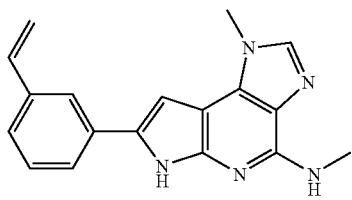
A553

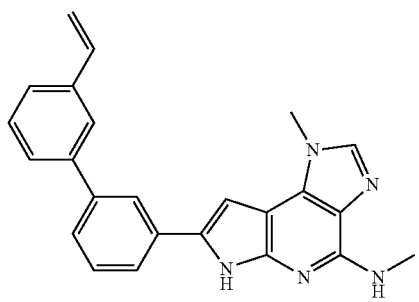
A553a

A553.1: tert-butyl 6-amino-7-((3-bromophenyl)ethynyl)-1-methyl-1H-imidazo[4,5-c]pyridin-4-yl(methyl)carbamate

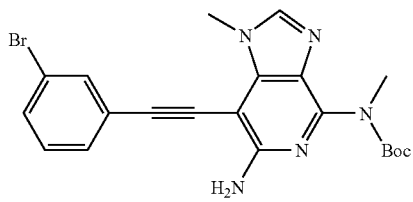
A75.1

During the production of A75.1 the product was found to contain ~20% of A553.1a. The mixture of products was used in the next step without further purification.

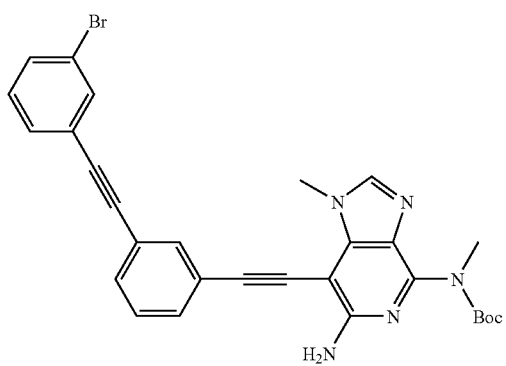
A553.1a

A553.2:

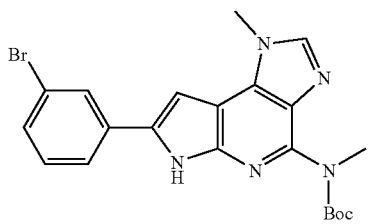

A75.2 was prepared in a similar manner as described previously HPLC: 82%, retention time. LC/MS (M+H)⁺=458. The product contains ~16% of A553.2a. The mixture of products was used in the next step without further purification.

A553.2a

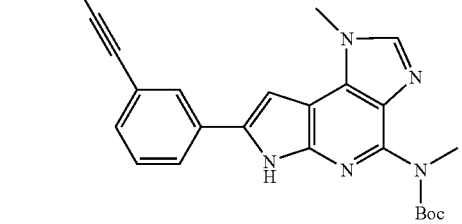

A553.3: tert-butyl methyl(1-methyl-7-(3-vinylphenyl)-1,6-dihydroimidazo[4,5-d]pyrrolo[2,3-b]pyridin-4-yl)carbamate

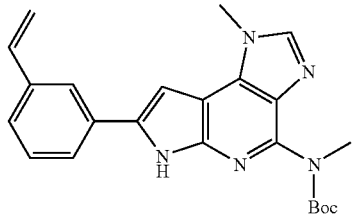
A553.3

A solution of A75.2 (444 mg, 0.974 mmol), triphenylphosphine (106 mg, 0.403 mmol), tetrakis(triphenylphosphine) Palladium(0) (106 mg, 0.098 mmol) and vinyltributyltin (0.314 ml, 1.07 mmol) in DMF (6 ml) was heated to 120° C. for 15 minutes under microwave. The reaction mixture was concentrated and purified on silica gel column with EtOAC to yield a mixture of A553.3 and A553.3a. The mixture of was purified on prep HPLC (condition G) to yield pure A553.3 (239 mg, 47%). HPLC: 99%, retention time: 3.328 minute (condition A). LC/MS (M+H)⁺=404. ¹H-NMR (400 MHz, CD₃OD) δ ppm 7.92 (1 H, s), 7.74 (1 H, dd, J=6.36, 2.80 Hz), 7.53-7.60 (1 H, m), 7.45-7.51 (1 H, m), 7.36-7.41 (2 H, m), 7.34 (1 H, s), 6.76 (1 H, dd, J=17.80, 10.68 Hz), 5.87 (1 H, d, J=18.31 Hz), 5.26 (1 H, d, J=11.19 Hz), 4.29 (3 H, s), 3.39 (3 H, s), 1.39 (9 H, s). It also afforded A553.3a (30 mg). HPLC: 99%, retention time: 4.136 minute (condition A). LC/MS (M+H)⁺=504. ¹H-NMR (400 MHz, CDCl₃) δ ppm 8.56 (1 H, s), 7.97 (1H, s), 7.77 (1 H, d, J=7.63 Hz), 7.61 (1 H, s), 7.43-7.56 (3 H, m), 7.38-7.43 (1 H, m), 7.34 (1 H, t, J=7.63 Hz), 7.11 (1 H, d, J=2.03 Hz), 6.71 (1 H, dd, J=17.55, 10.94 Hz), 5.81 (1 H, d, J=17.29 Hz), 5.32 (1 H, d, J=11.19 Hz), 4.25 (3 H, s), 3.56 (3 H, s), 1.51 (9 H, s).

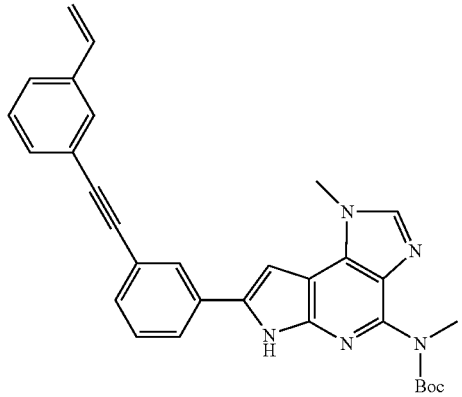

A553.3a

A553.4: N,1-dimethyl-7-(3-vinylphenyl)-1,6-dihydroimidazo[4,5-d]pyrrolo[2,3-b]pyridin-4-amine A553 was prepared in a similar manner as step A2.5. HPLC: >95%, retention time: 2.580 minute (condition A). LC/MS (M+H)⁺=304. ¹H-NMR (400 MHz, CD₃OD) δ ppm 8.08 (1 H, s), 7.74 (1 H, s), 7.54-7.59 (1 H, m), 7.29-7.35 (2 H, m), 7.11 (1 H, s), 6.72 (1 H, dd, J=17.80, 11.19 Hz), 5.82 (1 H, d, J=17.80 Hz), 5.22 (1 H, d, J=10.68 Hz), 4.06 (3 H, s), 3.17 (3 H, s).

A553.5: N,1-dimethyl-7-(3'-vinylbiphenyl-3-yl)-1,6-dihydroimidazo[4,5-d]pyrrolo[2,3-b]pyridin-4-amine A553a was prepared in a similar manner as step A2.5 HPLC: 96%, retention time: 3.941 minute (condition A). LC/MS (M+H)⁺=404. ¹H-NMR (400 MHz, CD₃OD) δ ppm 8.06 (1 H, s), 7.86 (1 H, s), 7.68 (1 H, s), 7.50 (1 H, s), 7.31-7.40 (4H, m), 7.26 (1 H, t, J=7.63 Hz), 7.15 (1 H, s), 6.66 (1 H, dd, J=17.80, 10.68 Hz), 5.75 (1 H, d, J=17.80 Hz), 5.21 (1 H, d, J=11.19 Hz), 4.05 (3 H, s), 3.16 (3 H, s)

Example A554

Racemic 1-(3-(1-methyl-4-(methylamino)-1,6-dihydroimidazo[4,5-d]pyrrolo[2,3-b]pyridin-7-yl)phenyl)ethane-1,2-diol

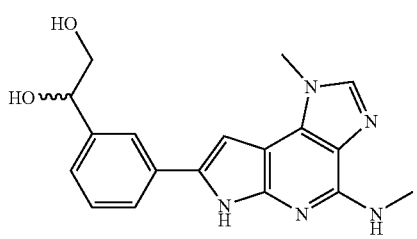

A554

A554.1: tert-butyl 7-(3-(1,2-dihydroxyethyl)phenyl)-1-methyl-1,6-dihydroimidazo[4,5-d]pyrrolo[2,3-b]pyridin-4-yl(methyl)carbamate

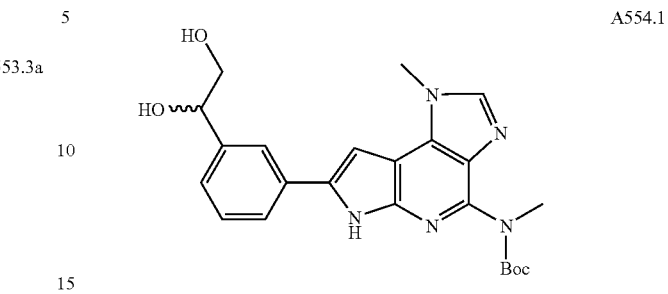

A554.1

A solution of A553.3 (110 mg, 0.273 mmol) in THF (4 mL) at 0-5° C. was added water (1 mL), 4-methylmorpholine-N-oxide (0.217 ml, 0.105 mmol; 50 wt % in water), followed by OSO₄ (0.231 ml; 2.5% in isopropanol). The reaction mixture was warmed up to RT and stirred for 4 hrs. The reaction was quenched with saturated NaHSO₃ solution (6 mL) which was extracted with EtOAC (10 mL×2). The combined organic phases was concentrated to give a crude product. It was added water (10 mL) and stirred for 5 minutes. The solid was collected as A554.1 (70 mg, 59%). HPLC: 94%, retention time: 2.278 minute (condition A). LC/MS (M+H)⁺=438. ¹H-NMR (400 MHz, CD₃OD) δ ppm 8.00 (1 H, s), 7.81 (1 H, s), 7.69 (1 H, d, J=8.14 Hz), 7.35 (1 H, t, J=7.63 Hz), 7.26 (1 H, d, J=7.63 Hz), 7.16 (1 H, s), 4.66-4.70 (1 H, m), 4.09 (3 H, s), 3.55-3.64 (2 H, m), 3.28 (3 H, s), 1.28 (9 H, s).

A554.2: 1-(3-(1-methyl-4-(methylamino)-1,6-dihydroimidazo[4,5-d]pyrrolo[2,3-b]pyridin-7-yl)phenyl)ethane-1,2-diol A suspension solution of A554.1 (70 mg, 0.16 mmol) in CH₂Cl₂ (5 ml) at 0-5° C. was added 4N HCl in dioxane (0.5 ml, 2 mmol) dropwise. The reaction mixture was warmed up to RT and stirred for 1 hrs. The solid was collected as A554 (55 mg, 92%). HPLC: 94%, retention time: 1.670 minute (condition A). LC/MS (M+H)⁺=338. ¹H-NMR (400 MHz, CD₃OD) δ ppm 8.10 (1 H, s), 7.68 (1 H, s), 7.56 (1 H, d, J=7.63 Hz), 7.33 (1 H, t, J=7.63 Hz), 7.25 (1 H, d, J=7.63 Hz), 7.07 (1 H, s), 4.66 (1 H, dd, J=6.87, 4.83 Hz), 4.05 (3 H, s), 3.53-3.62 (2 H, m), 3.16 (3 H, s)

Examples A555 and A556

1-(3-(1-methyl-4-(methylamino)-1,6-dihydroimidazo[4,5-d]pyrrolo[2,3-b]pyridin-7-yl)phenyl)ethane-1,2-diol

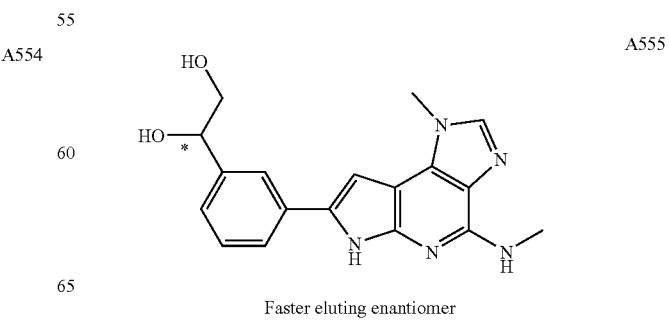

A555

Faster eluting enantiomer

329

-continued

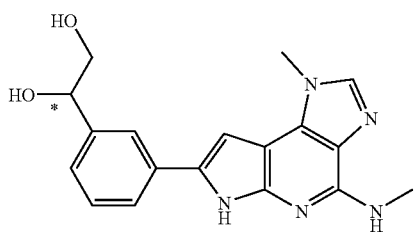

A556

Slower eluting enantiomer

A554 (55 mg, 0.147 mmol) was subjected to chiral separation (Chiralcel OJ 250×30 mm ID; 5 um, MeOH/IPA/DEA=50:50:0.1; 16 ml/min) to yield A555 (21.8 mg, 87%). HPLC: >95%, retention time: 1.690 minute (condition A). Chiral HPLC: >99.9% ee. retention time: 9.957 minute (Chiralcel OJ 10 um 4.6×250 mm; MeOH/IPA/DEA=50:50:0.1; 0.7 ml/min). LC/MS (M+H)$^+$=338, $^1$H NMR (500 MHz, CD$_3$OD) δ ppm 7.78 (1 H, s), 7.68 (1 H, s), 7.56 (1 H, d, J=7.70 Hz), 7.28 (1 H, t, J=7.70 Hz), 7.15 (1 H, d, J=7.70 Hz), 6.93 (1 H, s), 4.66 (1 H, dd, J=7.15, 4.67 Hz), 4.00 (3 H, s), 3.56-3.64 (2 H, m), 3.03 (3 H, s) and A556 (18.2 mg, 73%). HPLC: >95%, retention time: 1.687 minute (condition A). Chiral HPLC: 96.8% ee. retention time: 18.21 minute (Chiralcel OJ 10 um 4.6×250 mm; MeOH/IPA/DEA=50:50:0.1; 0.7 ml/min). LC/MS (M+H)$^+$=338, $^1$H NMR (500 MHz, CD$_3$OD) δ ppm 7.78 (1 H, s), 7.68 (1 H, s), 7.57 (1 H, d, J=7.70 Hz), 7.28 (1 H, t, J=7.70 Hz), 7.15 (1 H, d, J=7.70 Hz), 6.93 (1 H, s), 4.66 (1 H, dd, J=7.29, 4.81 Hz), 4.01 (3 H, s), 3.46-3.72 (2H, m), 3.03 (3 H, s).

Example A557

(R)-2-amino-2-(3-(1-methyl-4-(methylamino)-1,6-dihydroimidazo[4,5-d]pyrrolo[2,3-b]pyridin-7-yl)phenyl)ethanol

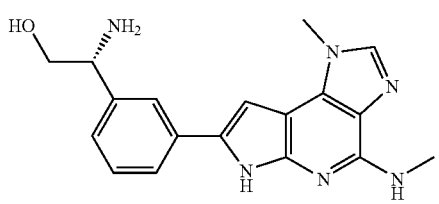

A557

A557.1: (R)-2-tert-butyloxycarbonylamino-2-(3-(1-methyl-4-(N-methyl-tert-butyloxycarbonylamino)-1,6-dihydroimidazo[4,5-d]pyrrolo[2,3-b]pyridin-7-yl)phenyl)ethanol

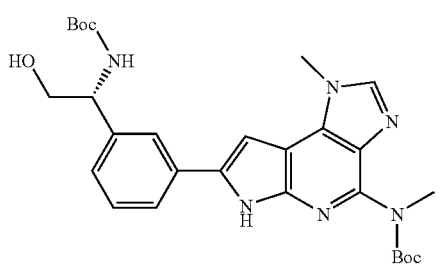

A557.1

330

A solution of tert-butyl carbamate (17.6 mg, 0.15 mmol) in n-propanol (0.2 ml) was added 1N NaOH solution (0.15 ml, 0.15 mmol), water (0.15 ml), followed by t-BuOCl (17 uL, 0.15 mmol) and stirred at RT for 20 minutes. The reaction mixture was cooled to 0-5° C. (DHQ)$_2$PHAL (1.95 mg, 0.0025 mmol) in n-propanol (0.16 ml) was added and then A553.3 (20 mg, 0.05 mmol) in n-propanol (0.4 ml) was added. Finally, to the reaction mixture was added K$_2$OsO$_4$o2H$_2$O (0.74 mg, 0.002 mmol) at 0-5° C. The color of solution was changed from faint yellow to green and then to yellow. The reaction mixture was stirred for 2 hrs from at 0° C. to at RT and the reaction was quenched with saturated NaHSO$_3$ solution (1 mL) and stirred for 15 minutes which was extracted with EtOAC (1 mL×3). The combined organic phases was washed with water (1 mL), brine (1 mL) and the organic layer was dried over sodium sulfate. Filtration and concentration to yield a crude product. It was purified on silica gel column with EtOAc/MeOH (20/1) to yield as A557.1 (11.6 mg, 43%). HPLC: 90%, retention time: 3.040 minute (condition A). LC/MS (M+H)$^+$=537. $^1$H NMR (400 MHz, CD$_3$OD) δ ppm 8.00 (1 H, s), 7.74 (1 H, s), 7.68 (1 H, d, J=7.63 Hz), 7.34 (1 H, t, J=7.63 Hz), 7.2.0 (1 H, d, J=7.63 Hz), 7.16 (1 H, s), 4.61-4.67 (1 H, m), 4.10 (3 H, s), 3.58-3.71 (2 H, m), 3.28 (3 H, s), 1.34 (9 H, s), 1.28 (9 H, s).

A557.2: (R)-2-amino-2-(3-(1-methyl-4-(methylamino)-1,6-dihydroimidazo[4,5-d]pyrrolo[2,3-b]pyridin-7-yl)phenyl)ethanol A suspension solution of A557.1 (11.6 mg, 0.022 mmol) in CH$_2$Cl$_2$ (1 ml) at 0-5° C. was added 4N HCl in dioxane (0.4 ml, 1.6 mmol) dropwise. The reaction mixture was warmed up to RT and stirred for 20 minutes. The solid was collected as A557 (5 mg, 56%). HPLC: 93%, retention time: 1.580 minute (condition A). Chiral HPLC: 88.2% ee. retention time: 12.05 minute (Chiralpak AD 10 um 4.6×250 mm; Hex/MeOH/IPA/DEA=60/20/20/0.1; 1.8 ml/min). LC/MS (M+H)$^+$=337. $^1$H-NMR (400 MHz, CD$_3$OD) δ ppm 8.15 (1 H, s), 7.82 (1 H, s), 7.73 (1 H, d, J=7.63 Hz), 7.45 (1 H, t, J=7.88 Hz), 7.30 (1 H, d, J=7.63 Hz), 7.15 (1 H, s), 4.33 (1 H, dd, J=7.88, 4.32 Hz), 4.07 (3 H, s), 3.83-3.89 (1 H, m), 3.74-3.81 (1 H, m), 3.16 (3 H, s).

Example A558

(R)-N-(2-hydroxy-1-(3-(1-methyl-4-(methylamino)-1,6-dihydroimidazo[4,5-d]pyrrolo[2,3-b]pyridin-7-yl)phenyl)ethyl)acetamide

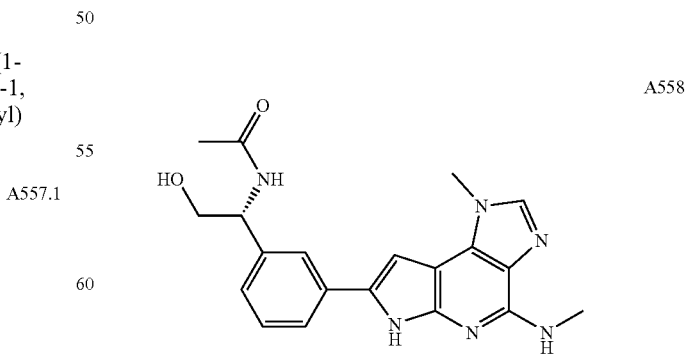

A558

A solution of A557 (4.5 mg, 0.0134 mmol) and triethylamine (6.51 uL, 0.0468 mmol) in dichloromethane (0.5 mL) at 0-5° C. was added acetyl chloride (0.99 uL, 0.014 mmol)

and the reaction mixture was stirred at 0-5° C. for 10 minutes, which was warmed up to room temperature and stirred for 10 minutes. The reaction mixture was concentrated and purified on prep. HPLC (condition G) to yield A558 (1.6 mg, 32%). HPLC: >95%, retention time: 1.712 minute (condition A). LC/MS (M+H)$^+$=379, $^1$H-NMR (400 MHz, CD$_3$OD) δ ppm 7.76 (1 H, s), 7.61 (1 H, s), 7.54 (1 H, d, J=7.63 Hz), 7.26 (1 H, t, J=7.88 Hz), 7.08 (1 H, d, J=8.14 Hz), 6.91 (1 H, s), 4.93 (1 H, dd, J=7.38, 5.34 Hz), 3.98 (3 H, s), 3.63-3.75 (2 H, m), 3.01 (3H, s), 1.94 (3 H, s).

Example A559

(R)-N-(2-hydroxy-1-(3-(1-methyl-4-(methylamino)-1,6-dihydroimidazo[4,5-d]pyrrolo[2,3-b]pyridin-7-yl)phenyl)ethyl)-2-methoxyacetamide

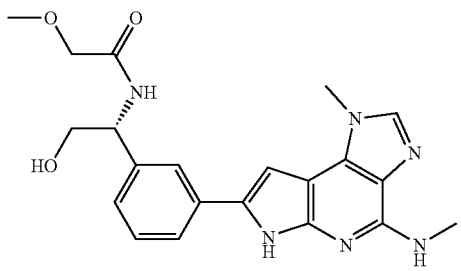

A559

A559 was prepared in a similar manner to A558. HPLC: 90%, retention time: 1.963 minute (condition A). LC/MS (M+H)$^+$=409. $^1$H NMR (500 MHz, CD$_3$OD) δ ppm 8.16-8.22 (1 H, m), 7.72-7.75 (1 H, m), 7.65-7.69 (1 H, m), 7.42-7.47 (1 H, m), 7.30-7.35 (1 H, m), 7.16-7.19 (1 H, s), 5.07-5.12 (1 H, m), 4.15 (3 H, s), 3.95-3.98 (2 H, m), 3.84-3.88 (2 H, m), 3.46 (3 H, s), 3.26 (3 H, s).

A560

(S)-2-amino-2-(3-(1-methyl-4-(methylamino)-1,6-dihydroimidazo[4,5-d]pyrrolo[2,3-b]pyridin-7-yl)phenyl)ethanol

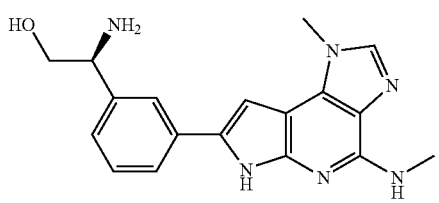

A560

A560.1: (S)-2-tert-butyloxycarbonylamino-2-(3-(1-methyl-4-(N-methyl-tert-butyloxycarbonylamino)-1,6-dihydroimidazo[4,5-d]pyrrolo[2,3-b]pyridin-7-yl)phenyl)ethanol

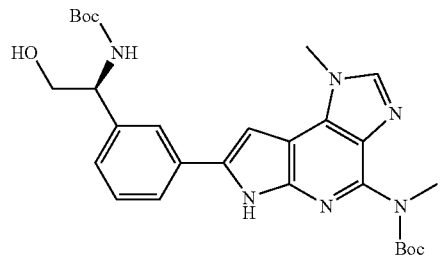

A560.1

A solution of tert-butyl carbamate (17.6 mg, 0.15 mmol) in n-propanol (0.2 ml) was added 1N NaOH solution (0.15 ml, 0.15 mmol), water (0.15 ml), followed by t-BuOCl (17 uL, 0.15 mmol) and stirred at RT for 20 minutes. The reaction mixture was cooled to 0-5° C. (DHQD)$_2$PHAL (1.95 mg, 0.0025 mmol) in n-propanol (0.16 ml) was added and then A553.3 (20 mg, 0.05 mmol) in n-propanol (0.4 ml) was added. Finally, to the reaction mixture was added K$_2$OsO$_4$o2H$_2$O (0.74 mg, 0.002 mmol) at 0-5° C. The color of solution was changed from faint yellow to green and then to yellow. The reaction mixture was stirred for 2 hrs from at 0° C. to at RT and the reaction was quenched with saturated NaHSO$_3$ solution (1 mL) and stirred for 15 minutes which was extracted with EtOAC (1 ml×3). The combined organic phases was washed with water (1 ml), brine (1 ml) and the organic layer was dried over sodium sulfate. Filtration and concentration to yield a crude product. It was purified on prep. silica gel TLC plate with EtOAc/MeOH (10/1) to yield as A560.1 (13.4 mg, 50%). HPLC: 89%, retention time: 3.051 minute (condition A). LC/MS (M+H)$^+$=537.

A560.2: (S)-2-amino-2-(3-(1-methyl-4-(methylamino)-1,6-dihydroimidazo[4,5-d]pyrrolo[2,3-b]pyridin-7-yl)phenyl)ethanol A suspension solution of A560.1 (13.4 mg, 0.025 mmol) in CH$_2$Cl$_2$ (1 ml) at 0-5° C. was added 4N HCl in dioxane (0.4 ml, 1.6 mmol) dropwise. The reaction mixture was warmed up to RT and stirred for 20 minute which was concentrated to yield a crude product. It was purified on prep. silica gel TLC plate with CH$_2$Cl$_2$/MeOH/NH$_4$OH (90/15/1.5) to yield A560 (5.2 mg, 62%). HPLC: 91%, retention time: 1.582 minute (condition A). Chiral HPLC: 88.8% ee. retention time: 15.69 minute (Chiralpak AD 10 um 4.6×250 mm; Hex/MeOH/IPA/DEA=60/20/20/0.1; 1.8 ml/min). LC/MS (M+H)$^+$=337. $^1$H-NMR (400 MHz, CD$_3$OD) δ ppm 7.90 (1 H, s), 7.80 (1 H, s), 7.71 (1 H, d, J=8.14 Hz), 7.42 (1 H, t, J=7.63 Hz), 7.25 (1 H, d, J=7.63 Hz), 7.07 (1 H, s), 4.07-4.16 (4H, m), 3.78-3.88 (1 H, m), 3.64-3.75 (1 H, m), 3.15 (3 H, s)

Example A561

1-(1-(3-(1-methyl-4-(methylamino)-1,6-dihydroimidazo[4,5-d]pyrrolo[2,3-b]pyridin-7-yl)phenyl)ethyl)pyrrolidin-2-one

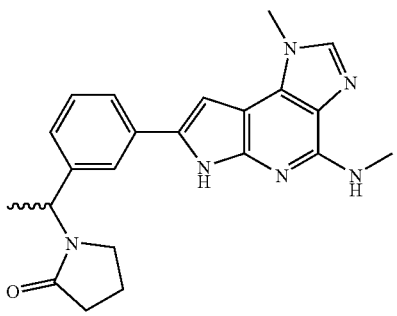

A561

To a solution A131 (8 mg, 0.02 mmol) in THF (5 mL) was added DIPEA (0.018 mL) followed by 4-chlorobutanoyl chloride (0.0072 mL, 0.06 mmol). The reaction was stirred at room temperature for 30 minutes then partitioned between EtOAc and saturated aq. NaHCO$_3$. The EtOAc layer was washed with water and brine then dried over MgSO$_4$, filtered, and evaporated to dryness. The residue thus obtained was dissolved in THF (5 mL), cooled with an ice bath, and excess sodium hydride (95%) was added. The reaction was warmed to room temperature overnight, then heated to gentle reflux. An additional portion of sodium hydride was added. After 3 hours at reflux, KOtBu (solid, excess amount) was added and heating continued for 48 hours. The material was then placed in a sealed tube along with fresh KOtBu and heated to 85° C. overnight. The reaction was quenched with water, extracted with EtOAc and the crude organics were concentrated and further purified by preparative reverse phase HPLC to afford the desired product (0.92 mg, 1×TFA) as a clear film. The compound had an HPLC retention time=2.7 min. (Column: Chromolith SpeedROD 4.6×50 mm—4 min.; Solvent A=10% MeOH, 90% H$_2$O, and 0.2% H$_3$PO$_4$; Solvent B=90% MeOH, 10% H$_2$O, and 0.2% H$_3$PO$_4$) and a LC/MS M$^{+1}$=389.4

Example A562

7-isopropyl-N,1-dimethyl-1,6-dihydroimidazo[4,5-d]pyrrolo[2,3-b]pyridin-4-amine

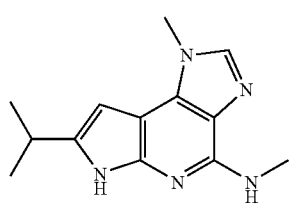

A562

A562.1: tert-butyl 7-iodo-1-methyl-6-(2,2,2-trifluoroacetamido)-1H-imidazo[4,5-c]pyridin-4-yl(methyl)carbamate

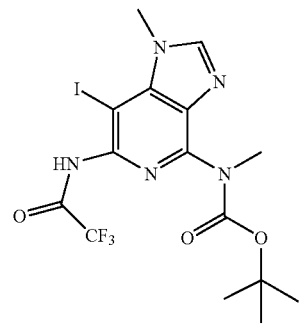

A562.1

To a solution of A1.12 (100 mg, 0.248 mmol) in THF (5 mL) and triethylamine (0.038 mL) at room temperature was added trifluoroacetic anhydride (0.070 mL, 0.496 mmol) dropwise. The reaction was stirred at room temperature overnight then diluted with EtOAc (15 mL) and washed with saturated aq. NaHCO$_3$ (10 mL). The EtOAc layer was washed with water (10 mL) and brine (10 mL) then dried over MgSO$_4$, filtered, and evaporated to dryness to afford A562.1 as a yellow solid (118 mg). The compound had an HPLC retention time=2.76 min. (Column: Chromolith SpeedROD 4.6×50 mm—4 min.; Solvent A=10% MeOH, 90% H$_2$O, and 0.2% H$_3$PO$_4$; Solvent B=90% MeOH, 10% H$_2$O, and 0.2% H$_3$PO$_4$) and a LC/MS M$^{+Na}$=522.01

A562.2: tert-butyl 7-isopropyl-1-methyl-1,6-dihydroimidazo[4,5-d]pyrrolo[2,3-b]pyridin-4-yl(methyl)carbamate

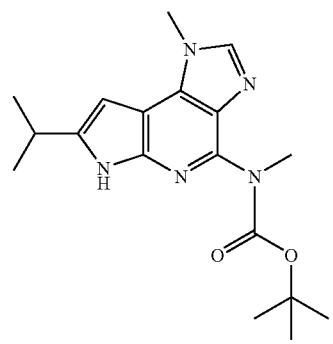

A562.2

A solution of A562.1 (20 mg, 0.04 mmol), 3-methylbut-1-yne (0.006 mL), polymer supported triphenylphosphine (3 mmol/g, 12 mg), CuI (2.3 mg, 0.012 mmol), and potassium carbonate (11.1 mg, 0.08 mmol) in DMF (0.6 mL) was heated in a Personal Chemistry microwave reactor for 1 hour at 160° C. followed by an additional processing time of 30 minutes at 160° C. The material was filtered through a glass frit, which was washed with methanol, and purified by preparative reverse phase HPLC to afford A562.2 (4.3 mg, 1×TFA). The compound had an HPLC retention time=2.68 min. (Column: Chromolith SpeedROD 4.6×50 mm—4 min.; Solvent A=10% MeOH, 90% H$_2$O, and 0.2% H$_3$PO$_4$; Solvent B=90% MeOH, 10% H$_2$O, and 0.2% H$_3$PO$_4$) and a LC/MS M$^{+1}$=344.2

A562: 7-isopropyl-N,1-dimethyl-1,6-dihydroimidazo[4,5-d]pyrrolo[2,3-b]pyridin-4-amine To a solution of A562.2 (4 mg, 1×TFA) in methanol (1 mL) was added HCl/Dioxane (4N, 2 mL). The reaction was stirred at room temperature until complete as judged by HPLC analysis, then evaporated and dried under high vacuum to afford the A562 as an off-white solid (2.5 mg, 1×HCl). The compound had an HPLC retention time=2.22 min. (Column: Chromolith SpeedROD 4.6×50 mm—4 min.; Solvent A=10% MeOH, 90% $H_2O$, and 0.2% $H_3PO_4$; Solvent B=90% MeOH, 10% $H_2O$, and 0.2% $H_3PO_4$) and a LC/MS $M^{+1}$=244.2

Examples A563-A565 described in Table A72 were prepared in a similar manner to Example A562.

TABLE A27

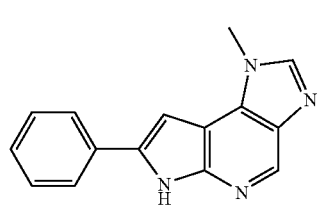

| Ex. | R | Name | HPLC Retention (min) | MS Reported |
|---|---|---|---|---|
| A563 | cyclohexyl | 7-cyclohexyl-N,1-dimethyl-1,6-dihydroimidazo[4,5-d]pyrrolo[2,3-b]pyridin-4-amine | 2.90 | 284.2 |
| A564 | pyridin-4-yl | N,1-dimethyl-7-(pyridin-4-yl)-1,6-dihydroimidazo[4,5-d]pyrrolo[2,3-b]pyridin-4-amine | 1.36 | 279.2 |
| A565 | 1-methyl-1H-imidazol-5-yl | N,1-dimethyl-7-(1-methyl-1H-imidazol-5-yl)-1,6-dihydroimidazo[4,5-d]pyrrolo[2,3-b]pyridin-4-amine | 0.69 | 282.3 |

Example B1

1,6-dihydro-1-methyl-7-phenyl imidazo[4,5-d]pyrrolo[2,3-b]pyridine

B1

B1.1: 4-chloro-5-nitropyridin-2-amine

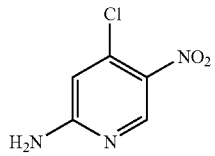

B1.1

Commercially available 3-nitro-4-chloropyridine (25 g, 157 mmol) was dissolved in liquid ammonia (1.4 L) and $KMnO_4$ (50 g, 316 mmol) was added and the mixture stirred for 5 h. at liq ammonia temperature. The reaction mixture was brought to RT and ammonia was allowed to evaporate. Water (1.5 L) was added and the mixture extracted with chloroform (10×2 L) for 20 h. The organic layer was washed with water, brine, separated, dried over sodium sulphate and concentrated under reduced pressure. The product was purified by 60-120 silica gel column chromatography using chloroform as eluent to give 11.2 g (40%) B1.1 as a yellow solid. $^1$H NMR (300 MHz, DMSO-$d_6$) δ 8.80 (s, 1H), 7.64 (s, 1H), 6.58 (s, 1H). LCMS $(M-H)^+$=173.

B1.2: tert-Butyl 4-chloro-5-nitropyridin-2-ylcarbamate

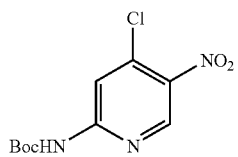

B1.2

B1.1 (10 g, 57.6 mmol) was dissolved in dry acetonitrile (750 mL) and DMAP (1.41 g, 12 mmol) was added. The reaction mixture was cooled at 0° C. and di-tert-butyldicarbonate (16.34 g, 75 mmol) was added drop-wise by addition funnel for 30 min. The reaction mixture was warmed to RT and stirred for overnight. The reaction mixture was concentrated and the residue was dissolved in ethyl acetate. The organic was layer washed with water and brine solution, separated, dried over sodium sulphate and concentrated. The product was purified by column chromatography using 5% of ethyl acetate in pet ether to give 9 g (57%) of B1.2 as a yellow. $^1$H NMR (300 MHz, DMSO-$d_6$) δ 10.93 (s, 1H), 9.03 (s, 1H), 8.09 (s, 1H) 1.49 (s, 9H). LCMS $(M-H)^+$=272.

B1.3: tert-Butyl 4-(methylamino)-5-nitropyridin-2-ylcarbamate

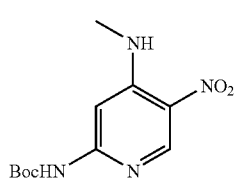

B1.3

B1.2 (9 g, 32.88 mmol) was dissolved in dry THF (50 ml) in an autoclave. Methyl amine solution (20% in THF, 2.59 g, 82 mmol) was added and the reaction mixture was heated at 80° C. for 3 h. The reaction mixture was concentrated under reduced pressure and methanol was added to the residue and cooled to 0° C. The solid was collected by filtration. The filtered cake was washed with cold MeOH to give 8 g (91%) of B1.3 as a yellow solid. $^1$H NMR (300 MHz, DMSO-$d_6$) δ 10.16 (s, 1H), 8.84 (s, 1H), 8.44 (bs, 1H) 7.27 (s, 1H), 2.92 (d, 3H), 1.47 (s, 9H). LCMS (M−H)$^+$=269.

B1.4: tert-Butyl 5-amino-4-(methylamino)pyridin-2-ylcarbamate

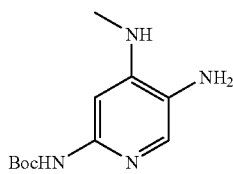

B1.3 (8 g, 30 mmol) was dissolved in methanol (1000 ml). Pd/C (1 g) was added cautiously and the mixture hydrogenated at 2 kg pressure for 12 h using a Parr shaker. The reaction mixture was filtered over Celite and concentrated to provide the crude product. The solid was washed with petrolium ether to give 6.55 g (92%) of B1.4 as a black solid. $^1$H NMR (300 MHz, DMSO-$d_6$) δ 9.12 (s, 1H), 7.33 (s, 1H), 6.83 (s, 1H) 5.59 (s, 1H), 4.25 (bs, 2H), 2.74 (d, 3H), 1.44 (s, 9H). LCMS (M−H)+239.

B1.5: tert-butyl 1-methyl-1H-imidazo[4,5-c]pyridin-6-ylcarbamate

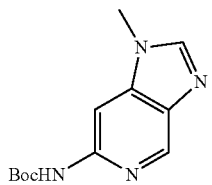

B1.4 (0.5 g, 2.1 mmol) was dissolved in diethoxymethyl acetate (5 ml) and stirred at room temperature for 16 h. Reaction mixture was poured into water (150 ml) and extracted with ethyl acetate (2×100 ml). The combined organic layers were washed with water, with brine, dried over sodium sulphate and concentrated to provide the crude product which was triturated with pet ether and filtered to yield 0.350 g (62%) of B1.5 as a brown solid. $^1$H NMR (300 MHz, DMSO-$d_6$) δ 9.71 (s, 1H), 8.59 (s, 1H), 8.19 (s, 1H) 7.91 (s, 1H), 3.79 (s, 3H), 1.48 (s, 9H). LCMS (M−H)$^+$=249.

B1.6: 1-methyl-1H-imidazo[4,5-c]pyridin-6-amine hydrochloride salt

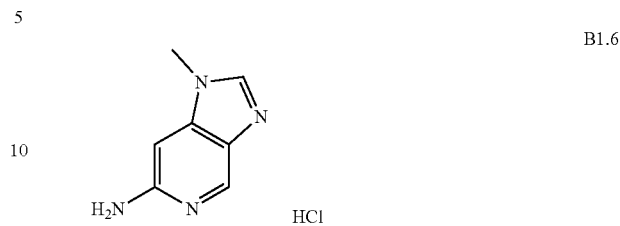

B1.5 (0.3 mg, 1.2 mmol) was taken in HCl in THF (10 ml, 4N solution) and stirred at room temperature overnight. The solvent was removed under reduced pressure and the solid obtained was washed with ethyl acetate and dried to provide B1.6, 200 mg (90%) as the hydrochloride salt. $^1$H NMR (300 MHz, DMSO-$d_6$) δ 8.66 (s, 1H), 8.41 (s, 1H), 7.31 (bs, 2H) 6.83 (s, 1H), 3.74 (s, 3H). LCMS (M−H)$^+$=149.

B1.7: 7-iodo-1-methyl-1H-imidazo[4,5-c]pyridin-6-amine

B1.6 (75 mg, 0.4 mmol) was dissolved in methanol (2.5 ml) and sodium acetate (66 mg, 0.8 mmol) was added. The reaction mixture was cooled to 0° C. and N-iodosuccinimide (100 mg, 0.44 mmol) was added in portions. The reaction mixture was stirred at room temperature for 3 h. Reaction mixture was concentrated to remove volatiles and the residue was purified by column chromatography over silica gel (60-120) using chloroform-methanol (95:5) as eluent to provide 70 mg (63%) of B1.7 as a yellow solid. $^1$H NMR (300 MHz, DMSO-$d_6$) δ 8.28 (s, 1H), 7.98 (s, 1H), 5.75 (s, 2H) 4.02 (s, 3H). LCMS (M−H)$^+$=275.

B1.8: 1-methyl-7-(2-phenylethynyl)-1H-imidazo[4,5-c]pyridin-6-amine

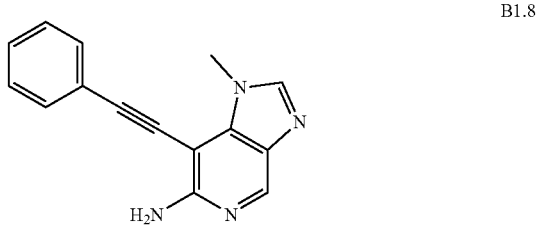

B1.7, (0.1 g, 0.364 mmol), bis(triphenylphosphine)palladium(II)chloride (0.012 g, 0.018 mmol), and triethylamine (0.5 mL) were dissolved in dry DMF (4 mL) and phenylacetylene (0.074 g, 0.73 mmol) was added. The reaction mixture was heated to 75° C. for 2 h. The reaction mixture was cooled to rt and poured into water and extracted with ethyl acetate (2×30 mL), washed with water and brine solution and the organic layer separated and evaporated under reduced pressure. The residue was purified by column chromatography using 5% of ethyl acetate in pet ether to provide 65 mg (72%) of B1.8. $^1$H NMR (400 MHz, CD$_3$OD) δ 8.36 (s, 1H), 7.99 (s, 1H), 7.64-7.62 (m, 2H) 7.44-7.42 (m, 3H), 4.17 (s, 1H). LCMS (M−H)$^+$=249.

B1.9: 1,6-dihydro-1-methyl-7-phenyl imidazo[4,5-d]pyrrolo[2,3-b]pyridine

B1.8 (40 mg, 0.16 mmol) was dissolved in N,N-dimethylacetamide (1 mL) and potassium tert-butoxide (40 mg, 0.36 mmol) was added. The reaction mixture was irradiated in a microwave reactor at 100° C. for 30 min. The reaction mixture was cooled to rt and poured into water and extracted with ethyl acetate (2×15 mL), washed with water and brine solution, the organic layer separated and concentrated under reduced pressure. The crude product was purified by crystallization from ethyl acetate to provide 22 mg (55%) of B1 as a white solid. $^1$H NMR (400 MHz, CD$_3$OD) δ 8.75 (s, 1H), 8.14 (s, 1H), 7.92 (d, 2H) 7.50-7.47 (t, 2H), 7.38-7.34 (m, 1H), 7.26 (s, 1H), 4.21 (s, 3H). LCMS (M−H)$^+$=249.

Example B2

3-(1,6-dihydro-1-methylimidazo[4,5-d]pyrrolo[2,3-b]pyridin-7-yl)-benzonitrile

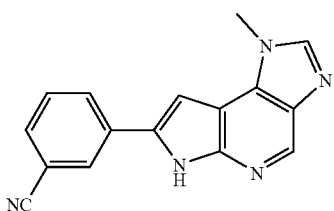

B2

B2.1: 3-(6-Amino-1-methyl-1H-imidazo[4,5-c]pyridin-7-ylethynyl)-benzonitrile

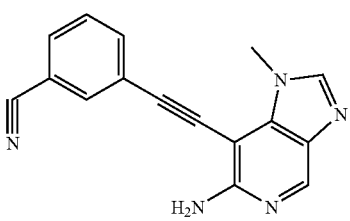

B2.1

A mixture of compound A1.7 (1 g, 3.65 mmol), 3-ethynylbenzonitrile (0.93 g, 7.3 mmol), bis(triphenylphosphine)palladium(II)chloride, (0.13 g, 0.18 mmol) and triethylamine (10 ml) were taken in DMF (20) ml and stirred at 85° C. for 6 h. The reaction mixture was cooled to rt, solvent was removed under reduced pressure and the crude product was recrystallised from ethylacetate to get 0.66 g (66%) of B1.1 as brown solid. $^1$H NMR (400 MHz, DMSO-d$_6$) δ 8.39 (s, 1H), 8.25 (s, 1H), 7.98-8.00 (m, 2H), 7.83-7.85 (d, 1H), 7.60-7.63 (t, 1H), 6.36 (bs 2H) 4.03 (s, 3H). LCMS (M−H)$^+$=274

B2.2: 3-(1,6-dihydro-1-methylimidazo[4,5-d]pyrrolo[2,3-b]pyridin-7-yl)benzonitrile 0.66 g (2.4 mmol) of B2.1 was taken in N,N-dimethylacetamide (15 ml) and added 0.6 g (5.4 mmol) of potassium tert-butoxide. The reaction mixture was irradiated in MW reactor at 110° C. for 30 min. Reaction mixture was cooled to rt and poured into water and extracted with ethyl acetate (3×250 ml), washed with water and brine solution. The product was purified by crystallization from ethyl acetate to give 350 mg (58%) of B2 as brown solid. $^1$H NMR (400 MHz, DMSO-d$_6$) δ 8.61 (s, 1H), 8.47 (s, 1H), 8.29-8.31 (d, 1H), 8.16 (s, 1H), 7.74-7.76 (d, 1H), 7.64-7.69 (t, 1H), 7.61 (s, 1H), 4.11 (s, 3H). LCMS (M−H)$^+$=274

Example B3

3-(1,6-dihydro-1-methylimidazo[4,5-d]pyrrolo[2,3-b]pyridin-7-yl)-benzenemethanamine

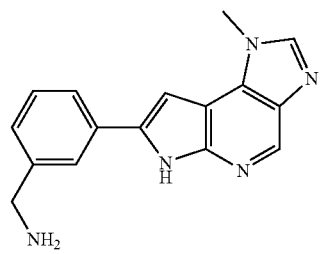

B3

325 mg (1.12 mmol) compound B2 was hydrogenated using Raney nickel (300 mg) in methanol (30 ml) and aq NH$_3$ (6 ml) at 5 kg pressure for 48 hours. (HPLC analysis shows the presence of starting material. Reaction mixture was filtered over Celite, filtrate was concentrated and the crude was once again taken for hydrogenation using 300 mg of Raney nickel in 30 ml methanol and aq NH$_3$ (6 ml) at 5 kg pressure for 48 h. Reaction mixture was filtered over Celite and the filtrate was concentrated. Crude material was recrystallised from ethylacetate to get 200 mg of the product, B3 as brown solid (61%). $^1$H NMR (400 MHz, CD$_3$OD) δ: 8.60 (s, 1H), 8.18 (s, 1H), 7.95 (s, 1H), 7.86-7.88 (d, 1H), 7.52-7.54 (t, 1H), 7.41 (d, 1H), 7.32 (s, 1 H), 4.24 (s, 3H), 4.0 (s, 2H). LCMS (M−H)$^+$=278.

Example B4

N-[1-[3-(1,6-dihydro-1-methylimidazo[4,5-d]pyrrolo[2,3-b]pyridin-7-yl)phenyl]ethyl]-acetamide

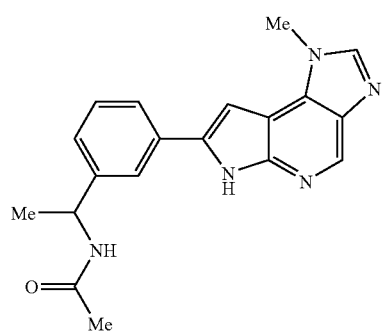

B4

B4.1: N-(1-(3-((6-Amino-1-methyl-1H-imidazo[4,5-c]pyridin-7-yl)ethynyl)phenyl)ethyl)acetamide

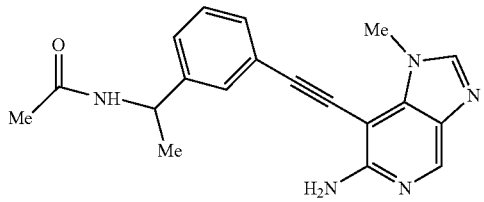

B4.1

A solution of B 1.7 (0.20 g, 0.73 mmol), dichlorobis(triphenylphosphine)palladium II (30.74 mg, 0.044 mmol), and triethylamine (2.94 mL, 21.2 mmol) in DMF (2.0 mL) was degassed for several minutes with argon. A56.1b (0.137 g, 0.73 mmol) was added over 7 minutes in small increments while heating at 90° C. under Ar. After completion of the addition, heating at 90° C. was continued for 1 h. A second portion of A56.1b (70.0 mg (0.37 mmol) was added in small portions, and heating at 90° C. was continued for 1 h. The reaction mixture was evaporated to dryness under vacuum. Flash chroma-tography on silica gel, eluting with an EtOAc:hexane gradient followed by an EtOAc:MeOH:ammonium hydroxide gradient and an ether trituration yielded 0.2113 g of B4.1 as a yellow solid (86.6%). HPLC (C): 86.05%, ret. time 1.83 min., LC/MS (M+H)$^+$=373.36.

B4.2: N-[1-[3-(1,6-dihydro-1-methylimidazo[4,5-d]pyrrolo[2,3-b]pyridin-7-yl)phenyl]ethyl]-acetamide A solution of B4.1 (0.155 g, 0.46 mmol) and potassium tert-butoxide (0.58 mL, 1.0M solution in THF, 0.58 mmol) in 2.61 mL of DMA was heated at 90° C. under Ar for 40 min. After removal of the DMA, the crude product was purified by reversed-phase preparative HPLC to yield 109.8 mg of B4 as a pale yellow solid (53% assuming 1.0 TFA salt). HPLC (C): 98.14%, ret. time 1.87 min., LC/MS (M+H)$^+$=334.33.

Example B5

3-(1,6-dihydro-1-methylimidazo[4,5-d]pyrrolo[2,3-b]pyridin-7-yl)-alpha-methyl-benzenemethanamine

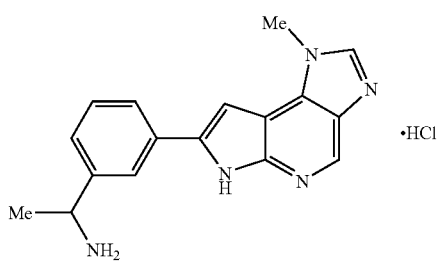

B5

A solution of B4 (103.1 mg, 0.23 mmol) in EtOH (3.0 mL) and con. HCl (3.0 mL) was heated in a sealed pressure tube at 150° C. for 4 hours and 15 minutes. The reaction mixture was evaporated to dryness under vacuum with toluene to yield B5 as a yellow solid (75.7 mg, 100%). HPLC (C): 97.0%, ret. time 1.50 min., LC/MS (M+H)$^+$=292.45.

Example B6

N-[1-[3-(1,6-dihydro-1-methylimidazo[4,5-d]pyrrolo[2,3-b]pyridin-7-yl)phenyl]ethyl]-3-methoxy-propanamide

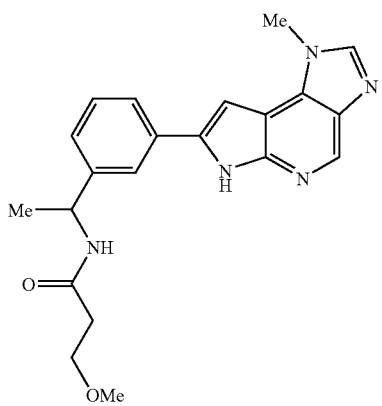

B6

Diisopropylethylamine (26.1 µL, 0.153 mmol) was added to a solution of B4 (10.0 mg, 0.0305 mmol), EDC (11.70 mg, 0.061 mmol), 1-Hydroxybenzotriazole hydrate (5.60 mg, 0.037 mmol), and 3-methoxypropionic acid (3.76 µL, 0.040 mmol) in DMF (0.70 mL). The reaction mixture was heated at 60° C. for 1 h and 10 min. in sealed vials on a platform shaker. After solvent removal, the crude product was purified by reversed-phase preparative HPLC to yield 11.60 mg of B6 as a pale yellow solid (68% assuming 1.0 mol TFA). HPLC (C): 95%, ret. time 1.97 min., LC/MS (M+H)$^+$=378.47.

Examples B7-B11

Examples B7-B11 were prepared in a manner similar to that used for example B6.

TABLE B1

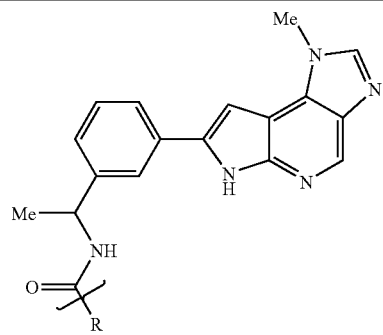

| Ex. | R | Name | HPLC Retention (min) | MS Reported |
|---|---|---|---|---|
| B7 |  | N-[1-[3-(1,6-dihydro-1-methylimidazo[4,5-d]pyrrolo[2,3-b]pyridin-7-yl)phenyl]ethyl]-1-hydroxy-cyclopropanecarboxamide | 1.96 | 376.47 |

TABLE B1-continued

| Ex. | R | Name | HPLC Retention (min) | MS Reported |
|---|---|---|---|---|
| B8 | –CH2–OH | N-[1-[3-(1,6-dihydro-1-methylimidazo[4,5-d]pyrrolo[2,3-b]pyridin-7-yl)phenyl]ethyl]-2-hydroxy-acetamide | 1.82 | 350.42 |
| B9 | –CH2–NH–C(O)–Me | 2-(acetylamino)-N-[1-[3-(1,6-dihydro-1-methylimidazo[4,5-d]pyrrolo[2,3-b]pyridin-7-yl)phenyl]ethyl]-acetamide | 1.81 | 391.46 |
| B10 | –CH2–OMe | N-[1-[3-(1,6-dihydro-1-methylimidazo[4,5-d]pyrrolo[2,3-b]pyridin-7-yl)phenyl]ethyl]-2-methoxy-acetamide | 1.99 | 364.44 |

Example B11

N-[[3-(1,6-dihydro-1-methylimidazo[4,5-d]pyrrolo[2,3-b]pyridin-7-yl)phenyl]methyl]-acetamide

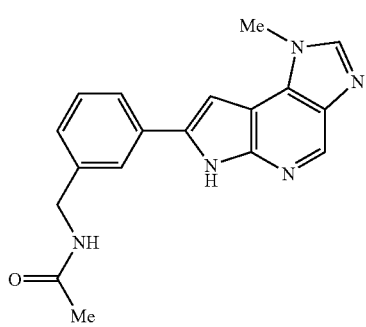

Diisopropylethylamine (24.7 μL, 0.184 mmol) was added to a solution of B3 (10.0 mg, 0.036 mmol), EDC (13.82 mg, 0.072 mmol), 1-Hydroxybenzotriazole hydrate (6.63 mg, 0.043 mmol), and acetic acid (2.68 μL, 0.046 mmol) in DMF (0.72 mL). The reaction mixture was heated at 60° C. for 50.0 min. in sealed vials on a platform shaker. After solvent removal, the crude product was purified by reversed-phase preparative HPLC to yield 9.3 mg of B11 as a tan solid (60% assuming 1.0 mol TFA). HPLC (C): 91.1%, ret. time 1.73 min., LC/MS (M+H)$^+$=320.36.

Examples B12-B16

Examples B12-B16 were prepared in a manner similar to that used for example B11.

TABLE B2

| Ex. | R | Name | HPLC Retention (min) | MS Reported |
|---|---|---|---|---|
| B12 | –CH2CH2–OMe | N-[[3-(1,6-dihydro-1-methylimidazo[4,5-d]pyrrolo[2,3-b]pyridin-7-yl)phenyl]methyl]-3-methoxy-propanamide | 1.73 | 364.39 |
| B13 | 2-pyridyl | N-[[3-(1,6-dihydro-1-methylimidazo[4,5-d]pyrrolo[2,3-b]pyridin-7-yl)phenyl]methyl]-2-pyridinecarboxamide | 2.22 | 383.37 |
| B14 | 2-(MeO2S)-phenyl | N-[[3-(1,6-dihydro-1-methylimidazo[4,5-d]pyrrolo[2,3-b]pyridin-7-yl)phenyl]methyl]-2-(methylsulfonyl)-benzamide | 2.00 | 460.33 |
| B15 | –CH2–CN | 2-cyano-N-[[3-(1,6-dihydro-1-methylimidazo[4,5-d]pyrrolo[2,3-b]pyridin-7-yl)phenyl]methyl]-acetamide | 1.67 | 345.38 |
| B16 | –CH(Me)2 | N-[[3-(1,6-dihydro-1-methylimidazo[4,5-d]pyrrolo[2,3-b]pyridin-7-yl)phenyl]methyl]-2-methyl-propanamide | 1.92 | 348.42 |

HPLC conditions used to determine retention times; LCMS conditions=B: 4 min gradient 0-100% B in A (A; 0.1% TFA in 90/10 water/methanol; B; 0.1% TFA in 10/90 water/methanol) using a Waters Sunfire C18 (4.6×50 mm) column at with a detection wavelength of 220 nanometers.

Example C1

3-(1,6-dimethyl-4-(methylamino)-1,6-dihydroimidazo[4,5-d]pyrrolo[2,3-b]pyridin-7-yl)-5-fluorobenzonitrile

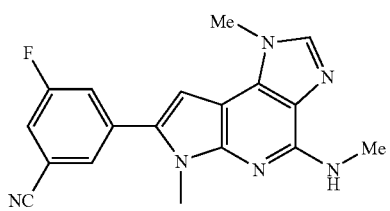

C1.1: 3-fluoro-5-((trimethylsilyl)ethynyl)benzonitrile

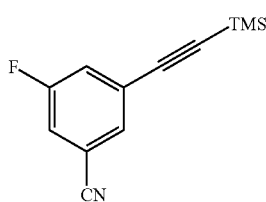

To a solution of commercially available 3-bromo-5-fluorobenzonitrile (5 g, 25 mmol) and triethylamine (35 ml) in 35 ml of THF was bubbled nitrogen for 10 min. Then added trimethylsilylacetylene (5.0 g, 50 mmol), copper iodide (60 mg, 0.31 mmol), and PdCl$_2$(PPh$_3$)$_2$ (80 mg, 0.11 mmol) and the reaction mixture was heated with a heating mantle. After an initial exotherm, the reaction was heated at reflux for 3 hrs. The reaction mixture was concentrated on a rotary evaporator and the dark residue diluted with hexane and washed with water three times. The hexane layer was filtered through Celite and the filtrate was concentrated to give a brown oil. The crude material was used without further purification. LCMS B: Ret time 3.96 min, (M+H)$^+$=218.14. $^1$H NMR, 400 MHz, CDCl$_3$: 7.57 (s, 1H), 7.43 (m, 1H), 7.35 (m, 1H), 0.26 (s, 9H).

C1.2: 3-ethynyl-5-fluorobenzonitrile

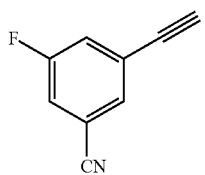

To a solution of 5.4 g (0.025 mol) of C1.1 in 40 ml of THF was added a 1 mL solution of 30% potassium hydroxide in water. The reaction mixture was stirred at RT for 1 hr. The reaction mixture was concentrated on a rotary evaporator and the dark residue diluted with ethyl acetate. The extract was washed with water, brine and concentrated. The product was purified on silica gel column using 5% of ethyl acetate in hexane to give 2.5 g (69%) of C1.2 as a white solid. LCMS B: Ret time 2.63 min, (M+H)$^+$=145.98. $^1$H NMR, 400 MHz, CDCl$_3$: 7.57 (s, 1H), 7.42 (dm, 1H), 7.35 (dm, 1H), 3.25 (s, 1H).

C1.3: tert-butyl 6-amino-7-((3-cyano-5-fluorophenyl)ethynyl)-1-methyl-1H-imidazo[4,5-c]pyridin-4-yl(methyl)carbamate

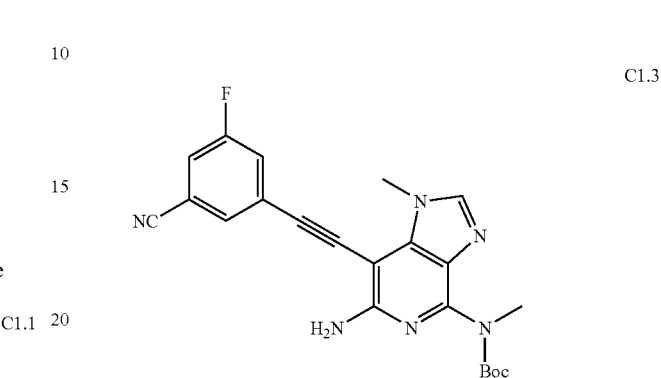

A1.12 tert-Butyl-6-amino-7-iodo-1-methyl-1H-imidazo[4,5-c]pyridin-4-yl (methyl)carbamate (3.2 g, 7.9 mmol), dichlorobis(triphenylphosphine)palladium (270 mg, 0.38 mmol), 3-ethynyl-5-fluorobenzonitrile (C1.2) (1.5 g, 10 mmol), CuI (75 mg, 0.39 mmol), diisopropylamine (15 mL) were added to N,N-dimethylformamide (15 mL). The reaction mixture was heated at 90° C. (in preheated oil bath) for 60 min. Additional 3-ethynyl-5-fluorobenzonitrile (C1.2) (0.5 g, 3.4 mmol) was added to the reaction mixture and heated for another 60 min. The reaction was cooled and diluted with ethyl acetate and washed several times with water. The solvent removed under reduced pressure and the residue was purified by silica gel column chromatography (50%-70% ethyl acetate/hexane) to give 3.0 g (90%) of C1.3. LCMS B: Ret time 2.98 min, (M+H)=421.31, $^1$H NMR, 400 MHz, CDCl$_3$: 7.62 (s, 1H), 7.57 (s, 1H), 7.42 (dm, 1H), 7.35 (dm, 1H), 5.00 (bs, 2H), 4.05 (s, 3 H), 3.39 (s, 3 H), 1.44 (s, 9 H).

C1.4: tert-butyl 7-((3-cyano-5-fluorophenyl)ethynyl)-1-methyl-6-(2,2,2-trifluoroacetamido)-1H-imidazo[4,5-c]pyridin-4-yl(methyl)carbamate

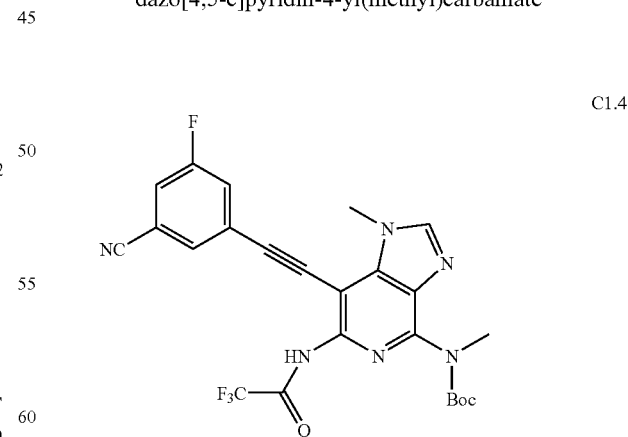

A solution of C1.3 (2.9 g, 6.9 mmol) and triethylamine (1.4 g, 14 mmol) in methylene chloride was cooled in an ice bath and treated dropwise with a solution of trifluoroacetic acid anhydride (2.9 g, 13.8 mmol) in 4 ml of methylene chloride. The reaction was stirred at 0° C. for 1 hr. The mixture was washed with water, sat'd NaHCO$_3$, and brine. Dried over Na$_2$SO$_4$, filtered and concentrated to give 3.5 g of C1.4 as tan solid. LCMS B: Ret time 3.38 min, (M+H−Boc)$^+$=417.18.

C1.5: tert-butyl 7-(3-cyano-5-fluorophenyl)-1-methyl-1,6-dihydroimidazo[4,5-d]pyrrolo[2,3-b]pyridin-4-yl(methyl)carbamate

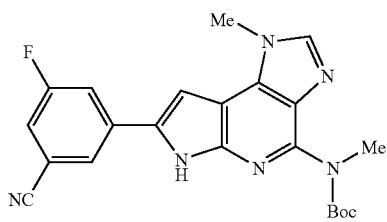

A solution of C1.4 (1.7 g, 3.3 mmol) in dimethylacetamide (18 mL) was treated with K$_2$CO$_3$ (0.63 g, 4.6 mmol) and dichlorobis(triphenylphosphine)palladium (55 mg, 0.08 mmol) and heated at 110° C. in an oil bath for 8 hrs. The reaction was cooled, diluted with ethyl acetate and washed several times with water. The solvent removed under reduced pressure and the residue titurated with methanol. The solid was filtered and rinsed with CH$_2$Cl$_2$/Hexane mixture to give 0.77 g of C1.5 as tan solid. The combined filtrates were concentrated and the residue was chromatographed on silica gel using ethyl acetate as the eluent to give an additional 200 mg of C1.5. LCMS B: Ret time 2.97 min, (M+H)$^+$=421.26, (M+H−Boc)$^+$=321.26.

C1.6: tert-butyl 7-(3-cyano-5-fluorophenyl)-1,6-dimethyl-1,6-dihydroimidazo[4,5-d]pyrrolo[2,3-b]pyridin-4-yl(methyl)carbamate

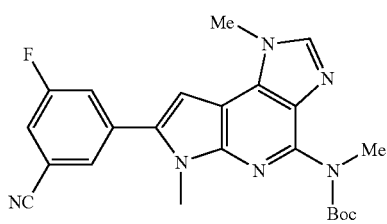

A solution of C1.5 (35 mg, 0.08 mmol) in DMF (2 ml) was cooled in an ice bath and treated with a 1 M solution of NaN(TMS)$_2$ (0.2 ml, 0.2 mmol) in THF and then with MeI (28 mg, 0.19 mmol). The mixture was stirred at 0° C. for 30 min and then at room temperature for 1 hour. The mixture was diluted with water and extracted into ethyl acetate. The organic extract was washed with water several times and concentrated to give C1.6 as a tan solid. LCMS B: Ret time 2.99 min, (M+H)$^+$=435.26, (M+H−Boc)$^+$=335.28. $^1$H NMR, 400 MHz, CDCl$_3$: 7.82 (s, 1H), 7.68 (s, 1H), 7.52 (dm, 1H), 7.41 (dm, 1H), 6.84 (s, 1H), 4.10 (s, 3 H), 3.97 (s, 3 H), 3.51 (s, 3H), 1.44 (s, 9 H).

C1: 3-(1,6-dimethyl-4-(methylamino)-1,6-dihydroimidazo[4,5-d]pyrrolo[2,3-b]pyridin-7-yl)-5-fluorobenzonitrile

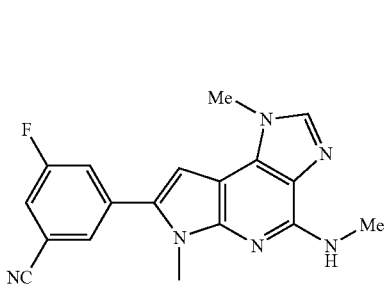

A solution of C1.6 (36 mg, 0.08 mmol) in CH$_2$Cl$_2$ (2 ml) was treated with 6 ml of TFA and stirred at room temperature for 1 hr. The mixture diluted with CH$_2$Cl$_2$ and concentrated on a rotary evaporator. The residue chromatographed on silica gel eluting with 8% NH$_4$OH/MeOH/CH$_2$Cl$_2$ (0.8:7.2:92) to give 20 mg of C1 as yellow solid. LCMS B: Ret time 2.65 min, (M+H)$^+$=335.27. $^1$H NMR, 400 MHz, CDCl$_3$: 7.63 (s, 1H), 7.62 (s, 1H), 7.47 (dm, 1H), 7.27 (dm, 1H), 6.70 (s, 1H), 5.50 (bs, 1 H), 4.03 (s, 3 H), 3.92 (s, 3 H), 3.23 (d, J=5 Hz, 3 H).

Example C2

3-[1,6-dihydro-1-methyl-4-(methylamino)imidazo[4,5-d]pyrrolo[2,3-b]pyridin-7-yl]-5-fluoro-benzonitrile

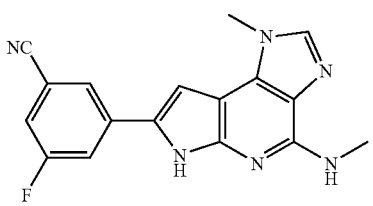

A solution of C1.5 (25 mg, 0.06 mmol) in CH$_2$Cl$_2$ (0.25 ml) was added TFA (0.25 ml) dropwise at 0-5° C. which was warmed up to RT and stirred for 20 minutes. The reaction mixture was concentrated and purified on prep. HPLC (condition G) to yield C2 (7.5 mg, 23%). HPLC: >95%, retention time: 2.382 minute LC/MS (M+H)$^+$=321, $^1$H-NMR (400 MHz, DMSO-d6) δ ppm 8.18 (1 H, s), 8.14 (1 H, s), 8.01 (1 H, d, J=10.17 Hz), 7.56 (1 H, d, J=7.63 Hz), 7.52 (1 H, s), 4.04 (3 H, s), 2.99 (3 H, s).

Example C3

3-(6-allyl-1-methyl-4-(methylamino)-1,6-dihydroimidazo[4,5-d]pyrrolo[2,3-b]pyridin-7-yl)-5-fluorobenzonitrile trifluoacetate salt

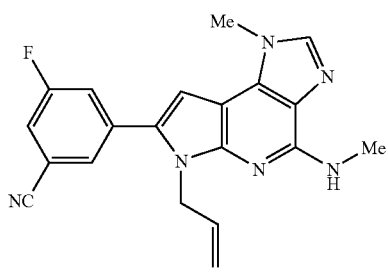

C3.1: tert-butyl 6-allyl-7-(3-cyano-5-fluorophenyl)-1-methyl-1,6-dihydroimidazo[4,5-d]pyrrolo[2,3-b]pyridin-4-yl(methyl)carbamate

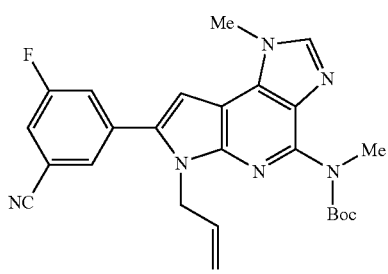

A solution of C1.5 (42 mg, 0.10 mmol) in DMF (3 ml) was cooled in an ice bath and treated with a 1 M solution of NaN(TMS)$_2$ (0.2 ml, 0.2 mmol) in THF and then with allyl iodide (33 mg, 0.20 mmol). The mixture was stirred at 0° C. for 30 min and then at room temperature for 1 hour. The mixture was diluted with water and extracted into ethyl acetate. The organic extract was washed with water several times and concentrated to give C3.1 as a tan solid. LCMS B: Ret time 3.20 min, (M+H)$^+$=461.26, (M+H−Boc)$^+$=361.26.

Alternate Preparation of C3.1

A solution of C2 (95 mg, 0.226 mmol) in DMF at 0-5° C. was added NaHMDS (0.407 ml, 0.407 mmol) and the reaction mixture was stirred at 0-5° C. for 10 minutes. Allyl bromide was added at 0-5° C. dropwise. The reaction mixture was warmed up to room temperature and stirred for 30 minutes. The reaction mixture was concentrated and then it was added water (2 ml) and stirred for 5 minutes. The solid was collected as C3.1 (100 mg, 96%). HPLC: 78%, retention time: 3.178 minute (condition B). LC/MS (M+H)$^+$=461, $^1$H-NMR (400 MHz, CD$_3$OD) δ ppm 8.03 (1 H, s), 7.78 (1 H, s), 7.66 (1 H, d, J=9.66 Hz), 7.53 (1 H, d, J=8.14 Hz), 7.08 (1 H, s), 5.83-6.00 (1 H, m), 4.93-5.04 (2 H, m), 4.58 (1 H, d, J=17.29 Hz), 4.02-4.12 (4 H, m), 3.27 (3 H, s), 1.19-1.34 (9 H, m).

Alternate Preparation of C3.1

A solution of C1.5 (500 mg, 1.19 mmol) in DMF (8 ml) was treated with Cs$_2$CO$_3$ (900 mg, 2.8 mmol) and allyl bromide (500 mg, 4.1 mmol) and stirred at room temperature overnight. The mixture was diluted with ethyl acetate (150 ml) and washed several times with water. The solution was concentrated on a rotary evaporator and the residue chromatographed on silica gel eluting with 2%-3% NH$_4$OH/MeOH/CH$_2$Cl$_2$ (0.2:1.8:98-0.3:2.7:97) to give C3.1 as a light yellow solid. LCMS B: Ret time 3.23 min, (M+H)$^+$=461.27. $^1$H NMR, 400 MHz, CDCl$_3$: 7.87 (s, 1H), 7.71 (s, 1H), 7.57 (dm, 1H), 7.39 (dm, 1H), 6.86 (s, 1H), 6.04 (m, 1H), 5.16 (m, 1H), 5.03 (m, 2H), 4.83 (m, 1H), 4.11 (s, 3H), 3.48 (s, 3H), 1.43 (s, 9H).

Also obtained was obtained from the column 100 mg of tert-butyl 8-allyl-7-(3-cyano-5-fluorophenyl)-1-methyl-1,6-dihydroimidazo[4,5-d]pyrrolo[2,3-b]pyridin-4-yl(methyl)carbamate C3.1a as an orange solid. LCMS B: Ret time 2.61 min, (M+H)$^+$=461.36

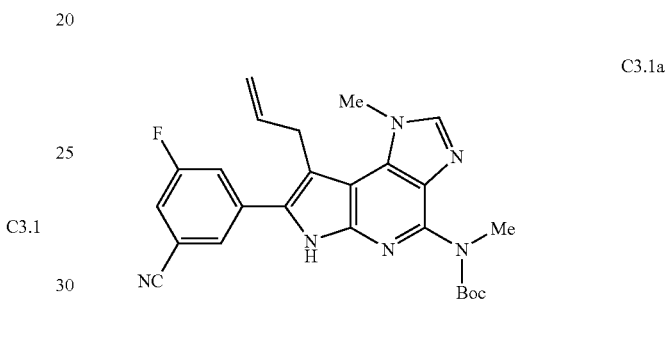

C3: 3-(6-allyl-1-methyl-4-(methylamino)-1,6-dihydroimidazo[4,5-d]pyrrolo[2,3-b]pyridin-7-yl)-5-fluorobenzonitrile trifluoacetate salt A solution of C2.1 (36 mg, 0.08 mmol) in CH$_2$Cl$_2$ (2 ml) was treated with 6 ml of TFA and stirred at room temperature for 1 hr. The mixture diluted with CH$_2$Cl$_2$ and concentrated on a rotary evaporator. The residue was purified by preparative HPLC and lyophilized to give 5 mg of C3 as yellow solid. LCMS B: Ret time 2.93 min, (M+H)$^+$=361.33.

Example C4 methyl 2-(7-(3-cyano-5-fluorophenyl)-1-methyl-4-(methylamino)imidazo[4,5-d]pyrrolo[2,3-b]pyridin-6 (1H)-yl)acetate

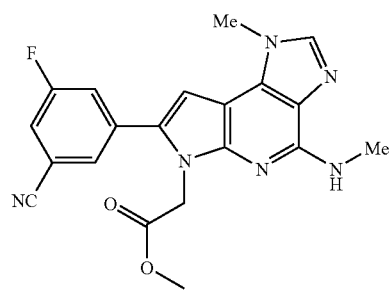

C4.1 methyl 2-(4-(tert-butoxycarbonyl(methyl)amino)-7-(3-cyano-5-fluorophenyl)-1-methylimidazo[4,5-d]pyrrolo[2,3-b]pyridin-6(1H)-yl)acetate

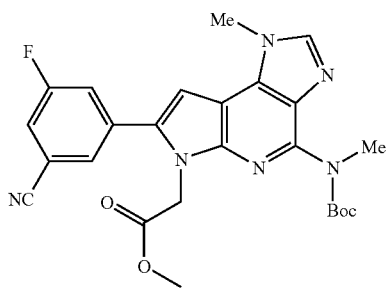

C4.1

A solution of C1.5 (200 mg, 0.47 mmol) in DMF (2 ml) was cooled in an ice bath and treated with a 1 M solution of NaN(TMS)$_2$ (1.0 ml, 1.0 mmol) in THF and then with methyl bromoacetate (250 mg, 1.6 mmol). The mixture was stirred at 0° C. for 30 min and then at room temperature for 1 hour. The mixture was diluted with water and extracted into ethyl acetate. The organic extract was washed with water several times and concentrated and the residue chromatographed on silica gel eluting with ethyl acetate to give 170 mg of C4.1 as a tan solid. LCMS B: Ret time 2.85 min, (M+H)$^+$=493.26, $^1$H NMR, 400 MHz, CDCl$_3$: 7.82 (s, 1H), 7.68 (m, 1H), 7.63 (s, 1H), 7.48 (m, 1H), 6.87 (s, 1H), 5.11 (s, 2H), 4.10 (s, 3 H), 3.75 (s, 3 H), 3.46 (s, 3H), 1.42 (s, 9H).

C4: methyl 2-(7-(3-cyano-5-fluorophenyl)-1-methyl-4-(methylamino)imidazo[4,5-d]pyrrolo[2,3-b]pyridin-6(1H)-yl)acetate A solution of C4.1 (20 mg, 0.04 mmol) in CH$_2$Cl$_2$ (2 ml) was treated with 6 ml of TFA and stirred at room temperature for 1 hr. The mixture diluted with CH$_2$Cl$_2$ and concentrated on a rotary evaporator. The residue chromatographed on silica gel eluting with 10% NH$_4$OH/MeOH/CH$_2$Cl$_2$ (1:9:90) to give 10 mg of C4 as yellow solid. LCMS B: Ret time 2.61 min, (M+H)$^+$=393.19. $^1$H NMR, 400 MHz, CDCl$_3$: 7.67 (s, 1H), 7.62 (s, 1H), 7.47 (m, 1H), 7.27 (m, 1H), 6.72 (s, 1H), 5.53 (bs, 1H), 5.05 (s, 2H), 4.01 (s, 3 H), 3.76 (s, 3 H), 3.15 (d, J=5 Hz, 3H).

Example C5

2-(7-(3-cyano-5-fluorophenyl)-1-methyl-4-(methylamino)imidazo[4,5-d]pyrrolo[2,3-b]pyridin-6(1H)-yl)acetamide trifluoacetate salt

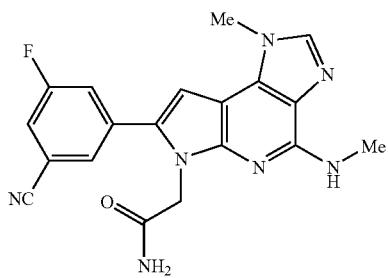

C5

C5.1: 2-(4-(tert-butoxycarbonyl(methyl)amino)-7-(3-cyano-5-fluorophenyl)-1-methylimidazo[4,5-d]pyrrolo[2,3-b]pyridin-6(1H)-yl)acetic acid

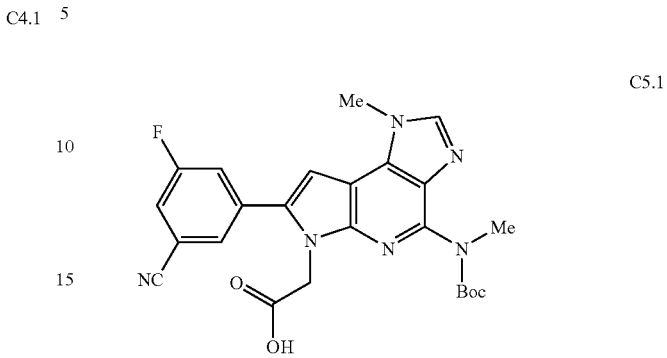

C5.1

A solution of C4.1 (150 mg, 0.3 mmol) in MeOH/THF (3 ml/3 ml) was treated with 3 ml of 1N NaOH and stirred at RT for 5 hours. Made acidic with 4 ml 1N HCl and extracted into ethyl acetate. Concentrated to give 100 mg of C5.1 as a solid. LCMS B: Ret time 2.67 min, (M+H)$^+$=479.20.

C5.2: tert-butyl 6-(2-amino-2-oxoethyl)-7-(3-cyano-5-fluorophenyl)-1-methyl-1,6-dihydroimidazo[4,5-d]pyrrolo[2,3-b]pyridin-4-yl(methyl)carbamate

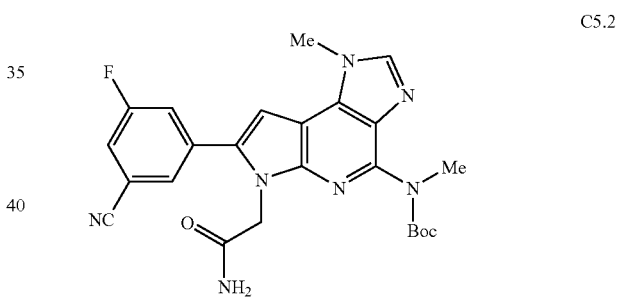

C5.2

A solution of C5.1 (50 mg, 0.10 mmol) in THF/DMF (3 ml/1 ml) was treated with EDC (24 mg, 0.12 mmol), HOBT (18 mg, 0.12 mmol), Et$_3$N (12 mg, 0.12 mmol) and 3 ml of a 0.5 M NH$_3$ (in dioxane) at RT and stirred overnight. The solvent was removed under vacuum and the residue dissolved in CH$_2$Cl$_2$ and washed with water. The CH$_2$Cl$_2$ was removed on a rotary evaporator and the residue chromatographed on silica gel eluting with 8% NH$_4$OH/MeOH/CH$_2$Cl$_2$ to give 20 mg of C5.2. LCMS B: Ret time 2.33 min, (M+H)$^+$=478.22.

C5: 2-(7-(3-cyano-5-fluorophenyl)-1-methyl-4-(methylamino)imidazo[4,5-d]pyrrolo[2,3-b]pyridin-6(1H)-yl)acetamide trifluoacetate salt A solution of C5.2 (20 mg, 0.04 mmol) in CH$_2$Cl$_2$ (2 ml) was treated with 6 ml of TFA and stirred at room temperature for 1 hr. The mixture diluted with CH$_2$Cl$_2$ and concentrated on a rotary evaporator. The residue was purified by preparative HPLC and lyophilized to give 4 mg of C5 as yellow solid. LCMS B: Ret time 2.05 min, (M+H)$^+$=378.20.

Example C6

3-(6-ethyl-1-methyl-4-(methylamino)-1,6-dihydroimidazo[4,5-d]pyrrolo[2,3-b]pyridin-7-yl)-5-fluorobenzonitrile

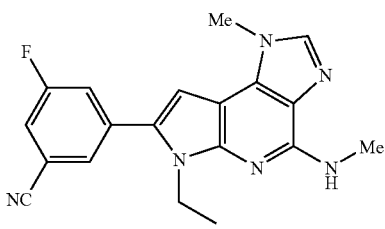

C6

This was obtained starting with intermediate C1.5 (20 mg, 0.048 mmol) and ethyl iodide (36 mg, 0.22 mmol) and using the procedure described for the synthesis of Example C1. Obtained 6 mg of C6 as a yellow solid. LCMS B: Ret time 2.93 min, $(M+H)^+=349.23$.

Example C7

3-fluoro-5-(1-methyl-4-(methylamino)-6-propyl-1,6-dihydroimidazo[4,5-d]pyrrolo[2,3-b]pyridin-7-yl)benzonitrile

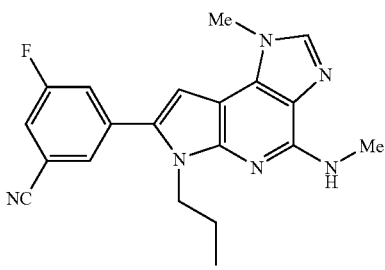

C7

This was obtained starting with intermediate C1.5 (20 mg, 0.048 mmol) and ethyl iodide (40 mg, 0.24 mmol) and using the procedure described for the synthesis of Example C1. Obtained 7 mg of C7 as a yellow solid. LCMS B: Ret time 3.11 min, $(M+H)^+=363.26$.

Example C8

3-fluoro-5-(6-(2-(2-hydroxyethylamino)ethyl)-1-methyl-4-(methylamino)-1,6-dihydroimidazo[4,5-d]pyrrolo[2,3-b]pyridin-7-yl)benzonitrile

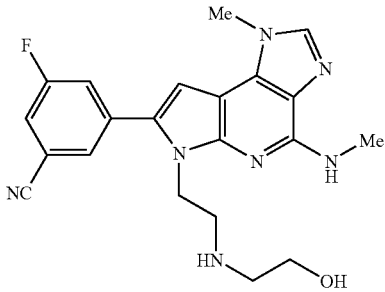

C8

C8.1: tert-butyl 7-(3-cyano-5-fluorophenyl)-6-(2,3-dihydroxypropyl)-1-methyl-1,6-dihydroimidazo[4,5-d]pyrrolo[2,3-b]pyridin-4-yl(methyl)carbamate

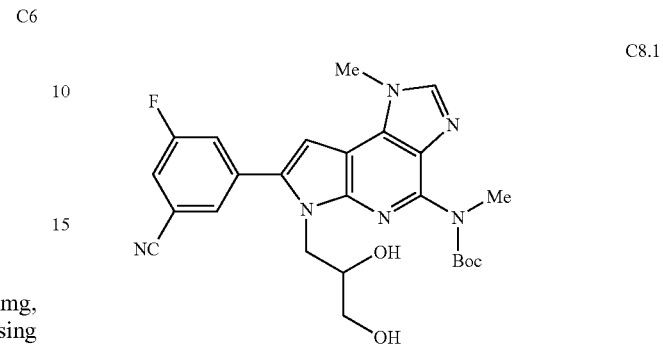

C8.1

A solution of C3.1 (480 mg, 1.04 mmol) in THF (10 ml) was treated with N-methylmorpholine N-oxide (257 mg, 2.19 mmol) in 2 ml of water and with 500 ul of a 4% aqueous $OsO_4$ solution. The solution was stirred at room temperature for 2 days and then concentrated on a rotary evaporator. The residue was dissolved in ethyl acetate and washed with water, a solution of $NaHSO_3$ and brine. The solution was concentrated on a rotary evaporator to give 490 mg of C8.1 as a solid. LCMS B: Ret time 2.61 min, $(M+H)^+=495.23$.

C8.2: tert-butyl 7-(3-cyano-5-fluorophenyl)-1-methyl-6-(2-oxoethyl)-1,6-dihydroimidazo[4,5-d]pyrrolo[2,3-b]pyridin-4-yl(methyl)carbamate

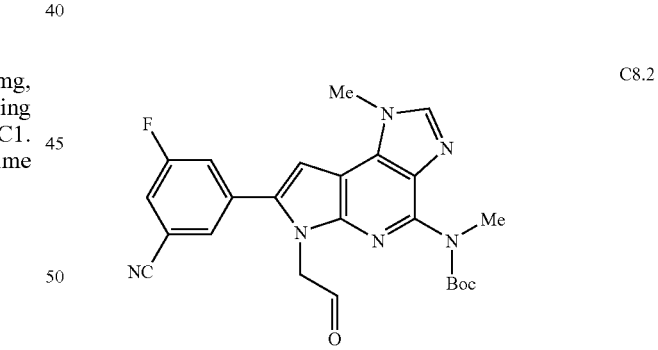

C8.2

A solution of C8.1 (450 mg, 0.91 mmol) in THF (15 ml) was treated with a 5 ml aqueous solution of $NaIO_4$ (500 mg, 2.34 mmol) and stirred overnight at RT. The solution was diluted with water and extracted into ethyl acetate. The extracts were washed with water and brine and concentrated to give 360 mg of C8.2 as a dark solid. This was used without further purification. LCMS B: Ret time 2.91 min. ES$^-$: $(M-H)^-=461.29$. $^1$H NMR, 400 MHz, $CDCl_3$: 9.77 (s, 1H), 7.85 (s, 1H), 7.58 (s, 1H), 7.41 (m, 2H), 6.91 (s, 1H), 5.23 (s, 2 H), 4.09 (s, 3 H), 3.43 (s, 3 H), 1.42 (s, 9H).

C8.3: tert-butyl 7-(3-cyano-5-fluorophenyl)-6-(2-(2-hydroxyethylamino)ethyl)-1-methyl-1,6-dihydroimidazo[4,5-d]pyrrolo[2,3-b]pyridin-4-yl(methyl)carbamate

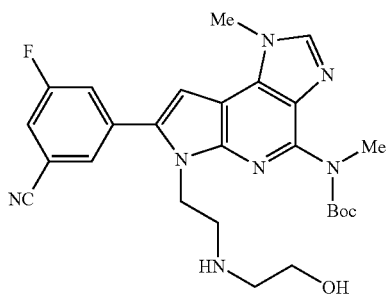

C8.3a

A solution of C8.2 (45 mg, 0.097 mmol) in MeOH (5 ml) was treated with ethanolamine (85 mg, 1.39 mmol), NaCNBH₃ (20 mg, 0.32 mmol), 1 drop of AcOH and stirred overnight at RT. The mixture was concentrated and the residue diluted with 1 N NaOH and extracted into ethyl acetate. The extracts were washed with water, brine and concentrated to give a solid which was chromatographed on silica gel eluting with 5% NH₄OH/MeOH/CH₂Cl₂ (0.5:4.5:95) to give 20 mg of C8.3a as a white solid. LCMS B: Ret time 2.16 min, (M+H)$^+$=508.28. $^1$H NMR, 400 MHz, CDCl₃: 7.83 (s, 1H), 7.75 (s, 1H), 7.63 (dm, 1H), 7.42 (dm, 1H), 6.82 (s, 1H), 4.56 (t, J=6 Hz, 2H), 4.10 (s, 3 H), 3.49 (s, 3H), 3.49 (m, 2H), 3.01 (t, J=6 Hz, 2H), 2.67 (t, J=5 Hz, 2H), 1.46 (s, 9 H).

Also obtained from the column was 15 mg of tert-butyl 6-(2-cyano-2-(2-hydroxyethylamino)ethyl)-7-(3-cyano-5-fluorophenyl)-1-methyl-1,6-dihydroimidazo[4,5-d]pyrrolo[2,3-b]pyridin-4-yl(methyl)carbamate C8.3b as a white solid. LCMS B: Ret time 2.50 min, (M+H)$^+$=533.27. $^1$H NMR, 400 MHz, CDCl₃: 7.86 (s, 1H), 7.71 (s, 1H), 7.59 (dm, 1H), 7.46 (dm, 1H), 6.85 (s, 1H), 4.75 (m, 1H), 4.64 (m, 1H), 4.41 (m, 1H), 4.10 (s, 3 H), 3.56 (m, 2H), 3.50 (s, 3H), 3.01 (m, 1), 2.67 (m, 1H), 1.49 (s, 9 H).

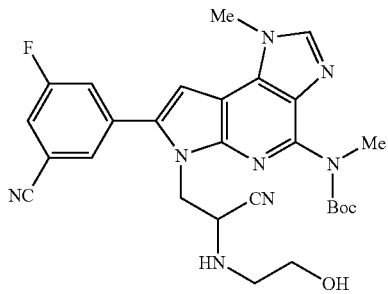

C8.3b

C8: 3-fluoro-5-(6-(2-(2-hydroxyethylamino)ethyl)-1-methyl-4-(methylamino)-1,6-dihydroimidazo[4,5-d]pyrrolo[2,3-b]pyridin-7-yl)benzonitrile A solution of C8.3a (20 mg, 0.039 mmol) in CH₂Cl₂ (2 ml) was treated with 6 ml of TFA and stirred at room temperature for 1 hr. The mixture diluted with CH₂Cl₂ and concentrated on a rotary evaporator. The residue was treated with 1 N NaOH and extracted into CH₂Cl₂ and washed with water and brine. The solvent was removed under vacuum to give 10 mg of C8 as yellow solid. LCMS B: Ret time 1.81 min, (M+H)$^+$=408.31. $^1$H NMR, 400 MHz, CDCl₃: 7.68 (s, 1H), 7.62 (s, 1H), 7.53 (dm, 1H), 7.29 (dm, 1H), 6.67 (s, 1H), 5.54 (t, J=5 Hz, 1H), 4.49 (t, J=4 Hz, 2H), 4.02 (s, 3H), 3.55 (t, J=5 Hz, 2H), 3.20 (d, J=5 Hz, 3H), 3.07 (t, J=6 Hz, 2H), 2.73 (t, J=5 Hz, 2H).

Example C9

3-(6-(2-cyano-2-(2-hydroxyethylamino)ethyl)-1-methyl-4-(methylamino)-1,6-dihydroimidazo[4,5-d]pyrrolo[2,3-b]pyridin-7-yl)-5-fluorobenzonitrile

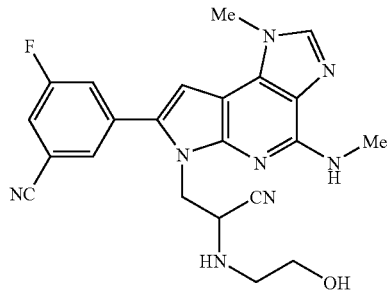

A solution of C8.3b (15 mg, 0.028 mmol) in CH₂Cl₂ (2 ml) was treated with 5 ml of TFA and stirred at room temperature for 1 hr. The mixture diluted with CH₂Cl₂ and concentrated on a rotary evaporator. The residue was treated with 1 N NaOH and extracted into CH₂Cl₂ and washed with water and brine. The solvent was removed under vacuum to give 10 mg of C9 as yellow solid. LCMS B: Ret time 2.10 min, (M+H)$^+$=433.28. $^1$H NMR, 400 MHz, CDCl₃: 7.66 (bs, 1H), 7.63 (s, 1H), 7.52 (dm, 1H), 7.32 (dm, 1H), 6.68 (s, 1H), 5.64 (bt, J=5 Hz, 1H), 4.64-4.45 (m, 3H), 4.02 (s, 3 H), 3.59 (t, J=5 Hz, 2H), 3.18 (d, J=5 Hz, 3H), 2.93 (m, 1H), 2.72 (m, 1H).

Example C10

3-(6-(3-(1,3-dioxoisoindolin-2-yl)propyl)-1-methyl-4-(methylamino)-1,6-dihydroimidazo[4,5-d]pyrrolo[2,3-b]pyridin-7-yl)-5-fluorobenzonitrile

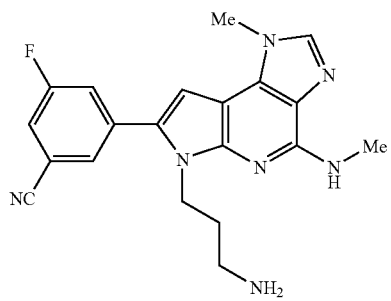

C10

C10.1: tert-butyl 7-(3-cyano-5-fluorophenyl)-6-(3-(1,3-dioxoisoindolin-2-yl)propyl)-1-methyl-1,6-dihydroimidazo[4,5-d]pyrrolo[2,3-b]pyridin-4-yl(methyl)carbamate

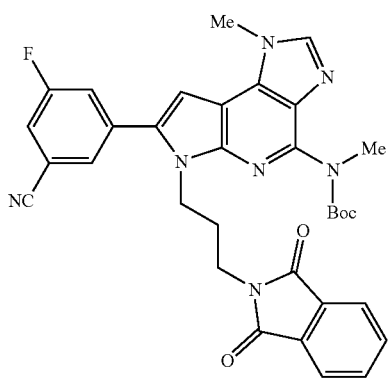

C10.1

A solution of C1.5 (42 mg, 0.10 mmol) in DMF (5 ml) was treated with $Cs_2CO_3$ (268 mg, 0.8 mmol) and N-(3-bromopropyl)phthalimide (120 mg, 0.45 mmol) and heated at 95° C. in an oil bath for 7 hrs. The mixture was diluted with ethyl acetate (150 ml) and washed several times with water. The solution was concentrated on a rotary evaporator and the residue chromatographed on silica gel eluting with 75% ethyl acetate/hexane to give 30 mg of C10.1 as a yellow solid. LCMS B: Ret time 3.27 min, $(M+H)^+=608.30$.

C10.2: 3-(6-(3-(1,3-dioxoisoindolin-2-yl)propyl)-1-methyl-4-(methylamino)-1,6-dihydroimidazo[4,5-d]pyrrolo[2,3-b]pyridin-7-yl)-5-fluorobenzonitrile A solution of C10.1 (30 mg, 0.05 mmol) in $CH_2Cl_2$ (2 ml) was treated with 6 ml of TFA and stirred at room temperature for 1 hr. The mixture diluted with $CH_2Cl_2$ and concentrated on a rotary evaporator. The residue was treated with sat'd $NaHCO_3$ and extracted into $CH_2Cl_2$. The solvent was evaporated under vacuum and the residue chromatographed on silica gel eluting with $NH_4OH/MeOH/CH_2Cl_2$ (0.5:4.5:95) to give 20 mg of C10.2 as yellow solid. LCMS B: Ret time 2.95 min, $(M+H)^+=508.22$.

C10.3: 3-(6-(3-aminopropyl)-1-methyl-4-(methylamino)-1,6-dihydroimidazo[4,5-d]pyrrolo[2,3-b]pyridin-7-yl)-5-fluorobenzonitrile A solution of C10.2 (10 mg, 0.02 mmol) in ethanol (6 ml) was treated with 1 ml of hydrazine and stirred heated to reflux for 1 hr. The mixture was concentrated on a rotary evaporator and the residue extracted into $CH_2Cl_2$ and washed with water. The solvent was evaporated under vacuum and the residue chromatographed on silica gel eluting with $NH_4OH/MeOH/CH_2Cl_2$ (1:9:90) to give 4 mg of C10 as yellow solid. LCMS B: Ret time 2.03 min, $(M+H)^+=378.26$.

Example C12

3-fluoro-5-(1-methyl-4-(methylamino)-6-(2-(pyrrolidin-1-yl)ethyl)-1,6-dihydroimidazo[4,5-d]pyrrolo[2,3-b]pyridin-7-yl)benzonitrile

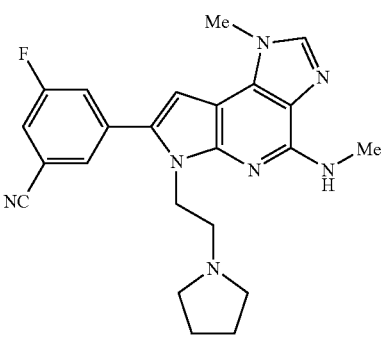

This was obtained, using the procedure described for the synthesis of Example C8, as a yellow solid. LCMS B: Ret time 1.92 min, $(M+H)^+=418.29$.

Example C13

3-fluoro-5-(6-(2-(3-hydroxypyrrolidin-1-yl)ethyl)-1-methyl-4-(methylamino)-1,6-dihydroimidazo[4,5-d]pyrrolo[2,3-b]pyridin-7-yl)benzonitrile

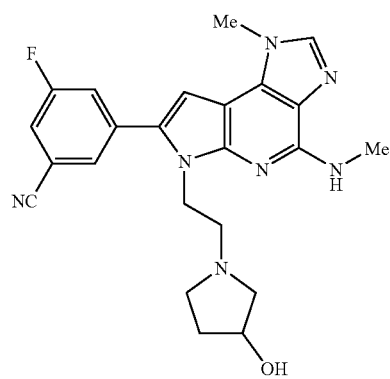

This was obtained, using the procedure described for the synthesis of Example C8, as a yellow solid. LCMS B: Ret time 1.86 min, $(M+H)^+=434.29$.

Example C14

3-(6-(2-cyano-2-(3-hydroxypyrrolidin-1-yl)ethyl)-1-methyl-4-(methylamino)-1,6-dihydroimidazo[4,5-d]pyrrolo[2,3-b]pyridin-7-yl)-5-fluorobenzonitrile

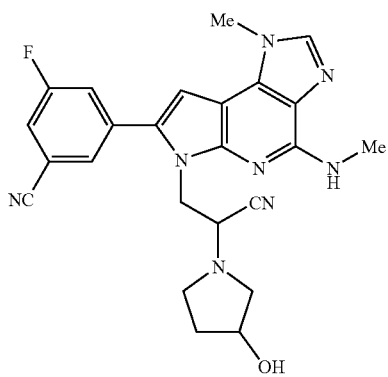

This was obtained, using the procedure described for the synthesis of Example C9, as a yellow solid. LCMS B: Ret time 2.52 min, (M+H)$^+$=459.27.

Example C15

3-(6-(2-(tert-butylamino)ethyl)-1-methyl-4-(methylamino)-1,6-dihydroimidazo[4,5-d]pyrrolo[2,3-b]pyridin-7-yl)-5-fluorobenzonitrile

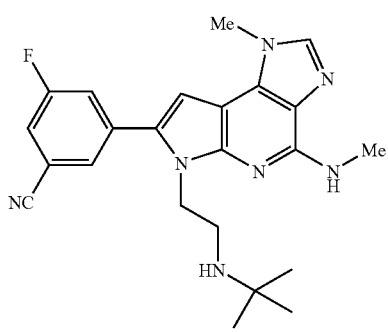

This was obtained, using the procedure described for the synthesis of Example C8, as a yellow solid. LCMS B: Ret time 2.06 min, (M+H)$^+$=420.30.

Example C16

3-(6-(2-(tert-butylamino)-2-cyanoethyl)-1-methyl-4-(methylamino)-1,6-dihydroimidazo[4,5-d]pyrrolo[2,3-b]pyridin-7-yl)-5-fluorobenzonitrile

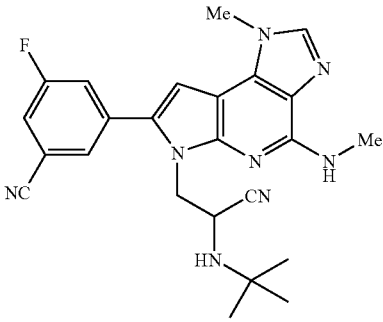

This was obtained, using the procedure described for the synthesis of Example C9, as a yellow solid. LCMS B: Ret time 2.55 min, (M+H)$^+$=445.31.

Example C17

3-(6-(2-(dimethylamino)ethyl)-1-methyl-4-(methylamino)-1,6-dihydroimidazo[4,5-d]pyrrolo[2,3-b]pyridin-7-yl)-5-fluorobenzonitrile

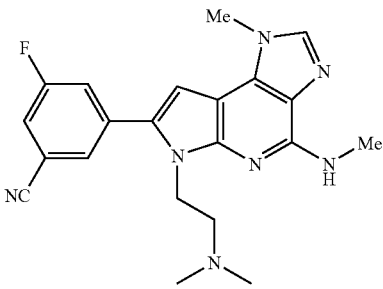

This was obtained, using the procedure described for the synthesis of Example C8, as a yellow solid. LCMS B: Ret time 1.82 min, (M+H)$^+$=392.30.

Example C18

3-(6-(2-cyano-2-(dimethylamino)ethyl)-1-methyl-4-(methylamino)-1,6-dihydroimidazo[4,5-d]pyrrolo[2,3-b]pyridin-7-yl)-5-fluorobenzonitrile

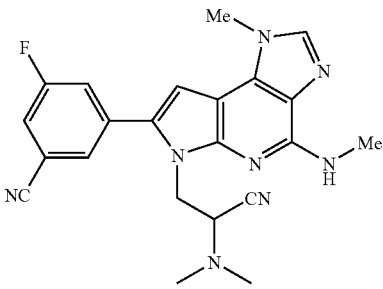

This was obtained, using the procedure described for the synthesis of Example C9, as a yellow solid. LCMS B: Ret time 2.55 min, (M+H)$^+$=418.34.

Example C19

(S)-3-fluoro-5-(6-(2-(1-hydroxypropan-2-ylamino)ethyl)-1-methyl-4-(methylamino)-1,6-dihydroimidazo[4,5-d]pyrrolo[2,3-b]pyridin-7-yl)benzonitrile

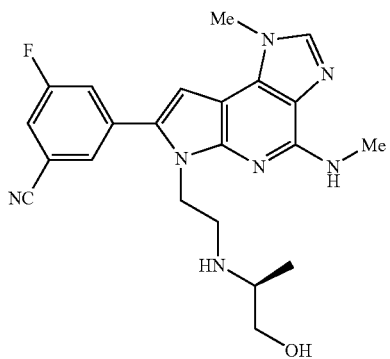

This was obtained, using the procedure described for the synthesis of Example C8, as a yellow solid. LCMS B: Ret time 1.91 min, (M+H)⁺=422.25.

Example C20

3-(6-(2-cyano-2-((S)-1-hydroxypropan-2-ylamino)ethyl)-1-methyl-4-(methylamino)-1,6-dihydroimidazo[4,5-d]pyrrolo[2,3-b]pyridin-7-yl)-5-fluorobenzonitrile

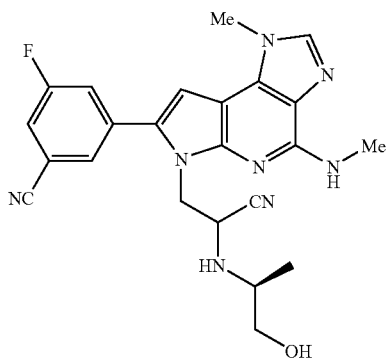

This was obtained, using the procedure described for the synthesis of Example C9, as a yellow solid (mixture of diastereomers). LCMS B: Ret time 2.29 and 2.22 min, (M+H)⁺=447.25.

Example C21

(S)-3-fluoro-5-(6-(2-(1-hydroxybutan-2-ylamino)ethyl)-1-methyl-4-(methylamino)-1,6-dihydroimidazo[4,5-d]pyrrolo[2,3-b]pyridin-7-yl)benzonitrile

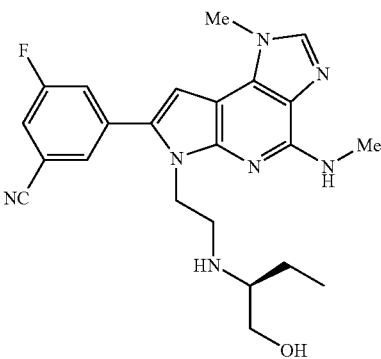

This was obtained, using the procedure described for the synthesis of Example C8, as a yellow solid. LCMS B: Ret time 1.99 min, (M+H)⁺=436.26.

Example C22

3-(6-(2-cyano-2-((S)-1-hydroxybutan-2-ylamino)ethyl)-1-methyl-4-(methylamino)-1,6-dihydroimidazo[4,5-d]pyrrolo[2,3-b]pyridin-7-yl)-5-fluorobenzonitrile

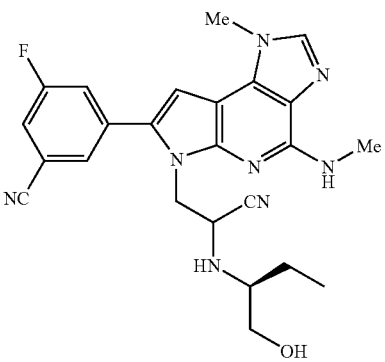

This was obtained, using the procedure described for the synthesis of Example C9, as a yellow solid (mixture of diastereomers). LCMS B: Ret time 2.42 and 2.51 min, (M+H)⁺=461.26.

Example C23

3-fluoro-5-(6-(2-hydroxyethyl)-1-methyl-4-(methylamino)-1,6-dihydroimidazo[4,5-d]pyrrolo[2,3-b]pyridin-7-yl)benzonitrile

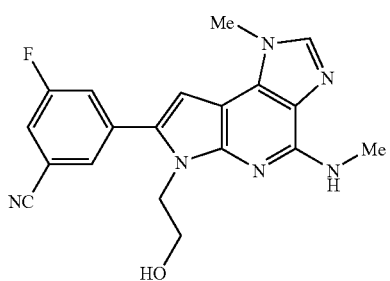

A solution of C8.3 (34 mg, 0.073 mmol) in ethanol (3 ml) was cooled to 0-5° C. and NaBH$_4$ (11 mg, 0.3 mmol) was added. The reaction mixture was warmed up to RT and stirred for 30 minutes. The reaction was quenched with acetone and concentrated to yield a crude product which was purified on prep HPLC (HPLC: Column: YMC 20×100 mm S-5; Gradient time: 10 min; Flow rate=20 ml/min; Solvent A=10% MeOH—90% Water—0.1% TFA; Solvent B=90% MeOH—10% water—0.1% TFA; Start % B=20; Final % B=100.) to provide the Boc protected intermediate, which dissolved in CH$_2$Cl$_2$ (0.25 ml) and added TFA (0.25 ml) dropwise at 0-5° C. The reaction mixture was warmed up to RT, stirred for 10 minutes and concentrated to yield C23 (8 mg, 19%). HPLC: 99%, retention time: 2.277 minute (condition B). LC/MS (M+H)$^+$=365, $^1$H-NMR (400 MHz, CD$_3$OD) δ ppm 8.29 (1 H, s), 7.73 (1 H, s), 7.58-7.67 (1 H, m), 7.51 (1 H, s), 6.94 (1 H, s), 4.29 (2 H, m), 4.05 (3 H, s), 3.99-4.03 (2 H, m), 3.09 (3 H, s).

Example C24 ethyl 4-((7-(3-cyano-5-fluorophenyl)-1-methyl-4-(methylamino)imidazo[4,5-d]pyrrolo[2,3-b]pyridin-6(1H)-yl)methyl)benzoate

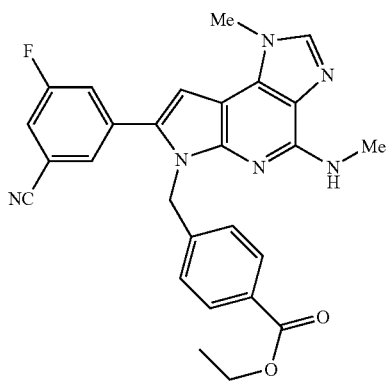

This was obtained, using the procedure described for the synthesis of Example C10, as a yellow solid. LCMS B: Ret time 3.28 min, (M+H)$^+$=469.21.

Example C25

3-fluoro-5-(6-(2-methoxyethyl)-1-methyl-4-(methylamino)-1,6-dihydroimidazo[4,5-d]pyrrolo[2,3-b]pyridin-7-yl)benzonitrile

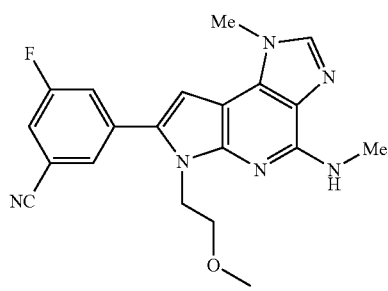

This was obtained, using the procedure described for the synthesis of Example C10, as a yellow solid. LCMS B: Ret time 2.72 min, (M+H)$^+$=379.23.

Example C26

3-(6-(3,4-dihydroxybutyl)-1-methyl-4-(methylamino)-1,6-dihydroimidazo[4,5-d]pyrrolo[2,3-b]pyridin-7-yl)-5-fluorobenzonitrile

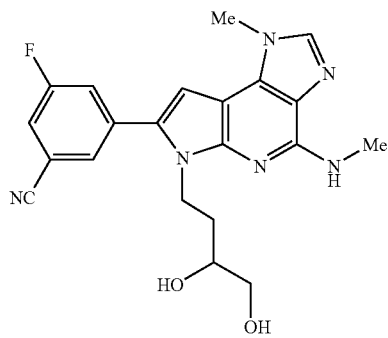

This was obtained, using the procedure described for the synthesis of Example C8.2, as a yellow solid. LCMS B: Ret time 2.28 min, (M+H)$^+$=409.23.

Example C27

3-(6-(3-amino-2-hydroxypropyl)-1-methyl-4-(methylamino)-1,6-dihydroimidazo[4,5-d]pyrrolo[2,3-b]pyridin-7-yl)-5-fluorobenzonitrile

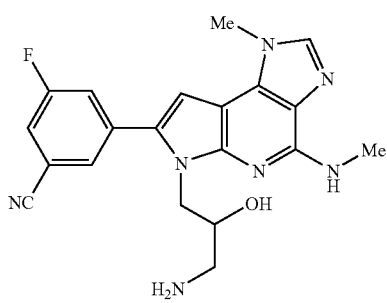

C27

C27.1: tert-butyl 7-(3-cyano-5-fluorophenyl)-1-methyl-6-(oxiran-2-ylmethyl)-1,6-dihydroimidazo[4,5-d]pyrrolo[2,3-b]pyridin-4-yl(methyl)carbamate

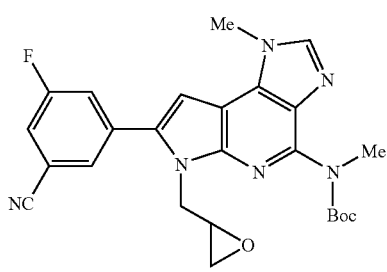

C27.1

A solution of C1.5 (300 mg, 0.71 mmol) in DMF (2 ml) was treated with $Cs_2CO_3$ (698 mg, 2.1 mmol) and epibromohydrin (195 mg, 1.4 mmol) and heated at 95° C. in an oil bath for 2 hrs. The mixture was diluted with ethyl acetate (150 ml) and washed several times with water. The solution was concentrated on a rotary evaporator and the residue chromatographed on silica gel eluting with ethyl acetate/hexane to give 200 mg of C27.1 as a solid. LCMS B: Ret time 2.95 min, $(M+H)^+=477.20$.

C27.2: 3-fluoro-5-(1-methyl-4-(methylamino)-6-(oxiran-2-ylmethyl)-1,6-dihydroimidazo[4,5-d]pyrrolo[2,3-b]pyridin-7-yl)benzonitrile

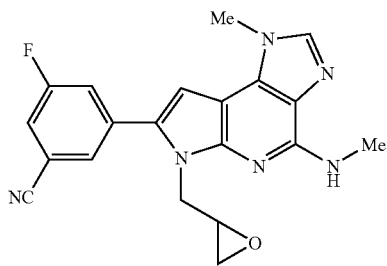

C27.2

A solution of C27.1 (100 mg, 0.21 mmol)) in $CH_2Cl_2$ (2 ml) was treated with 6 ml of TFA and stirred at room temperature for 1 hr. The mixture diluted with $CH_2Cl_2$ and concentrated on a rotary evaporator. The residue chromatographed on silica gel eluting with ethyl acetate to give 22 mg of CC27.2 as yellow solid. LCMS B: Ret time 2.58 min, $(M+H)^+=377.23$.

C27: 3-(6-(3-amino-2-hydroxypropyl)-1-methyl-4-(methylamino)-1,6-dihydroimidazo[4,5-d]pyrrolo[2,3-b]pyridin-7-yl)-5-fluorobenzonitrile A solution of C27.2 (22 mg, 0.06 mmol) in MeOH (2 mL) and 1 mL of NH4OH was heated in a microwave at 80° C. for 200 seconds. The solution was concentrated and chromatographed on silica gel eluting with 10% $NH_4OH/MeOH/CH_2Cl_2$ to give 8 mg of C27 as yellow solid. LCMS B: Ret time 2.17 min, $(M+H)^+=395.26$.

Example C28

3-(6-(2-aminoethyl)-1-methyl-4-(methylamino)-1,6-dihydroimidazo[4,5-d]pyrrolo[2,3-b]pyridin-7-yl)-5-fluorobenzonitrile trifluoacetate salt

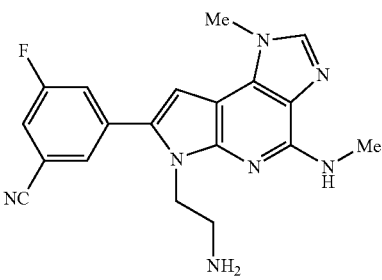

This was obtained, using the procedure described for the synthesis of Example C10 and C11, after HPLC purification and lypholization as a yellow solid. LCMS B: Ret time 1.88 min, $(M+H)^+=364.24$. $^1H$ NMR, 500 MHz, $CDCl_3/CD_3OD$: 7.55 (s, 1H), 7.38 (m, 2H), 7.26 (m, 1H), 6.65 (s, 1H), 4.46 (t, J=6 Hz, 2H), 4.09 (s, 3 H), 3.51 (t, J=5 Hz, 2H), 3.16 (bs, 3H).

Example 29

3-fluoro-5-(6-(2-hydroxypropyl)-1-methyl-4-(methylamino)-1,6-dihydroimidazo[4,5-d]pyrrolo[2,3-b]pyridin-7-yl)benzonitrile

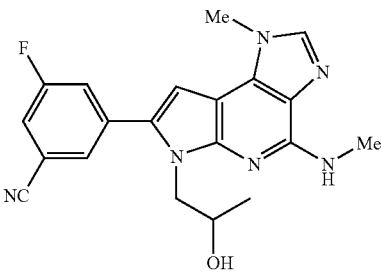

C29

C29.1: tert-butyl 7-(3-cyano-5-fluorophenyl)-6-(2-hydroxypropyl)-1-methyl-1,6-dihydroimidazo[4,5-d]pyrrolo[2,3-b]pyridin-4-yl(methyl)carbamate

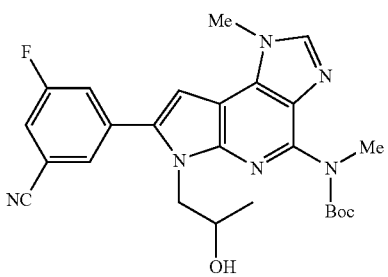

C29.1

A solution of C8.3 (50 mg, 0.10 mmol) in THF (5 ml) was cooled in an ice bath and treated with 0.1 ml of a 3 M solution of MeMgBr in ether. The solution was stirred at 0° C. for 1.5 hours and then quenched with water and extracted into ethyl acetate. The extract was washed with water, brine and concentrated to give 50 mg C29.1 as a solid. LCMS B: Ret time 2.91 min, (M+H)$^+$=479.34.

C29: 3-fluoro-5-(6-(2-hydroxypropyl)-1-methyl-4-(methylamino)-1,6-dihydroimidazo[4,5-d]pyrrolo[2,3-b]pyridin-7-yl)benzonitrile A solution of C29.1 (50 mg, 0.10 mmol) in CH$_2$Cl$_2$ (2 ml) was treated with 6 ml of TFA and stirred at room temperature for 1 hr. The mixture diluted with CH$_2$Cl$_2$ and concentrated on a rotary evaporator. The residue was treated with sat'd NaHCO3 and extracted into CH$_2$Cl$_2$. The solvent was evaporated under vacuum and the residue chromatographed on silica gel eluting with NH$_4$OH/MeOH/CH$_2$Cl$_2$ (0.5:2.5:97) to give 20 mg of C29 as yellow solid. LCMS B: Ret time 2.51 min, (M+H)$^+$=379.24. $^1$H NMR, 400 MHz, CDCl$_3$: 7.64 (s, 1H), 7.54 (s, 1H), 7.38 (m, 1H), 7.32 (m, 1H), 6.67 (s, 1H), 5.72 (bs, 1 H), 4.38 (m, 1H), 4.21 (m, 2H), 4.02 (s, 3 H), 3.17 (d, J=5 Hz, 3H), 1.28 (d, 7 Hz, 3H).

Example C30

7-(3-(aminomethyl)-5-fluorophenyl)-N,1,6-trimethyl-1,6-dihydroimidazo[4,5-d]pyrrolo[2,3-b]pyridin-4-amine

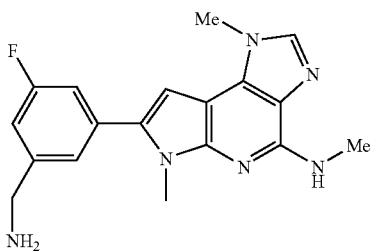

C30

C30.1: tert-butyl 7-(3-(aminomethyl)-5-fluorophenyl)-1-methyl-1,6-dihydroimidazo[4,5-d]pyrrolo[2,3-b]pyridin-4-yl(methyl)carbamate

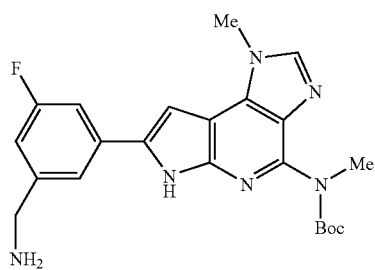

C30.1

A slurry of Raney-Nickel (1 g) was put in a Parr bottle and rinsed with ethanol and decanted. Then a solution of C1.5 (330 mg, 0.78 mmol) in 20 ml of ethanol and 3 ml of aqueous NH$_4$OH was added and the mixture hydrogenated overnight at 50 psi in a Parr shaker. The mixture was filtered and concentrated to give 320 mg of C30.1 as a light yellow solid. This was used without further purification. LCMS B: Ret time 2.16 min, (M+H)$^+$=425.27.

C30.2: tert-butyl 7-(3-(tert-butoxycarbonylaminomethyl)-5-fluorophenyl)-1-methyl-1,6-dihydroimidazo[4,5-d]pyrrolo[2,3-b]pyridin-4-yl(methyl)carbamate

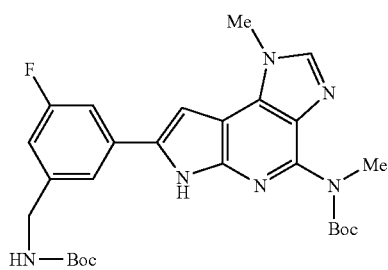

C30.2

A solution of C30.1 (320 mg, 0.78 mmol) in THF (20 ml) was treated with Et$_3$N (140 mg, 0.94 mmol), di-tert-butyl dicarbonate (240 mg, 1.1 mmol) and stirred at room temperature for 2 hours. The solvent removed under vacuum and the residue dissolved in ethyl acetate and washed with water, 1N NaOH, and brine. The solvent removed under vacuum to give 390 mg of C30.2 as a yellow solid. This was used without further purification. LCMS B: Ret time 3.24 min, (M+H)$^+$=525.36.

C30.3: tert-butyl 7-(3-(tert-butoxycarbonylaminomethyl)-5-fluorophenyl)-1,6-dimethyl-1,6-dihydroimidazo[4,5-d]pyrrolo[2,3-b]pyridin-4-yl(methyl)carbamate

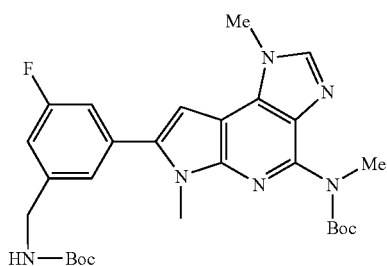

C30.3

A solution of C30.2 (48 mg, 0.09 mmol) in DMF (3 ml) was treated with Cs₂CO₃ (59 mg, 0.18 mmol) and MeI (40 mg, 0.18 mmol) and stirred at room temperature for 2 hours. The mixture was diluted with water and extracted into ethyl acetate. The extract was washed with water, concentrated and the residue chromatographed on silica gel, eluting with ethyl acetate to give 30 mg of C30.3 as a yellow solid. LCMS B: Ret time 3.39 min, $(M+H)^+=539.32$.

C30: 7-(3-(aminomethyl)-5-fluorophenyl)-N,1,6-trimethyl-1,6-dihydroimidazo[4,5-d]pyrrolo[2,3-b]pyridin-4-amine A solution of C30.3 (30 mg, 0.056 mmol) in CH₂Cl₂ (2 ml) was treated with 6 ml of TFA and stirred at room temperature for 1 hr. The mixture diluted with CH₂Cl₂ and concentrated on a rotary evaporator. The residue was treated with sat'd NaHCO₃ and extracted into CH₂Cl₂. The solvent was evaporated under vacuum and the residue chromatographed on silica gel eluting with NH₄OH/MeOH/CH₂Cl₂ (1:9:90) to give 12 mg of C30 as yellow solid. LCMS B: Ret time 1.92 min, $(M+H)^+=339.29$. ¹H NMR, 400 MHz, CDCl₃/CD₃OD: 7.65 (s, 1H), 7.33 (s, 1H), 7.20 (m, 1H), 7.06 (m, 1H), 6.67 (s, 1H), 4.03 (s, 3H), 4.01 (s, 2H), 3.90 (s, 3H), 2.97 (s, 3H).

Example C31

(S)-3-(7-(3-(aminomethyl)-5-fluorophenyl)-1-methyl-4-(methylamino)imidazo[4,5-d]pyrrolo[2,3-b]pyridin-6(1H)-yl)propane-1,2-diol

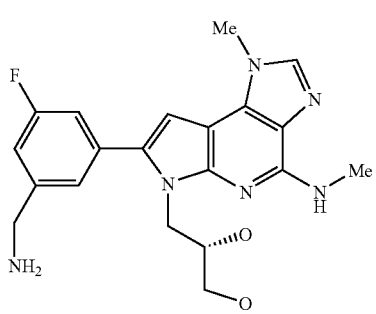

C31

C31.1: (S)-tert-butyl 7-(3-(tert-butoxycarbonylaminomethyl)-5-fluorophenyl)-6-((2,2-dimethyl-1,3-dioxolan-4-yl)methyl)-1-methyl-1,6-dihydroimidazo[4,5-d]pyrrolo[2,3-b]pyridin-4-yl(methyl)carbamate

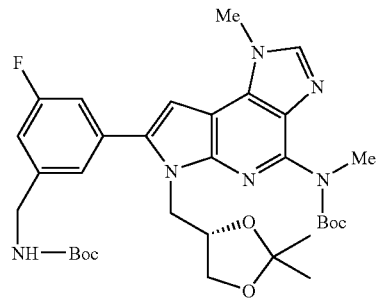

C31.1

A solution of C30.2 (48 mg, 0.09 mmol) in DMF (3 ml) was treated with Cs₂CO₃ (60 mg, 0.18 mmol) and (R)-(2,2-dimethyl-1,3-dioxolan-4-yl)methyl 4-methylbenzenesulfonate (85 mg, 0.29 mmol) and heated in an oil bath at 95° C. for 3 hours. The mixture was diluted with water and extracted into ethyl acetate. The extract was washed with water, concentrated and the residue chromatographed on silica gel, eluting with ethyl acetate to give 20 mg of C31.1 as a yellow solid. LCMS B: Ret time 3.48 min, $(M+H)^+=639.34$.

C31: (S)-3-(7-(3-(aminomethyl)-5-fluorophenyl)-1-methyl-4-(methylamino)imidazo[4,5-d]pyrrolo[2,3-b]pyridin-6(1H)-yl)propane-1,2-diol A solution of C31.1 (30 mg, 0.056 mmol) in CH₂Cl₂ (2 ml) was treated with 6 ml of TFA and stirred at room temperature for 1 hr. The mixture diluted with CH₂Cl₂ and concentrated on a rotary evaporator. The residue was treated with sat'd NaHCO₃ and extracted into CH₂Cl₂. The solvent was evaporated under vacuum and the residue chromatographed on silica gel eluting with NH₄OH/MeOH/CH₂Cl₂ (1:9:90) to give 8 mg of C31 as yellow solid. LCMS B: Ret time 1.63 min, $(M+H)^+=399.28$.

Example C32

(S)-3-(7-cyclohexyl-1-methyl-4-(methylamino)imidazo[4,5-d]pyrrolo[2,3-b]pyridin-6(1H)-yl)propane-1,2-diol

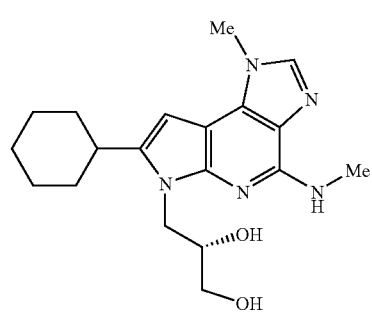

C32

C32.1: tert-butyl 6-amino-7-(cyclohexylethynyl)-1-methyl-1H-imidazo[4,5-c]pyridin-4-yl(methyl)carbamate

C32.3: (S)-tert-butyl 7-cyclohexyl-6-((2,2-dimethyl-1,3-dioxolan-4-yl)methyl)-1-methyl-1,6-dihydroimidazo[4,5-d]pyrrolo[2,3-b]pyridin-4-yl(methyl)carbamate

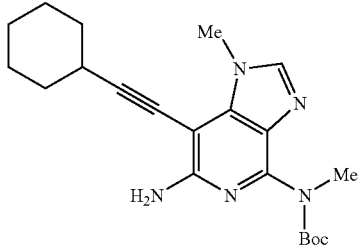

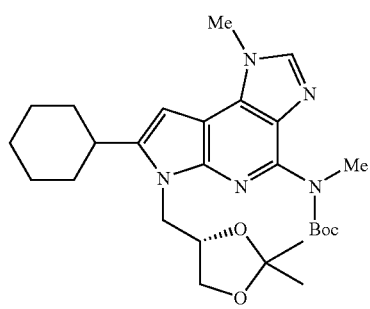

A1.12 tert-Butyl-6-amino-7-iodo-1-methyl-1H-imidazo[4,5-c]pyridin-4-yl(methyl)carbamate (1.0 g, 2.48 mmol), dichlorobis(triphenylphosphine)palladium (75 mg, 0.11 mmol), ethynylcyclohexane (0.3 g, 2.8 mmol), CuI (25 mg, 0.13 mmol), and diisopropylamine (5 mL) were added to N,N-dimethylformamide (7 mL). The reaction mixture was heated at 95° C. (in preheated oil bath) for 60 min. Additional ethynylcyclohexane (0.3 g, 2.8 mmol) was added to the reaction mixture and heated for another 60 min. The reaction was cooled and diluted with ethyl acetate and washed several times with water. The solvent removed under reduced pressure and the residue was chromatographed on a silica gel column (50%-70% ethyl acetate/hexane) to give 400 mg of C32.1 as a yellow solid. LCMS B: Ret time 3.15 min, $(M+H)^+=384.41$.

C32.2: tert-butyl 7-cyclohexyl-1-methyl-1,6-dihydroimidazo[4,5-d]pyrrolo[2,3-b]pyridin-4-yl(methyl)carbamate

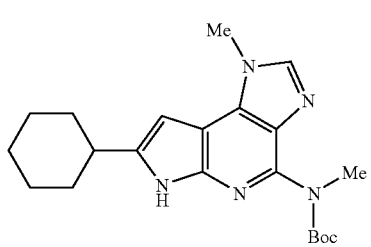

A solution of C32.1 (300 mg, 0.78 mmol) in DMA (8 ml) was treated with solid potassium t-butoxide (123 mg, 1.1 mmol) and heated at 85° C. (in preheated oil bath) for 3 hours. The reaction was cooled and diluted with ethyl acetate and washed several times with water. The solvent removed under reduced pressure and the residue was chromatographed on a silica gel column (75-100% ethyl acetate/hexane) to give 180 mg of C32.2. LCMS B: Ret time 2.99 min, $(M+H)^+=384.37$.

A solution of C32.2 (180 mg, 0.47 mmol) in DMF (5 ml) was treated with $Cs_2CO_3$ (450 mg, 1.38 mmol) and (R)-(2,2-dimethyl-1,3-dioxolan-4-yl)methyl 4-methylbenzenesulfonate (400 mg, 1.4 mmol) and heated in an oil bath at 95° C. for 8 hours. The mixture was diluted with water and extracted into ethyl acetate. The extract was washed with water, concentrated and the residue chromatographed on silica gel, eluting with ethyl acetate to give 130 mg of C32.3 as a yellow solid. LCMS B: Ret time 3.48 min, $(M+H)^+=498.42$.

C32: (S)-3-(7-cyclohexyl-1-methyl-4-(methylamino)imidazo[4,5-d]pyrrolo[2,3-b]pyridin-6(1H)-yl)propane-1,2-diol A solution of C32.3 (130 mg, 0.26 mmol) in $CH_2Cl_2$ (2 ml) was treated with 6 ml of TFA and stirred at room temperature for 1 hr. The mixture diluted with $CH_2Cl_2$ and concentrated on a rotary evaporator. The residue was treated with sat'd $NaHCO_3$ and extracted into $CH_2Cl_2$. The solvent was evaporated under vacuum and the residue chromatographed on silica gel eluting with 5% $NH_4OH/MeOH/CH_2Cl_2$ to give 80 mg of C32 as yellow solid. LCMS B: Ret time 2.47 min, $(M+H)^+=358.37$.

Example C33

(S)-3-(6-(2,3-dihydroxypropyl)-1-methyl-4-(methylamino)-1,6-dihydroimidazo[4,5-d]pyrrolo[2,3-b]pyridin-7-yl)-5-fluorobenzonitrile

C33.1: (S)-tert-butyl 7-(3-cyano-5-fluorophenyl)-6-((2,2-dimethyl-1,3-dioxolan-4-yl)methyl)-1-methyl-1,6-dihydroimidazo[4,5-d]pyrrolo[2,3-b]pyridin-4-yl(methyl)carbamate

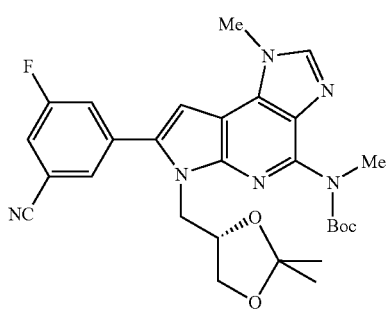

A solution of C1.5 (150 mg, 0.36 mmol) in DMF (5 ml) was treated with $Cs_2CO_3$ (450 mg, 1.38 mmol) and (R)-(2,2-dimethyl-1,3-dioxolan-4-yl)methyl 4-methylbenzenesulfonate (310 mg, 1.1 mmol) and heated in an oil bath at 95° C. for 8 hours. The mixture was diluted with water and extracted into ethyl acetate. The extract was washed with water, concentrated and the residue chromatographed on silica gel, eluting with 75% ethyl acetate/hexane to give 180 mg of C33.1 as a yellow solid. LCMS B: Ret time 3.24 min, $(M+H)^+=535.27$.

C33: (S)-3-(6-(2,3-dihydroxypropyl)-1-methyl-4-(methylamino)-1,6-dihydroimidazo[4,5-d]pyrrolo[2,3-b]pyridin-7-yl)-5-fluorobenzonitrile A solution of C33.1 (160 mg, 0.30 mmol) in $CH_2Cl_2$ (2 ml) was treated with 6 ml of TFA and stirred at room temperature for 1 hr. The mixture diluted with $CH_2Cl_2$ and concentrated on a rotary evaporator. The residue was treated with sat'd $NaHCO_3$ and extracted into $CH_2Cl_2$. The solvent was evaporated under vacuum and the residue chromatographed on silica gel eluting with $NH_4OH/MeOH/CH_2Cl_2$ (0.5:4.5:95) to give 90 mg of C33 as yellow solid. LCMS B: Ret time 2.16 min, $(M+H)^+=395.27$. Chiral HPLC Retention time: 6.97 min. Chiral HPLC conditions: Column: Chiralpak AD 250×4.6 mm ID, 10 μm; Mobil Phase: Hex/MeOH/IPA/DEA=30:35:35:0.1; Flow rate: 1.0 ml/min; UV detection: 220 nm. $^1$H NMR, 500 MHz, $CDCl_3$: 7.65 (s, 1H), 7.62 (s, 1H), 7.46 (m, 1H), 7.33 (m, 1H), 6.68 (s, 1H), 5.73 (bs, 1 H), 4.48 (m, 1H), 4.29 (m, 1H), 4.09 (m, 1H), 4.04 (s, 3 H), 3.58 (m, 2H), 3.19 (d, J=5 Hz, 3H), 1.61 (bs, 3 H).

Example C34

(R)-3-(6-(2,3-dihydroxypropyl)-1-methyl-4-(methylamino)-1,6-dihydroimidazo[4,5-d]pyrrolo[2,3-b]pyridin-7-yl)-5-fluorobenzonitrile

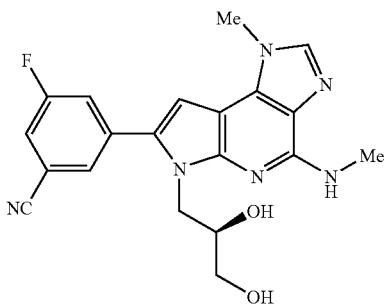

This was obtained using the procedure describe for Example C33 except using (S)(2,2-dimethyl-1,3-dioxolan-4-yl)methyl 4-methylbenzenesulfonate to give C34 as a yellow solid. LCMS B: Ret time 2.16 min, $(M+H)^+=395.28$. Chiral HPLC Retention time: 5.52 min. Chiral HPLC conditions: Column: Chiralpak AD 250×4.6 mm ID, 10 μm; Mobil Phase: Hex/MeOH/IPA/DEA=30:35:35:0.1; Flow rate: 1.0 ml/min; UV detection: 220 nm.

Alternate Preparation of C33 and C34

C8.2 (20 mg, 0.04 mmol) was subjected to chiral separation (Chiralpak AD 500×20 mm ID; 10 um, Hex/EtOH/IPA/DEA=82:9:9:0.1; 25 ml/min) to yield a Boc protected product. It was dissolved in $CH_2Cl_2$ (0.25 ml) and added TFA (0.25 ml) dropwise at 0-5° C. The reaction mixture was warmed up to RT, stirred for 10 minutes and concentrated to yield C33 (8 mg, 78%). HPLC: 85%, retention time: 2.115 minute (condition B). Chiral HPLC: >99.9% ee. retention time: 5.577 minute (Chiralpak AD 10 um 4.6×250 mm; Hex/MeOH/IPA/DEA=30/37.5/37.5/0.1; 1.0 ml/min). LC/MS $(M+H)^+=395$, $^1$H-NMR (400 MHz, $CD_3OD$) δ ppm 8.12 (1 H, s), 7.76 (1 H, s), 7.67 (1 H, d, J=9.16 Hz), 7.49 (1 H, d, J=7.12 Hz), 6.94 (1 H, s), 4.42 (1 H, d, J=12.21 Hz), 4.09-4.20 (1 H, m), 3.99-4.07 (4 H, m), 3.45-3.56 (1 H, m), 3.38 (1 H, dd, J=11.19, 6.61 Hz), 3.08 (3 H, s) and C34 HPLC: 85%, retention time: 2.113 minute (condition B). Chiral HPLC: 90% ee. retention time: 7.394 minute (Chiralpak AD 10 um 4.6×250 mm; Hex/MeOH/IPA/DEA=30/37.5/37.5/0.1; 1.0 ml/min). LC/MS $(M+H)^+=395$, $^1$H-NMR (400 MHz, $CD_3OD$) δ ppm 8.11 (1 H, s), 7.76 (1 H, s), 7.67 (1 H, d, J=8.65 Hz), 7.49 (1 H, d, J=111.70 Hz), 6.94 (1H, s), 4.42 (1 H, d, J=12.21 Hz), 4.13 (1 H, d, J=11.19 Hz), 3.99-4.07 (4 H, m), 3.51 (1 H, d, J=13.23 Hz), 3.37 (1 H, s), 3.08 (3 H, s).

Example C35

3-fluoro-5-(6-(2-(2-methoxyethylamino)ethyl)-1-methyl-4-(methylamino)-1,6-dihydroimidazo[4,5-d]pyrrolo[2,3-b]pyridin-7-yl)benzonitrile

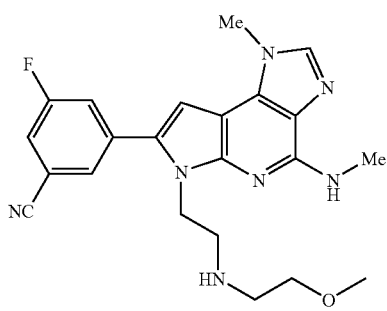
C35

This was obtained, using the procedure described for the synthesis of Example C8, as a yellow solid. LCMS B: Ret time 1.96 min, (M+H)$^+$=422.35. $^1$H NMR, 500 MHz, CDCl$_3$: 7.71 (s, 1H), 7.61 (s, 1H), 7.58 (dm, 1H), 7.29 (dm, 1H), 6.65 (s, 1H), 5.51 (m, 1H), 4.46 (t, J=6 Hz, 2H), 4.01 (s, 3 H), 3.41 (t, J=5 Hz, 2H), 3.20 (d, J=5 Hz, 3H), 3.08 (t, J=6 Hz, 2H), 2.74 (t, J=5 Hz, 2H).

Example C36

3-(6-(2-cyano-2-(2-methoxyethylamino)ethyl)-1-methyl-4-(methylamino)-1,6-dihydroimidazo[4,5-d]pyrrolo[2,3-b]pyridin-7-yl)-5-fluorobenzonitrile

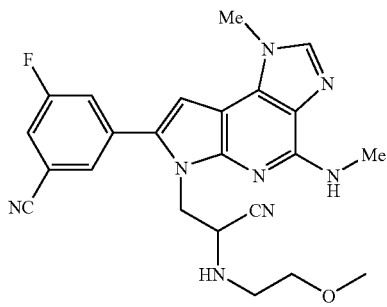
C36

This was obtained, using the procedure described for the synthesis of Example C9, as a yellow solid. LCMS B: Ret time 2.41 min, (M+H)$^+$=447.27. $^1$H NMR, 500 MHz, CDCl$_3$: 7.66 (bs, 2H), 7.55 (dm, 1H), 7.344 (dm, 1H), 6.67 (s, 1H), 5.64 (m, 1H), 4.57 (m, 3H), 4.03 (s, 3 H), 3.44 (m, 2H), 3.30 (s, 3H), 3.19 (m, 3H), 2.93 (m, 1H), 2.75 (m, 1H).

Example C37

3-fluoro-5-(6-(2-((2-hydroxyethyl)(methyl)amino)ethyl)-1-methyl-4-(methylamino)-1,6-dihydroimidazo[4,5-d]pyrrolo[2,3-b]pyridin-7-yl)benzonitrile

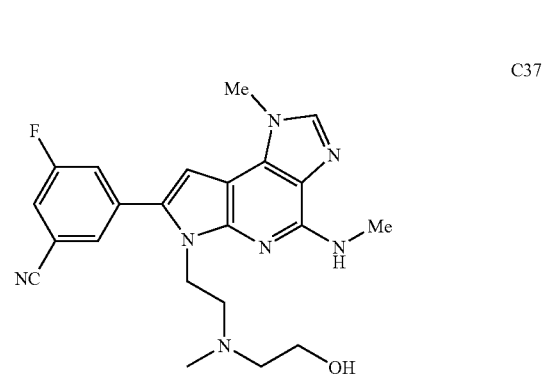
C37

This was obtained, using the procedure described for the synthesis of Example C8, as a yellow solid. LCMS B: Ret time 1.81 min, (M+H)$^+$=422.30.

Example C38

3-(6-(2-(1,3-dihydroxypropan-2-ylamino)ethyl)-1-methyl-4-(methylamino)-1,6-dihydroimidazo[4,5-d]pyrrolo[2,3-b]pyridin-7-yl)-5-fluorobenzonitrile

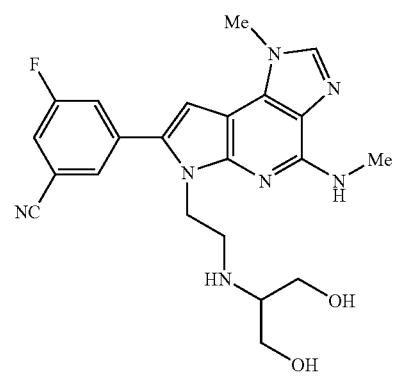
C38

This was obtained, using the procedure described for the synthesis of Example C8, as a yellow solid. LCMS B: Ret time 1.83 min, (M+H)$^+$=438.28.

Example C39

3-fluoro-5-(1-methyl-4-(methylamino)-6-(2-morpholinoethyl)-1,6-dihydroimidazo[4,5-d]pyrrolo[2,3-b]pyridin-7-yl)benzonitrile

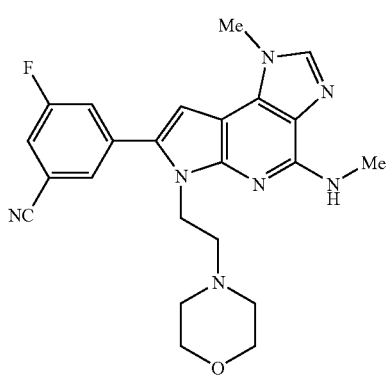

This was obtained, using the procedure described for the synthesis of Example C8, as a yellow solid. LCMS B: Ret time 1.83 min, (M+H)$^+$=434.32.

Example C40

3-fluoro-5-(1-methyl-4-(methylamino)-6-(2-(piperazin-1-yl)ethyl)-1,6-dihydroimidazo[4,5-d]pyrrolo[2,3-b]pyridin-7-yl)benzonitrile

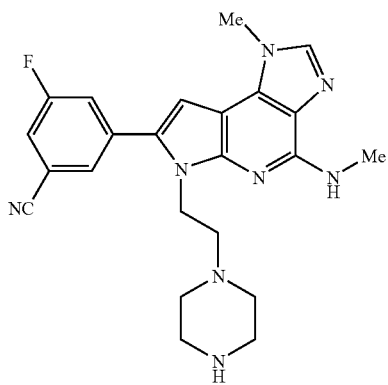

This was obtained, using the procedure described for the synthesis of Example C8, as a yellow solid. LCMS B: Ret time 2.00 min, (M+H)$^+$=433.33.

Example C41

3-(6-(2-(bis(2-hydroxyethyl)amino)ethyl)-1-methyl-4-(methylamino)-1,6-dihydroimidazol-[4,5-d]pyrrolo[2,3-b]pyridin-7-yl)-5-fluorobenzonitrile

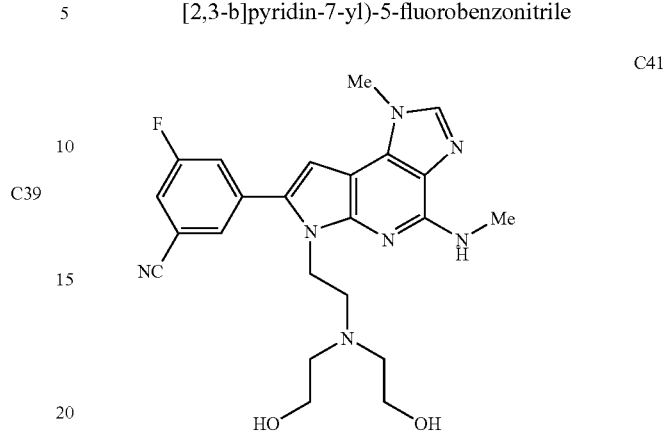

This was obtained, using the procedure described for the synthesis of Example C8, as a yellow solid. LCMS B: Ret time 1.82 min, (M+H)$^+$=452.30.

Example C42

3-fluoro-5-(6-(2-(2-(2-hydroxyethoxy)ethylamino)ethyl)-1-methyl-4-(methylamino)-1,6-dihydroimidazo[4,5-d]pyrrolo[2,3-b]pyridin-7-yl)benzonitrile

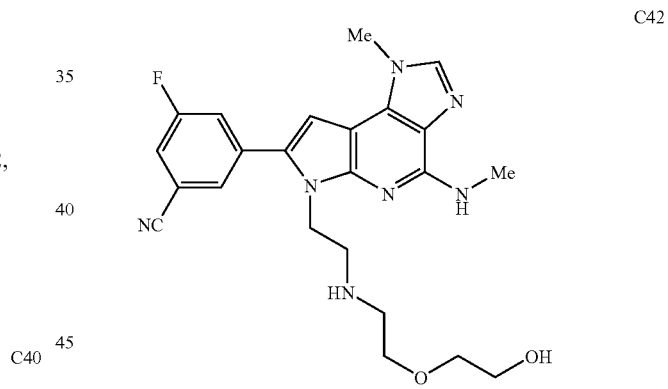

This was obtained, using the procedure described for the synthesis of Example C8, as a yellow solid. LCMS B: Ret time 1.88 min, (M+H)$^+$=452.33.

Example C43

1,6-dihydro-N,1,6-trimethyl-7-phenyl-imidazo[4,5-d]pyrrolo[2,3-b]pyridin-4-amine

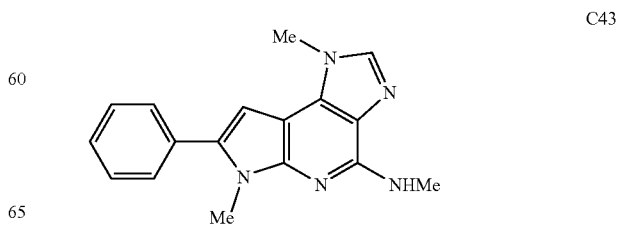

Sodium bis(trimethylsilyl)amide (0.11 mL of a 1.0M THF solution, 0.11 mmol) was added to a solution of A1.14 (20.0 mg, 0.053 mmol) in DMF (0.70 mL) at 0° C. After 10 min., iodomethane was added (16.2 µL, 0.053 mmol), the flask was sealed, and stirring at 0° C. was continued for 25 min. The reaction mixture was concentrated under vacuum. TFA was added (2.0 mL), followed by heating at 50° C. for 35 min. TFA was removed under vacuum. The crude product was purified by reversed-phase preparative HPLC and trituration with ether to yield 10.8 mg of C43 as an off-white solid (50% assuming 1.0 TFA salt). HPLC (C): 95.0%, ret. Time 2.73 min., LC/MS (M+H)$^+$=292.32.

Example C44

6-ethyl-1,6-dihydro-N,1-dimethyl-7-phenyl-imidazo[4,5-d]pyrrolo[2,3-b]pyridin-4-amine

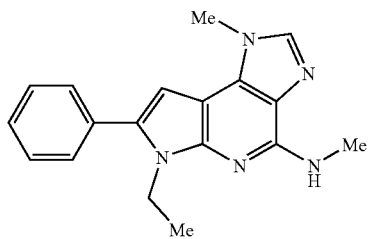

C44

Sodium bis(trimethyl)amide (0.10 mL of a 1.0M solution in THF, 0.10 mmol) was added to a solution of A1.14 (15.0 mg, 0.040 mmol) in DMF (0.60 mL) at 0° C. under Ar. After 20 min., iodoethane was added (15.9 µL, 0.20 mmol), and stirring was continued at room temperature for 50 min. DMF was removed under vacuum. TFA was added (2.0 mL), and the reaction mixture was stirred at 50° C. for 30 min. TFA was removed under vacuum. The crude product was purified by reversed-phase preparative HPLC to yield 13.2 mg of C44 as a pale green solid which was suspended in ether, sonicated briefly, collected by filtration, and rinsed with ether. Yield after drying: 4.20 mg of C44 as an off-white solid (21% assuming a 1.0 TFA salt). HPLC (C): 96.1%, ret. Time 2.97 min., LC/MS (M+H)$^+$=306.35.

Example C45

3-[1-methyl-4-(methylamino)-7-phenylimidazo[4,5-d]pyrrolo[2,3-b]pyridin-6(1H)-yl]-1,2-propanediol

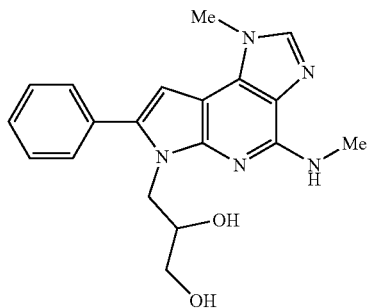

C45

C45.1: tert-butyl 6-allyl-1-methyl-7-phenyl-1,6-dihydroimidazo[4,5-d]pyrrolo[2,3-b]pyridin-4-yl(methyl)carbamate

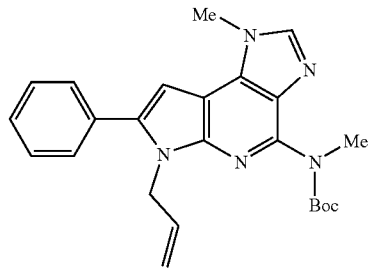

C45.1

Sodium bis(trimethyl)amide (0.81 mL of a 10M solution in THF, 0.81 mmol) was added to a solution of A1.14 (0.17 g, 0.045 mmol) in DMF (13.6 mL) at 0° C. under Ar. After 20 min., allyl bromide was added (0.16 mL, 1.85 mmol), and stirring was continued at room temperature for 45 min. The reaction was quenched with saturated aqueous NH$_4$Cl solution (0.20 mL), and DMF was removed under vacuum. The residue was partitioned between 2:1 EtOAc:THF (40.0 mL) and water (10 mL). After separation, the organic layer was washed with water, brine, dried (Na$_2$SO$_4$), and concentrated under vacuum to yield 0.22 g of a viscous tan oil. Flash chromatography on silica gel, eluting with an EtOAc:hexane gradient followed by EtOAc:MeOH yielded C45.1 (0.1345 g, 72%) as a solid. HPLC (C): 92.3%, ret. Time 3.32 min., LC/MS (M+H)$^+$=418.4.

C45.2: tert-butyl 6-(2,3-dihydroxypropyl)-1-methyl-7-phenyl-1,6-dihydroimidazo[4,5-d]pyrrolo[2,3-b]pyridin-4-yl(methyl)carbamate

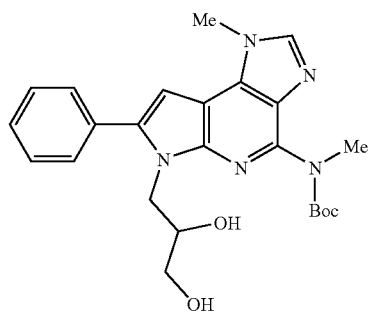

C45.2

A solution of C45.1 (120.6 mg, 0.29 mmol), 4-methylmorpholine-N-oxide (0.10 g, 0.87 mmol), and OsO$_4$ (0.24 mL of a 2% aqueous solution) in THF (3.26 mL) and water (0.60 mL) was stirred for 16 h. Saturated aqueous NaHCO$_3$ solution was added (2.0 mL), and the reaction mixture was stirred for 30 min. EtOAc and water were added; after separation, the aqueous layer was extracted with EtOAc, the combined organic layers were washed with water (3×), brine, dried (Na$_2$SO$_4$), and evaporated under vacuum to yield 124.5 mg of C45.2 as a pale yellow solid (95%).

C45.3: 3-[1-methyl-4-(methylamino)-7-phenylimidazo[4,5-d]pyrrolo[2,3-b]pyridin-6(1H)-yl]-1,2-propanediol A solution of C45.2 (10.0 mg, 0.022 mmol) in TFA (1.0 mL) was stirred at 0° C. to room temperature for 25 min. TFA was removed under vacuum. The crude product was triturated with ether to yield C45 as a pale tan solid (5.0 mg, 49%, assuming a 1.0 TFA salt). HPLC): 93.5%, ret. time 2.15 min., LC/MS (M+H)$^+$=352.35.

Example C46

1-methyl-4-(methylamino)-7-phenyl-imidazo[4,5-d]pyrrolo[2,3-b]pyridine-6(1H)-ethanol

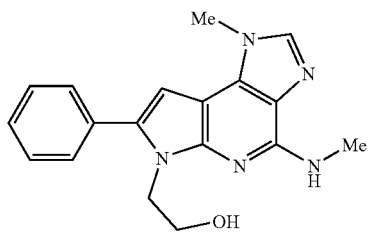

C46

C46.1: tert-butyl methyl(1-methyl-6-(2-oxoethyl)-7-phenyl-1,6-dihydroimidazo[4,5-d]pyrrolo[2,3-b]pyridin-4-yl)carbamate

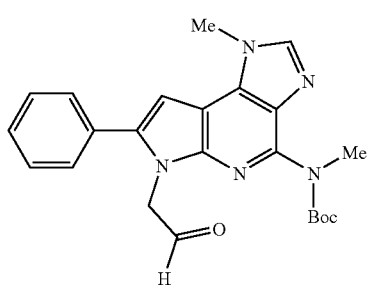

C46.1

A solution of NaIO$_4$ (78.94 mg, 0.37 mmol) in water (1.25 mL) was added slowly to a solution of C45.2 (0.11 g, 0.246 mmol) in acetone (4.85 mL) at 0° C. After 16 h at 0° C., more NaIO$_4$ was added (26.31 mg, 0.12 mmol), followed by the same amount several hours later. Water (1.25 mL), acetone (4.0 mL), and MeOH (1.0 mL) were added, and stirring was continued at room temperature for 2 days. The reaction mixture was diluted with water and EtOAc. After separation, the aqueous layer was extracted with EtOAc, the combined organic layers were washed with water, brine, dried (Na$_2$SO$_4$), and evaporated under vacuum to yield 0.12 g of a viscous tan oil. Trituration with 80:20 ether:hexane yielded C46.1 as an off white solid (61.6 mg, 59%). HPLC (C): 93.4%, ret. time 2.86 min., LC/MS (M+H)$^+$=420.40.

C46.2: tert-butyl 6-(2-hydroxyethyl)-1-methyl-7-phenyl-1,6-dihydroimidazo[4,5-d]pyrrolo[2,3-b]pyridin-4-yl(methyl)carbamate

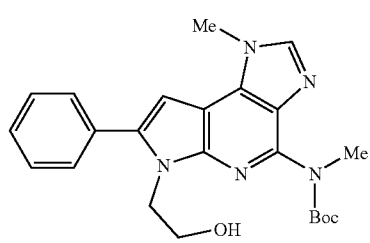

C46.2

Sodium borohydride (8.9 mg, 0.24 mmol) was added to a solution of C46.1 (25.0 mg, 0.06 mmol) in EtOH (3.0 mL). The reaction mixture was stirred for 1.25 hr. EtOH was removed under vacuum. Saturated aqueous KHSO$_4$ solution was slowly added at 0° C. with stirring until H$_2$ gas evolution ceased. After several minutes, NaHCO$_3$ was slowly added at 0° C. to pH 8.5. EtOAc was added. After separation, the EtOAc layer was washed with water, brine, dried (Na$_2$SO$_4$), and evaporated under vacuum to yield 20.6 mg of C46.2 as an oily solid (81%). HPLC (C): 93.4%, ret. time 2.77 min., LC/MS (M+H)$^+$=422.41

C46.3: 1-methyl-4-(methylamino)-7-phenyl-imidazo[4,5-d]pyrrolo[2,3-b]pyridine-6(1H)-ethanol TFA (1.5 mL) was added to C46.2 (20.6 mg) at 0° C. The ice bath was removed and the reaction mixture was stirred for 20 min. TFA was removed under vacuum and the crude product was triturated with 70:30 ether:hexane to yield 15.90 mg of C46 as a white solid (75% assuming a 1.0 TFA salt). HPLC (C): 95.0%, ret. time 2.35 min., LC/MS (M+H)$^+$=322.3.

Example C47

(R)-N-((6-(6-(2,3-dihydroxypropyl)-1-methyl-4-(methylamino)-1,6-dihydroimidazo[4,5-d]pyrrolo[2,3-b]pyridin-7-yl)pyridin-2-yl)methyl)-2-methoxyacetamide

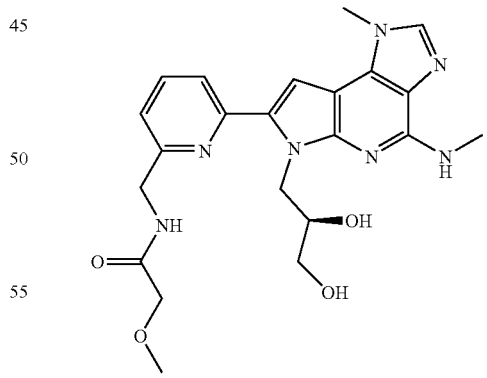

C47

To a solution of A228.5 (50 mg, 0.104 mmol) in DMF (1 mL) at room temperature was added tBuOK/THF (1 M, 0.136 mL, 0.136 mmol) followed 5 minutes later by the addition of (S)-(2,2-dimethyl-1,3-dioxolan-4-yl)methyl 4-methylbenzenesulfonate (90 mg, 0.392 mmol) in one portion. The reaction was heated to 60° C. with stirring overnight. Water (0.1 mL) was added to quench the reaction and the solution was evaporated to near dryness under a stream of nitrogen then dissolved in methanol and purified by preparative reverse phase HPLC to afford a mixture of protected and deprotected products along with Tosyl starting material. The mixture was treated with neat trifluoroacetic acid at room temperature for 5 minutes then evaporated to dryness. The residue was dissolved in methanol and purified by preparative reverse phase HPLC followed by evaporation and purification of the resulting residue on an SCX column (eluting with 1N NH$_3$/MeOH) to afford C47 as a yellow solid (4.9 mg). The compound had an HPLC retention time=2.08 min. (Column: Chromolith SpeedROD 4.6×50 mm—4 min.; Solvent A=10% MeOH, 90% H$_2$O, and 0.2% H$_3$PO$_4$; Solvent B=90% MeOH, 10% H$_2$O, and 0.2% H$_3$PO$_4$) and a LC/MS M+H$^+$=454.2

The examples described in Table Cl were prepared in a manner similar to that of Example C47.

TABLE C1

| Ex. | R | Name | HPLC Retention (min) | MS Reported |
|---|---|---|---|---|
| C48 | | (S)-N-((6-(6-(2,3-dihydroxypropyl)-1-methyl-4-(methylamino)-1,6-dihydroimidazo[4,5-d]pyrrolo[2,3-b]pyridin-7-yl)pyridin-2-yl)methyl)-2-methoxyacetamide | 2.08 | 454.2 |
| C49 | | N-((6-(6-(2-hydroxyethyl)-1-methyl-4-(methylamino)-1,6-dihydroimidazo[4,5-d]pyrrolo[2,3-b]pyridin-7-yl)pyridin-2-yl)methyl)-2-methoxyacetamide | 2.05 | 424.3 |
| C50 | | N-((6-(6-allyl-1-methyl-4-(methylamino)-1,6-dihydroimidazo[4,5-d]pyrrolo[2,3-b]pyridin-7-yl)pyridin-2-yl)methyl)-2-methoxyacetamide | 2.54 | 420.3 |

TABLE C1-continued

| Ex. | R | Name | HPLC Retention (min) | MS Reported |
|---|---|---|---|---|
| C51 | | 6-allyl-7-(6-(aminomethyl)pyridin-2-yl)-N,1-dimethyl-1,6-dihydroimidazo[4,5-d]pyrrolo[2,3-b]pyridin-4-amine | 1.83 | 348.3 |

Utility

Compounds herein are inhibitors of IKK. Accordingly, compounds of formula (I) have utility in treating conditions were a decrease in NF-κB activity would be beneficial. Such conditions include diseases or disorders in which cytokine levels are modulated as a consequence of intracellular signaling via IKK, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its sypmtoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "IKK," this means that either or both IKK-2 and IKK-1 are inhibited.

In view of their activity as inhibitors of IKK, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to infectious diseases such as sepsis, septic shock, Shigellosis, and *Heliobacter Pylori*.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS/ARC or malignancy, and herpes.

The compounds also may be used to treat angiogenic disorders including solid tumors, ocular neovasculization, and infantile haemangiomas.

In addition, the compounds may be used to treat Lupus, Multiple Scelrosis, Alzheimer's disease, Cachexia, Hodgkin's disease, Stroke, Diabetes, Osteoporosis, Osteoarthritis, Alkylosing spondylitis, Psoriasis, Atopic dermatitis, Atherosclerosis, restenosis, Glomerulonephritis, Inflammation associated with infection and certain viral infections including AIDS, Adult respiratory distress syndrome, Ataxia telangiestasia In addition, IKK inhibitors omay inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

In addition, IKK (+/−) mice when fed a high fat diet have reduced insulin levels and reduced blood glucose levels.

Accordingly compound of this invention are useful in the treatment of Type II diabetes (also known as non-insulin dependant diabetes).

Additionally, the compounds are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

The compounds also may be used in treating oncological diseases, in treating cancer and tumors, such as solid tumors, lymphomas and leukemia, and in particular, breast cancer, prostate cancer, and Hodgkin's lymphoma.

Additionally this invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid or liquid tumors which are associated with IKK, especially those tumors which are significantly dependent on IKK for their growth and spread, including for example, hematopoietic tumors, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of the skin, including melanoma;

hematopoietic tumors including those of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

hematopoietic tumors including those of plasma cell lineage such as multiple myeloma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Additionally, the compounds of formula I are useful in the treatment of the following cancers.

Breast and other cancers: Hu, M C-T, and Hung, M C. "Role of IkB kinase in tumorigenesis" Future Oncology (2005) 1(1), 67-78.

Colon, lung, and other cancers: Jun-Li Luo, Hideaki Kamata, and Michael Karin. "IKK/NF-κB signaling: balancing life and death—a new approach to cancer therapy" J Clin Invest. 2005 115(10): 2625-2632.

Colon, lung, stomach, oesophagus, ovarian and other cancers: Michael Karin1 & Florian R. Greten2 "NF-κB: LINKING INFLAMMATION AND IMMUNITY TO CANCER DEVELOPMENT AND PROGRESSION" Nature Reviews Immunology 5, 749-759 (2005).

Lung, pancreatic, colon and other cancers: Greten F R, Karin M. "The IKK/NF-kappaB activation pathway-a target for prevention and treatment of cancer." Cancer Lett. 2004; 206(2):193-9.

Multiple Myeloma: Hideshima T, Chauhan D, Richardson P, Mitsiades C, Mitsiades N, Hayashi T, Munshi N, Dang L, Castro A, Palombella V, Adams J, Anderson KC. "NF-kappa B as a therapeutic target in multiple myeloma." J Biol. Chem. 2002; 277(19):16639-47.

Lymphoma: Lam L T, Davis R E, Pierce J, Hepperle M, Xu Y, Hottelet M, Nong Y, Wen D, Adams J, Dang L, Staudt L M. "Small molecule inhibitors of IkappaB kinase are selectively toxic for subgroups of diffuse large B-cell lymphoma defined by gene expression profiling." Clin Cancer Res. 2005; 11(1): 28-40.

Melanoma: Burke J R. "Targeting I kappa B kinase for the treatment of inflammatory and other disorders." Curr Opin Drug Discov Devel. 2003; 6(5):720-8. and a paper in press: Jinming Yang, Katayoun I. Amiri, James R. Burke, Johannes A. Schmid, and Ann Richmond. "BMS-345541 Targets IkappaB Kinase to Induce Apoptosis in Melanoma: Involvement of Nuclear Factor-kappaB and Mitochondria Pathways." Clin. Cancer Res., in press. The above references are hereby incorporated by reference.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of IKK kinase activity, such as melanomas, and multiple myeloma. By the administration of a composition (or a combination) of the compounds of this invention, development of tumors in a mammalian host is reduced.

Also provided is a pharmaceutical composition comprising a compound of formula I in combination with pharmaceutically acceptable carrier and an anti-cancer or cytotoxic agent. In another embodiment said anti-cancer or cytotoxic agent is selected from the group consisting of linomide; inhibitors of integrin αvβ3 function; angiostatin; razoxin; tamoxifen; toremifen; raloxifene; droloxifene; iodoxyfene; megestrol acetate; anastrozole; letrazole; borazole; exemestane; flutamide; nilutamide; bicalutamide; cyproterone acetate; gosereline acetate; luprolide; finasteride; metalloproteinase inhibitors; inhibitors of urokinase plasminogen activator receptor function; growth factor antibodies; growth factor receptor antibodies such as Avastin® and Erbitux®; tyrosine kinase inhibitors; serine/threonine kinase inhibitors); methotrexate; 5-fluorouracil; purine and adenosine analogues; cytosine arabinoside; doxorubicin; daunomycin; epirubicin; idarubicin; mitomycin-C; dactinomycin; mithramycin); cisplatin; carboplatin; nitrogen mustard; melphalan; chlorambucil; busulphan; cyclophosphamide; ifosfamide nitrosoureas; thiotephan; vincristine; Taxol®; Taxotere®; epothilone analogs; discodermolide analogs; eleutherobin analogs; etoposide; teniposide; amsacrine; topotecan; and flavopyridols.

In the field of medical oncology it is normal practice to use a combination of different forms of treatment to treat each patient with cancer. In medical oncology the other component (s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

1: antiangiogenic agents such as inhibitors of VEGF or related kinases (such as FLT, or KDR), linomide, antibodies which block angiogenesis, inhibitors of integrin αvβ3 function, angiostatin, razoxin;

2: cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antiharmones, antiprogestogens, antiandrogens (for example flutamide, nilutamide, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® and Erbitux®, tyrosine kinase inhibitors and serine/threonine kinase inhibitors);

3: antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like Taxol®, Taxotere® and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols).

Herein are provided methods for treating such conditions, comprising administering to a subject in need thereof an effective amount of at least one compound of formula I or a salt thereof. Other therapeutic agents such as those described herein may be employed in combination with compounds of formula I. In the methods of the present invention, such other therapeutic agent(s) may be administered prior to, simultaneously with, or following administration of the inventive compound(s).

When the terms "IKK associated condition" or "IKK associated disease or disorder" are used herein, each is intended to encompass all of the conditions identified above as if repeated at length, as well as any other condition that is modulated by IKK kinase activity.

The disclosure provides methods for treating such conditions, comprising administering to a subject in need thereof an effective amount of at least one compound of Formula (I), or a pharmaceutically-acceptable salt, hydrate, or prodrug thereof. The methods of treating IKK kinase-associated conditions may comprise administering compounds of Formula (I) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, therapies for the treatment of irritable bowel syndrome (e.g., Zelmac®, Zelnorm®, and Maxi-K® openers such as those disclosed in U.S. Pat. No. 6,184,231 B1), corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan, or with opioids (e.g. morphine, codeine, hydomorphone).

Examples of suitable diabetic agents with which the inventive compounds may be used include insulin (of porcine or recombinant human origin including, short acting insulins such as Humalog®, Regular, intermediate acting insulins such NPH, lente, and long acting insulins such as ultralente or glarginine (Lantus®)); sulfonylureas such as glyburide and glipizide; secretegogues such as repaginide, and nateglinide; Peroisome proliferators-activated receptor (PPAR) agonists such as rosiglitazole and pioglitazone, and mixed PPAR alpha/gamma dual agonists agonists such as muriglitazar; biquanides such as metformin, and glucosidase inhibitors such as acarbose and miglitol, PPAR-alpha agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorphenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

Additionally, the compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal $Na^+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760, 246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The disclosure also provides pharmaceutical compositions capable of treating p38-kinase associated conditions, including TNF-α, IL-1, and/or IL-8 mediated conditions, as described above. The compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®. Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. Alternatively, the compound may be administered 1 or 2 times per day. In another embodiment, the total amount administered per day is less than about 500 mg, alternatively about 100-350 mg, or alternatively, about 130-350 mg per day in either a once a day dose or in a twice a day dose. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of IKK enzyme activity.

At least one or more of the compounds described herein have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells ($1.4 \times 10^6$/mL, $2.5 \times 10^5$ cells/well) in 180 µL RPMI-1640 was added 10 µL of the test compound in 10% DMSO. Typically, test compound concentrations of 0.1-100 µM were used in the assay. After one hour at 37° C., 10 µL of 1000 ng/mL lipopolysaccharide (LPS from *Salmonella typhosa*, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFα secretion model. Likewise, assays known in the field are applied to establish the activity of the compounds as inhibitors of IKK, IkB, and/or the NF-κB pathway.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells ($2 \times 10^5$/well in U-bottom 96 well plates) were pre-incubated with compounds for 30 min at 37 C prior to addition of lipopolysaccharide (LPS) at a final concentration of 6.25 ng/ml in a total volume of 200 µL. After 4 h at 37° C., 50 µL of supernatant was carefully aspirated for detection of soluble TNFα. Soluble TNFα was detected by ELISA developed by R&D Systems (Minneapolis, Minn.) according to the manufacturer's instructions.

We claim:

1. A compound of formula (I),

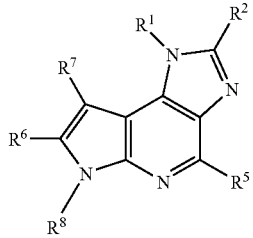

(I)

and salts thereof wherein
$R^1$ is, $C_{1-3}$ alkyl;
$R^2$ is hydrogen;
$R^5$ is
—$NR^3R^4$;

$R^3$ and $R^4$ are independently selected from
(a) hydrogen,
(b) alkyl;
$R^6$ is
which may be optionally independently substituted as valence allows with one or more $Z^{1^d}$, $Z^{2^d}$ and $Z^{3^d}$;
$R^7$ is
(a) hydrogen, or halo;
$R^8$ is
(a) hydrogen,
(b) alkyl, alkenyl, any of which may be optionally independently substituted as valence allows with one or more $Z^{1^d}$, $Z^{2^d}$ and $Z^{3^d}$; or
$Z^{1^{a\text{-}1^e}}$, $Z^{2^{a\text{-}2^e}}$, and $Z^{3^{a\text{-}3^e}}$ are optional substituents at each occurrence independently selected from —$W^1$—$V^1$; —$W^2$—$V^2$; —$W^3$—$V^3$; —$W^4$—$V^4$; —$W^5$—$V^5$;
where $W^{1\text{-}5}$ are independently
(1) a bond
(2) alkyl, alkenyl, or aryl, any of which may be optionally independently substituted as valence allows with one or more $V^{1\text{-}5}$; or
where $V^{1\text{-}5}$ are independently
(1) H
(2) alkyl, alkenyl, aryl, heterocyclo, wherein the heterocyclo is pyrrolidinyl or morpholinyl, any of which may be optionally independently substituted as valence allows with one or more of groups (3)-(20) of $V^{1\text{-}5}$;
(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—SO$_3$—H, or —$U^1$—S(O)$_t$$Y^5$,
(7) —$U^1$-halo,
(8) —$U^1$-cyano,
(9) —$U^1$-nitro,
(10) —$U^1$—$NY^2Y^3$,
(11) —$U^1$—$N(Y^4)$—C(O)—$Y^1$,
(12) —$U^1$—$N(Y^4)$—C(O)—$NY^2Y^3$,
(13) —$U^1$—$N(Y^4)$—C(O)—C(O)—$NY^2Y^3$,
(14) —$U^1$—$N(Y^4)$—C(O)—C(O)—$OY^5$,
(15) —$U^1$—$N(Y^4)$—C(O)O—$Y^5$,
(16) —$U^1$—$N(Y^4)$—S(O)$_2$—$Y^1$,
(17) —$U^1$—C(O)—$NY^2Y^3$,
(18) —$U^1$—OC(O)—$NY^2Y^3$,
(19) —$U^1$—$N(Y^4)$—C(=$NV^{1^a}$)—$NY^2Y^3$,
(20) oxo;
$V^{1a}$ is independently hydrogen, alkyl, —CN, or —C(O)$NY^2Y^3$;
$Y^1$, $Y^2$, $Y^3$, $Y^4$ and $Y^5$
(1) are each independently hydrogen, alkyl, cycloalkyl, aryl, heterocyclo, wherein the heterocyclo is pyrrolidinyl, thiomorpholinyl, piperidinyl, piperazinyl, piperazinonyl, morpholinyl; or heteroaryl, wherein the heteroaryl is isoxazolyl, pyrazinyl, pyridinyl, tetrazolyl, thophene, thiadiazolyl, thiazolyl; any of which may be optionally independently substituted as valence allows with one or more $Z^4$, $Z^5$ and $Z^6$; or
(2) $Y^2$ and $Y^3$ together with the nitrogen atom to which they are attached combine to form a 3 to 8 membered heterocyclic ring, selected from pyrrolidinyl, piperidinyl, morpholinyl, piperazinyl, diazepanyl, optionally independently substituted as valence allows with one or more $Z^4$, $Z^5$ and $Z^6$, $Z^4$, $Z^5$, and $Z^6$ are optional substituents at each occurrence independently selected from
(1) H
(2) alkyl, cycloalkyl, aryl, heterocyclo, wherein the heterocyclo is tetrahydrofuranyl, piperidinyl, pyrrolidinyl, pyrrolidinonyl, or imidazolidinyl, or heteroaryl, wherein the heteroaryl is furanyl, or pyridinyl;
(3) —$U^1$—O—$Y^{5a}$,
(4) —$U^1$—C(O)$_t$—H, —$U^1$—C(O)$_t$—$Y^{5a}$ where t is 1 or 2,
(5) —$U^1$—$SO_3$—H, or —$U^1$—S(O)$_t Y^{5a}$,
(6) —$U^1$-halo,
(7) —$U^1$-cyano,
(8) —$U^1$—$NY^{2a}Y^{3a}$,
(9) —$U^1$—N($Y^{4a}$)—C(O)—$Y^{1a}$,
(10) —$U^1$—C(O)—$NY^{2a}Y^{3a}$,
(11) —$U^1$—S(O)$_2$—N($Y^{4a}$)—$Y^{1a}$,
(12) oxo;
$Y^{1a}$, $Y^{2a}$, $Y^{3a}$, $Y^{4a}$ and $Y^{5a}$
(1) are each independently hydrogen, alkyl, (alkoxy) alkyl, or aryl;
$U^1$ is independently
(1) a single bond,
(2) alkylene,
(3) alkenylene, or
(4) alkynylene.

2. A compound of claim 1 wherein
$R^1$ is, methyl, ethyl, propyl, or i-propyl; and
$R^2$ is hydrogen.

3. A compound of claim 1 wherein
$Z^{1d}$, $Z^{2d}$ and $Z^{3d}$ are optional substituents independently selected from
(a) cyano, halo, —OH, —$OY^5$, —$U^1$—$NY^2Y^3$, —C(O)$_t$H, —C(O)$_t Y^1$, —$U^1$—C(O)—$NY^2Y^3$, —S(O)$_t Y^5$;
(b) alkyl or alkoxy optionally substituted with one or more cyano, halo, —OH, —$OY^5$, —$U^1$—$NY^2Y^3$, —C(O)$_t$H, —C(O)$_t Y^1$, —$U^1$—C(O)—$NY^2Y^3$, —OC(O)—$NY^2Y^3$, OC(O)—$OY^5$, —$U^1$—N($Y^4$)—C(O)—$Y^1$, —$U^1$—N($Y^4$)—C(O)—$NY^2Y^3$, —$U^1$—N($Y^4$)—C(O)O—$Y^5$, —N($Y^4$)—S(O)$_2$—$Y^1$, —N($Y^4$)—C(O)—C(O)—$NY^2Y^3$, —N($Y^4$)—C(O)—C(O)—$OY^5$, —$U^1$—N($Y^4$)—C(=$NV^{1a}$)—$NY^2Y^3$, —$U^1$—N($Y^4$)—C(=$NV^{1a}$)—$Y^1$, —S(O)$_t$Y, or heterocyclo wherein the heterocyclo is pyrrolidinyl or morpholinyl, and wherein heterocyclo are substituted as valence allows with one or more of groups (3)-(20) of $V^{1-5}$.

4. A compound of claim 3 wherein $R^3$ is hydrogen;
$R^4$ is alkyl
$R^6$ is
aryl optionally independently substituted as valence allows with one or more $Z^{1d}$, $Z^{2d}$ and $Z^{3d}$;
where
$U^1$ is a bond or alkylene.

5. The compound of claim 1, wherein
$R^6$ is

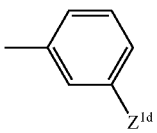

which may be further substituted with with one or more $Z^{1d}$, $Z^{2d}$ and $Z^{3d}$.

6. A pharmaceutical composition comprising (a) at least one compound according to claim 1, or a pharmaceutically acceptable salt, thereof, and (b) a pharmaceutically-acceptable carrier or diluent.

7. A compound or pharmaceutically acceptable salt thereof according to claim 1, wherein the compound is:
1,6-dihydro-N,1-dimethyl-7-phenyl imidazo[4,5-d]pyrrolo[2,3-b]pyridin-4-amine;
3-[1,5-dihydro-1-methyl-4-(methylamino)imidazo[4,5-d]pyrrolo[2,3-b]pyridin-7-yl]benzonitrile;
7-[3-(Aminomethyl)phenyl]-1,6-dihydro-N,1-dimethyl-imidazo[4,5-d]pyrrolo[2,3-b]pyridin-4-amine;
N-[[3-[1,6-dihydro-1-methyl-4-(methylamino)imidazo[4,5-d]pyrrolo[2,3-b]pyridin-7-yl]phenyl]methyl]acetamide;
N-[[3-[1,6-dihydro-1-methyl-4-(methylamino)imidazo[4,5-d]pyrrolo[2,3-b]pyridin-7-yl]phenyl]methyl]-2-methyl-propanamide;
N-[[3-[1,6-dihydro-1-methyl-4-(methylamino)imidazo[4,5-d]pyrrolo[2,3-b]pyridin-7-yl]phenyl]methyl]-2,2-dimethyl propanamide;
N-[[3-[1,6-dihydro-1-methyl-4-(methylamino)imidazo[4,5-d]pyrrolo[2,3-b]pyridin-7-yl]phenyl]methyl]-1-methyl-cyclopropanecarboxamide;
N-[[3-[1,6-dihydro-1-methyl-4-(methylamino)imidazo[4,5-d]pyrrolo[2,3-b]pyridin-7-yl]phenyl]methyl]-1-hydroxy-cyclopropanecarboxamide;
1-cyano-N-[[3-[1,6-dihydro-1-methyl-4-(methylamino)imidazo[4,5-d]pyrrolo[2,3-b]pyridin-7-yl]phenyl]methyl]-cyclopropanecarboxamide;
N-[[3-[1,6-dihydro-1-methyl-4-(methylamino)imidazo[4,5-d]pyrrolo[2,3-b]pyridin-7-yl]phenyl]methyl]-2-hydroxy-acetamide;
acetamide2-(acetylamino)-N-[[3-[1,6-dihydro-1-methyl-4-(methylamino)imidazo[4,5-d]pyrrolo[2,3-b]pyridin-7-yl]phenyl]methyl]-acetamide;
N-[[3-[1,6-dihydro-1-methyl-4-(methylamino)imidazo[4,5-d]pyrrolo[2,3-b]pyridin-7-yl]phenyl]methyl]-2-(dimethylamino)-acetamide;
N-[[3-[1,6-dihydro-1-methyl-4-(methylamino)imidazo[4,5-d]pyrrolo[2,3-b]pyridin-7-yl]phenyl]methyl]butanediamide;
N-[[3-[1,6-dihydro-1-methyl-4-(methylamino)imidazo[4,5-d]pyrrolo[2,3-b]pyridin-7-yl]phenyl]methyl]-3-methyl butanamide;
N-[[3-[1,6-dihydro-1-methyl-4-(methylamino)imidazo[4,5-d]pyrrolo[2,3-b]pyridin-7-yl]phenyl]methyl]-3,3-dimethyl-butanamide;
N-[[3-[1,6-dihydro-1-methyl-4-(methylamino)imidazo[4,5-d]pyrrolo[2,3-b]pyridin-7-yl]phenyl]methyl]-4-methyl-pentanamide;
N-[[3-[1,6-dihydro-1-methyl-4-(methylamino)imidazo[4,5-d]pyrrolo[2,3-b]pyridin-7-yl]phenyl]methyl]-3-methoxy-propanamide;
4-(aminosulfonyl)-N-[[3-[1,6-dihydro-1-methyl-4-(methylamino)imidazo[4,5-d]pyrrolo[2,3-b]pyridin-7-yl]phenyl]methyl]-butanamide;
2-chloro-N-[[3-[1,6-dihydro-1-methyl-4-(methylamino)imidazo[4,5-d]pyrrolo[2,3-b]pyridin-7-yl]phenyl]methyl]-benzamide;
3-chloro-N-[[3-[1,6-dihydro-1-methyl-4-(methylamino)imidazo[4,5-d]pyrrolo[2,3-b]pyridin-7-yl]phenyl]methyl]-benzamide;
4-chloro-N-[[3-[1,6-dihydro-1-methyl-4-(methylamino)imidazo[4,5-d]pyrrolo[2,3-b]pyridin-7-yl]phenyl]methyl]-benzamide;

N-[[3-[1,6-dihydro-1-methyl-4-(methylamino)imidazo[4,5-d]pyrrolo[2,3-b]pyridin-7-yl]phenyl]methyl]benzeneacetamide;
N-[[3-[1,6-dihydro-1-methyl-4-(methylamino)imidazo[4,5-d]pyrrolo[2,3-b]pyridin-7-yl]phenyl]methyl]benzenepropanamide;
N-[[3-[1,6-dihydro-1-methyl-4-(methylamino)imidazo[4,5-d]pyrrolo[2,3-b]pyridin-7-yl]phenyl]methyl]-benzenebutanamide;
N-[[3-[1,6-dihydro-1-methyl-4-(methylamino)imidazo[4,5-d]pyrrolo[2,3-b]pyridin-7-yl]phenyl]methyl]-3-thiophenecarboxamide;
N-[[3-[1,6-dihydro-1-methyl-4-(methylamino)imidazo[4,5-d]pyrrolo[2,3-b]pyridin-7-yl]phenyl]methyl]-4-thiazolecarboxamide;
N-[[3-[1,6-dihydro-1-methyl-4-(methylamino)imidazo[4,5-d]pyrrolo[2,3-b]pyridin-7-yl]phenyl]methyl]-4-methyl-1,2,3-thiadiazole-5-carboxamide;
N-[[3-[1,6-dihydro-1-methyl-4-(methylamino)imidazo[4,5-d]pyrrolo[2,3-b]pyridin-7-yl]phenyl]methyl]-5-methyl-3-isoxazolecarboxamide;
N-[[3-[1,6-dihydro-1-methyl-4-(methylamino)imidazo[4,5-d]pyrrolo[2,3-b]pyridin-7-yl]phenyl]methyl]-1H-tetrazole-5-acetamide;
N-[[3-[1,6-dihydro-1-methyl-4-(methylamino)imidazo[4,5-d]pyrrolo[2,3-b]pyridin-7-yl]phenyl]methyl]-cyclopropanecarboxamide;
N-[[3-[1,6-dihydro-1-methyl-4-(methylamino)imidazo[4,5-d]pyrrolo[2,3-b]pyridin-7-yl]phenyl]methyl]-1,2,3-thiadiazole-4-carboxamide;
N-[[3-[1,6-dihydro-1-methyl-4-(methylamino)imidazo[4,5-d]pyrrolo[2,3-b]pyridin-7-yl]phenyl]methyl]-benzamide;
N-[[3-[1,6-dihydro-1-methyl-4-(methylamino)imidazo[4,5-d]pyrrolo[2,3-b]pyridin-7-yl]phenyl]methyl]-alpha,alpha-dimethylbenzeneacetamide;
2-amino-N-[[3-[1,6-dihydro-1-methyl-4-(methylamino)imidazo[4,5-d]pyrrolo[2,3-b]pyridin-7-yl]phenyl]methyl]-acetamide;
N-[[3-[1,6-dihydro-1-methyl-4-(methylamino)imidazo[4,5-d]pyrrolo[2,3-b]pyridin-7-yl]phenyl]methyl]-2-(methylamino)-acetamide;
2-amino-N-[[3-[1,6-dihydro-1-methyl-4-(methylamino)imidazo[4,5-d]pyrrolo[2,3-b]pyridin-7-yl]phenyl]methyl]-,(2S)-propanamide;
2-amino-N-[[3-[1,6-dihydro-1-methyl-4-(methylamino)imidazo[4,5-d]pyrrolo[2,3-b]pyridin-7-yl]phenyl]methyl]-,(2R)-propanamide;
N-[[3-[1,6-dihydro-1-methyl-4-(methylamino)imidazo[4,5-d]pyrrolo[2,3-b]pyridin-7-yl]phenyl]methyl]-2-(methylamino)-,(2S)-propanamide;
3-amino-N-[[3-[1,6-dihydro-1-methyl-4-(methylamino)imidazo[4,5-d]pyrrolo[2,3-b]pyridin-7-yl]phenyl]methyl]-propanamide;
1-amino-N-[[3-[1,6-dihydro-1-methyl-4-(methylamino)imidazo[4,5-d]pyrrolo[2,3-b]pyridin-7-yl]phenyl]methyl]-cyclopropanecarboxamide;
2-amino-N-[[3-[1,6-dihydro-1-methyl-4-(methylamino)imidazo[4,5-d]pyrrolo[2,3-b]pyridin-7-yl]phenyl]methyl]-2-methyl-propanamide;
2-amino-N-[[3-[1,6-dihydro-1-methyl-4-(methylamino)imidazo[4,5-d]pyrrolo[2,3-b]pyridin-7-yl]phenyl]methyl]-,(2S)-butanamide;
2-amino-N-[[3-[1,6-dihydro-1-methyl-4-(methylamino)imidazo[4,5-d]pyrrolo[2,3-b]pyridin-7-yl]phenyl]methyl]-3-methyl-,(2S)-butanamide;
2-amino-N-[[3-[1,6-dihydro-1-methyl-4-(methylamino)imidazo[4,5-d]pyrrolo[2,3-b]pyridin-7-yl]phenyl]methyl]-3-methyl-,(2R)-butanamide;
2-amino-N-[[3-[1,6-dihydro-1-methyl-4-(methylamino)imidazo[4,5-d]pyrrolo[2,3-b]pyridin-7-yl]phenyl]methyl]-3,3-dimethyl-,(2S)-butanamide;
2-amino-N-[[3-[1,6-dihydro-1-methyl-4-(methylamino)imidazo[4,5-d]pyrrolo[2,3-b]pyridin-7-yl]phenyl]methyl]-4-methyl-,(2S)-pentanamide;
alpha-amino-N-[[3-[1,6-dihydro-1-methyl-4-(methylamino)imidazo[4,5-d]pyrrolo[2,3-b]pyridin-7-yl]phenyl]methyl]-,(alphaS)-benzeneacetamide;
alpha-amino-N-[[3-[1,6-dihydro-1-methyl-4-(methylamino)imidazo[4,5-d]pyrrolo[2,3-b]pyridin-7-yl]phenyl]methyl]-,(alphaS)-benzenepropanamide;
alpha-amino-N-[[3-[1,6-dihydro-1-methyl-4-(methylamino)imidazo[4,5-d]pyrrolo[2,3-b]pyridin-7-yl]phenyl]methyl]-,(alphaR)-benzenepropanamide;
N-[[3-[1,6-dihydro-1-methyl-4-(methylamino)imidazo[4,5-d]pyrrolo[2,3-b]pyridin-7-yl]phenyl]methyl]-,(2R)-2-pyrrolidinecarboxamide;
$N^1$-[[3-[1,6-dihydro-1-methyl-4-(methylamino)imidazo[4,5-d]pyrrolo[2,3-b]pyridin-7-yl]phenyl]methyl]-L-aspartamide;
N-[[3-[1,6-dihydro-1-methyl-4-(methylamino)imidazo[4,5-d]pyrrolo[2,3-b]pyridin-7-yl]phenyl]methyl]-alpha-phenyl-benzeneacetamide;
N-[[3-[1,5-dihydro-1-methyl-4-(methylamino)imidazo[4,5-d]pyrrolo[2,3-b]pyridin-7-yl]phenyl]methyl]trimethylacetamide;
N-[[3-[1,5-dihydro-1-methyl-4-(methylamino)imidazo[4,5-d]pyrrolo[2,3-b]pyridin-7-yl]phenyl]methyl]-3-methoxypropanamide;
N,1-dimethyl-7-(3-methylphenyl)-imidazo[4,5-d]pyrrolo[2,3-b]pyridin-4-amine,1,6-dihydro-;
7-(3-chlorophenyl)-1,6-dihydro-N,1-dimethyl-imidazo[4,5-d]pyrrolo[2,3-b]pyridin-4-amine;
7-(3-fluorophenyl)-1,6-dihydro-N,1-dimethyl-imidazo[4,5-d]pyrrolo[2,3-b]pyridin-4-amine;
N-[1-[3-[1,6-dihydro-1-methyl-4-(methylamino)imidazo[4,5-d]pyrrolo[2,3-b]pyridin-7-yl]phenyl]ethyl]acetamide;
1,6-dihydro-7-(3-methoxyphenyl)-N,1-dimethyl-imidazo[4,5-d]pyrrolo[2,3-b]pyridin-4-amine;
7-(4-chloro-3-methoxyphenyl)-1,6-dihydro-N,1-dimethyl-imidazo[4,5-d]pyrrolo[2,3-b]pyridin-4-amine;
1,6-dihydro-N,1-dimethyl-7-[3-(trifluoromethyl)phenyl]-imidazo[4,5-d]pyrrolo[2,3-b]pyridin-4-amine;
7-(4-fluorophenyl)-1,6-dihydro-N,1-dimethyl-imidazo[4,5-d]pyrrolo[2,3-b]pyridin-4-amine;
1,6-dihydro-7-(4-methoxyphenyl)-N,1-dimethyl-imidazo[4,5-d]pyrrolo[2,3-b]pyridin-4-amine;
7-(4-chlorophenyl)-1,6-dihydro-N,1-dimethyl-imidazo[4,5-d]pyrrolo[2,3-b]pyridin-4-amine;
1,6-dihydro-1-methyl-4-(methylamino)-7-phenyl-methyl ester imidazo[4,5-d]pyrrolo[2,3-b]pyridine-8-carboxylic acid;
N-[[3-[1,6-dihydro-1-methyl-4-(methylamino)imidazo[4,5-d]pyrrolo[2,3-b]pyridin-7-yl]phenyl]methyl]urea;
N-[[3-[1,6-dihydro-1-methyl-4-(methylamino)imidazo[4,5-d]pyrrolo[2,3-b]pyridin-7-yl]phenyl]methyl]guanidine;
7[3-(aminomethyl)phenyl]-1,6-dihydro-1-methyl-imidazo[4,5-d]pyrrolo[2,3-b]pyridin-4-amine;
N-[[3-(4-Amino-1,6-dihydro-1-methylimidazo[4,5-d]pyrrolo[2,3-b]pyridin-7-yl)phenyl]methyl]acetamide;

7-(3-fluorophenyl)-1,6-dihydro-1-methylimidazo[4,5-d]pyrrolo[2,3-b]pyridin-4-amine;

8-chloro-7-(3-fluorophenyl)-1,6-dihydro-1-methylimidazo[4,5-d]pyrrolo[2,3-b]pyridin-4-amine;

3-(1-Methyl-4-methylamino-1,6-dihydro-1,3,5,6-tetraaza-as-indacen-7-yl)-benzoic acid N-Cyclopropyl-3-(1-methyl-4-methylamino-1,6-dihydro-1,3,5,6-tetraaza-as-indacen-7-yl)-benzamide;

[3-(1-Methyl-4-methylamino-1,6-dihydro-1,3,5,6-tetraaza-as-indacen-7-yl)-phenyl]-morpholin-4-yl-methanone;

7-(3-bromophenyl)-1,6-dihydro-N,1-dimethyl-imidazo[4,5-d]pyrrolo[2,3-b]pyridin-4-amine;

3-[1,6-dihydro-1-methyl-4-(methylamino)imidazo[4,5-d]pyrrolo[2,3-b]pyridin-7-yl]-benzoic acid, ethyl ester;

3-[1,6-dihydro-1-methyl-4-(methylamino)imidazo[4,5-d]pyrrolo[2,3-b]pyridin-7-yl]-N-(2-furanylmethyl)-benzamide;

(2S)-1-[3-[1,6-dihydro-1-methyl-4-(methylamino)imidazo[4,5-d]pyrrolo[2,3-b]pyridin-7-yl]benzoyl]-2-pyrrolidinecarboxamide;

1-[3-[1,6-dihydro-1-methyl-4-(methylamino)imidazo[4,5-d]pyrrolo[2,3-b]pyridin-7-yl]benzoyl]-3-pyrrolidinol;

3-[1,6-dihydro-1-methyl-4-(methylamino)imidazo[4,5-d]pyrrolo[2,3-b]pyridin-7-yl]-N-[(tetrahydro-2-furanyl)methyl]-benzamide;

4-[3-[1,6-dihydro-1-methyl-4-(methylamino)imidazo[4,5-d]pyrrolo[2,3-b]pyridin-7-yl]benzoyl]-thiomorpholine;

1-[3-[1,6-dihydro-1-methyl-4-(methylamino)imidazo[4,5-d]pyrrolo[2,3-b]pyridin-7-yl]benzoyl]-piperidine;

1-[3-[1,6-dihydro-1-methyl-4-(methylamino)imidazo[4,5-d]pyrrolo[2,3-b]pyridin-7-yl]benzoyl]-3-piperidinecarboxamide;

1[-3-[1,6-dihydro-1-methyl-4-(methylamino)imidazo[4,5-d]pyrrolo[2,3-b]pyridin-7-yl]benzoyl]-4-piperidinol;

3-[1,6-dihydro-1-methyl-4-(methylamino)imidazo[4,5-d]pyrrolo[2,3-b]pyridin-7-yl]-N-(3-pyridinylmethyl)-benzamide;

3-[1,6-dihydro-1-methyl-4-(methylamino)imidazo[4,5-d]pyrrolo[2,3-b]pyridin-7-yl]-N-[2-(1-piperidinyl)ethyl]-benzamide;

3-[1,6-dihydro-1-methyl-4-(methylamino)imidazo[4,5-d]pyrrolo[2,3-b]pyridin-7-yl]-N-(2-methylpropyl)-benzamide;

3-[1,6-dihydro-1-methyl-4-(methylamino)imidazo[4,5-d]pyrrolo[2,3-b]pyridin-7-yl]-N-ethyl-benzamide;

N-[2-(acetylamino)ethyl]-3-[1,6-dihydro-1-methyl-4-(methylamino)imidazo[4,5-d]pyrrolo[2,3-b]pyridin-7-yl]-benzamide;

3-[1,6-dihydro-1-methyl-4-(methylamino)imidazo[4,5-d]pyrrolo[2,3-b]pyridin-7-yl]-N-(4-hydroxybutyl)-benzamide;

3-[1,6-dihydro-1-methyl-4-(methylamino)imidazo[4,5-d]pyrrolo[2,3-b]pyridin-7-yl]-N,N-diethyl-benzamide;

3-[1,6-dihydro-1-methyl-4-(methylamino)imidazo[4,5-d]pyrrolo[2,3-b]pyridin-7-yl]-N-methyl-N-propyl-benzamide;

N-[3-[1,6-dihydro-1-methyl-4-(methylamino)imidazo[4,5-d]pyrrolo[2,3-b]pyridin-7-yl]benzoyl]-glycine, ethyl ester;

N-[3-[1,6-dihydro-1-methyl-4-(methylamino)imidazo[4,5-d]pyrrolo[2,3-b]pyridin-7-yl]benzoyl]-beta-alanine, ethyl ester;

4-[[3-[1,6-dihydro-1-methyl-4-(methylamino)imidazo[4,5-d]pyrrolo[2,3-b]pyridin-7-yl]benzoyl]amino]-butanoic acid, ethyl ester;

1-[3-[1,6-dihydro-1-methyl-4-(methylamino)imidazo[4,5-d]pyrrolo[2,3-b]pyridin-7-yl]benzoyl]-4-piperidinecarboxamide;

1-acetyl-4-[3-[1,6-dihydro-1-methyl-4-(methylamino)imidazo[4,5-d]pyrrolo[2,3-b]pyridin-7-yl]benzoyl]-piperazine;

N-[1-[3-[1,6-dihydro-1-methyl-4-(methylamino)imidazo[4,5-d]pyrrolo[2,3-b]pyridin-7-yl]benzoyl]-3-pyrrolidinyl]-acetamide;

1-[3-[1,6-dihydro-1-methyl-4-(methylamino)imidazo[4,5-d]pyrrolo[2,3-b]pyridin-7-yl]benzoyl]-4-piperidinemethanol;

4-[3-[1,6-dihydro-1-methyl-4-(methylamino)imidazo[4,5-d]pyrrolo[2,3-b]pyridin-7-yl]benzoyl]-2-piperazinone;

3-[1,6-dihydro-1-methyl-4-(methylamino)imidazo[4,5-d]pyrrolo[2,3-b]pyridin-7-yl]-5-fluoro-benzoic acid, methyl ester;

3-[1,6-dihydro-1-methyl-4-(methylamino)imidazo[4,5-d]pyrrolo[2,3-b]pyridin-7-yl]-5-fluoro-benzoic acid;

4-[3-[1,6-dihydro-1-methyl-4-(methylamino)imidazo[4,5-d]pyrrolo[2,3-b]pyridin-7-yl]-5-fluorobenzoyl]-morpholine;

3-[1,6-dihydro-1-methyl-4-(methylamino)imidazo[4,5-d]pyrrolo[2,3-b]pyridin-7-yl]-5-fluoro-N-(2-methoxyethyl)-benzamide;

N-[[4-[1,6-dihydro-1-methyl-4-(methylamino)imidazo[4,5-d]pyrrolo[2,3-b]pyridin-7-yl]phenyl]methyl]-acetamide;

N-[[4-[1,6-dihydro-1-methyl-4-(methylamino)imidazo[4,5-d]pyrrolo[2,3-b]pyridin-7-yl]phenyl]methyl]-propanamide;

N-[[4-[1,6-dihydro-1-methyl-4-(methylamino)imidazo[4,5-d]pyrrolo[2,3-b]pyridin-7-yl]phenyl]methyl]-2-methyl-propanamide;

N-[[4-[1,6-dihydro-1-methyl-4-(methylamino)imidazo[4,5-d]pyrrolo[2,3-b]pyridin-7-yl]phenyl]methyl]-2,2-dimethyl-propanamide;

N-[[4-[1,6-dihydro-1-methyl-4-(methylamino)imidazo[4,5-d]pyrrolo[2,3-b]pyridin-7-yl]phenyl]methyl]-cyclopropanecarboxamide;

N-[[4-[1,6-dihydro-1-methyl-4-(methylamino)imidazo[4,5-d]pyrrolo[2,3-b]pyridin-7-yl]phenyl]methyl]-1-methyl-cyclopropanecarboxamide;

N-[[4-[1,6-dihydro-1-methyl-4-(methylamino)imidazo[4,5-d]pyrrolo[2,3-b]pyridin-7-yl]phenyl]methyl]-1-hydroxy-cyclopropanecarboxamide;

1-cyano-N-[[4-[1,6-dihydro-1-methyl-4-(methylamino)imidazo[4,5-d]pyrrolo[2,3-b]pyridin-7-yl]phenyl]methyl]-cyclopropanecarboxamide;

N-[[4-[1,6-dihydro-1-methyl-4-(methylamino)imidazo[4,5-d]pyrrolo[2,3-b]pyridin-7-yl]phenyl]methyl]-2-hydroxy-acetamide;

2-cyano-N-[[4-[1,6-dihydro-1-methyl-4-(methylamino)imidazo[4,5-d]pyrrolo[2,3-b]pyridin-7-yl]phenyl]methyl]-acetamide;

N-[[4-[1,6-dihydro-1-methyl-4-(methylamino)imidazo[4,5-d]pyrrolo[2,3-b]pyridin-7-yl]phenyl]methyl]-3-methoxy-propanamide;

4-(aminosulfonyl)-N-[[4-[1,6-dihydro-1-methyl-4-(methylamino)imidazo[4,5-d]pyrrolo[2,3-b]pyridin-7-yl]phenyl]methyl]-butanamide;

N-[[4-[1,6-dihydro-1-methyl-4-(methylamino)imidazo[4,5-d]pyrrolo[2,3-b]pyridin-7-yl]phenyl]methyl]-benzamide;

N-[[4-[1,6-dihydro-1-methyl-4-(methylamino)imidazo[4,5-d]pyrrolo[2,3-b]pyridin-7-yl]phenyl]methyl]-benzeneacetamide;

N-[[4-[1,6-dihydro-1-methyl-4-(methylamino)imidazo[4,5-d]pyrrolo[2,3-b]pyridin-7-yl]phenyl]methyl]-3-thiophenecarboxamide;

N-[[4-[1,6-dihydro-1-methyl-4-(methylamino)imidazo[4,5-d]pyrrolo[2,3-b]pyridin-7-yl]phenyl]methyl]-1,2,3-thiadiazole-4-carboxamide;

N-[[4-[1,6-dihydro-1-methyl-4-(methylamino)imidazo[4,5-d]pyrrolo[2,3-b]pyridin-7-yl]phenyl]methyl]-4-methyl-1,2,3-thiadiazole-5-carboxamide;

N-[[4-[1,6-dihydro-1-methyl-4-(methylamino)imidazo[4,5-d]pyrrolo[2,3-b]pyridin-7-yl]phenyl]methyl]-1H-tetrazole-5-acetamide;

2-amino-N-[[4-[1,6-dihydro-1-methyl-4-(methylamino)imidazo[4,5-d]pyrrolo[2,3-b]pyridin-7-yl]phenyl]methyl]-acetamide;

N-[[4-[1,6-dihydro-1-methyl-4-(methylamino)imidazo[4,5-d]pyrrolo[2,3-b]pyridin-7-yl]phenyl]methyl]-2-(methylamino)-acetamide;

3-amino-N-[[4-[1,6-dihydro-1-methyl-4-(methylamino)imidazo[4,5-d]pyrrolo[2,3-b]pyridin-7-yl]phenyl]methyl]-propanamide;

(2S)-N-[[4-[1,6-dihydro-1-methyl-4-(methylamino)imidazo[4,5-d]pyrrolo[2,3-b]pyridin-7-yl]phenyl]methyl]-2-(methylamino)propanamide;

(2S)-2-amino-N-[[4-[1,6-dihydro-1-methyl-4-(methylamino)imidazo[4,5-d]pyrrolo[2,3-b]pyridin-7-yl]phenyl]methyl]-4-methylpentanamide;

(alphaS)-alpha-amino-N-[[4-[1,6-dihydro-1-methyl-4-(methylamino)imidazo[4,5-d]pyrrolo[2,3-b]pyridin-7-yl]phenyl]methyl]benzeneacetamide;

(2S)-N-[[4-[1,6-dihydro-1-methyl-4-(methylamino)imidazo[4,5-d]pyrrolo[2,3-b]pyridin-7-yl]phenyl]methyl]-2-pyrrolidinecarboxamide;

(2S,4R)-N-[[4-[1,6-dihydro-1-methyl-4-(methylamino)imidazo[4,5-d]pyrrolo[2,3-b]pyridin-7-yl]phenyl]methyl]-4-hydroxy-2-pyrrolidinecarboxamide;

7-[3-(1-aminoethyl)phenyl]-1,6-dihydro-N,1-dimethyl-imidazo[4,5-d]pyrrolo[2,3-b]pyridin-4-amine;

7-[3-(1-tert-butyloxycarbonylaminoethyl)phenyl]-1,6-dihydro-N,1-dimethyl-imidazo[4,5-d]pyrrolo[2,3-b]pyridin-4-amine;

N-[1-[3-[1,6-dihydro-1-methyl-4-(methylamino)imidazo[4,5-d]pyrrolo[2,3-b]pyridin-7-yl]phenyl]ethyl]-propanamide;

N-[1-[3-[1,6-dihydro-1-methyl-4-(methylamino)imidazo[4,5-d]pyrrolo[2,3-b]pyridin-7-yl]phenyl]ethyl]-2-hydroxy-acetamide;

2-cyano-N-[1-[3-[1,6-dihydro-1-methyl-4-(methylamino)imidazo[4,5-d]pyrrolo[2,3-b]pyridin-7-yl]phenyl]ethyl]-acetamide;

N-[1-[3-[1,6-dihydro-1-methyl-4-(methylamino)imidazo[4,5-d]pyrrolo[2,3-b]pyridin-7-yl]phenyl]ethyl]-cyclopropanecarboxamide;

N-[1-[3-[1,6-dihydro-1-methyl-4-(methylamino)imidazo[4,5-d]pyrrolo[2,3-b]pyridin-7-yl]phenyl]ethyl]-2-methyl-propanamide;

N-[1-[3-[1,6-dihydro-1-methyl-4-(methylamino)imidazo[4,5-d]pyrrolo[2,3-b]pyridin-7-yl]phenyl]ethyl]-1-methyl-cyclopropanecarboxamide;

N-[1-[3-[1,6-dihydro-1-methyl-4-(methylamino)imidazo[4,5-d]pyrrolo[2,3-b]pyridin-7-yl]phenyl]ethyl]-1-hydroxy-cyclopropanecarboxamide;

N-[1-[3-[1,6-dihydro-1-methyl-4-(methylamino)imidazo[4,5-d]pyrrolo[2,3-b]pyridin-7-yl]phenyl]ethyl]-3-methyl-butanamide;

N-[1-[3-[1,6-dihydro-1-methyl-4-(methylamino)imidazo[4,5-d]pyrrolo[2,3-b]pyridin-7-yl]phenyl]ethyl]-2,2-dimethyl-propanamide;

N-[1-[3-[1,6-dihydro-1-methyl-4-(methylamino)imidazo[4,5-d]pyrrolo[2,3-b]pyridin-7-yl]phenyl]ethyl]-2-ethoxy-acetamide;

N-[1-[3-[1,6-dihydro-1-methyl-4-(methylamino)imidazo[4,5-d]pyrrolo[2,3-b]pyridin-7-yl]phenyl]ethyl]-3-methoxy-propanamide;

1-cyano-N-[1-[3-[1,6-dihydro-1-methyl-4-(methylamino)imidazo[4,5-d]pyrrolo[2,3-b]pyridin-7-yl]phenyl]ethyl]-cyclopropanecarboxamide;

N-[1-[3-[1,6-dihydro-1-methyl-4-(methylamino)imidazo[4,5-d]pyrrolo[2,3-b]pyridin-7-yl]phenyl]ethyl]-3,3-dimethyl-butanamide;

2-(acetylamino)-N-[1-[3-[1,6-dihydro-1-methyl-4-(methylamino)imidazo[4,5-d]pyrrolo[2,3-b]pyridin-7-yl]phenyl]ethyl]-acetamide;

2-(acetyloxy)-N-[1-[3-[1,6-dihydro-1-methyl-4-(methylamino)imidazo[4,5-d]pyrrolo[2,3-b]pyridin-7-yl]phenyl]ethyl]-acetamide;

N-[1-[3-[1,6-dihydro-1-methyl-4-(methylamino)imidazo[4,5-d]pyrrolo[2,3-b]pyridin-7-yl]phenyl]ethyl]-3-hydroxy-3-methyl-butanamide;

N-[1-[3-[1,6-dihydro-1-methyl-4-(methylamino)imidazo[4,5-d]pyrrolo[2,3-b]pyridin-7-yl]phenyl]ethyl]-3-ethoxy-propanamide;

N-[1-[3-[1,6-dihydro-1-methyl-4-(methylamino)imidazo[4,5-d]pyrrolo[2,3-b]pyridin-7-yl]phenyl]ethyl]-2-methoxy-acetamide;

N-[[3-[1,6-dihydro-1-methyl-4-(methylamino)imidazo[4,5-d]pyrrolo[2,3-b]pyridin-7-yl]phenyl]methyl]-N'-(1,1-dimethylethyl)-urea;

N-[[3-[1,6-dihydro-1-methyl-4-(methylamino)imidazo[4,5-d]pyrrolo[2,3-b]pyridin-7-yl]phenyl]methyl]-N'-(4-methoxyphenyl)-urea;

N-[[3-[1,6-dihydro-1-methyl-4-(methylamino)imidazo[4,5-d]pyrrolo[2,3-b]pyridin-7-yl]phenyl]methyl]-1-propanesulfonamide;

N-[[3-[1,6-dihydro-1-methyl-4-(methylamino)imidazo[4,5-d]pyrrolo[2,3-b]pyridin-7-yl]phenyl]methyl]-ethanesulfonamide;

N-[[3-[1,6-dihydro-1-methyl-4-(methylamino)imidazo[4,5-d]pyrrolo[2,3-b]pyridin-7-yl]phenyl]methyl]-benzeneethanesulfonamide;

N-[[3-[1,6-dihydro-1-methyl-4-(methylamino)imidazo[4,5-d]pyrrolo[2,3-b]pyridin-7-yl]phenyl]methyl]-4-methoxy-benzenesulfonamide;

N-[[3-[1,6-dihydro-1-methyl-4-(methylamino)imidazo[4,5-d]pyrrolo[2,3-b]pyridin-7-yl]phenyl]methyl]-3-methoxy-benzeneacetamide;

N-[[3-[1,6-dihydro-1-methyl-4-(methylamino)imidazo[4,5-d]pyrrolo[2,3-b]pyridin-7-yl]phenyl]methyl]-N'-(phenylmethyl)-urea;

N-[[3-[1,6-dihydro-1-methyl-4-(methylamino)imidazo[4,5-d]pyrrolo[2,3-b]pyridin-7-yl]phenyl]methyl]-benzenemethanesulfonamide;

4-chloro-N-[[3-[1,6-dihydro-1-methyl-4-(methylamino)imidazo[4,5-d]pyrrolo[2,3-b]pyridin-7-yl]phenyl]methyl]-benzenesulfonamide;

N-[[3-[1,6-dihydro-1-methyl-4-(methylamino)imidazo[4,5-d]pyrrolo[2,3-b]pyridin-7-yl]phenyl]methyl]-4-methoxy-benzamide;
N-(4-chlorophenyl)-N'-[[3-[1,6-dihydro-1-methyl-4-(methylamino)imidazo[4,5-d]pyrrolo[2,3-b]pyridin-7-yl]phenyl]methyl]-urea;
N-[[3-[1,6-dihydro-1-methyl-4-(methylamino)imidazo[4,5-d]pyrrolo[2,3-b]pyridin-7-yl]phenyl]methyl]-N'-(2-phenylethyl)-urea;
N-[[3-[1,6-dihydro-1-methyl-4-(methylamino)imidazo[4,5-d]pyrrolo[2,3-b]pyridin-7-yl]phenyl]methyl]-butanamide;
[[3-[1,6-dihydro-1-methyl-4-(methylamino)imidazo[4,5-d]pyrrolo[2,3-b]pyridin-7-yl]phenyl]methyl]-carbamic acid, phenyl ester;
[[3-[1,6-dihydro-1-methyl-4-(methylamino)imidazo[4,5-d]pyrrolo[2,3-b]pyridin-7-yl]phenyl]methyl]-carbamic acid, phenylmethyl ester;
[[3-[1,6-dihydro-1-methyl-4-(methylamino)imidazo[4,5-d]pyrrolo[2,3-b]pyridin-7-yl]phenyl]methyl]-carbamic acid, ethyl ester;
[[3-[1,6-dihydro-1-methyl-4-(methylamino)imidazo[4,5-d]pyrrolo[2,3-b]pyridin-7-yl]phenyl]methyl]-carbamic acid, 2-methylpropyl ester;
[[3-[1,6-dihydro-1-methyl-4-(methylamino)imidazo[4,5-d]pyrrolo[2,3-b]pyridin-7-yl]phenyl]methyl]-carbamic acid, 4-methoxyphenyl ester;
[[3-[1,6-dihydro-1-methyl-4-(methylamino)imidazo[4,5-d]pyrrolo[2,3-b]pyridin-7-yl]phenyl]methyl]-carbamic acid, methyl ester;
[[3-[1,6-dihydro-1-methyl-4-(methylamino)imidazo[4,5-d]pyrrolo[2,3-b]pyridin-7-yl]phenyl]methyl]-carbamic acid, 4-chlorophenyl ester;
N-[[3-[1,6-dihydro-1-methyl-4-(methylamino)imidazo[4,5-d]pyrrolo[2,3-b]pyridin-7-yl]phenyl]methyl]-N'-phenyl-urea;
N-[[3-[1,6-dihydro-1-methyl-4-(methylamino)imidazo[4,5-d]pyrrolo[2,3-b]pyridin-7-yl]phenyl]methyl]-benzenesulfonamide;
(2R)-2-amino-N-[[3-[1,6-dihydro-1-methyl-4-(methylamino)imidazo[4,5-d]pyrrolo[2,3-b]pyridin-7-yl]phenyl]methyl]-3-hydroxy-3-methylbutanamide;
(2S)-2-amino-N-[[3-[1,6-dihydro-1-methyl-4-(methylamino)imidazo[4,5-d]pyrrolo[2,3-b]pyridin-7-yl]phenyl]methyl]-3-hydroxy-3-methylbutanamide;
N-[[3-[1,6-dihydro-1-methyl-4-(methylamino)imidazo[4,5-d]pyrrolo[2,3-b]pyridin-7-yl]phenyl]methyl]-3-(dimethylamino)-propanamide;
N-[2-[[[3-[1,6-dihydro-1-methyl-4-(methylamino)imidazo[4,5-d]pyrrolo[2,3-b]pyridin-7-yl]phenyl]methyl]amino]-2-oxoethyl]-benzamide;
N-[[3-[1,6-dihydro-1-methyl-4-(methylamino)imidazo[4,5-d]pyrrolo[2,3-b]pyridin-7-yl]phenyl]methyl]-3-pyridinecarboxamide;
N-[[3-[1,6-dihydro-1-methyl-4-(methylamino)imidazo[4,5-d]pyrrolo[2,3-b]pyridin-7-yl]phenyl]methyl]-3-pyridinecarboxamide;
2-cyano-N-[[3-[1,6-dihydro-1-methyl-4-(methylamino)imidazo[4,5-d]pyrrolo[2,3-b]pyridin-7-yl]phenyl]methyl]-acetamide;
N-[[3-[1,6-dihydro-1-methyl-4-(methylamino)imidazo[4,5-d]pyrrolo[2,3-b]pyridin-7-yl]phenyl]methyl]-2-methoxy-acetamide;
(alphaS)-N-[[3-[1,6-dihydro-1-methyl-4-(methylamino)imidazo[4,5-d]pyrrolo[2,3-b]pyridin-7-yl]phenyl]methyl]-alpha-(dimethylamino)benzenepropanamide;
N-[[3-[1,6-dihydro-1-methyl-4-(methylamino)imidazo[4,5-d]pyrrolo[2,3-b]pyridin-7-yl]phenyl]methyl]-4-(dimethylamino)-butanamide;
N-[[3-[1,6-dihydro-1-methyl-4-(methylamino)imidazo[4,5-d]pyrrolo[2,3-b]pyridin-7-yl]phenyl]methyl]-1-piperidinepropanamide;
N-[[3-[1,6-dihydro-1-methyl-4-(methylamino)imidazo[4,5-d]pyrrolo[2,3-b]pyridin-7-yl]phenyl]methyl]-cyclohexaneacetamide;
(alphaS)-N-[[3-[1,6-dihydro-1-methyl-4-(methylamino)imidazo[4,5-d]pyrrolo[2,3-b]pyridin-7-yl]phenyl]methyl]-alpha-methoxy-alpha-(trifluoromethyl)benzeneacetamide;
(alphaR)-N-[[3-[1,6-dihydro-1-methyl-4-(methylamino)imidazo[4,5-d]pyrrolo[2,3-b]pyridin-7-yl]phenyl]methyl]-alpha-methoxy-alpha-(trifluoromethyl)benzeneacetamide;
N-[[3-[1,6-dihydro-1-methyl-4-(methylamino)imidazo[4,5-d]pyrrolo[2,3-b]pyridin-7-yl]phenyl]methyl]-alpha-hydroxy-alpha-methyl-benzeneacetamide;
N-[[3-[1,6-dihydro-1-methyl-4-(methylamino)imidazo[4,5-d]pyrrolo[2,3-b]pyridin-7-yl]phenyl]methyl]-2,5-dioxo-4-imidazolidineacetamide;
N-[[3-[1,6-dihydro-1-methyl-4-(methylamino)imidazo[4,5-d]pyrrolo[2,3-b]pyridin-7-yl]phenyl]methyl]-3,3,3-trifluoro-2-hydroxy-2-methyl-propanamide;
N-[[3-[1,6-dihydro-1-methyl-4-(methylamino)imidazo[4,5-d]pyrrolo[2,3-b]pyridin-7-yl]phenyl]methyl]-2-hydroxy-2-methyl-propanamide;
5-[1,6-dihydro-1-methyl-4-(methylamino)imidazo[4,5-d]pyrrolo[2,3-b]pyridin-7-yl]-2-fluoro-benzonitrile7-[3-(aminomethyl)-4-fluorophenyl]-1,6-dihydro-N,1-dimethyl-imidazo[4,5-d]pyrrolo[2,3-b]pyridin-4-amine;
N-[[5-[1,6-dihydro-1-methyl-4-(methylamino)imidazo[4,5-d]pyrrolo[2,3-b]pyridin-7-yl]-2-fluorophenyl]methyl]-2-hydroxy-acetamide;
(2S)-N-[[5-[1,6-dihydro-1-methyl-4-(methylamino)imidazo[4,5-d]pyrrolo[2,3-b]pyridin-7-yl]-2-fluorophenyl]methyl]-,2-pyrrolidinecarboxamide
N-[[5-[1,6-dihydro-1-methyl-4-(methylamino)imidazo[4,5-d]pyrrolo[2,3-b]pyridin-7-yl]-2-fluorophenyl]methyl]-2-hydroxy-2-methyl-propanamide;
N-[[5-[1,6-dihydro-1-methyl-4-(methylamino)imidazo[4,5-d]pyrrolo[2,3-b]pyridin-7-yl]-2-fluorophenyl]methyl]-3-hydroxy-butanamide;
N-[[5-[1,6-dihydro-1-methyl-4-(methylamino)imidazo[4,5-d]pyrrolo[2,3-b]pyridin-7-yl]-2-fluorophenyl]methyl]-2-methoxy-acetamide;
2-cyano-N-[[5-[1,6-dihydro-1-methyl-4-(methylamino)imidazo[4,5-d]pyrrolo[2,3-b]pyridin-7-yl]-2-fluorophenyl]methyl]-acetamide;
N-[[5-[1,6-dihydro-1-methyl-4-(methylamino)imidazo[4,5-d]pyrrolo[2,3-b]pyridin-7-yl]-2-fluorophenyl]methyl]-acetamide;
N-[[5-[1,6-dihydro-1-methyl-4-(methylamino)imidazo[4,5-d]pyrrolo[2,3-b]pyridin-7-yl]-2-fluorophenyl]methyl]-1-hydroxy-cyclopropanecarboxamide;
1-cyano-N-[[5-[1,6-dihydro-1-methyl-4-(methylamino)imidazo[4,5-d]pyrrolo[2,3-b]pyridin-7-yl]-2-fluorophenyl]methyl]-cyclopropanecarboxamide;
(2S)-2-amino-N-[[5-[1,6-dihydro-1-methyl-4-(methylamino)imidazo[4,5-d]pyrrolo[2,3-b]pyridin-7-yl]-2-fluorophenyl]methyl]-3-hydroxypropanamide;
N-[[5-[1,6-dihydro-1-methyl-4-(methylamino)imidazo[4,5-d]pyrrolo[2,3-b]pyridin-7-yl]-2-fluorophenyl]methyl]-3-methoxy-propanamide;

N-[[5-[1,6-dihydro-1-methyl-4-(methylamino)imidazo[4,5-d]pyrrolo[2,3-b]pyridin-7-yl]-2-fluorophenyl]methyl]-propanamide;
N-[[5-[1,6-dihydro-1-methyl-4-(methylamino)imidazo[4,5-d]pyrrolo[2,3-b]pyridin-7-yl]-2-fluorophenyl]methyl]-2-(2-methoxyethoxy)-acetamide;
(2R)-N-[[5-[1,6-dihydro-1-methyl-4-(methylamino)imidazo[4,5-d]pyrrolo[2,3-b]pyridin-7-yl]-2-fluorophenyl]methyl]2-pyrrolidinecarboxamide;
N-[[5-[1,6-dihydro-1-methyl-4-(methylamino)imidazo[4,5-d]pyrrolo[2,3-b]pyridin-7-yl]-2-fluorophenyl]methyl]-3,3,3-trifluoro-propanamide;
(2S,4R)-N-[[5-[1,6-dihydro-1-methyl-4-(methylamino)imidazo[4,5-d]pyrrolo[2,3-b]pyridin-7-yl]-2-fluorophenyl]methyl]-4-hydroxy-2-pyrrolidinecarboxamide;
N-[[5-[1,6-dihydro-1-methyl-4-(methylamino)imidazo[4,5-d]pyrrolo[2,3-b]pyridin-7-yl]-2-fluorophenyl]methyl]-cyclopropanecarboxamide;
N-[[5-[1,6-dihydro-1-methyl-4-(methylamino)imidazo[4,5-d]pyrrolo[2,3-b]pyridin-7-yl]-2-fluorophenyl]methyl]-4-pyridinecarboxamide;
N-[[5-[1,6-dihydro-1-methyl-4-(methylamino)imidazo[4,5-d]pyrrolo[2,3-b]pyridin-7-yl]-2-fluorophenyl]methyl]-2-pyridinecarboxamide;
N-[[5-[1,6-dihydro-1-methyl-4-(methylamino)imidazo[4,5-d]pyrrolo[2,3-b]pyridin-7-yl]-2-fluorophenyl]methyl]-2,2-dimethyl-propanamide;
N-[[5-[1,6-dihydro-1-methyl-4-(methylamino)imidazo[4,5-d]pyrrolo[2,3-b]pyridin-7-yl]-2-fluorophenyl]methyl]-3-pyridinecarboxamide;
(2S)-2-amino-N-[[5-[1,6-dihydro-1-methyl-4-(methylamino)imidazo[4,5-d]pyrrolo[2,3-b]pyridin-7-yl]-2-fluorophenyl]methyl]-3-(phenylmethoxy)propanamide;
(2S,4R)-N-[[5-[1,6-dihydro-1-methyl-4-(methylamino)imidazo[4,5-d]pyrrolo[2,3-b]pyridin-7-yl]-2-fluorophenyl]methyl]-4-(phenylmethoxy)2-pyrrolidinecarboxamide;
(2S)-N-[[5-[1,6-dihydro-1-methyl-4-(methylamino)imidazo[4,5-d]pyrrolo[2,3-b]pyridin-7-yl]-2-fluorophenyl]methyl]-3-hydroxy-2-(methylamino)propanamide;
(3S)-N-[[5-[1,6-dihydro-1-methyl-4-(methylamino)imidazo[4,5-d]pyrrolo[2,3-b]pyridin-7-yl]-2-fluorophenyl]methyl]-3-hydroxybutanamide;
N-[[5-[1,6-dihydro-1-methyl-4-(methylamino)imidazo[4,5-d]pyrrolo[2,3-b]pyridin-7-yl]-2-fluorophenyl]methyl]-3-hydroxy-3-methyl-butanamide;
(2S,3R)-2-amino-N-[[5-[1,6-dihydro-1-methyl-4-(methylamino)imidazo[4,5-d]pyrrolo[2,3-b]pyridin-7-yl]-2-fluorophenyl]methyl]-3-methoxybutanamide;
N-[[5-[1,6-dihydro-1-methyl-4-(methylamino)imidazo[4,5-d]pyrrolo[2,3-b]pyridin-7-yl]-2-fluorophenyl]methyl]-2-oxo-1-pyrrolidinebutanamide;
(2S)-2-amino-N-[[5-[1,6-dihydro-1-methyl-4-(methylamino)imidazo[4,5-d]pyrrolo[2,3-b]pyridin-7-yl]-2-fluorophenyl]methyl]-3-methoxypropanamide;
7-[3-(aminomethyl)-5-fluorophenyl]-1,6-dihydro-N,1-dimethyl-imidazo[4,5-d]pyrrolo[2,3-b]pyridin-4-amine;
N-[[3-[1,6-dihydro-1-methyl-4-(methylamino)imidazo[4,5-d]pyrrolo[2,3-b]pyridin-7-yl]-5-fluorophenyl]methyl]-cyclopropanecarboxamide;
2-cyano-N-[[3-[1,6-dihydro-1-methyl-4-(methylamino)imidazo[4,5-d]pyrrolo[2,3-b]pyridin-7-yl]-5-fluorophenyl]methyl]-acetamide;
N-[[3-[1,6-dihydro-1-methyl-4-(methylamino)imidazo[4,5-d]pyrrolo[2,3-b]pyridin-7-yl]-5-fluorophenyl]methyl]-propanamide;
N-[[3-[1,6-dihydro-1-methyl-4-(methylamino)imidazo[4,5-d]pyrrolo[2,3-b]pyridin-7-yl]-5-fluorophenyl]methyl]-2,2-dimethyl-propanamide;
2-(acetylamino)-N-[[3-[1,6-dihydro-1-methyl-4-(methylamino)imidazo[4,5-d]pyrrolo[2,3-b]pyridin-7-yl]-5-fluorophenyl]methyl]-acetamide;
N-[[3-[1,6-dihydro-1-methyl-4-(methylamino)imidazo[4,5-d]pyrrolo[2,3-b]pyridin-7-yl]-5-fluorophenyl]methyl]-2-methoxy-acetamide;
N-[[3-[1,6-dihydro-1-methyl-4-(methylamino)imidazo[4,5-d]pyrrolo[2,3-b]pyridin-7-yl]-5-fluorophenyl]methyl]-2-hydroxy-acetamide;
N-[[3-[1,6-dihydro-1-methyl-4-(methylamino)imidazo[4,5-d]pyrrolo[2,3-b]pyridin-7-yl]-5-fluorophenyl]methyl]-2-hydroxy-2-methyl-propanamide;
N-[[3-[1,6-dihydro-1-methyl-4-(methylamino)imidazo[4,5-d]pyrrolo[2,3-b]pyridin-7-yl]-5-fluorophenyl]methyl]-1-hydroxy-cyclopropanecarboxamide;
(2S)-1-acetyl-N-[[3-[1,6-dihydro-1-methyl-4-(methylamino)imidazo[4,5-d]pyrrolo[2,3-b]pyridin-7-yl]-5-fluorophenyl]methyl]-2-pyrrolidinecarboxamide;
N-[[3-[1,6-dihydro-1-methyl-4-(methylamino)imidazo[4,5-d]pyrrolo[2,3-b]pyridin-7-yl]-5-fluorophenyl]methyl]-acetamide;
(2S)-N-[[3-[1,6-dihydro-1-methyl-4-(methylamino)imidazo[4,5-d]pyrrolo[2,3-b]pyridin-7-yl]-5-fluorophenyl]methyl]-2-pyrrolidinecarboxamide;
(2S,4R)-N-[[3-[1,6-dihydro-1-methyl-4-(methylamino)imidazo[4,5-d]pyrrolo[2,3-b]pyridin-7-yl]-5-fluorophenyl]methyl]-4-(phenylmethoxy)-2-pyrrolidinecarboxamide;
N-[[3-[1,6-dihydro-1-methyl-4-(methylamino)imidazo[4,5-d]pyrrolo[2,3-b]pyridin-7-yl]-5-fluorophenyl]methyl]-2-(2-methoxyethoxy)-acetamide;
(2S,4R)-N-[[3-[1,6-dihydro-1-methyl-4-(methylamino)imidazo[4,5-d]pyrrolo[2,3-b]pyridin-7-yl]-5-fluorophenyl]methyl]-4-hydroxy-2-pyrrolidinecarboxamide;
(2R)-1-acetyl-N-[[3-[1,6-dihydro-1-methyl-4-(methylamino)imidazo[4,5-d]pyrrolo[2,3-b]pyridin-7-yl]-5-fluorophenyl]methyl]-2-pyrrolidinecarboxamide;
N-[[3-[1,6-dihydro-1-methyl-4-(methylamino)imidazo[4,5-d]pyrrolo[2,3-b]pyridin-7-yl]-5-fluorophenyl]methyl]-3,3,3-trifluoro-propanamide;
N-[[3-[1,6-dihydro-1-methyl-4-(methylamino)imidazo[4,5-d]pyrrolo[2,3-b]pyridin-7-yl]-5-fluorophenyl]methyl]-4-methyl-1,2,3-thiadiazole-5-carboxamide;
1-cyano-N-[[3-[1,6-dihydro-1-methyl-4-(methylamino)imidazo[4,5-d]pyrrolo[2,3-b]pyridin-7-yl]-5-fluorophenyl]methyl]-cyclopropanecarboxamide;
N-[[3-[1,6-dihydro-1-methyl-4-(methylamino)imidazo[4,5-d]pyrrolo[2,3-b]pyridin-7-yl]-5-fluorophenyl]methyl]-3-morpholinecarboxamide;
1,6-dihydro-N,1-dimethyl-7-[3-[(methylamino)methyl]phenyl]-imidazo[4,5-d]pyrrolo[2,3-b]pyridin-4-amine;
1,6-dihydro-N,1-dimethyl-7-[3-[(methylamino)methyl]phenyl]-imidazo[4,5-d]pyrrolo[2,3-b]pyridin-4-amine;
N-[[3-[1,6-dihydro-1-methyl-4-(methylamino)imidazo[4,5-d]pyrrolo[2,3-b]pyridin-7-yl]phenyl]methyl]-N-methyl-acetamide;
N-[[3-[1,6-dihydro-1-methyl-4-(methylamino)imidazo[4,5-d]pyrrolo[2,3-b]pyridin-7-yl]phenyl]methyl]-N-methyl-methanesulfonamide;

N-[[3-[1,6-dihydro-1-methyl-4-(methylamino)imidazo[4,5-d]pyrrolo[2,3-b]pyridin-7-yl]phenyl]methyl]-2-(2-methoxyethoxy)-N-methyl-acetamide;

1-cyano-N-[[3-[1,6-dihydro-1-methyl-4-(methylamino)imidazo[4,5-d]pyrrolo[2,3-b]pyridin-7-yl]phenyl]methyl]-N-methyl-cyclopropanecarboxamide;

N-[[3-[1,6-dihydro-1-methyl-4-(methylamino)imidazo[4,5-d]pyrrolo[2,3-b]pyridin-7-yl]phenyl]methyl]-2-methoxy-N-methyl-acetamide;

N-[[3-[1,6-dihydro-1-methyl-4-(methylamino)imidazo[4,5-d]pyrrolo[2,3-b]pyridin-7-yl]phenyl]methyl]-N,2,2-trimethyl-propanamide;

N-[[3-[1,6-dihydro-1-methyl-4-(methylamino)imidazo[4,5-d]pyrrolo[2,3-b]pyridin-7-yl]phenyl]methyl]-N-methyl-propanamide;

N-[[3-[1,6-dihydro-1-methyl-4-(methylamino)imidazo[4,5-d]pyrrolo[2,3-b]pyridin-7-yl]phenyl]methyl]-N-methyl-cyclopropanecarboxamide;

N-[[3-[1,6-dihydro-1-methyl-4-(methylamino)imidazo[4,5-d]pyrrolo[2,3-b]pyridin-7-yl]phenyl]methyl]-1-hydroxy-N-methyl-cyclopropanecarboxamide;

2-(acetylamino)-N-[[3-[1,6-dihydro-1-methyl-4-(methylamino)imidazo[4,5-d]pyrrolo[2,3-b]pyridin-7-yl]phenyl]methyl]-N-methyl-acetamide;

N-[[3-[1,6-dihydro-1-methyl-4-(methylamino)imidazo[4,5-d]pyrrolo[2,3-b]pyridin-7-yl]phenyl]methyl]-2-hydroxy-N,2-dimethyl-propanamide;

N-[[3-[1,6-dihydro-1-methyl-4-(methylamino)imidazo[4,5-d]pyrrolo[2,3-b]pyridin-7-yl]phenyl]methyl]-3,3,3-trifluoro-N-methyl-propanamide;

(2R)-1-acetyl-N-[[3-[1,6-dihydro-1-methyl-4-(methylamino)imidazo[4,5-d]pyrrolo[2,3-b]pyridin-7-yl]phenyl]methyl]-N-methyl-2-pyrrolidinecarboxamide;

N-[[3-[1,6-dihydro-1-methyl-4-(methylamino)imidazo[4,5-d]pyrrolo[2,3-b]pyridin-7-yl]phenyl]methyl]-N,4-dimethyl-1,2,3-thiadiazole-5-carboxamide;

N-[[3-[1,6-dihydro-1-methyl-4-(methylamino)imidazo[4,5-d]pyrrolo[2,3-b]pyridin-7-yl]phenyl]methyl]-2-hydroxy-N-methyl-acetamide;

(2S)-1-acetyl-N-[[3-[1,6-dihydro-1-methyl-4-(methylamino)imidazo[4,5-d]pyrrolo[2,3-b]pyridin-7-yl]phenyl]methyl]-N-methyl-2-pyrrolidinecarboxamide;

3-(1-methyl-4-(methylamino)-1,6-dihydroimidazo[4,5-d]pyrrolo[2,3-b]pyridin-7-yl)benzyl 4-isopropylpiperazine-1-carboxylate;

3-[1,6-dihydro-1-methyl-4-(methylamino)imidazo[4,5-d]pyrrolo[2,3-b]pyridin-7-yl]-benzenemethanol;

3-(1-methyl-4-(methylamino)-1,6-dihydroimidazo[4,5-d]pyrrolo[2,3-b]pyridin-7-yl)benzyl 2-methoxyethylcarbamate;

3-(1-methyl-4-(methylamino)-1,6-dihydroimidazo[4,5-d]pyrrolo[2,3-b]pyridin-7-yl)benzyl methylcarbamate;

3-(1-methyl-4-(methylamino)-1,6-dihydroimidazo[4,5-d]pyrrolo[2,3-b]pyridin-7-yl)benzyl cyclopropylcarbamate;

3-(1-methyl-4-(methylamino)-1,6-dihydroimidazo[4,5-d]pyrrolo[2,3-b]pyridin-7-yl)benzyl 5-methyl-1,3,4-thiadiazol-2-ylcarbamate;

3-(1-methyl-4-(methylamino)-1,6-dihydroimidazo[4,5-d]pyrrolo[2,3-b]pyridin-7-yl)benzyl tert-butylcarbamate;

3-(1-methyl-4-(methylamino)-1,6-dihydroimidazo[4,5-d]pyrrolo[2,3-b]pyridin-7-yl)benzyl 2-fluorobenzylcarbamate;

3-(1-methyl-4-(methylamino)-1,6-dihydroimidazo[4,5-d]pyrrolo[2,3-b]pyridin-7-yl)benzyl 2-hydroxyethylcarbamate;

3-(1-methyl-4-(methylamino)-1,6-dihydroimidazo[4,5-d]pyrrolo[2,3-b]pyridin-7-yl)benzyl bis(2-methoxyethyl)carbamate;

3-(1-methyl-4-(methylamino)-1,6-dihydroimidazo[4,5-d]pyrrolo[2,3-b]pyridin-7-yl)benzyl isoxazol-3-ylcarbamate;

3-(1-methyl-4-(methylamino)-1,6-dihydroimidazo[4,5-d]pyrrolo[2,3-b]pyridin-7-yl)benzyl 2-isopropoxyethylcarbamate;

3-(1-methyl-4-(methylamino)-1,6-dihydroimidazo[4,5-d]pyrrolo[2,3-b]pyridin-7-yl)benzyl 3-oxopiperazine-1-carboxylate;

3-(1-methyl-4-(methylamino)-1,6-dihydroimidazo[4,5-d]pyrrolo[2,3-b]pyridin-7-yl)benzyl 4-(hydroxymethyl)piperidine-1-carboxylate;

(R)-3-(1-methyl-4-(methylamino)-1,6-dihydroimidazo[4,5-d]pyrrolo[2,3-b]pyridin-7-yl)benzyl 3-hydroxypyrrolidine-1-carboxylate;

3-(1-methyl-4-(methylamino)-1,6-dihydroimidazo[4,5-d]pyrrolo[2,3-b]pyridin-7-yl)benzyl methyl(1-methylpyrrolidin-3-yl)carbamate;

3-(1-methyl-4-(methylamino)-1,6-dihydroimidazo[4,5-d]pyrrolo[2,3-b]pyridin-7-yl)benzyl 4-acetylpiperazine-1-carboxylate;

2-((3-(1-methyl-4-(methylamino)-1,6-dihydroimidazo[4,5-d]pyrrolo[2,3-b]pyridin-7-yl)benzyloxy)carbonylamino)acetic acid;

3-(1-methyl-4-(methylamino)-1,6-dihydroimidazo[4,5-d]pyrrolo[2,3-b]pyridin-7-yl)benzyl 3-(dimethylamino)propyl(methyl)carbamate;

3-(1-methyl-4-(methylamino)-1,6-dihydroimidazo[4,5-d]pyrrolo[2,3-b]pyridin-7-yl)benzyl 2-(dimethylamino)ethyl(methyl)carbamate;

(S)-3-(1-methyl-4-(methylamino)-1,6-dihydroimidazo[4,5-d]pyrrolo[2,3-b]pyridin-7-yl)benzyl 3-(methoxymethyl)pyrrolidine-1-carboxylate;

3-(1-methyl-4-(methylamino)-1,6-dihydroimidazo[4,5-d]pyrrolo[2,3-b]pyridin-7-yl)benzyl methyl(propyl)carbamate;

3-(1-methyl-4-(methylamino)-1,6-dihydroimidazo[4,5-d]pyrrolo[2,3-b]pyridin-7-yl)benzyl diethylcarbamate;

3-(1-methyl-4-(methylamino)-1,6-dihydroimidazo[4,5-d]pyrrolo[2,3-b]pyridin-7-yl)benzyl ethyl(methyl)carbamate;

3-(1-methyl-4-(methylamino)-1,6-dihydroimidazo[4,5-d]pyrrolo[2,3-b]pyridin-7-yl)benzyl methyl(phenethyl)carbamate;

3-(1-methyl-4-(methylamino)-1,6-dihydroimidazo[4,5-d]pyrrolo[2,3-b]pyridin-7-yl)benzyl benzyl(methyl)carbamate;

3-(1-methyl-4-(methylamino)-1,6-dihydroimidazo[4,5-d]pyrrolo[2,3-b]pyridin-7-yl)benzyl isopentylcarbamate;

3-(1-methyl-4-(methylamino)-1,6-dihydroimidazo[4,5-d]pyrrolo[2,3-b]pyridin-7-yl)benzyl phenethylcarbamate;

3-(1-methyl-4-(methylamino)-1,6-dihydroimidazo[4,5-d]pyrrolo[2,3-b]pyridin-7-yl)benzyl 2-acetamidoethylcarbamate;

3-(1-methyl-4-(methylamino)-1,6-dihydroimidazo[4,5-d]pyrrolo[2,3-b]pyridin-7-yl)benzyl ethylcarbamate;

3-(1-methyl-4-(methylamino)-1,6-dihydroimidazo[4,5-d]pyrrolo[2,3-b]pyridin-7-yl)benzyl 4-fluorobenzylcarbamate;

3-(1-methyl-4-(methylamino)-1,6-dihydroimidazo[4,5-d]pyrrolo[2,3-b]pyridin-7-yl)benzyl isopropylcarbamate;

3-(1-methyl-4-(methylamino)-1,6-dihydroimidazo[4,5-d]pyrrolo[2,3-b]pyridin-7-yl)benzyl methyl(1-methylpiperidin-4-yl)carbamate;

3-(1-methyl-4-(methylamino)-1,6-dihydroimidazo[4,5-d]pyrrolo[2,3-b]pyridin-7-yl)benzyl pyridin-4-ylmethylcarbamate;

3-(1-methyl-4-(methylamino)-1,6-dihydroimidazo[4,5-d]pyrrolo[2,3-b]pyridin-7-yl)benzyl pyridin-3-ylmethylcarbamate;

3-(1-methyl-4-(methylamino)-1,6-dihydroimidazo[4,5-d]pyrrolo[2,3-b]pyridin-7-yl)benzyl pyridin-2-ylmethylcarbamate;

3-(1-methyl-4-(methylamino)-1,6-dihydroimidazo[4,5-d]pyrrolo[2,3-b]pyridin-7-yl)benzyl4-(2-hydroxyethyl)piperidine-1-carboxylate;

3-(1-methyl-4-(methylamino)-1,6-dihydroimidazo[4,5-d]pyrrolo[2,3-b]pyridin-7-yl)benzyl3-(hydroxymethyl)piperidine-1-carboxylate;

3-(1-methyl-4-(methylamino)-1,6-dihydroimidazo[4,5-d]pyrrolo[2,3-b]pyridin-7-yl)benzyl morpholine-4-carboxylate;

3-(1-methyl-4-(methylamino)-1,6-dihydroimidazo[4,5-d]pyrrolo[2,3-b]pyridin-7-yl)benzyl4-(2-hydroxyethyl)piperazine-1-carboxylate;

3-(1-methyl-4-(methylamino)-1,6-dihydroimidazo[4,5-d]pyrrolo[2,3-b]pyridin-7-yl)benzyl4-methylpiperazine-1-carboxylate;

3-(1-methyl-4-(methylamino)-1,6-dihydroimidazo[4,5-d]pyrrolo[2,3-b]pyridin-7-yl)benzyl pyrrolidine-1-carboxylate;

3-(1-methyl-4-(methylamino)-1,6-dihydroimidazo[4,5-d]pyrrolo[2,3-b]pyridin-7-yl)benzyl benzyl(methyl)carbamate;

3-(1-methyl-4-(methylamino)-1,6-dihydroimidazo[4,5-d]pyrrolo[2,3-b]pyridin-7-yl)benzyl2-hydroxyethyl(methyl)carbamate;

3-(1-methyl-4-(methylamino)-1,6-dihydroimidazo[4,5-d]pyrrolo[2,3-b]pyridin-7-yl)benzyl2-cyanoethyl(methyl)carbamate;

3-(1-methyl-4-(methylamino)-1,6-dihydroimidazo[4,5-d]pyrrolo[2,3-b]pyridin-7-yl)benzyl4-phenylpiperazine-1-carboxylate;

3-(1-methyl-4-(methylamino)-1,6-dihydroimidazo[4,5-d]pyrrolo[2,3-b]pyridin-7-yl)benzyl sec-butylcarbamate;

3-(1-methyl-4-(methylamino)-1,6-dihydroimidazo[4,5-d]pyrrolo[2,3-b]pyridin-7-yl)benzyl3-fluorobenzylcarbamate;

3-(1-methyl-4-(methylamino)-1,6-dihydroimidazo[4,5-d]pyrrolo[2,3-b]pyridin-7-yl)benzyl isobutylcarbamate;

3-(1-methyl-4-(methylamino)-1,6-dihydroimidazo[4,5-d]pyrrolo[2,3-b]pyridin-7-yl)benzyl3-hydroxypiperidine-1-carboxylate;

3-(1-methyl-4-(methylamino)-1,6-dihydroimidazo[4,5-d]pyrrolo[2,3-b]pyridin-7-yl)benzyl cyclopropylmethylcarbamate;

3-(1-methyl-4-(methylamino)-1,6-dihydroimidazo[4,5-d]pyrrolo[2,3-b]pyridin-7-yl)benzyl4-methyl-1,4-diazepane-1-carboxylate;

(S)-3-(1-methyl-4-(methylamino)-1,6-dihydroimidazo[4,5-d]pyrrolo[2,3-b]pyridin-7-yl)benzyl 3-acetamidopyrrolidine-1-carboxylate;

3-(1-methyl-4-(methylamino)-1,6-dihydroimidazo[4,5-d]pyrrolo[2,3-b]pyridin-7-yl)benzyl2-methoxyethyl(methyl)carbamate;

3-(1-methyl-4-(methylamino)-1,6-dihydroimidazo[4,5-d]pyrrolo[2,3-b]pyridin-7-yl)benzyl4-(2-methoxyethyl)piperazine-1-carboxylate;

(S)-3-(1-methyl-4-(methylamino)-1,6-dihydroimidazo[4,5-d]pyrrolo[2,3-b]pyridin-7-yl)benzyl 3-hydroxypyrrolidine-1-carboxylate;

(R)-2-((3-(1-methyl-4-(methylamino)-1,6-dihydroimidazo[4,5-d]pyrrolo[2,3-b]pyridin-7-yl)benzyloxy)carbonylamino)propanoicacid;

3-(1-methyl-4-(methylamino)-1,6-dihydroimidazo[4,5-d]pyrrolo[2,3-b]pyridin-7-yl)benzyl4-isopropylpiperazine-1-carboxylate;

(S)-3-methyl-2-((3-(1-methyl-4-(methylamino)-1,6-dihydroimidazo[4,5-d]pyrrolo[2,3-b]pyridin-7-yl)benzyloxy)carbonylamino)butanoic acid;

N-[[3-[1,6-dihydro-1-methyl-4-(methylamino)imidazo[4,5-d]pyrrolo[2,3-b]pyridin-7-yl]phenyl]methyl]-N-(2-methoxyethyl)-methanesulfonamide;

7-(2-fluorophenyl)-1,6-dihydro-N,1-dimethyl-imidazo[4,5-d]pyrrolo[2,3-b]pyridin-4-amine;

7-(3-chloro-2-fluorophenyl)-1,6-dihydro-N,1-dimethyl-imidazo[4,5-d]pyrrolo[2,3-b]pyridin-4-amine;

7-(3,4-difluorophenyl)-1,6-dihydro-N,1-dimethyl-imidazo[4,5-d]pyrrolo[2,3-b]pyridin-4-amine;

1,6-dihydro-N,1-dimethyl-7-(3,4,5-trifluorophenyl)-imidazo[4,5-d]pyrrolo[2,3-b]pyridin-4-amine;

1,6-dihydro-N,1-dimethyl-7-[3-(methylthio)phenyl]-imidazo[4,5-d]pyrrolo[2,3-b]pyridin-4-amine;

1,6-dihydro-N,1-dimethyl-7-[3-(methylsulfonyl)phenyl]-imidazo[4,5-d]pyrrolo[2,3-b]pyridin-4-amine;

7-(3,4-difluoro-5-methoxyphenyl)-1,6-dihydro-N,1-dimethyl-imidazo[4,5-d]pyrrolo[2,3-b]pyridin-4-amine;

1,6-dihydro-N,1-dimethyl-7-(2,4,5-trifluorophenyl)-imidazo[4,5-d]pyrrolo[2,3-b]pyridin-4-amine;

7-(3-chloro-5-fluorophenyl)-1,6-dihydro-N,1-dimethyl-imidazo[4,5-d]pyrrolo[2,3-b]pyridin-4-amine;

1,6-dihydro-N,1-dimethyl-7-[3-(methylsulfinyl)phenyl]-imidazo[4,5-d]pyrrolo[2,3-b]pyridin-4-amine;

N-[[3-[1,6-dihydro-1-methyl-4-(methylamino)imidazo[4,5-d]pyrrolo[2,3-b]pyridin-7-yl]-5-fluorophenyl]methyl]-3-methoxy-propanamide;

N-[[3-[1,6-dihydro-1-methyl-4-(methylamino)imidazo[4,5-d]pyrrolo[2,3-b]pyridin-7-yl]-5-fluorophenyl]methyl]-4-morpholinecarboxamide;

N-[[3-[1,6-dihydro-1-methyl-4-(methylamino)imidazo[4,5-d]pyrrolo[2,3-b]pyridin-7-yl]-5-fluorophenyl]methyl]-N'-(2-methoxyethyl)-urea;

N-[[3-[1,6-dihydro-1-methyl-4-(methylamino)imidazo[4,5-d]pyrrolo[2,3-b]pyridin-7-yl]-5-fluorophenyl]methyl]-N'-(2-hydroxyethyl)-urea;

N-[[3-[1,6-dihydro-1-methyl-4-(methylamino)imidazo[4,5-d]pyrrolo[2,3-b]pyridin-7-yl]-5-fluorophenyl]methyl]-1-piperazinecarboxamide;

N-[[3-[1,6-dihydro-1-methyl-4-(methylamino)imidazo[4,5-d]pyrrolo[2,3-b]pyridin-7-yl]-5-fluorophenyl]methyl]-N'-methyl-urea;

N-[[3-[1,6-dihydro-1-methyl-4-(methylamino)imidazo[4,5-d]pyrrolo[2,3-b]pyridin-7-yl]-5-fluorophenyl]methyl]-4-hydroxy-1-piperidinecarboxamide;

N-(2-cyanoethyl)-N'-[[3-[1,6-dihydro-1-methyl-4-(methylamino)imidazo[4,5-d]pyrrolo[2,3-b]pyridin-7-yl]-5-fluorophenyl]methyl]-N-methyl-urea;

N'-[[3-[1,6-dihydro-1-methyl-4-(methylamino)imidazo[4,5-d]pyrrolo[2,3-b]pyridin-7-yl]-5-fluorophenyl]methyl]-N-(2-methoxyethyl)-N-methyl-urea;

3-(acetylamino)-N-[[3-[1,6-dihydro-1-methyl-4-(methylamino)imidazo[4,5-d]pyrrolo[2,3-b]pyridin-7-yl]-5-fluorophenyl]methyl]-1-pyrrolidinecarboxamide;

N-[[3-[1,6-dihydro-1-methyl-4-(methylamino)imidazo[4,5-d]pyrrolo[2,3-b]pyridin-7-yl]-5-fluorophenyl]methyl]-3-hydroxy-1-pyrrolidinecarboxamide;

N-[[3-[1,6-dihydro-1-methyl-4-(methylamino)imidazo[4,5-d]pyrrolo[2,3-b]pyridin-7-yl]-5-fluorophenyl]methyl]-3-morpholinecarboxamide;

N''-cyano-N-[[3-[1,6-dihydro-1-methyl-4-(methylamino)imidazo[4,5-d]pyrrolo[2,3-b]pyridin-7-yl]-5-fluorophenyl]methyl]-N'-methyl-guanidine;

N'-cyano-N-[[3-[1,6-dihydro-1-methyl-4-(methylamino)imidazo[4,5-d]pyrrolo[2,3-b]pyridin-7-yl]-5-fluorophenyl]methyl]-4-morpholinecarboximidamide;

N''-cyano-N-[[3-[1,6-dihydro-1-methyl-4-(methylamino)imidazo[4,5-d]pyrrolo[2,3-b]pyridin-7-yl]-5-fluorophenyl]methyl]-N'-(2-methoxyethyl)-guanidine;

N''-cyano-N'-[[3-[1,6-dihydro-1-methyl-4-(methylamino)imidazo[4,5-d]pyrrolo[2,3-b]pyridin-7-yl]-5-fluorophenyl]methyl]-N-(2-methoxyethyl)-N-methyl-guanidine;

N-[1-[(E)-(cyanoimino)[[[3-[1,6-dihydro-1-methyl-4-(methylamino)imidazo[4,5-d]pyrrolo[2,3-b]pyridin-7-yl]-5-fluorophenyl]methyl]amino]methyl]-3-pyrrolidinyl]-acetamide;

N'-cyano-N-[[3-[1,6-dihydro-1-methyl-4-(methylamino)imidazo[4,5-d]pyrrolo[2,3-b]pyridin-7-yl]-5-fluorophenyl]methyl]-4-hydroxy-1-piperidinecarboximidamide;

N''-cyano-N-[[3-[1,6-dihydro-1-methyl-4-(methylamino)imidazo[4,5-d]pyrrolo[2,3-b]pyridin-7-yl]-5-fluorophenyl]methyl]-N'-(2-hydroxyethyl)-guanidine;

N'-cyano-N-[[3-[1,6-dihydro-1-methyl-4-(methylamino)imidazo[4,5-d]pyrrolo[2,3-b]pyridin-7-yl]-5-fluorophenyl]methyl]-4-methyl-1-piperazinecarboximidamide;

N''-cyano-N-cyclopropyl-N'-[[3-[1,6-dihydro-1-methyl-4-(methylamino)imidazo[4,5-d]pyrrolo[2,3-b]pyridin-7-yl]-5-fluorophenyl]methyl]-guanidine;

[[[3-[1,6-dihydro-1-methyl-4-(methylamino)imidazo[4,5-d]pyrrolo[2,3-b]pyridin-7-yl]-5-fluorophenyl]methyl]amino]oxo-acetic acid, methyl ester;

[[[3-[1,6-dihydro-1-methyl-4-(methylamino)imidazo[4,5-d]pyrrolo[2,3-b]pyridin-7-yl]-5-fluorophenyl]methyl]amino]oxo-acetic acid;

N-cyclopropyl-N'-[[3-[1,6-dihydro-1-methyl-4-(methylamino)imidazo[4,5-d]pyrrolo[2,3-b]pyridin-7-yl]-5-fluorophenyl]methyl]-ethanediamide;

N-[[3-[1,6-dihydro-1-methyl-4-(methylamino)imidazo[4,5-d]pyrrolo[2,3-b]pyridin-7-yl]-5-fluorophenyl]methyl]-alpha-oxo-4-morpholineacetamide;

N-[[3-[1,6-dihydro-1-methyl-4-(methylamino)imidazo[4,5-d]pyrrolo[2,3-b]pyridin-7-yl]-5-fluorophenyl]methyl]-alpha-oxo-1-piperazineacetamide;

N-[[3-[1,6-dihydro-1-methyl-4-(methylamino)imidazo[4,5-d]pyrrolo[2,3-b]pyridin-7-yl]-5-fluorophenyl]methyl]-N'-(2-hydroxyethyl)-ethanediamide;

N-[(1E)-[[[3-[1,6-dihydro-1-methyl-4-(methylamino)imidazo[4,5-d]pyrrolo[2,3-b]pyridin-7-yl]-5-fluorophenyl]methyl]amino][(2-methoxyethyl)amino]methylene]-urea;

N-[(1Z)-[[[3-[1,6-dihydro-1-methyl-4-(methylamino)imidazo[4,5-d]pyrrolo[2,3-b]pyridin-7-yl]-5-fluorophenyl]methyl]amino](methylamino)methylene]-urea;

N,1-dimethyl-7-(3-vinylphenyl)-1,6-dihydroimidazo[4,5-d]pyrrolo[2,3-b]pyridin-4-amine;

N,1-dimethyl-7-(3'-vinylbiphenyl-3-yl)-1,6-dihydroimidazo[4,5-d]pyrrolo[2,3-b]pyridin-4-amine;

1-(3-(1-methyl-4-(methylamino)-1,6-dihydroimidazo[4,5-d]pyrrolo[2,3-b]pyridin-7-yl)phenyl)ethane-1,2-diol;

1-(3-(1-methyl-4-(methylamino)-1,6-dihydroimidazo[4,5-d]pyrrolo[2,3-b]pyridin-7-yl)phenyl)ethane-1,2-diol;

(R)-2-amino-2-(3-(1-methyl-4-(methylamino)-1,6-dihydroimidazo[4,5-d]pyrrolo[2,3-b]pyridin-7-yl)phenyl)ethanol;

(R)-N-(2-hydroxy-1-(3-(1-methyl-4-(methylamino)-1,6-dihydroimidazo[4,5-d]pyrrolo[2,3-b]pyridin-7-yl)phenypethyl)acetamide;

(R)-N-(2-hydroxy-1-(3-(1-methyl-4-(methylamino)-1,6-dihydroimidazo[4,5-d]pyrrolo[2,3-b]pyridin-7-yl)phenyl)ethyl)-2-methoxyacetamide;

(S)-2-amino-2-(3-(1-methyl-4-(methylamino)-1,6-dihydroimidazo[4,5-d]pyrrolo[2,3-b]pyridin -7-yl)phenyl)ethanol;

1-(1-(3-(1-methyl-4-(methylamino)-1,6-dihydroimidazo[4,5-d]pyrrolo[2,3-b]pyridin-7-yl)phenyl)ethyl)pyrrolidin-2-one;

3(1,6-dimethyl-4-(methylamino)-1,6-dihydroimidazo[4,5-d]pyrrolo[2,3-b]pyridin-7-yl)-5-fluorobenzonitrile;

3-[1,6-dihydro-1-methyl-4-(methylamino)imidazo[4,5-d]pyrrolo[2,3-b]pyridin-7-yl]-5-fluoro-benzonitrile;

3-(6-allyl-1-methyl-4-(methylamino)-1,6-dihydroimidazo[4,5-d]pyrrolo[2,3-b]pyridin-7-yl)-5-fluorobenzonitrile;

methyl2-(7-(3-cyano-5-fluorophenyl)-1-methyl-4-(methylamino)imidazo[4,5-d]pyrrolo[2,3-b]pyridin-6(1H)-yl)acetate;

2-(7-(3-cyano-5-fluorophenyl)-1-methyl-4-(methylamino)imidazo[4,5-d]pyrrolo[2,3-b]pyridin-6(1H)-yl)acetamide;

3-(6-ethyl-1-methyl-4-(methylamino)-1,6-dihydroimidazo[4,5-d]pyrrolo[2,3-b]pyridin-7-yl)-5-fluorobenzonitrile;

3-fluoro-5-(1-methyl-4-(methylamino)-6-propyl-1,6-dihydroimidazo[4,5-d]pyrrolo[2,3-b]pyridin-7-yl)benzonitrile;

3-fluoro-5-(6-(2-(2-hydroxyethylamino)ethyl)-1-methyl-4-(methylamino)-1,6-dihydroimidazo[4,5-d]pyrrolo[2,3-b]pyridin-7-yl)benzonitrile;

3-(6-(2-cyano-2-(2-hydroxyethylamino)ethyl)-1-methyl-4-(methylamino)-1,6-dihydroimidazo[4,5-d]pyrrolo[2,3-b]pyridin-7-yl)-5-fluorobenzonitrile;

3-(6-(3-(1,3-dioxoisoindolin-2-yl)propyl)-1-methyl-4-(methylamino)-1,6-dihydroimidazo[4,5-d]pyrrolo[2,3-b]pyridin-7-yl)-5-fluorobenzonitrile;

3-fluoro-5-(1-methyl-4-(methylamino)-6-(2-(pyrrolidin-1-yl)ethyl)-1,6-dihydroimidazo[4,5-d]pyrrolo[2,3-b]pyridin-7-yl)benzonitrile;

3-fluoro-5-(6-(2-(3-hydroxypyrrolidin-1-yl)ethyl)-1-methyl-4-(methylamino)-1,6-dihydroimidazo[4,5-d]pyrrolo[2,3-b]pyridin-7-yl)benzonitrile;

3-(6-(2-cyano-2-(3-hydroxypyrrolidin-1-yl)ethyl)-1-methyl-4-(methylamino)-1,6-dihydroimidazo[4,5-d]pyrrolo[2,3-b]pyridin-7-yl)-5-fluorobenzonitrile;

3-(6-(2-(tert-butylamino)ethyl)-1-methyl-4-(methylamino)-1,6-dihydroimidazo[4,5-d]pyrrolo[2,3-b]pyridin-7-yl)-5-fluorobenzonitrile;

3-(6-(2-(tert-butylamino)-2-cyanoethyl)-1-methyl-4-(methylamino)-1,6-dihydroimidazo[4,5-d]pyrrolo[2,3-b]pyridin-7-yl)-5-fluorobenzonitrile;

3-(6-(2-(dimethylamino)ethyl)-1-methyl-4-(methylamino)-1,6-dihydroimidazo[4,5-d]pyrrolo[2,3-b]pyridin-7-yl)-5-fluorobenzonitrile;

3-(6-(2-cyano-2-(dimethylamino)ethyl)-1-methyl-4-(methylamino)-1,6-dihydroimidazo[4,5-d]pyrrolo[2,3-b]pyridin-7-yl)-5-fluorobenzonitrile;

(S)-3-fluoro-5-(6-(2-(1hydroxypropan-2-ylamino)ethyl)-1-methyl-4-(methylamino)-1,6-dihydroimidazo[4,5-d]pyrrolo[2,3-b]pyridin-7-yl)benzonitrile;

3-(6-(2-cyano-2-((S)-1-hydroxypropan-2-ylamino)ethyl)-1-methyl-4-(methylamino)-1,6-dihydroimidazo[4,5-d]pyrrolo[2,3-b]pyridin-7-yl)-5-fluorobenzonitrile;

(S)-3-fluoro-5-(6-(2-(1hydroxybutan-2-ylamino)ethyl)-1-methyl-4-(methylamino)-1,6-dihydroimidazo[4,5-d]pyrrolo[2,3-b]pyridin-7-yl)benzonitrile;

3-(6-(2-cyano-2-((S)-1-hydroxybutan-2-ylamino)ethyl)-1-methyl-4-(methylamino)-1,6-dihydroimidazo[4,5-d]pyrrolo[2,3-b]pyridin-7-yl)-5-fluorobenzonitrile;

3-fluoro-5-(6-(2-hydroxyethyl)-1-methyl-4-(methylamino)-1,6-dihydroimidazo[4,5-d]pyrrolo[2,3-b]pyridin-7-yl)benzonitrile;

ethyl4-((7-(3-cyano-5-fluorophenyl)-1-methyl-4-(methylamino)imidazo[4,5-d]pyrrolo[2,3-b]pyridin-6(1H)-yl)methyl)benzoate;

3-fluoro-5-(6-(2-methoxyethyl)-1-methyl-4-(methylamino)-1,6-dihydroimidazo[4,5-d]pyrrolo[2,3-b]pyridin-7-yl)benzonitrile;

3-(6-(3,4-dihydroxybutyl)-1-methyl-4-(methylamino)-1,6-dihydroimidazo[4,5-d]pyrrolo[2,3-b]pyridin-7-yl)-5-fluorobenzonitrile;

3-(6-(3-amino-2-hydroxypropyl)-1-methyl-4-(methylamino)-1,6-dihydroimidazo[4,5-d]pyrrolo[2,3-b]pyridin-7-yl)-5-fluorobenzonitrile;

3-(6-(2-aminoethyl)-1-methyl-4-(methylamino)-1,6-dihydroimidazo[4,5-d]pyrrolo[2,3-b]pyridin-7-yl)-5-fluorobenzonitrile;

3-fluoro-5-(6-(2-hydroxypropyl)-1-methyl-4-(methylamino)-1,6-dihydroimidazo[4,5-d]pyrrolo[2,3-b]pyridin-7-yl)benzonitrile;

7-(3-(aminomethyl)-5-fluorophenyl)-N,1,6-trimethyl-1,6-dihydroimidazo[4,5-d]pyrrolo[2,3-b]pyridin-4-amine;

(S)-3-(7-(3-(aminomethyl)-5-fluorophenyl)-1-methyl-4-(methylamino)imidazo[4,5-d]pyrrolo[2,3-b]pyridin-6(1H)-yl)propane-1,2-diol;

(S)-3-(6-(2,3-dihydroxypropyl)-1-methyl-4-(methylamino)-1,6-dihydroimidazo[4,5-d]pyrrolo[2,3-b]pyridin-7-yl)-5-fluorobenzonitrile (R)-3-(6-(2,3-dihydroxypropyl)-1-methyl-4-(methylamino)-1,6-dihydroimidazo[4,5-d]pyrrolo[2,3-b]pyridin-7-yl)-5-fluorobenzonitrile;

3-fluoro-5-(6-(2-(2-methoxyethylamino)ethyl)-1-methyl-4-(methylamino)-1,6-dihydroimidazo[4,5-d]pyrrolo[2,3-b]pyridin-7-yl)benzonitrile;

3-(6-(2-cyano-2-(2-methoxyethylamino)ethyl)-1-methyl-4-(methylamino)-1,6-dihydroimidazo[4,5-d]pyrrolo[2,3-b]pyridin-7-yl)-5-fluorobenzonitrile;

3-fluoro-5-(6-(2-((2-hydroxyethyl)(methyl)amino)ethyl)-1-methyl-4-(methylamino)-1,6-dihydroimidazo[4,5-d]pyrrolo[2,3-b]pyridin-7-yl)benzonitrile;

3-(6-(2-(1,3-dihydroxypropan-2-ylamino)ethyl)-1-methyl-4-(methylamino)-1,6-dihydroimidazo[4,5-d]pyrrolo[2,3-b]pyridin-7-yl)-5-fluorobenzonitrile;

3-fluoro-5-(1-methyl-4-(methylamino)-6-(2-morpholinoethyl)-1,6-dihydroimidazo[4,5-d]pyrrolo[2,3-b]pyridin-7-yl)benzonitrile;

3-fluoro-5-(1-methyl-4-(methylamino)-6-(2-(piperazin-1-yl)ethyl)-1,6-dihydroimidazo[4,5-d]pyrrolo[2,3-b]pyridin-7-yl)benzonitrile;

3-(6-(2-(bis(2-hydroxyethyl)amino)ethyl)-1-methyl-4-(methylamino)-1,6-dihydroimidazo[4,5-d]pyrrolo[2,3-b]pyridin-7-yl)-5-fluorobenzonitrile;

3-fluoro-5-(6-(2-(2-(2-hydroxyethoxy)ethylamino)ethyl)-1-methyl-4-(methylamino)-1,6-dihydroimidazo[4,5-d]pyrrolo[2,3-b]pyridin-7-yl)benzonitrile;

1,6-dihydro-N,1,6-trimethyl-7-phenyl-imidazo[4,5-d]pyrrolo[2,3-b]pyridin-4-amine;

6-ethyl-1,6-dihydro-N,1-dimethyl-7-phenyl-imidazo[4,5-d]pyrrolo[2,3-b]pyridin-4-amine;

3-[1-methyl-4-(methylamino)-7-phenylimidazo[4,5-d]pyrrolo[2,3-b]pyridin-6(1H)-yl]-1,2-propanediol; or 1-methyl-4-(methylamino)-7-phenyl-imidazo[4,5-d]pyrrolo[2,3-b]pyridine-6(1H)-ethanol.

8. A pharmaceutical composition comprising (a) at least one compound according to claim 7, or a pharmaceutically acceptable salt thereof, and (b) a pharmaceutically-acceptable carrier or diluent.

* * * * *

UNITED STATES PATENT AND TRADEMARK OFFICE
CERTIFICATE OF CORRECTION

| PATENT NO. | : 7,737,279 B2 |
|---|---|
| APPLICATION NO. | : 11/430215 |
| DATED | : June 15, 2010 |
| INVENTOR(S) | : Pitts et al. |

It is certified that error appears in the above-identified patent and that said Letters Patent is hereby corrected as shown below:

In Column 395, Line 64:

Delete "$R^1$ is," and insert -- $R^1$ is --

In Column 396, Line 4:

After "$R^6$ is" insert -- aryl --

In Column 396, Line 59:

Delete "thophene" and insert -- thiophene --

In Column 397, Line 28:

Delete "$R^1$ is," and insert -- $R^1$ is --

In Column 397, Line 49:

After "$R^4$ is alkyl" insert -- ; --

In Column 397, Line 66:

In claim 5, before "one" delete "with"

Signed and Sealed this
Seventh Day of June, 2011

David J. Kappos
*Director of the United States Patent and Trademark Office*

CERTIFICATE OF CORRECTION (continued)
U.S. Pat. No. 7,737,279 B2

In Column 406, Line 40:

Delete ",2-pyrrolidinecarboxamide" and insert -- 2-pyrrolidinecarboxamide; --

In Column 414, Line 8:

Delete "phenypethyl)" and insert -- phenyl)ethyl) --

In Column 415, Line 7:

Delete "(2-(1hydroxybutan" and insert -- (2-(1-hydroxybutan --

In Column 415, Line 42:

Delete "fluorobenzonitrile" and insert -- fluorobenzonitrile; --